United States Patent
Gao et al.

(10) Patent No.: US 10,669,252 B2
(45) Date of Patent: Jun. 2, 2020

(54) BENZAZEPINE DERIVATIVE, PREPARATION METHOD, PHARMACEUTICAL COMPOSITION AND USE THEREOF

(71) Applicant: SHANGHAI DE NOVO PHARMATECH CO., LTD., Shanghai (CN)

(72) Inventors: Daxin Gao, Shanghai (CN); Yuxun Wang, Shanghai (CN); Shoujun Chen, Shanghai (CN); Heping Yang, Shanghai (CN)

(73) Assignee: SHANGHAI DE NOVO PHARMATECH CO., LTD., Shanghai (CN)

( * ) Notice: Subject to any disclaimer, the term of this patent is extended or adjusted under 35 U.S.C. 154(b) by 0 days.

(21) Appl. No.: 16/098,972

(22) PCT Filed: May 4, 2017

(86) PCT No.: PCT/CN2017/083031
§ 371 (c)(1),
(2) Date: Nov. 5, 2018

(87) PCT Pub. No.: WO2017/190669
PCT Pub. Date: Nov. 9, 2017

(65) Prior Publication Data
US 2019/0152941 A1    May 23, 2019

(30) Foreign Application Priority Data

May 6, 2016   (CN) .......................... 2016 1 0296748
Jul. 25, 2016  (CN) .......................... 2016 1 0589219
Nov. 4, 2016   (CN) .......................... 2016 1 0965360
Jan. 12, 2017  (CN) .......................... 2017 1 0020298
Jan. 24, 2017  (CN) .......................... 2017 1 0054038

(51) Int. Cl.
*C07D 401/04*  (2006.01)
*C07D 495/04*  (2006.01)
*C07D 471/04*  (2006.01)
*C07D 413/04*  (2006.01)
*C07D 403/04*  (2006.01)
(Continued)

(52) U.S. Cl.
CPC ............ *C07D 401/04* (2013.01); *A61K 31/55* (2013.01); *C07D 401/14* (2013.01); *C07D 403/04* (2013.01); *C07D 403/06* (2013.01); *C07D 403/14* (2013.01); *C07D 413/04* (2013.01); *C07D 413/14* (2013.01); *C07D 417/14* (2013.01); *C07D 471/04* (2013.01); *C07D 491/048* (2013.01); *C07D 495/04* (2013.01); *C07F 9/65583* (2013.01)

(58) Field of Classification Search
CPC .. C07D 401/14; C07D 401/04; C07D 403/04; C07D 471/04; C07D 491/048; C07D 417/14; C07D 413/14; C07D 413/04; C07D 403/14; C07D 403/06; C07D 495/04; C07D 413/413; C07F 9/65583; A61K 31/55
See application file for complete search history.

(56) References Cited

U.S. PATENT DOCUMENTS

2011/0118235 A1   5/2011   Howbert et al.
2014/0066432 A1   3/2014   Howbert et al.

FOREIGN PATENT DOCUMENTS

CA    2771609 A1    2/2011
CN    102753542    * 10/2012
(Continued)

OTHER PUBLICATIONS

Taro Kawai et al., "The role of pattern-recognition receptors in innate immunity: update on Toll-like receptors", Nature Immunology, vol. 11, No. 5, 2010, pp. 373-384.
(Continued)

*Primary Examiner* — Alexander R Pagano
*Assistant Examiner* — Ebenezer O Sackey
(74) *Attorney, Agent, or Firm* — Harness, Dickey & Pierce, P.L.C.

(57) ABSTRACT

Disclosed are a benzazepine derivative, a preparation method, a pharmaceutical composition and the use thereof. A compound as shown in formula (I) of the present invention, and an isomer, a prodrug, a stable isotope derivative or a pharmaceutically acceptable salt thereof have the following structure. The benzazepine derivative of the present invention has a good regulation effect on the TLR family and the related signaling pathway, and in particular, has a good regulation effect on TLR8, can effectively treat, relieve and/or prevent various diseases mediated by TLR family and the TLR-related signaling pathway, and in particular, can effectively treat, relieve and/or prevent various diseases mediated by TLR8, such as cancers, autoimmune diseases, infections, inflammations, transplantation rejections, graft-versus-host diseases, etc.

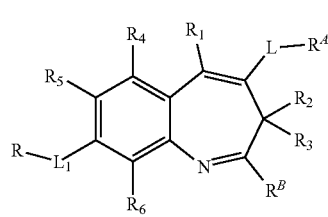

(I)

17 Claims, No Drawings

(51) Int. Cl.
| | | |
|---|---|---|
| C07D 403/06 | (2006.01) | |
| C07D 417/14 | (2006.01) | |
| C07D 403/14 | (2006.01) | |
| C07D 413/14 | (2006.01) | |
| C07D 401/14 | (2006.01) | |
| C07F 9/6558 | (2006.01) | |
| A61K 31/55 | (2006.01) | |
| C07D 491/048 | (2006.01) | |

(56) References Cited

FOREIGN PATENT DOCUMENTS

| | | |
|---|---|---|
| CN | 102753542 A | 10/2012 |
| CN | 102781933 A | 11/2012 |
| CN | 103562186 A | 2/2014 |
| JP | 2008515798 A | 5/2008 |
| JP | 2013502430 A | 1/2013 |
| JP | 2013502431 A | 1/2013 |
| JP | 2014505692 A | 3/2014 |
| WO | WO-2006041773 A2 | 4/2006 |
| WO | 2011022508 A2 | 2/2011 |
| WO | 2011022509 A2 | 2/2011 |
| WO | 2012097173 A2 | 7/2012 |

OTHER PUBLICATIONS

Gerty Schreibelt et al., "Toll-like receptor expression and function in human dendritic cell subsets: implications for dendritic cell-based anti-cancer immunotherapy", Cancer Immunol Immunother, vol. 59, 2010, pp. 1573-1582.
MS Hayden et al., "NF-kappaB and the immune response", Oncogene, vol. 25, 2006, pp. 6758-6780.
Holger Kanzler et al., "Therapeutic targeting of innate immunity with Toll-like receptor agonists and antagonists", Nature Medicine, vol. 3, No. 5, 2007, pp. 552-559.
Evelien L. J. M. Smits et al., "The use of TLR7 and TLR8 ligands for the enhancement of cancer immunotherapy", The Oncologist, vol. 13, 2008, pp. 859-875.
Elizabeth J. Hennessy et al., "Targeting Toll-like receptors: emerging therapeutics", Nature Reviews Drug Discovery, vol. 9, 2010, pp. 293-307.
Sabina Kaczanowska et al., "TLR agonists: our best frenemy in cancer immunotherapy", Journal of Leukocyte Biology, vol. 93, 2013, pp. 847-863.
Mallesh Beesu et al., "Identification of a human Toll-like receptor (TLR) 8-specific agonist and a functional Pan-TLR Inhibitor in 2-aminoimidazoles", Journal of Medicinal Chemistry, vol. 59, 2016, pp. 3311-3330.

Wei Cao et al., "Regulation of TLR7/9 responses in plasmacytoid dendritic cells by BST2 and ILT7 receptor Interaction", The Journal of Experimental Medicine, vol. 206, No. 7, 2009, pp. 1603-1614.
Keith B. Gorden et al., "Synthetic TLR agonists reveal functional differences between TLR7 and TLR8", The Journal of Immunology, vol. 174, 2005, pp. 1259-1268.
Anne Krug et al., "Interferon-producing cells fail to induce proliferation of naive T cells but can promote expansion and T helper 1 differentiation of antigen-experienced unpolarized T cells", The Journal of Experimental Medicine, vol. 197, No. 7, 2003, pp. 899-906.
Max Schnurr et al., "Extracellular nucleotide signaling by P2 receptors IL-12 and enhances IL-23 expression in human dendritic cells: a novel role for the cAMP pathway", Blood, vol. 105, No. 4, 2005, pp. 1582-1589.
Frederic Berard et al., "Cross-priming of naive CD8 T cells against melanoma antigens using dendritic cells loaded with killed allogeneic melanoma cells", The Journal of Experimental Medicine, vol. 192, No. 11, 2000, pp. 1535-1543.
Jakob Dalgaard et al., "Differential capability for phagocytosis of apoptotic and necrotic leukemia cells by human peripheral blood dendritic cell subsets", Journal of Leukocyte Biology, vol. 77, 2005, pp. 689-698.
Robert L. Ferris et al., "Tumor antigen-targeted, monoclonal antibody-based immunotherapy: clinical response, cellular immunity, and immunoescape", Journal of Clinical Oncology, vol. 28, No. 28, 2010, pp. 4390-4399.
Robert L. Ferris, "Immunology and immunotherapy of head and neck cancer", Journal of Clinical Oncology, vol. 33, No. 29, 2015, pp. 3293-3304.
Jj Ignatz-Hoover et al., "The role of TLR8 signaling in acute myeloid leukemia dfferentiation", Leukemia, vol. 29, 2015, pp. 918-926.
R.L. Miller et al., "Immunomodulation as a treatment strategy for genital herpes: review of the evidence", International Immunopharmacology, vol. 2, 2002, pp. 443-451.
International Search Report and Written Opinion of PCT/CN2017/083031 dated Aug. 3, 2017.
Examination Report issued in Australian patent application No. 2017259654 dated May 23, 2019.
Office Action issued in the counterpart Japanese application No. 2018-558270 dated Nov. 19, 2019.
Office Action issued in the counterpart Canadian application No. 3,023,154 dated Jan. 20, 2020.
Extended European Search Report issued in the counterpart European application No. 17792495.8 dated Dec. 5, 2019.
Written Opinion and Search Report issued in the counterpart Singaporean application No. 11201809859V dated Dec. 26, 2019.

* cited by examiner

BENZAZEPINE DERIVATIVE, PREPARATION METHOD, PHARMACEUTICAL COMPOSITION AND USE THEREOF

CROSS-REFERENCE TO RELATED APPLICATIONS

This application is a 371 National Phase of PCT/CN2017/083031 filed May 4, 2017, which claims the benefit of Chinese Patent Application No. CN201610296748.X filed on May 6, 2016, Chinese Patent Application No. CN201610589219.9 filed on Jul. 25, 2016, the Chinese Patent Application No. CN201610965360.4 filed on Nov. 4, 2016, Chinese Patent Application No. CN201710020298.6 filed on Jan. 12, 2017 and Chinese Patent Application No. CN201710054038.0 filed on Jan. 24, 2017. The entire disclosures of the above application applications are incorporated herein by reference.

FIELD OF INVENTION

The present invention relates to a benzazepine derivative, a preparation method, a pharmaceutical composition and a use thereof.

PRIOR ARTS

Toll-like receptors (TLRs) are important proteins that recognize pathogen-associated molecular patterns, sense and initiate innate immune responses, and promote the development of adaptive immune responses. TLRs are mainly expressed in immune cells such as myeloid dendritic cells (mDC), plasma-like dendritic cells (pDC), monocytes, B cells and lungs. In humans, more than 10 TLRs are considered to have significant functions. TLR1, TLR2, TLR4, TLR5 and TLR6 are located in the cell membrane and their primary function is to recognize extracellular macromolecular ligands from bacteria and fungi. In contrast, TLR3, TLR7, TLR8 and TLR9 are located in the endosomal membrane of cells, which main function is to recognize exogenous nucleic acids from pathogen cells. Although most TLRs work through specific signaling pathways (primarily through the MyD88-dependent pathway), different TLRs can coordinate different downstream molecules. The addition of specific TLRs leads to activation of different cell populations and production of different cytokines and other inflammatory mediators, resulting in different immune responses. For Embodiment, when bound to a ligand, TLR8 forms a dimer and conformational changes result in the involvement of the adaptor protein MyD88, which recruits an interleukin-1 receptor-associated kinase, leading to activation of downstream signaling pathways, including mitogen-associated protein kinases and transcription factor NF-κB.

TLRs, mainly TLR7, TLR8 and TLR9, located in connotations, have been considered as attractive new targets for anti-cancer immunotherapy (Kanzler, et al, 2007; Kreig 2008; Smits, et al, 2008; Hennessy, et al, 2010; Kaczanowska, et al, 2013; Beesu, et al, 2016). For Embodiment, TLR7 activates pDCs in response to viral infections, induces high levels of interferon alpha, and induces adaptive T cell responses of major cells to endogenous viral antigens (Liu, et al, 2009). Compared to TLR7 and TLR9, TLR8 is more widely expressed in immune cells of different subtypes. Regulatory T cells (Treg) have potent immune response inhibition and are major obstacles to effective cancer immunotherapy. The TLR8 signaling pathway has been shown to be necessary and sufficient for reversion of the Treg cell suppressor function and suppression of strong tumor. TLR8 selective agonists effectively activate a variety of immune cells, including mDCs and monocytes (Gorden, et al, 2005), and promote adaptive immune responses to cancer cells (Krug, et al, 2003; Schnurr, et al, 2005). Activated mDCs phagocytize apoptotic and dead tumor cells, and then cross-present tumor-associated antigensto $CD8^+CTLs$ more effectively than pDCs (Berard, et al, 2000; Dalgaard, et al, 2005). In addition, activation of mDCs leads to the release of TNFα and interleukin 12 (IL-12), which stimulates the activation of T cells and NK cells. Activation of NK cells is the primary mechanism of antibody-dependent cell-mediated cytotoxicity (ADCC). Thus, enhanced killing of tumor cells by ADCC may present an important therapeutic opportunity for TLR8 selective inhibitors (Lu, et al, 2011). Some monoclonal antibody therapies are widely used in cancer patients, such as rituximab and trastuzumab, which can be treated by ADCC (Ferris, et al, 2010). In fact, the addition of TLR8 agonists to mAb therapy can enhance ADCC and increase the efficacy of mAb therapy (Ferris, et al, 2015). In addition, recent studies have shown that TLR8 agonists have a direct antitumor effect, independent of their immunomodulatory function (Ignatz-Hoover, et al, 2015). Therefore, TLR8 agonists can not only act as a single drug for therapy, but also enhance the host immune response to improve the efficacy of a variety of chemotherapy and targeted anticancer drugs.

Among the TLRs family members that recognize the nucleic acid of pathogenic microorganisms, TLR7 and TLR8 have high homology and can recognize some synthetic small molecules with antiviral activity, such as Imidazoquinolines (ligands of TLR7 and TLR8). Imidazoquinolines were studied in a model of genital herpes of HSV-infected guinea pigs and were found to have a small effect on viral replication in vitro, but it had a strong effect in vivo, indicating that these compounds may promote proinflammatory cytokines and regulate cytokines in immune cells and lead to antiviral response (Int Immunopharmacol 2002; 2: 443-451). More importantly, TLR7 and TLR8 can recognize viral ssRNA. Studies have shown that ssRNA viruses are natural ligands of TLR7 and TLR8, such as type I human immunodeficiency virus (HIV), influenza virus, Sendai virus, dengue virus, Newcastle disease virus (NDV), vesicular stomatitis virus (VSV) and hepatitis C virus (HCV), etc. TLR8 recognizes antiviral compounds, ssRNA viruses, synthetic oligonucleotides, etc., induces Th1, inhibits Th2 cytokine secretion and Tregs proliferation through MyD88-dependent signaling pathway, mediates antiviral immunity, and exerts anti-infective and anti-allergic effects.

The X-ray crystal structure of the TLR8 protein and its associated TLR family members have been extensively studied, which will further promote structure-based drug design and optimization.

Therefore, TLR8 is currently an attractive therapeutic target. Although there have been more studies on TLRs, there are still huge opportunities for further expansion of their applications and advantages. The compounds and applications described herein will contribute to the development of TLR8 agonists to meet clinically unmet needs.

CONTENT OF THE PRESENT INVENTION

The technical problem to be solved in the present invention is to provide a novel benzazepine derivative, a preparation method, a pharmaceutical composition and the use thereof. The benzazepine derivative of the present invention has a good regulatory effect on TLRs, and can effectively treat, alleviate and/or prevent various related diseases caused by immunosuppression, such as cancer, autoimmune diseases, infection, inflammation, transplantation rejection, graft-versus-host disease, etc.

The present invention provides a compound of formula (I), an isomer, a prodrug, a stable isotopic derivative or a pharmaceutically acceptable salt thereof, $$\text{(I)}$$

wherein;

L is —C(O)—, —C(S)— or —S(O)$_2$—;

$L_1$ is a bond, $C_{2-6}$ alkenylene, $C_{2-6}$ alkynylene, —(CR$_a$R$_b$)$_m$—, —(CR$_a$R$_b$)$_u$O(CR$_a$R$_b$)$_v$—, —(CR$_a$R$_b$)$_u$C(O)(CR$_a$R$_b$)$_v$—, —(CR$_a$R$_b$)$_u$C(O)O(CR$_a$R$_b$)$_v$—, —(CR$_a$R$_b$)$_u$OC(O)(CR$_a$R$_b$)$_v$—, —(CR$_a$R$_b$)$_u$N(R$_c$)C(O)(CR$_a$R$_b$)$_v$—, —(CR$_a$R$_b$)$_u$C(O)N(R$_c$)(CR$_a$R$_b$)$_v$—, —(CR$_a$R$_b$)$_u$N(R$_c$)C(O)N(R$_c$)(CR$_a$R$_b$)$_v$—, —(CR$_a$R$_b$)$_u$C(S)(CR$_a$R$_b$)$_v$—, —(CR$_a$R$_b$)$_u$S(O)$_{0-2}$(CR$_a$R$_b$)$_v$, —(CR$_a$R$_b$)$_u$S(O)$_{1-2}$N(R$_c$)(CR$_a$R$_b$)$_v$, —(CR$_a$R$_b$)$_u$N(R$_c$)S(O)$_2$N(R$_c$)(CR$_a$R$_b$)$_v$ or —(CR$_a$R$_b$)$_u$N(R$_c$)S(O)$_{1-2}$(CR$_a$R$_b$)$_v$; each of u is independently 0, 1, 2 or 3; each of v is independently 0, 1, 2 or 3; m is 1, 2, 3, 4, 5 or 6;

R is selected from a bicyclic, tricyclic or tetracyclic fused ring, and the fused ring is unsubstituted or selectively substituted at any position by one or more than one substituent selected from the group consisting of halogen, alkyl, haloalkyl, haloalkoxy, alkenyl, alkynyl, Cy$^1$, -L$_2$-Cy$^1$, —CN, —NO$_2$, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —C(O)N(R$_d$)OR$_e$, —C(O)NR$_d$ S(O)$_2$R$_e$, —C(=NH)R$_e$, —C(=NH)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$ and —NR$_d$S(O)$_2$NR$_d$R$_e$; the alkyl, alkenyl or alkynyl is unsubstituted or selectively substituted at any position by one or more than one substituent selected from the group consisting of —CN, —NO$_2$, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —C(O)NR$_d$S(O)$_2$R$_e$, —NR$_d$R$_e$, —NR$_d$C(O)R$_e$, —N(R$_d$)C(O)OR$_e$, —N(R$_d$)C(O)NR$_d$R$_e$, —NR$_d$C(=NH)R$_e$, —NR$_d$C(=NH)NR$_d$R$_e$, —NR$_d$S(O)$_2$R$_e$, —NR$_d$S(O)$_2$NR$_d$R$_e$, —N(R$_d$)C(O)N(R$_d$)S(O)$_2$R$_e$, —(O)$_{1-2}$R$_e$, —S(O)$_2$NR$_d$R$_e$, —S(O)(=NCN)R$_e$, —S(O)(=NR$_d$)R$_e$, —S(O)(=NSO$_2$R$_d$)R$_e$, —S(O)$_2$N(R$_d$)C(O)R$_e$, —S(O)$_2$N(R$_d$)C(O)NR$_d$R$_e$, —P(O)(OR$_d$)$_2$, —OP(O)(OR$_d$)$_2$ or —B(OR$_d$)$_2$;

$L_2$ is a bond, $C_{2-6}$ alkenylene, $C_{2-6}$ alkynylene, —(CR$_{a1}$R$_{b1}$)$_m$—, —(CR$_{a1}$R$_{b1}$)$_u$O(CR$_{a1}$R$_{b1}$)$_v$—, —(CR$_{a1}$R$_{b1}$)$_u$C(O)(CR$_{a1}$R$_{b1}$)$_v$—, —(CR$_{a1}$R$_{b1}$)$_u$C(O)O(CR$_{a1}$R$_{b1}$)$_v$—, —(CR$_a$R$_b$)$_u$OC(O)(CR$_{a1}$R$_{b1}$)$_v$—, —(CR$_{a1}$R$_{b1}$)$_u$N(R$_{c1}$)C(O)(CR$_{a1}$R$_{b1}$)$_v$—, —(CR$_a$R$_b$)$_u$C(O)N(R$_{c1}$)(CR$_{a1}$R$_{b1}$)$_v$—, —(CR$_{a1}$R$_{b1}$)$_u$N(R$_c$)C(O)N(R$_{c1}$)(CR$_{a1}$R$_{b1}$)$_v$—, —(CR$_{a1}$R$_{b1}$)$_u$C(S)(CR$_{a1}$R$_{b1}$)$_v$—, —(CR$_{a1}$R$_{b1}$)$_u$S(O)$_{0-2}$(CR$_{a1}$R$_{b1}$)$_v$, —(CR$_{a1}$R$_{b1}$)$_u$S(O)$_{1-2}$N(R$_{c1}$)(CR$_{a1}$R$_{b1}$)$_v$, —(CR$_{a1}$R$_{b1}$)$_u$N(R$_{c1}$)S(O)$_2$N(R$_{c1}$)(CR$_{a1}$R$_{b1}$)$_v$ or —(CR$_{a1}$R$_{b1}$)$_u$N(R$_{c1}$)S(O)$_{1-2}$(CR$_{a1}$R$_{b1}$)$_v$; each of u is independently 0, 1, 2, or 3; each of v is independently 0, 1, 2, or 3; m is 1, 2, 3, 4, 5, or 6;

each of Cy$^1$ is independently cycloalkyl, heterocycloalkyl, aryl or heteroaryl; the Cy$^1$ is unsubstituted or selectively substituted at any position by one or more than one substituent selected from the group consisting of halogen, alkyl, haloalkyl, haloalkoxy, hydroxyalkyl, aminoalkyl, alkenyl, alkynyl, —CN, —NO$_2$, —SR$_{d2}$, —OR$_{d2}$, —OC(O)R$_{d2}$, —OC(O)OR$_{d2}$, —OC(O)NR$_{d2}$R$_{e2}$, —C(O)OR$_{d2}$, —C(O)R$_{d2}$, —C(O)NR$_{d2}$R$_{e2}$, —NR$_{d2}$R$_{e2}$, —NR$_{d2}$C(O)R$_{e2}$, —N(R$_{d2}$)C(O)OR$_{e2}$, —N(R$_{d2}$)C(O)NR$_{d2}$R$_{e2}$, —NR$_{d2}$S(O)$_2$R$_{e2}$, —NR$_{d2}$C(=NH)R$_{e2}$, —NR$_{d2}$C(=NH)NR$_{d2}$R$_{e2}$, —S(O)$_{1-2}$R$_{e2}$, —S(O)$_2$NR$_{d2}$R$_{e2}$ and —NR$_{d2}$S(O)$_2$NR$_{d2}$R$_{e2}$;

$R_1$, $R_2$ and $R_3$ are independently selected from hydrogen, deuterium, alkyl, alkenyl, alkynyl, cycloalkyl, heterocycloalkyl, aryl and heteroaryl, and the alkyl, alkenyl, alkynyl, cycloalkyl, heterocycloalkyl, aryl or heteroaryl is unsubstituted or selectively substituted at any position by 1 to 3 substituent selected from the group consisting of halogen, alkyl, haloalkyl, haloalkoxy, hydroxyalkyl, aminoalkyl, alkenyl, alkynyl, —CN, —NO$_2$, —SR$_{d2}$, —OR$_{d2}$, —OC(O)R$_{d2}$, —OC(O)OR$_{d2}$, —OC(O)NR$_{d2}$R$_{e2}$, —C(O)OR$_{d2}$, —C(O)R$_{d2}$, —C(O)NR$_{d2}$R$_{e2}$, —NR$_{d2}$R$_{e2}$, —NR$_{d2}$C(O)R$_{e2}$, —N(R$_{d2}$)C(O)OR$_{e2}$, —N(R$_{d2}$)C(O)NR$_{d2}$R$_{e2}$, —NR$_{d2}$S(O)$_2$R$_{e2}$, —NR$_{d2}$C(=NH)R$_{e2}$, —NR$_{d2}$C(=NH)NR$_{d2}$R$_{e2}$, —S(O)$_{1-2}$R$_{e2}$, —S(O)$_2$NR$_{d2}$R$_{e2}$ and —NR$_{d2}$S(O)$_2$NR$_{cu}$R$_{e2}$;

or, $R_2$ and $R_3$ together with the C atom to which they are attached, form a $C_{3-8}$ cycloalkyl or a 3 to 8 membered heterocycloalkyl; the $C_{3-8}$ cycloalkyl or 3 to 8 membered heterocycloalkyl is unsubstituted or selectively substituted at any position by 1 to 3 substituent selected from the group consisting of halogen, alkyl, haloalkyl, haloalkoxy, hydroxyalkyl, aminoalkyl, alkenyl, alkynyl, —CN, —NO$_2$, —SR$_{d2}$, —OR$_{d2}$, —OC(O)R$_{d2}$, —OC(O)OR$_{d2}$, —OC(O)NR$_{d2}$R$_{e2}$, —C(O)OR$_{d2}$, —C(O)R$_{d2}$, —C(O)NR$_{d2}$R$_{e2}$, —NR$_{d2}$R$_{e2}$, —NR$_{d2}$C(O)R$_{e2}$, —N(R$_{d2}$)C(O)OR$_{e2}$, —N(R$_{d2}$)C(O)NR$_{d2}$R$_{e2}$, —NR$_{d2}$S(O)$_2$R$_{e2}$, —NR$_{d2}$C(=NH)R$_{e2}$, —NR$_{d2}$C(=NH)NR$_{d2}$R$_{e2}$, —S(O)$_{1-2}$R$_{e2}$, —S(O)$_2$NR$_{d2}$R$_{e2}$ and —NR$_{d2}$S(O)$_2$NR$_{d2}$R$_{e2}$;

$R_4$, $R_5$ and $R_6$ are independently selected from hydrogen, deuterium, halogen, amino, cyano, nitro, $C_{1-6}$ alkyl, $C_{1-6}$ haloalkyl, $C_{1-6}$ haloalkoxy, $C_{1-6}$ alkoxy, $C_{2-6}$ alkenyl, $C_{2-6}$ alkynyl, $C_{1-6}$ hydroxyalkyl $C_{3-8}$ cycloalkyl, 3 to 8 membered heterocycloalkyl, phenyl or 5 to 6 membered heteroaryl;

$R^A$ is selected from —OR$_{d1}$ or —NR$_{d1}$R$_{e1}$;

$R^B$ is —NR$_{d1}$R$_{e1}$;

each of R$_a$, R$_b$, R$_{a1}$ and R$_{b1}$ is independently selected from hydrogen, deuterium, halogen, $C_{1-6}$ alkyl, $C_{1-6}$ alkoxy, $C_{2-6}$ alkenyl, $C_{2-6}$ alkynyl, $C_{3-8}$ cycloalkyl, 3 to 8 membered heterocycloalkyl, $C_{6-10}$ aryl, 5 to 6 membered heteroaryl, $C_{3-8}$ cycloalkyl $C_{1-6}$ alkyl, 3 to 8 membered heterocycloalkyl $C_{1-6}$ alkyl, phenyl $C_{1-6}$ alkyl or 5 to 6 membered heteroaryl $C_{1-6}$ alkyl; the $C_{1-6}$ alkyl, $C_{1-6}$ alkoxy, $C_{2-6}$ alkenyl, $C_{2-6}$ alkynyl, $C_{3-8}$ cycloalkyl, 3 to 8 membered heterocycloalkyl, $C_{6-10}$ aryl or 5 to 6 membered heteroaryl is unsubstituted or selectively substituted at any position by 1 to 3 substituent selected from the group consisting of halogen, hydroxyl, amino, carboxyl, $C_{2-6}$ alkenyl, $C_{2-6}$ alkynyl, $C_{1-6}$ alkyl, $C_{1-6}$ haloalkyl, $C_{1-6}$ alkoxy and $C_{1-6}$ haloalkoxy;

or, R$_a$ and R$_b$, or R$_{a1}$ and R$_{b1}$ together with the C atom to which they are attached, form a $C_{3-8}$ cycloalkyl or a 3 to 8 membered heterocycloalkyl;

each of R$_e$ and R$_{e1}$ is independently selected from hydrogen, $C_{1-4}$ alkyl, $C_{3-8}$ cycloalkyl or 3 to 8 membered heterocycloalkyl;

each of $R_d$, $R_e$, $R_{d1}$ and $R_{e1}$ is independently selected from hydrogen, $C_{1-6}$ alkyl, $C_{2-6}$ alkenyl, $C_{2-6}$ alkynyl, $C_{3-8}$ cycloalkyl, 3 to 8 membered heterocycloalkyl, $C_{6-10}$ aryl, 5 to 6 membered heteroaryl, $C_{3-8}$ cycloalkyl $C_{1-6}$ alkyl, 3 to 8 membered heterocycloalkyl $C_{1-6}$ alkyl, phenyl $C_{1-6}$ alkyl or 5 to 6 membered heteroaryl $C_{1-6}$ alkyl; $R_d$, $R_e$, $R_{d1}$ or $R_{e1}$ is unsubstituted or selectively substituted at any position by 1 to 3 substituent selected from the group consisting of halogen, hydroxyl, amino, carboxyl, $C_{1-6}$ alkyl, $C_{1-6}$ alkoxy, $C_{1-6}$ alkylamino, $C_{1-6}$ haloalkyl, $C_{1-6}$ haloalkoxy, $C_{2-6}$ alkenyl and $C_{2-6}$ alkynyl;

or, $R_d$ and $R_e$, or $R_{d1}$ and $R_{e1}$ together with the N atom to which they are attached, form a 3 to 8 membered heterocycloalkyl; the heterocycloalkyl can further contain 1 to 3 heteroatom selected from the group consisting of N, O and S; the heterocycloalkyl is unsubstituted or selectively substituted at any position by 1 to 3 substituent selected from the group consisting of halogen, amino, hydroxyl, carboxyl, cyano, $C_{1-6}$ alkyl, $C_{1-6}$ haloalkyl, $C_{2-6}$ alkenyl, $C_{2-6}$ alkynyl, $C_{1-3}$ alkyl, amino $C_{1-3}$ alkyl, —$OR_{d2}$, —$OC(O)R_{d2}$, —$OC(O)OR_{d2}$, —$OC(O)NR_{d2}R_{e2}$, —$C(O)OR_{d2}$, —$C(O)R_{d2}$, —$C(O)NR_{d2}R_{e2}$, —$NR_{d2}R_{e2}$, —$NR_{d2}C(O)R_{e2}$, —$N(R_{d2})C(O)OR_{e2}$, —$N(R_{d2})C(O)NR_{d2}R_{e2}$, —$NR_{d2}S(O)_2R_{e2}$, —$NR_{d2}C(=NH)R_{e2}$, —$NR_{d2}C(=NH)NR_{de}R_{e2}$, —$NR_{d2}S(O)_2NR_{d2}R_{e2}$, —$S(O)_{1-2}R_{d2}$ and —$S(O)_2NR_{d2}R_{e2}$;

each of $R_{d2}$ and $R_{ee}$ is independently selected from hydrogen, $C_{1-6}$ alkyl, $C_{2-6}$ alkenyl, $C_{2-6}$ alkynyl, $C_{3-8}$ cycloalkyl, 3 to 8 membered heterocycloalkyl, $C_{6-10}$ aryl, 5 to 6 membered heteroaryl, $C_{3-8}$ cycloalkyl $C_{1-6}$ alkyl, 3 to 8 membered heterocycloalkyl $C_{1-6}$ alkyl, phenyl $C_{1-6}$ alkyl or 5 to 6 membered heteroaryl $C_{1-6}$ alkyl; $R_{d2}$ or $R_{e2}$ is unsubstituted or selectively substituted at any position by 1 to 3 substituent selected from the group consisting of halogen, hydroxyl, amino, carboxyl, $C_{1-6}$ alkyl, $C_{1-6}$ alkoxy, $C_{1-6}$ alkylamino, $C_{1-6}$ haloalkyl, $C_{1-6}$ haloalkoxy, $C_{2-6}$ alkenyl and $C_{2-6}$ alkynyl; or, $R_{d2}$ and $R_{e2}$ together with the N atom attached form a 3 to 8 membered heterocycloalkyl.

In a preferred embodiment of the present invention, L is preferably —C(O)— or —S(O)$_2$—; R is preferably defined as above except for —C(O)N($R_d$)O$R_e$, wherein the alkyl, alkenyl or alkynyl in the definition of R is unsubstituted or selectively substituted at any position by one or more than one substituent as defined above except for —P(O)(O$R_d$)$_2$—, —OP(O)(O$R_d$)$_2$— and —B(O$R_d$)$_2$.

In a preferred embodiment of the present invention, L is preferably —C(O)—; R is preferably defined as above except for —C(O)N($R_d$)O$R_e$, wherein the alkyl, alkenyl or alkynyl in the definition of R is unsubstituted or selectively substituted at any position by one or more than one substituent as defined above except for —S(O)(=NCN)$R_e$, —S(O)(=N$R_d$)$R_e$, —S(O)(=NSO$_2R_d$)$R_e$, —P(O)(O$R_d$)$_2$—, —OP(O)(O$R_d$)$_2$— and —B(O$R_d$)$_2$.

In a preferred embodiment of the present invention, $L_1$ is preferably a bond, —CH$_2$—, —O—, —NH—, —OCH$_2$— or —CH$_2$O—.

In a preferred embodiment of the present invention, $R_1$ is preferably H.

In a preferred embodiment of the present invention, $R_2$ is preferably H.

In a preferred embodiment of the present invention, $R_3$ is preferably H.

In a preferred embodiment of the present invention, each of $R_4$, $R_5$ and $R_6$ is preferably selected from H, D, F, Cl, Br, —CH$_3$, —OCH$_3$, —CF$_3$, —CH$_2$F, —CHF$_2$, —OCF$_3$, —CN or —NH$_2$;

in another preferred embodiment of the present invention, each of $R_4$, $R_5$ and $R_6$ is preferably selected from H, I, F, Cl, Br, —CH$_3$, —OCH$_3$, —CF$_3$, —CH$_2$F, —CHF$_2$, —OCF$_3$, —CN or —NH$_2$;

in another preferred embodiment of the present invention, each of $R_4$, $R_5$ and $R_6$ is preferably selected from H, F, Cl, Br, —CH$_3$, —OCH$_3$, —CF$_3$, —CH$_2$F, —CHF$_2$, —OCF$_3$, —CN or —NH$_2$.

In a preferred embodiment of the present invention, in $R^A$, each of $R_{d1}$ and $R_{e1}$ is preferably selected from hydrogen, $C_{1-6}$ alkyl, $C_{1-6}$ haloalkyl, $C_{3-8}$ cycloalkyl or 3 to 8 membered heterocycloalkyl; $R_{d1}$ or $R_{e1}$ is unsubstituted or selectively substituted at any position by one hydroxyl.

Or, $R_{d1}$ and $R_{e1}$ together with the N atom to which they are attached, form a $C_{3-8}$ heterocycloalkyl; the heterocycloalkyl may further contain 1-3 hetero atoms selected from the group consisting of N, O, and S; the heterocycloalkyl is unsubstituted or further substituted at any position by one substituent selected from the group consisting of $C_{1-4}$ alkyl, $C_{1-3}$ haloalkyl, $C_{1-3}$ hydroxyalkyl or $C_{1-3}$ aminoalkyl.

In a preferred embodiment of the present invention, $R^B$ is preferably —NH$_2$.

In a preferred embodiment of the present invention, R is preferably selected from a 8 to 20 membered bicyclic, tricyclic or tetracyclic fused ring.

In another preferred embodiment of the present invention, R is preferably selected from a 9 to 15 membered bicyclic or tricyclic fused ring, and at least one ring of which is an aromatic ring.

In another preferred embodiment of the present invention, R is 9 to 15 membered bicyclic or tricyclic fused ring, one ring of which is an aromatic ring, the other 1 to 2 ring is non-aromatic ring, and the 9 to 15 membered bicyclic or tricyclic fused ring contains 1 to 3 N atom, and the non-aromatic ring further contains 1 to 2 oxo

and/or thio

In a preferred embodiment of the present invention, R is unsubstituted, or preferably substituted at any position by 1 to 4 substituent; more preferably substituted at any position substituted by 1, 1 to 2 or 1 to 3 substituent.

In a preferred embodiment of the present invention, when R is substituted, halogen as a substituent is preferably F, Cl or Br.

In a preferred embodiment of the present invention, when R is substituted, the alkyl as a substituent is preferably $C_{1-6}$ alkyl, such as methyl, ethyl, n-propyl, isopropyl, n-butyl, isobutyl, tert-butyl, neopentyl, tert-amyl or 2,2-dimethyl butyl.

In a preferred embodiment of the present invention, when R is substituted, the haloalkyl as a substituent is preferably $C_{1-6}$ haloalkyl, such as —CF$_3$, —CHF$_2$ or —CH$_2$F.

In a preferred embodiment of the present invention, when R is substituted, the haloalkoxy as a substituent is preferably $C_{1-6}$ haloalkoxy, such as —OCF$_3$, —OCHF$_2$ or —OCH$_2$F.

In a preferred embodiment of the present invention, when R is substituted, the alkenyl as a substituent is preferably $C_{2-6}$ alkenyl.

In a preferred embodiment of the present invention, when R is substituted, the alkynyl as a substituent is preferably $C_{2-6}$ alkynyl.

In a preferred embodiment of the present invention, when R is substituted, the alkyl, alkenyl or alkynyl as a substituent is unsubstituted or preferably substituted at any position by 1 to 3 substituent.

In a preferred embodiment of the present invention, when R is substituted, in the definition of -$L_2$-$Cy^1$, $L_2$ is preferably a bond or —$(CR_{a1}R_{b1})_m$—, and m, $R_{a1}$, $R_{b1}$ are defined as above; $L_2$ is more preferably a bond, —$CH_2$—, —$CH_2CH_2$—, —$CH_2CH_2CH_2$—, —$CH_2CH_2C(CH_3)_2$—, —$CH_2CH_2CH_2CH_2$— or —$CH_2CH(CH_3)CH_2$—;

in a preferred embodiment of the present invention, when R is substituted, the $Cy^1$ as a substituent is preferably $C_{3-10}$ cycloalkyl, 3 to 10 membered heterocycloalkyl, $C_{6-10}$ aryl or 5 to 10 membered heteroaryl;

In a preferred embodiment of the present invention, when R is substituted, in the definition of $Cy^1$ in the substituent, the 5 to 10 membered heteroaryl is preferably 5 to 6 membered heteroaryl, such as pyridyl, pyrimidinyl, pyrazinyl, furyl, thienyl, thiazolyl, pyrrolyl, imidazolyl, pyrazolyl, oxazolyl, isoxazolyl, 1,2,5-oxadiazolyl, 1,2,4-oxadiazolyl, 1,3,4-oxadiazolyl, 1,3,4-thiadiazole, 1,2,4-triazolyl, 1,2,3-triazolyl or tetrazolyl;

in a preferred embodiment of the invention, when R is substituted, in the definition of $Cy^1$ of the substituent, the $C_{6-10}$ aryl is more preferably phenyl;

In a preferred embodiment of the present invention, when R is substituted, in the definition of substituent, the $Cy^1$ is unsubstituted or selectively substituted at any position by 1 to 3 substituent selected from the group consisting of F, Cl, Br, $C_{1-4}$ alkyl (such as, methyl, ethyl, n-propyl, isopropyl or butyl, etc.), $C_{1-3}$ haloalkyl, $C_{1-3}$ haloalkoxy, $C_{1-3}$ hydroxyalkyl, $C_{1-3}$ aminoalkyl, $C_{2-6}$ alkenyl, $C_{2-6}$ alkynyl, —CN, —$NO_2$, —$SR_{d2}$, —$OR_{d2}$, —$OC(O)R_{d2}$, —$OC(O)OR_{d2}$, —$OC(O)NR_{d2}$, —$C(O)OR_{d2}$, —$C(O)R_{d2}$, —$C(O)NR_{d2}R_{e2}$, —$NR_{d2}R_{e2}$, —$NR_{d2}C(O)R_{e2}$, —$N(R_{d2})C(O)OR_{e2}$, —$N(R_{d2})C(O)NR_{d2}R_{e2}$, —$NR_{d2}S(O)_2R_{e2}$, —$NR_{d2}C(=NH)R_{e2}$, —$NR_{d2}C(=NH)NR_{d2}R_{e2}$, —$S(O)_{1-2}R_{e2}$, —$S(O)_2NR_{d2}R_{e2}$ and —$NR_{d2}S(O)_2NR_{d2}R_{e2}$; wherein $R_{d2}$ and $R_{e2}$ are defined as above.

In a preferred embodiment of the present invention, R is more preferably selected from the group consisting of R-1 to R-19:

R-1
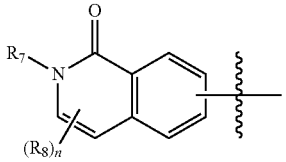

R-2
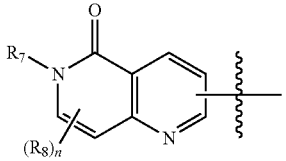

R-3
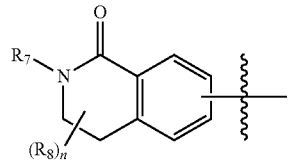

R-4
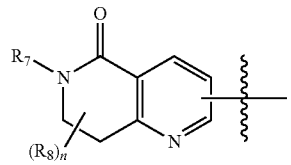

R-5
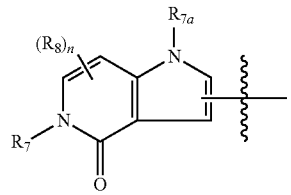

R-6
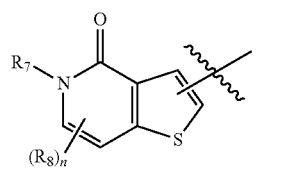

R-7
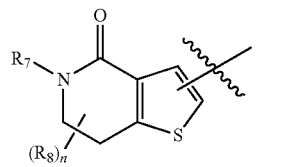

R-8
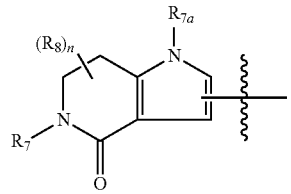

R-9
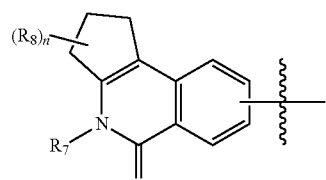

R-10
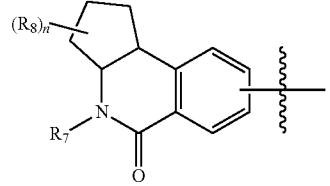

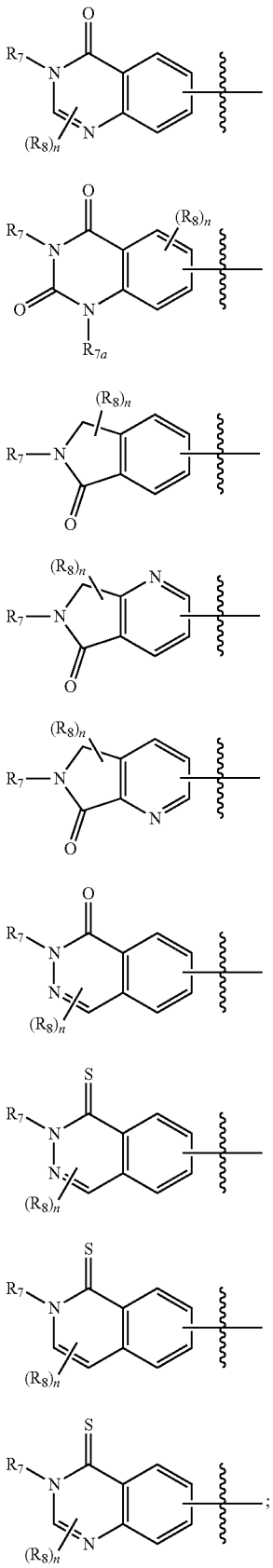

wherein, each of $R_7$ and $R_{7a}$ is independently selected from hydrogen, halogen, alkyl, haloalkyl, alkenyl, alkynyl, $Cy^1$, $-L_2-Cy^1$, $-SR_d$, $-OR_d$, $-C(O)OR_d$, $-C(O)R_d$, $-C(O)NR_dR_e$, $-C(O)N(R_d)OR_e$, $-C(O)NR_dS(O)_2R_e$, $-C(=NH)R_e$, $-C(=NH)NR_dR_e$, $-S(O)_2R_e$ and $-S(O)_2NR_dR_e$; wherein, the alkyl, alkenyl or alkynyl is unsubstituted or selectively substituted at any position by one or more than one substituent selected from the group consisting of $-CN$, $-NO_2$, $-SR_d$, $-OR_d$, $-OC(O)R_d$, $-OC(O)OR_d$, $-OC(O)NR_dR_e$, $-C(O)OR_d$, $-C(O)R_d$, $-C(O)NR_dR_e$, $-C(O)NR_dS(O)_2R_e$, $-NR_dR_e$, $-NR_dC(O)R_e$, $-N(R_d)C(O)OR_e$, $-N(R_d)C(O)NR_dR_e$, $-NR_dC(=NH)R_e$, $-NR_dC(=NH)NR_dR_e$, $-NR_dS(O)_2R_e$, $-NR_dS(O)_2NR_dR_e$, $-N(R_d)C(O)N(R_d)S(O)_2R_e$, $-S(O)_{1-2}R_e$, $-S(O)_2NR_dR_e$, $-S(O)(=NCN)R_e$, $-S(O)(=NR_d)R_e$, $-S(O)(=NSO_2R_d)R_e$, $-S(O)_2N(R_d)C(O)R_e$, $-S(O)_2N(R_d)C(O)NR_dR_e$, $-P(O)(OR_d)_2$, $-OP(O)(OR_d)_2$ or $-B(OR_d)_2$;

each of $R_8$ is independently hydrogen, halogen, alkyl, haloalkyl, haloalkoxy, alkenyl, alkynyl, $Cy^1$, $-L_2-Cy^1$, $-CN$, $-NO_2$, $-SR_d$, $-OR_d$, $-OC(O)R_d$, $-OC(O)OR_d$, $-OC(O)NR_dR_e$, $-C(O)OR_d$, $-C(O)R_d$, $-C(O)NR_dR_e$, $-C(O)N(R_d)OR_e$, $-C(O)NR_d S(O)_2R_e$, $-C(=NH)R_e$, $-C(=NH)NR_dR_e$, $-NR_dR_e$, $-NR_dC(O)R_e$, $-N(R_d)C(O)OR_e$, $-N(R_d)C(O)NR_dR_e$, $-NR_dS(O)_2R_e$, $-NR_dC(=NH)R_e$, $-NR_dC(=NH)NR_dR_e$, $-S(O)_{1-2}R_e$, $-S(O)_2NR_dR_e$ and $-NR_dS(O)_2NR_dR_e$; wherein, the alkyl, alkenyl or alkynyl is unsubstituted or selectively substituted at any position by one or more than one substituent selected from the group consisting of $-CN$, $-NO_2$, $-SR_d$, $-OR_d$, $-OC(O)R_d$, $-OC(O)OR_d$, $-OC(O)NR_dR_e$, $-C(O)OR_d$, $-C(O)R_d$, $-C(-)NR_dR_e$, $-(C(O)NR_dS(O)_2R_e$, $-NR_dR_e$, $-NR_dC(O)R_e$, $N(R_d)C(O)OR_2$, $-N(R_d)C(O)NR_dR_e$, $-NR_dC(=NH)R_e$, $-NR_dC(=NH)NR_dR_e$, $-NR_dS(O)_2R_e$, $-NR_dS(O)_2NR_dR_e$, $-N(R_d)C(O)N(R_d)S(O)_2R_e$, $-S(O)_{1-2}R_e$, $-S(O)_2NR_dR_e$, $-S(O)_2N(R_d)C(O)R_e$ or $-S(O)_2N(R_d)C(O)NR_dR_e$; each of n is independently 1, 2 or 3; $L_2$, $Cy^1$, $R_d$ and $R_e$ are defined as above.

In a preferred embodiment of the present invention, R is preferably selected from the group consisting of R-1 to R-11, and R-13 to R-16; each of $R_7$ and $R_{7a}$ is preferably defined as above other than $-C(O)N(R_d)OR_e$, wherein the alkyl, alkenyl or alkynyl in the definition of $R_7$ or $R_{7a}$ is unsubstituted or selectively substituted at any position by one or more than one substituent as described above except for $-S(O)(=NCN)R_e$, $-S(O)(=NROR_e$, $-S(O)(=NSO_2R_d)R_e$, $-P(O)(OR_d)_2$, $-OP(O)(OR_d)_2$ or $-B(OR_d)_2$; $R_8$ is preferably defined as above except for $-C(O)N(R_d)OR_e$.

In a preferred embodiment of the present invention, R is preferably selected from the group consisting of R-1 to R-16; each of $R_7$ and $R_{7a}$ is preferably defined as above except for $-C(O)N(R_d)OR_e$, wherein the alkyl, alkenyl or alkynyl in the definition of $R_7$ or $R_{7a}$ is unsubstituted or selectively substituted at any position by one or more than one substituent except for $-P(O)(OR_d)_2$, $-OP(O)(OR_d)_2$ or $-B(OR_d)_2$; $R_8$ is preferably defined as above except for $-C(O)N(R_d)OR_e$.

In a preferred embodiment of the present invention, R is preferably selected from the group consisting of R-1 to R-18; each of $R_7$ and $R_{7a}$ is preferably defined as above except for $-C(O)N(R_d)OR_e$.

In a preferred embodiment of the present invention, in the definition of R, $R_7$ is preferably hydrogen, $C_{1-6}$ alkyl, $C_{1-6}$ haloalkyl, $C_{2-6}$ alkenyl, $C_{2-6}$ alkynyl, $Cy^1$, $-L_2-Cy^1$, $-SR_d$, $-OR_d$, $-C(O)OR_d$, $-C(O)R_d$, $-C(O)NR_dR_e$, $-C(O)N(R_d)OR_e$, $-C(=NH)R_e$, $-C(=NH)NR_dR_e$, $-S(O)_2R_e$ or $-S(O)_2NR_dR_e$; wherein the $C_{1-6}$ alkyl, $C_{2-6}$ alkenyl or $C_{2-6}$ alkynyl is unsubstituted or selectively substituted at any position by 1 to 3 substituent selected from the group consisting of —CN, —NO$_2$, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)(=NCN)R$_e$, —S(O)(=NR$_d$)R$_e$, —S(O)(=NSO$_2$R$_d$)R$_e$, —S(O)$_2$NR$_d$R$_e$, —NR$_d$S(O)$_2$NR$_d$R$_e$, —P(O)(OR$_d$)$_2$, —OP(O)(OR$_d$)$_2$ or —B(OR$_d$)$_2$; L$_2$, Cy$^1$, R$_d$ and R$_e$ are defined as above.

In a preferred embodiment of the present invention, in the definition of R, R$_7$ preferably is defined as above except for —C(O)N(R$_d$)OR$_e$, wherein the C$_{1-6}$ alkyl, C$_{2-6}$ alkenyl or C$_{2-6}$ alkynyl is unsubstituted or selectively substituted at any position by 1 to 3 substituent as defined above other than —S(O)(=NCN)R$_e$, —S(O)(=NR$_d$)R$_e$, —S(O)(=NSO$_2$R$_d$)R$_e$, —P(O)(OR$_d$)$_2$, —OP(O)(OR$_d$)$_2$ or —B(OR$_d$)$_2$.

In another preferred embodiment of the invention, in the definition of R, R$_7$ is preferably defined as above except for —C(O)N(R$_d$)OR$_e$, wherein the C$_{1-6}$ alkyl, C$_{2-6}$ alkenyl or C$_{2-6}$ alkynyl is unsubstituted or selectively substituted at any position by 1 to 3 substituent other than —P(O)(OR$_d$)$_2$, —OP(O)(OR$_d$)$_2$ or —B(OR$_d$)$_2$.

In another preferred embodiment of the present invention, in the definition of R, R$_7$ is preferably as defined above other than —C(O)N(R$_d$)OR$_e$.

In a preferred embodiment of the present invention, in the definition of R, R$_7$ is preferably hydrogen, methyl, ethyl, propyl, butyl, isopropyl, isobutyl, n-butyl, neopentyl, tert-amyl, cyclopropyl, cyclobutyl, cyclopentyl, cyclohexyl,

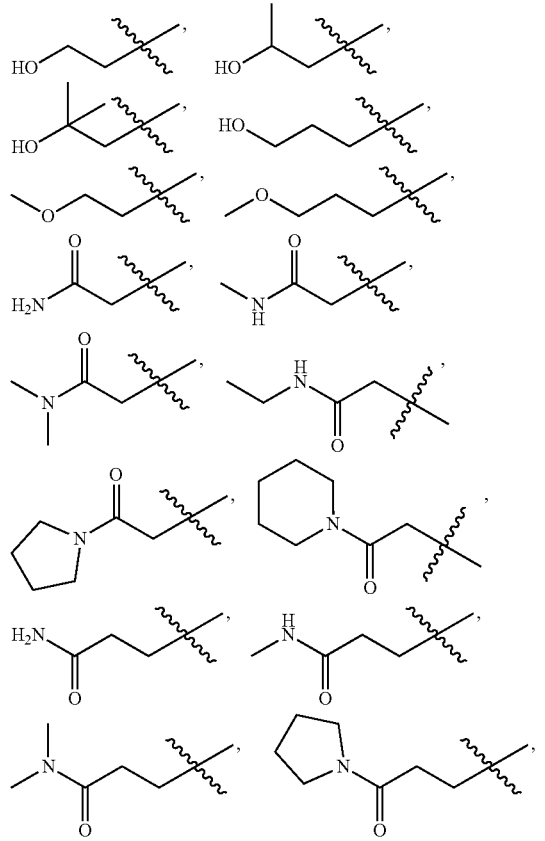

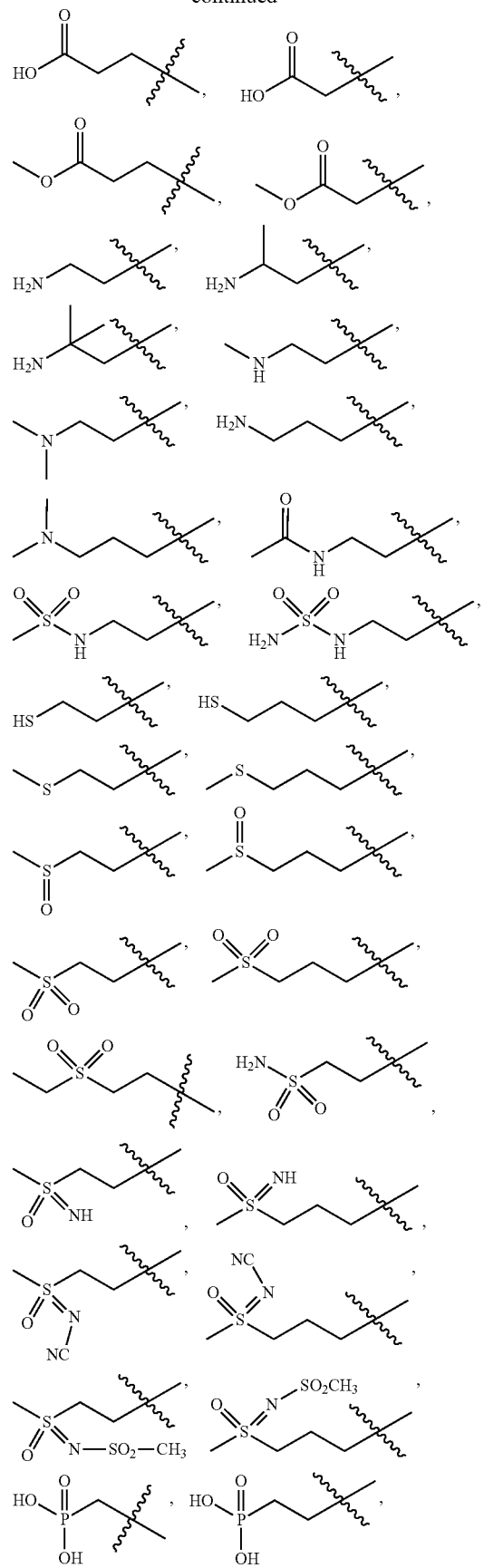

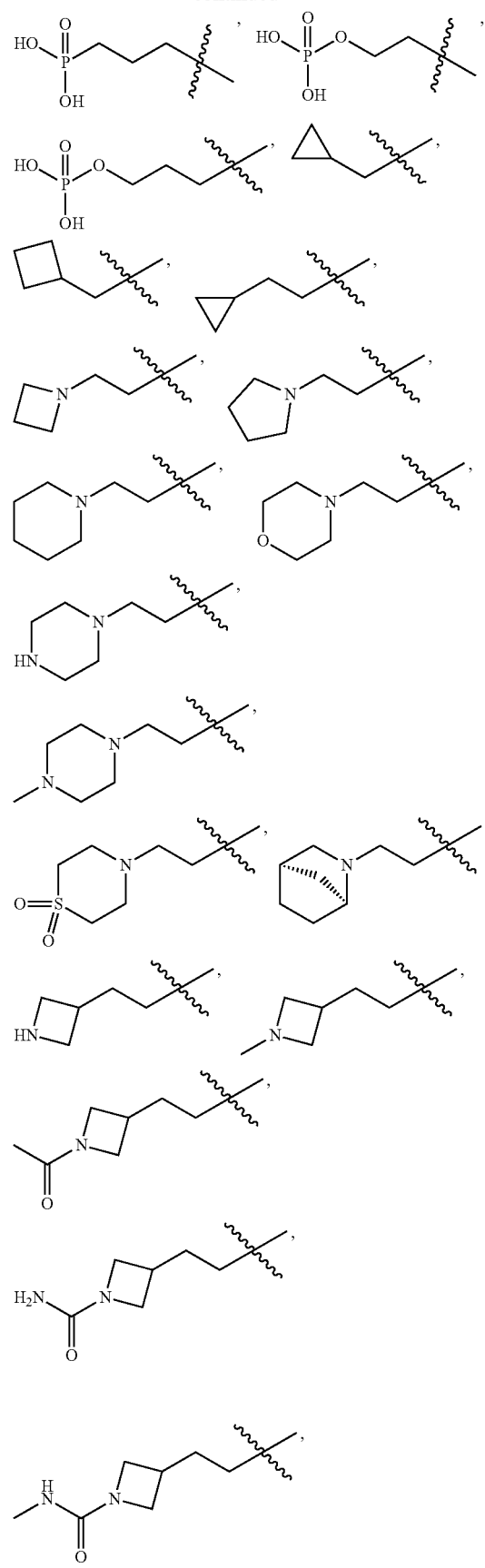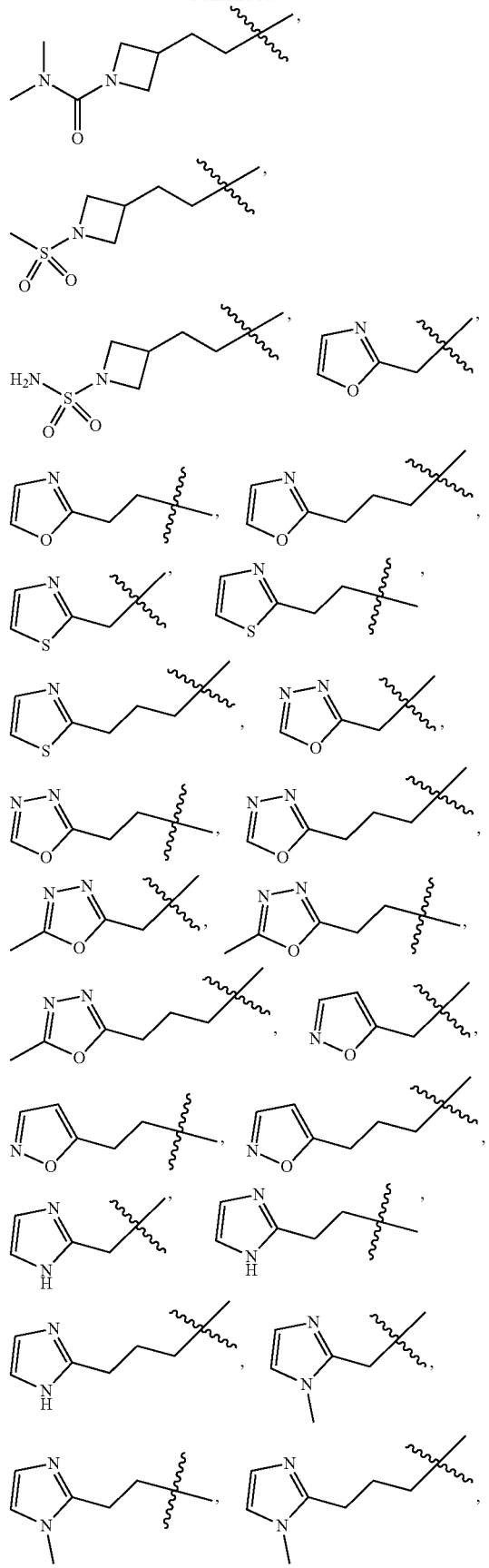

-continued
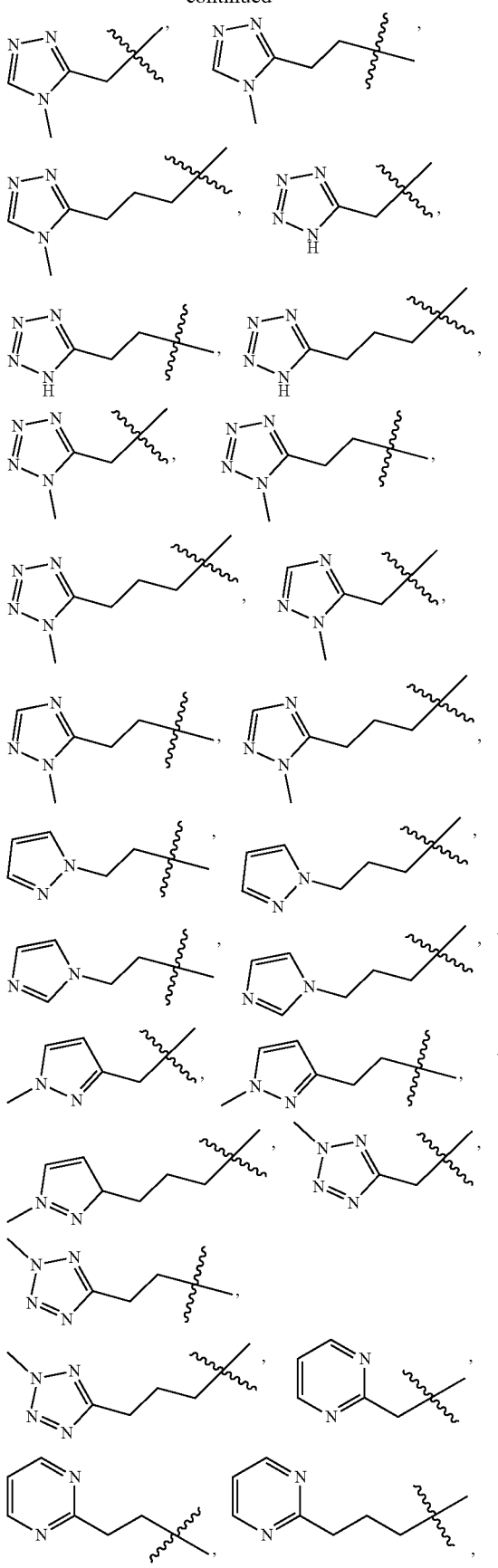
-continued
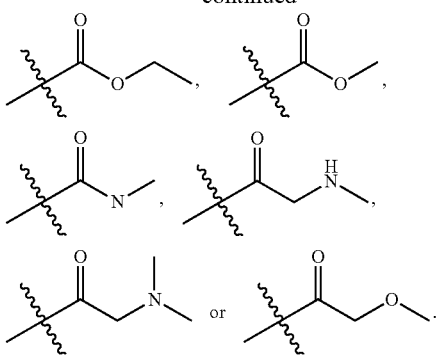
In a preferred embodiment of the present invention, in the definition of R, $R_7$ is more preferably
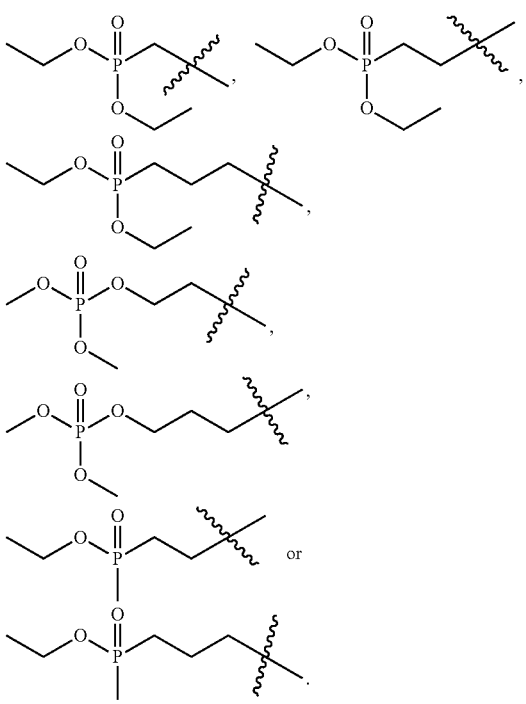
In a preferred embodiment of the present invention, in the definition of R, $R_7$ is more preferably benzyl,
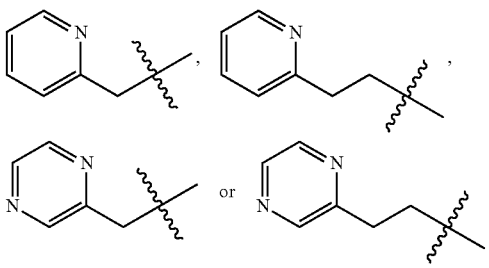
In another preferred embodiment of the present invention, in the definition of R, $R_7$ is more preferably benzyl, pyridyl, pyrimidinyl,

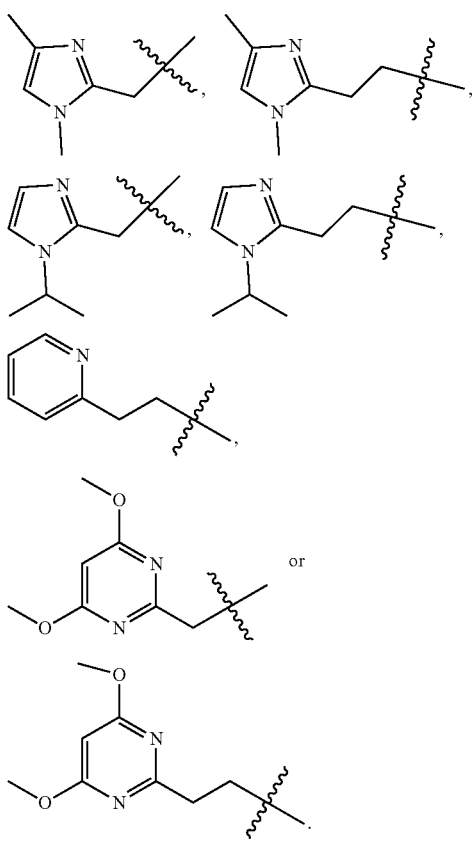

In a preferred embodiment of the invention, in the definition of R, $R_7$ is more preferably

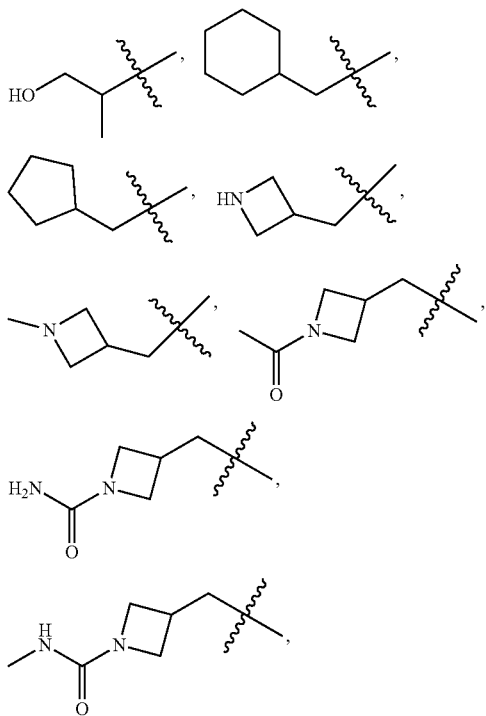

In a preferred embodiment of the present invention, in the definition of R, $R_{7a}$ is preferably hydrogen, $C_{1-6}$ alkyl, $C_{1-6}$ haloalkyl, $C_{2-6}$ alkenyl, $C_{2-6}$ alkynyl, $Cy^1$ or $-L_2-Cy^1$, wherein the $C_{1-6}$ alkyl, $C_{2-6}$ alkenyl or $C_{2-6}$ alkynyl is unsubstituted or selectively substituted at any position by 1 to 3 substituent selected from the group consisting of —CN, —$NO_2$, —CN, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(\!=\!NH)R_e$, —$NR_dC(\!=\!NH)NR_dR_e$, —$S(O)_{1\text{-}2}R_e$, —$S(O)_2NR_dR_e$ and —$NR_dS(O)_2NR_dR_e$; $L_2$, $Cy^1$, $R_d$ and $R_e$ are defined as above.

In a preferred embodiment of the present invention, in the definition of R, $R_{7a}$ is more preferably hydrogen or $C_{1-6}$ alkyl (such as, methyl or ethyl).

In a preferred embodiment of the present invention, in the definition of R, $R_8$ is more preferably hydrogen, methyl, ethyl, n-propyl, tert-butyl, isopropyl, isobutyl, n-butyl, —CN, —$NO_2$, —$NH_2$, —$CF_3$, —$OCF_3$, —$CH_3$, —$OCH_3$, F, Cl or Br; or $R_8$ is preferably a substituent other than —$OCH_3$.

In the definition of R, n is preferably 1 or 2; n is more preferably 1.

In a preferred embodiment of the present invention, $L_2$ is preferably a bond or —$(CR_{a1}R_{b1})_m$—.

In another preferred embodiment of the present invention, $L_2$ is preferably a bond,
—$CH_2$—, —$CH_2CH_2$—, —$CH_2$—$CH_2CH_2$—, —$CH_2CH_2CH_2CH_2$—, —$CH_2CH(CH_2)CH_2$— or In another preferred embodiment of the present invention, $L_2$ is preferably a bond, —$CH_2$—, —$CH_2CH_2$—, —$CH_2CH_2CH_2$—, —$CH_2CH_2CH_2CH_2$— or —$CH_2CH(CH_2)CH_2$—.

In a preferred embodiment of the present invention, $R_d$, $R_e$, $R_{d1}$, $R_{e1}$, $R_{d2}$ or $R_{e2}$ is preferably unsubstituted or selectively substituted at any position by 1 to 3 substituent selected from the group consisting of halogen, hydroxyl, amino, carboxyl, $C_{1-4}$ alkyl, $C_{1-3}$ haloalkyl, $C_{1-3}$ haloalkoxy, $C_{2-6}$ alkenyl and $C_{2-6}$ alkynyl.

In a preferred embodiment of the present invention, $R_d$, $R_e$, $R_{d1}$, $R_{e1}$, $R_{d2}$ or $R_{e2}$ is preferably unsubstituted or selectively substituted at any position by 1 to 3 substituent selected from the group consisting of halogen, hydroxyl, amino, carboxyl, $C_{1-4}$ alkyl, $C_{1-3}$ haloalkyl, $C_{1-3}$ haloalkoxy, $C_{1-3}$ alkoxy, $C_{1-3}$ alkylamino, $C_{2-6}$ alkenyl and $C_{2-6}$ alkynyl.

In a preferred embodiment of the present invention, $R_d$ and $R_e$, or $R_{d1}$ and $R_{e1}$, or $R_{d2}$ and $R_{e2}$ together with the N atom to which they are attached, form a 3 to 8 membered heterocycloalkyl; the heterocycloalkyl further contains 1 to 3 hetero atom selected from the group consisting of N, O and S; the heterocycloalkyl is preferably unsubstituted or substituted at any position by 1 to 3 substituent selected from the group consisting of halogen, amino, carboxyl, cyano, $C_{1-4}$ alkyl, $C_{1-3}$ haloalkyl, $C_{1-3}$ haloalkoxy, $C_{2-6}$ alkenyl, $C_{2-6}$ alkynyl, hydroxyalkyl, aminoalkyl, $-OR_{d2}$, $-OC(O)R_{d2}$, $-OC(=)OR_{d2}$, $-OC(O)NR_{d2}R_{e2}$, $-C(O)OR_{d2}$, $-C(O)R_{d2}$, $-C(O)NR_{d2}R_{e2}$, $-NR_{d2}R_{e2}$, $-NR_{d2}C(O)R_{e2}$, $-N(R_{d2})C(O)OR_{e2}$, $-N(R_{d2})C(O)OR_{e2}$, $-N(R_{d2})C(O)NR_{d2}R_{e2}$, $-NR_{d2}S(O)_2R_{e2}$, $-NR_{d2}C(=NH)R_{e2}$, $-NR_{d2}C(=NH)NR_{d2}R_{e2}$, $-S(O)_{1-2}R_{d2}$ and $-S(O)_2NR_{d2}R_{e2}$.

A compound of formula I, an isomer, a prodrug, a stable isotopic derivative or a pharmaceutically acceptable salt is preferably a compound of formula IA, a isomer, a prodrug, a stable isotopic derivative or a pharmaceutically acceptable salt thereof;

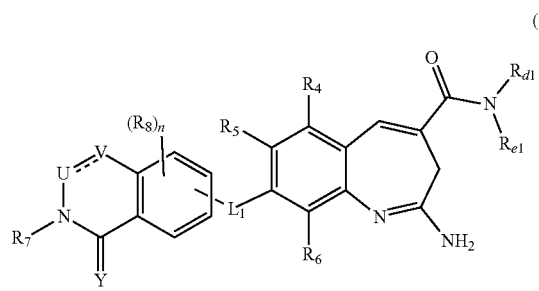

(IA)

wherein, ==== is a single bond or a double bond, U is N, $C(R_8)$ or $C(O)$, V is N, $C(R_8)$ or $N(R_{7a})$; U and V are any combination of the following:

==== is a double bond, U is N, V is $C(R_8)$;
==== is a double bond, U is $C(R_8)$, V is N;
==== is a double bond, U is $C(R_8)$, V is $C(R_8)$;
==== is a single bond, U is $C(R_8)$, V is $C(R_8)$;
==== is a single bond, U is $C(O)$, V is $N(R_{7a})$;

Y is O or S;
n is 1;
$L_1$, $R_{d1}$, $R_{e1}$, $R_4$, $R_5$, $R_6$, $R_7$, $R_8$ and X are defined as above.

A compound of formula I, an isomer, a prodrug, a stable isotopic derivative or a pharmaceutically acceptable salt is preferably a compound of formula IB or IC, an isomer, a prodrug, a stable isotopic derivative or a pharmaceutically acceptable salt thereof;

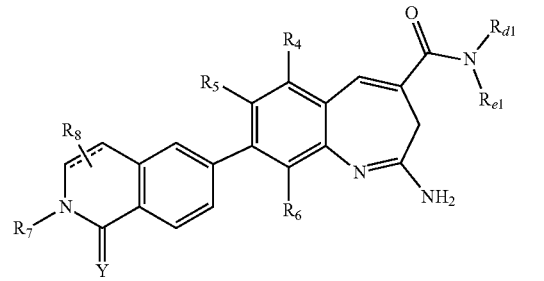

(IB)

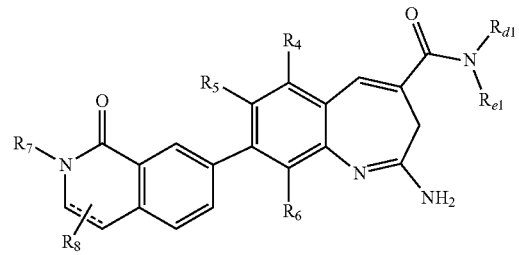

(IC)

wherein, ==== is a single bond or a double bond;
$R_{d1}$, $R_{e1}$, $R_4$, $R_5$, $R_6$, $R_7$, $R_8$ and Y are defined as above.

In a preferred embodiment of the present invention, in the compound of formula IB or IC, the isomer, the prodrug, the stable isotopic derivative or the pharmaceutically acceptable salt, Y is preferably O.

In a preferred embodiment of the present invention, the compound of formula I, the isomer, the prodrug, the stable isotopic derivative or the pharmaceutically acceptable salt is preferably a compound of formula ID, IE, IF, IG, IH or II, an isomer, a prodrug, a stable isotopic derivative or a pharmaceutically acceptable salt thereof:

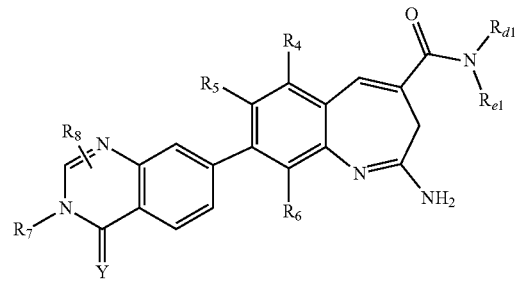

(ID)

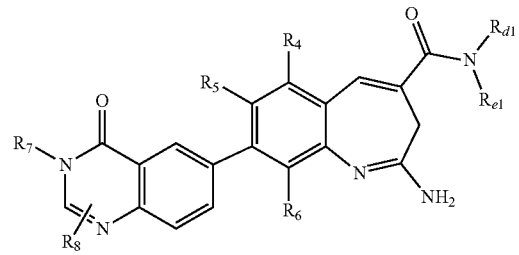

(IE)

(IF)
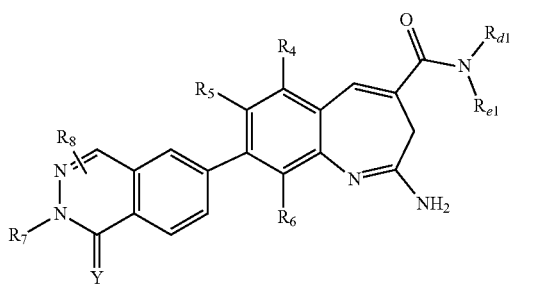

(IJ)
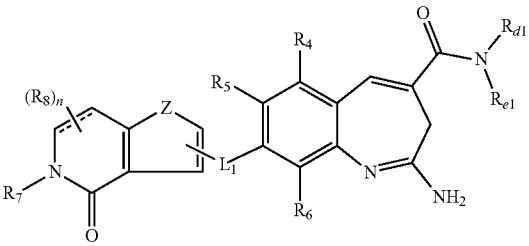

(IG)
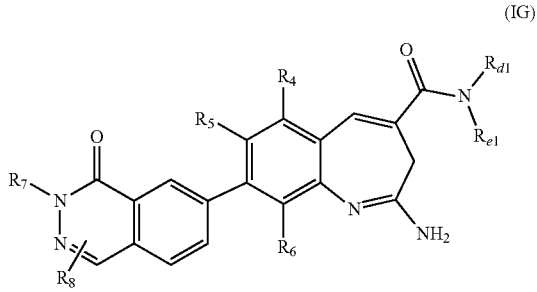

wherein, ==== is a single bond or a double bond; Z is N($R_{7a}$) or S;

n is 1 or 2;

$L_1$, $R_{d1}$, $R_{e1}$, $R_4$, $R_5$, $R_6$, $R_7$ and $R_8$ are defined as above.

The compound of formula I, the isomer, the prodrug, the stable isotopic derivative or the pharmaceutically acceptable salt thereof is preferably a compound of formula IK or IL, an isomer, a prodrug, a stable isotopic derivative or a pharmaceutically acceptable salt thereof:

(IH)
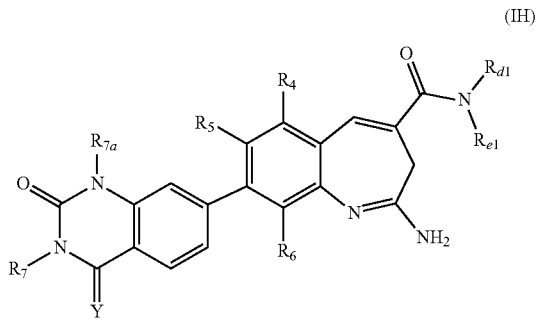

(IK)
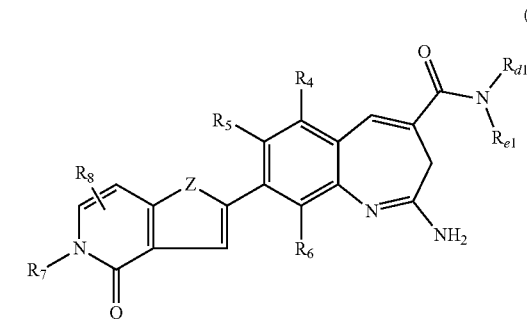

(II)
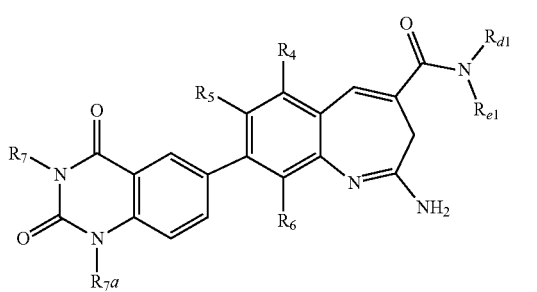

(IL)
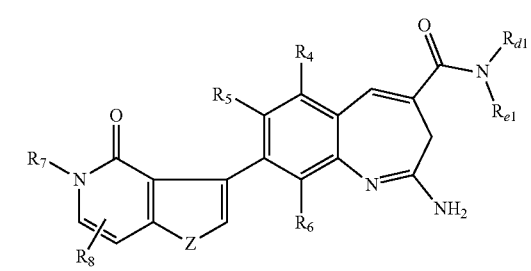

wherein, $R_{d1}$, $R_{e1}$, $R_4$, $R_5$, $R_6$, $R_7$, $R_{7a}$, $R_8$ and Y are defined as above.

In a preferred embodiment of the present invention, in the compound of formula ID or IF, the isomer, the prodrug, a stable isotopic derivative or the pharmaceutically acceptable salt thereof, Y is preferably O.

In a preferred embodiment of the present invention, the compound of formula I, the isomer, the prodrug, the stable isotopic derivative or the pharmaceutically acceptable salt thereof is preferably a compound of formula IJ, an isomer, a prodrug, a stable isotopic derivative or a pharmaceutically acceptable salt thereof:

wherein, Z is NH, N(CH$_3$) or S;

$R_{d1}$, $R_{e1}$, $R_4$, $R_5$, $R_6$, $R_7$ and $R_8$ are defined as above.

The compound of formula (I), the isomer, the prodrug, the stable isotopic derivative or the pharmaceutically acceptable salt thereof is preferably selected from the group consisting of:

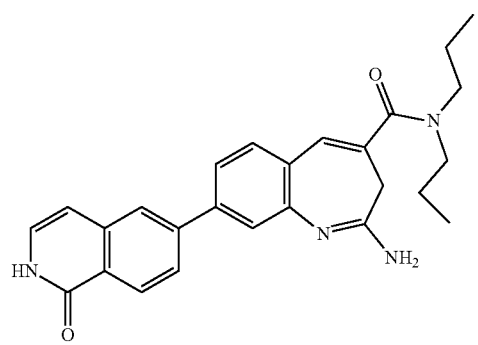
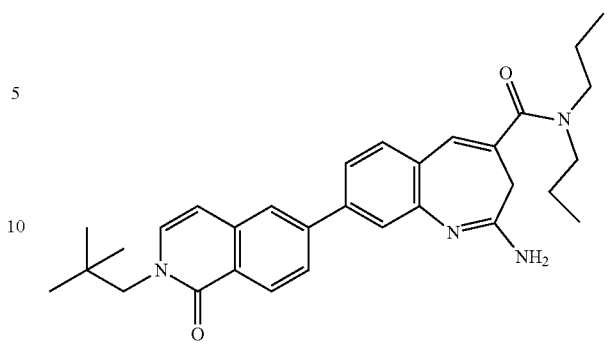
-continued
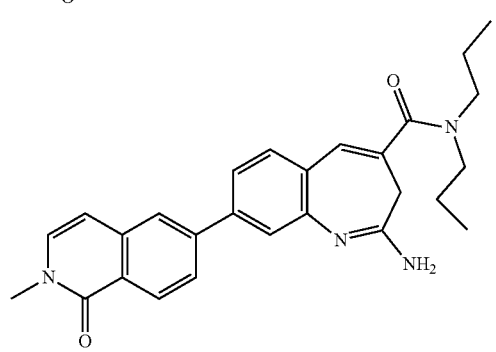
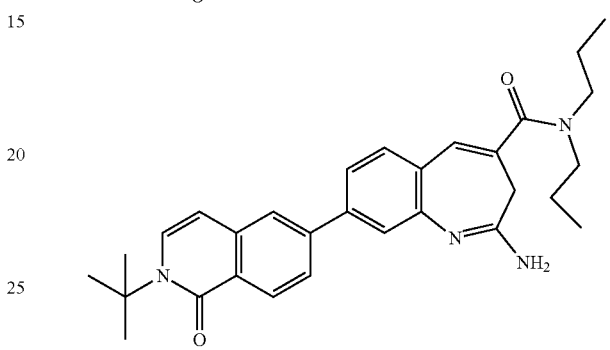
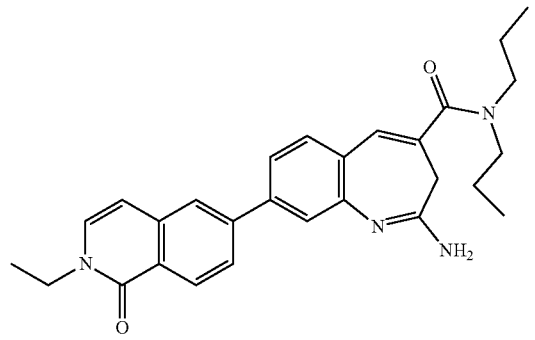
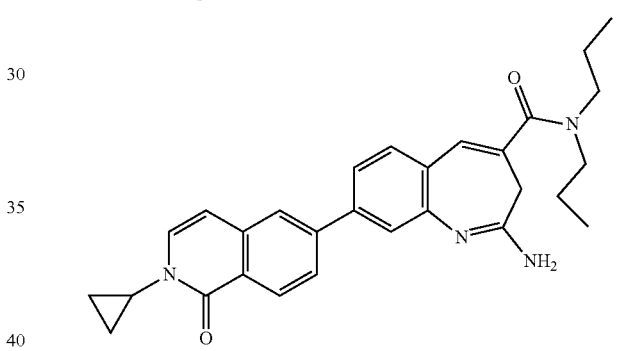
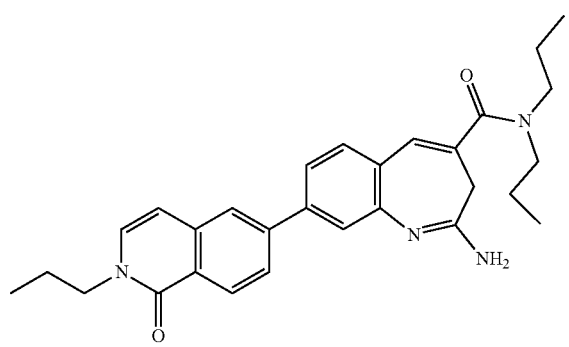
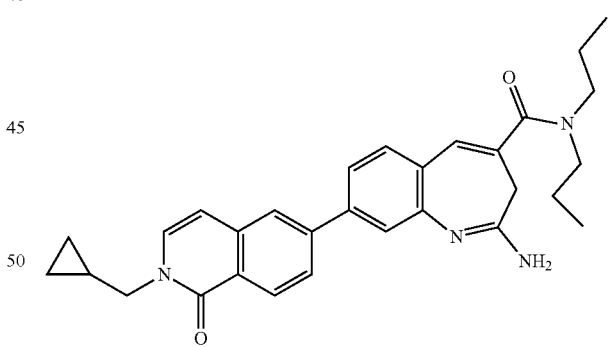
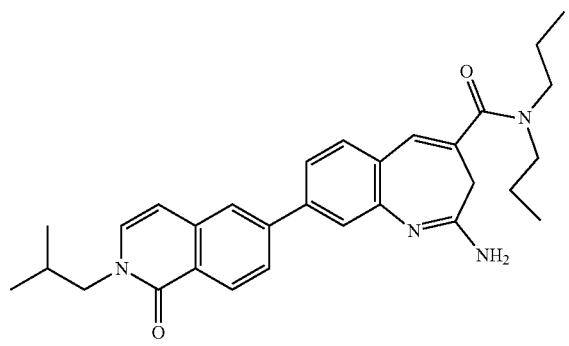
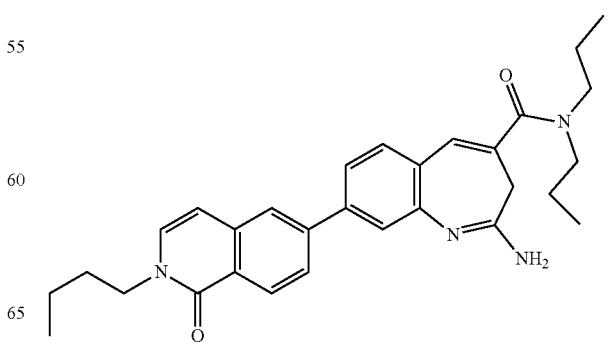

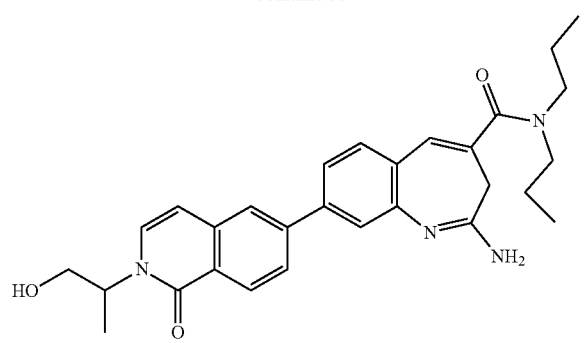
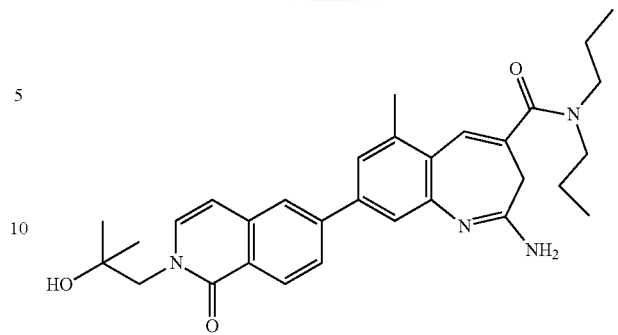
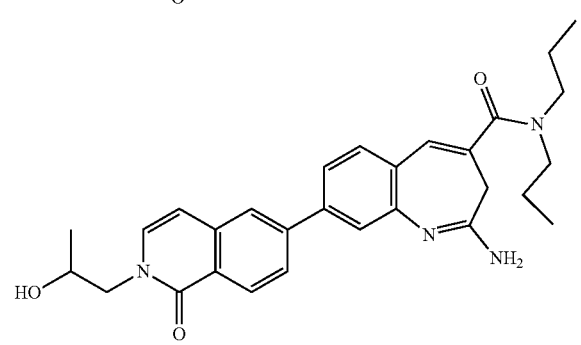
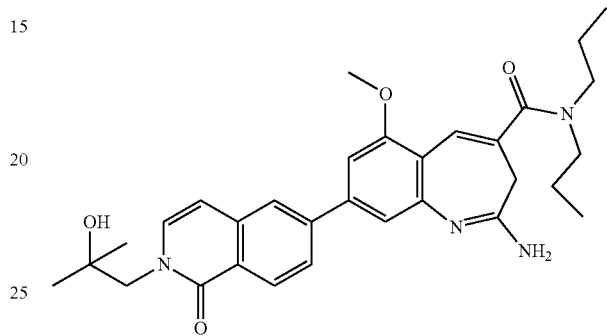
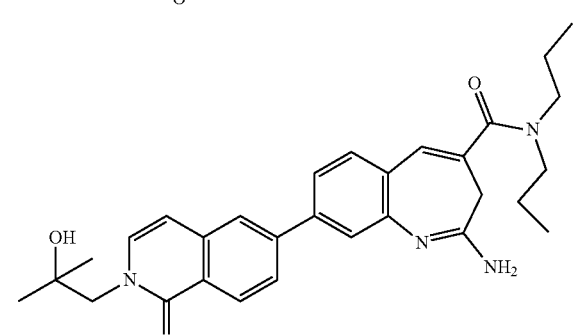
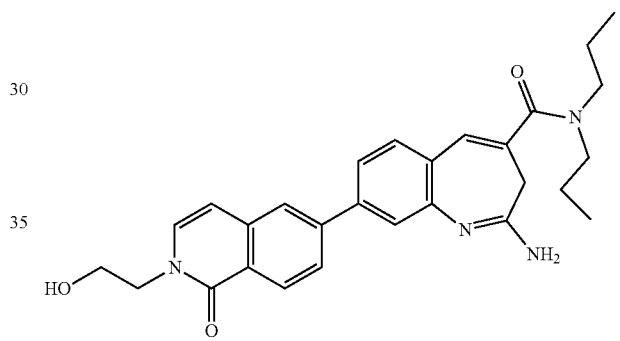
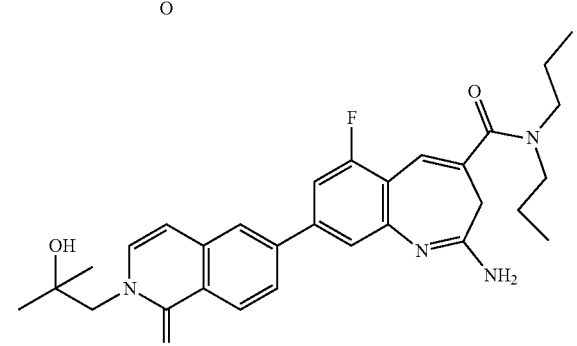
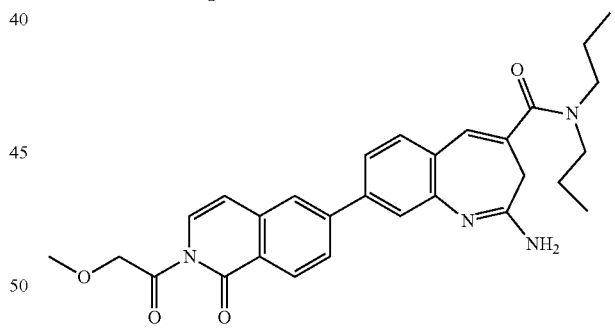
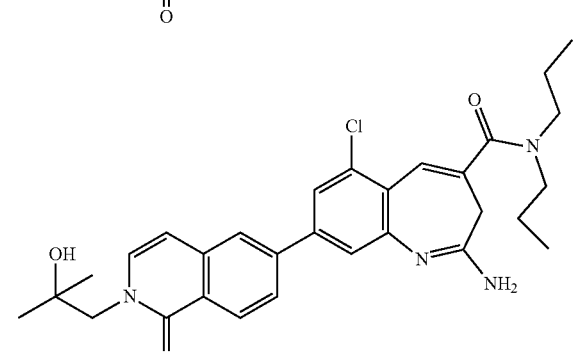
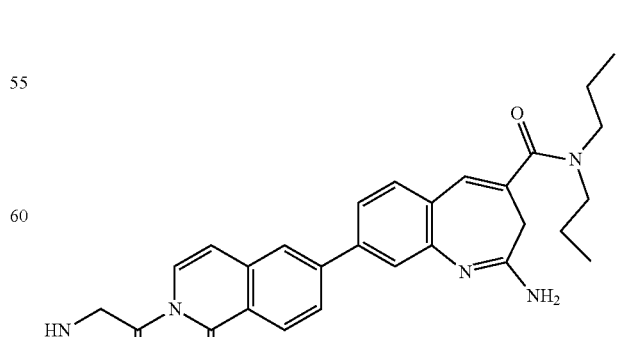

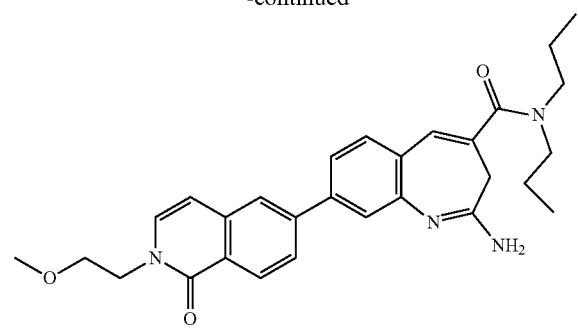
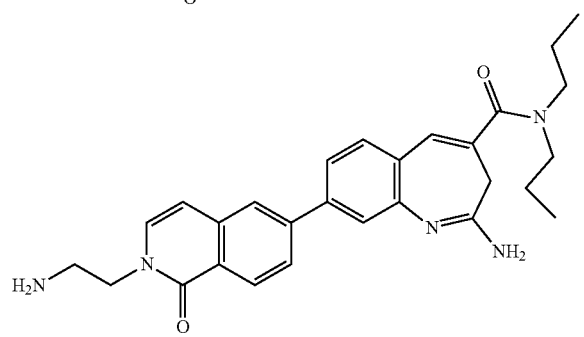
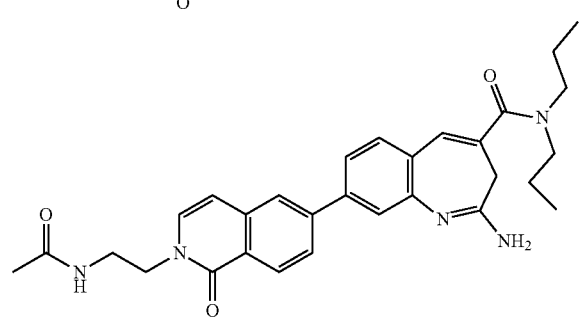
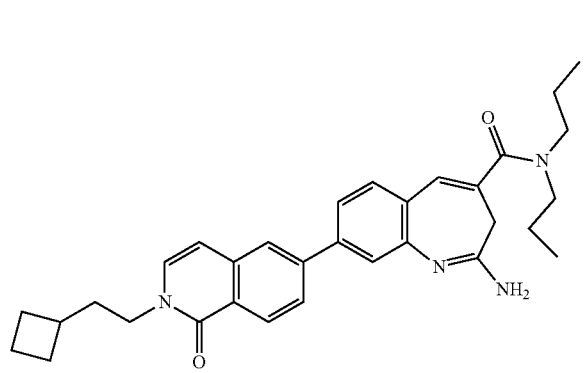
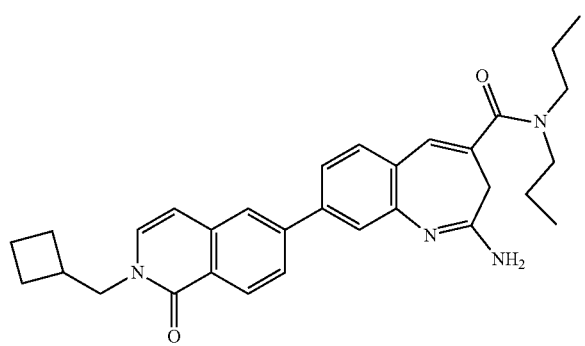
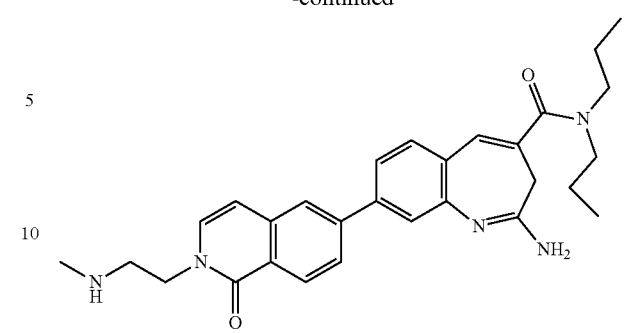
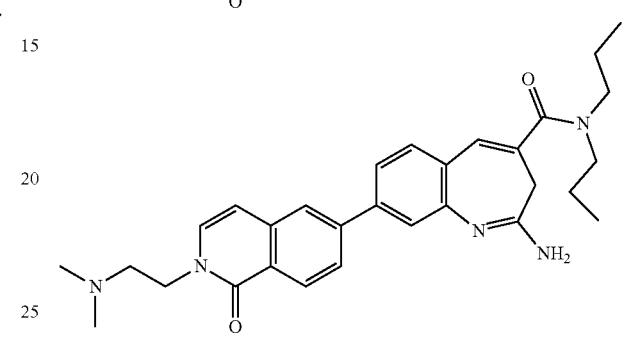
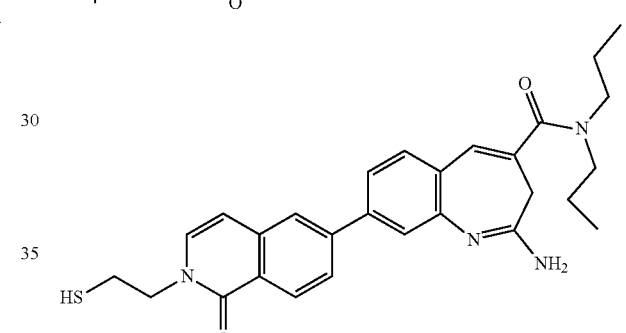
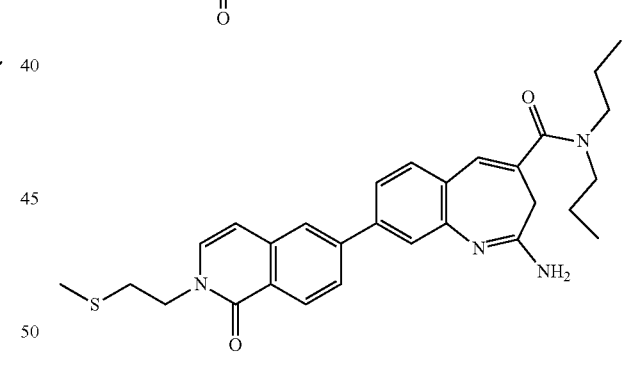
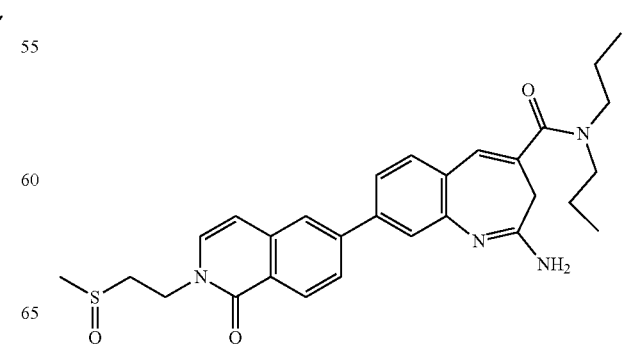

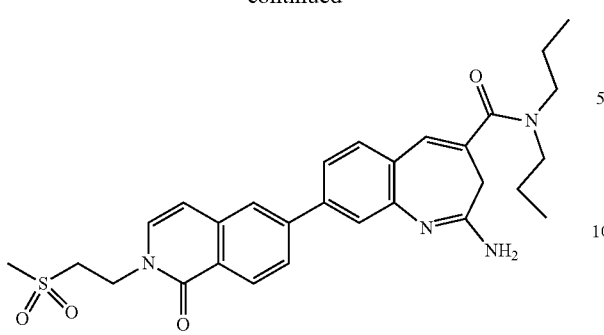
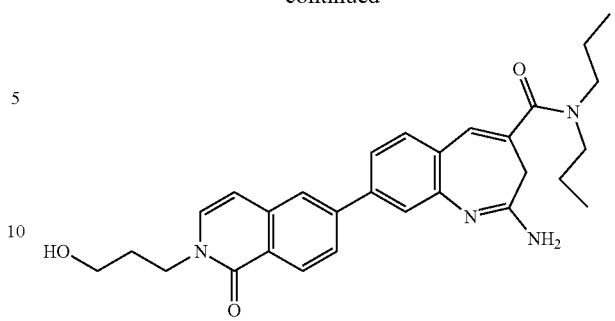
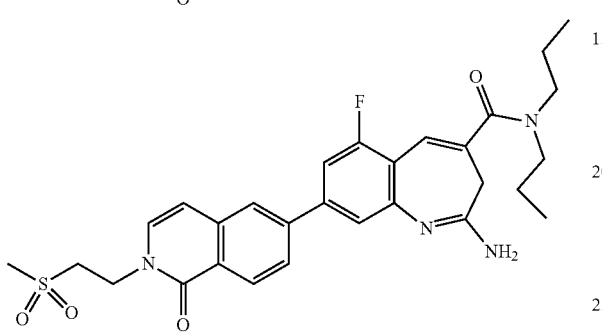
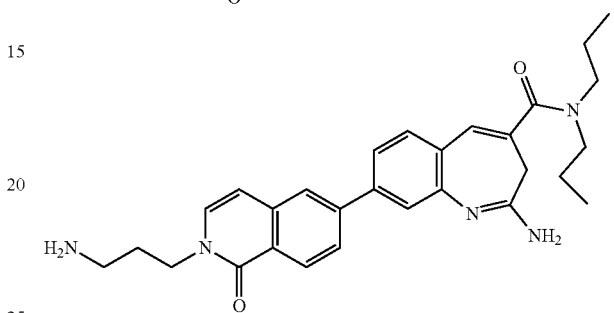
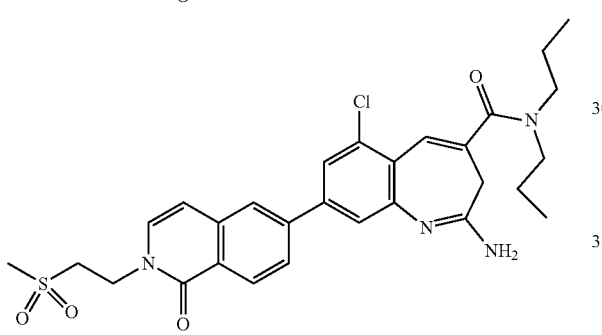
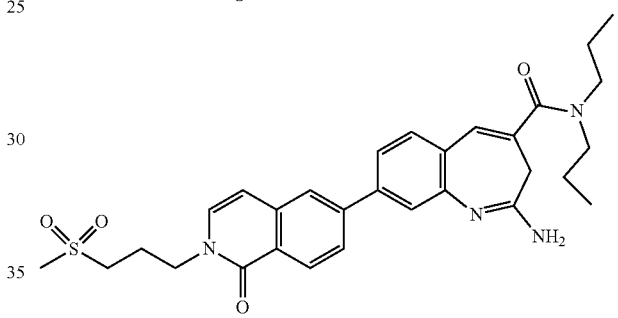
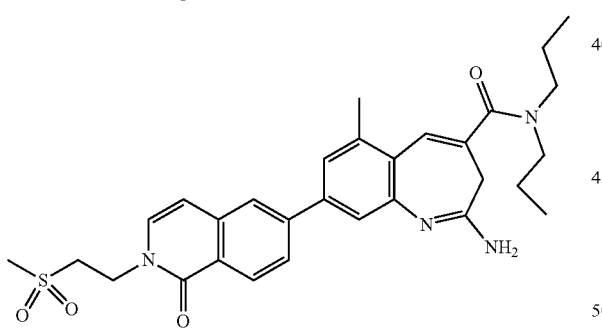
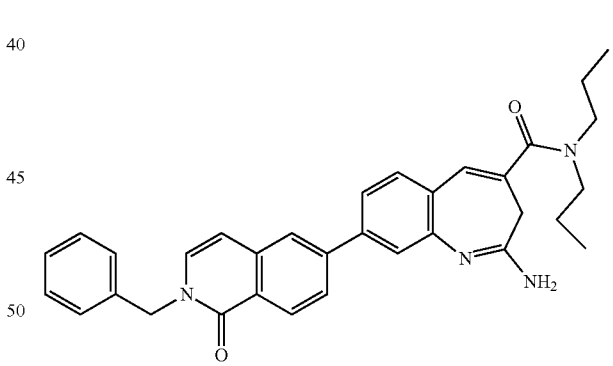
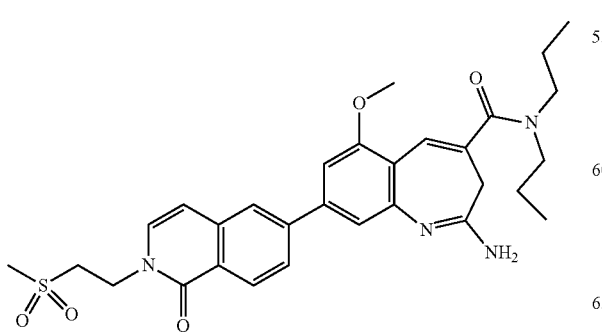
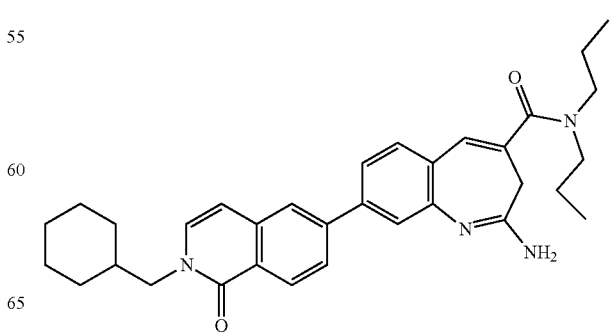

31
-continued
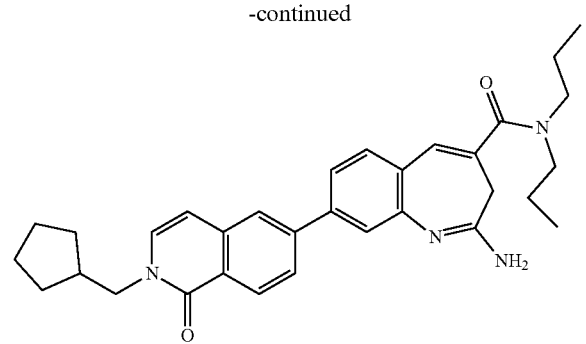
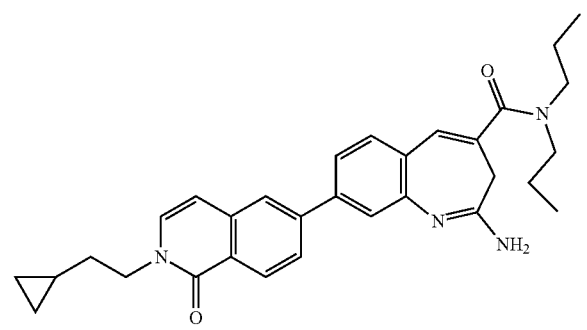
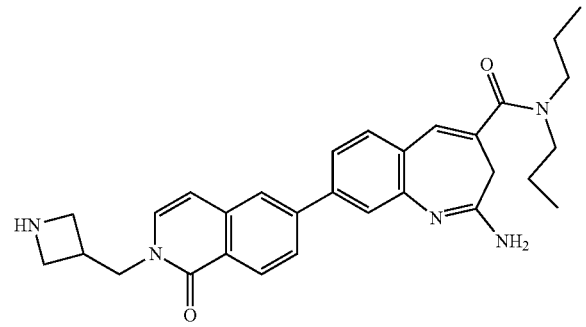
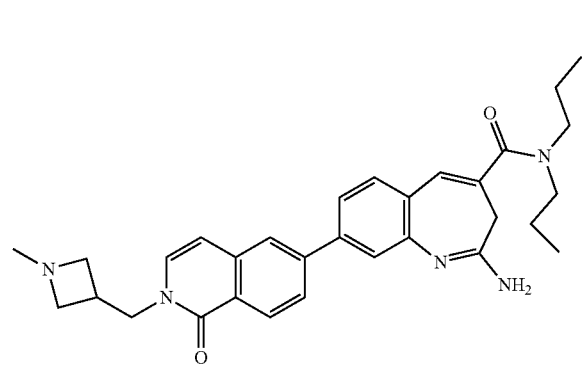
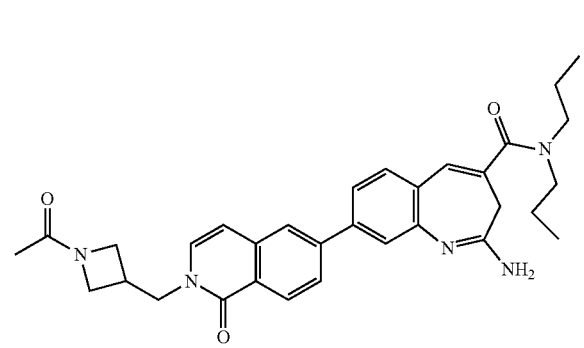
32
-continued
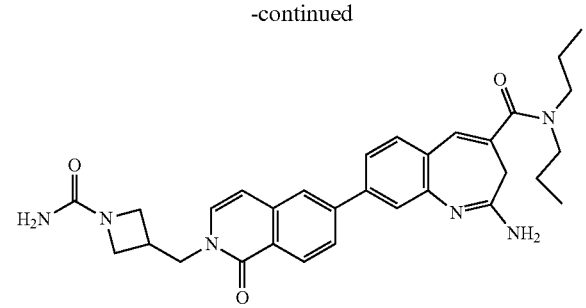
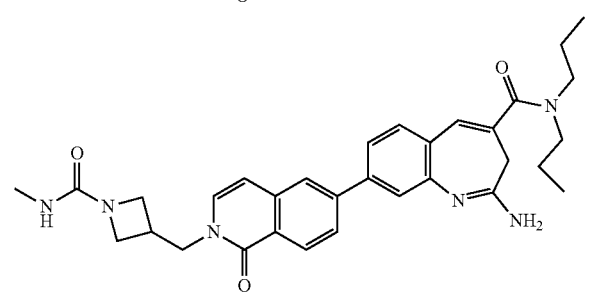
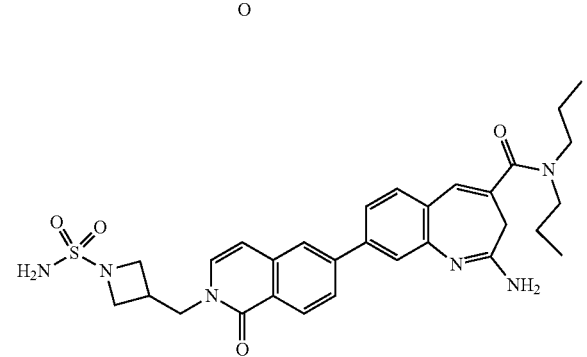
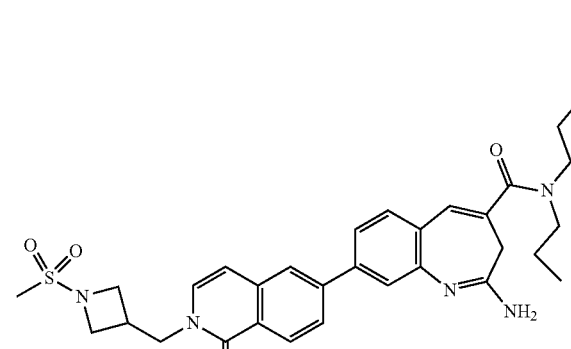
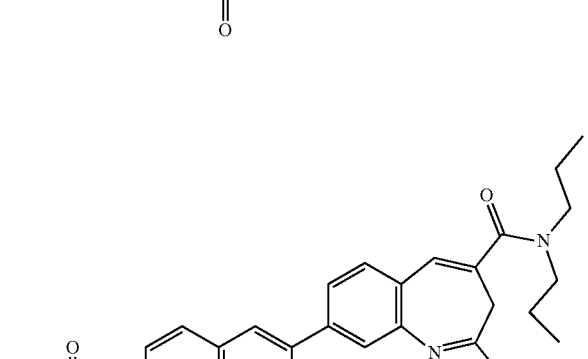

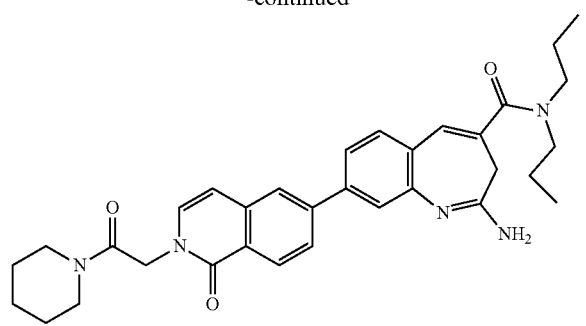
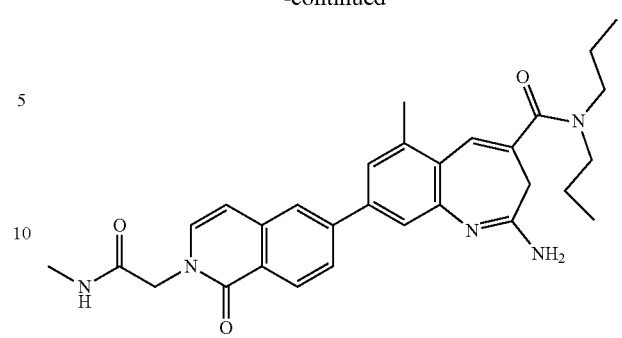
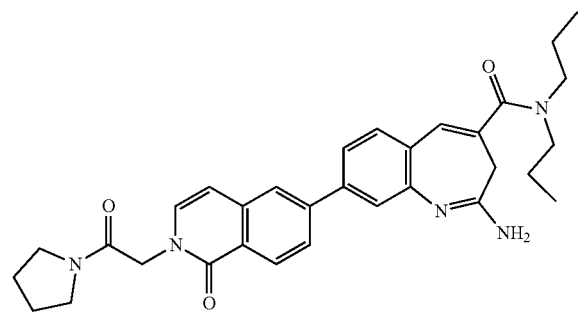
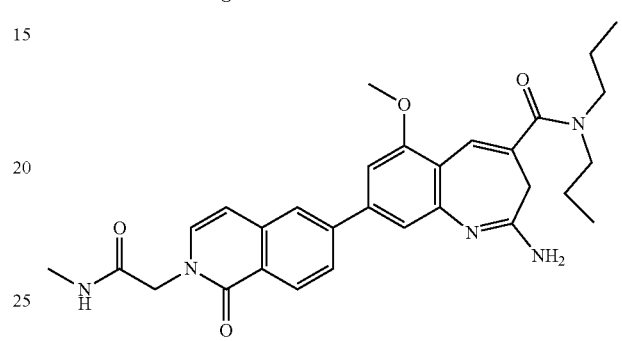
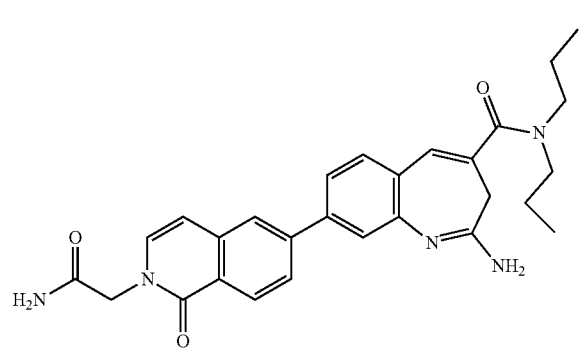
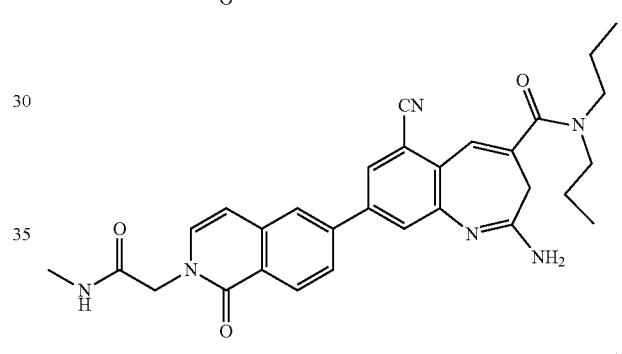
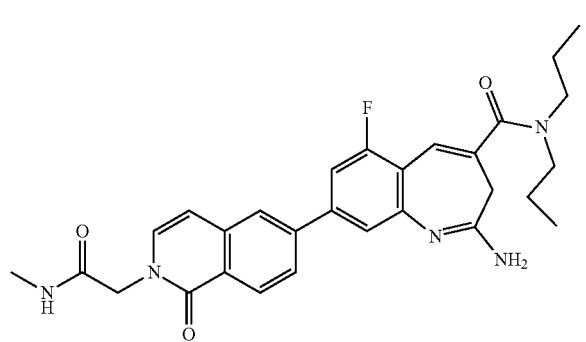
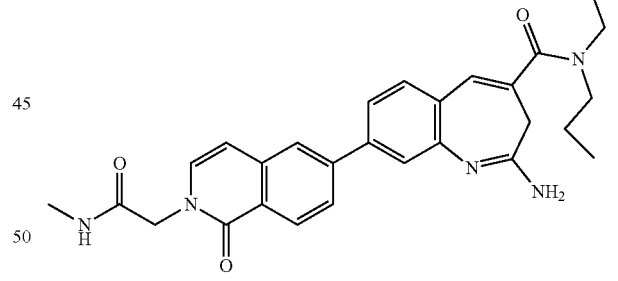
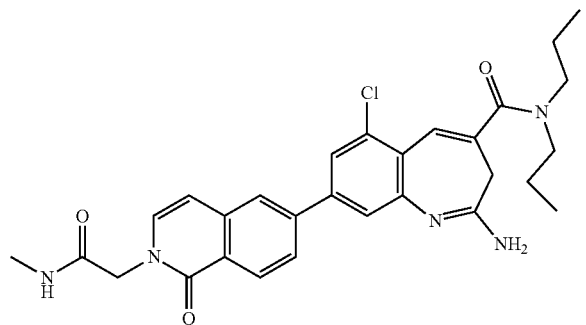
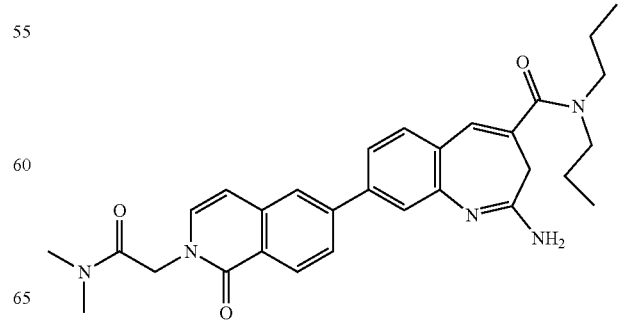

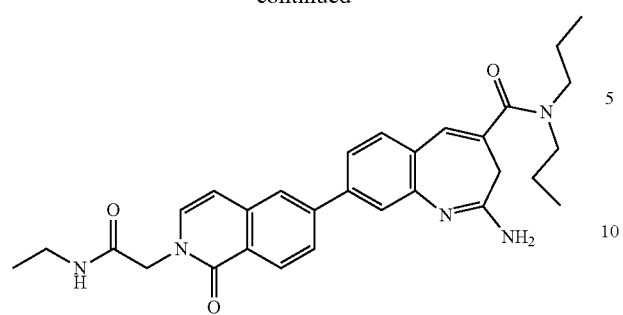
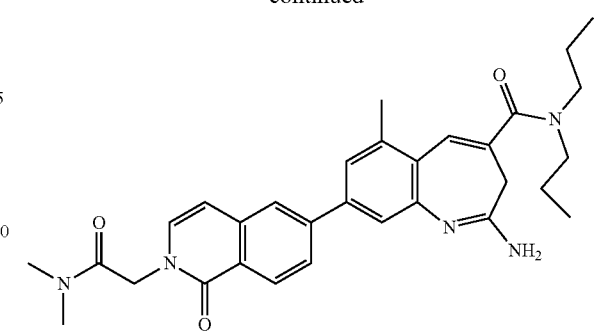
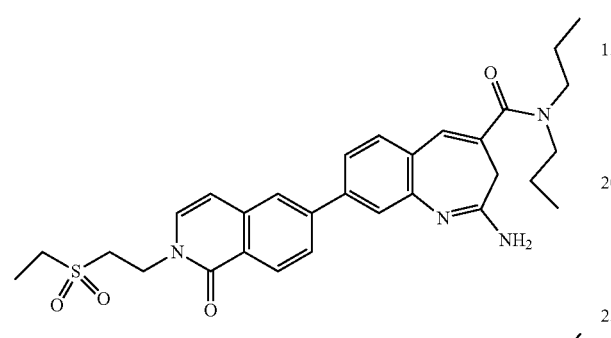
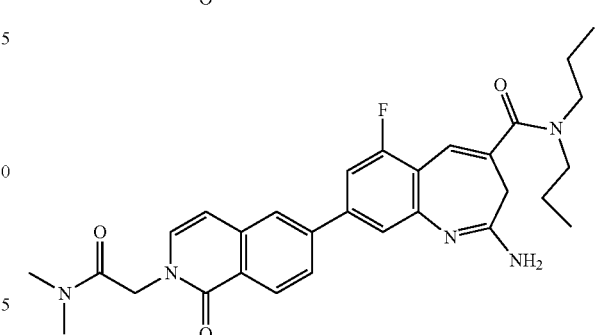
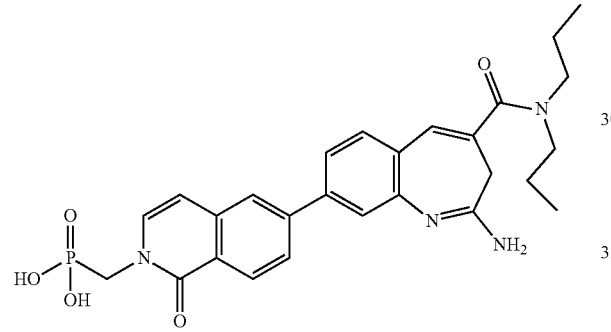
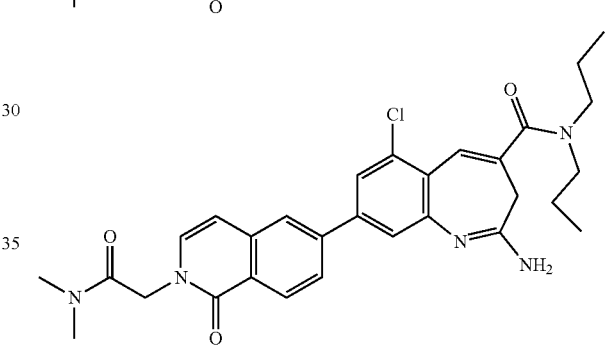
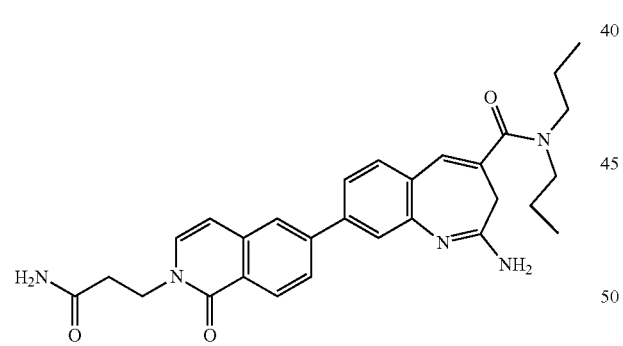
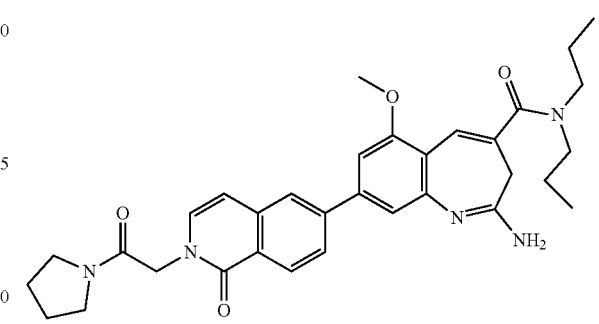
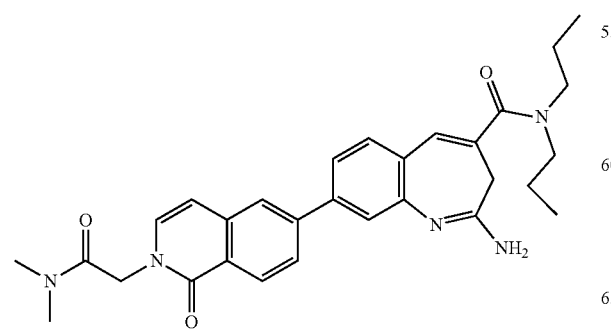
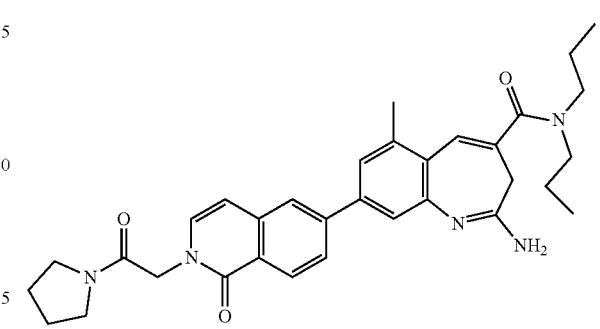

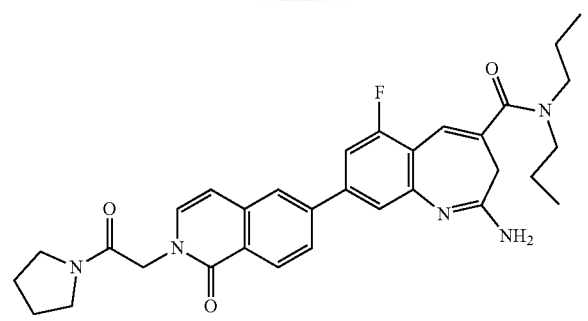
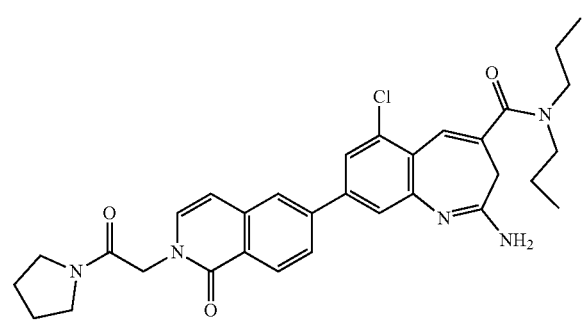
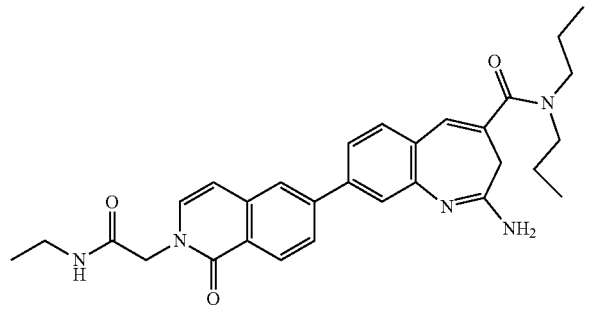
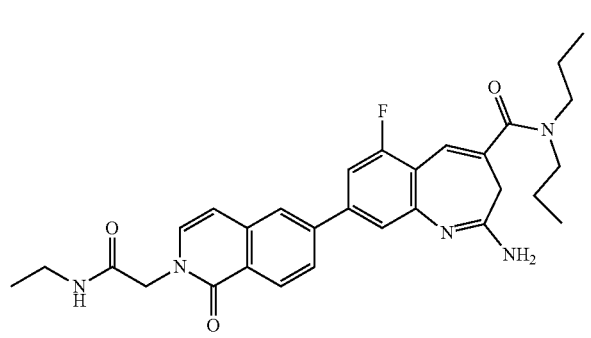
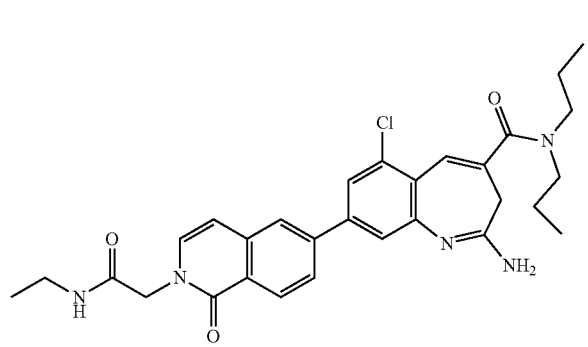

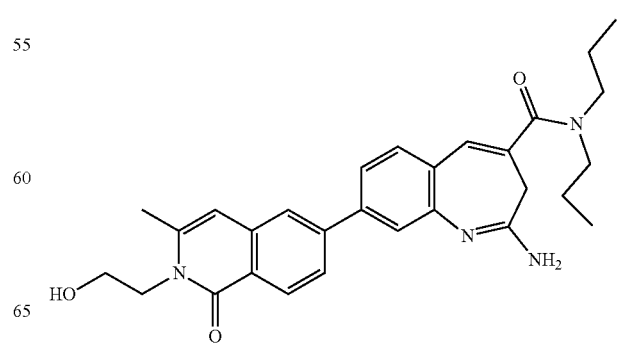

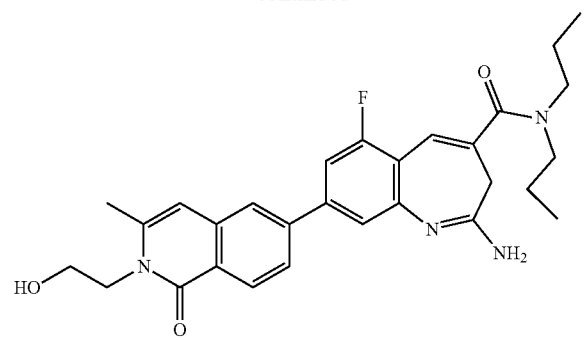
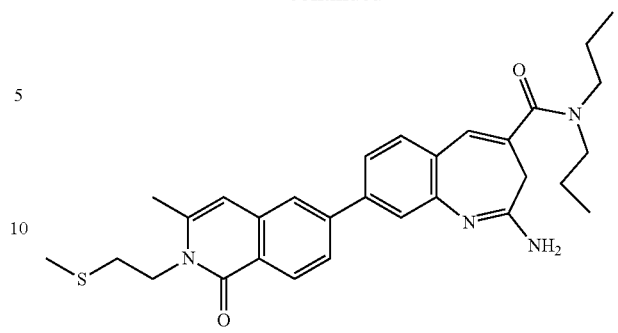
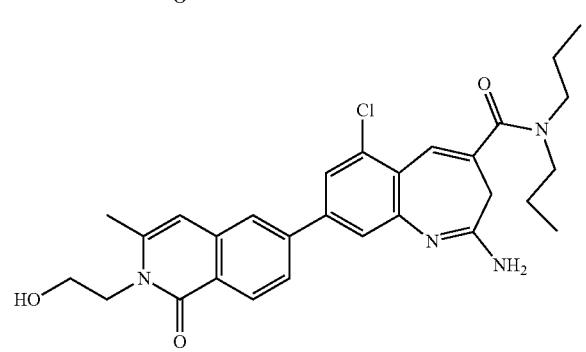
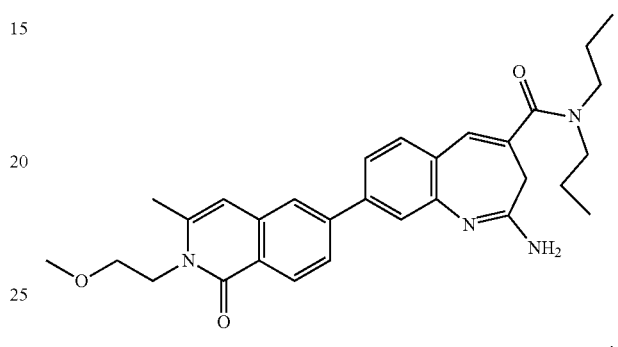
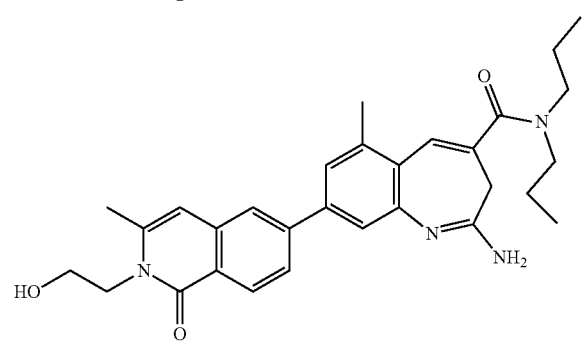
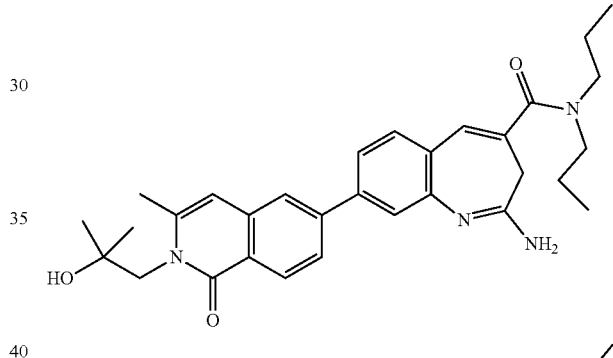
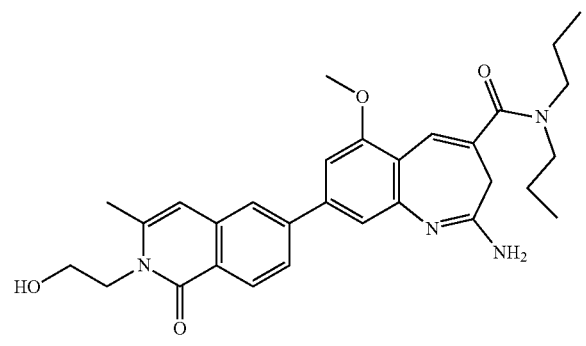
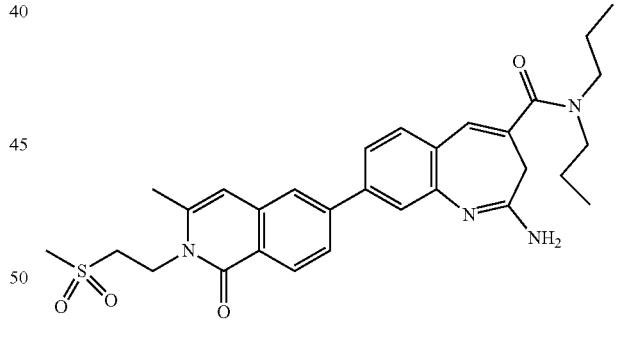
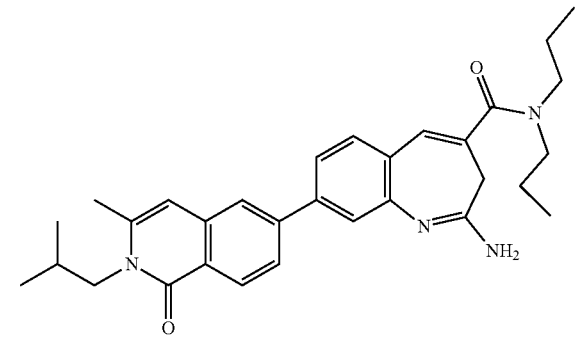
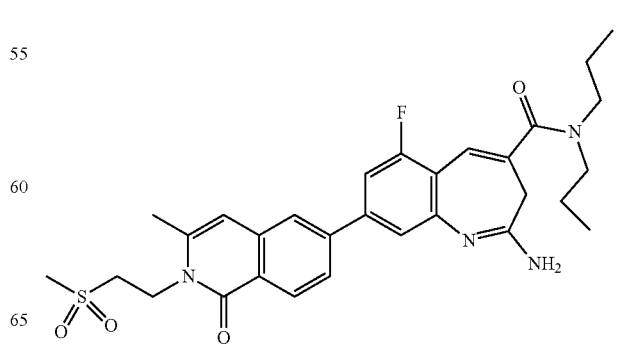

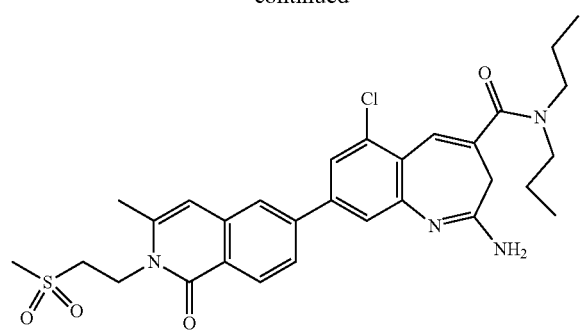
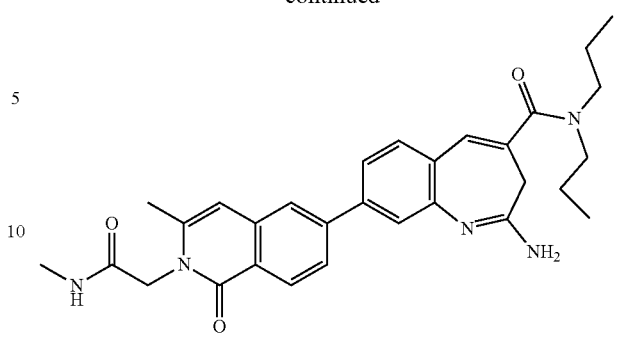
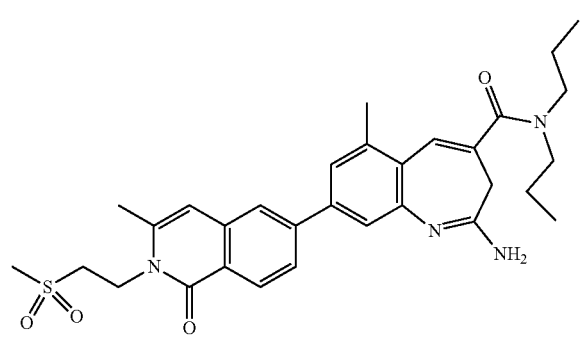
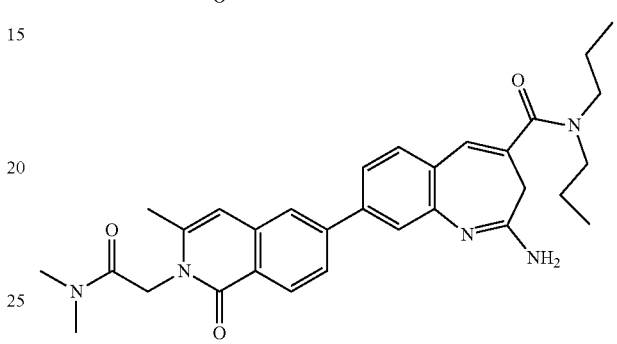
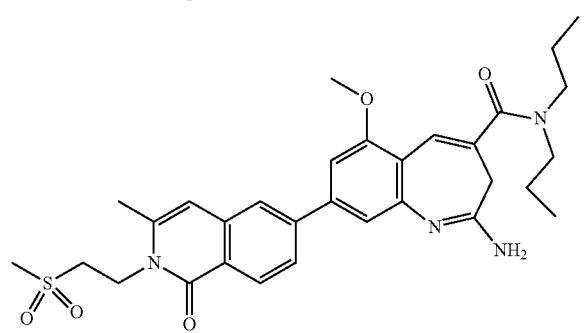
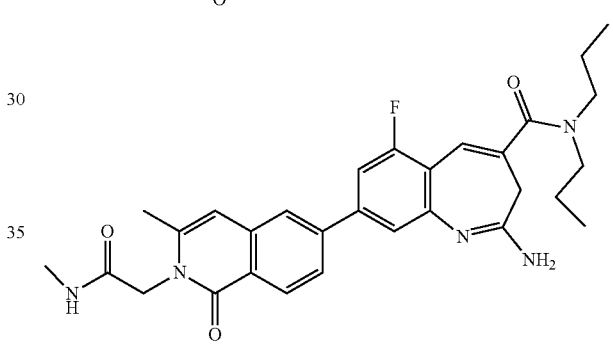
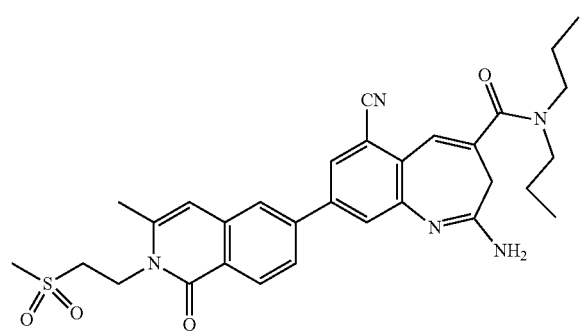
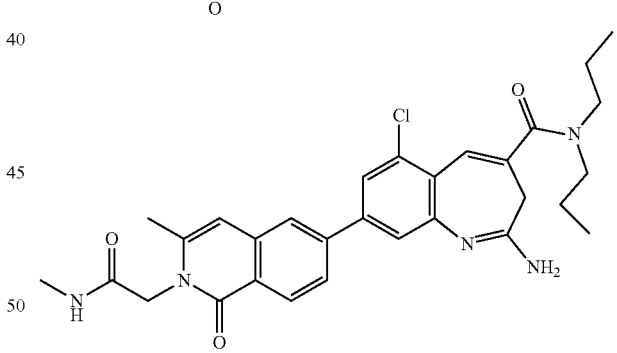
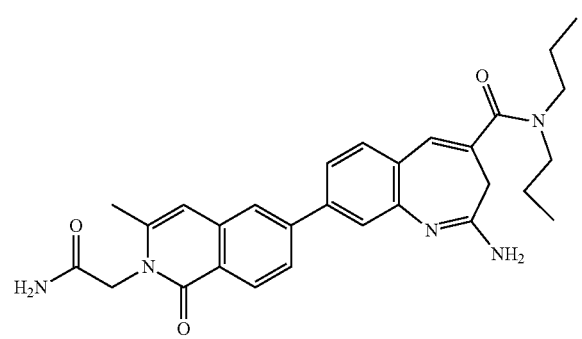
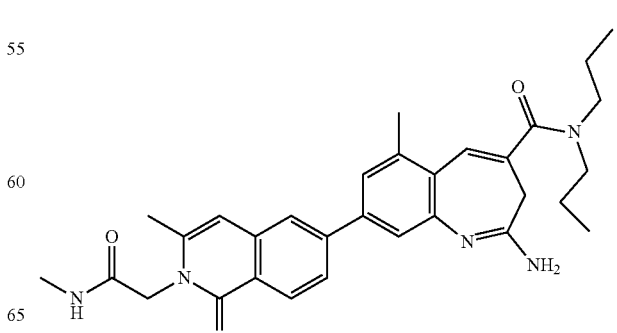

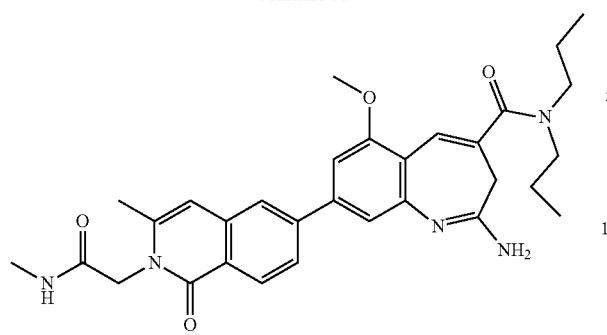
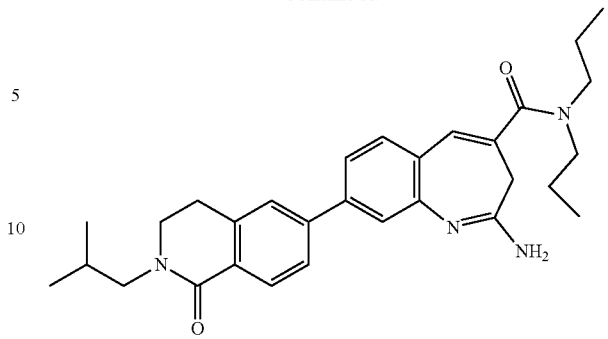
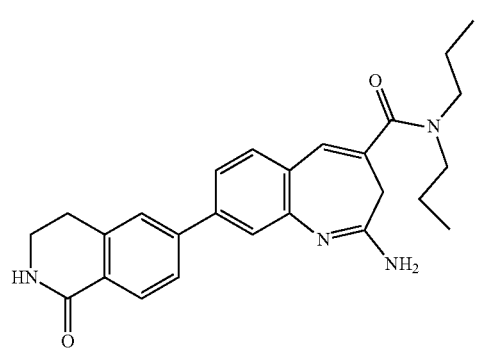
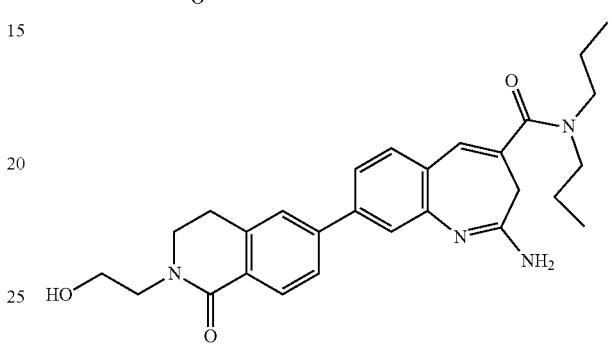
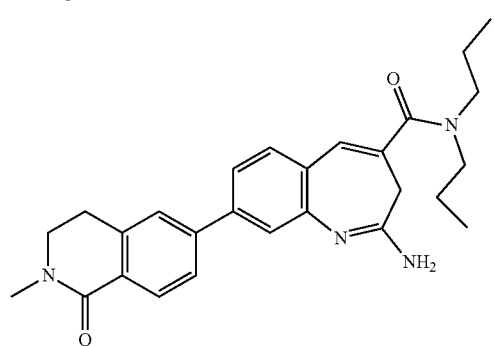
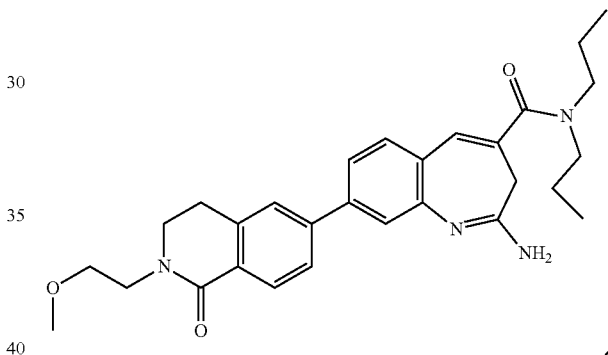
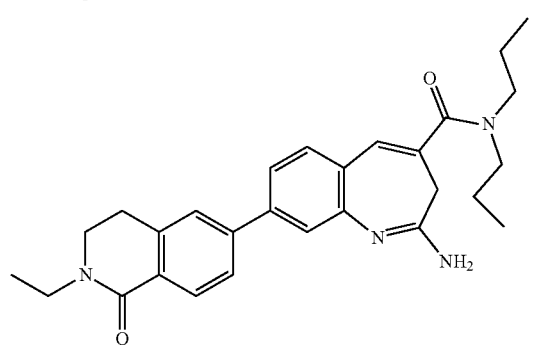
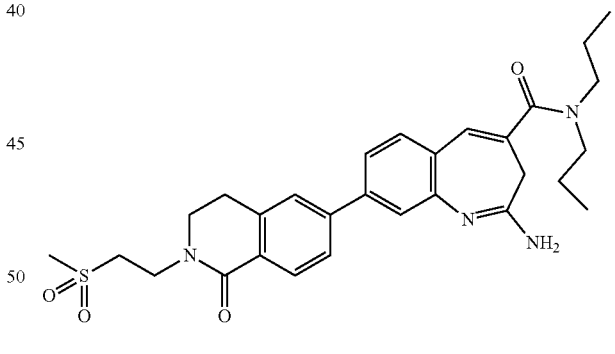
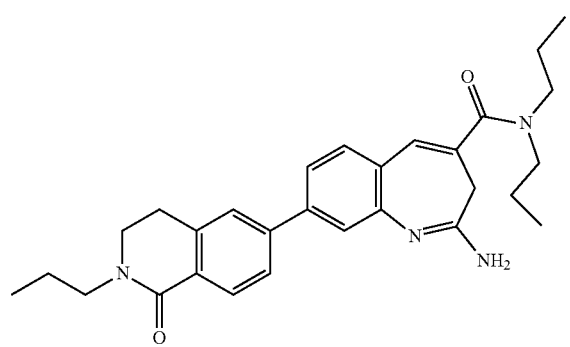
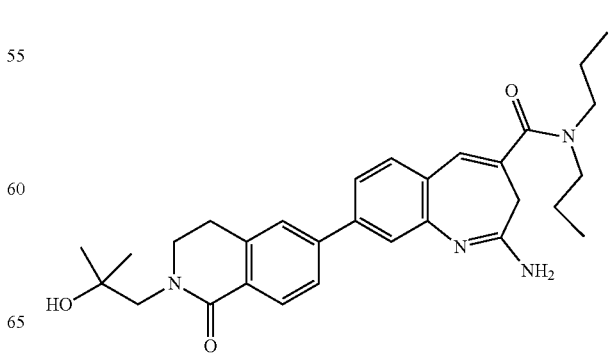

45
-continued
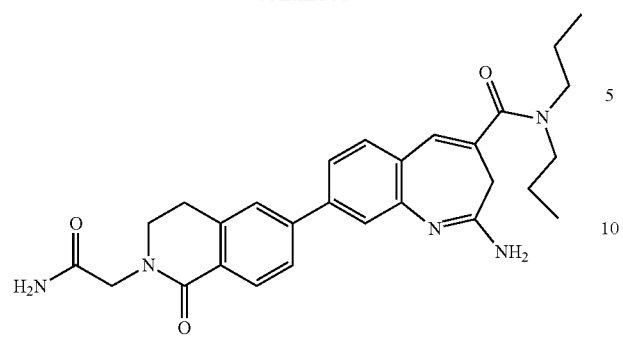
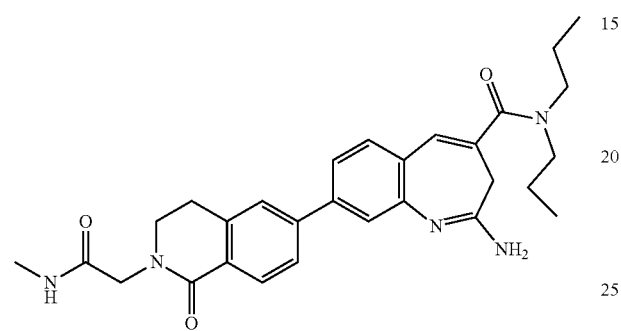
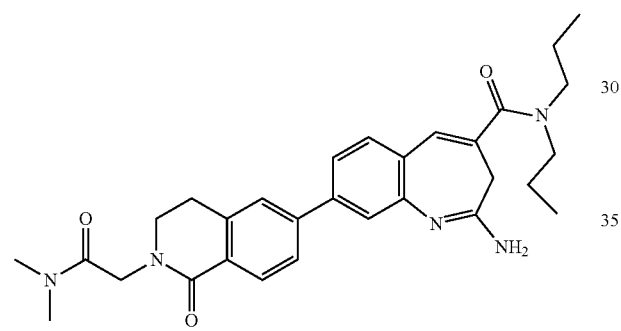
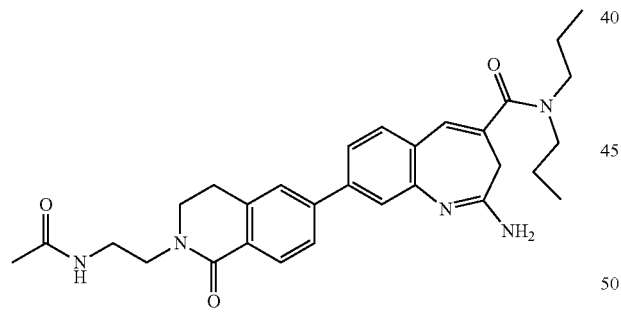
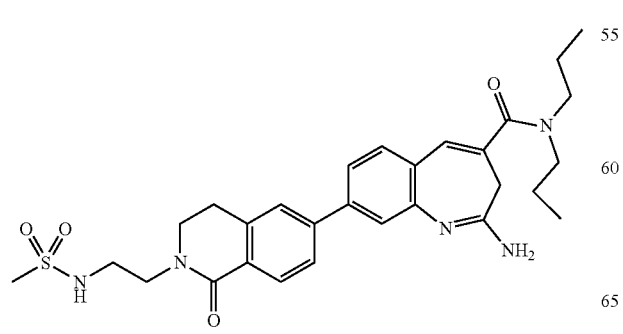
46
-continued
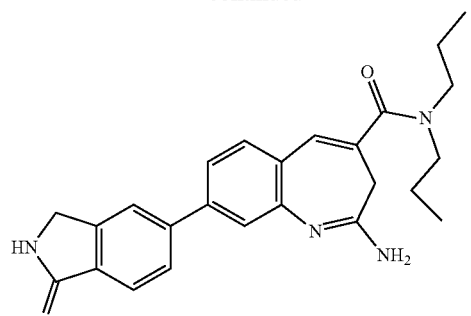
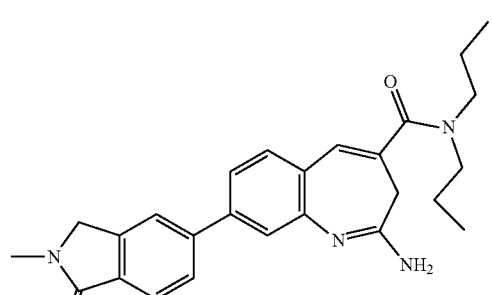
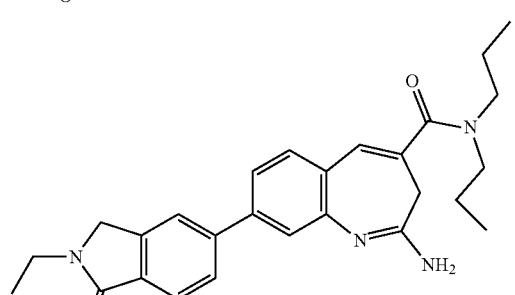
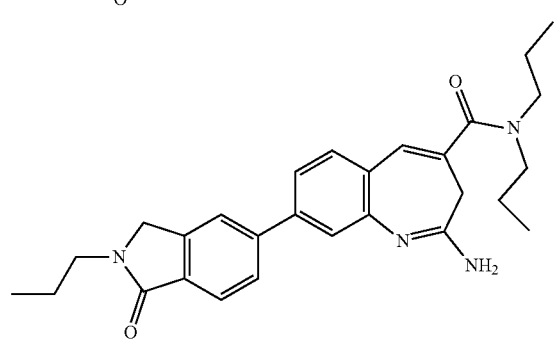
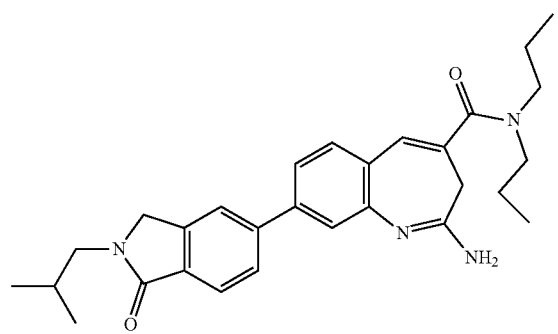

-continued
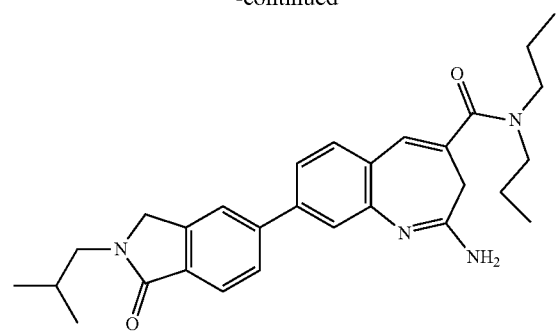
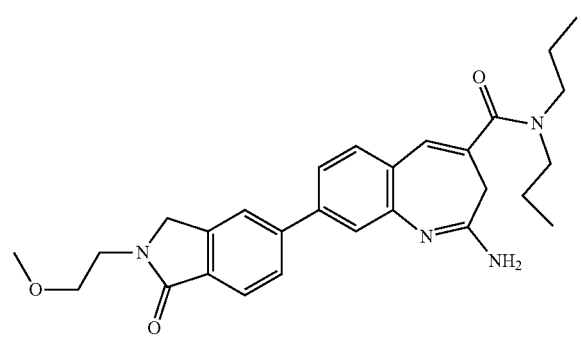
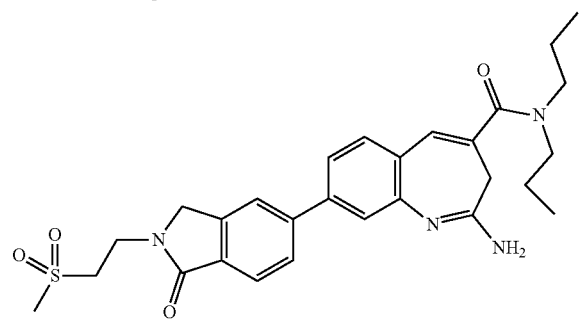
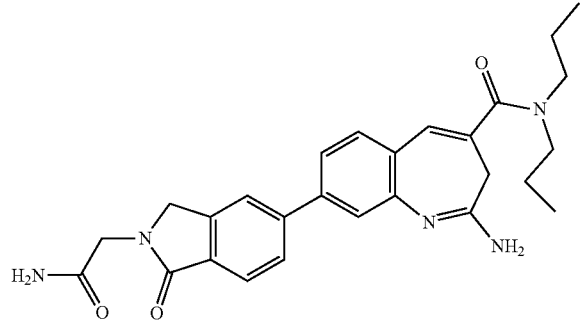
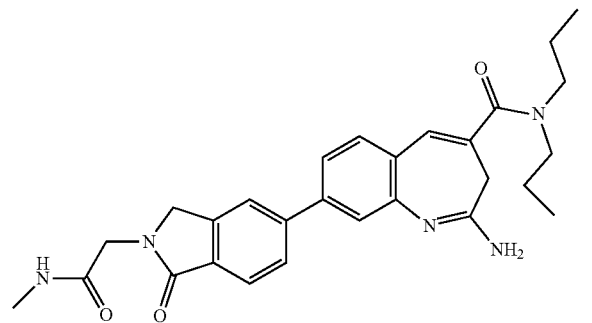
-continued
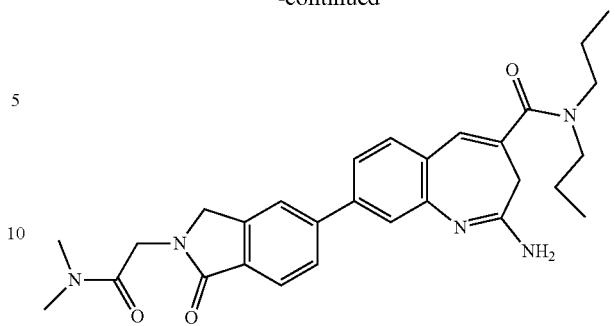
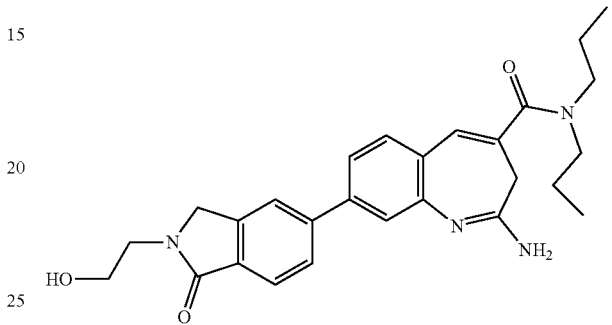
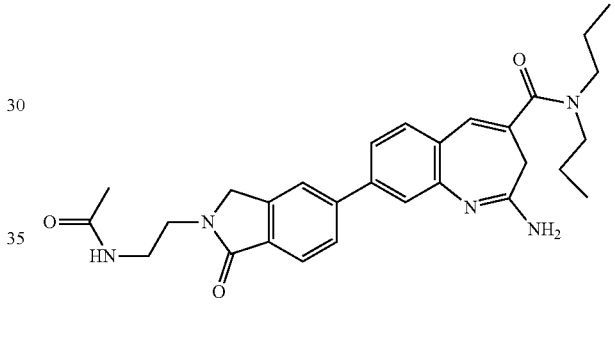
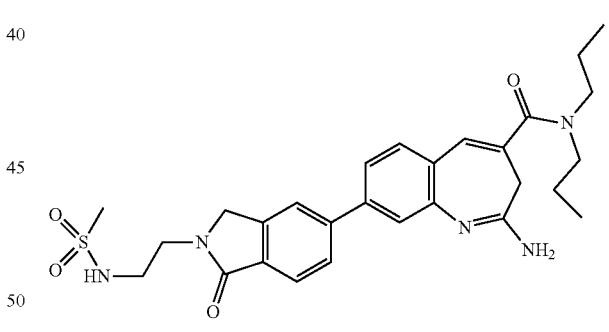
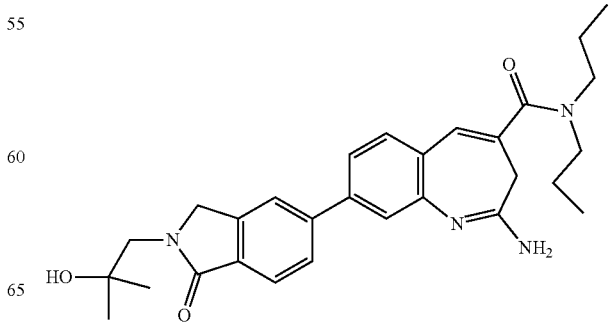

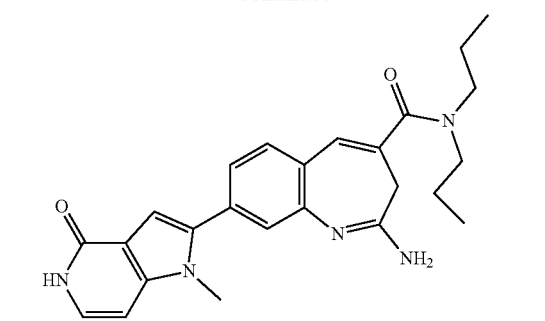
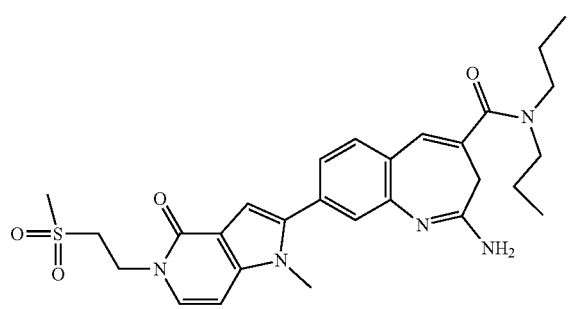
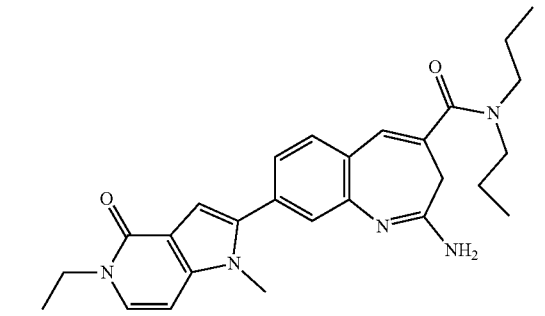
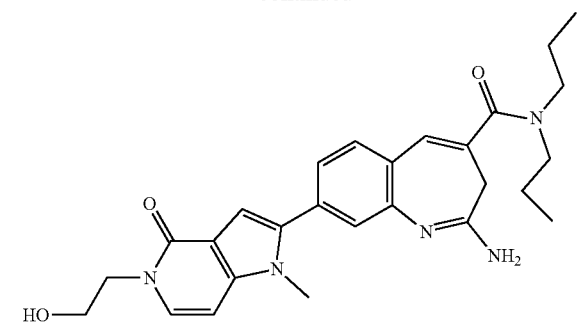
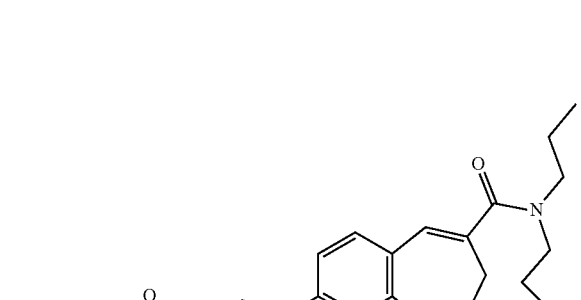
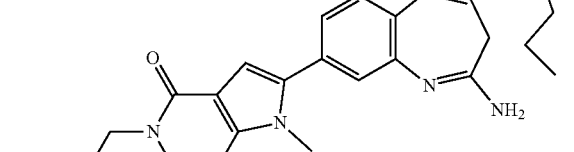
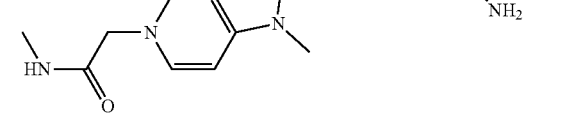

51
-continued
52
-continued
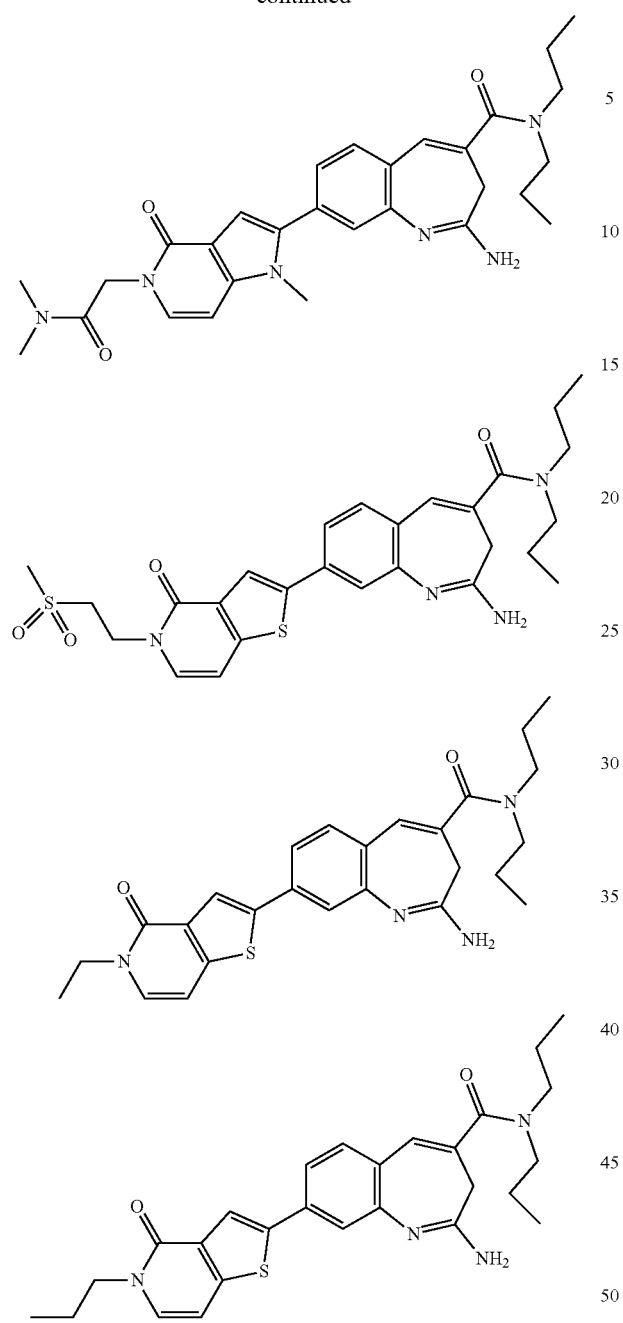
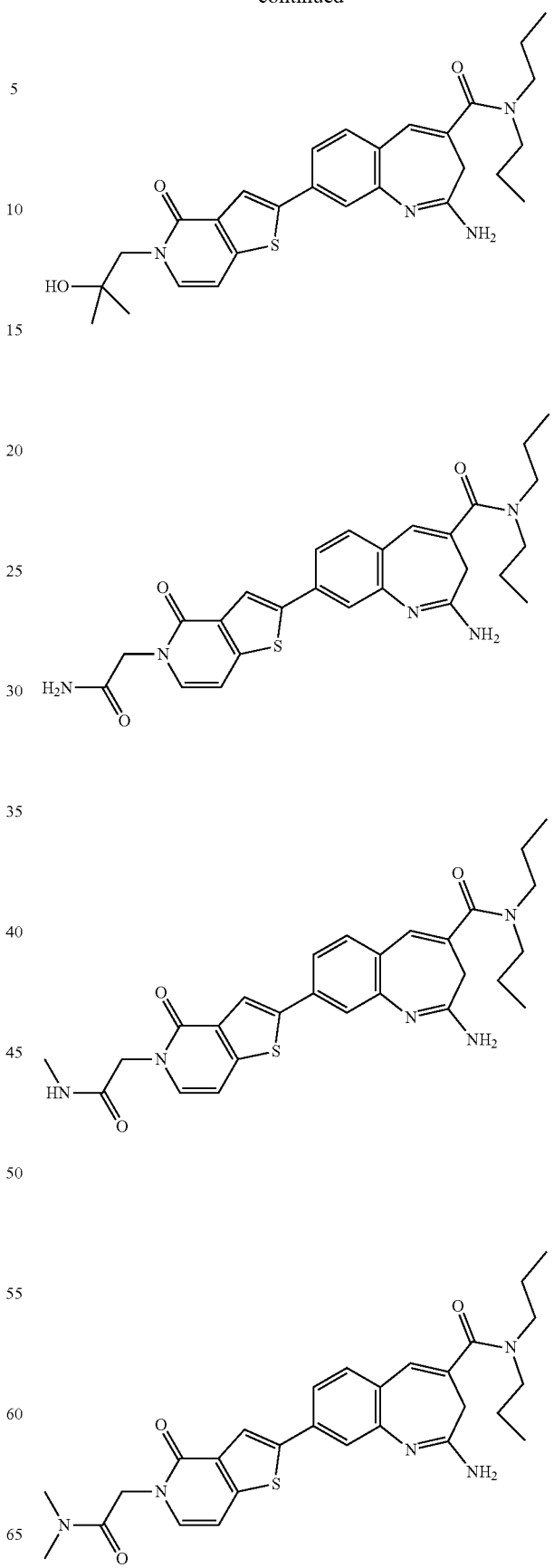

53
-continued
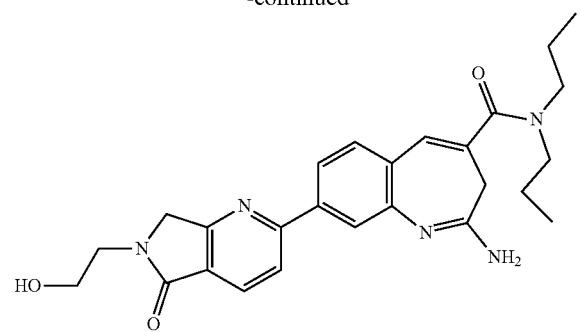
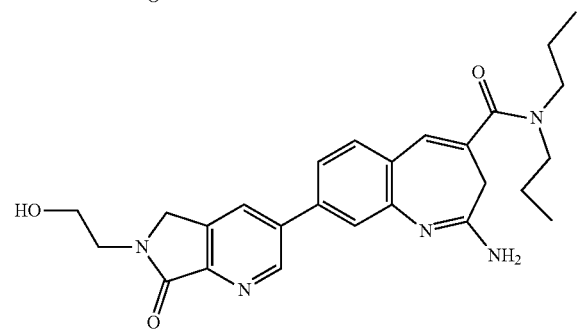
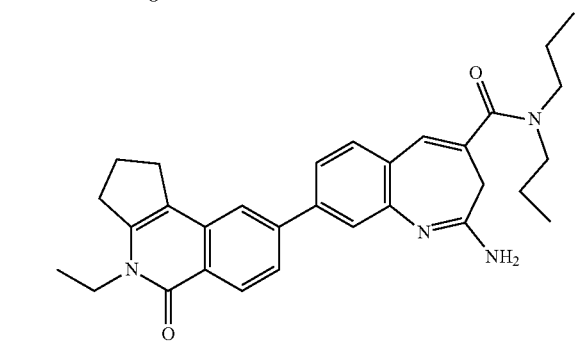
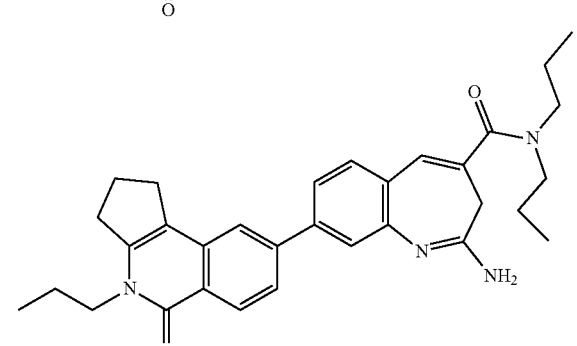
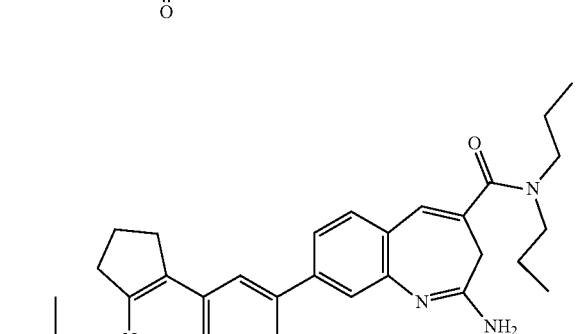
54
-continued
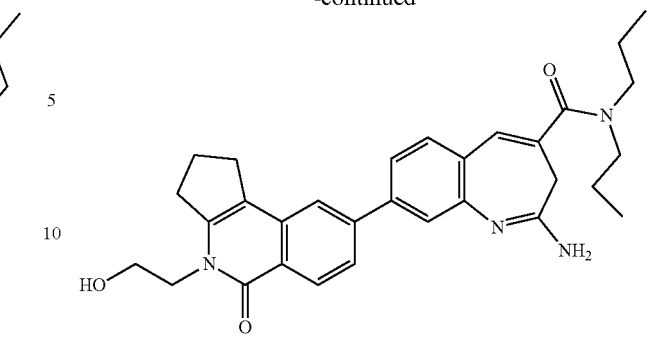
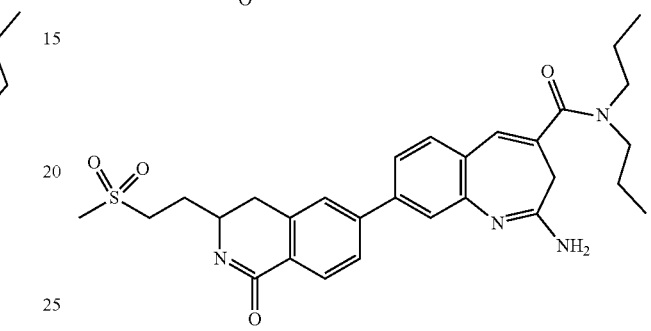
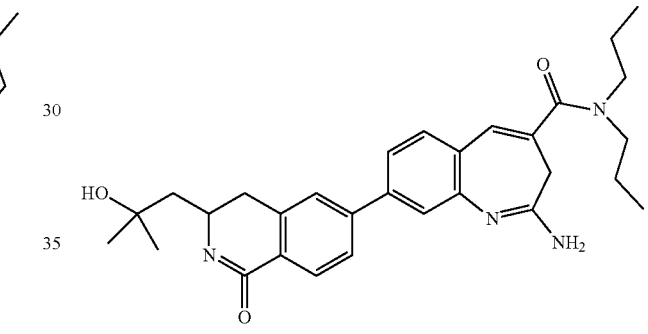
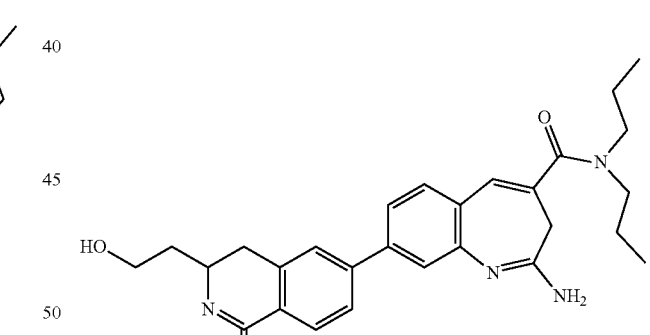
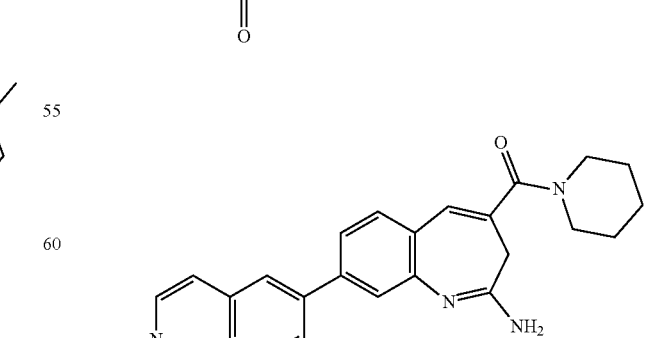

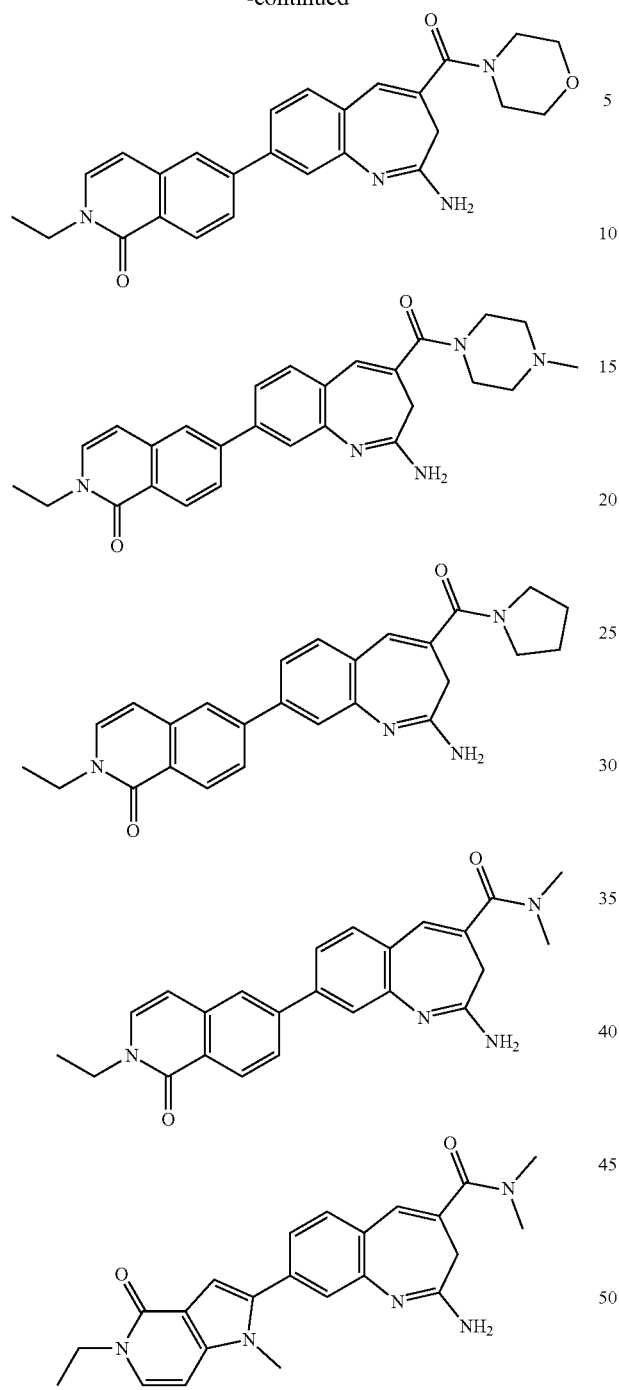
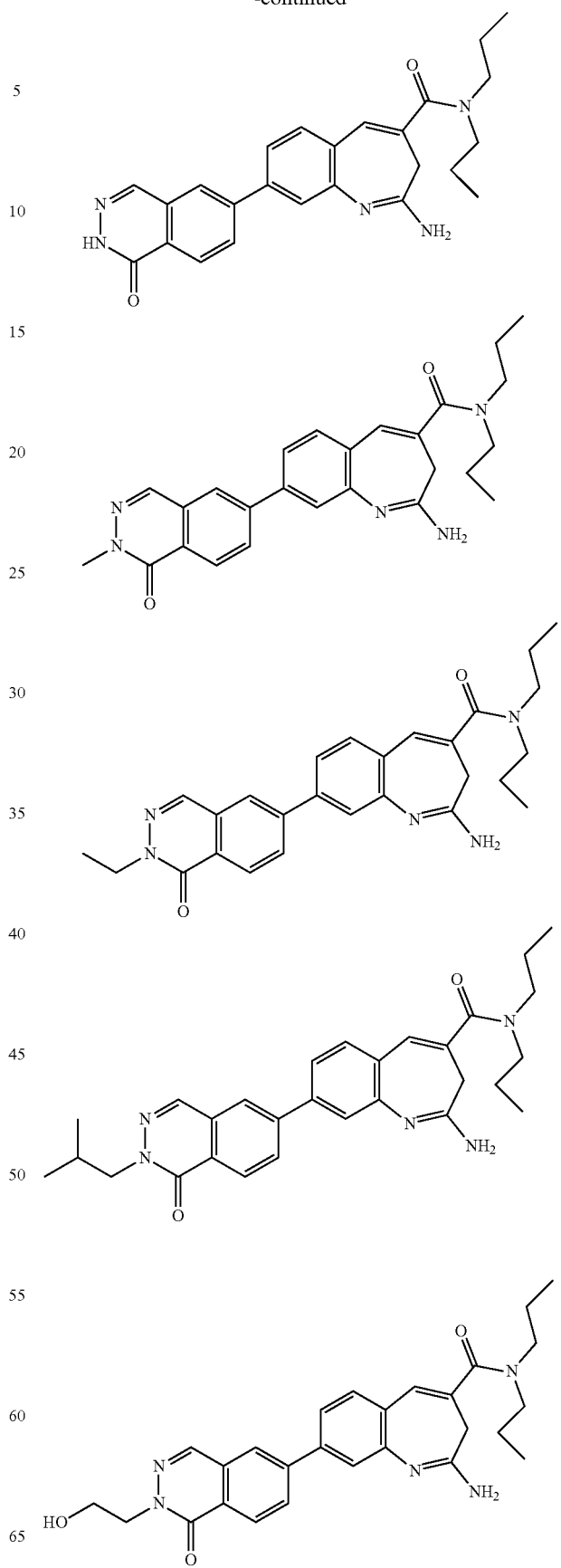

57
-continued
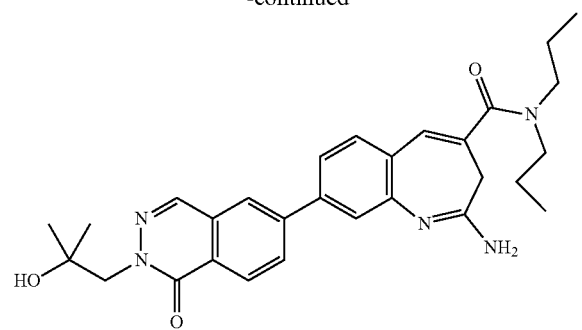
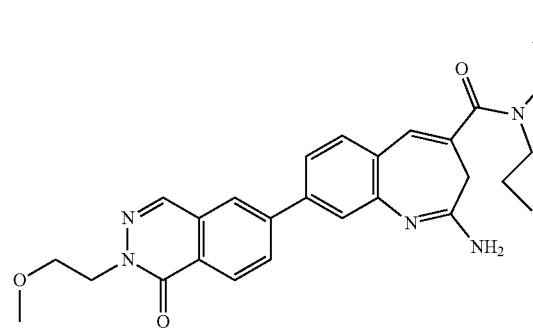
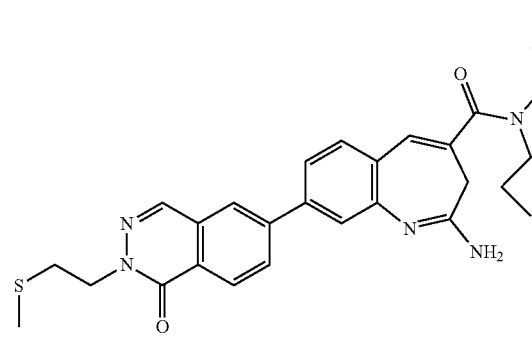
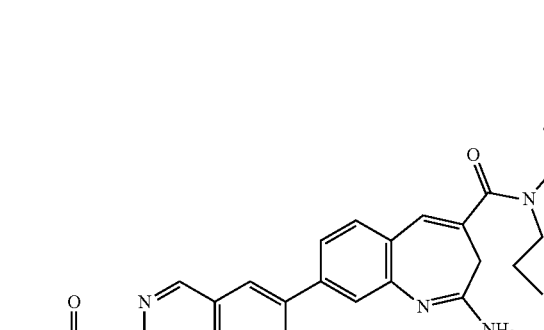
58
-continued
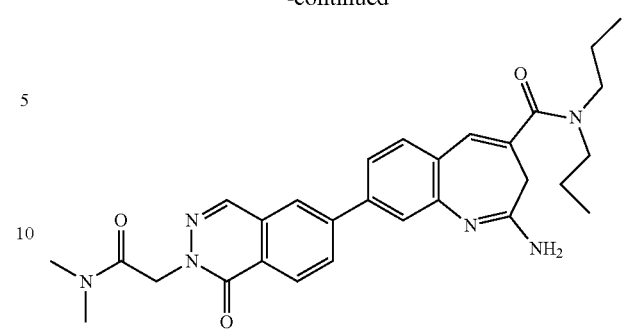
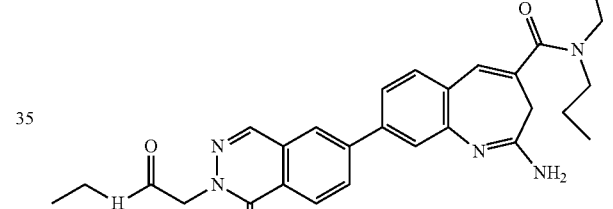
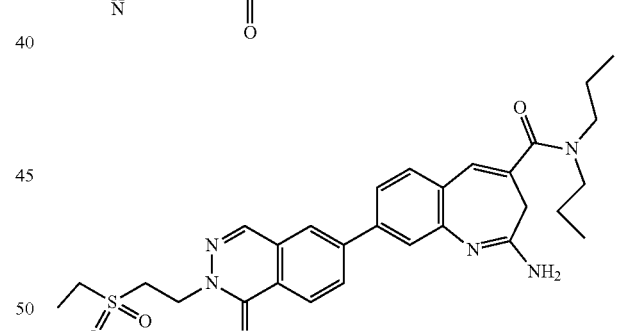
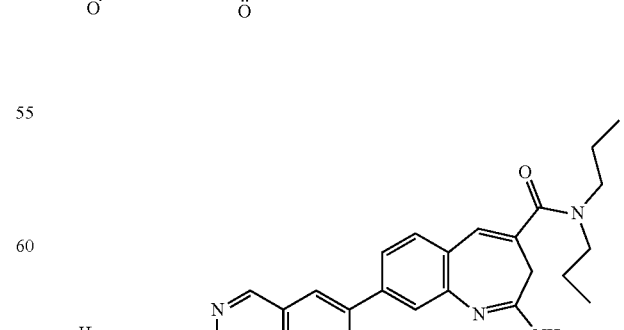

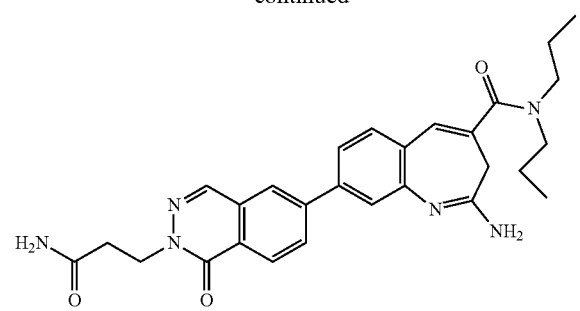
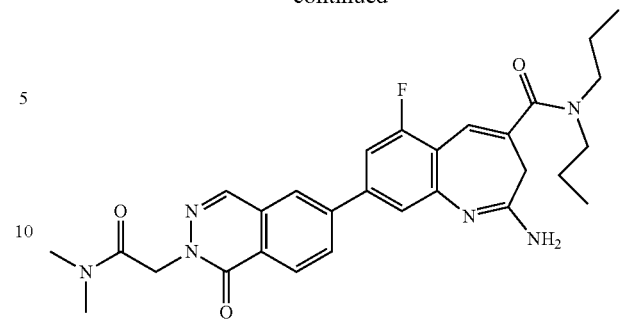
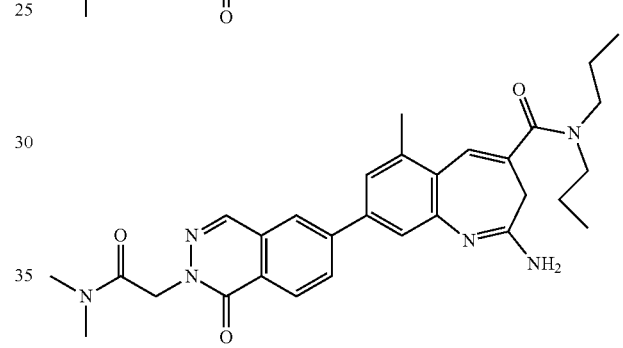

61
-continued
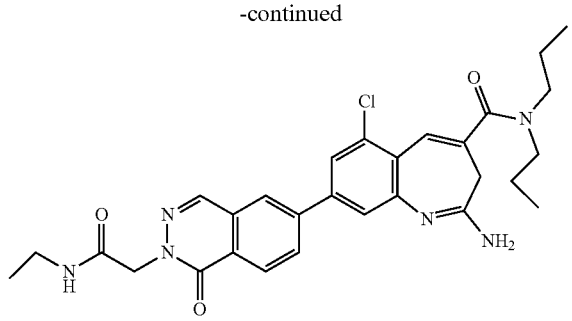
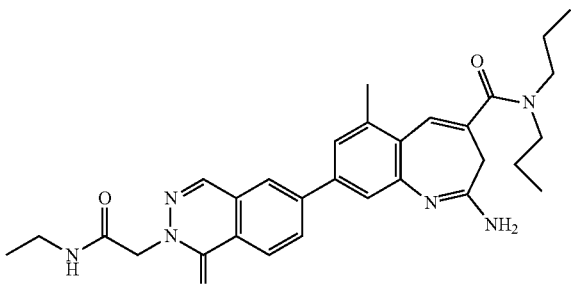
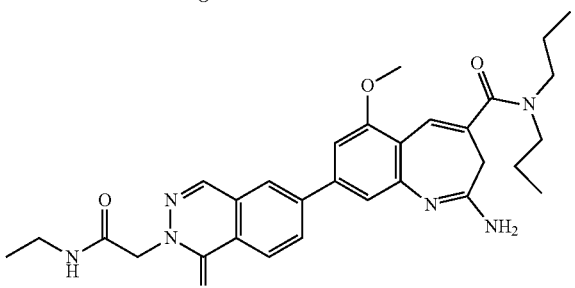
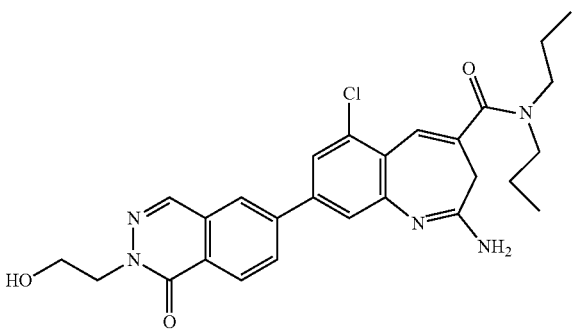
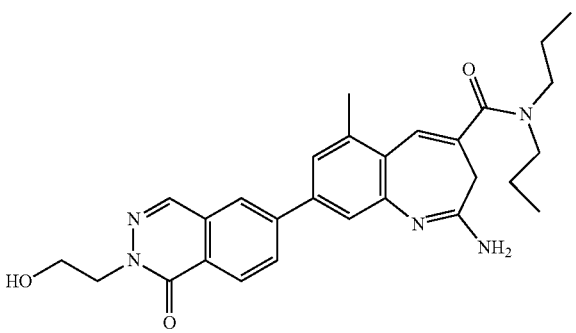
62
-continued
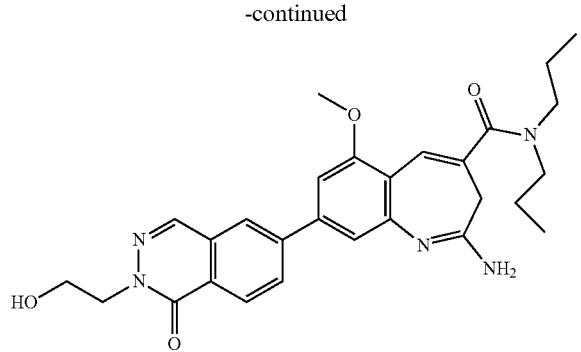
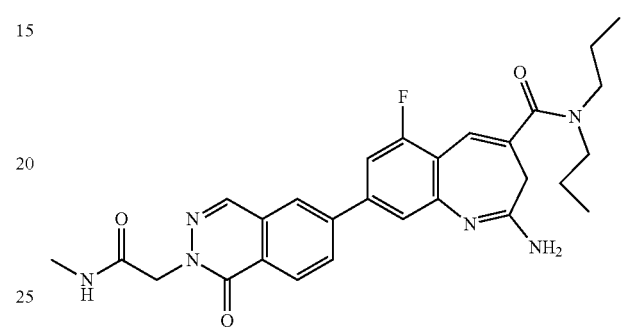
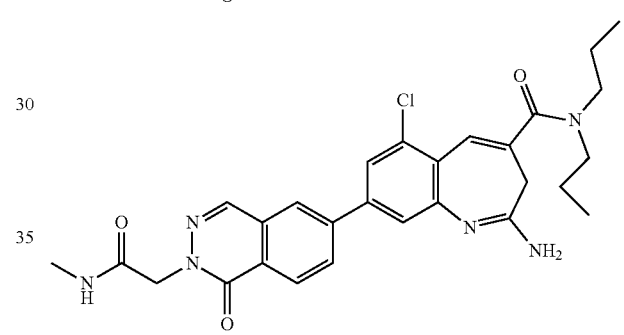
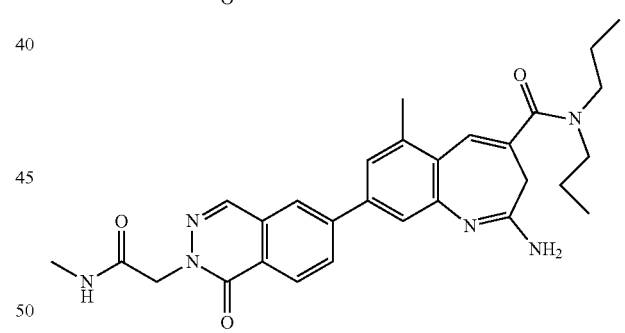
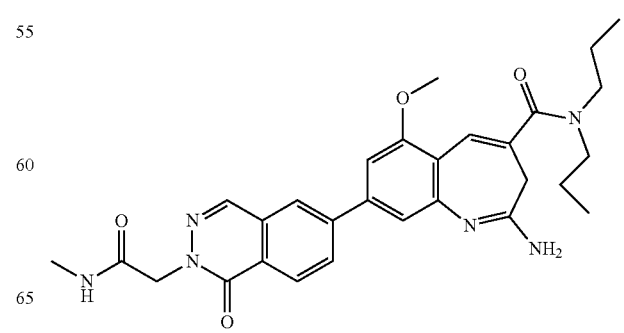

63
-continued
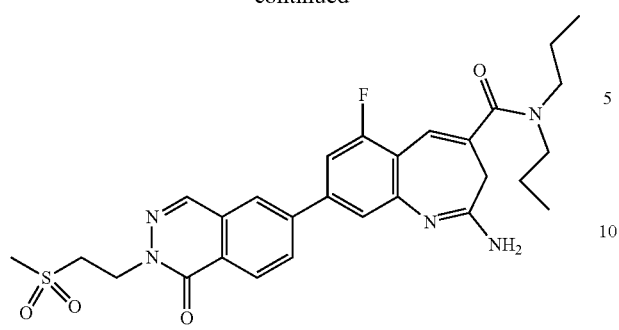
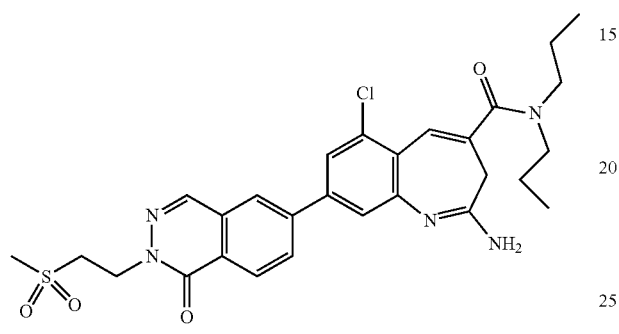
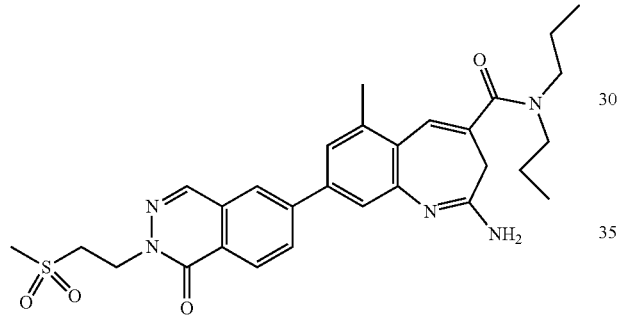
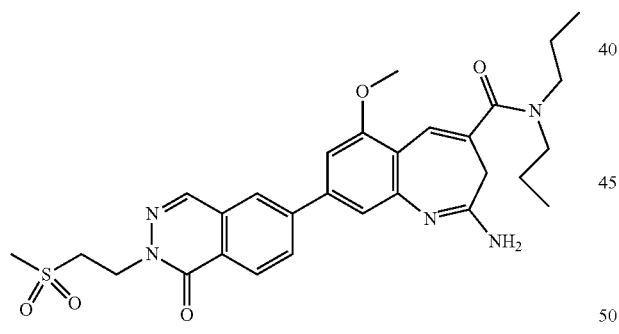
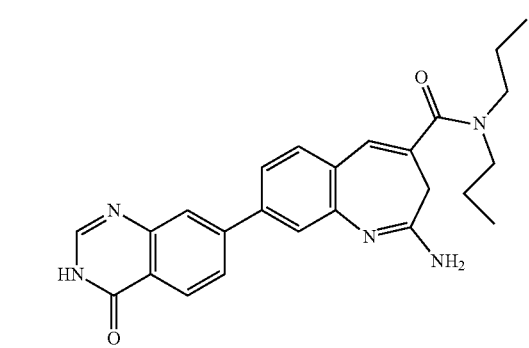
64
-continued
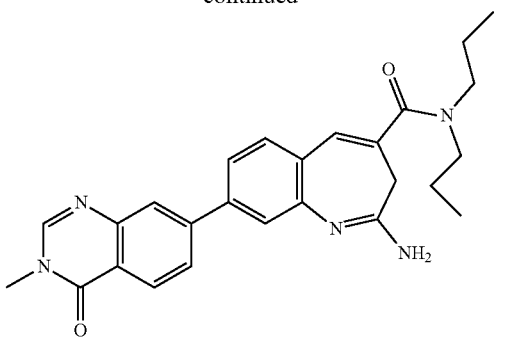
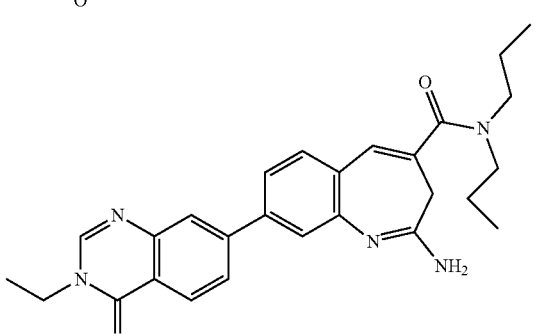
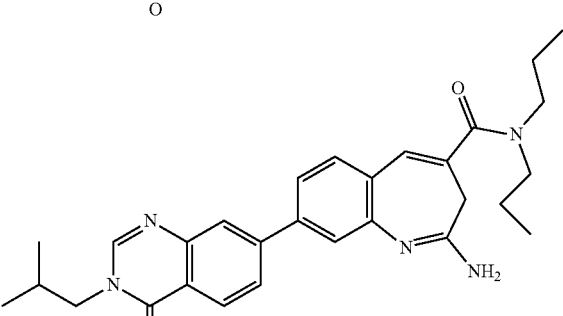
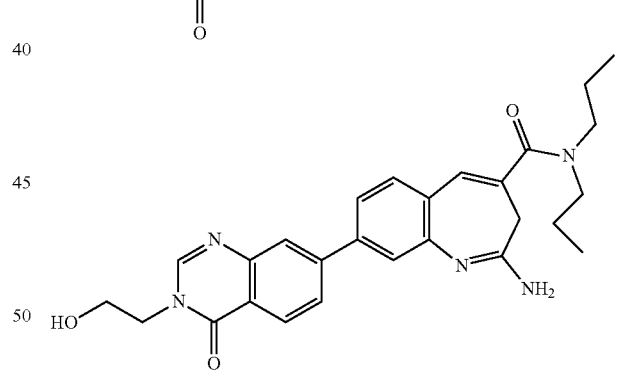
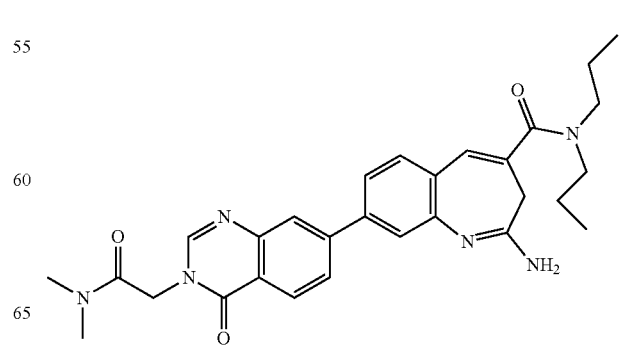

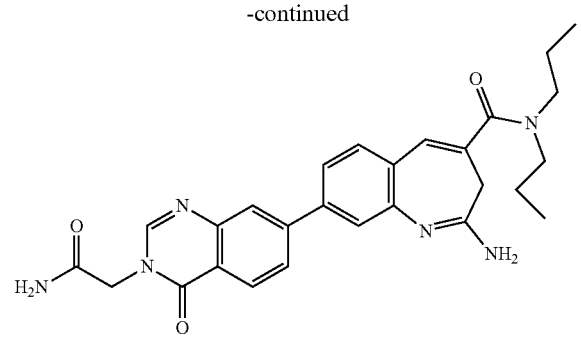
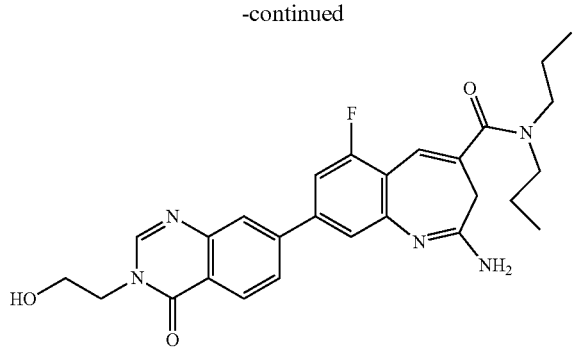
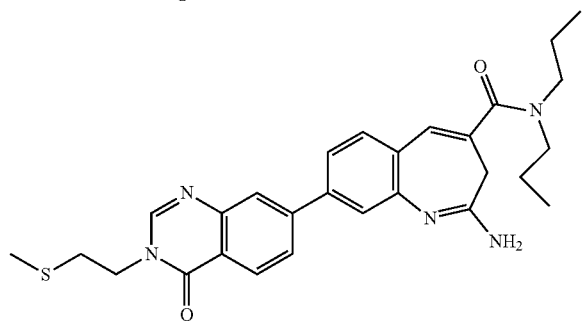
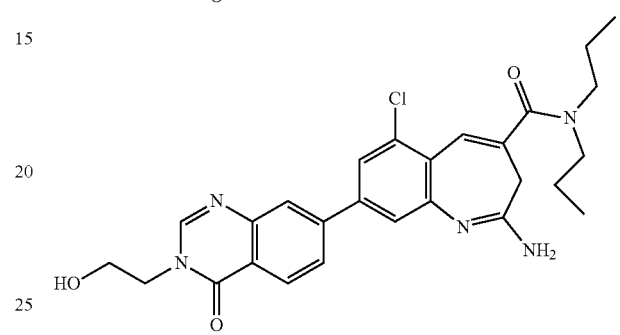
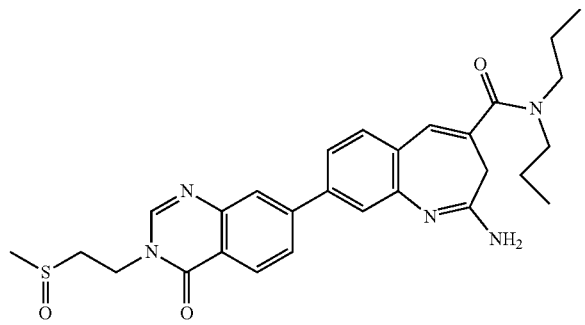
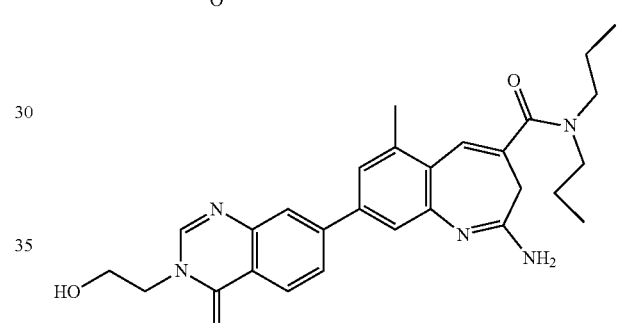
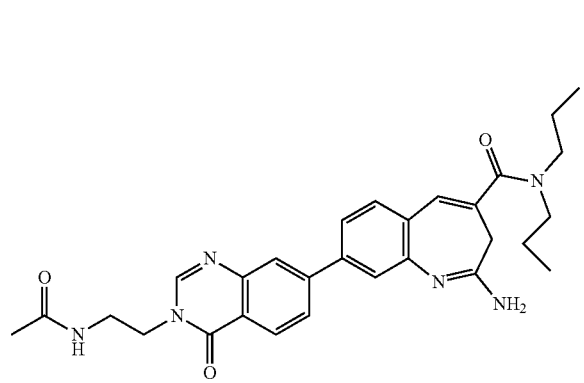
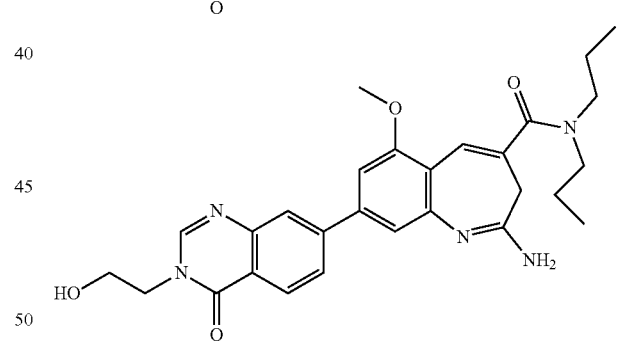
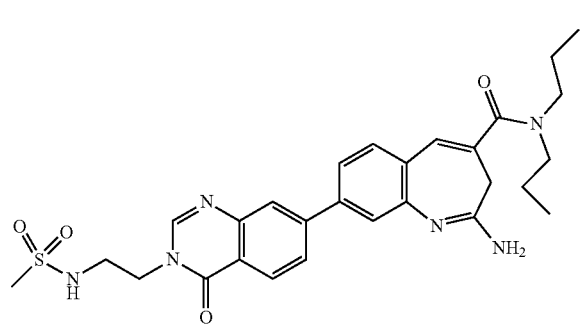
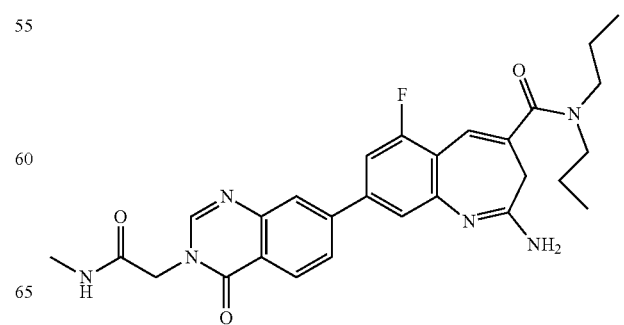

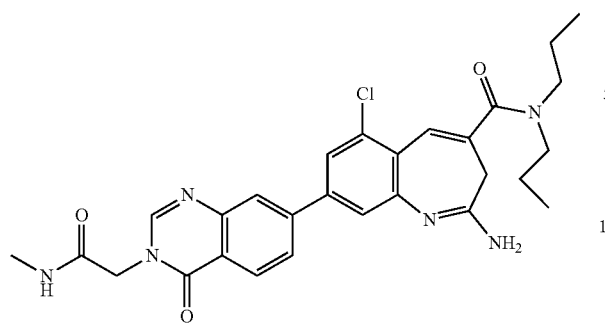
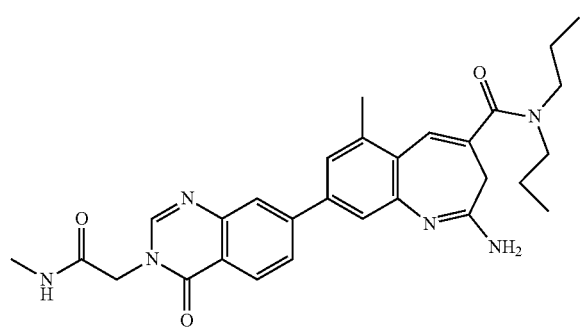
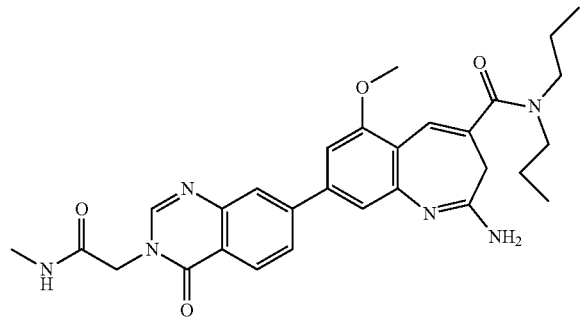
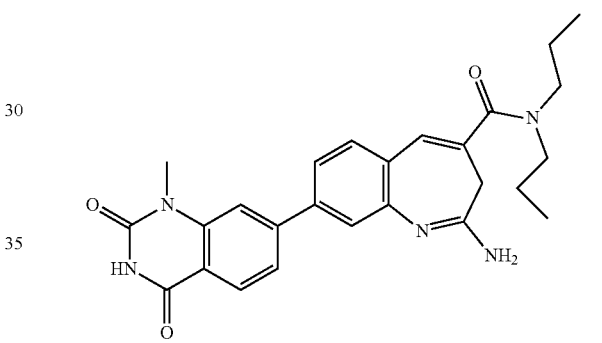
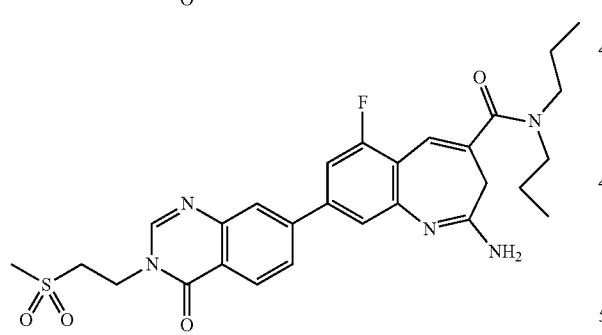
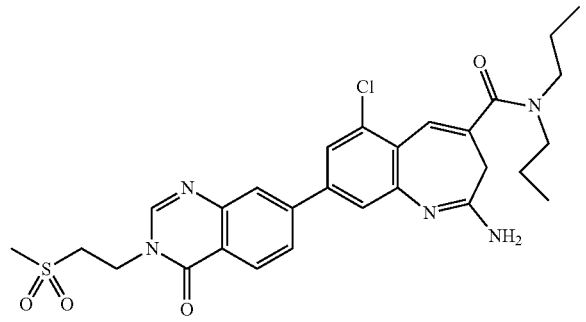

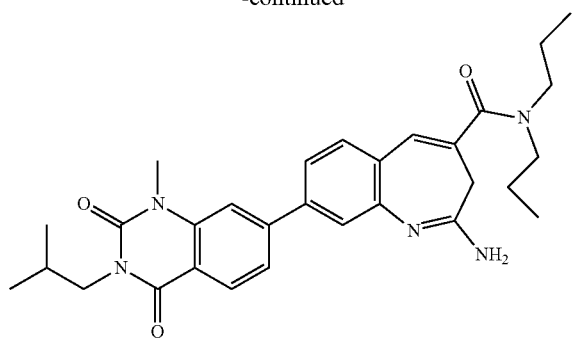
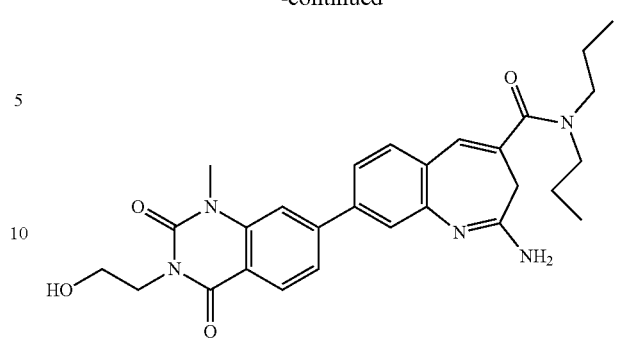
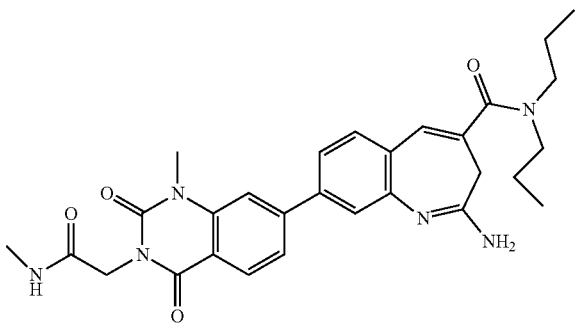
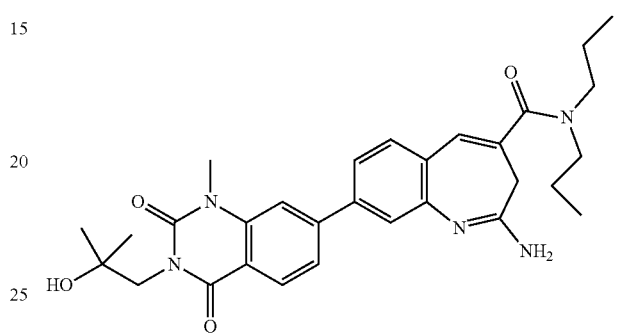
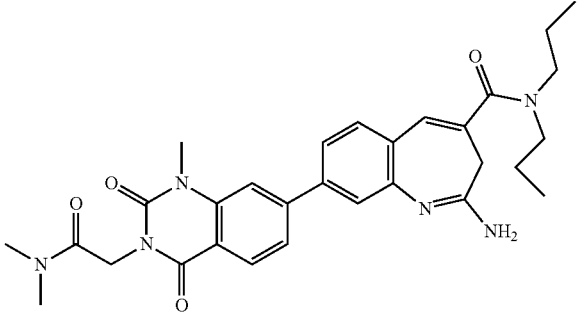
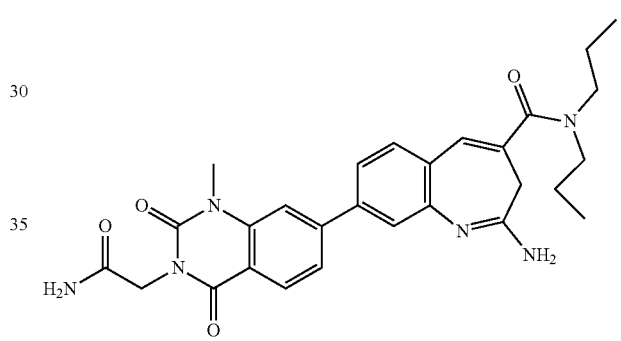
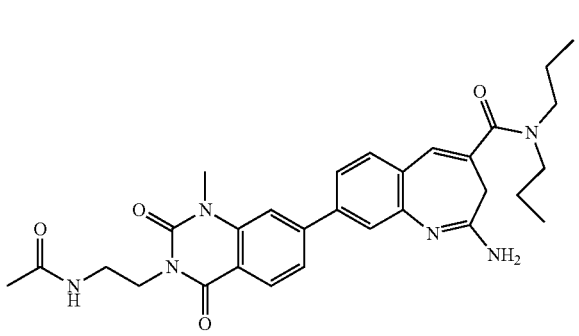
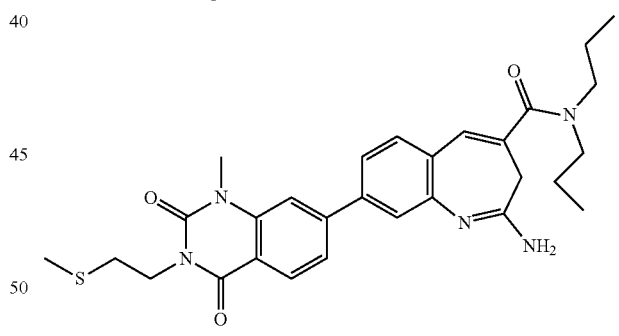
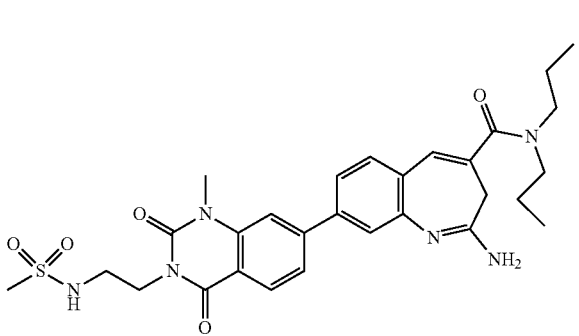
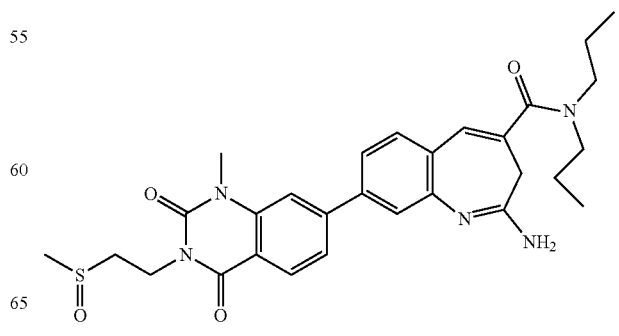

71
-continued
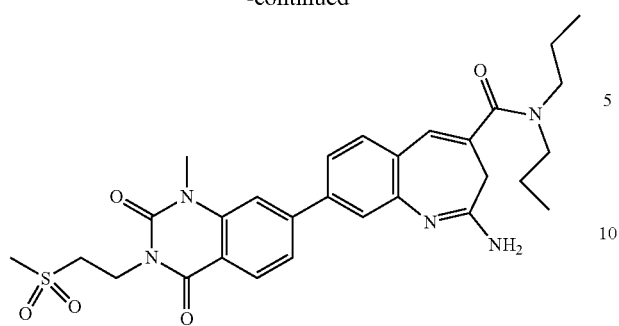
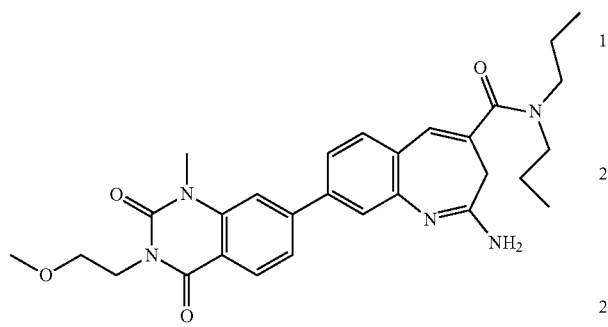
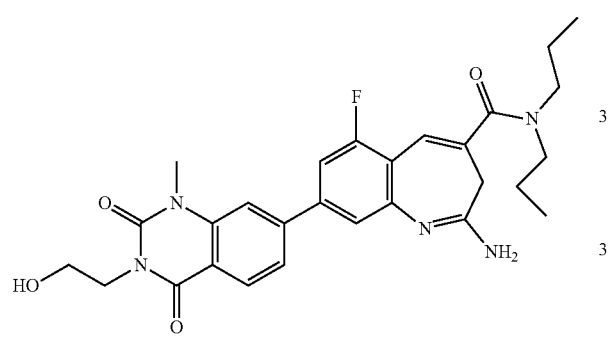
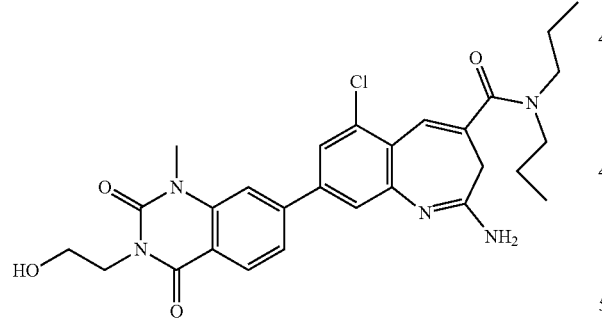
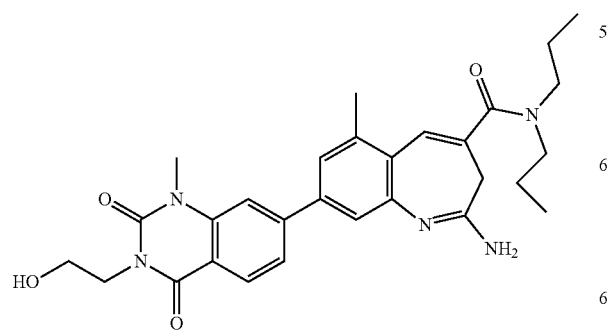
72
-continued
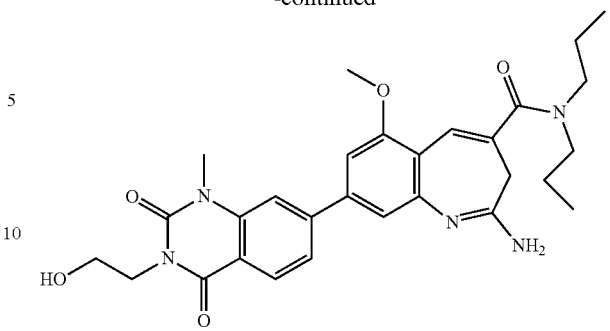
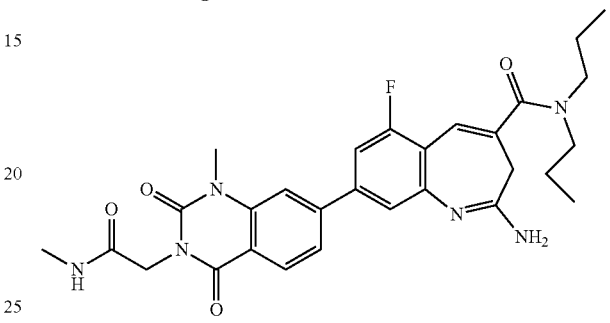
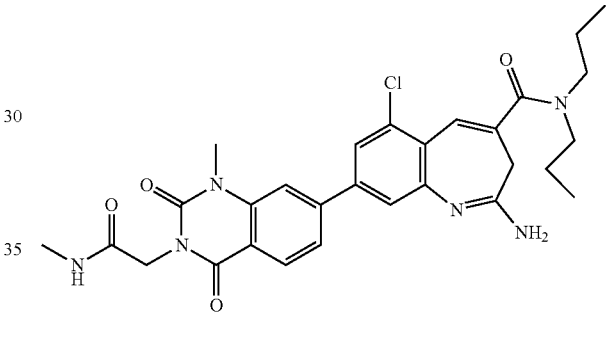
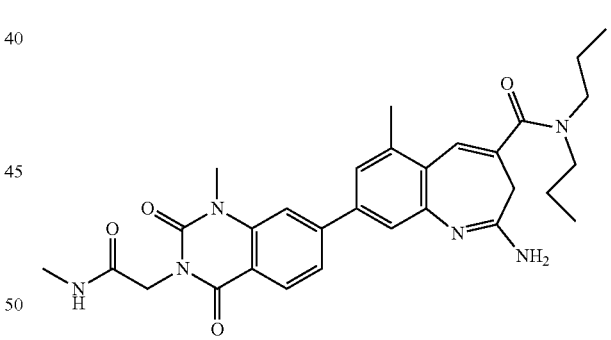
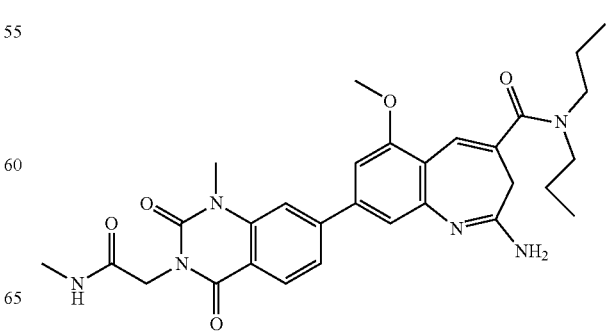

73
-continued
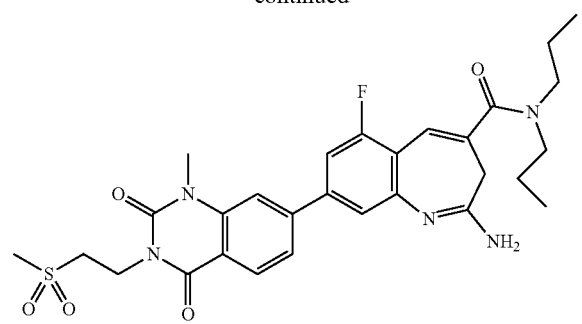
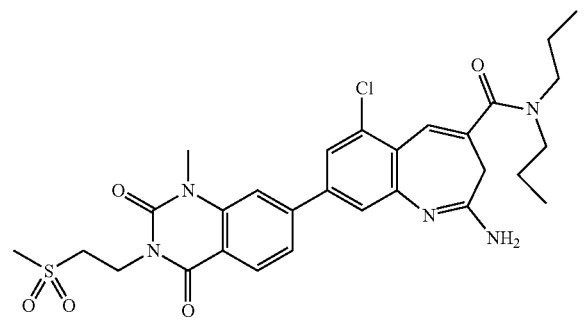
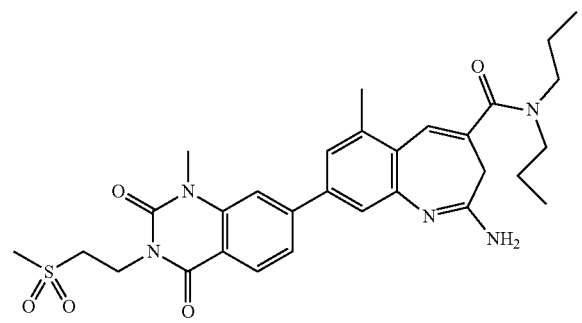
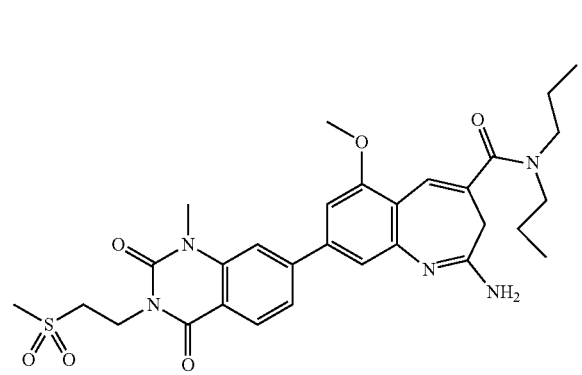
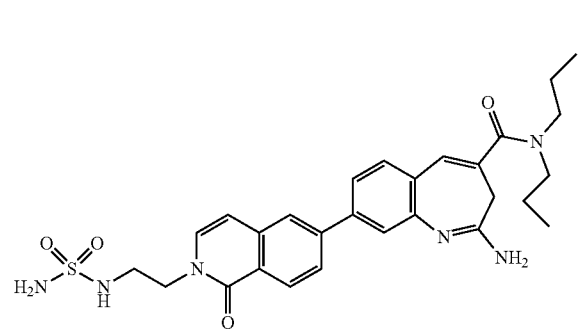
74
-continued
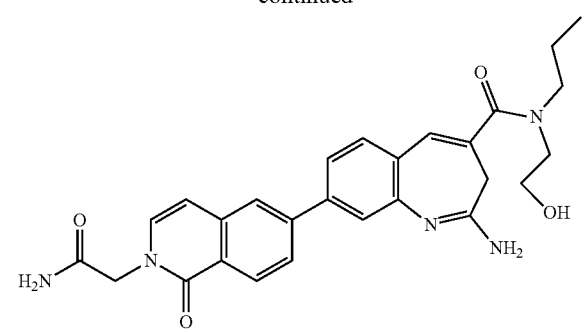
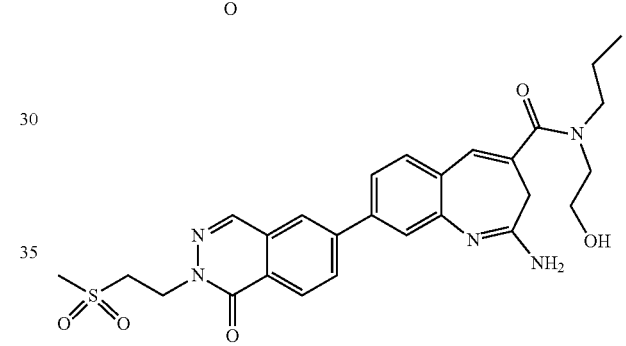
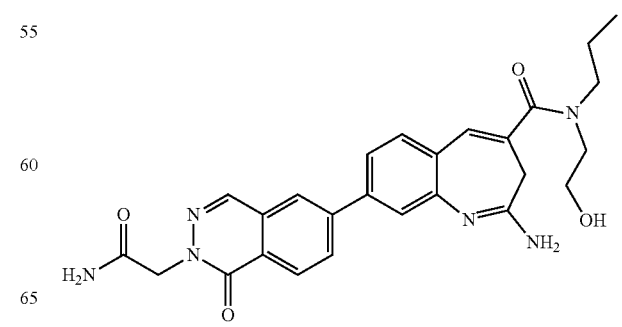

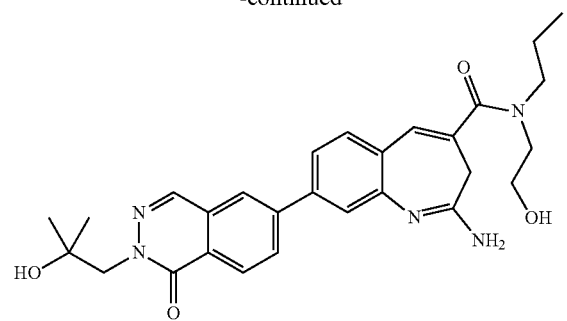
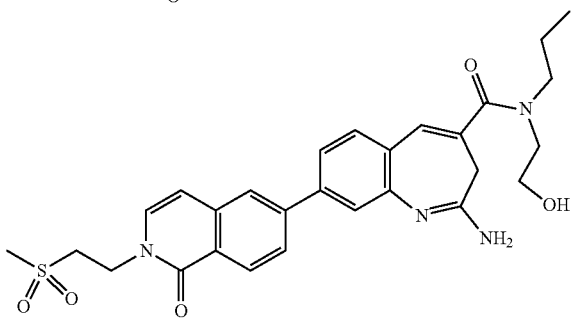
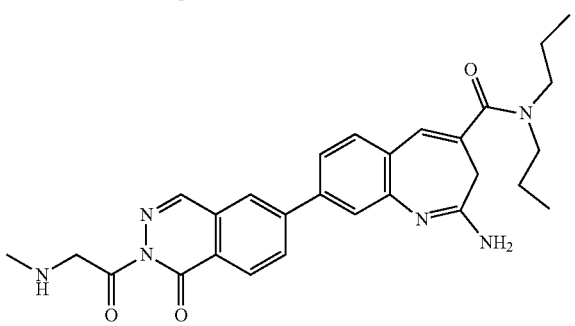
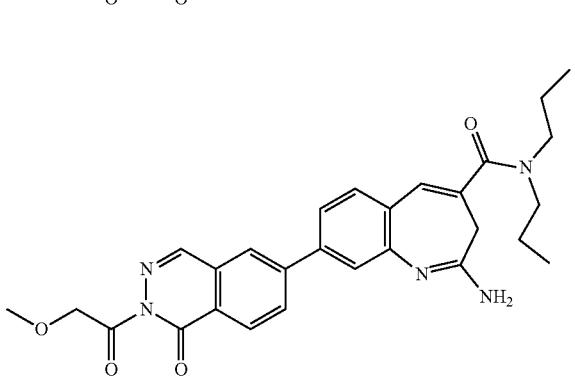
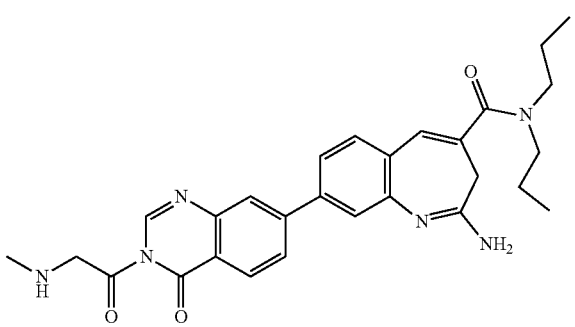
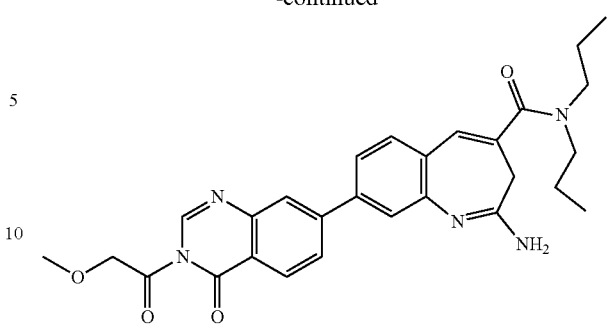

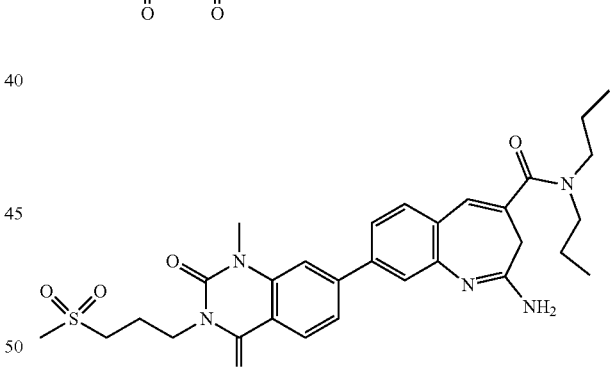
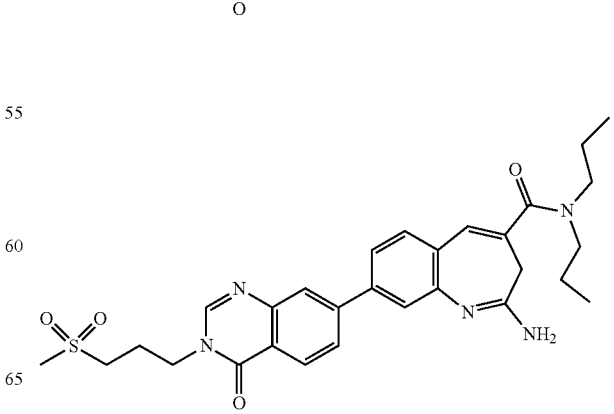

77
-continued
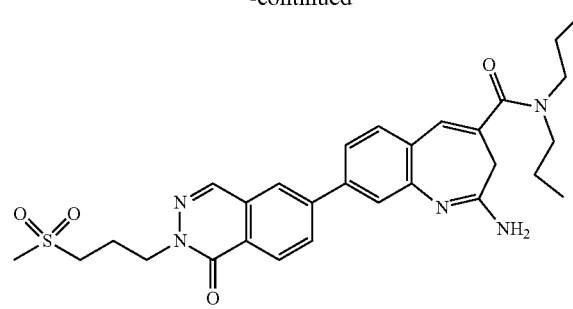
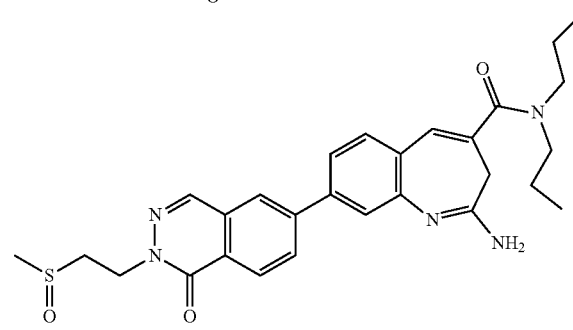
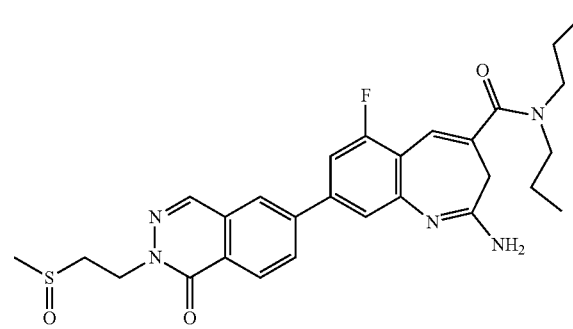
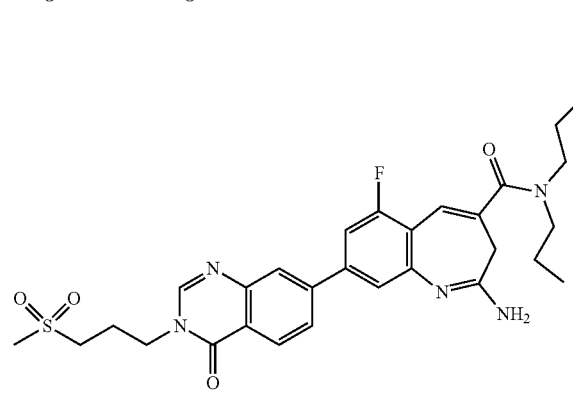
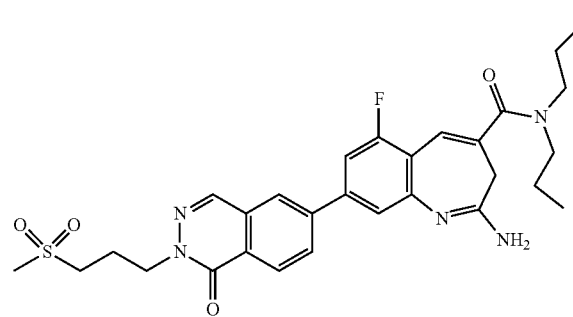
78
-continued
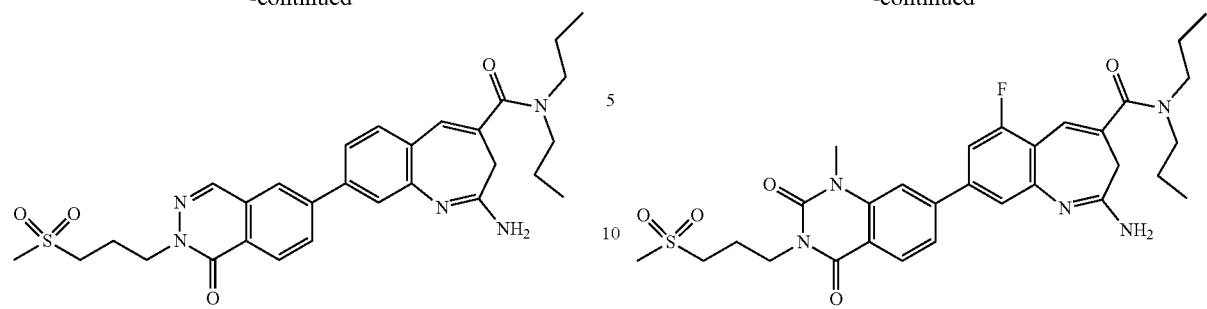
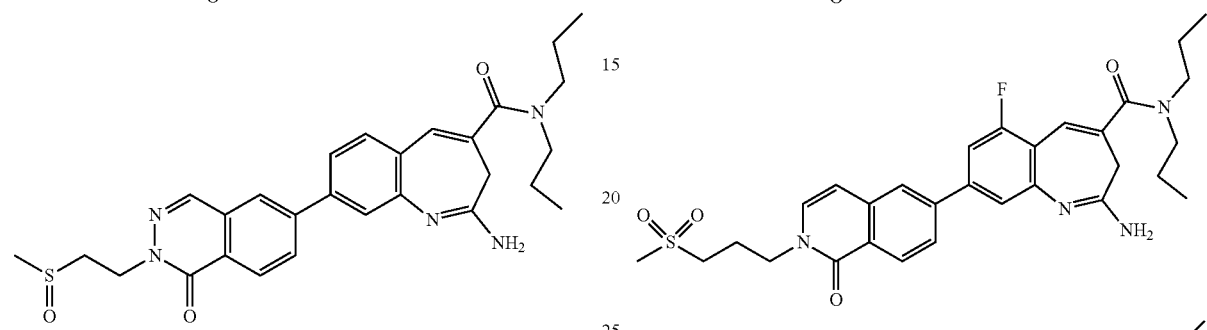
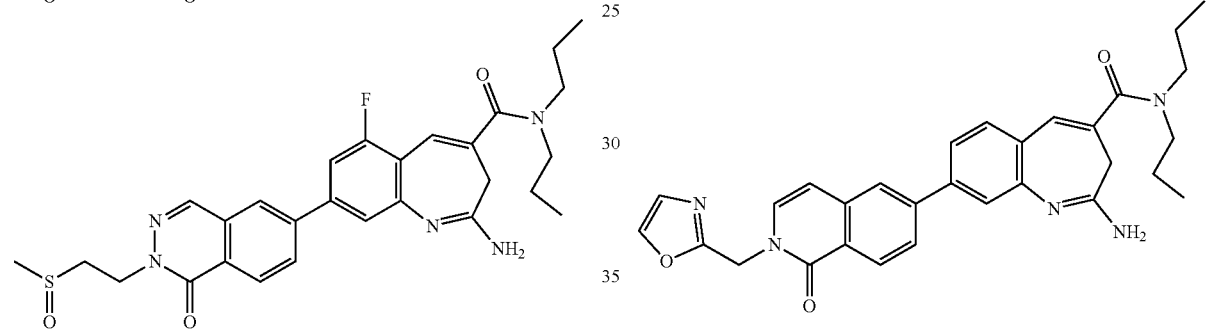
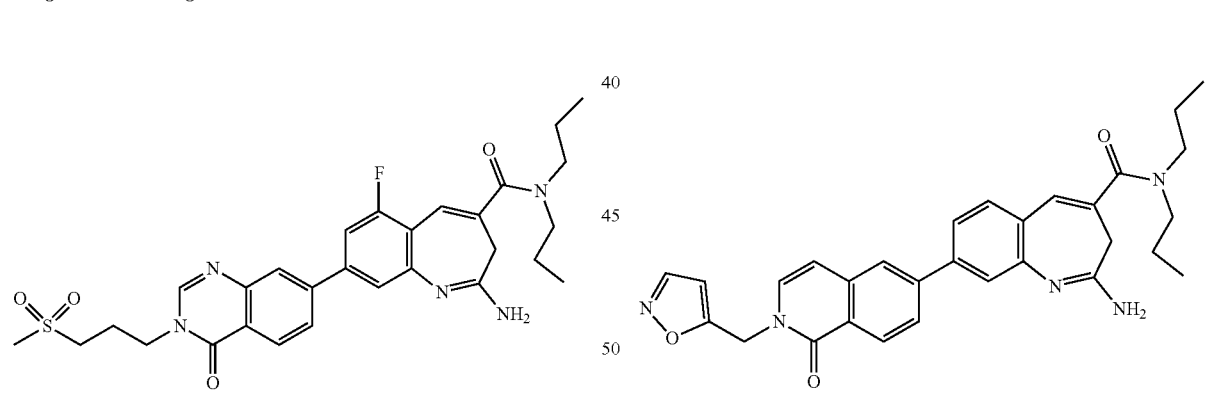
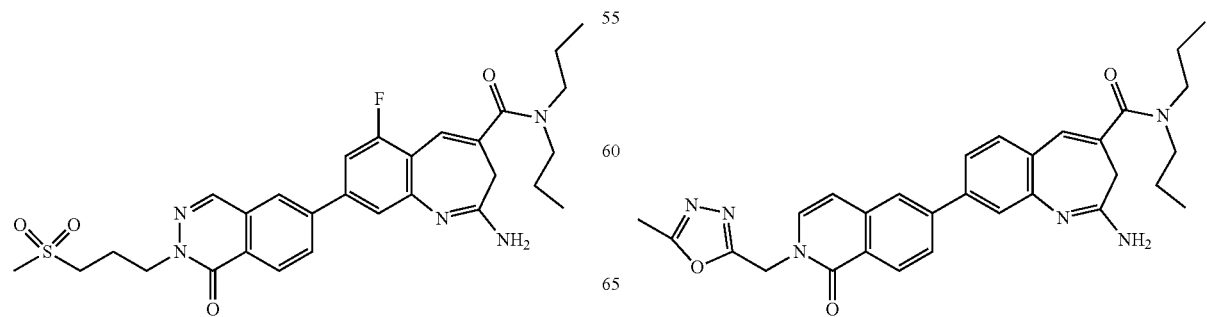

79
-continued
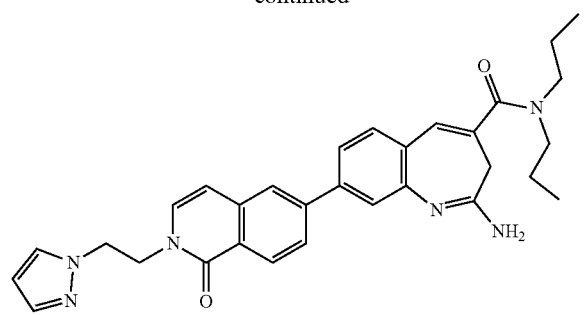
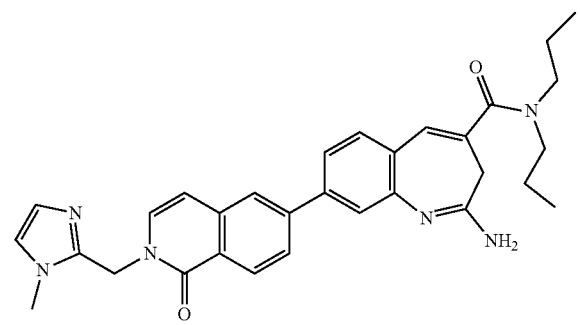
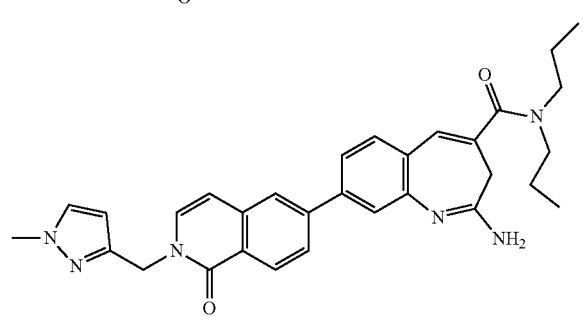
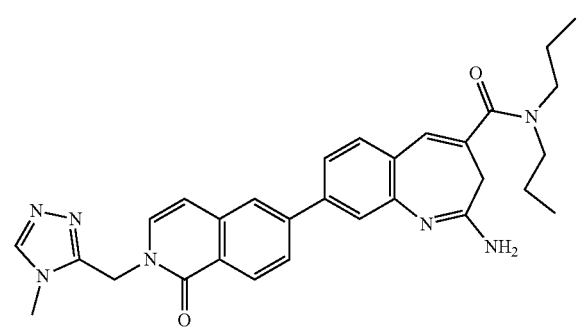
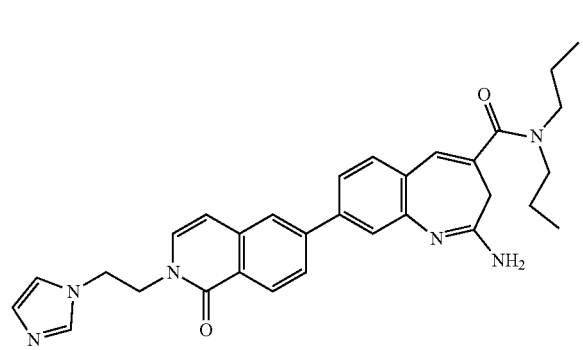
80
-continued
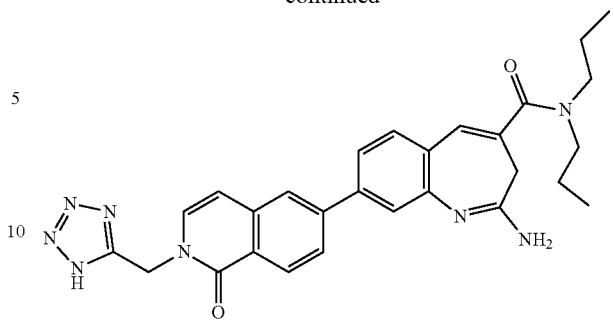
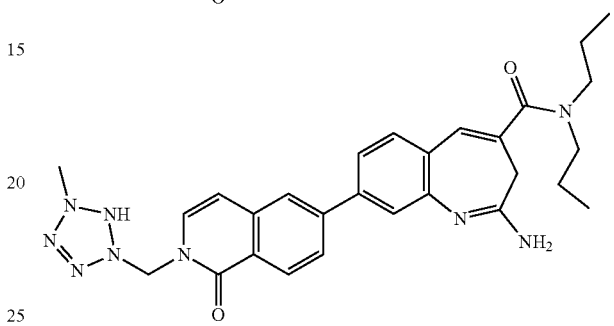
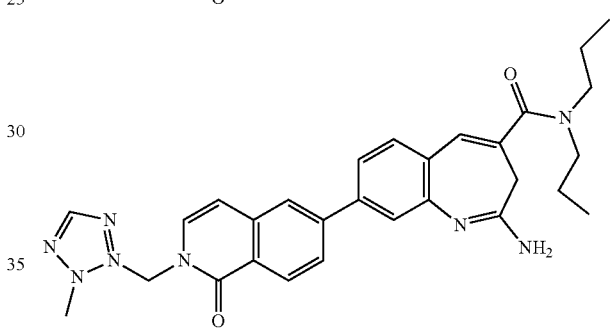
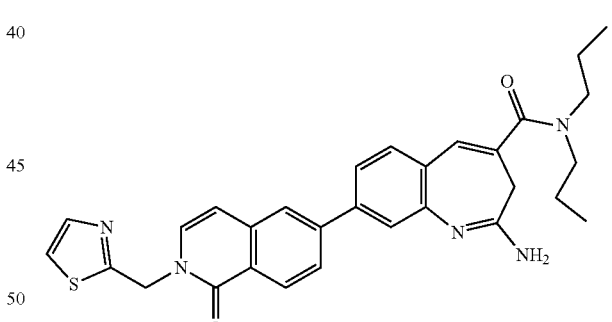

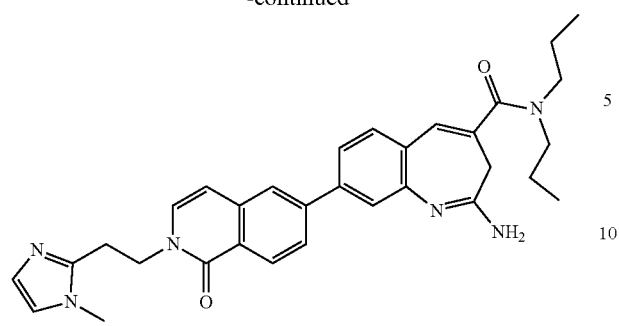
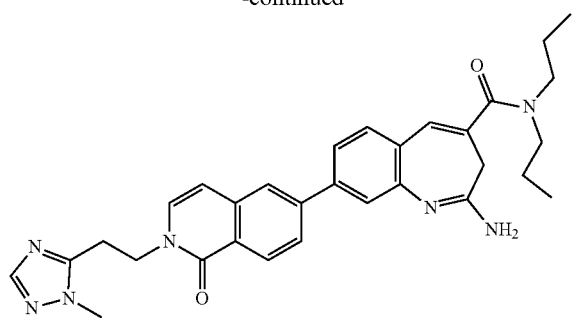
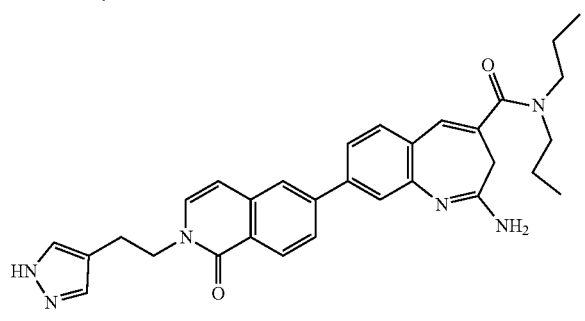
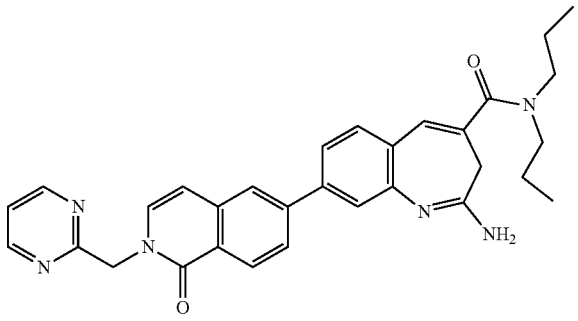
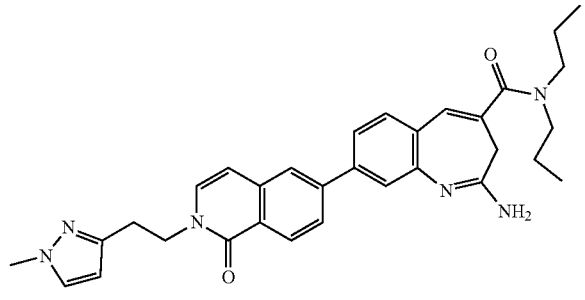
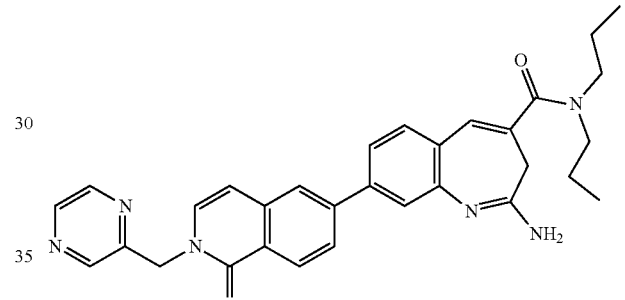
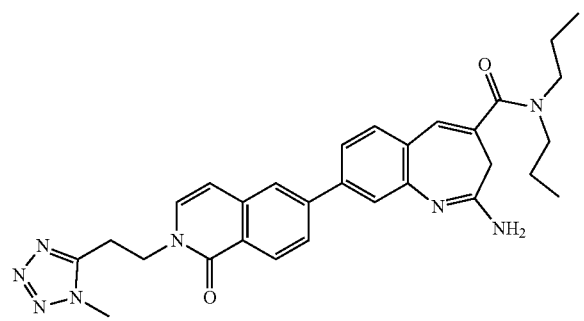
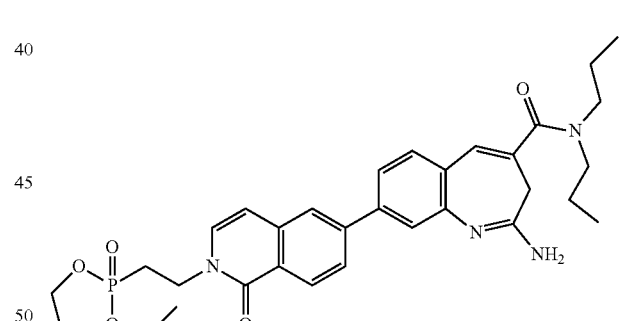
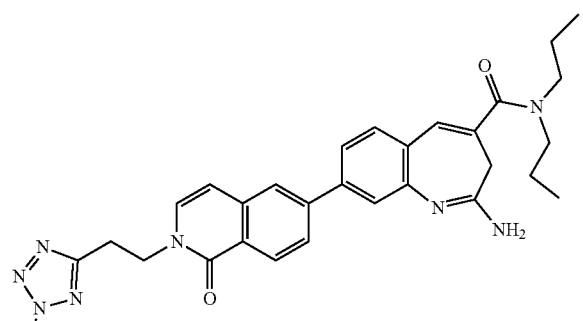
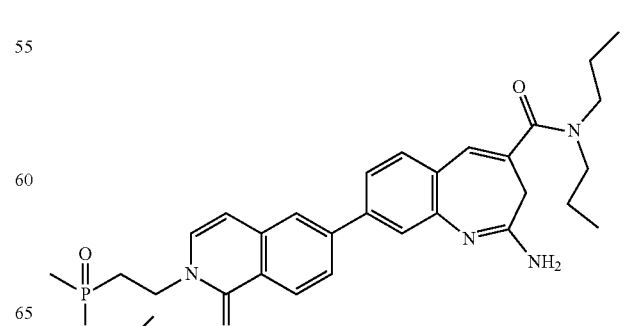

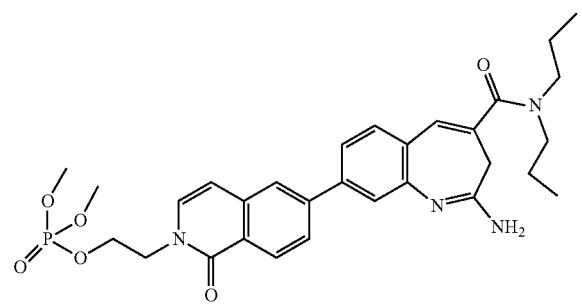
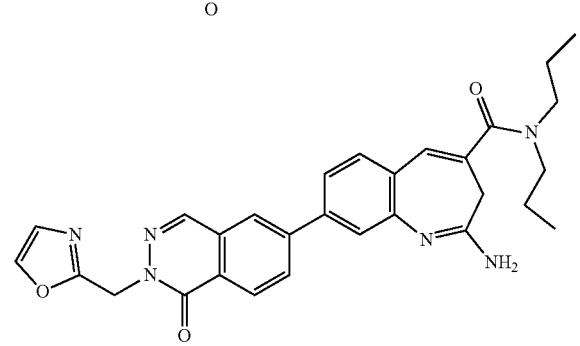
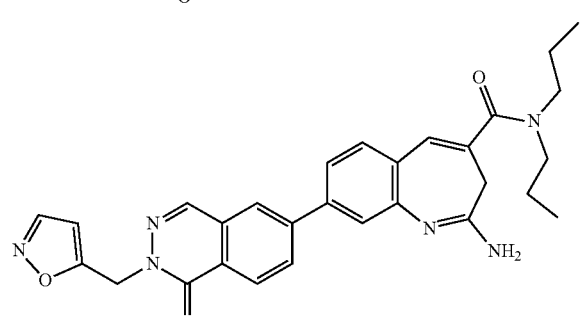
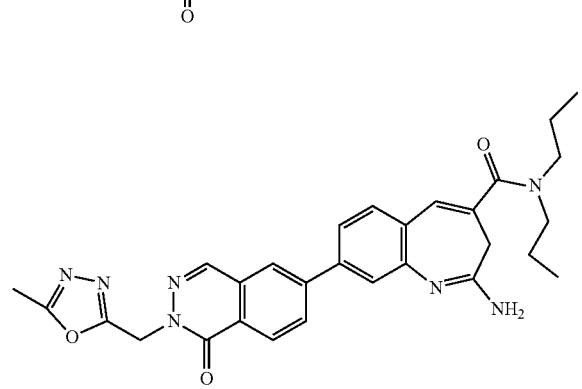
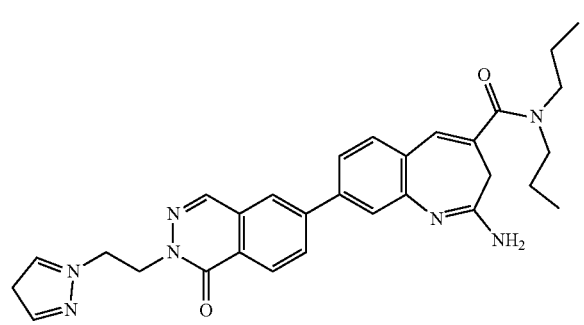
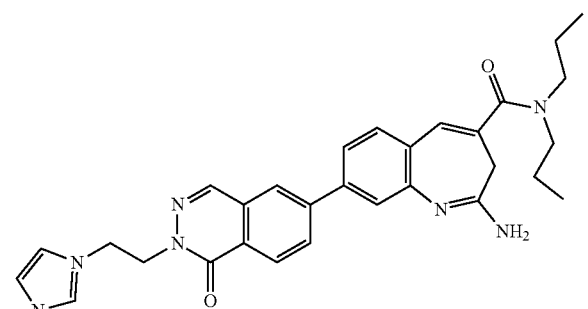
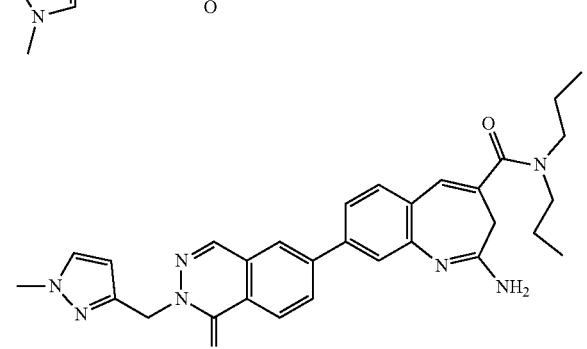
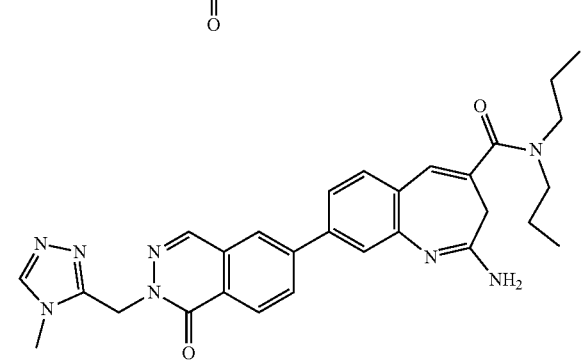
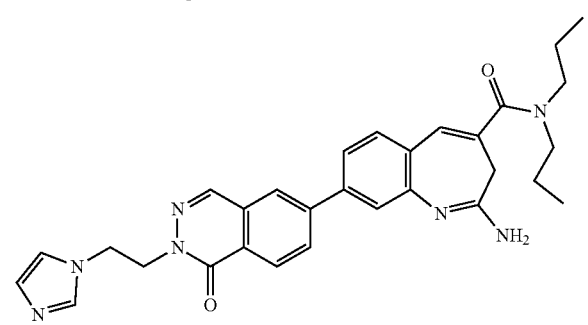
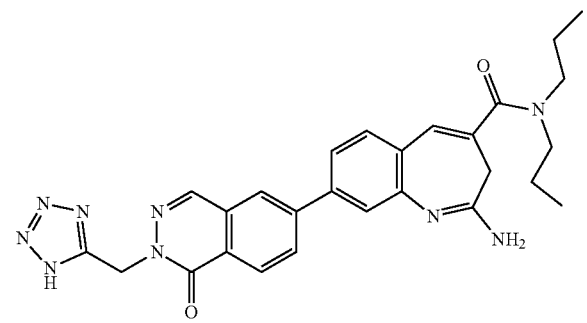

85
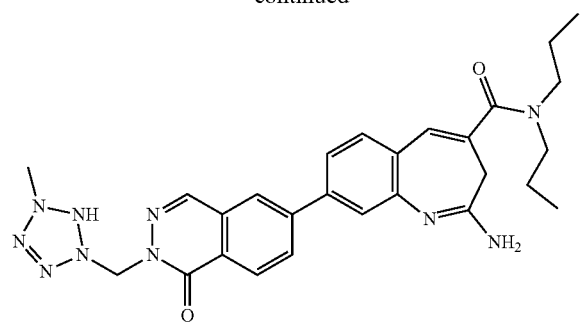
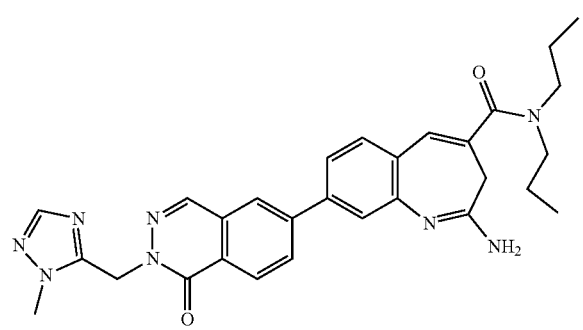
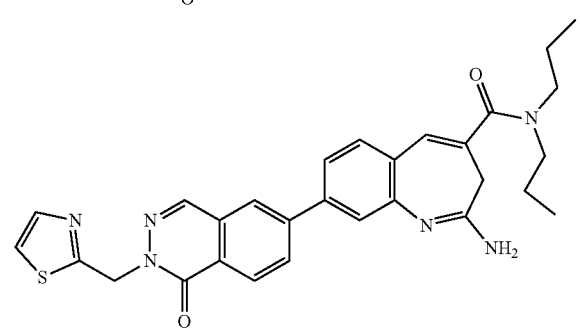

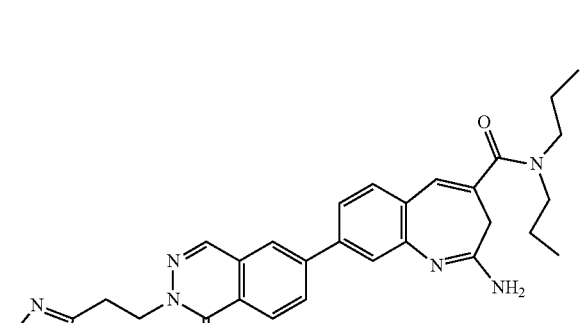
86
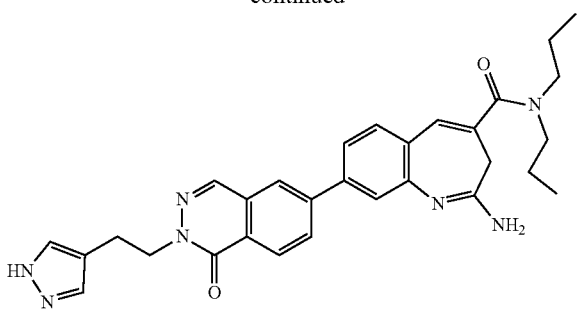
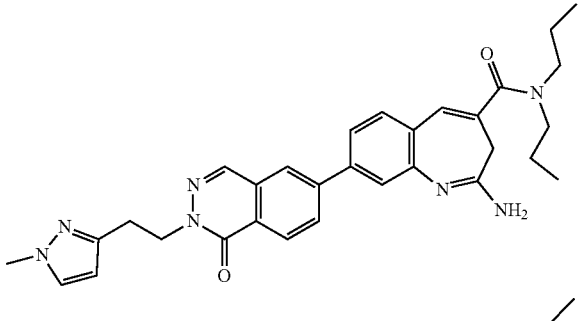
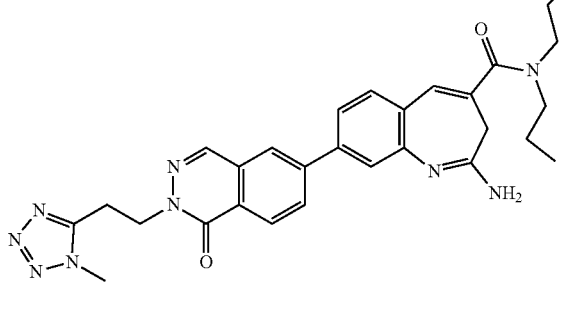
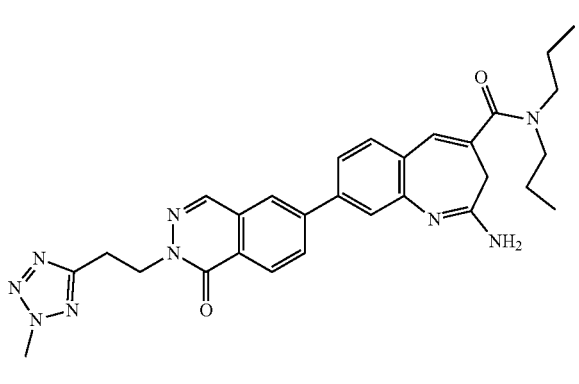
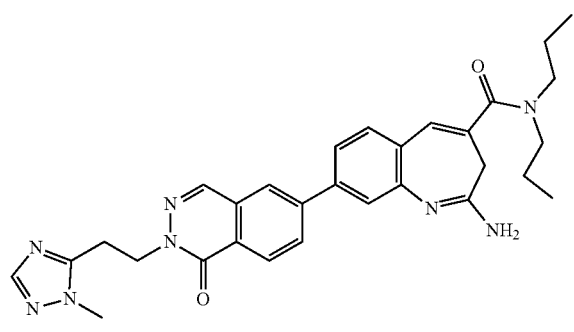

87
-continued
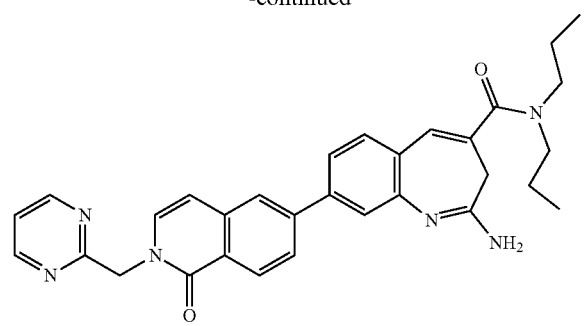
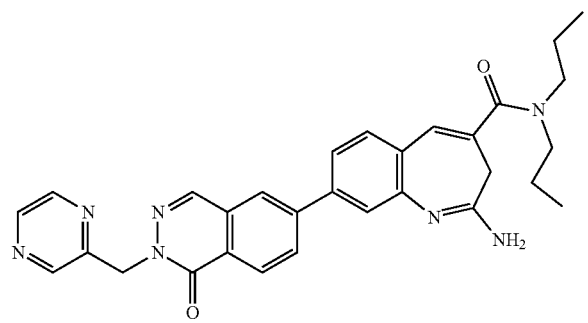
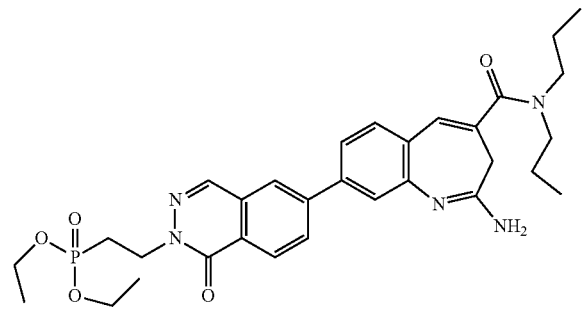
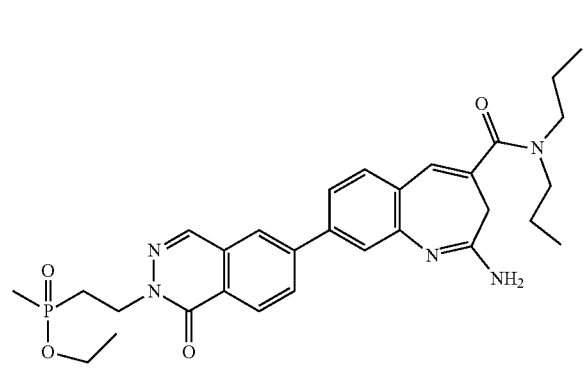
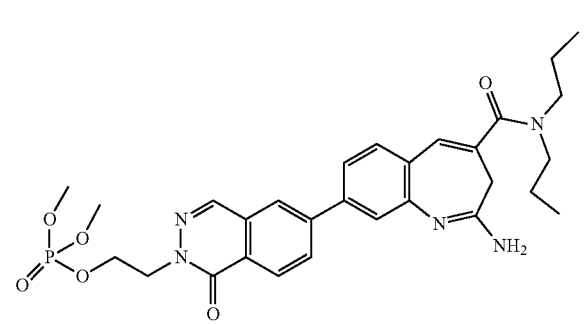
88
-continued
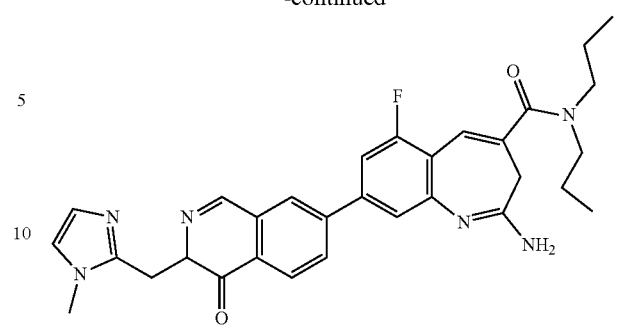
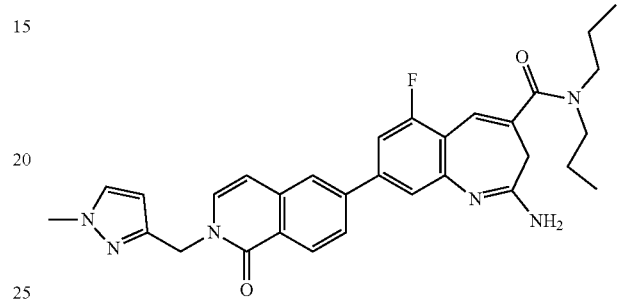
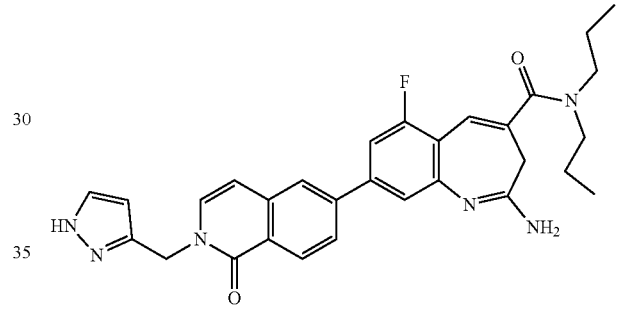
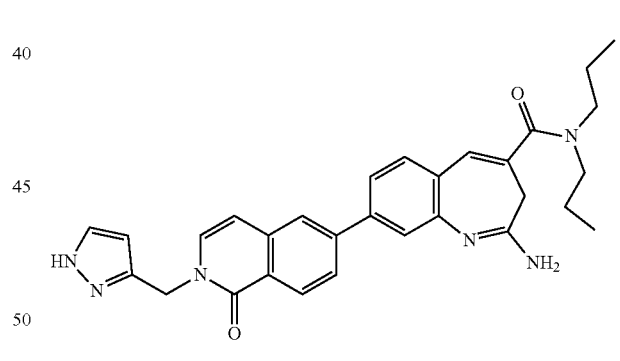
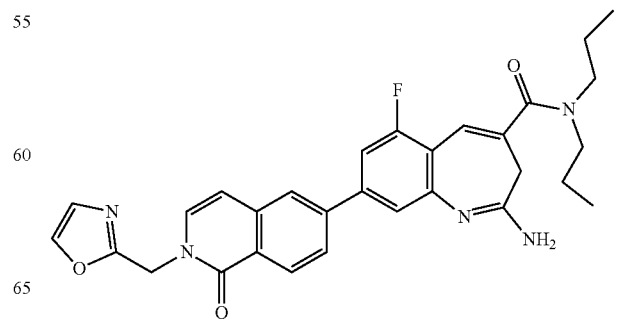

89
-continued
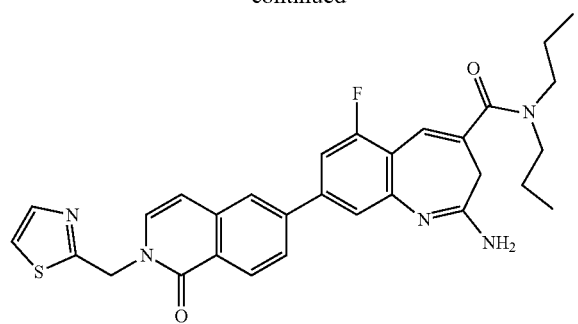
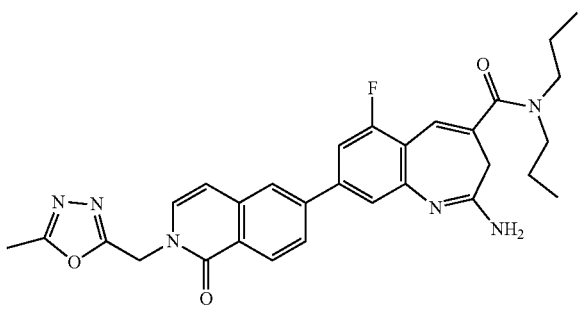
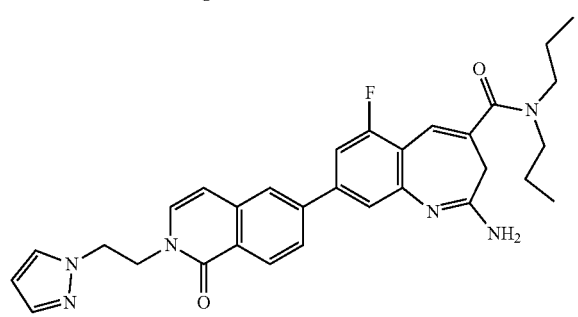
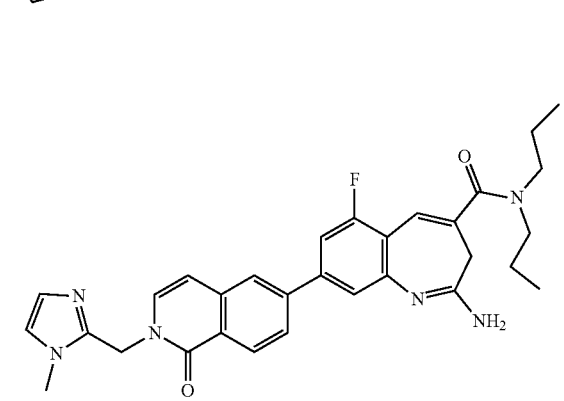
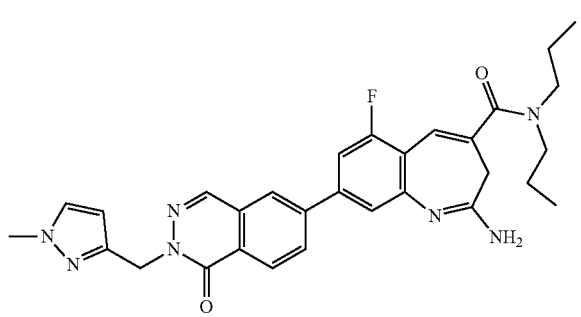
90
-continued
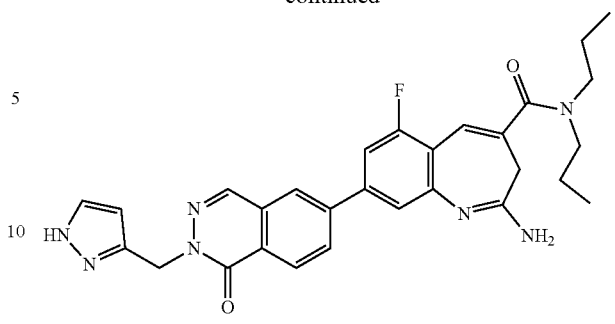
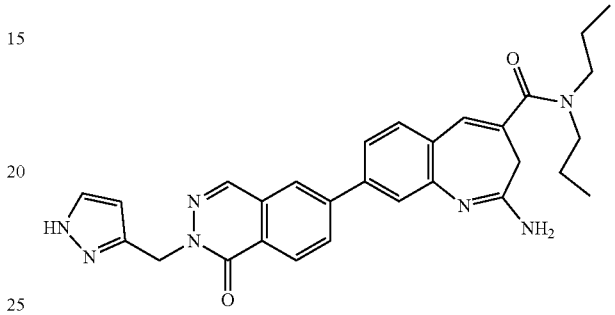
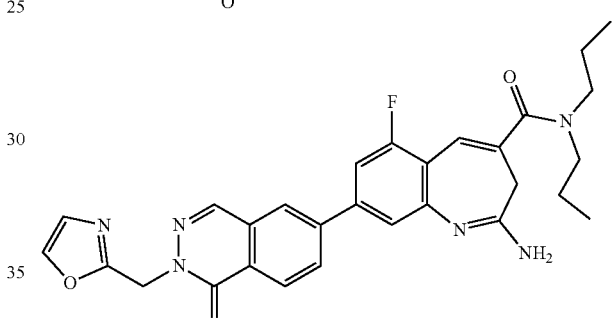
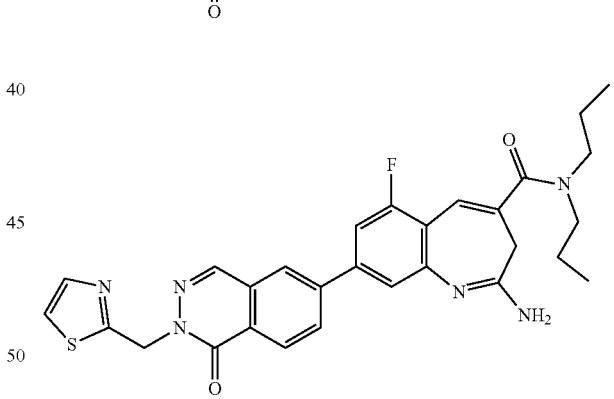
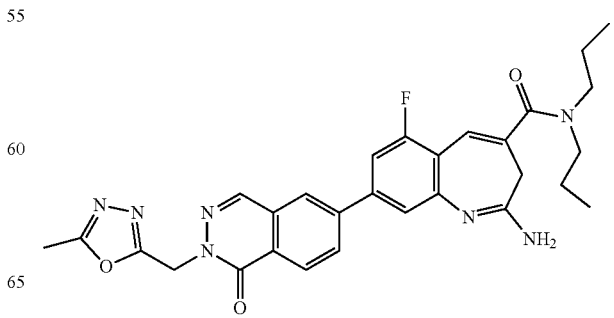

91
-continued
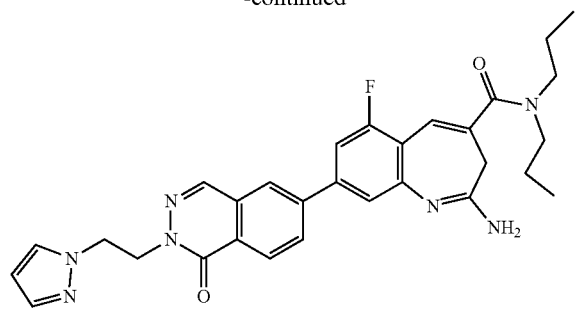
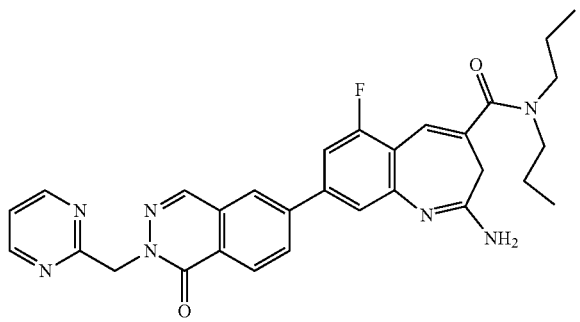
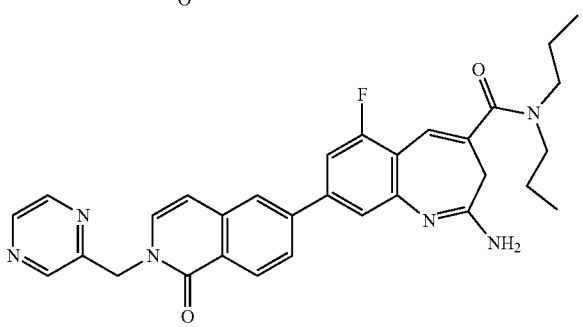
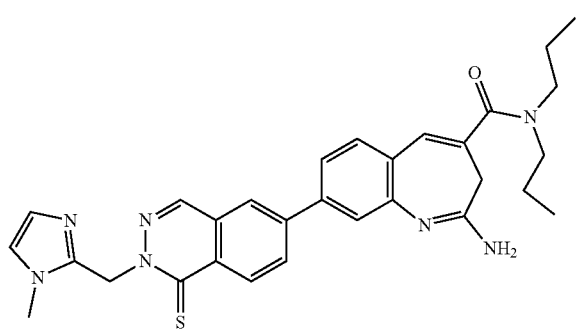
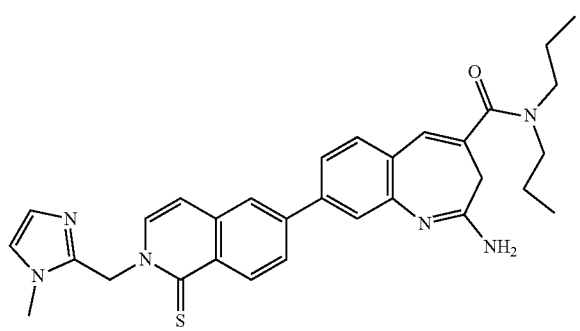
92
-continued
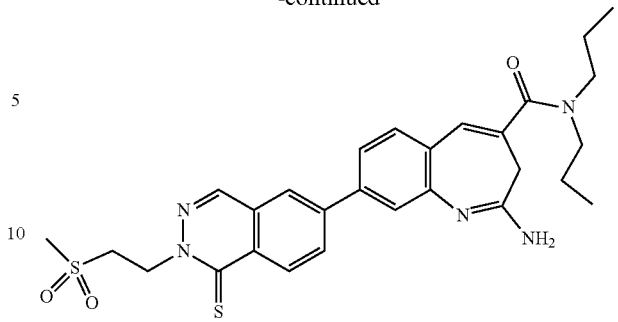
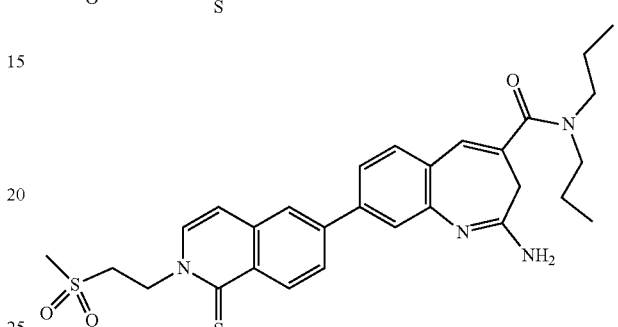
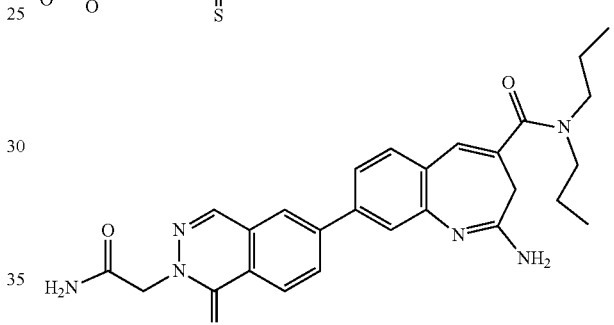
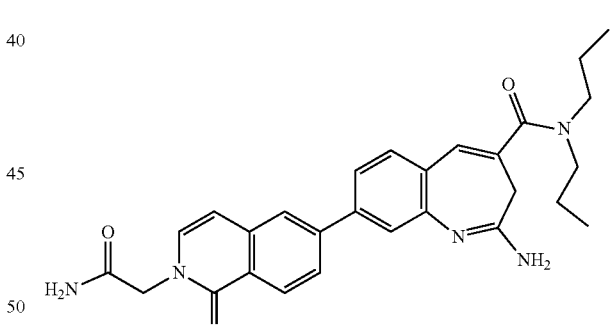
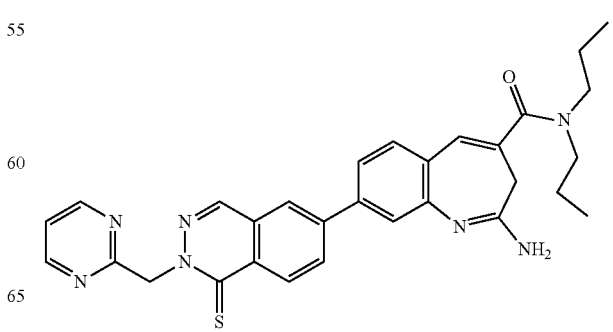

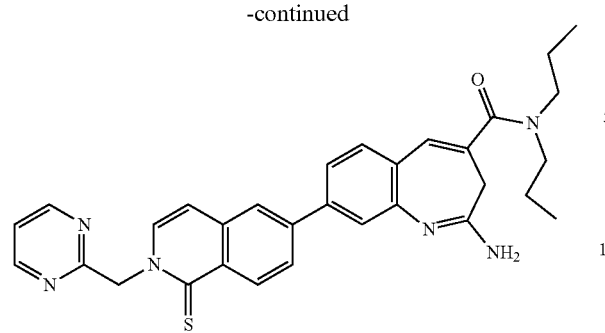
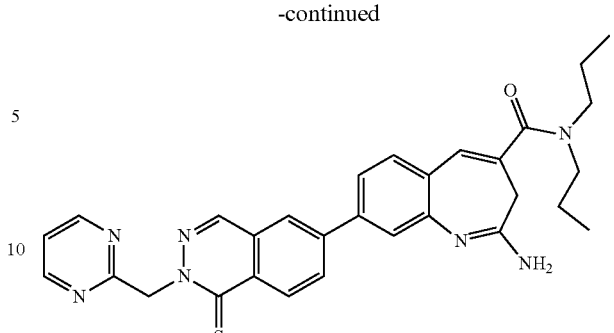
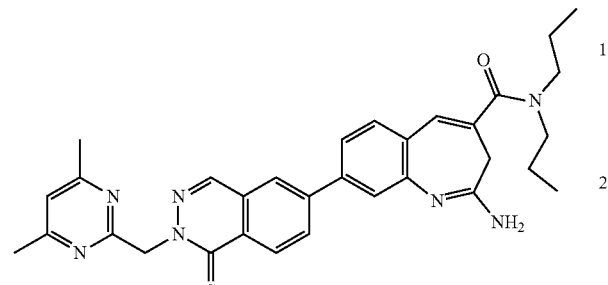
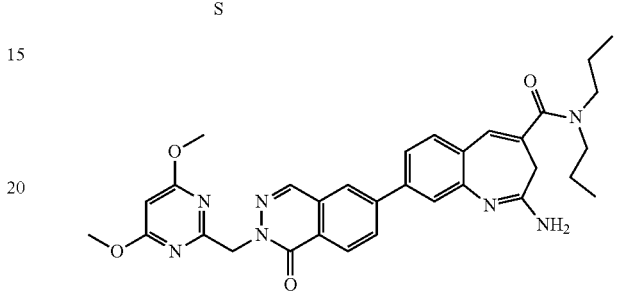
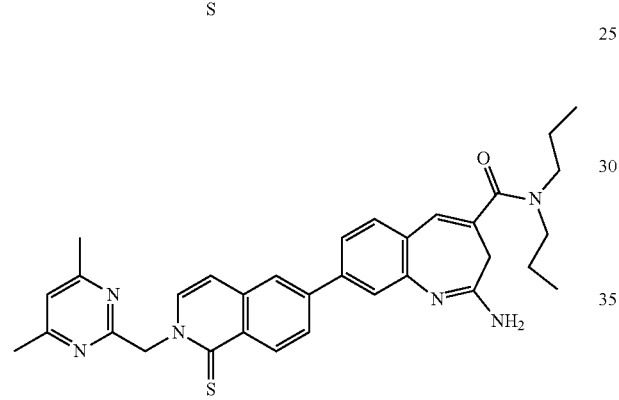
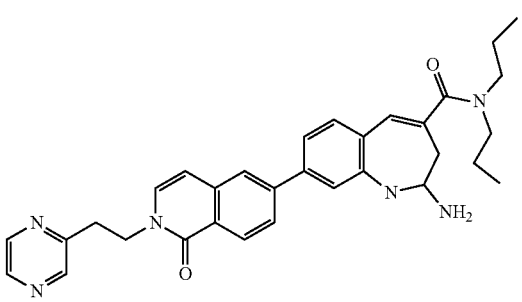
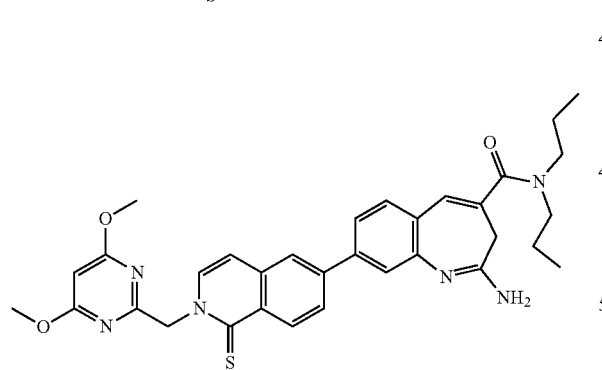
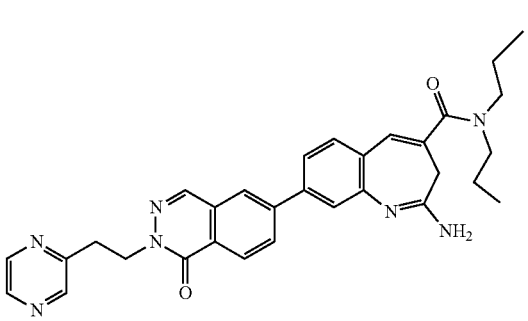
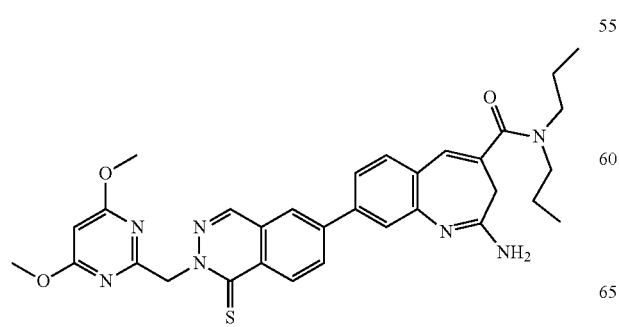
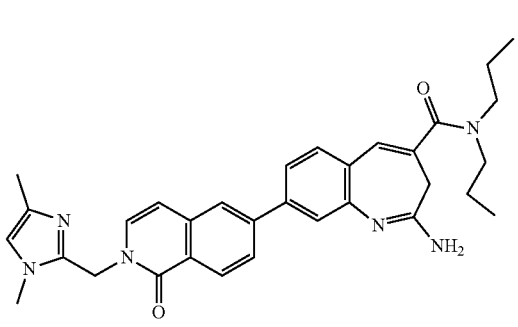

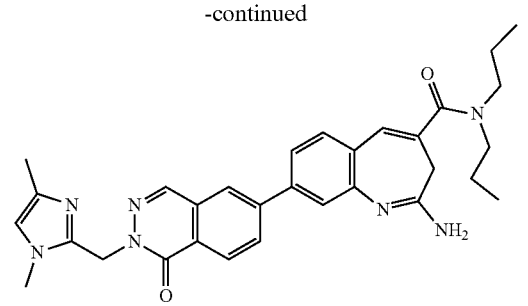

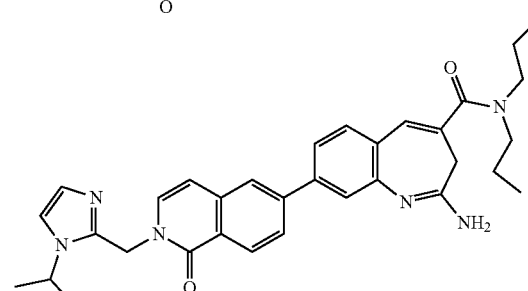

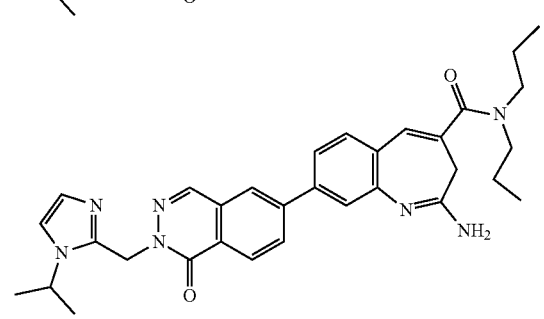

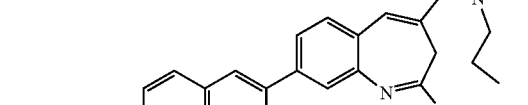

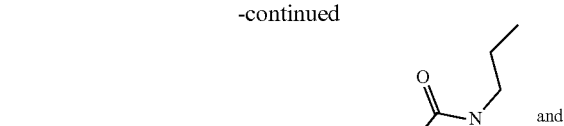

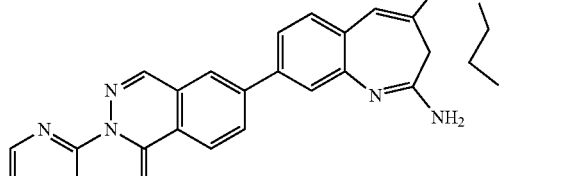

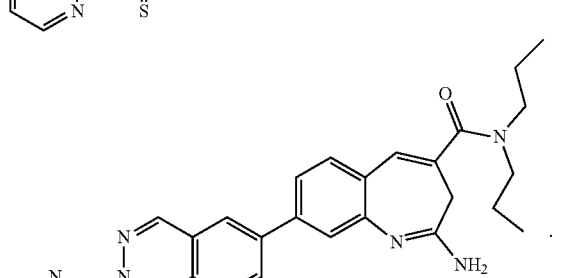

The present invention also provides a preparation method of the compound of formula (I), the isomer, the prodrug, the stable isotopic derivative or the pharmaceutically acceptable salt thereof, wherein, the preparation method is any one of the following methods:

Method 1 comprising conducting a suzuki coupling reaction with compound I-a and

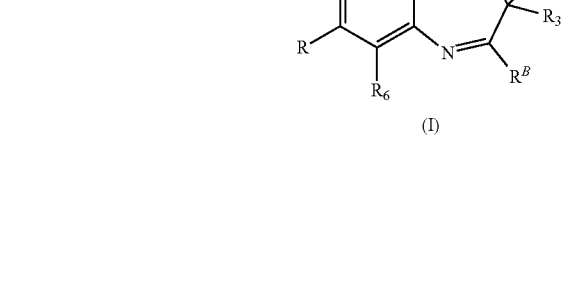

to obtain the compound of formula (I);

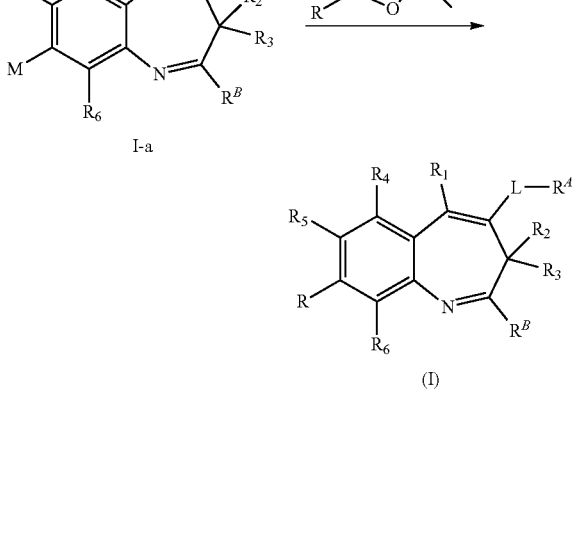

Method 2 comprising conducting a suzuki coupling reaction with compound I-b and R-M to obtain the compound of formula (I);

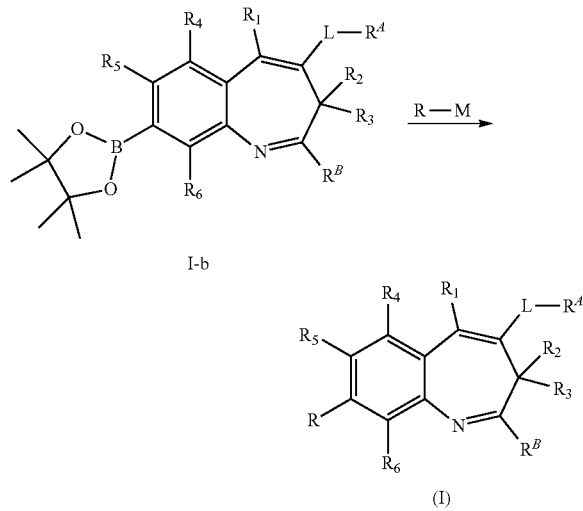

wherein, M is bromine, chlorine, iodine or —OS(O)$_2$CF$_3$; R$_1$, R$_3$, R$_4$, R$_5$, R$_6$, R$^A$, R$^B$, R and L are defined as above.

In method 1 and method 2, the conditions for the suzuki coupling reaction may be those conventional conditions in this type of reaction in the art, and the following reaction conditions are particularly preferred in the present invention: under nitrogen, in a mixed solvent (such as, tetrahydrofuran/water, acetonitrile/water, or N,N-dimethylformamide/water), base (potassium carbonate, cesium carbonate or diethyl isopropyl amine) and catalyst (preferably [1,1'-bis(diphenylphosphino)ferrocene]palladium dichloride (Pd(dppf)Cl$_2$) or [1,1'-bis(diphenylphosphino)ferrocene] palladium chloride dichloromethane complex (Pd(dppf)$_2$Cl$_2$), the mixed solvent is preferably used in an amount of 1 to 50 mL/mmol of compound I-a or I-b, and the reaction time is preferably 0 to 24 hours, and the temperature is preferably at room temperature to refluxing, more preferably 60 to 90° C., and the molar ratio of the compound I-a or I-b to the catalyst is preferably 1:0.01 to 1:0.1.

In the final step of the preparation method, an acidic system such as p-toluenesulfonic acid, hydrochloric acid, hydrogen chloride or trifluoroacetic acid etc. is used, or in the purification process, for example, when the above-mentioned acidic system is present in the mobile phase of prep-HPLC, the compound I-1 will be the corresponding p-toluenesulfonate, hydrochloride or trifluoroacetate, etc.

In the above method, when an amino, a hydroxyl or a carboxyl is present in the compound of formula I-a, I-b,

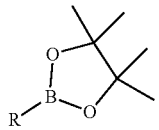

or R-M, the amino, hydroxyl or carboxyl can be protected by a protective group to avoid any side reactions. If the amino protecting group or hydroxy protecting group is present, it is necessary to undergo a subsequent deprotection step to give the compound I-1. Any suitable amino protecting group, for example, a tert-butoxycarbonyl (Boc), can be used to protect the amino. If Boc is used as a protecting group, subsequent deprotection reactions can be carried out under standard conditions, for example, p-toluenesulfonic acid/methanol system, dichloromethane/trifluoroacetic acid system, saturated hydrogen chloride ether solution, or trimethylsilyl trifluoromethanesulfonate/2,6-lutidine/dichloromethane system; any suitable hydroxyl protecting group, such as a benzyl, can be used to protect the amino group, and subsequent deprotection reactions can be carried out under standard conditions, for example, palladium on carbon/hydrogen; any suitable carboxyl protecting group, for example, to form a carboxylate group (such as, methyl carboxylate, ethyl carboxylate), can be used to protect the carboxyl group, and subsequent deprotection can be carried out under standard conditions, such as using sodium hydroxide, potassium hydroxide, lithium hydroxide to deprotect in tetrahydrofuran, water and/or methanol. The above deprotection is preferably carried out in the last step.

The compound of formula (I), the pharmaceutically acceptable salt thereof can be synthesized according to a general chemical synthesis method.

In general, the preparation of the salt can be carried out by reacting the free base or acid with an equivalent chemical equivalent or an excess of an acid (inorganic or organic acid) or a base (inorganic or organic base) in a suitable solvent or solvent composition.

The present invention also provides a pharmaceutical composition, which comprises a component selected from the group consisting of the therapeutically effective amount of the compound of formula (I), the isomer, the prodrug, the stable isotope derivative, and the pharmaceutically acceptable salt thereof, and a pharmaceutically acceptable excipient.

The pharmaceutical composition may also include other therapeutic agents for the treatment, alleviation and/or prevention of cancer, viral infections or autoimmune diseases.

In the pharmaceutical composition, the pharmaceutically acceptable excipient may include a pharmaceutically acceptable carrier, diluent, and/or excipient.

According to the purpose of the treatment, the pharmaceutical composition can be formulated into various types of unit dosage, such as tablets, pills, powders, liquids, suspensions, emulsions, granules, capsules, suppositories, and injections (solutions and suspensions) and the like, and preferably liquids, suspensions, emulsions, suppositories and injections (solutions and suspensions), etc.

In order to shape the pharmaceutical composition in the form of a tablet, any excipient known and widely used in the art can be used. For Embodiment, carriers such as lactose, white sugar, sodium chloride, glucose, urea, starch, calcium carbonate, kaolin, crystalline cellulose, and silicic acid; binders such as water, ethanol, propanol, common syrup, dextrose solution, starch solution, gelatin solution, carboxymethyl cellulose, shellac, methyl cellulose and potassium phosphate, polyvinylpyrrolidone, etc.; disintegrating agents, such as dry starch, sodium alginate, agar powder, kelp powder, sodium bicarbonate, calcium carbonate, polyethylene sorbitan, sodium lauryl sulfate, monoglyceryl stearate, starch and lactose; disintegration inhibitors such as white sugar, glyceryl tristearate, coconut oil and hydrogenation oil; adsorption promoters such as quaternary ammonium bases and sodium lauryl sulfate; wetting agents such as glycerin, starch, etc.; adsorbents such as starch, lactose, kaolin, bentonite and colloidal silicic acid; such as pure talc, stearate, boric acid powder and polyethylene glycol. It is also possible to use a usual coating material to formulate a sugar-coated tablet, a gelatin film tablet, a casing tablet, a film-coated tablet, a two-layer film tablet, and a multilayer tablet.

In order to shape the pharmaceutical composition in the form of a pill, any excipient known and widely used in the art may be used, for Embodiment, carriers such as lactose, starch, coconut oil, hardened vegetable oil, kaolin and talc, etc.; binders such as gum arabic powder, tragacanth powder, gelatin and ethanol, etc.; disintegrating agents such as agar and kelp powder.

In order to shape the pharmaceutical composition in the form of a suppository, any excipient known and widely used in the art can be used, for Embodiment, polyethylene glycol, coconut oil, higher alcohols, esters of higher alcohols, gelatin and semi-synthetic glycerides, etc.

For the preparation of a pharmaceutical composition in the form of an injection, the solution or suspension may be sterilized (preferably by adding an appropriate amount of sodium chloride, glucose or glycerin, etc.) to prepare an injection which is isotonic with blood. Any of the commonly used carriers in the art can also be used. For example, water, ethanol, propylene glycol, ethoxylated isostearyl alcohol, polyoxylated isostearyl alcohol, and fatty acid esters of polyethylene sorbitan. In addition, usual solubilizers, buffers, analgesics etc. can be added.

In the present invention, the content of the compound of formula (I), the isomer, the prodrug, the stable isotope derivative and the pharmaceutically acceptable salt thereof, and/or the other therapeutic agent comprised in the pharmaceutical composition does not have specific limitation, which can be selected within a wide range, typically 5 wt. %-95 wt. %, preferably 30 wt. % to 80 wt. %.

In the present invention, the administration method of the pharmaceutical composition is not particularly limited. Formulations of various dosage forms can be selected depending on the age, sex and other conditions and symptoms of the patient. For Embodiment, tablets, pills, solutions, suspensions, emulsions, granules or capsules are administered orally; injections can be administered alone or in combination with injectable solutions (eg, glucose solution and amino acid solution); suppositories are given to the rectum.

The invention also provides the use of the compound of formula (I), the isomer, the prodrug, the stable isotope derivative or the pharmaceutically acceptable salt thereof for the preparation of a TLRs modulator. The TLRs modulator is preferably a TLRs agonist or a TLRs partial agonist. The TLRs are preferably selected from the group consisting of TLR7, TLR8 and TLR9.

The present invention also provides the use of the compound of formula (I), the isomer, the prodrug, the stable isotope derivative or the pharmaceutically acceptable salt thereof for the preparation of a medicament for modulating T cells and other immune cells.

The present invention also provides a use of the compound of formula (I), the isomer, the prodrug, the stable isotope derivative or the pharmaceutically acceptable salt thereof in the preparation of a medicament for the treatment, alleviation and/or prevention of a disease mediated by TLRs; the present invention preferably provides a use of the compound of formula (I), the isomer, the prodrug, the stable isotope derivative or the pharmaceutically acceptable salt thereof in the preparation of a medicament for the treatment, alleviation and/or prevention of related diseases mediated by TLR8; the diseases include tumors and non-neoplastic diseases. Such diseases include, but are not limited to, cancer, viruses and other infections, diseases caused by immunosuppression, and autoimmune diseases, etc.

The present invention preferably provides the use of the compound of formula (I), the isomer, the prodrug, the stable isotope derivative or the pharmaceutically acceptable salt thereof for the preparation of a medicament for the treatment and/or alleviation of cancers. The cancers are preferably associated with immunological inhibition, which refers to tumor-specific immunosuppression.

The present invention further provides a method for treating cancers, virus and other infections, autoimmune diseases by using the compound of formula (I), the isomer, the prodrug, the stable isotope derivative or the pharmaceutically acceptable salt thereof, which comprises administering a therapeutically required amount of the compound of formula (I), the isomer, the prodrug, the stable isotope derivative or the pharmaceutically acceptable salt thereof, or the pharmaceutical composition, to a mammal.

Mammal is preferably a human.

The present invention further provides a use of the compound of formula (I), the isomer, the prodrug, the stable isotope derivative or the pharmaceutically acceptable salt thereof in combination with one or more than one other therapeutic agents and/or therapeutic methods for the treatment, alleviation and/or prevention of related diseases mediated by TLRs, in particular by TLR8. The TLR8-mediated related disease refers to a disease caused by TLR8-mediated immunosuppression, which may include cancers, viral infections, inflammations, autoimmune diseases, transplant rejections, transplant-versus-host diseases, etc.

The present invention preferably provides a use of the compound of formula (I), the isomer, the prodrug, the stable isotope derivative or the pharmaceutically acceptable salt thereof in combination with one or more than one other therapeutic agents and/or therapeutic methods for the treatment and/or alleviation of diseases mediated by TLR8, preferably cancers.

The other therapeutic agent (such as, other therapeutic agents for treating cancers) may be formulated to a single dosage form with the compound of formula (I), or to be administered sequentially.

The viral infections may include: the infection caused by influenza virus, Sendai virus, Coxsackie virus, dengue virus, Newcastle disease virus (NDV), vesicular stomatitis virus (VSV), hepatitis C virus (HCV), human papillary Infections caused by viruses such as neoplastic virus (HPV), cytomegalovirus (CMV), Epstein-Barr virus (EBV), poliovirus, varicella-zoster virus or type I human immunodeficiency virus (HIV) and so on.

Such cancers include metastatic and non-metastatic cancers, as well as familial hereditary and sporadic cancers, and may also include solid tumors and non-solid tumors.

Specific embodiments of the solid tumor may include, but are not limited to, cancers selected from the group consisting of eye cancer, bone cancer, lung cancer, stomach cancer, pancreatic cancer, breast cancer, prostate cancer, brain cancer (including malignant glioma, medulloblastoma), ovary cancer, bladder cancer, cervical cancer, testicular cancer, kidney cancer (including adenocarcinoma and nephroblast cancer), oral cancer (including squamous cell carcinoma), tongue cancer, laryngeal cancer, nasopharyngeal cancer, head and neck cancer, colon cancer, small bowel cancer, rectal cancer, parathyroid cancer, thyroid cancer, esophageal cancer, gallbladder cancer, cholangiocarcinoma, cervical cancer, liver cancer, lung cancer, sarcoma, and skin cancer.

Specific embodiments of the non-solid tumors (including hematological tumors) may include, but are not limited to, one or more of lymphocytic leukemia (including acute lymphocytic leukemia, lymphoma, myeloma, chronic lymphocytic leukemia, Hodgkin's lymphoma, non-Hodgkin lymphoma, T cell chronic lymphocytic leukemia, B cell chronic lymphocytic leukemia), myeloid associated leukemia (including acute myeloid leukemia, chronic myeloid leukemia), and AIDs associated leukemia.

The autoimmune diseases may include, but are not limited to, rheumatoid arthritis, systemic lupus erythematosus, mixed connective tissue disease (MCTD), systemic scleroderma (including: CREST syndrome), dermatomyositis, knot Segmental vasculitis, nephropathy (including: pulmonary hemorrhagic nephritis syndrome, acute glomerulonephritis, primary membrane proliferative glomerulonephritis, etc.), endocrine-related diseases (including: type I diabetes, gonadal insufficiency, pernicious anemia, hyperthyroidism, etc.), liver disease (including: primary biliary cirrhosis, autoimmune cholangitis, autoimmune hepatitis, primary sclerosing cholangitis, etc.) and autoimmune response due to infection (such as: one or more of AIDS, malaria, etc.).

In the present invention, unless otherwise indicated, the term "selectively substituted at any position by a substituent selected from the group consisting of" refers to that one or more than one hydrogen atoms attached to one or more than one indicated atom is replaced with indicated substituent, provided that the bond attached to the atom does not exceed the valence of the indicated atom, the position of substitution is any reasonable position in the art.

In the present invention, unless otherwise indicated, a chemical bond represented by a dashed line indicates that the bond is optionally present or absent. For example, a dashed line drawn parallel to a solid single bond indicates a single bond or a double bond.

In the present invention, when a bond of a substituent is intersected with a bond formed by two ring atoms, such substituent may be bonded to any bondable ring atom.

Unless otherwise indicated, the following terms when used in the descriptions and the claims of the present invention have the following meanings:

The term "alkyl" refers to saturated branched or straight-chain hydrocarbon groups comprising 1 to 20 carbon atoms, preferably 1 to 10 carbon atoms, more preferably 1 to 8, 1 to 6, 1 to 4, 1 to 3 carbon atoms, such as methyl, ethyl, n-propyl, isopropyl, n-butyl, sec-butyl, t-butyl, isobutyl, pentyl, hexyl, heptyl, octyl, nonyl, decyl, 4,4-dimethylpentyl, 2,2,4-trimethylpentyl, undecyl, dodecyl and various isomers thereof. When "alkyl" is used as a linking group for other groups, such as —($CH_2$)$_m$—, it may be a branched or straight chain, embodiments including but not limited to, —$CH_2$—, —$CH_2CH_2$—, —$CH_2CH(CH_3)$—.

The term "cycloalkyl" refers to a saturated or partially unsaturated (containing 1 or 2 double bond) monocyclic or polycyclic group comprising 3 to 20 carbon atoms. "monocycloalkyl" is preferably a 3 to 10 membered monocycloalkyl, more preferably a 3 to 8 membered monocycloalkyl, such as cyclopropyl, cyclobutyl, cyclopentyl, cyclohexyl, cycloheptyl, cyclooctyl, cyclodecyl, cyclododecyl, cyclohexenyl. "polycycloalkyl" includes "bridged ring", "fused cycloalkyl" and "spirocycloalkyl", and representative embodiments of "bridged cycloalkyl" include, but are not limited to, borneol, bicyclo[2.2.1]heptenyl, bicyclo[3.1.1]heptyl, bicyclo[2.2.1] heptyl, bicyclo[2.2.2]octyl, bicyclo[3.2.2]nonyl, bicyclo[3.3.1]nonyl, bicyclo[4.2.1]nonanyl, adamantyl, etc. "Fused cycloalkyl" includes a cycloalkyl fused to a phenyl, a cycloalkyl or a heteroaryl, including but not limited to, benzocyclobutene, 2,3-dihydro-1-H-oxime, 2,3-cyclopentenopyridine, 5,6-dihydro-4H-cyclopenta[B]thiophene, naphthane and the like. Monocycloalkyl or polycycloalkyl can be attached to the parent molecular moiety through any carbon atom on the ring.

The term "heterocycloalkyl" refers to saturated or partially unsaturated non-aromatic cyclic groups comprising carbon atoms and hetero atoms selected from nitrogen, oxygen or sulfur etc. The cyclic group can be monocyclic or polycyclic. In the present invention, the number of hetero atoms in the heterocycloalkyl is preferably 1, 2, 3 or 4, and the nitrogen, carbon or sulfur atom in the heterocycloalkyl group may be optionally oxidized. The nitrogen atom can be optionally further substituted with other groups to form a tertiary amine or a quaternary ammonium salt. The "monocyclic heterocycloalkyl" is preferably a 3 to 10 membered monocyclic heterocycloalkyl, more preferably a 3 to 8 membered monocyclic heterocycloalkyl. Such as: aziridinyl, tetrahydrofuran-2-yl, morpholin-4-yl, thiomorpholin-4-yl, thiomorpholine-S-oxide-4-yl, piperidin-1-yl, N-alkylpiperidin-4-yl, pyrrolidin-1-yl, N-alkylpyrrolidin-2-yl, piperazin-1-yl, 4-alkylpiperazin-1-yl and the like. "polycycloheterocycloalkyl" includes "fused heterocycloalkyl", "spiroheterocyclyl" and "bridge heterocycloalkyl". "Fused heterocycloalkyl" includes a monocyclic heterocycloalkyl ring fused to a phenyl, cycloalkyl, heterocycloalkyl or heteroaryl, including but not limited to: 2,3-dihydrobenzofuranyl, 1,3-dihydroisobenzofuranyl, indanyl, 2,3-dihydrobenzo[b]thienyl, dihydrobenzopyranyl, 1,2,3,4-tetrahydroquinolyl and the like. Monocyclic heterocycloalkyl and polycyclic heterocycloalkyl can be attached to the parent molecular moiety through any atom on the ring. The above ring atoms specifically refer to carbon atoms and/or nitrogen atoms constituting the ring.

The term "cycloalkylalkyl" refers to an alkyl linkage between a cycloalkyl and a parent molecular moiety. Thus, "cycloalkylalkyl" includes the definition of alkyl and cycloalkyl as described above.

The term "heterocycloalkylalkyl" refers to an alkyl linkage between a heterocycloalkyl group and a parent molecular moiety. Thus, "heterocycloalkylalkyl" includes the definitions of alkyl and heterocycloalkyl as described above.

The term "alkoxy" refers to a cyclic or acyclic alkyl having indicated carbon atoms attached through an oxygen bridge, and includes alkyloxy, cycloalkyloxy, and heterocycloalkyloxy. Thus, "alkoxy" includes the definitions of alkyl, heterocycloalkyl and cycloalkyl as described above.

The term "hydroxyalkyl" refers to any one of the hydrogen atoms on the alkyl is replaced by a hydroxyl, including but not limited to, —$CH_2OH$, —$CH_2CH_2OH$, —$CH_2CH_2C(CH_3)_2OH$.

The term "alkenyl" refers to a straight, branched or cyclic non-aromatic hydrocarbon containing at least one carbon-carbon double bond. There may be 1 to 3 carbon-carbon double bonds, preferably one carbon-carbon double bond. The term "$C_{2-4}$ alkenyl" refers to an alkenyl having 2 to 4 carbon atoms, and the term "$C_{2-6}$ alkenyl" refers to an alkenyl group having 2 to 6 carbon atoms, including vinyl, propenyl, and butenyl, 2-methylbutenyl and cyclohexenyl. The alkenyl may be substituted.

The term "alkynyl" refers to a straight, branched or cyclic hydrocarbon containing at least one carbon to carbon triple bond. There may be 1 to 3 carbon-carbon triple bonds, preferably one carbon-carbon triple bond. The term "$C_{2-6}$ alkynyl" refers to an alkynyl having 2 to 6 carbon atoms and includes ethynyl, propynyl, butynyl and 3-methylbutynyl.

The term "aryl" refers to any stable 6 to 20 membered monocyclic or polycyclic aromatic groups such as phenyl, naphthyl, tetrahydronaphthyl, indanyl or biphenyl.

The term "heteroaryl" refers to an aromatic ring that at least one carbon atom is replaced by a heteroatom selected from nitrogen, oxygen or sulfur, which may be a 5-7 membered monocyclic ring or 7 to 20 membered fused ring, preferably a 5 to 6 membered heteroaryl. In the present invention, the number of hetero atoms is preferably 1, 2 or 3, and includes: pyridyl, pyrimidinyl, piperazinyl, pyridazine-3(2H)-one, furyl, thienyl, thiazolyl, pyrrolyl, imidazolyl, pyrazolyl, oxazolyl, isoxazolyl, 1,2,5-oxadiazolyl, 1,2,4-oxadiazolyl, 1,3,4-oxadiazolyl, 1,3,4-thiadiazole, 1,2,4-triazolyl, 1,2,3-triazolyl, tetrazolyl, oxazolyl, isoxazolyl, fluorenyl, isoindolyl, benzofuranyl, benzothienyl, benzo[d][1,3]dioxolanyl, benzothiazolyl, benzoxazolyl, quinolyl, isoquinolinyl, isoquinolinone, quinazolinyl, 4-hydroxythieno[3,2-c]pyridyl, 4,5-dihydro-4-oxofuro[3,2]pyridinyl, 4-hydroxyl-5-azaindolyl, furo[2,3-c]pyridin-7(6H)-one, thieno[2,3-c]pyridin-7(6H)-one, and the like.

The term "fused ring" refer to a cyclic structure in which two, three or four rings share two adjacent atoms, and each of which may be a monocyclic aryl, monocyclic heteroaryl, monocycloalkyl or monocyclic heterocycloalkyl. The fused ring referred to in the present invention is a saturated, unsaturated or partially saturated fused ring structure, and preferably at least one ring is an aromatic ring. More preferably, a bicyclic or tricyclic fused ring, and at least one ring is an aromatic ring. The non-aromatic ring in the fused ring may further comprise 1 to 2 oxo or thio groups. In the present invention, the fused ring is 8 to 20 membered fused ring, preferably 8 to 15 membered fused group. Specific embodiments of the fused ring include, but are not limited to, benzocyclobutenyl, 2,3-dihydro-1-H-indenyl, 1,2,3,4-tetrahydronaphthyl, 6,7,8,9-tetrahydro-5H-benzo[7]annulenyl, 6,9-dihydro-5H-benzo[7]annulenyl, 5,6,7,8,9,10-hexahydrobenzo[8]annulenyl, 2,3-cyclopentenopyridyl, 5,6-dihydro-4H-cyclopenta[B]thienyl, 5,6-dihydro-4H-cyclopenta[B]furanyl, 2,3-dihydrobenzofuranyl, 1,3-dihydroisobenzofuranyl, indanyl, 2,3-dihydrobenzo[b]thienyl, dihydrobenzopipenyl, 1,2,3,4-tetrahydroquinolyl, 2,3-dihydro-1,4-benzodioxyl, 3,4-dihydro-2H-1,4-benzoxazinyl, naphthyridinyl, naphthyl, benzofuranyl, benzothienyl, benzopyrrolyl, benzothiazolyl, benzoxazolyl, indazolyl, benzopyridazinyl, benzimidazolyl, indolyl, quinolyl, isoquinolyl, purinly, pteridinyl,

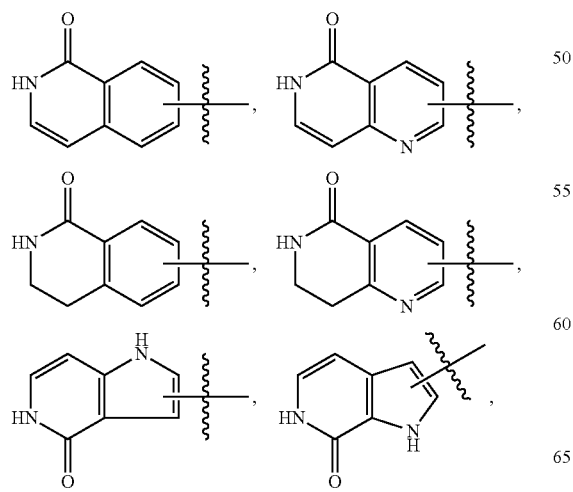

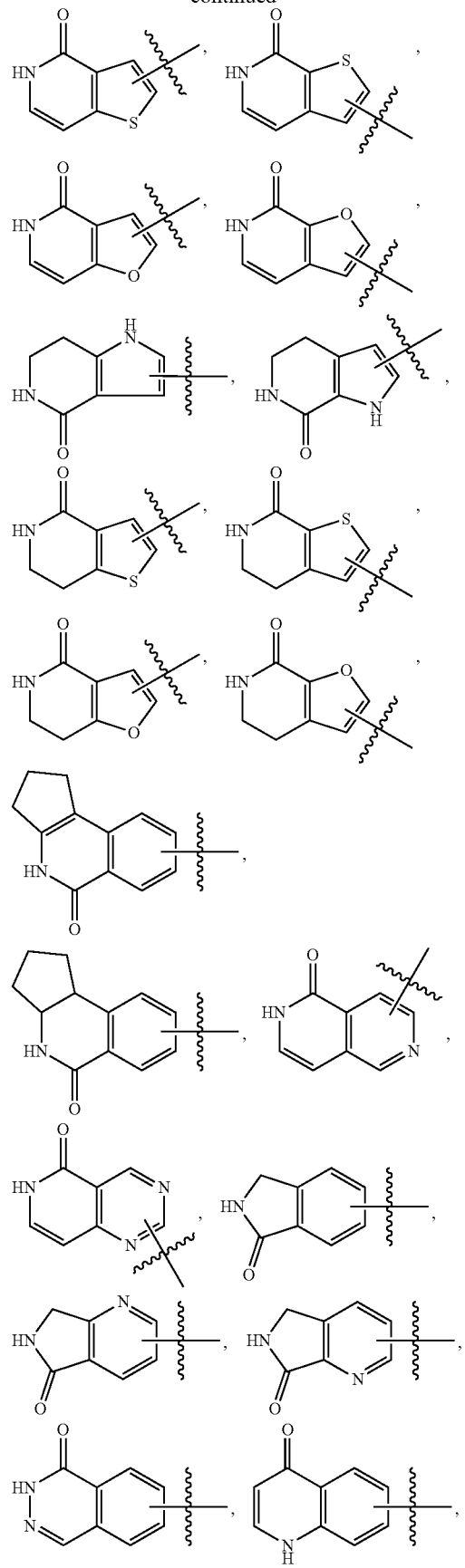

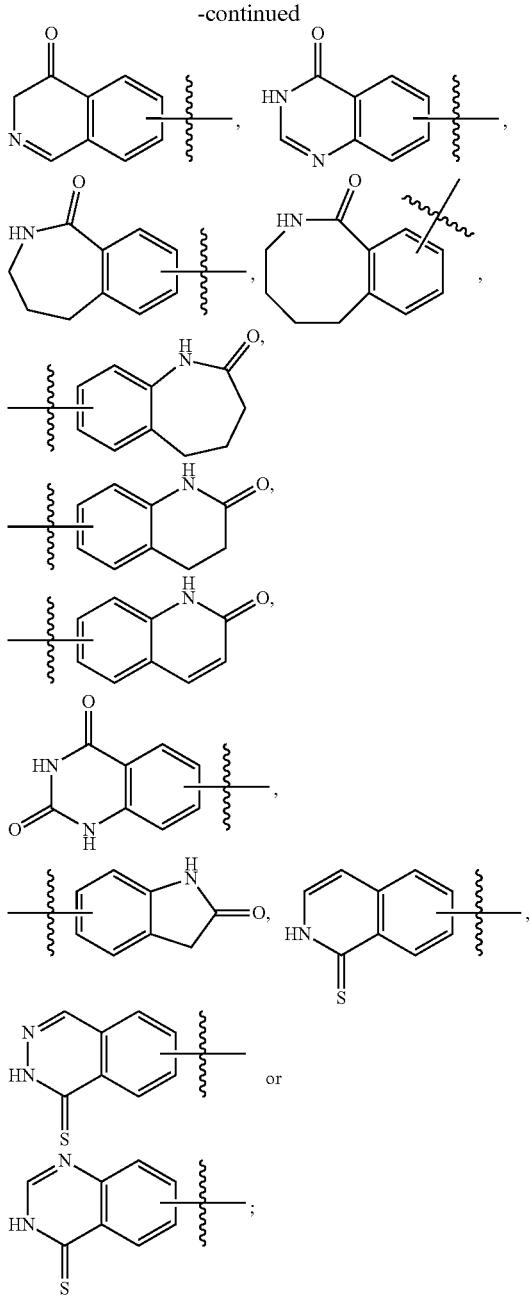

the fused ring can be attached to the parent molecular moiety through a ring carbon atom, preferably through a carbon atom comprised in the aromatic ring. The fused ring may be unsubstituted optionally substituted at any position by one or more than one substituent.

The term "aromatic ring" includes "aryl" and "heteroaryl".

The term "arylalkyl" refers to an aryl attached to the parent molecular moiety through an alkyl. Thus, "arylalkyl" includes the definition of alkyl and aryl as defined above.

The term "heteroarylalkyl" refers to a heterocycloalkyl attached to the parent molecular moiety through an alkyl. Thus, "heteroarylalkyl" includes the definitions of alkyl and heteroaryl as defined above.

The term "halogen" refers to fluorine, chlorine, bromine or iodine.

The term "haloalkyl" refers to an alkyl optionally substituted by halogen. Thus, "haloalkyl" includes the definitions of the halogen and alkyl as defined above.

The term "haloalkoxy" refers to an alkoxy group optionally substituted by halogen. Thus, "haloalkoxy" includes the definitions of the halogen and alkoxy as defined above.

The term "amino" refers to —NH$_2$, and the term "alkylamino" refers to that at least one hydrogen atom on the amino group is substituted by an alkyl, including but not limited to —NHCH$_3$, —N(CH$_3$)$_2$, —NHCH$_2$CH$_3$, —N(CH$_2$CH$_3$)$_2$. The term "aminoalkyl" means that any one of the hydrogen atoms on the alkyl is substituted by an amino group, including but not limited to —CH$_2$NH$_2$, —CH$_2$CH$_2$NH$_2$. Thus, "aminoalkyl" and "alkylamino" include the definition of alkyl and amino as defined above.

The term "nitro" refers to —NO$_2$.

The term "cyano" refers to —CN.

The symbol "═" refers to a double bond; the symbol "⸺" refers to a double bond or a single bond.

"Room temperature" used herein means 15 to 30° C.

The isotope-substituted derivative includes an isotope-substituted derivative that any hydrogen atom of the compound of formula I is replaced by 1 to 5 deuterium atoms, or any carbon atom of the compound of formula I is replaced by 1-3 C$^{14}$ atom, or any oxygen atom of the compound of formula I is replaced by 1 to 3 O$^{18}$ atom.

The term "prodrug" refers to the compound is capable of being converted to the original active compound after being subject to metabolism in the body. Typically, the prodrug is inactive or less active than the active parent compound, but can provide convenient preparation, administration or improve metabolic properties.

"Pharmaceutically acceptable salts" as described herein are discussed in Berge, et al., "Pharmaceutically acceptable salts", J. Pharm. Sci., 66, 1-19 (1977), and it's apparent for pharmaceutical chemists that the salts are substantially non-toxic and can provide the desired pharmacokinetic properties, palatability, absorption, distribution, metabolism or excretion, and the like. The compounds of the present invention may have an acidic group, a basic group or an amphoteric group, and typical pharmaceutically acceptable salts include those prepared by reacting the compound of the present invention with an acid, for example, hydrochloride, hydrobromide, sulfate, pyrosulfate, bisulfate, sulfite, bisulfite, phosphate, monohydrogen phosphate, dihydrogen phosphate, metaphosphate, pyrophosphate, nitrate, acetate, propionate, citrate, octanoate, formate, acrylate, isobutyrate, hexanoate, heptanoate, oxalate, malonate, succinate, suberate, benzoate, methyl benzoate, phthalate, maleate, methanesulfonate, p-toluenesulfonate, (D,L)-tartaric acid, citric acid, maleic acid, (D,L)-malic acid, fumaric acid, succinic acid, succinate, lactate, triflate, naphthalene-1-sulfonate, mandelate, pyruvate, stearate, ascorbate, salicylate. When the compound of the present invention contains an acidic group, the pharmaceutically acceptable salt thereof may further include an alkali metal salt such as a sodium or potassium salt; an alkaline earth metal salt such as a calcium or magnesium salt; an organic base salt such as formed by ammonia, alkylamines, hydroxyalkylamines, amino acids (lysine, arginine) or N-methylglucamine and so on.

As used herein, "isomer" means that the compound of formula (I) of the present invention may have asymmetric centers and racemates, racemic mixtures and individual diastereomers, all of which including stereoisomers, geometric isomers are all included in the present invention. In the present invention, when the compound of formula I or a salt thereof is present in stereoisomeric form (for example, when it contains one or more asymmetric carbon atoms), individual stereoisomers (enantiomers and diastereomers) and mixtures thereof are included within the scope of the invention. The present invention also includes individual isomers of the compounds of formula I or salts, as well as mixtures with isomers in which one or more chiral centers are inverted. The scope of the invention includes mixtures of stereoisomers, as well as purified enantiomers or enantiomerically/diastereomerically enriched mixtures. The present invention includes mixtures of stereoisomers of all possible different combinations of all enantiomers and diastereomers. The present invention includes all combinations and subsets of stereoisomers of all the specific groups defined above. The present invention also includes geometric isomers of the compound of formula I or the salt thereof, including cis or trans isomers.

The above preferred conditions of the present invention may be arbitrarily combined without departing from the general knowledge in the art to obtain the preferred embodiments of the present invention.

The reagents and raw materials used in the present invention are commercially available.

DETAILED DESCRIPTION OF THE PREFERRED EMBODIMENT

All the structures of the compounds in the present disclosure were confirmed by Nuclear Magnetic Resonance ($^1$H NMR) and/or Mass Spectra (MS).

$^1$H NMR chemical shifts (δ) were recorded in ppm ($10^{-6}$). NMR Spectra were recorded on Bruker AVANCE-400 spectrometer. The proper solvents are Chloroform-d (CDCl$_3$), Methanol-D$_4$ (CD$_3$OD), Dimethyl sulfoxide-D$_6$ (DMSO-d$_6$). Tetramethylsilane as internal standard (TMS).

The analytical low-resolution mass spectra (MS) were recorded on Agilent 1200 HPLC/6120 using a)(Bridge C18, 4.6×50 mm, 3.5 μm. The gradient elution method 1:80-5% solvent A$_1$ and 20-95% solvent B$_1$ (1.8 min), and then 95% solvent B$_1$ and 5% solvent A$_1$ (over 3 min). "%" as used herein is volume percentage of the volume of a solvent in the total solvent volume. Solvent A$_1$: 0.01% trifluoroacetic acid (TFA) aqueous solution; Solvent B$_1$: 0.01% trifluoroacetic acid acetonitrile solution. "%" is the volume of a solvent in the total solvent volume. The gradient elution method 2: 80-5% solvent A$_2$ and 20-95% solvent B$_2$ (1.5 min), and then 95% solvent B$_2$ and 5% solvent A$_2$ (over 2 min), "%" is the volume of a solvent in the total solvent volume. Solvent A$_2$:10 mM ammonium bicarbonate aqueous solution; Solvent B$_2$: acetonitrile.

All the compounds in the present disclosure were separated by preparative high-performance liquid chromatography, column chromatography, or flash column chromatography.

Preparative high-performance liquid chromatography purification (prep-HPLC) was performed on Shimadzu LC-20 HPLC, chromatographic column: waters xbridge Pre C18, 10 um, 19 mm*250 mm. Preparative method: mobile phase A: 0.05% trifluoroacetic acid aqueous solution (% is volume percentage), mobile phase B: acetonitrile; the gradient elution method: 25-75% solvent A and 75-25% solvent B; detection wavelength: 214, and/or 254, and/or 262 nM. the flow rate: 10.0 mL/min;

Flash column chromatography (flash system/Cheetah™) was performed on Agela Technologies MP200, the separation column was used Flash columm Silica-CS (80 g), Cat No. CS140080-0.

Thin layer chromatography was used Yantai xinnuo chemical, thickness of the coating is 0.2±0.03 mm. Column chromatography generally used Yantai Huanghai 200-300 mesh silica gel as carrier.

Embodiment 1: Synthesis of Compounds 1.7 and 1.8

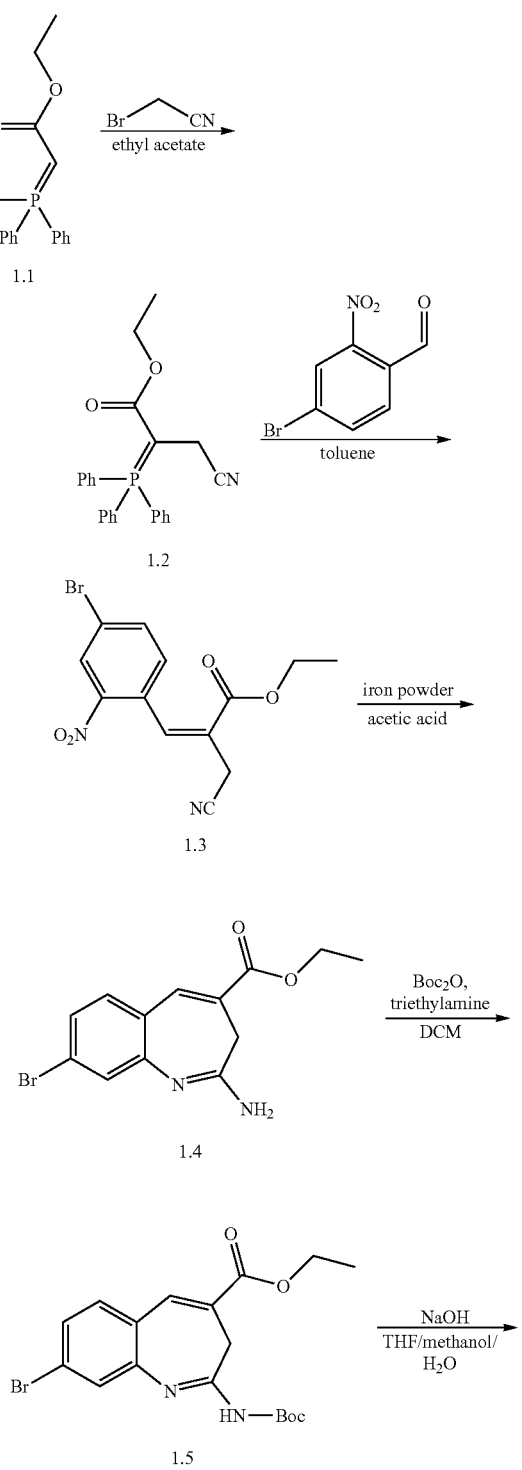

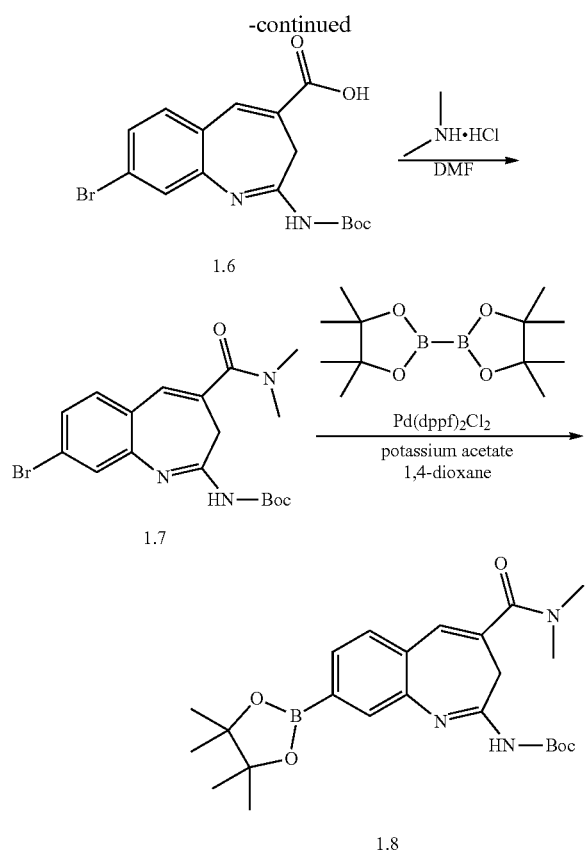

Step 1: Synthesis of Compound 1.2

Compound 1.1 (20 g, 57.4 mmol) and bromoacetonitrile (6.9 g, 57.4 mmol) were dissolved in ethyl acetate (200 mL), the reaction system was heated to reflux and stirred for 3 h, the solid was removed by filtration. The filter cake was washed twice with ethyl acetate. The filtrate was concentrated under reduced pressure to removed the solvent and afford compound 1.2 (17 g, yield: 76%) as a light-yellow solid, which can directly used for next step.

Step 2: Synthesis of Compound 1.3

The mixture solution of 4-bromo-2-nitrobenzaldehyde (10 g, 43.9 mmol), compound 1.2 (17 g, 43.9 mmol) and toluene (170 mL) was stirred at reflux for 2 h, the resulting mixture was cooled down to room temperature and filtered through a short silica gel pad, eluted with 25% ethyl acetate petroleum ether solution until the product could not be detected by TLC, most of the eluent was removed by concentrated under reduced pressure, residual solution was placed at −18° C. for 16 h. Filtered, the filter cake was dried over to afford compound 1.3 (8.2 g, yield: 55%) as an off-white solid.

Step 3: Synthesis of Compound 1.4

The mixture of compound 1.3 (4.2 g, 12.4 mmol) and acetic acid (80 mL) was heated to 80° C., to the above mixture was added iron powder (4.1 g, 74.3 mmol) in 15 min, the reaction temperature was kept no more than 90° C. and stirred for 3 h. The reaction system was cooled down to room temperature, filtered through celite, rinsed 3 times with ethyl acetate. The filtrate was concentrated under reduced pressure, the residue was diluted with cooled water and adjusted to pH>8 with the aqueous solution of saturated sodium bicarbonate, the combined organic layers were washed with brine, separation of organic layer and dried over anhydrous sodium sulfate, filtered and concentrated, the residue was triturated with 10% ethyl acetate petroleum ether solution, filtered, the filter cake was dried over to afford compound 1.4 (3.0 g, yield: 78%) as an off-white solid.

Step 4: Synthesis of Compound 1.5

To a solution of compound 1.4 (3.0 g, 9.7 mmol) and triethylamine (1.47 g, 14.6 mmol) in dichloromethane (50 mL) was added di-tert-butyl decarbonate ((BOC)$_2$O, 3.2 g, 14.6 mmol). The reaction system was stirred at room temperature for 2d and then diluted with dichloromethane (100 mL), the organic layer was successively washed with hydrochloric acid (3.0 M), aqueous solution of saturated sodium bicarbonate and brine, separation of organic layer and dried over anhydrous sodium sulfate, filtered and concentrated, the residue was triturated with 10% ethyl acetate petroleum ether solution, filtered, the fiter cake was dried over to afford compound 1.5 (1.6 g, yield: 40%) as an off-white solid.

m/z: [M+H]$^+$409

Step 5: Synthesis of Compound 1.6

To an ice-cooling solution of compound 1.5 (1.6 g, 3.91 mmol) in tetrahydrofuran (THF) (50 mL) was added an aqueous solution of sodium hydroxide (1.0 M, 5.9 mL, 5.9 mmol). The reaction system was stirred at room temperature for 16 h and then adjusted pH to 6 with hydrochloric acid (0.5 M), the resulting mixture was extracted twice with ethyl acetate, the combined organic layers were washed with brine, separation of organic phase and dried over anhydrous sodium sulfate, filtered and concentrated to afford compound 1.6 (1.1 g, yield: 74%) as a light-yellow foam.

m/z: [M+H]$^+$381

Step 6: Synthesis of Compound 1.7

The mixture of compound 1.6 (1.1 g, 2.8 mmol), 2-(7-azabenzotriazol-1-yl)-N,N,N',N'-tetramethyluronium hexafluorophosphate (1.6 g, 4.33 mmol), dimethylamine hydrochloride (470 mg, 5.77 mmol) and N,N-diisopropylethylamine (560 mg, 4.37 mmol) in N,N-dimethylformamide (DIVIF) (10 mL) was stirred at room temperature for 3 h. The reaction system was diluted with ethyl acetate (100 mL) and successively washed with water and brine, separation of organic phase and dried over anhydrous sodium sulfate, filtered and concentrated, the residue was purified by column chromatography on silica gel (methanol/dichloromethane (DCM)=1/20) to afford compound 1.7 (400 mg, yield: 34%) as a light-yellow solid.

m/z: [M+H]$^+$408

Step 8: Synthesis of Compound 1.8

The mixture of compound 1.7 (380 mg, 0.93 mmol), potassium acetate (274 mg, 2.79 mmol), bis(pinacolato)diboron (354 mg, 1.40 mmol) and Pd(dppf)$_2$Cl$_2$ in 1,4-dioxane (10 mL) was stirred at 80° C. for 5 h under N$_2$ protection. The reaction system was cooled down to room temperature, filtered through celite, the celite was rinsed with 10% methanol DCM solution, the filtrate was concentrated, the residue was purified by column chromatography on silica gel (methanol/DCM=1/20~1/10) to afford compound 1.8 (208 mg, yield: 49%) as a red solid.

m/z: [M+H]$^+$456

Embodiment 2: Synthesis of Compound 2.4

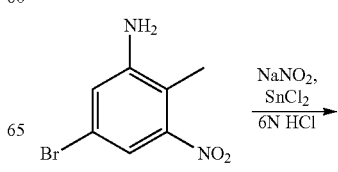

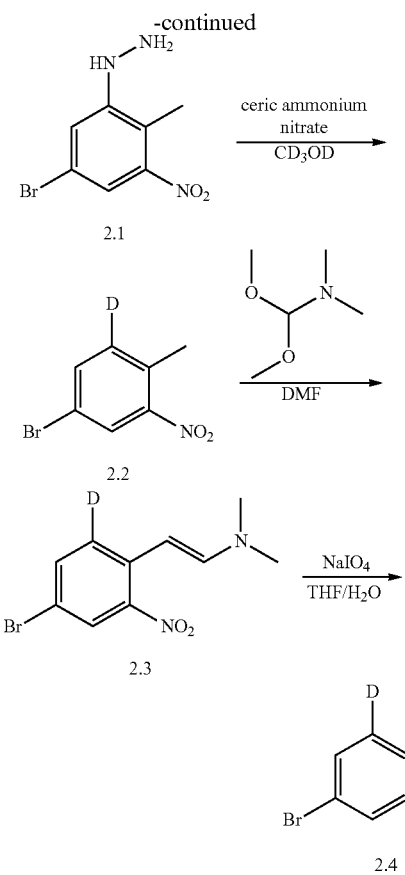

Step 1: Synthesis of Compound 2.1

To an ice-cooling suspension of 5-bromo-2-methyl-3-nitroaniline (2.0 g, 8.66 mmol), water (8 mL) and hydrochloric acid (6 N, 8 mL) was added the aqueous solution of sodium nitrite (627 mg, 9.09 mmol, 5 mL), and then concentrated hydrochloric acid solution of stannous chloride (5.4 g, 25.9 mmol, 5 mL) was added, the reaction system was stirred at 0° C. for 30 min. The reaction solution was neutralized with concentrated ammonia solution to pH=8, and then extracted with ethyl acetate. The combined organic layers were washed with brine, dried over anhydrous sodium sulfate, filtered and concentrated. The crude product was triturated with tert-butyl methyl ether, filtered to afford compound 2.1 (700 mg, yield: 33%) as a light-yellow solid.

m/z: [M+H]$^+$246

Step 2: Synthesis of Compound 2.2

To a solution of ceric ammonium nitrate (3.28 g, 5.97 mmol) in methanol-D$_4$ (7 mL) was added compound 2.1 (700 mg, 2.84 mmol) in one portion. The reaction system was stirred at room temperature for 10 min and then filtered through celite, the filtrate was concentrated and purified by column chromatography on silica gel (100% petroleum ether) to afford compound 2.2 (300 mg, yield: 49%) as a light-yellow oil.

Step 3: Synthesis of Compound 2.3

Compound 2.2 (0.85 g, 3.92 mmol) and N,N-dimethylformamide dimethyl acetal (5 mL) were dissolved in DMF (10 mL), the reaction system was stirred at 105° C. for overnight, and then concentrated under reduced pressure to afford compound 2.3 (1.0 g, yield: 94%) as a red solid.

m/z: [M+H]$^+$272

Step 4: Synthesis of Compound 2.4

To a solution of compound 2.3 (1.0 g, 3.93 mmol) in a mixed solvent of THF and H$_2$O (5 mL/5 mL) was added sodium periodate (2.5 g, 11.8 mmol), the reaction system was stirred at room temperature for 16 h, undissolved substance was filtered, the filtrate was extracted with ethyl acetate, the combined organic layers were washed with brine, dried over anhydrous sodium sulfate, concentrated, the residue was purified by column chromatography on silica gel (petroleum ether/ethyl acetate=10/1-5/1) to afford compound 2.4 (200 mg, yield: 22%) as a light-yellow solid.

$^1$H NMR (400 MHz, CDCl$_3$): δ 10.38 (s, 1H), 8.26 (s, 1H), 7.93 (s, 1H).

Embodiment 3: Synthesis of Compounds 1.9~1.13

Compounds 1.9~1.13 were synthesized following the synthetic method to the one used for Embodiment 1 compound 1.7, by replacing dimethylamine hydrochloride to corresponding amines in step 6:

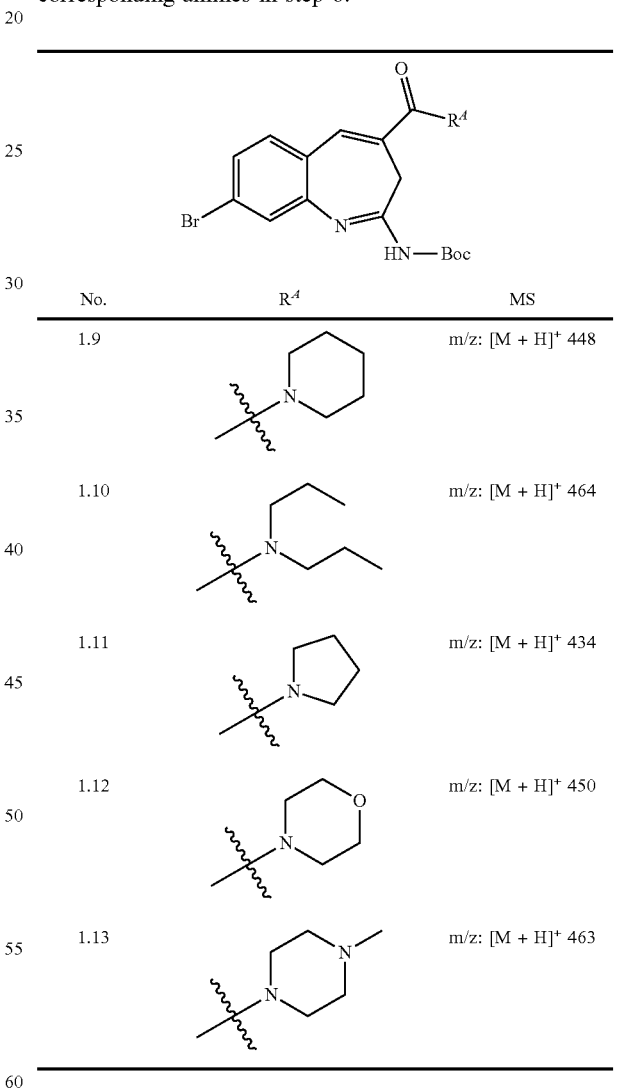

Embodiment 4: Synthesis of Compounds 1.14~1.17

Compounds 1.14~1.17 were synthesized following the synthetic method to the one used for Embodiment 1 compound 1.7, by replacing 4-bromo-2-nitrobenzaldehyde to 4-bromo-2-methoxy-6-nitrobenzaldehyde, 4-bromo-2- methyl-6-nitrobenzaldehyde, 4-bromo-2-chloro-6-nitrobenzaldehyde, or compound 2.4 in step 2:

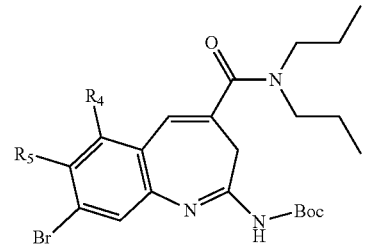

| No. | R₄ | R₅ | MS |
|---|---|---|---|
| 1.14 | —OCH₃ | H | m/z: [M + H]⁺ 494 |
| 1.15 | —CH₃ | H | m/z: [M + H]⁺ 478 |
| 1.16 | —Cl | H | m/z: [M + H]⁺ 498 |
| 1.17 | —D | H | m/z: [M + H]⁺ 465 |

Embodiment 5: Synthesis of Compound 1.19

Compound 1.19 was synthesized following the synthetic method to the one used for Embodiment 1 compound 1.8, by replacing dimethylamine hydrochloride to 2-(propylamino)ethanol in step 6:

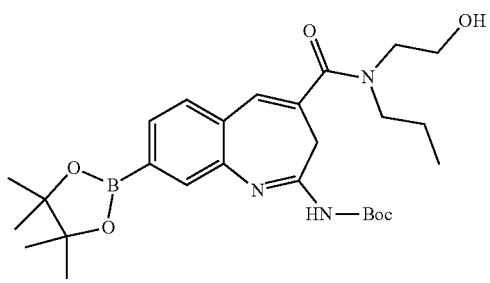

1.19 m/z: [M+H]⁺514

Embodiment 6: Synthesis of Compounds 1.20~1.22

Compound 1.20 was synthesized following the synthetic method to the one used for Embodiment 1 compound 1.8, by replacing compound 1.7 to compound 1.10 in step 7:
Compounds 1.21 and 1.22 were synthesized following the synthetic method to the one used for Embodiment 1 compound 1.8, by replacing 4-bromo-2-nitrobenzaldehyde to 4-bromo-5-fluoro-2-nitrobenzaldehyde or 4-bromo-2-fluoro-6-nitrobenzaldehyde in step 2:

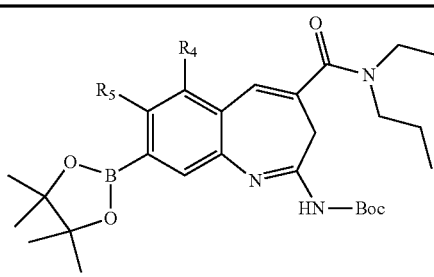

| No. | R₄ | R₅ | MS |
|---|---|---|---|
| 1.20 | H | H | m/z: [M + H]⁺ 512 |
| 1.21 | H | F | m/z: [M + H]⁺ 530 |
| 1.22 | F | H | m/z: [M + H]⁺ 530 |

Embodiment 7: Synthesis of Compound 3.8

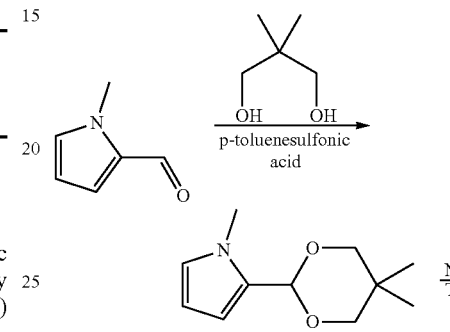

3.1

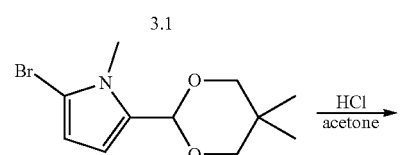

3.2

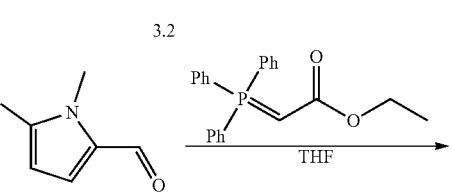

3.3

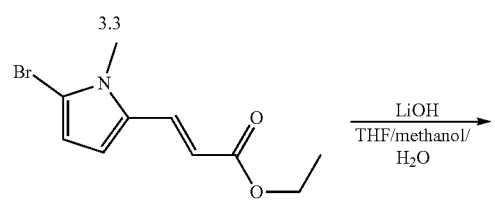

3.4

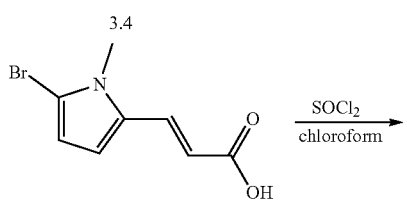

3.5

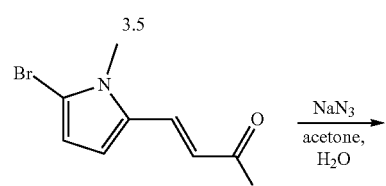

3.6

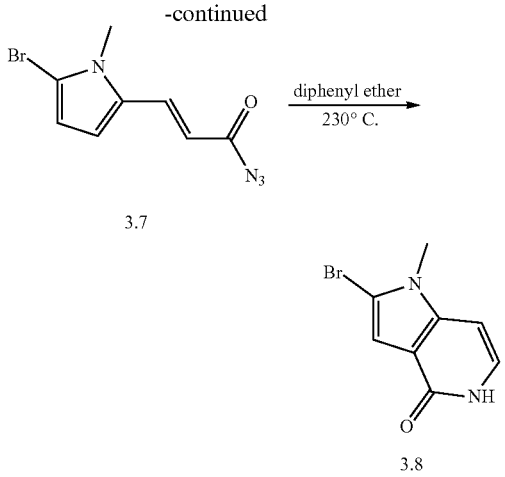

Step 1: Synthesis of Compound 3.1

1, Synthesis of p-toluenesulfonic acid catalyst: p-toluenesulfonic acid monohydrate (100 mg) and benzene (20 mL) were heated to reflux for 2 h in Dean-stark apparatus until the solution became clear.

2, The solution of 1-methyl-1H-pyrrole-2-carbaldehyde (2.0 g, 18.3 mmol) and 2,2-dimethylpropane-1,3-diol (4.9 g, 47.6 mmol) in benzene (20 mL) was heated to reflux for 15 min in Dean-stark apparatus, the prepared p-toluenesulfonic acid catalyst is slowly added dropwise to the above solution, after the addition, the reaction system was stirred at 85° C. for 2 h, and cooled down to room temperature, filtered, the filterate was concentrated under reduced pressure, the residue was purified by column chromatography on silica gel (ethyl acetate/petroleum ether=1/100) to afford compound 3.1 (1.0 g, yield: 28%) as a colorless oil.

$^1$H NMR (400 MHz, CDCl$_3$): δ 6.59-6.58 (m, 1H), 6.25-6.23 (m, 1H), 6.06-6.05 (m, 1H), 5.45 (s, 1H), 3.80 (s, 3H), 3.78 (d, J=11.2 Hz, 2H), 3.63 (d, J=10.8 Hz, 2H), 1.33 (s, 3H), 0.82 (s, 3H).

Step 2: Synthesis of Compound 3.2

To a solution of compound 3.1 (1.0 g, 5.12 mmol) in THF (10 mL) was added N-bromosuccinimide (NBS) (960 mg, 5.38 mmol) in small protions, the reaction system was stirred at room temperature for 1 h and then diluted with ethyl acetate (100 mL), the organic layer was washed with the aqueous solution of sodium hydroxide (2.0 M) and brine, separation of organic layer, dried over sodium sulfate, filtered and concentrated, the residue was purified by column chromatography on silica gel (ethyl acetate/petroleum ether=1/100~1/10) to afford compound 3.2 (800 mg, yield: 57%) as a colorless oil, which can directly used for next step.

Step 3: Synthesis of Compound 3.3

To a solution of compound 3.2 (800 mg, 2.92 mmol) in acetone (4 mL) was added concentrated hydrochloric acid (1 mL), the reaction system was stirred at 40° C. for 1 h and then diluted with water (50 mL), the mixture was extracted 3 times with ethyl acetate, the combined organic layers were washed with brine, dried over anhydrous sodium sulfate, filtered and concentrated, the residue was purified by column chromatography on silica gel (ethyl acetate/petroleum ether=1/9) to afford compound 3.3 (145 mg, yield: 26%) as a brown oil.

$^1$HNMR (400 MHz, CDCl$_3$): δ 9.45 (s, 1H), 6.90 (d, J=4.0 Hz, 1H), 6.23 (d, J=4.4 Hz, 1H), 3.96 (s, 3H).

Step 4: Synthesis of Compound 3.4

To a solution of compound 3.3 (145 mg, 0.77 mmol) in THF (10 mL) was added ethyl (triphenylphosphoranylidene) acetate (537 g, 1.54 mmol) in small portions. The reaction system was stirred at room temperature for 2 d until TLC detected the reaction was completed, the reaction was quenched by addition of water (30 mL), the mixture was extracted with ethyl acetate (20 mL×2). The combined organic layers were washed with brine, separation of organic layer, dried over anhydrous sodium sulfate, filtered and concentrated, the residue was purified by column chromatography on silica gel (25% ethyl acetate petroleum ether solution) to afford compound 3.4 (200 mg, yield: 100%) as an off-white solid.

Step 5: Synthesis of Compound 3.5

To a solution of compound 3.4 (200 mg, 0.77 mmol) in a mixed solvent of methanol (2 mL), THF (0.5 mL) and H$_2$O (0.5 mL) was added lithium hydroxide hydrate (162 mg, 3.87 mmol). The reaction system was stirred at room temperature for 16 h, and then quenched by addition of hydrochloric acid (3.0 M) and adjusted pH to 5. the mixture was extracted twice with ethyl acetate, the combined organic layers were washed with brine, separation of organic phase, dried over anhydrous sodium sulfate, filtered and concentrated to afford compound 3.5 (170 mg, yield: 95%) as an off-yellow solid, which can directly used for next step.

Step 6: Synthesis of Compound 3.6

To a solution of compound 3.5 (170 mg, 0.74 mmol) in chloroform (2 mL) was added thionyl chloride (1 mL) and a drop of DMF under N$_2$ protection, after the addition, the reaction system was heated to reflux and stirred for 1 h. The reaction system was cooled down to room temperature and concentrate under reduced pressure to afford compound 3.6 (165 mg, yield: 90%) as a brown solid, which can directly used for next step.

Step 7: Synthesis of Compound 3.7

To an ice-cooling solution of compound 3.6 (165 mg, 0.66 mmol) in acetone (5.0 mL) was added the aqueous solution of saturated sodium azide (1 mL). The reaction system was stirred vigorously under ice bath until TLC detected the reaction was completed. The reaction system was diluted with dichloromethane and washed with water and brine, separation of organic phase, dried over anhydrous sodium sulfate, filtered and concentrated to afford compound 3.7 (188 mg, yield: 100%) as an off-yellow solid, which can directly used for next step.

Step 8: Synthesis of Compound 3.8

Diphenyl ether (3 mL) was added into a 10 mL round bottom flask with an air condensation tube, the flask was heated to 240° C., to above solution was slowly injected a solution of compound 3.7 (188 mg, 0.74 mmol) in dichloromethane (3 mL) by a syringe, the reaction system was stirred at 240° C. for 20 min and then cooled down to 50° C., the reaction system was poured into petroleum ether (50 mL) and stirred for 2 h, the resulting mixture was filtered, the filter cake was rinsed with petroleum ether, dried over to afford compound 3.8 (90 mg, yield: 54%) as a dark grey solid.

m/z: [M+H]$^+$227

Embodiment 8: Synthesis of Compound 3.9

Compound 3.9 was synthesized following the synthetic method to the one used for Embodiment 7 compound 3.8, by replacing compound 3.3 to 5-bromothiophene-2-carbaldehyde in step 4:

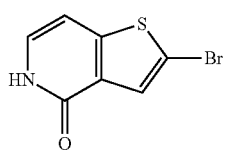

3.9 m/z: [M+H]⁺230

Embodiment 9: Synthesis of Compound 4.2

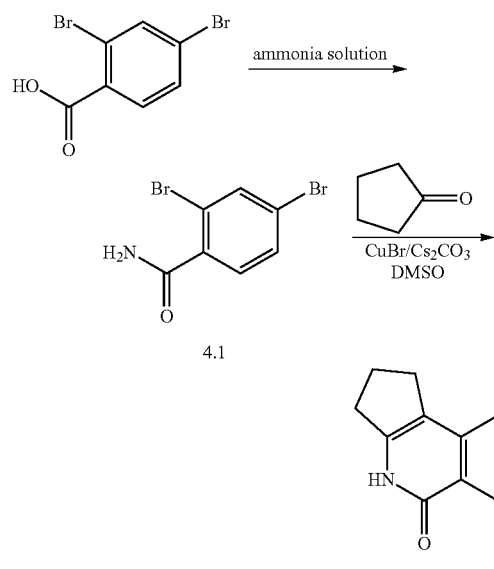

Step 1: Synthesis of Compound 4.1

To a solution of 2,4-dibromobenzoic acid (1.0 g, 3.57 mmol) in DMF (10 mL) was successively added 1-hydroxybenzotriazole (530 mg, 3.93 mmol) and 1-(3-dimethyl aminopropyl)-3-ethylcarbodiimide hydrochloride (820 mg, 4.29 mmol). The reaction system was cooled down to 0° C. and ammonia solution (20 mL, 25%) was added, after the addition, the reaction system was warmed up to room temperature and stirred for overnight. To the reaction system was added water (50 mL), filtered, the filter cake was washed 3 times with water, dried over to afford compound 4.1 (660 mg, yield: 66%) as a white solid.

m/z: [M+H]⁺278

Step 2: Synthesis of Compound 4.2

Cuprous bromide (15.4 mg, 0.11 mmol), cesium carbonate (701 mg, 2.15 mmol), compound 4.1 (300 mg, 1.08 mmol), cyclopentanone (136 mg, 1.61 mmol) and dimethyl sulfoxide (Dmso) (10 mL) were added into a sealing tube (20 mL), the tube was replaced 3 times with N₂. The reaction system was stirred at 80° C. for overnight and then cooled down to room temperature, to the reaction system was added brine (50 mL) and ethyl acetate (50 mL), separation of organic layer, the aqueous layer was extracted with ethyl acetate (20 mL×2). The combined organic layers were washed with brine, dried over anhydrous sodium sulfate, filtered and concentrated, the residue was triturated with a mixed solvent of tert-butyl methyl ether (50 mL) and dichloromethane (5 mL), filtered, the filtered cake was dried over to afford compound 4.2 (150 mg, yield: 42%) as a yellow solid.

m/z: [M+H]⁺264

Embodiment 10: Synthesis of Compound 4.3

Compound 4.3 was synthesized following the synthetic method to the one used for Embodiment 9 compound 4.2, by replacing cyclopentanone to acetone in step 2:

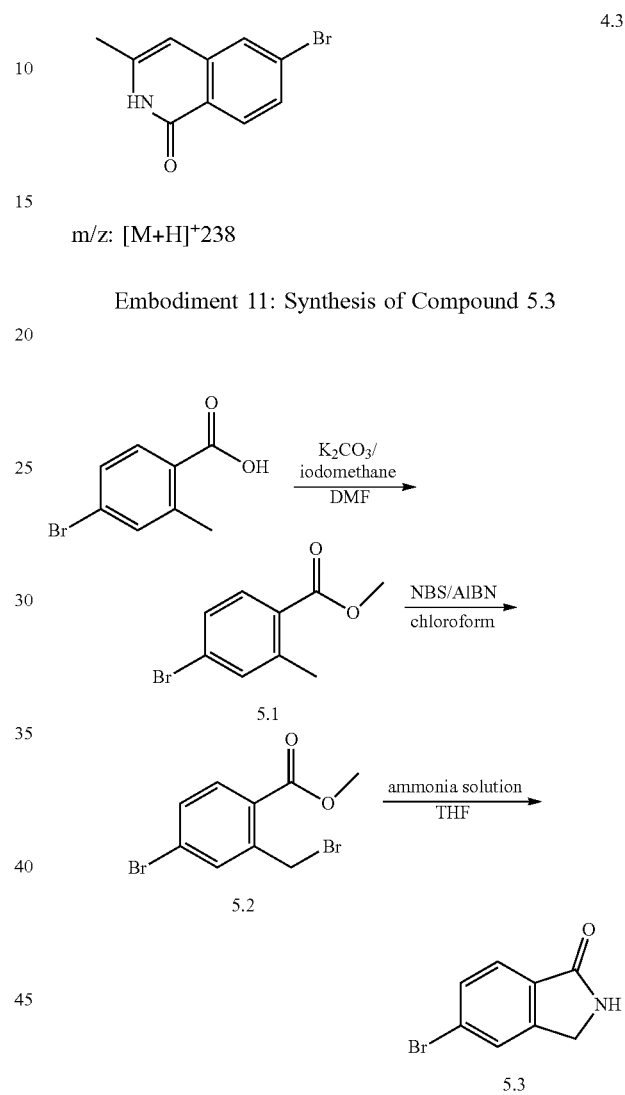

m/z: [M+H]⁺238

Embodiment 11: Synthesis of Compound 5.3

Step 1: synthesis of compound 5.1

To a solution of 4-bromo-2-methylbenzoic acid (1.0 g, 4.65 mmol) in DMF (10 mL) was successively added potassium carbonate (670 mg, 4.89 mmol) and iodomethane (900 mg, 6.98 mmol). The reaction system was stirred at room temperature for 2 h and then quenched by addition of water (60 mL), the mixture was extracted with ethyl acetate (40 mL×2), the combined organic layers were washed with brine, separation of organic layer, dried over sodium sulfate, filtered and concentrated to afford compound 5.1 (1.0 g, yield: 93%) as a light-red oil, which can directly used for next step.

Step 2: Synthesis of Compound 5.2

To a solution of compound 5.1 (300 mg, 1.31 mmol) in chloroform (10 mL) was added NBS (350 mg, 1.96 mmol) and azodiisobutyronitrile (100 mg, 0.65 mmol) in one portion. The reaction system was heated to 80° C. and stirred for 2 h and then cooled down to room temperature, filtered, the filtrate was washed with brine, separation of organic phase, dried over sodium sulfate, filtered and concentrated to afford compound 5.2 (300 mg, yield: 75%) as a red oil, which can directly used for next step.

Step 3: Synthesis of Compound 5.3

To a solution of compound 5.2 (300 mg, 0.97 mmol) in THF (2 mL) was added ammonia solution (2 mL). The reaction system was stirred at 20° C. for 12 h. The resulting solid was filtered, after vacuum drying treatment to afford compound 5.3 (100 mg, yield: 50%) as an off-white solid.
m/z: [M+H]$^+$212

Embodiment 12: Synthesis of Compound 5.4

Compound 5.4 was synthesized following the synthetic method to the one used for Embodiment 11 compound 5.3, by replacing 4-bromo-2-methylbenzoic acid to 5-bromo-3-methylpyridine-2-carboxylic acid in step 1:

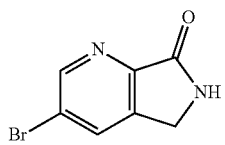

5.4 m/z: [M+H] $^+$213

Embodiment 13: Synthesis of Compound 6.2

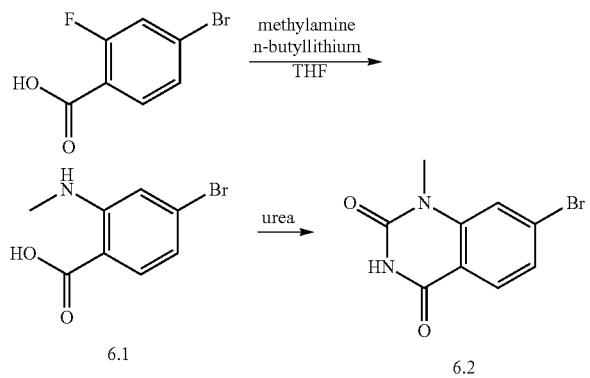

Step 1: Synthesis of Compound 6.1

A solution of methylamine in tetrahydrofuran (2.0 M, 11 mL, 27.8 mmol) was dissolved in THE (10 mL) under ice-water bath, to the system was added n-butyllithium (8.2 mL, 20.5 mmol) dropwise. After the addition, the reaction was stirred at 0° C. for 1 h, and then the reaction system was cooled down to −78° C. To the system was added a solution of 4-bromo-2-fluorobenzoic acid (1.0 g, 4.57 mmol) in THF (5 mL), stirred at −78° C. for 0.5 h and quenched by addition of hydrochloric acid (1.0 M), extracted with ethyl acetate (5 mL×3). The combined organic layers were washed with brine, dried over sodium sulfate, filtered and concentrated to afford compound 6.1 (700 mg, yield: 68%) as a light-yellow solid.
m/z: [M+H]$^+$230

Step 2: Synthesis of Compound 6.2

The compound 6.1 (580 mg, 2.52 mmol) and urea (3 g) were heated to melt, and stirred at 150° C. for 7 h. The reaction system was cooled down to room temperature and then quenched by addition of water, extracted with ethyl acetate. The combined organic layers were washed with brine, dried over sodium sulfate. Filtered, concentrated to afford compound 6.2 (320 mg, yield: 35%) as a grew solid.
m/z: [M+H]$^+$255

Embodiment 14: Synthesis of Compounds 15.1 and 15.2

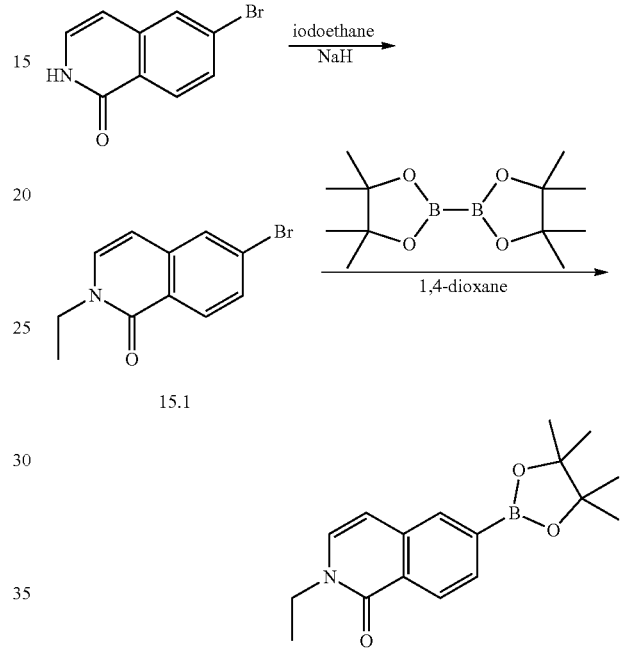

Step 1: Synthesis of Compound 15.1

To an ice-cooling solution of 6-bromoisoquinolin-1(2H)-one (800 mg, 3.57 mmol) in DMF (8 mL) was added sodium hydride (160 mg, 3.93 mmol, 60%) in small portions, after the addition, the reaction system was warmed up to room temperature and stirred for 20 min, iodoethane (800 mg, 5.36 mmol) was added. After the addition, the reaction system was stirred at room temperature for 2 h, the reaction was quenched by addition of water (20 mL), extracted with ethyl acetate (20 mL×2), the combined organic layers were washed with brine, dried over sodium sulfate, separation of organic phase, dried over anhydrous sodium sulfate, filtered and concentrated, the residue was purified by column chromatography on silica gel (ethyl acetate:petroleum ether=1:4) to afford compound 15.1 (800 mg, yield: 91%) as a white solid.

$^1$H NMR (400 MHz, CDCl$_3$): δ 8.30 (d, J=8.8 Hz, 1H), 7.67 (s, 1H), 7.58 (d, J=8.8 Hz, 1H), 7.12 (d, J=7.2 Hz, 1H), 6.43 (d, J=7.2 Hz, 1H), 4.08-4.02 (m, 2H), 1.40 (t, 3H).

Step 2: Synthesis of Compound 15.2

To a solution of compound 15.1 (500 mg, 1.98 mmol) in 1,4-dioxane (6 mL) was successively added potassium acetate (580 mg, 5.95 mmol), bis(pinacolato)diboron (760 mg, 2.97 mmol) and Pd(dppf)Cl$_2$ (160 mg, 0.19 mmol) under N$_2$ protection. The reaction system was stirred at 80° C. for 2 h. The reaction was cooled down to room temperature and quenched by addition of water (60 mL), extracted with ethyl acetate (40 mL×2), the combined organic layers were washed with brine, separation of organic phase, dried over anhydrous sodium sulfate, filtered and concentrated, the residue was purified by column chromatography on silica gel (ethyl acetate:petroleum ether=1:4) to afford compound 15.2 (500 mg, yield: 83%) as a yellow solid.

m/z: [M+H]⁺300

Embodiment 15: Synthesis of Compounds 15.3~45.10

Compounds 15.3~15.10 were synthesized following the synthetic method to the one used for Embodiment 14 compound 15.1, by reaction of 6-bromoisoquinolin-1(2H)-one, 6-bromo-3,4-dihydroisoquinolin-1(2H)-one, compound 3.9, 4.2, 4.3 or 5.4 with corresponding iodides or bromides:

| No. | Chemical Name | MS |
|---|---|---|
| 15.3 | 6-bromo-2-ethyl-3,4-dihydroisoquinolin-1(2H)-one | m/z: [M + H]⁺254 |
| 15.4 | 5-bromo-2-ethylisoindolin-1-one | m/z: [M + H]⁺239 |
| 15.5 | 6-bromo-2-ethyl-3-methylisoquinolin-1(2H)-one | m/z: [M + H]⁺266 |
| 15.6 | 6-bromo-2-isobutylisoquinolin-1(2H)-one | m/z: [M + H]⁺280 |
| 15.7 | 6-bromo-2-propylisoquinolin-1(2H)-one | m/z: [M + H]⁺266 |
| 15.8 | 8-bromo-4-ethyl-2,3-dihydro-1H-cyclopenta[c]isoquinolin-5(4H)-one | m/z: [M + H]⁺292 |
| 15.9 | 2-bromo-5-ethylthieno[3,2-c]pyridin-4(5H)-one | m/z: [M + H]⁺258; ¹H NMR (400 MHz, CD₃OD): δ7.60 (s, 1 H), 7.55 (d, J = 1.6 Hz, 1 H), 6.85 (d, J = 1.6 Hz, 1 H), 4.12 (m, 2 H), 1.35 (t, 3 H). |
| 15.10 | 2-bromo-5-ethyl-1-methyl-1H-pyrrolo[3,2-c]pyridin-4(5H)-one | m/z: [M + H]⁺256 |

Embodiment 16: Synthesis of Compound 16.1

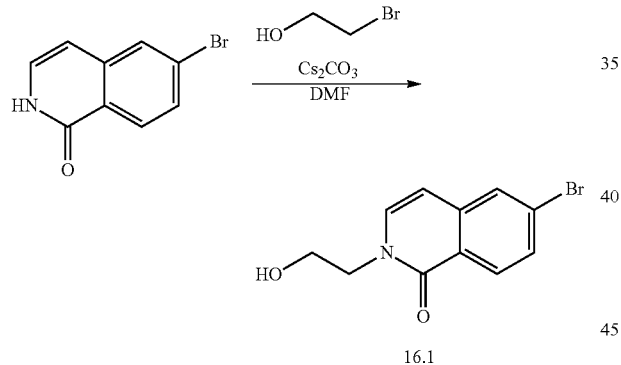

16.1

The solution of 6-bromoisoquinolin-1(2H)-one (150 mg, 0.67 mmol), cesium carbonate (650 mg, 2.01 mmol) and 2-bromoethanol (170 mg, 1.34 mmol) in DMF (2 mL) was stirred at room temperature for 2 d, the reaction system was diluted with ethyl acetate (100 mL), the mixture was washed with water and brine, the organic layer was separated and dried over anhydrous sodium sulfate, filtered and concentrated, the residue was triturated with petroleum ether, filtered, the filter cake was dried over to afford compound 16.1 (120 mg, yield: 60%) as an off-white solid.

m/z: [M+H]⁺268

Embodiment 17: Synthesis of Compounds 16.2~16.75

Compounds 16.2~16.75 were synthesized following the synthetic method to the one used for Embodiment 16 compound 16.1, by reaction of 6-bromoisoquinolin-1(2H)-one, 6-bromo-3,4-dihydroisoquinolin-1(2H)-one, 7-bromoquinazolin-4(3H)-one, 6-bromophthalazin-1(2H)-one, compound 4.3, 5.3, 5.4 or 6.2 with corresponding bromides or chlorides:

| No. | Chemical Name | MS |
|---|---|---|
| 16.2 | 6-bromo-2-(3-hydroxypropyl)isoquinolin-1(2H)-one | m/z: [M + H]$^+$282 |
| 16.3 | 6-bromo-2-(2-hydroxyethyl)-3-methylisoquinolin-1(2H)-one | m/z: [M + H]$^+$282 |
| 16.4 | 6-bromo-2-(2-((tert-butyldimethylsilyl)oxy)ethyl)-3,4-dihydroisoquinolin-1(2H)-one | m/z: [M + H]$^+$384 |
| 16.5 | ethyl 2-(6-bromo-3-methyl-1-oxoisoquinolin-2(1H)-yl)acetate | m/z: [M + H]$^+$324 |
| 16.6 | ethyl 2-(6-bromo-1-oxo-3,4-dihydroisoquinolin-2(1H)-yl)acetate | m/z: [M + H]$^+$312 |
| 16.7 | ethyl 2-(6-bromo-1-oxoisoquinolin-2(1H)-yl)acetate | m/z: [M + H]$^+$310 |
| 16.8 | 2-(6-bromo-1-oxoisoquinolin-2(1H)-yl)acetonitrile | m/z: [M + H]$^+$263 |
| 16.9 | 7-bromo-2-(2-hydroxyethyl)isoquinolin-1(2H)-one | m/z: [M + H]$^+$268 |
| 16.10 | ethyl 2-(5-bromo-1-oxoisoindolin-2-yl)acetate | m/z: [M + H]$^+$298 |
| 16.11 | 6-bromo-2-(2-(dimethylamino)ethyl)isoquinolin-1(2H)-one | m/z: [M + H]$^+$295 |
| 16.12 | 6-bromo-2-(2-methoxyethyl)isoquinolin-1(2H)-one | m/z: [M + H]$^+$282 |
| 16.13 | 6-bromo-2-neopentylisoquinolin-1(2H)-one | m/z: [M + H]$^+$294 |
| 16.14 | 2-(6-bromo-3-methyl-1-oxoisoquinolin-2(1H)-yl)acetonitrile | m/z: [M + H]$^+$277 |
| 16.15 | 2-(7-bromo-4-oxoquinazolin-3(4H)-yl)acetonitrile | m/z: [M + H]$^+$264 |
| 16.16 | tert-butyl (2-(6-bromo-1-oxoisoquinolin-2(1H)-yl)ethyl)carbamate | / |
| 16.17 | 7-bromo-3-(2-(methylthio)ethyl)quinazolin-4(3H)-one | m/z: [M + H]$^+$299 |
| 16.18 | 2-(7-bromo-4-oxoquinazolin-3(4H)-yl)-N-methylacetamide | m/z: [M + H]$^+$296 |
| 16.19 | 2-(6-bromo-1-oxophthalazin-2(1H)-yl)acetonitrile | m/z: [M + H]$^+$264 |
| 16.20 | 7-bromo-3-(2-hydroxyethyl)quinazolin-4(3H)-one | m/z: [M + H]$^+$269 |
| 16.21 | 2-(6-bromo-1-oxophthalazin-2(1H)-yl)-N-methylacetamide | m/z: [M + H]$^+$296 |
| 16.22 | 2-(6-bromo-1-oxoisoquinolin-2(1H)-yl)-N-methylacetamide | m/z: [M + H]$^+$295 |
| 16.23 | 7-bromo-1-methyl-3-(2-(methylthio)ethyl)quinazoline-2,4(1H,3H)-dione | m/z: [M + H]$^+$329 |
| 16.24 | 6-bromo-2-(2-hydroxyethyl)phthalazin-1(2H)-one | m/z: [M + H]$^+$269 |
| 16.25 | 6-bromo-2-(2-(methylthio)ethyl)isoquinolin-1(2H)-one | m/z: [M + H]$^+$298 |
| 16.26 | ethyl 2-(6-bromo-1-oxophthalazin-2(1H)-yl)acetate | m/z: [M + H]$^+$311 |
| 16.27 | ethyl 2-(7-bromo-4-oxoquinazolin-3(4H)-yl)acetate | m/z: [M + H]$^+$311 |
| 16.28 | 6-bromo-2-(2-(methylthio)ethyl)phthalazin-1(2H)-one | m/z: [M + H]$^+$299 |
| 16.29 | ethyl 2-(3-bromo-7-oxo-5H-pyrrolo[3,4-b]pyridin-6(7H)-yl)acetate | m/z: [M + H]$^+$299 |
| 16.30 | ethyl 2-(7-bromo-1-methyl-2,4-dioxo-1,2-dihydroquinazolin-3(4H)-yl)acetate | m/z: [M + H]$^+$341 |
| 16.31 | 6-bromo-2-(3-(methylthio)propyl)phthalazin-1(2H)-one | m/z: [M + H]$^+$313 |
| 16.32 | 3-(6-bromo-1-oxophthalazin-2(1H)-yl)prop anamide | m/z: [M + H]$^+$296 |
| 16.33 | 2-(6-bromo-1-oxoisoquinolin-2(1H)-yl)-N,N-dimethylacetamide | m/z: [M + H]$^+$309 |
| 16.34 | 2-(6-bromo-1-oxoisoquinolin-2(1H)-yl)-N-ethylacetamide | m/z: [M + H]$^+$309 |
| 16.35 | 6-bromo-2-(2-oxo-2-(pyrrolidin-1-yl)ethyl)isoquinolin-1(2H)-one | m/z: [M + H]$^+$335 |
| 16.36 | 6-bromo-2-(2-methoxyethyl)phthalazin-1(2H)-one | m/z: [M + H]$^+$283 |
| 16.37 | 6-bromo-2-butylisoquinolin-1(2H)-one | m/z: [M + H]$^+$280 |
| 16.38 | 6-bromo-2-(oxazol-2-ylmethyl)isoquinolin-1(2H)-one | m/z: [M + H]$^+$305 |
| 16.39 | 6-bromo-2-(thiazol-2-ylmethyl)phthalazin-1(2H)-one | m/z: [M + H]$^+$322 |
| 16.40 | 6-bromo-2-(isoxazol-5-ylmethyl)isoquinolin-1(2H)-one | m/z: [M + H]$^+$305 |
| 16.41 | 6-bromo-2((5-methyl-1,3,4-oxadiazol-2-yl)methyl)isoquinolin-1(2H)-one | m/z: [M + H]$^+$320 |
| 16.42 | 6-bromo-2-(pyrimidin-2-ylmethyl)isoquinolin-1(2H)-one | m/z: [M + H]$^+$316 |
| 16.43 | 2-(2-(1H-pyrazol-1-yl)ethyl)-6-bromoisoquinolin-1(2H)-one | m/z: [M + H]$^+$318 |
| 16.44 | 2-(2-(1H-pyrazol-1-yl)ethyl)-6-bromophthalazin-1(2H)-one | m/z: [M + H]$^+$319 |
| 16.45 | 6-bromo-2-((1-methyl-1H-imidazol-2-yl)methyl)isoquinolin-1(2H)-one | m/z: [M + H]$^+$318 |
| 16.46 | 2-((1H-pyrazol-3-yl)methyl)-6-bromoisoquinolin-1(2H)-one | m/z: [M + H]$^+$304 |
| 16.47 | 6-bromo-2-((1-methyl-1H-pyrazol-3-yl)methyl)isoquinolin-1(2H)-one | m/z: [M + H]$^+$318 |
| 16.48 | 6-bromo-2-((4-methyl-4H-1,2,4-triazol-3-yl)methyl)isoquinolin-1(2H)-one | m/z: [M + H]$^+$319 |
| 16.49 | 2-(2-(1H-imidazol-1-yl)ethyl)-6-bromoisoquinolin-1(2H)-one | m/z: [M + H]$^+$318 |
| 16.50 | 2-((1H-tetrazol-5-yl)methyl)-6-bromoisoquinolin-1(2H)-one | m/z: [M + H]$^+$306 |
| 16.51 | 6-bromo-2((2-methyl-2H-tetrazol-5-yl)methyl)isoquinolin-1(2H)-one | m/z: [M + H]$^+$320 |
| 16.52 | 6-bromo-2-((1-methyl-1H-tetrazol-5-yl)methyl)isoquinolin-1(2H)-one | m/z: [M + H]$^+$320 |
| 16.53 | 6-bromo-2-((1-methyl-1H-1,2,4-triazol-5-yl)methyl)isoquinolin-1(2H)-one | m/z: [M + H]$^+$319 |
| 16.54 | 2-(6-bromo-1-oxoisoquinolin-2(1H)-yl)acetic acid | m/z: [M + H]$^+$282 |
| 16.55 | tert-butyl (2-(7-bromo-1-methyl-2,4-dioxo-1,2-dihydroquinazolin-3(4H)-yl)ethyl)carbamate | / |
| 16.56 | tert-butyl (2-(7-bromo-4-oxoquinazolin-3(4H)-yl)ethyl)carbamate | / |
| 16.57 | tert-butyl (2-(6-bromo-1-oxophthalazin-2(1H)-yl)ethyl)carbamate | / |
| 16.58 | 6-bromo-2-(2-(ethylthio)ethyl)phthalazin-1(2H)-one | m/z: [M + H]$^+$313 |
| 16.59 | diethyl ((6-bromo-1-oxoisoquinolin-2(1H)-yl)methyl)phosphonate | m/z: [M + H]$^+$374 |

| No. | Chemical Name | MS |
|---|---|---|
| 16.60 | diethyl (2-(6-bromo-1-oxoisoquinolin-2(1H)-yl)ethyl)phosphonate | m/z: [M + H]⁺388 |
| 16.61 | diethyl (2-(6-bromo-1-oxophthalazin-2(1H)-yl)ethyl)phosphonate | m/z: [M + H]⁺389 |
| 16.62 | 6-bromo-2-(pyrazin-2-ylmethyl)isoquinolin-1(2H)-one | m/z: [M + H]⁺316 |
| 16.63 | 6-bromo-2-(oxazol-2-ylmethyl)phthalazin-1(2H)-one | m/z: [M + H]⁺306 |
| 16.64 | 6-bromo-2-(pyrimidin-2-ylmethyl)phthalazin-1(2H)-one | m/z: [M + H]⁺317 |
| 16.65 | 6-bromo-2-((4,6-dimethylpyrimidin-2-yl)methyl)phthalazin-1(2H)-one | m/z: [M + H]⁺345 |
| 16.66 | 2-benzyl-6-bromophthalazin-1(2H)-one | m/z: [M + H]⁺315 |
| 16.67 | 6-bromo-2-(pyridin-2-ylmethyl)phthalazin-1(2H)-one | m/z: [M + H]⁺316 |
| 16.68 | 6-bromo-2-((4,6-dimethoxypyrimidin-2-yl)methyl)isoquinolin-1(2H)-one | m/z: [M + H]⁺376 |
| 16.69 | 6-bromo-2-(pyrazin-2-ylmethyl)isoquinolin-1(2H)-one | m/z: [M + H]⁺330 |
| 16.70 | 6-bromo-2((1,4-dimethyl-1H-imidazol-2-yl)methyl)isoquinolin-1(2H)-one | m/z: [M + H]⁺332 |
| 16.71 | 6-bromo-2-((1-isopropyl-1H-imidazol-2-yl)methyl)isoquinolin-1(2H)-one | m/z: [M + H]⁺346 |
| 16.72 | 6-bromo-2-(2-(pyridin-2-yl)ethyl)isoquinolin-1(2H)-one | m/z: [M + H]⁺329 |
| 16.73 | 6-bromo-2-(pyrimidin-2-yl)phthalazin-1(2H)-one | m/z: [M + H]⁺303 |
| 16.74 | 6-bromo-2-(pyrazin-2-ylmethyl)phthalazin-1(2H)-one | m/z: [M + H]⁺317 |
| 16.75 | 6-bromo-2-((4,6-dimethoxypyrimidin-2-yl)methyl)phthalazin-1(2H)-one | m/z: [M + H]⁺377 |

Embodiment 18: Synthesis of Compound 17.1

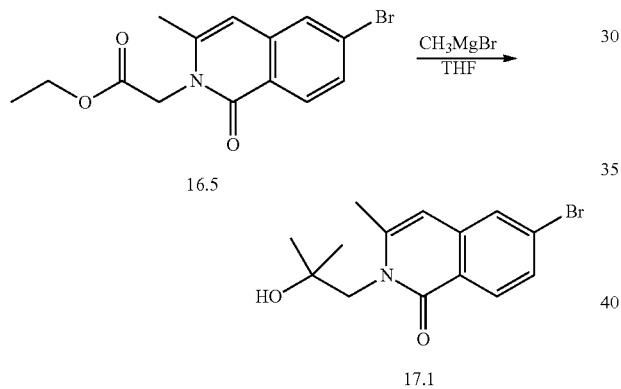

Compound 16.5 (50.0 mg, 0.154 mmol) was dissolved in THF (5 mL), the solution was cooled down to 0° C. with an ice-water bath, to this solution was added methyl magnesium bromide (0.18 mL, 3 M, 0.54 mmol) under N₂ protection. And then removed the ice-water bath and stirred at room temperature for 1.5 h, the aqueous solution of saturated ammonium chloride was added (20 mL), the mixture was extracted with ethyl acetate (20 mL×2), the combined organic layers were washed with brine, dried over anhydrous sodium sulfate, filtered and concentrated under reduced pressure. The residue was purified by prep-TLC (petroleum ether/ethyl acetate=1/1) to afford compound 17.1 (13 mg, yield: 27%) as a yellow solid.

m/z: [M+H] ⁺310

Embodiment 19: Synthesis of Compounds 17.2~17.5

Compounds 17.2~17.5 were synthesized following the synthetic method to the one used for Embodiment 18 compound 17.1, by replacing compound 16.5 to 16.6, 16.23, 16.26 or 16.27:

| No. | Chemical Name | MS |
|---|---|---|
| 17.2 | 6-bromo-2-(2-hydroxy-2-methylpropyl)isoquinolin-1(2H)-one | m/z: [M + H]$^+$296 |
| 17.3 | 6-bromo-2-(2-hydroxy-2-methylpropyl)-3,4-dihydroisoquinolin-1(2H)-one | m/z: [M + H]$^+$298 |
| 17.4 | 6-bromo-2-(2-hydroxy-2-methylpropyl)phthalazin-2(1H)-one | m/z: [M + H]$^+$297 |
| 17.5 | 7-bromo-3-(2-hydroxy-2-methylpropyl)quinazolin-4(3H)-one | m/z: [M + H]$^+$297 |

Embodiment 20: Synthesis of Compound 18.1

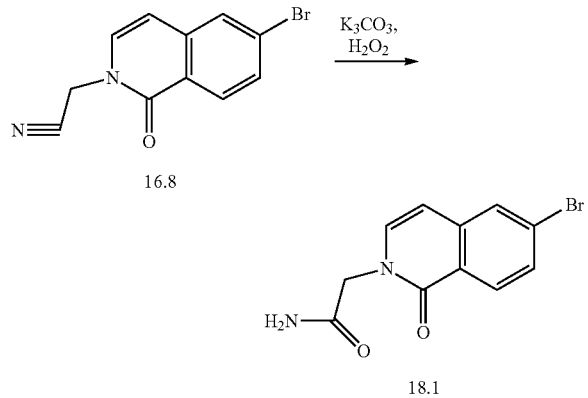

Compound 16.8 (0.2 g, 0.76 mmol), potassium carbonate (0.21 g, 1.52 mmol), hydrogen peroxide (0.5 mL, 30%) and DMSO (2.0 mL) were added into a 25 mL flask. The reaction system was stirred at room temperature for 1 h. Water was added, and then filtered, the filter cake was washed, afford compound 18.1 (160 mg, yield: 80%) as a light-yellow solid. m/z: [M+H]$^+$281

Embodiment 21: Synthesis of Compounds 18.2~18.4

Compounds 18.2~18.4 were synthesized following the synthetic method to the one used for Embodiment 20 compound 11.1, by replacing compound 16.8 to 16.14, 16.15 or 16.19:

| No. | Chemical Name | MS |
|---|---|---|
| 18.2 | 2-(6-bromo-3-methyl-1-oxoisoquinolin-2(1H)-yl)acetamide | m/z: [M + H]$^+$295 |
| 18.3 | 2-(7-bromo-4-oxoquinazolin-3(4H)-yl)acetamide | m/z: [M + H]$^+$282 |
| 18.4 | 2-(6-bromo-1-oxophthalazin-2(1H)-yl)acetamide | m/z: [M + H]$^+$282 |

Embodiment 22: Synthesis of Compound 19.1

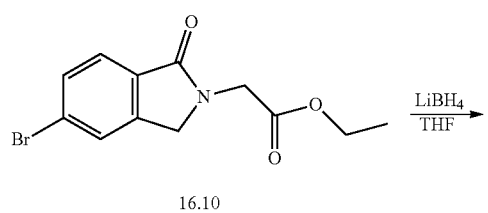

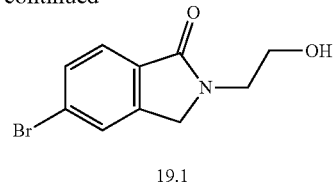

19.1

Compound 16.10 (55 mg, 0.18 mmol), lithium borohydride (0.5 mL, 2 M THF solution) and THF (1.0 mL) were added into a 25 mL, flask. The reaction system was stirred at room temperature for 2 h. Filtered, the filtrate was added into water (10 mL), the mixture was extracted with ethyl acetate (10 mL×2), the combined organic layers were washed with brine, dried over anhydrous sodium sulfate, filtered, the solvent was evaporated under reduced pressure, the residue was purified by column chromatography on silica gel (methanol/DCM=1/10) to afford compound 19.1 (23 mg, yield: 50%) as a white solid.
m/z: [M+H]$^+$256

Embodiment 23: Synthesis of Compound 19.2

Compound 19.2 was synthesized following the synthetic method to the one used for Embodiment 22 compound 19.1, by replacing compound 16.10 to 16.29:

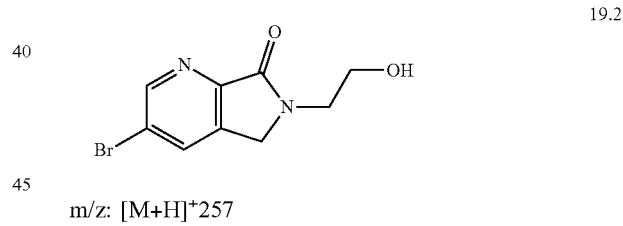

m/z: [M+H]$^+$257

Embodiment 24: Synthesis of Compound 20.2

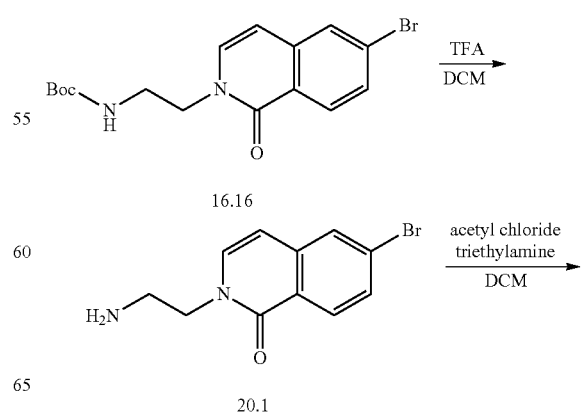

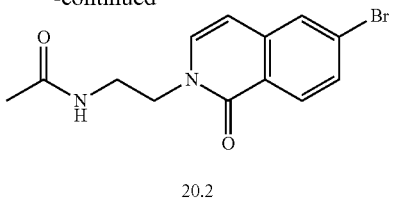

20.2

Step 1: Synthesis of Compound 20.1

Compound 16.16 (2.80 g, 7.62 mmol) was dissolved in DCM (30 mL), trifluoroacetic acid (TFA) (15 mL) was added under an ice-water bath, and then removed the ice-water bath and stirred at room temperature for 1 h. The mixture was directly concentrated to dryness under reduced pressure. The residue was adjusted to pH=7-8 with the aqueous solution of saturated sodium carbonate, extracted with ethyl acetate (50 mL×2), the combined organic layers were washed with brine, dried over anhydrous sodium sulfate. Filtered, the solvent was evaporated under reduced pressure to afford compound 20.1 (2.00 g, yield: 98%) as a yellow solid.

m/z: [M+H] $^+$267

Step 2: Synthesis of Compound 20.2

Compound 20.1 (150 mg, 0.56 mmol) and triethylamine (284 mg, 2.81 mmol) were added into DCM (3 mL), acetyl chloride (66 mg, 0.84 mmol) was added under an ice-water bath, and then removed the ice-water bath and stirred at room temperature for 2 h. To this solution was added water (5 mL), and extracted with DCM (10 mL×2), the combined organic layers were washed with brine, dried over anhydrous sodium sulfate. Filtered, the solvent was evaporated under reduced pressure to afford compound 20.2 (90 mg, yield: 52%) as a yellow solid.

m/z: [M+H] $^+$309

Embodiment 25: Synthesis of Compounds 20.3~20.6

Compounds 20.3~20.6 were synthesized following the synthetic method to the one used for Embodiment 24 compound 20.2, by reaction of methanesulfonyl chloride which was used in place of acetyl chloride in step 2, with compound 16.16, 16.55, 16.56 or 16.57:

| No. | Chemical Name | MS |
|---|---|---|
| 20.3 | N-(2-(6-bromo-1-oxoquinolin-2(1H)-yl)ethyl)methanesulfonamide | m/z: [M + H]$^+$345 |
| 20.4 | N-(2-(7-bromo-1-methyl-2,4-dioxo-1,2-dihydroquinazolin-3(4H)-yl)ethyl)methanesulfonamide | m/z: [M + H]$^+$376 |
| 20.5 | N-(2-(7-bromo-4-oxoquinazolin-3(4H)-yl)ethyl)methanesulfonamide | m/z: [M + H]$^+$346 |
| 20.6 | N-(2-(6-bromo-1-oxophthalazin-2(1H)-yl)ethyl)methanesulfonamide | m/z: [M + H]$^+$346 |

Embodiment 26: Synthesis of Compound 21.5

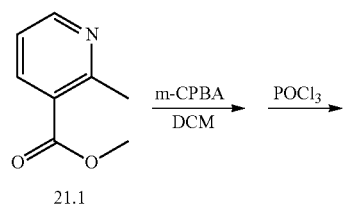

21.1

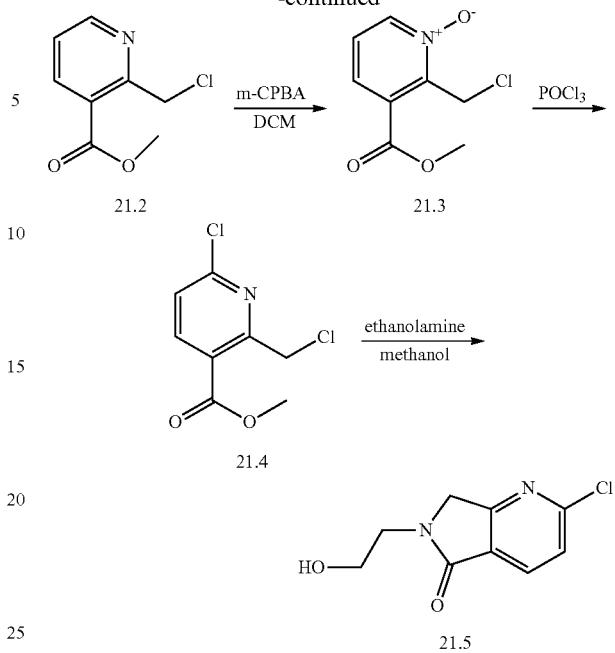

Step 1: Synthesis of Compound 21.2

Compound 21.1 (10.0 g, 66.2 mmol), m-chloroperbenzoic acid (m-CPBA) (16.3 g, 94.5 mmol) and DCM (140 mL) were added into a 250 mL flask. And stirred at room temperature for overnight, the aqueous solution of saturated sodium bicarbonate was added to adjusted pH to 7-8, the mixture was extracted with DCM (50 mL×2), the combined organic layers were washed with brine, dried over anhydrous sodium sulfate. Filtered, the solvent was distilled under reduced pressure. To the residue was added phosphorus oxychloride (60 mL), and heated to reflux and stirred for 4 h. The phosphorus oxychloride was evaporated under reduced pressure, the residue was poured into ice water and adjusted pH to neutral with sodium carbonate. Filtered, the solvent was evaporated under reduced pressure, the residue was purified by Flash column chromatography (petroleum ether/ethyl acetate=0%-30%) to afford compound 21.2 (1.94 g, yield: 16%) as an organe oil.

m/z: [M+H]$^+$186

Step 2: Synthesis of Compound 21.3

Compound 21.3 (1.94 g, 40.5 mmol), m-CPBA (2.25 g, 13.1 mmol) and DCM (25 mL) were added into a 100 mL flask. Stirred at room temperature for overnight, the aqueous solution of saturated sodium bicarbonate was added to adjusted pH to 7-8, the mixture was extracted with DCM (50 mL×2), the combined organic layers were washed with brine, dried over anhydrous sodium sulfate. Filtered and concentrated under reduced pressure to afford compound 21.3 (1.90 g, yield: 90%) as a white solid.

m/z: [M+H]$^+$202

Step 3: Synthesis of Compound 21.4

The compound 21.3 (1.90 g, 9.42 mmol) was added into phosphorus oxychloride (20 mL), and stirred at reflux for 4 h. The phosphorus oxychloride was evaporated under reduced pressure, the residue was poured into ice water and adjusted pH to neutral with sodium carbonate, the resulting mixture was extracted with ethyl acetate (50 mL×3), the combined organic layers were washed with brine, dried over anhydrous sodium sulfate, filtered and concentrated under reduced pressure, the residue was purified by Flash column chromatography (elution: ethyl acetate/petroleum ether=0%-50%) to afford compound 21.4 (1.40 g, yield: 68%) as a yellow solid.

m/z: [M+H]$^+$220

Step 4: Synthesis of Compound 21.5

Compound 21.4 (0.40 g, 1.82 mmol), ethanolamine (1.8 mL) and methanol (40 mL) were added into a 100 mL flask. Stirred at room temperature for overnight, the solvent was evaporated under reduced pressure, the residue was purified by Flash column chromatography (methanol/DCM=0%~5%) to afford compound 21.5 (0.37 g, yield: 95%) as a yellow oil.

m/z: [M+H]$^+$213

Embodiment 27: Synthesis of Compound 22.1

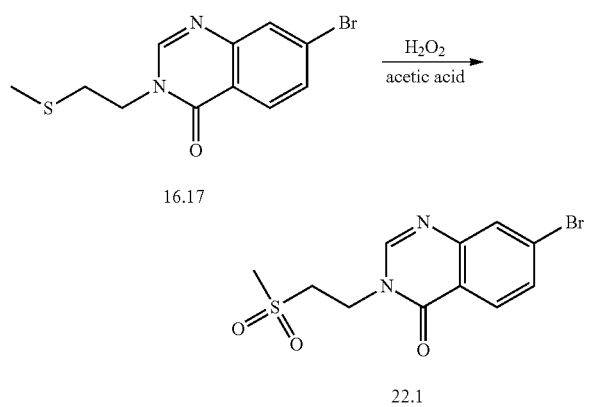

Compound 16.17 (500 mg, 1.67 mmol) was dissolved in acetic acid (2.5 mL), hydrogen peroxide (2.5 mL) was added dropwise under an ice-water bath, the system was stirred at room temperature for overnight. Part of the solvent was evaporated under reduced pressure by using a water pump, the residue was poured into water (100 mL), cooled down to 0° C. and stirred for 15 min and then filtered by using Buchner funnel, the obtained solid was washed with water (10 mL×2) and petroleum ether (10 mL×2) and dried over to afford compound 22.1 (460 mg, yield: 83%) as a white solid.

m/z: [M+H]$^+$331

Embodiment 28: Synthesis of Compounds 22.2~22.6

Compounds 22.2~22.6 were synthesized following the synthetic method to the one used for Embodiment 27 compound 22.1, by replacing compound 16.7 to 16.23, 16.25, 16.28, 16.31 or 16.58:

| No. | Chemical Name | MS |
|---|---|---|
| 22.2 | 7-bromo-1-methyl-3-(2-(methylsulfonyl)ethyl)quinazoline-2,4(1H,3H)-dione | m/z: [M + H]$^+$361 |
| 22.3 | 6-bromo-2-(2-(methylsulfonyl)ethyl)isoquinolin-1(2H)-one | m/z: [M + H]$^+$330 |
| 22.4 | 6-bromo-2-(2-(methylsulfonyl)ethyl)phthalazin-1(2H)-one | m/z: [M + H]$^+$331 |
| 22.5 | 6-bromo-2-(2-(methylsulfonyl)propyl)phthalazin-1(2H)-one | m/z: [M + H]$^+$345 |
| 22.6 | 6-bromo-2-(2-(ethylsulfonyl)ethyl)phthalazin-1(2H)-one | m/z: [M + H]$^+$345 |

Embodiment 29: Synthesis of Compounds 22.7-22.8

Compounds 22.7~22.8 were synthesized following the synthetic method to the one used for Embodiment 14 compound 24.1 in step 2, by reaction of compound 22.4 or 16.64 with bis(pinacolato)diboron:

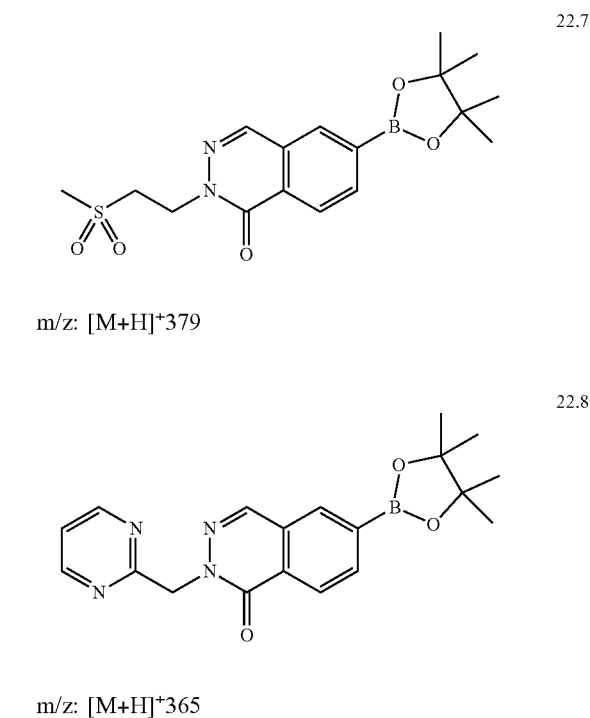

m/z: [M+H]$^+$379 m/z: [M+H]$^+$365

Embodiment 30: Synthesis of Compound 22.11

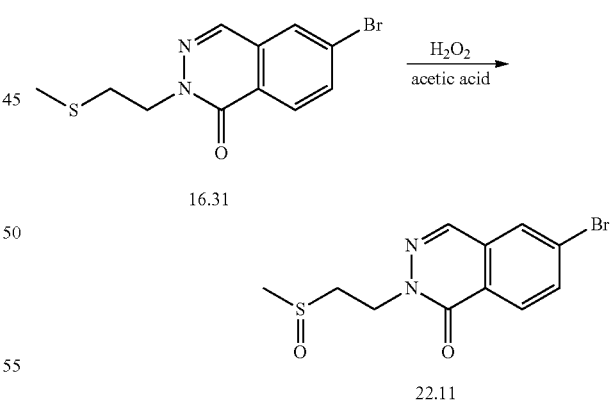

Compound 16.31 (1.22 g, 4.08 mmol) was dissolved in acetic acid (10 mL), hydrogen peroxide (10 mL) was added under an ice-water bath, the system was stirred at room temperature for 1.5 h. The reaction solution was poured into water (100 mL), the mixture was cooled down to 0° C. and adjusted pH to weak alkalinity with the aqueous solution of saturated sodium bicarbonate, extracted with 10% solution of methanol in DCM (30 mL×3), the combined organic layers were washed with brine, dried over anhydrous sodium sulfate, filtered and concentrated under reduced pressure to afford compound 22.11 (1.15 g, yield: 89%) as a light-yellow solid.

m/z: [M+H]⁺315

Embodiment 31: Synthesis of Compound 23.1

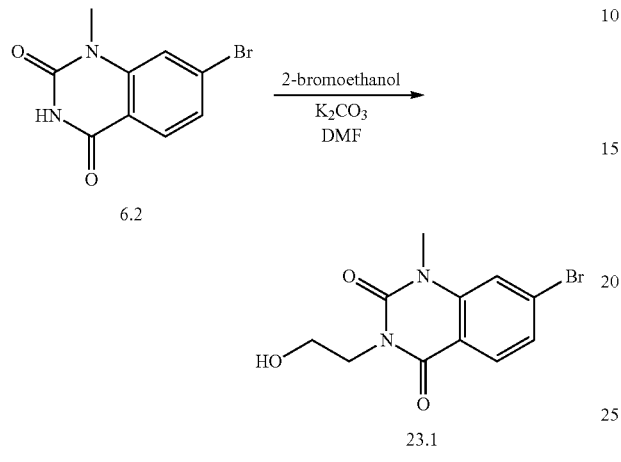

Compound 6.2 (150 mg, 0.59 mmol), 2-bromoethanol (81 mg, 0.65 mmol) and potassium carbonate (122 mg, 0.88 mmol) were added into DMF (8 mL), the system was stirred at 90° C. for 1 h. The reaction was quenched by addition of water after cooling down to room temperature, extracted with ethyl acetate, the combined organic layers were washed with brine, dried over anhydrous sodium sulfate. Filtered and concentrated, the residue was purified by column chromatography on silica gel (petroleum ether/ethyl acetate=1/1) to afford compound 23.1 (70 mg, yield: 27%) as a white solid.

m/z: [M+H]⁺299

Embodiment 32: Synthesis of Compound 24.1

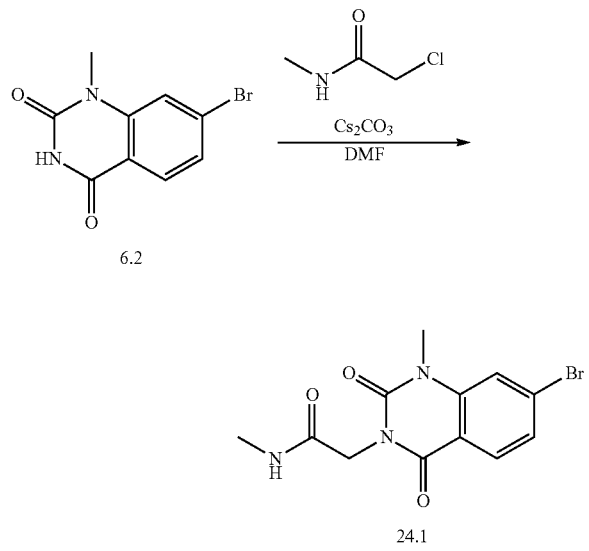

Compound 6.2 (150 mg, 0.59 mmol), 2-chloro-N-methylacetamide (70 mg, 0.65 mmol) and cesium carbonate (287 mg, 0.88 mmol) were dissolved in DMF (5 mL), the system was stirred at 75° C. for 2 h. The reaction was quenched by addition of water, and the solids precipitated out. Filtered and washed with water, the filter cake was dried over to afford compound 24.1 (85 mg, yield: 44%) as a gray solid.

m/z: [M+H]⁺326

Embodiment 33: Synthesis of Compound 24.2

Compound 24.2 was synthesized following the synthetic method to the one used for Embodiment 32 compound 24.1, by replacing 2-chloro-N-methylacetamide to 1-chloro-2-methyl-2-propanol:

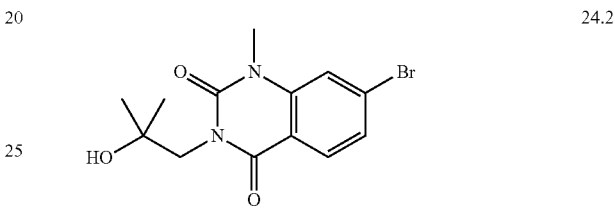

m/z: [M+H]⁺327

Embodiment 34: Synthesis of Compound 25.1

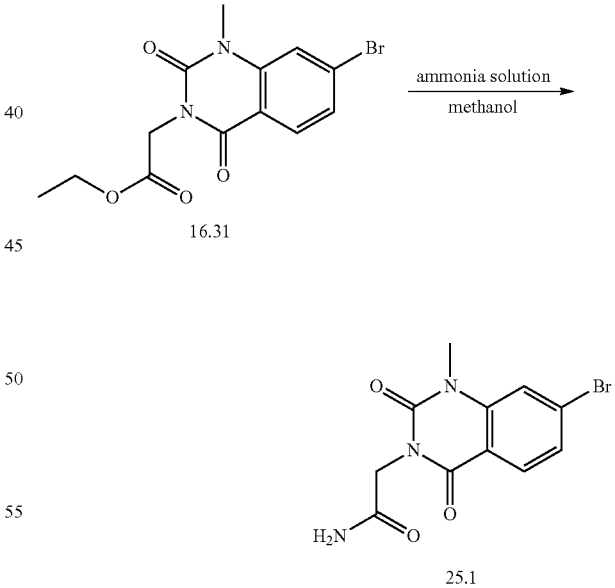

Compound 16.30 (0.3 g, 0.8 mmol), a solution of methylaminein in tetrahydrofuran (2.0 M, 10.0 mL) were added into a 25 mL sealing tube. The reaction system was stirred at room temperature for 12 h, and then filtered. The filter cake was washed with petroleum ether, dried over to afford compound 25.1 (180 mg, yield: 66%) as a white solid.

m/z: [M+H]⁺312

Embodiment 35: Synthesis of Compound 26.1

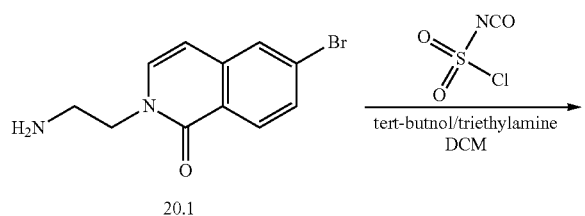

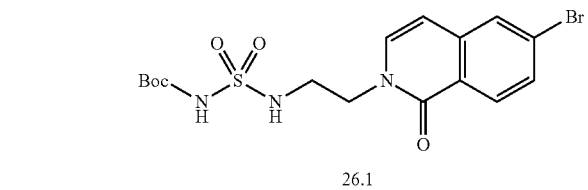

Chlorosulfonyl isocyanate (0.2 g, 1.41 mmol), tert-butanol (0.19 g, 2.54 mmol), DCM (3.0 mL) were added into a 25 mL flask. The reaction system was stirred at 0° C. for 1.5 h. And then to this solution was added compound 20.1 (0.38 g, 1.41 mmol) and a solution of triethylamine (0.71 g, 7.0 mmol) in DCM (2 mL) at 0° C. The resulting mixture was stirred at room temperature for 3 h. the reaction was quenched by addition of H$_2$O (20 mL), extracted with ethyl acetate (20 mL×2), the combined organic layers were washed with brine, dried over anhydrous sodium sulfate, filtered, the solvent was evaporated under reduced pressure, the residue was purified by column chromatography on silica gel (DCM/methanol=10/1) to afford compound 26.1 (0.26 g, yield: 42%) as a white solid.

m/z: [M+H]$^+$446

Embodiment 36: Synthesis of Compound 27.1

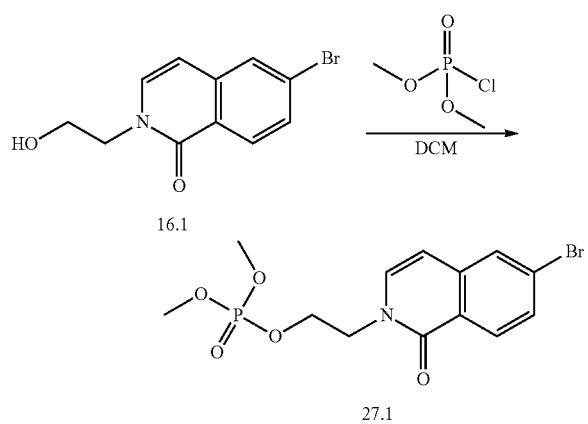

To an ice-cooling solution of compound 16.1 (100 mg, 0.373 mmol) and dimethyl phosphorochloridate (108 mg, 0.746 mmol) in DCM (5 mL) was added pyridine (148 mg, 1.86 mmol). The reaction system was stirred at room temperature for 1 h. Concentrated under reduced pressure, the residue was purified by prep-TLC (petroleum ether:ethyl acetate=1:1) to afford compound 27.1 (140 mg, yield: 99%) as a colorless oil.

m/z: [M+H]$^+$376

Embodiment 37: Synthesis of Compound 28.3

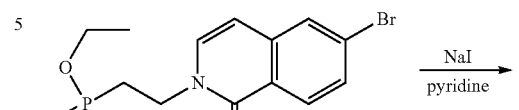

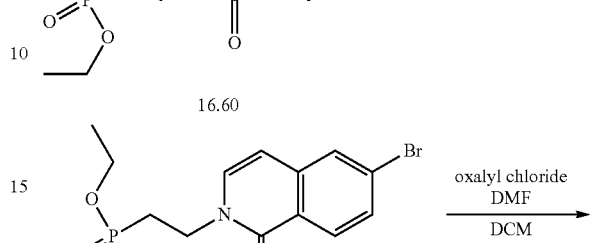

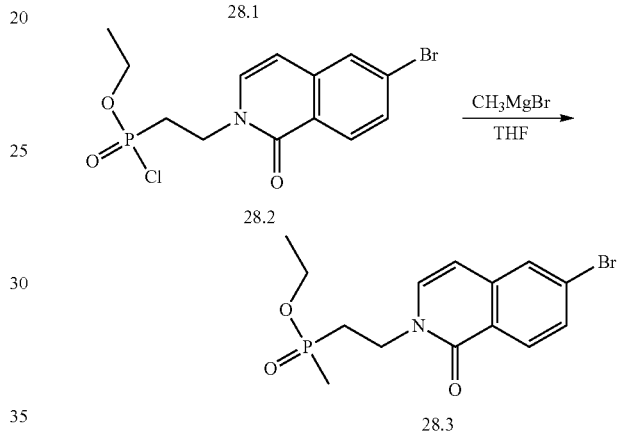

Step 1: Synthesis of Compound 28.1

Compound 16.60 (1.55 g, 3.99 mmol) and sodium iodide (1.79 g, 8.93 mmol) were added into pyridine (15 mL), the system was stirred at 115° C. for overnight. The system was cooled down to room temperature, and then concentrated under reduced pressure, the residue was dissolved in water, extracted with tert-butyl methyl ether to get rid of the impurity. The aqueous layer was adjusted to pH=2 with 2N hydrochloric acid, and then extracted with DCM. The combined organic layers were washed with brine, dried over anhydrous sodium sulfate, filtered and concentrated to afford compound 28.1 (1.15 g, yield: 80%) as a white solid.

m/z: [M+H]$^+$360

Step 2: Synthesis of Compound 28.2

Oxalyl chloride (0.81 g, 6.39 mmol) was added into DCM (20 mL), 2 drops DMF was added and then stirred at room temperature for 15 min. To this solution was added a solution of compound 28.1 (1.15 g, 3.19 mmol) in DCM (20 mL) dropwise. After stirred at room temperature for 40 min, then concentrated under reduced pressure to afford compound 1.4 (1.21 g, yield: 100%) as a yellow oil.

Step 3: Synthesis of Compound 28.3

To a solution of compound 28.2 (1.21 g, 3.19 mmol) in THF (50 mL) was added a solution of methyl magnesium bromide in ethyl ether (2.1 mL, 6.30 mmol, 3 M) at −30° C. The reaction system was stirred at −30° C. for 1.5 h and then quenched by addition of the aqueous solution of saturated ammonium chloride, extracted with ethyl acetate. The combined organic layers were washed with brine, dried over anhydrous sodium sulfate. Filtered and concentrated, the residue was purified by column chromatography on silica gel (DCM/methanol=10/1) to afford compound 28.3 (1.0 g, yield: 87%) as a yellow oil.

m/z: [M+H]$^+$358

Embodiment 38: Synthesis of Compound 28.4

Compound 28.4 was synthesized following the synthetic method to the one used for Embodiment 37 compound 28.3, by replacing compound 16.60 to compound 16.61:

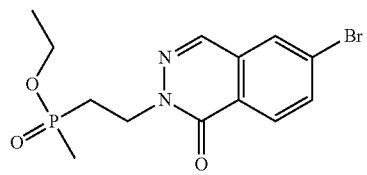

28.4 m/z: [M+H]$^+$359

Embodiment 39: Synthesis of Compound 29.1

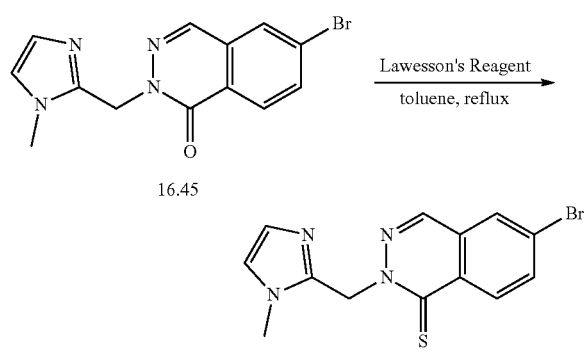

Compound 16.45 (100 mg, 0.314 mmol) and Lawesson's Reagent (380 mg, 0.942 mmol) were dissolved in toluene (3 mL), the system was stirred at 110° C. for 7 d. Concentrated under reduced pressure. The residue was purified by prep-TLC (DCM/methanol=20/1) to afford compound 29.1 (75 mg, yield: 71%) as a light-brown solid.

m/z: [M+H]$^+$334

Embodiment 40: Synthesis of Compound 29.2

Compound 29.2 was synthesized following the synthetic method to the one used for Embodiment 39 compound 29.1, by replacing compound 16.45 to compound 16.64:

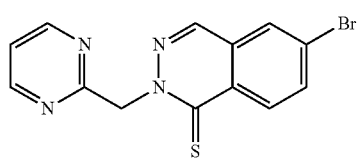

29.2 m/z: [M+H]$^+$335

Embodiment 41: Synthesis of Compound 30.1

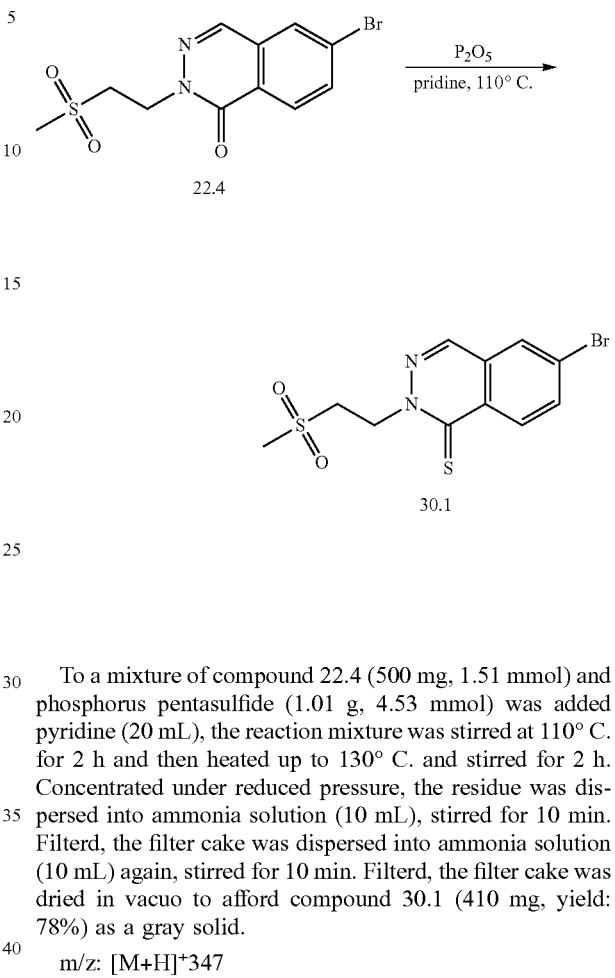

To a mixture of compound 22.4 (500 mg, 1.51 mmol) and phosphorus pentasulfide (1.01 g, 4.53 mmol) was added pyridine (20 mL), the reaction mixture was stirred at 110° C. for 2 h and then heated up to 130° C. and stirred for 2 h. Concentrated under reduced pressure, the residue was dispersed into ammonia solution (10 mL), stirred for 10 min. Filterd, the filter cake was dispersed into ammonia solution (10 mL) again, stirred for 10 min. Filterd, the filter cake was dried in vacuo to afford compound 30.1 (410 mg, yield: 78%) as a gray solid.

m/z: [M+H]$^+$347

Embodiment 42: Synthesis of Compounds 30.2~30.6

Compounds 30.2~30.6 were synthesized following the synthetic method to the one used for Embodiment 41 compound 30.1, by replacing compound 22.4 to compounds 16.42, 16.62, 16.68, 16.74 or 16.75:

| No. | Chemical Name | MS |
|---|---|---|
| 30.2 | 6-bromo-2-(pyrimidin-2-ylmethyl)isoquinoline-1(2H)-thione | m/z: [M + H]$^+$332 |
| 30.3 | 6-bromo-2-((4,6-dimethoxypyrimidin-2-yl)methyl)isoquinoline-1(2H)-thione | m/z: [M + H]$^+$392 |
| 30.4 | 6-bromo-2-(pyrazin-2-ylmethyl)isoquinoline-1(2H)-thione | m/z: [M + H]$^+$332 |
| 30.5 | 6-bromo-2-(pyrazin-2-ylmethyl)phthalazine-1(2H)-thione | m/z: [M + H]$^+$333 |
| 30.6 | 6-bromo-2-((4,6-dimethoxypyrimidin-2-yl)methyl)phthalazine-1(2H)-thione | m/z: [M + H]$^+$393 |

Embodiment 43: Synthesis of Compound 1-1-1

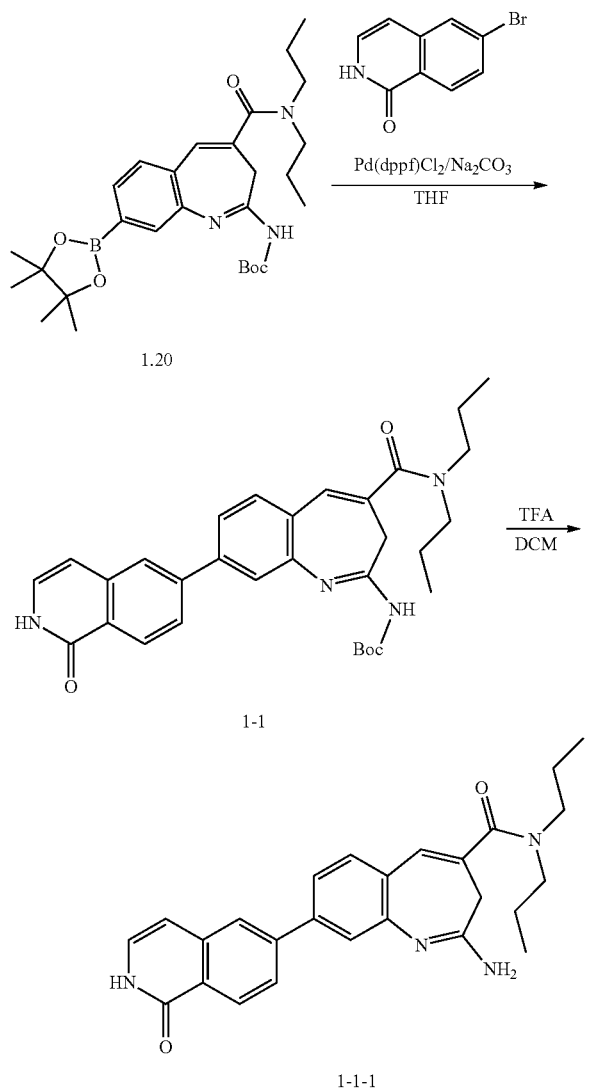

Step 1: Synthesis of Compound 1-1

To a solution of compound 1.20 (101 mg, 0.19 mmol) in THF (5 mL) was successively added 6-bromoisoquinolin-1 (2H)-one (44 mg, 0.2 mmol), aqueous solution of sodium carbonate (2.0 M, 2.0 mL) and Pd(dppf)Cl$_2$ (10 mg) under N$_2$ protection, after the addition, the reaction system was replaced 3 times by N$_2$, stirred at 70° C. for 20 min to 2 h, until TLC detected the reaction was completed. The reaction was quenched by addition of water (10 mL), the mixture was extracted with ethyl acetate (10 mL×2), the combined organic layers were washed with brine, separation of organic layer, dried over anhydrous sodium sulfate, filtered and concentrated, the residue was purified by column chromatography on silica gel (petroleum ether/ethyl acetate=1/1) to afford compound 1-1 (44 mg, yield: 43%) as a colorless oil.

Step 2: Synthesis of Compound 1-1-1

To an ice-cooling solution of compound 1-1 (20 mg, 0.04 mmol) in DCM (2 mL) was added TFA (2 mL), after the addition, the reaction system was stirred at 0° C. for 20 min. Concentrated under reduced pressure to remove the solvent, the residue was washed by a solution of 50% ethyl acetate in petroleum ether, filtered to afford compound 1-1-1 (9.4 mg, yield: 44%) as a white solid.

$^1$H NMR (400 MHz, CD$_3$OD): δ 8.37 (d, J=8.0 Hz, 1H), 7.95 (s, 1H), 7.84 (d, J=8.0 Hz, 1H), 7.54 (s, 1H), 7.46 (s, 2H), 7.21 (d, J=8.0 Hz, 1H), 6.91 (s, 1H), 6.77 (d, J=8.0 Hz, 1H), 3.43 (t, J=7.0 Hz, 4H), 3.30 (s, 2H), 1.76-1.61 (m, 4H), 1.08-0.79 (m, 6H); m/z: [M+H]$^+$ 429.

Embodiment 44: Synthesis of Compounds 1-1-2~1-2-4

Compounds 1-1-2~1-1-4 were synthesized following the synthetic method to the one used for Embodiment 43 compound 1-1-1, by reaction of compound 1.8 which was used in place of compound 1.20 in step 1, with compound 15.1, 15.9 or 15.10:

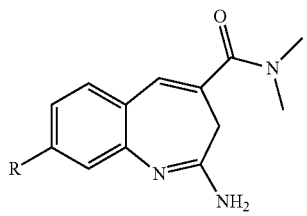

1-1-2~1-1-4

| No. | R | $^1$H NMR and/or MS |
|---|---|---|
| 1-1-2 | ![structure: 2-ethyl-1-oxo-1,2-dihydroisoquinolin-6-yl] | $^1$H NMR (400 MHz, CD$_3$OD): δ 8.43 (d, J = 8.0 Hz, 1 H), 7.97 (d, J = 1.6 Hz, 1 H), 7.87-7.81 (m, 2 H), 7.75 (d, J = 1.6 Hz, 1 H), 7.71-7.69 (m, 1 H), 7.45 (d, J = 4.0 Hz, 1 H), 7.18 (s, 1 H), 6.80 (d, J = 8.0 Hz, 1 H), 4.12 (q, J = 8.0 Hz, 2 H), 3.37 (s, 2 H), 3.24-3.09 (m, 6 H), 1.38 (t, J = 8.0 Hz, 3 H); m/z: [M + H]$^+$ 401. |

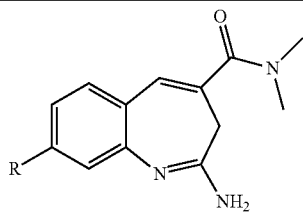

1-1-2~1-1-4

| No. | R | ¹H NMR and/or MS |
|---|---|---|
| 1-1-3 | (5-ethyl-4-oxo-thieno[3,2-c]pyridin-2-yl) | ¹H NMR (400 MHz, CD₃OD): δ 7.99 (s, 1 H), 7.78 (d, J = 8.4 Hz, 1 H), 7.73 (s, 1 H), 7.64 (d, J = 8.4 Hz, 1 H), 7.57 (d, J = 6.8 Hz, 1 H), 7.15 (s, 1 H), 6.98 (d, J = 7.2 Hz, 1 H), 4.15 (q, J = 7.2 Hz, 2 H), 3.39 (s, 2 H), 3.24 (br. s, 3 H), 3.10 (br. s, 3 H), 1.40 (t, J = 7.6 Hz, 3 H); m/z: [M + H]⁺ 407. |
| 1-1-4 | (1,5-diethyl-4-oxo-pyrrolo[3,2-c]pyridin-2-yl) | ¹H NMR (400 MHz, CD₃OD): δ 7.70 (d, J = 7.6 Hz, 1 H), 7.63 (d, J = 7.6 Hz, 1 H), 7.58 (s, 1 H), 7.45 (d, J = 7.2 Hz, 1 H), 7.20 (s, 1 H), 6.92 (s, 1 H), 6.78 (d, J = 7.2 Hz, 1 H), 4.15 (q, J = 7.2 Hz, 2 H), 3.83 (s, 3 H), 3.40 (s, 2 H), 3.26 (br. s, 3 H), 3.11 (br. s, 3 H), 1.39 (t, J = 7.2 Hz, 3 H); m/z: [M + H]⁺ 404. |

Embodiment 45: Synthesis of Compounds 1-2-1~1-2-51

Compounds 1-2-1~1-2-51 were synthesized following the synthetic method to the one used for Embodiment 43 compound 1-1-1, by reaction of corresponding compound 15.1, 15.5, 15.6, 15.7, 15.8, 16.1, 16.2, 16.3, 16.9, 16.11, 16.12, 16.13, 16.16, 16.22, 16.25, 17.1, 17.2, 18.1, 18.2, 20.3, 22.3, 26.1, 16.33, 16.34, 16.35, 16.37, 16.38, 16.40, 16.41, 16.42, 16.43, 16.45, 16.46, 16.47, 16.48, 16.49, 16.50, 16.51, 16.52, 16.53, 16.54, 16.59, 16.62, 16.68, 16.69, 16.70, 16.71, 16.72, 27.1 or 28.3 which was used in place of 6-bromoisoquinolin-1(2H)-one in step 1, with compound 1.20:

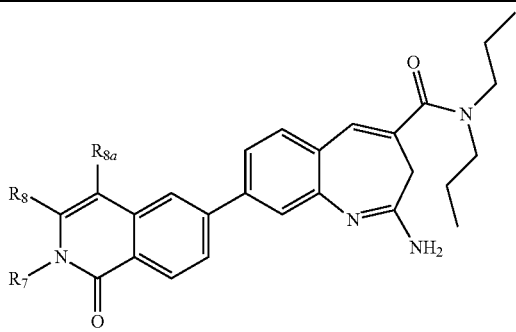

1-2-1~1-2-50

| No. | R₇ | R₈ | R₈ₐ | ¹H NMR and/or MS |
|---|---|---|---|---|
| 1-2-1 | ethyl | (cyclopentyl-methyl fused) | | ¹H NMR (400 MHz, CD₃OD): δ 8.44-8.38 (m, 1 H), 7.85-7.75 (m, 4 H), 7.70-7.66 (m, 1 H), 7.10 (s, 1 H), 4.15 (q, J = 7.2 Hz, 2 H), 3.54-3.42 (m, 4 H), 3.38 (s, 2 H), 3.20-3.13 (m, 2 H), 3.12-3.06 (m, 2 H), 2.36-2.25 (m, 2 H), 1.78-1.65 (m, 4 H), 1.36 (t, J = 7.2 Hz, 3 H), 1.04-0.87 (m, 6 H); m/z: [M + H]⁺ 497 |
| 1-2-2 | ethyl | methyl | H | ¹H NMR (400 MHz, CD₃OD): δ 8.36 (d, J = 8.4 Hz, 1 H), 7.89-7.72 (m, 4 H), 7.67 (d, J = 8.0 Hz, 1 H), 7.10 (s, 1 H), 6.67 (s, 1 H), 4.24 (q, J = 7.2 Hz, 2 H), 3.54-3.41 (m, 4 H), 3.37 (s, 2 H), 2.55 (s, 3 H), 1.77-1.65 (m, 4 H), 1.35 (t, J = 7.2 Hz, 3 H), 1.05-0.86 (m, 6 H); m/z: [M + H]⁺ 471. |

-continued

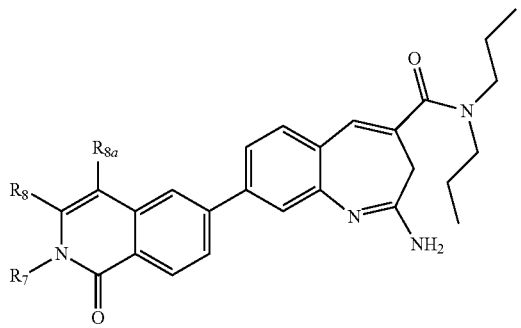

1-2-1~1-2-50

| No. | R$_7$ | R$_8$ | R$_{8a}$ | $^1$H NMR and/or MS |
|---|---|---|---|---|
| 1-2-3 | ethyl | H | H | $^1$H NMR (400 MHz, CD$_3$OD): δ 8.43-8.39 (m, 1 H), 7.94 (s, 1 H), 7.85-7.84 (m, 1 H), 7.66-7.65 (m, 2 H), 7.58-7.57 (m, 1 H), 7.44-7.43 (m, 1 H), 7.01 (s, 1 H), 6.81-6.79 (m, 1 H), 4.12 (q, J = 6.0 Hz, 2 H), 3.74-3.73 (m, 2 H), 3.46 (br. s, 2 H), 3.03-3.01 (m, 2 H), 1.71-1.68 (m, 4 H), 1.39 (t, J = 4.8 Hz, 3 H), 0.98-0.91 (m, 6 H); m/z: [M + H]$^+$ 457. |
| 1-2-4 | propyl | H | H | $^1$H NMR (400 MHz, CD$_3$OD): δ 8.42 (d, J = 7.6 Hz, 1 H), 7.97 (br. s, 1 H), 7.88-7.78 (m, 2 H), 7.75 (br. s, 1 H), 7.68 (d, J = 7.6 Hz, 1 H), 7.44 (d, J = 8.0 Hz, 1 H), 7.10 (br. s, 1 H), 6.79 (d, J = 7.0 Hz, 1 H), 4.04 (br. s, 2 H), 3.47 (br. s, 4 H), 3.37 (br. s, 2 H), 1.88-1.62 (m, 6 H), 1.02-0.87 (m, 9 H); m/z: [M + H]$^+$ 471. |
| 1-2-5 | Iso-propyl | H | H | $^1$H NMR (400 MHz, CD$_3$OD): δ 8.43 (d, J = 8.4 Hz, 1 H), 7.98 (s, 1 H), 7.89-7.81 (m, 2 H), 7.76 (s, 1 H), 7.68 (d, J = 8.4 Hz, 1 H), 7.41 (d, J = 7.2 Hz, 1 H), 7.10 (s, 1 H), 6.78 (d, J = 7.2 Hz, 1 H), 3.90 (d, J = 7.2 Hz, 2 H), 3.57-3.41 (m, 4 H), 3.37 (s, 2 H), 2.29-2.16 (m, 1 H), 1.78-1.64 (m, 4 H), 1.05-0.88 (m, 12 H); m/z: [M + H]$^+$ 485. |
| 1-2-6 | ![HO-CH2-CH(-)-CH3] | H | H | $^1$H NMR (400 MHz, CD$_3$OD): δ 8.45 (d, J = 8.8 Hz, 1 H), 8.00 (s, 1 H), 7.89-7.84 (m, 2 H), 7.78 (s, 1 H), 7.71 (d, J = 8.0 Hz, 1H), 7.46 (d, J = 7.2 Hz, 1 H), 7.13 (s, 1 H), 6.80 (d, J = 7.6 Hz, 1 H), 4.21 (t, J = 5.6 Hz, 2 H), 3.92 (t, J = 5.6 Hz, 2 H), 3.50 (br. s, 4 H), 3.32 (overlapping with solvent, 2 H), 1.77-1.68 (m, 4 H), 0.93 (br. s, 6 H); m/z: [M + H]$^+$ 473. |
| 1-2-7 | ![HO-CH2CH2CH2-CH(-)-CH3] | H | H | $^1$H NMR (400 MHz, CD$_3$OD): δ 8.44 (d, J = 8.4 Hz, 1 H), 7.98 (d, J = 1.6 Hz, 1 H), 7.89-7.81 (m, 2 H), 7.76 (d, J = 1.6 Hz, 1 H), 7.69 (d, J = 8.4 Hz, 1 H), 7.46 (d, J = 7.2 Hz, 1 H), 7.11 (s, 1 H), 6.81 (d, J = 7.6 Hz, 1 H), 4.18 (t, J = 7.2 Hz, 2 H), 3.63 (t, J = 6.0 Hz, 2 H), 3.56-3.42 (m, 4 H), 3.40-3.34 (m, 2 H), 2.06-1.97 (m, 2 H), 1.77-1.65 (m, 4 H), 1.06-0.84 (m, 6 H); m/z: [M + H]$^+$ 487. |
| 1-2-8 | ![HO-CH2-CH(-)-CH3] | methyl | H | $^1$H NMR (400 MHz, CD$_3$OD): δ 8.38-8.33 (m, 1 H), 7.89-7.85 (m, 1 H), 7.84-7.80 (m, 1 H), 7.79-7.76 (m, 1 H), 7.75-7.73 (m, 1 H), 7.70-7.67 (m, 1 H), 7.11 (s, 1 H), 6.67, 6.55 (two s, 1 H), 4.31 (t, J = 5.6 Hz, 2 H), 3.90 (t, J = 5.6 Hz, 2 H), 3.56-3.42 (m, 4 H), 3.40-3.36 (m, 2 H), 2.59, 2.35 (two s, 3 H), 1.77-1.65 (m, 4 H), 1.04-0.85 (m, 6 H); m/z: [M + H]$^+$ 487. |
| 1-2-9 | ![HO-C(CH3)2-CH2-CH(-)-CH3] | methyl | H | $^1$H NMR (400 MHz, CD$_3$OD): δ 8.37 (d, J = 8.8 Hz, 1 H), 7.88-7.73 (m, 4 H), 7.68 (d, J = 8.0 Hz, 1 H), 7.11 (s, 1 H), 6.68 (s, 1 H), 4.37-4.28 (m, 2 H), 3.55-3.42 (m, 4 H), 3.39-3.34 (m, 2 H), 2.66, 2.62 (two, s, 3 H), 1.77-1.65 (m, 4 H), 1.28 (s, 6 H), 1.05-0.86 (m, 6 H); m/z: [M + H]$^+$ 515. |
| 1-2-10 | ![H2N-C(=O)-CH2-] | H | H | $^1$H NMR (400 MHz, CD$_3$OD): δ 8.38 (d, J = 8.0 Hz, 1 H), 7.96 (s, 1 H), 7.84-7.89 (m, 2 H), 7.74 (s, 1 H), 7.66 (d, J = 8.0 Hz, 1 H), 7.36 (d, J = 4.0 Hz, 1 H), 7.08 (s, 1 H), 6.77 (d, J = 4.0 Hz, 1 H), 4.74 (s, 2 H), 3.47 (br. s, 4 H), 3.34 (s, 2 H), 1.73-1.67 (m, 4 H), 0.93 (br. s, 6 H); m/z: [M + H]$^+$ 486. |

-continued

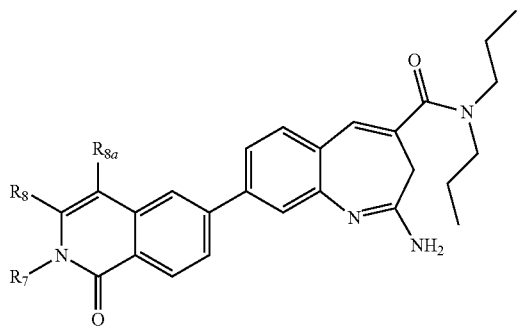

1-2-1~1-2-50

| No. | R$_7$ | R$_8$ | R$_{8a}$ | $^1$H NMR and/or MS |
|---|---|---|---|---|
| 1-2-11 | ethyl(methyl)phosphinyl-ethyl | H | H | $^1$H NMR (400 MHz, CD$_3$OD): δ 8.42 (d, J = 8.8 Hz, 1 H), 7.98 (d, J = 1.6 Hz, 1 H), 7.89-7.84 (m, 1 H), 7.84-7.79 (m, 1 H), 7.76 (d, J = 1.6 Hz, 1 H), 7.68 (d, J = 8.0 Hz, 1 H), 7.48 (d, J = 7.2 Hz, 1 H), 7.10 (s, 1 H), 6.81 (d, J = 7.6 Hz, 1 H), 4.41-4.21 (m, 2 H), 4.06 (q, J = 7.2 Hz, 2 H), 3.48 (br. s, 4 H), 3.40-3.34 (m, 2 H), 2.51-2.31 (m, 2 H), 1.76-1.65 (m, 4 H), 1.60 (d, J = 14.0 Hz, 3 H), 1.26 (t, J = 7.2 Hz, 3 H), 0.95 (br. s, 6 H); m/z: [M + H]$^+$ 563. |
| 1-2-12 | 2-(dimethylamino)ethyl | H | H | $^1$H NMR (400 MHz, CD$_3$OD): δ 8.45-8.39 (m, 1 H), 7.98 (s, 1 H), 7.91-7.85 (m, 1 H), 7.76-7.70 (m, 2 H), 7.63-7.61 (m, 1 H), 7.45 (d, J = 8.0 Hz, 1 H), 7.04 (s, 1 H), 6.83 (d, J = 8.0 Hz, 1 H), 4.60 (br. s, 2 H), 4.35 (t, J = 6.4 Hz, 2 H), 3.52-3.38 (m, 4 H), 3.25-3.24 (m, 2 H), 2.74 (s, 6 H), 1.74-1.64 (m, 4 H), 1.00-0.85 (m, 6 H); m/z: [M + H]$^+$ 500. |
| 1-2-13 | 3-hydroxy-3-methylbutyl | H | H | $^1$H NMR (400 MHz, CD$_3$OD): δ 8.44 (d, J = 8.4 Hz, 1 H), 8.00 (s, 1 H), 7.88-7.83 (m, 2 H), 7.78 (s, 1 H), 7.70 (d, J = 8.0 Hz, 1 H), 7.51 (d, J = 7.6 Hz, 1 H), 7.12 (s, 1 H), 6.77 (d, J = 7.2 Hz, 1 H), 4.15 (s, 2 H), 3.50 (br. s, 4 H), 3.39 (s, 2 H), 1.75-1.70 (m, 4 H), 1.27 (s, 6 H) 0.98 (br. s, 6 H); m/z: [M + H]$^+$ 501. |
| 1-2-14 | 2-methoxyethyl | H | H | $^1$H NMR (400 MHz, CD$_3$OD): δ 8.44 (d, J = 8.4 Hz, 1 H), 8.00 (s, 1 H), 7.89-7.84 (m, 2 H), 7.79 (s, 1 H), 7.71 (d, J = 8.4 Hz, 1 H), 7.44 (d, J = 7.2 Hz, 1 H), 7.12 (s, 1 H), 6.78 (d, J = 7.6 Hz, 1 H), 4.27 (t, J = 5.2 Hz, 2 H), 3.76 (t, J = 5.2 Hz, 2 H), 3.50 (br. s, 4 H), 3.37 (s, 3 H), 3.33 (overlapping with solvent, 2 H), 1.76-1.70 (m, 4 H), 0.98 (br. s, 6 H); m/z: [M + H]$^+$ 487. |
| 1-2-15 | tert-butyl | H | H | $^1$H NMR (400 MHz, CD$_3$OD): δ 8.44 (d, J = 8.8 Hz, 1 H), 8.00 (s, 1 H), 7.89-7.84 (m, 2 H), 7.79 (s, 1 H), 7.71 (d, J = 8.4 Hz, 1 H), 7.41 (d, J = 7.2 Hz, 1 H), 7.12 (s, 1 H), 6.71 (d, J = 7.6 Hz, 1 H), 4.00 (s, 2 H), 3.50 (br. s, 4 H), 3.38 (s, 2 H), 1.77-1.68 (m, 4 H), 1.05 (s, 9 H), 0.98 (br. s, 6 H); m/z: [M + H]$^+$ 499. |
| 1-2-16 | 3-amino-3-oxopropyl | methyl | H | $^1$H NMR (400 MHz, CD$_3$OD): δ 8.35 (d, J = 8.4 Hz, 1 H), 7.89-7.86 (m, 1 H), 7.84-7.80 (m, 1 H), 7.80-7.76 (m, 1 H), 7.76-7.73 (m, 1 H), 7.68 (d, J = 8.4 Hz, 1 H), 7.11 (s, 1 H), 6.68 (s, 1 H), 4.91 (s, 2 H), 3.56-3.41 (m, 4 H), 3.40-3.33 (m, 2 H), 2.45 (s, 3 H), 1.79-1.64 (m, 4 H), 1.06-0.85 (m, 6 H); m/z: [M + H]$^+$ 500. |
| 1-2-17 | 2-aminoethyl | H | H | $^1$H NMR (400 MHz, CD$_3$OD): δ 8.46 (d, J = 8.4 Hz, 1 H), 8.03-8.00 (m, 1 H), 7.93-7.88 (m, 1 H), 7.85-7.81 (m, 1 H), 7.80-7.77 (m, 1 H), 7.69 (d, J = 8.4 Hz, 1 H), 7.42 (d, J = 7.6 Hz, 1 H), 7.10 (s, 1 H), 6.85 (d, J = 7.6 Hz, 1 H), 4.36 (t, J = 5.8 Hz, 2 H), 3.56-3.42 (m, 4 H), 3.42-3.35 (m, 4 H), 1.77-1.65 (m, 4 H), 1.06-0.85 (m, 6 H); m/z: [M + H]$^+$ 472. |

-continued

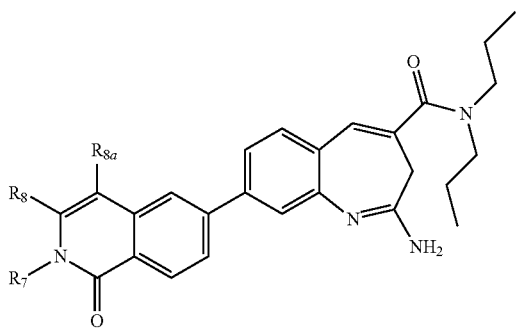

1-2-1~1-2-50

| No. | R_7 | R_8 | R_{8a} | $^1$H NMR and/or MS |
|---|---|---|---|---|
| 1-2-18 | (acetamido-ethyl) | H | H | $^1$H NMR (400 MHz, CD$_3$OD): δ 8.43 (d, J = 8.4 Hz, 1 H), 7.97 (d, J = 1.6 Hz, 1 H), 7.89-7.80 (m, 2 H), 7.76 (d, J = 1.6 Hz, 1 H), 7.69 (d, J = 8.0 Hz, 1 H), 7.35 (d, J = 7.2 Hz, 1 H), 7.11 (s, 1 H), 6.78 (d, J = 7.2 Hz, 1 H), 4.17 (t, J = 6.0 Hz, 2 H), 3.59 (t, J = 5.8 Hz, 2 H), 3.56-3.39 (m, 4 H), 3.38-3.32 (m, 2 H), 1.89 (s, 3 H), 1.77-1.64 (m, 4 H), 1.06-0.85 (m, 6 H); m/z: [M + H]$^+$ 514. |
| 1-2-19 | (methanesulfonamido-ethyl) | H | H | $^1$H NMR (400 MHz, CD$_3$OD): δ 8.43 (d, J = 8.4 Hz, 1 H), 7.97 (d, J = 1.6 Hz, 1 H), 7.87-7.81 (m, 2 H), 7.76 (s, 1 H), 7.68 (d, J = 8.0 Hz, 1 H), 7.43 (d, J = 7.2 Hz, 1 H), 7.10 (s, 1 H), 6.79 (d, J = 7.2 Hz, 1 H), 4.19 (t, J = 6.0 Hz, 2 H), 3.56-3.39 (m, 6 H), 3.36-3.32 (m, 2 H), 2.90 (s, 3 H), 1.78-1.64 (m, 4 H), 1.08-0.84 (m, 6 H); m/z: [M + H]$^+$ 550. |
| 1-2-20 | (sulfamoylamino-ethyl) | H | H | $^1$H NMR (400 MHz, CD$_3$OD): δ 8.42 (d, J = 8.0 Hz, 1 H), 7.97 (d, J = 4.0 Hz, 1 H), 7.85 (dd, J = 4.0, 8.0 Hz, 1 H), 7.79 (dd, J = 8.0, 4.0 Hz, 1 H), 7.73 (s, 1 H), 7.66 (d, J = 8.0 Hz, 1 H), 7.46 (d, J = 8.0 Hz, 1 H), 7.08 (s, 1 H), 6.82-6.72 (m, 1 H), 4.27-4.17 (m, 2 H), 3.77-3.69 (m, 1 H), 3.59-3.36 (m, 6 H), 3.04-2.97 (m, 1H), 1.65-1.75 (m, 4 H), 1.01-0.84 (m, 6 H); m/z: [M + H]$^+$ 551. |
| 1-2-21 | (N-methylcarbamoyl-methyl) | H | H | $^1$H NMR (400 MHz, CD$_3$OD): δ 8.40 (d, J = 8.4 Hz, 1 H), 7.98 (d, J = 1.6 Hz, 1 H), 7.84-7.81 (m. 2 H), 7.75 (d, J = 1.6 Hz, 1 H), 7.68 (d, J = 8.4 Hz, 1 H), 7.38 (d, J = 7.2 Hz, 1 H), 7.10 (s, 1 H), 6.79 (d, J = 7.2 Hz, 1 H), 4.70 (s, 2 H), 3.47 (br. s, 4 H), 3.37 (s, 2 H), 2.78 (s, 3 H), 1.73-1.68 (m, 4 H), 0.95-0.90 (m, 6 H); m/z: [M + H]$^+$ 500. |
| 1-2-22 | (methylthio-ethyl) | H | H | $^1$H NMR (400 MHz, CD$_3$OD): δ 8.43 (d, J = 8.4 Hz, 1 H), 7.99 (s, 1 H), 7.88-7.82 (m, 2 H), 7.76 (s, 1 H), 7.68 (d, J = 8.8 Hz, 1 H), 7.48 (d, J = 7.2 Hz, 1 H), 7.11 (s, 1 H), 6.79 (d, J = 6.8 Hz, 1 H), 4.27 (t, J = 7.2 Hz, 2 H), 3.48 (br. s, 4 H), 3.31 (overlapping with solvent, 2 H), 2.93 (t, J = 6.8 Hz, 2 H), 2.15 (s, 3 H), 1.74-1.66 (m, 4 H), 0.98 (br. s, 6 H); m/z: [M + H]$^+$ 503. |
| 1-2-23 | (methylsulfonyl-ethyl) | H | H | $^1$H NMR (400 MHz, CD$_3$OD): δ 8.41 (d, J = 8.8 Hz, 1 H), 7.95 (d, J = 1.6 Hz, 1 H), 7.84 (dd, J = 8.0, 2.0 Hz, 1 H), 7.80 (dd, J = 8.0, 2.0 Hz, 1H), 7.74 (d, J = 1.6 Hz, 1 H), 7.67 (d, J = 8.0 Hz, 1 H), 7.47 (d, J = 7.6 Hz, 1 H), 7.08 (s, 1 H), 6.78 (d, J = 7.2 Hz, 1 H), 4.53 (t, J = 6.4 Hz, 2 H), 3.69 (t, J = 6.4 Hz, 2 H), 3.50 (br. s, 4 H), 3.33 (overlapping with solvent, 2 H), 3.06 (s, 3 H), 1.76-1.70 (m, 4 H), 0.98 (br. s, 6 H); m/z: [M + H]$^+$ 535. |
| 1-2-24 | (N,N-dimethylcarbamoyl-methyl) | H | H | $^1$H NMR (400 MHz, CD$_3$OD): δ 8.43 (d, J = 8.4 Hz, 1 H), 8.00 (d, J = 1.6 Hz, 1 H), 7.88-7.83 (m, 2 H), 7.78 (d, J = 1.6 Hz, 1 H), 7.70 (d, J = 8.2 Hz, 1 H), 7.36 (d, J = 7.4 Hz, 1 H), 7.12 (s, 1 H), 6.81 (d, J = 7.2 Hz, 1 H), 4.99 (s, 2 H), 3.50 (br. s, 4 H), 3.42-3.36 (m, 2 H), 3.23 (s, 3 H), 3.03 (s, 3 H), 1.79-1.67 (m, 4 H), 0.98 (br. s, 6 H); m/z: [M + H]$^+$ 514. |

-continued

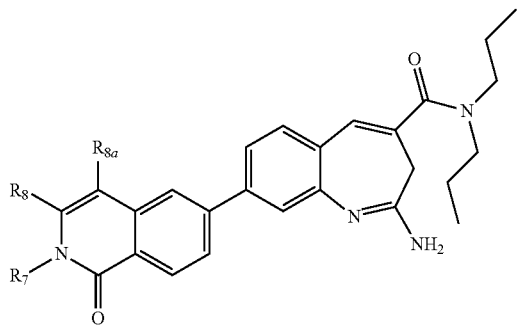

1-2-1~1-2-50

| No. | R₇ | R₈ | R₈ₐ | ¹H NMR and/or MS |
|---|---|---|---|---|
| 1-2-25 | ethylcarbamoylmethyl (CH₂C(O)NHEt) | H | H | ¹H NMR (400 MHz, CD₃OD): δ 8.42 (d, J = 8.4 Hz, 1 H), 8.00 (d, J = 1.6 Hz, 1 H), 7.89-7.86 (m, 1 H), 7.82-7.79 (m, 1 H), 7.75 (d, J = 1.4 Hz, 1 H), 7.68 (d, J = 8.4 Hz, 1 H), 7.40 (d, J = 7.6 Hz, 1 H), 7.10 (s, 1 H), 6.81 (d, J = 7.6 Hz, 1 H), 4.72 (s, 2 H), 3.50 (br. s, 4 H), 3.34 (overlapping with solvent, 2 H), 3.31-3.27 (m, 2 H), 1.78-1.69 (m, 4 H), 1.19 (t, J = 7.2 Hz, 3 H), 0.97 (br. s, 6 H); m/z: [M + H]⁺ 514. |
| 1-2-26 | pyrrolidin-1-yl-carbonylmethyl | H | H | ¹H NMR (400 MHz, CD₃OD): δ 8.42 (d, J = 8.4 Hz, 1 H), 8.00 (d, J = 1.6 Hz, 1 H), 7.88-7.83 (m, 2 H), 7.77 (d, J = 1.6 Hz, 1 H), 7.70 (d, J = 8.4 Hz, 1 H), 7.39 (d, J = 7.2 Hz, 1 H), 7.12 (s, 1 H), 6.81 (d, J = 7.6 Hz, 1 H), 4.85 (overlapping with solvent, 2 H), 3.71 (t, J = 6.8 Hz, 2 H), 3.59-3.43 (m, 6 H), 3.38 (s, 2 H), 2.14-2.07 (m, 2 H), 2.00-1.93 (m, 2 H), 1.77-1.68 (m, 4 H), 0.97 (br. s, 6 H); m/z: [M + H]⁺ 540. |
| 1-2-27 | n-butyl | H | H | ¹H NMR (400 MHz, CD₃OD): δ 8.43 (d, J = 8.0 Hz, 1 H), 7.99-7.95 (m, 1 H), 7.89-7.80 (m, 2 H), 7.78-7.73 (m, 1 H), 7.68 (d, J = 8.0 Hz, 1 H), 7.44 (d, J = 7.2 Hz, 1 H), 7.10 (s, 1 H), 6.79 (d, J = 7.6 Hz, 1 H), 4.08 (t, J = 7.4 Hz, 2 H), 3.48 (br. s, 4 H), 3.31 (overlapping with solvent, 2 H), 1.84-1.65 (m, 6 H), 1.49-1.37 (m, 2 H), 1.05-0.86 (m, 9 H); m/z: [M + H]⁺ 485. |
| 1-2-28 | oxazol-2-ylmethyl | H | H | ¹H NMR (400 MHz, CD₃OD): δ 8.39 (d, J = 8.4 Hz, 1 H), 8.02-7.96 (m, 1 H), 7.93-7.89 (m, 1 H), 7.88-7.79 (m, 2 H), 7.78-7.74 (m, 1 H), 7.68 (d, J = 8.0 Hz, 1 H), 7.52 (d, J = 7.6 Hz, 1 H), 7.15 (s, 1 H), 7.10 (s, 1 H), 6.83 (d, J = 7.2 Hz, 1 H), 5.40 (s, 2 H), 3.48 (br. s, 4 H), 3.31 (overlapping with solvent, 2 H), 1.78-1.63 (m, 4 H), 0.96 (br. s, 6 H); m/z: [M + H]⁺ 510. |
| 1-2-29 | isoxazol-5-ylmethyl | H | H | m/z: [M + H]⁺ 510. |
| 1-2-30 | (5-methyl-1,3,4-oxadiazol-2-yl)methyl | H | H | ¹H NMR (400 MHz, CD₃OD): δ 8.41 (d, J = 8.4 Hz, 1 H), 8.01 (m, 1 H), 7.90-7.82 (m, 2 H), 7.78 (m, 1 H), 7.70 (d, J = 8.0 Hz, 1 H), 7.55 (d, J = 7.2 Hz, 1 H), 7.11 (s, 1 H), 6.86 (d, J = 7.2 Hz, 1 H), 5.49 (s, 2 H), 3.50 (br. s, 4 H), 3.33 (overlapping with solvent, 2 H), 2.54 (s, 3 H), 1.77-1.68 (m, 4 H), 0.97 (br. s, 6 H); m/z: [M + H]⁺ 525. |
| 1-2-31 | pyrimidin-2-ylmethyl | H | H | ¹H NMR (400 MHz, CD₃OD): δ 8.74 (d, J = 4.8 Hz, 2 H), 8.38 (d, J = 8.4 Hz, 1 H), 8.02 (d, J = 1.6 Hz, 1 H), 7.87-7.83 (m, 2 H), 7.78 (d, J = 1.6 Hz, 1 H), 7.70 (d, J = 8.4 Hz, 1 H), 7.55 (t, J = 7.2 Hz, 1 H), 7.39 (t, J = 5.2 Hz, 1 H), 7.12 (s, 1 H), 6.85 (d, J = 7.6 Hz, 1 H), 5.49 (s, 2 H), 3.50 (br. s, 4 H), 3.33 (overlapping with solvent, 2 H), 1.77-1.68 (m, 4 H), 0.97 (br. s, 6 H); m/z: [M + H]⁺ 521. |

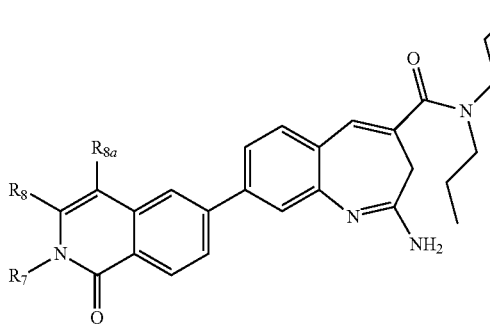

1-2-1~1-2-50

| No. | R₇ | R₈ | R₈ₐ | ¹H NMR and/or MS |
|---|---|---|---|---|
| 1-2-32 | pyrazol-1-yl-CH₂CH₂- | H | H | ¹H NMR (400 MHz, CD₃OD): δ 8.42 (d, J = 8.8 Hz, 1 H), 7.93-7.89 (m, 1 H), 7.87-7.83 (m, 1 H), 7.83-7.78 (m, 1 H), 7.75-7.72 (m, 1 H), 7.67 (d, J = 8.4 Hz, 1 H), 7.52-7.48 (m, 1 H), 7.47-7.43 (m, 1 H), 7.10 (s, 1 H), 6.78 (d, J = 7.6 Hz, 1 H), 6.56 (d, J = 7.2 Hz, 1 H), 6.22 (t, J = 2.0 Hz, 1 H), 4.59 (t, J = 5.6 Hz, 2 H), 4.46 (t, J = 5.6 Hz, 2 H), 3.48 (br. s, 4 H), 3.40-3.33 (m, 2 H), 1.77-1.64 (m, 4 H), 0.95 (br. s, 6 H); m/z: [M + H]⁺ 523. |
| 1-2-33 | 1-methylimidazol-2-yl-CH₂- | H | H | ¹H NMR (400 MHz, CD₃OD): δ 8.39 (d, J = 8.4 Hz, 1 H), 8.04 (d, J = 1.2 Hz, 1 H), 7.92-7.89 (m, 1 H), 7.82-7.80 (m, 2 H), 7.68 (d, J = 7.6 Hz, 1 H), 7.63 (d, J = 7.6 Hz, 1 H), 7.59 (d, J = 2.4 Hz, 1 H), 7.51 (d, J = 2.0 Hz, 1 H), 7.09 (s, 1 H), 6.91 (d, J = 7.2 Hz, 1 H), 5.55 (s, 2 H), 4.07 (s, 3 H), 3.49 (br. s, 4 H), 3.42-3.36 (m, 2 H), 1.77-1.68 (m, 4 H), 0.97 (br. s, 6 H); m/z: [M + H]⁺ 523. |
| 1-2-34 | 1H-pyrazol-3-yl-CH₂- | H | H | ¹H NMR (400 MHz, CD₃OD): δ 8.44 (d, J = 8.4 Hz, 1 H), 7.99-7.93 (m, 1 H), 7.89-7.79 (m, 2 H), 7.77-7.73 (m, 1 H), 7.68 (d, J = 8.0 Hz, 1 H), 7.63-7.57 (m, 1 H), 7.47 (d, J = 7.2 Hz, 1 H), 7.10 (s, 1 H), 6.78 (d, J = 7.2 Hz, 1 H), 6.37-6.29 (m, 1 H), 5.29 (s, 2 H), 3.50 (br. s, 4 H), 3.39-3.34 (m, 2 H), 1.77-1.64 (m, 4 H), 0.97 (br. s, 6 H); m/z: [M + H]⁺ 509. |
| 1-2-35 | 1-methylpyrazol-3-yl-CH₂- | H | H | ¹H NMR (400 MHz, CD₃OD): δ 8.43 (d, J = 8.8 Hz, 1 H), 7.97-7.94 (m, 1 H), 7.88-7.79 (m, 2 H), 7.77-7.73 (m, 1 H), 7.68 (d, J = 8.0 Hz, 1 H), 7.55-7.51 (m, 1 H), 7.46 (d, J = 7.2 Hz, 1 H), 7.10 (s, 1 H), 6.77 (d, J = 7.2 Hz, 1 H), 6.29-6.23 (m, 1 H), 5.22 (s, 2 H), 3.86 (s, 3 H), 3.50 (br. s, 4 H), 3.40-3.34 (m, 2 H), 1.77-1.64 (m, 4 H), 0.97 (br. s, 6 H); m/z: [M + H]⁺ 523. |
| 1-2-36 | 4-methyl-1,2,4-triazol-3-yl-CH₂- | H | H | ¹H NMR (400 MHz, CD₃OD): δ 8.62 (s, 1 H), 8.41 (d, J = 8.0 Hz, 1 H), 8.03-7.99 (m, 1 H), 7.89-7.82 (m, 2 H), 7.79-7.76 (m, 1 H), 7.70 (d, J = 8.0 Hz, 1 H), 7.59 (d, J = 6.8 Hz, 1 H), 7.11 (s, 1 H), 6.86 (d, J = 7.2 Hz, 1 H), 5.46 (s, 2 H), 3.95 (s, 3 H), 3.50 (br. s, 4 H), 3.39-3.33 (m, 2 H), 1.77-1.64 (m, 4 H), 0.97 (br. s, 6 H); m/z: [M + H]⁺ 524. |
| 1-2-37 | imidazol-1-yl-CH₂CH₂- | H | H | ¹H NMR (400 MHz, CD₃OD): δ 8.88 (s, 1 H), 8.37 (d, J = 8.8 Hz, 1 H), 8.01-7.96 (m, 1 H), 7.90-7.85 (m, 1 H), 7.83-7.78 (m, 1 H), 7.78-7.74 (m, 1 H), 7.68 (d, J = 8.4 Hz, 1 H), 7.58 (s, 1 H), 7.52 (s, 1 H), 7.25 (d, J = 7.2 Hz, 1 H), 7.10 (s, 1 H), 6.77 (d, J = 7.6 Hz, 1 H), 4.71 (t, J = 5.6 Hz, 2 H), 4.54 (t, J = 5.8 Hz, 2 H), 3.50 (br. s, 4 H), 3.39-3.33 (m, 2 H), 1.77-1.64 (m, 4 H), 0.97 (br. s, 6 H); m/z: [M + H]⁺ 523. |
| 1-2-38 | 1H-tetrazol-5-yl-CH₂- | H | H | ¹H NMR (400 MHz, CD₃OD): δ 8.42 (d, J = 8.4 Hz, 1 H), 8.01 (s, 1 H), 7.83-7.83 (m, 2 H), 7.78 (d, J = 1.2 Hz, 1 H), 7.71 (d, J = 8.4 Hz, 1 H), 7.60 (d, J = 7.2 Hz, 1 H), 7.12 (s, 1 H), 6.87 (d, J = 7.2 Hz, 1 H), 5.59 (s, 2 H), 3.50 (br. s, 4 H), 3.33 (overlapping with solvent, 2 H), 1.77-1.68 (m, 4 H), 0.97 (br. s, 6 H); m/z: [M + H]⁺ 511. |

| No. | R₇ | R₈ | R₈ₐ | ¹H NMR and/or MS |
|---|---|---|---|---|
| 1-2-39 | 2-methyl-tetrazol-5-ylmethyl | H | H | ¹H NMR (400 MHz, CD₃OD): δ 8.38 (d, J = 8.4 Hz, 1 H), 8.03-7.99 (m, 1 H), 7.88-7.81 (m, 2 H), 7.78-7.75 (m, 1 H), 7.70-7.64 (m, 2 H), 7.11 (s, 1 H), 6.88 (d, J = 7.6 Hz, 1 H), 5.55 (s, 2 H), 4.30 (s, 3 H), 3.49 (br. s, 4 H), 3.34 (overlapping with solvent, 2 H), 1.77-1.68 (m, 4 H), 0.96 (br. s, 6 H); m/z: [M + H]⁺ 525. |
| 1-2-40 | 1-methyl-tetrazol-5-ylmethyl | H | H | ¹H NMR (400 MHz, CD₃OD): δ 8.40 (d, J = 8.4 Hz, 1 H), 8.04-7.97 (m, 1 H), 7.88-7.81 (m, 2 H), 7.80-7.75 (m, 1 H), 7.69 (d, J = 8.4 Hz, 1 H), 7.58 (d, J = 7.6 Hz, 1 H), 7.11 (s, 1 H), 6.85 (d, J = 7.2 Hz, 1 H), 5.54 (s, 2 H), 4.35 (s, 3 H), 3.49 (br. s, 4 H), 3.33 (overlapping with solvent, 2 H), 1.77-1.68 (m, 4 H), 0.96 (br. s, 6 H); m/z: [M + H]⁺ 525. |
| 1-2-41 | 1-methyl-1,2,4-triazol-5-ylmethyl | H | H | ¹H NMR (400 MHz, CD₃OD): δ 8.38 (d, J = 8.0 Hz, 1 H), 8.01-7.97 (m, 1 H), 7.87-7.80 (m, 3 H), 7.78-7.75 (m, 1 H), 7.68 (d, J = 8.0 Hz, 1 H), 7.60 (d, J = 7.2 Hz, 1 H), 7.11 (s, 1 H), 6.85 (d, J = 7.6 Hz, 1 H), 5.41 (s, 2 H), 4.12 (s, 3 H), 3.50 (br. s, 4 H), 3.40-3.33 (m, 2 H), 1.77-1.68 (m, 4 H), 0.98 (br. s, 6 H); m/z: [M + H]⁺ 524. |
| 1-2-42 | carboxymethyl (HOOC-CH₂-) | H | H | ¹H NMR (400 MHz, CD₃OD): δ 8.38 (d, J = 8.4 Hz, 1 H), 7.96 (d, J = 1.6 Hz, 1 H), 7.87-7.81 (m, 2 H), 7.75 (d, J = 1.6 Hz, 1 H), 7.66 (d, J = 8.4 Hz, 1 H), 7.39 (d, J = 7.2 Hz, 1 H), 7.09 (s, 1 H), 6.78 (d, J = 7.2 Hz, 1 H), 4.80 (s, 2 H), 3.50 (br. s, 4 H), 3.31 (overlapping with solvent, 2 H), 1.76-1.64 (m, 4 H), 0.95 (br. s, 6 H); m/z: [M + H]⁺ 487. |
| 1-2-43 | diethylphosphonoethyl (EtO)₂P(O)CH₂CH₂- | H | H | ¹H NMR (400 MHz, CD₃OD): δ 8.42 (d, J = 8.6 Hz, 1 H), 7.98 (s, 1 H), 7.89-7.79 (m, 2 H), 7.76 (s, 1 H), 7.68 (d, J = 8.2 Hz, 1 H), 7.45 (d, J = 7.4 Hz, 1 H), 7.10 (s, 1 H), 6.79 (d, J = 7.4 Hz, 1 H), 4.35-4.23 (m, 2 H), 4.10 (m, 4 H), 3.48 (s, 4 H), 3.37-3.35 (m, 2 H), 2.42 (m, 2 H), 1.77-1.64 (m, 4 H), 1.27 (t, J = 6.8 Hz, 6 H), 0.95 (br. s, 6 H); m/z: [M + H]⁺ 593. |
| 1-2-44 | pyrazin-2-ylmethyl | H | H | ¹H NMR (400 MHz, CD₃OD): δ 8.69 (s, 1 H), 8.54 (d, J = 14.2 Hz, 2 H), 8.37 (d, J = 8.4 Hz, 1 H), 7.99 (d, J = 1.4 Hz, 1 H), 7.87-7.77 (m, 2 H), 7.76 (d, J = 1.4 Hz, 1 H), 7.67 (d, J = 8.2 Hz, 1 H), 7.61 (d, J = 7.4 Hz, 1 H), 7.09 (s, 1 H), 6.83 (d, J = 7.4 Hz, 1 H), 5.40 (s, 2 H), 3.48 (s, 4 H), 3.31 (overlapping with solvent, 2 H), 1.76-1.64 (m, 4 H), 0.92 (br. s, 6 H); m/z: [M + H]⁺ 521. |
| 1-2-45 | dimethylphosphonopropyl (MeO)₂P(O)OCH₂CH₂CH₂- | H | H | ¹H NMR (400 MHz, CD₃OD): δ 8.46 (d, J = 8.4 Hz, 1 H), 8.01 (d, J = 1.6 Hz, 1 H), 7.89 (dd, J = 8.4, 2.0 Hz, 1 H), 7.85 (dd, J = 8.4, 2.0 Hz, 1 H), 7.79 (d, J = 2.0 Hz, 1 H), 7.70 (d, J = 8.0 Hz, 1 H), 7.47 (d, J = 7.2 Hz, 1 H), 7.12 (s, 1 H), 6.82 (d, J = 7.6 Hz, 1 H), 4.50-4.42 (m, 2 H), 4.43-4.36 (m, 2 H), 3.70 (s, 3 H), 3.67 (s, 3 H), 3.50 (br. s, 4 H), 3.39 (d, J = 8.8 Hz, 2 H), 1.73 (h, J = 7.4 Hz, 4 H), 0.97 (br. s, 6 H); m/z: [M + H]⁺ 581. |

-continued

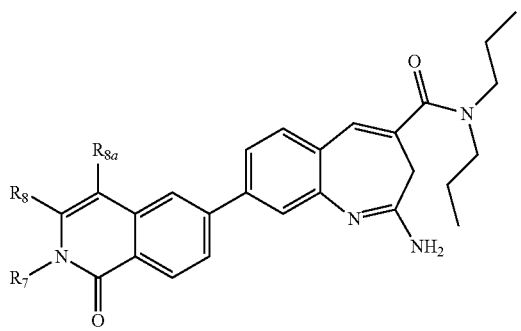

1-2-1~1-2-50

| No. | R_7 | R_8 | R_{8a} | ¹H NMR and/or MS |
|---|---|---|---|---|
| 1-2-46 | 4,6-dimethoxypyrimidin-2-ylmethyl | H | H | ¹H NMR (400 MHz, CD$_3$OD) δ 8.42 (d, J = 8.4 Hz, 1 H), 8.02 (d, J = 1.6 Hz, 1 H), 7.88-7.82 (m, 2 H), 7.77 (d, J = 1.6 Hz, 1 H), 7.69 (d, J = 8.0 Hz, 1 H), 7.53 (d, J = 7.6 Hz, 1 H), 7.11 (s, 1 H), 6.84 (d, J = 7.6 Hz, 1 H), 6.00 (s, 1 H), 5.29 (s, 2 H), 3.78 (s, 6 H), 3.48 (br. s., 4 H), 3.38 (s, 2 H), 1.78-1.65 (m, 4 H), 0.96 (br. s, 6 H); m/z: [M + H]$^+$ 581. |
| 1-2-47 | pyrazin-2-ylethyl | H | H | ¹H NMR (400 MHz, CD$_3$OD): δ 8.57-8.53 (m, 1 H), 8.47-8.42 (m, 2 H), 8.39 (d, J = 8.8 Hz, 1 H), 7.94 (d, J = 1.6 Hz, 1 H), 7.88-7.78 (m, 2 H), 7.75 (d, J = 1.6 Hz, 1 H), 7.67 (d, J = 8.4 Hz, 1 H), 7.28 (d, J = 7.6 Hz, 1 H), 7.10 (s, 1 H), 6.70 (d, J = 7.6 Hz, 1 H), 4.48 (t, J = 7.0 Hz, 2 H), 3.48 (br. s., 4 H), 3.39-3.32 (m, 4 H), 1.77-1.63 (m, 4 H), 0.95 (br. s, 6 H); m/z: [M + H]$^+$ 535. |
| 1-2-48 | 1,4-dimethylimidazol-2-ylmethyl | H | H | ¹H NMR (400 MHz, CD$_3$OD): δ 8.40 (d, J = 8.4 Hz, 1 H), 8.04 (d, J = 1.2 Hz, 1 H), 7.91 (dd, J = 1.6, 8.4 Hz, 1 H), 7.82 (dd, J = 1.6, 8.0 Hz, 1 H), 7.80-7.77 (m, 1 H), 7.69 (d, J = 8.4 Hz, 1 H), 7.59 (d, J = 7.2 Hz, 1 H), 7.24 (s, 1 H), 7.10 (s, 1 H), 6.91 (d, J = 7.6 Hz, 1 H), 5.47 (s, 2 H), 3.97 (s, 3 H), 3.48 (br. s., 4 H), 3.38 (s, 2 H), 2.27 (s, 3 H), 1.77-1.64 (m, 4 H), 0.95 (br. s., 6 H); m/z: [M + H]$^+$ 537. |
| 1-2-49 | 1-isopropylimidazol-2-ylmethyl | H | H | ¹H NMR (400 MHz, CD$_3$OD): δ 8.42 (d, J = 8.4 Hz, 1H), 8.07 (d, J = 1.6 Hz, 1H), 7.93 (dd, J = 8.4, 2.0 Hz, 1H), 7.88-7.79 (m, 3H), 7.71 (d, J = 8.4 Hz, 1H), 7.63 (d, J = 7.6 Hz, 1H), 7.57 (d, J = 2.0 Hz, 1H), 7.13 (s, 1H), 6.95 (d, J = 7.6 Hz, 1H), 5.61 (s, 2H), 4.95 (overlapping with solvent, 1 H), 3.49 (br. s, 4H), 3.39 (d, J = 8.8 Hz, 2H), 1.79-1.67 (m, 4H), 1.59 (d, J = 6.8 Hz, 6H), 0.98 (br. s., 6H); m/z: [M + H]$^+$ 551. |
| 1-2-50 | pyridin-2-ylethyl | H | H | ¹H NMR (400 MHz, CD$_3$OD): δ 8.72 (d, J = 5.6 Hz, 1H), 8.34 (d, J = 8.4 Hz, 1H), 8.32-8.26 (td, J = 8.0, 1.6 Hz, 1H), 7.99 (d, J = 1.6 Hz, 1H), 7.87 (dd, J = 8.4, 1.6 Hz, 1H), 7.84-7.75 (m, 4H), 7.69 (d, J = 8.4 Hz, 1H), 7.38 (d, J = 7.2 Hz, 1H), 7.11 (s, 1H), 6.79 (d, J = 7.6 Hz, 1H), 4.52 (t, J = 6.8 Hz, 2H), 3.58-3.43 (m, 6H), 3.38 (d, J = 8.8 Hz, 2H), 1.78-1.66 (m, 4H), 0.97 (d, J = 17.6 Hz, 6H); m/z: [M + H]$^+$ 534. |

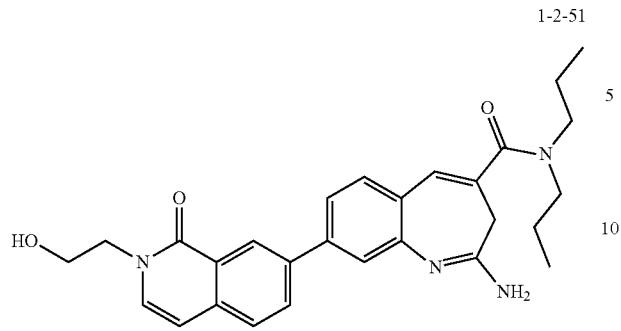

¹H NMR (400 MHz, CD₃OD): δ 8.68 (s, 1H), 8.10 (dd, J=8.0, 4.0 Hz, 1H), 7.82-7.76 (m, 3H), 7.67 (d, J=8.0 Hz, 1H), 7.44 (d, J=8.0 Hz, 1H), 7.12 (s, 1H), 6.78 (d, J=4.0 Hz, 1H), 4.22 (t, J=5.2 Hz, 2H), 3.93 (t, J=5.2 Hz, 2H), 3.50 (br. s, 4H), 3.42-3.37 (m, 2H), 1.73-1.65 (m, 4H), 0.95 (br. s, 6H); m/z: [M+H]⁺473.

Embodiment 46: Synthesis of Compound 1-2-52

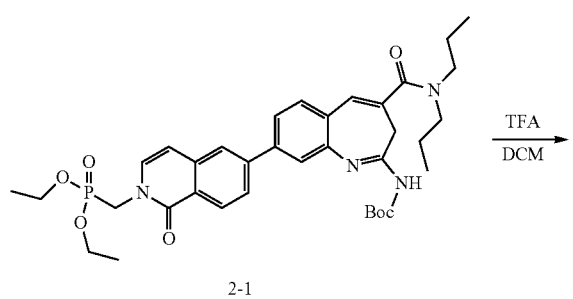

Compound 2-1 was synthesized following the synthetic method to the one used for Embodiment 43 compound 1-1, by reaction of corresponding compound 16.59 which was used in place of 6-bromoisoquinolin-1(2H)-one in step 1, with compound 1.20.

To a solution of compound 2-1 (100 mg, 0.15 mmol) in DCM (3.0 mL) was added TFA (1.5 mL), the reaction system was stirred at room temperature for 1.5 h. Concentrated under reduced pressure, the residue was recrystallization with ethanol to afford compound 1-2-52 (50 mg, yield: 53%) as a white solid.

¹H NMR (400 MHz, DMSO-d₆): δ 9.88 (s, 1H), 9.12 (s, 1H), 8.35 (d, J=8.8 Hz, 1H), 8.03 (d, J=1.6 Hz, 1H), 7.89-7.80 (m, 3H), 7.72 (d, J=8.4 Hz, 1H), 7.48 (d, J=7.2 Hz, 1H), 7.06 (s, 1H), 6.74 (d, J=7.2 Hz, 1H), 4.37 (d, J=12.4 Hz, 2H), 3.57 (s, 2H), 3.35 (s, 6H), 1.61-1.54 (m, 4H), 0.91-0.82 (m, 6H); m/z: [M+H]⁺523.

Embodiment 47: Synthesis of Compounds 1-3-1~1-3-2

Compounds 1-3-1~1-3-2 were synthesized following the synthetic method to the one used for Embodiment 43 compound 1-1-1, by reaction of corresponding compound 15.4 or 19.1 which was used in place of 6-bromoisoquinolin-1(2H)-one in step 1, with compound 1.20:

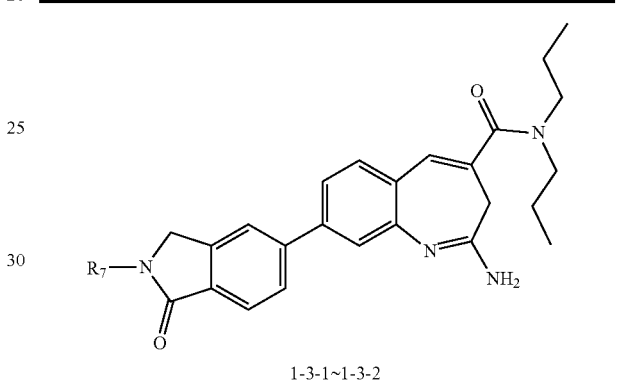

1-3-1~1-3-2

| No. | R₇ | ¹H NMR and/or MS |
|---|---|---|
| 1-3-1 | ethyl | ¹H NMR (400 MHz, DMSO-d₆): δ 9.88 (s, 1 H), 9.53 (s, 1 H), 7.93 (s, 1 H), 7.88-7.68 (m, 5 H), 7.05 (s, 1 H), 4.57 (s, 2 H), 3.66-3.56 (m, 2 H), 3.35-3.29 (m, 6 H), 1.62-1.55 (m, 4 H), 1.24-1.16 (m, 3 H), 0.94-0.78 (m, 6 H); m/z: [M + H]⁺ 445. |
| 1-3-2 | 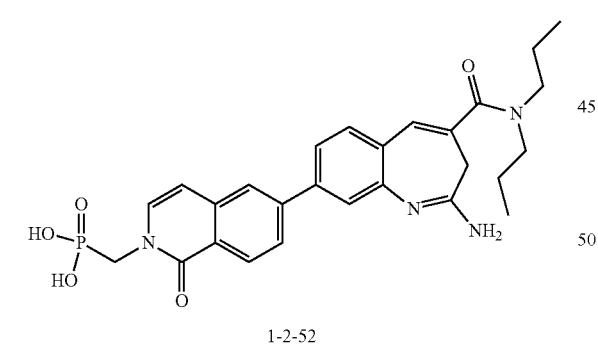 | ¹H NMR (400 MHz, CD₃OD): δ 7.91-7.88 (m, 2 H), 7.85-7.81 (m, 1 H), 7.78-7.76 (m, 1 H), 7.71-7.64 (m, 2 H), 7.09 (s, 1 H), 4.71 (s, 2 H), 3.86-3.81 (m, 2 H), 3.79-3.74 (m, 2 H), 3.47 (br. s, 4 H), 3.36 (s, 2 H), 1.73-1.67 (m, 4 H), 0.94 (br. s, 6 H); m/z: [M + H]⁺ 461. |

Embodiment 48: Synthesis of Compounds 1-4-1~1-4-2

Compounds 1-4-1~1-4-2 were synthesized following the synthetic method to the one used for Embodiment 43 compound 1-1-1, by reaction of corresponding compound 15.3 or 17.3 which was used in place of 6-bromoisoquinolin-1(2H)-one in step 1, with compound 1.20

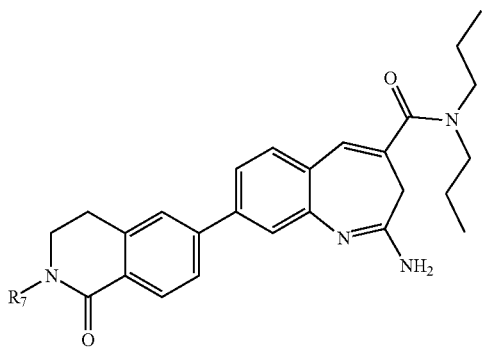

1-4-1~1-4-2

| No. | R$_7$ | $^1$H NMR and/or MS |
|---|---|---|
| 1-4-1 | ethyl | $^1$H NMR (400 MHz, CD$_3$OD): δ8.05 (d, J = 8.0 Hz, 1 H), 7.78-7.73 (m, 1 H), 7.72-7.58 (m, 4 H), 7.09 (s, 1 H), 3.71-3.61 (m, 4 H), 3.48 (br. s, 4 H), 3.12 (t, J = 8.0 Hz, 2 H), 1.71 (qd, J = 15.0, 7.0 Hz, 4 H), 1.25 (t, J = 7.2 Hz, 3 H), 1.04-0.86 (m, 6 H); m/z: [M + H]$^+$ 459. |
| 1-4-2 | 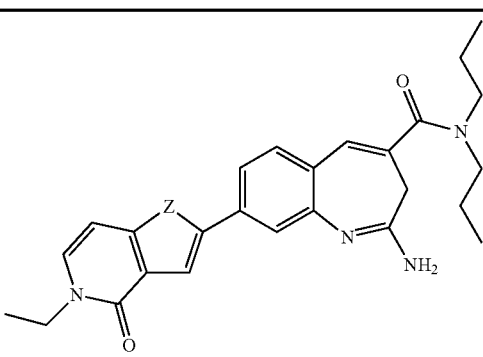 | $^1$H NMR (400 MHz, CD$_3$OD): δ8.06 (d, J = 8.8 Hz, 1 H), 7.78-7.75 (m, 1 H), 7.72-7.63 (m, 4 H), 7.09 (s, 1 H), 3.84 (t, J = 6.4 Hz, 2 H), 3.62 (s, 2 H), 3.55-3.40 (m, 4 H), 3.39-3.32 (m, 2 H), 3.13 (t, J = 6.4 Hz, 2 H), 1.76-1.64 (m, 4 H), 1.27 (s, 6 H), 1.02-0.87 (m, 6 H); m/z: [M + H]$^+$ 503. |

Embodiment 49: Synthesis of Compounds 1-6-1 and 1-6-2

Compounds 1-5-1 and 1-5-2 were synthesized following the synthetic method to the one used for Embodiment 43 compound 1-1-1, by reaction of corresponding compound 15.9 or 15.10 which was used in place of 6-bromoisoquinolin-1(2H)-one in step 1, with compound 1.20

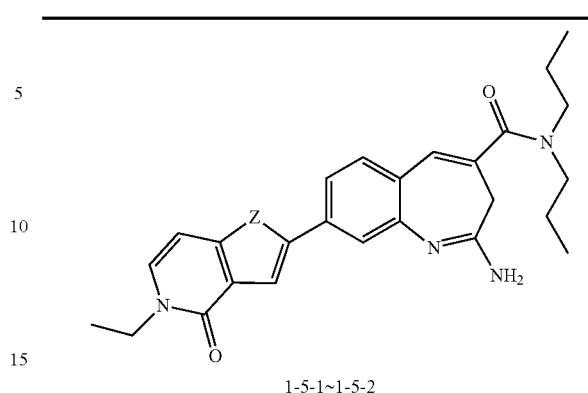

1-5-1~1-5-2

| No. | Z | $^1$H NMR and/or MS |
|---|---|---|
| 1-5-1 | N(CH$_3$) | $^1$H NMR (400 MHz, CD$_3$OD): δ 7.45 (d, J = 8.0 Hz 1 H), 7.41 (d, J = 7.6 Hz, 1 H), 7.32 (s, 1 H), 7.24 (d, J = 8.0 Hz, 1 H), 6.92 (s, 1 H), 6.82 (s, 1 H), 6.77 (d, J = 7.6 Hz, 1 H), 4.14 (q, J = 7.2 Hz, 2 H), 3.80 (s, 3 H), 3.51-3.44 (m, 4 H), 1.71-0.91 (m, 15 H); m/z: [M + H]$^+$ 460. |
| 1-5-2 | S | $^1$H NMR (400 MHz, CD$_3$OD): δ 7.97 (s, 1 H), 7.79-7.74 (m, 1 H), 7.73-7.70 (m, 1 H), 7.62 (d, J = 8.4 Hz, 1 H), 7.56 (d, J = 6.8 Hz, 1 H), 7.06 (s, 1 H), 6.97 (d, J = 7.6 Hz, 1 H), 4.14 (q, J = 7.2 Hz, 2 H), 3.54-3.39 (m, 4 H), 3.38-3.32 (m, 2 H), 1.75-1.64 (m, 4 H), 1.38 (t, J = 7.2 Hz, 3 H), 1.03-0.86 (m, 6 H); m/z: [M + H]$^+$ 463. |

Embodiment 50: Synthesis of Compounds 1-6-1 and 1-6-2

Compounds 1-6-1 and 1-6-2 were synthesized following the synthetic method to the one used for Embodiment 43 compound 1-1-1, by reaction of corresponding compound 19.2 or 21.5 which was used in place of 6-bromoisoquinolin-1(2H)-one in step 1, with compound 1.20:

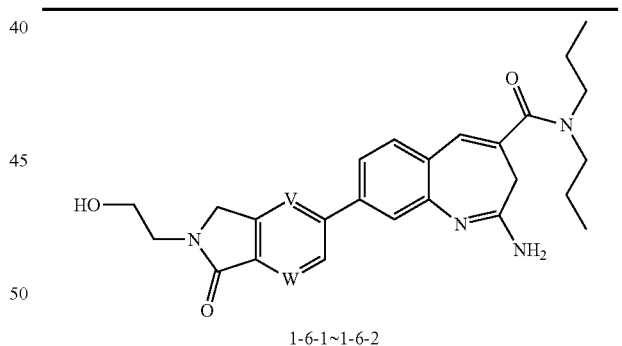

1-6-1~1-6-2

| No. | W | V | $^1$H NMR and/or MS |
|---|---|---|---|
| 1-6-1 | N | CH | $^1$H NMR (400 MHz, CD$_3$OD): δ9.04 (s, 1 H), 8.38 (s, 1 H), 7.85-7.79 (m, 1 H), 7.78-7.69 (m, 2 H), 7.11 (s, 1 H), 4.76 (s, 2 H), 3.91-3.78 (m, 4 H), 3.56-3.41 (m, 4 H), 3.40-3.34 (m, 2 H), 1.77-1.65 (m, 4 H), 1.07-0.83 (m, 6 H); m/z: [M + H]$^+$ 462. |
| 1-6-2 | CH | N | $^1$H NMR (400 MHz, CD$_3$OD): δ8.24 (d, J = 8.4 Hz, 1 H), 8.22-8.19 (m, 1 H), 8.18-8.14 (m, 1 H), 8.11 (d, J = 8.0 Hz, 1 H), 7.69 (d, J = 8.4 Hz, 1 H), 7.10 (s, 1 H), 4.73 (s, 2 H), 3.90-3.77 (m, 4 H), 3.55-3.40 (m, 4 H), 3.40-3.34 (m, 2 H), 1.77-1.64 (m, 4 H), 1.05-0.84 (m, 6 H); m/z: [M + H]$^+$ 462. |

Embodiment 51: Synthesis of Compounds 1-7-1~1-7-6

Compounds 1-7-1~1-7-6 were synthesized following the synthetic method to the one used for Embodiment 43 compound 1-1-1, by reaction of corresponding compound 16.18, 16.20, 17.5, 18.3, 22.1 or 20.5 which was used in place of 6-bromoisoquinolin-1(2H)-one in step 1, with compound 1.20:

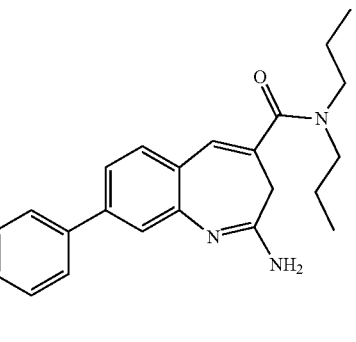

1-7-1~1-7-6

| No. | R$_7$ | $^1$H NMR and/or MS |
|---|---|---|
| 1-7-1 | H$_2$N-C(O)-CH$_2$-CH$_2$- | $^1$H NMR (400 MHz, CD$_3$OD): δ 8.38-8.30 (m, 2 H), 8.00 (d, J = 1.6 Hz, 1 H), 7.93-7.89 (m, 1 H), 7.84-7.80 (m, 1 H), 7.76 (d, J = 1.6 Hz, 1 H), 7.69 (d, J = 8.4 Hz, 1 H), 7.10 (s, 1 H), 4.79 (s, 2 H), 3.57-3.40 (m, 4 H), 3.40-3.34 (m, 2 H), 1.76-1.65 (m, 4 H), 1.05-0.86 (m, 6 H); m/z: [M + H]$^+$ 487. |
| 1-7-2 | CH$_3$-S(O)$_2$-CH$_2$-CH$_2$- | $^1$H NMR (400 MHz, CD$_3$OD): δ 8.42 (s, 1 H), 8.35 (d, J = 8.4 Hz, 1 H), 7.98-7.95 (m, 1 H), 7.92-7.88 (m, 1 H), 7.83-7.78 (m, 1 H), 7.77-7.74 (m, 1 H), 7.68 (d, J = 8.0 Hz, 1 H), 7.09 (s, 1 H), 4.54 (t, J = 6.4 Hz, 2 H), 3.70 (t, J = 6.4 Hz, 2 H), 3.56-3.40 (m, 4 H), 3.40-3.31 (m, 2 H), 3.08 (s, 3 H), 1.77-1.63 (m, 4 H), 1.05-0.84 (m, 6 H); m/z: [M + H]$^+$ 536. |
| 1-7-3 | CH$_3$-NH-C(O)-CH$_2$-CH$_2$- | $^1$H NMR (400 MHz, CD$_3$OD): δ 8.37 (d, J = 8.2 Hz, 2 H), 8.03 (d, J = 1.6 Hz, 1 H), 7.94 (dd, J = 8.4, 1.8 Hz, 1 H), 7.86 (dd, J = 8.2, 1.8 Hz, 1 H), 7.79 (d, J = 1.7 Hz, 1 H), 7.72 (d, J = 8.3 Hz, 1 H), 7.13 (s, 1 H), 4.77 (s, 2 H), 3.50 (br. s, 4 H), 3.39 (d, J = 8.6 Hz, 2 H), 2.83 (s, 3 H), 1.79-1.67 (m, 4 H), 0.97 (br. s, 6 H); m/z: [M + H]$^+$ 501. |
| 1-7-4 | HO-CH$_2$-CH$_2$- | $^1$H NMR (400 MHz, CD$_3$OD): δ8.43-8.30 (m, 2 H), 7.99 (s, 1 H), 7.91 (d, J = 8.0 Hz, 1 H), 7.83 (d, J = 8.0 Hz, 1 H), 7.76 (s, 1 H), 7.69 (d, J = 8.0 Hz, 1 H), 7.10 (s, 1 H), 4.19 (t, J = 4.0 Hz, 2 H), 3.87 (t, J = 4.0 Hz, 2 H), 3.47 (br. s, 4 H), 3.37 (s, 2 H), 1.77-1.61 (m, 4 H), 1.01-0.86 (m, 6 H); m/z: [M + H]$^+$ 474. |
| 1-7-5 | HO-C(CH$_3$)$_2$-CH$_2$- | $^1$H NMR (400 MHz, CD$_3$OD): δ 8.41-8.39 (m, 2 H), 8.01 (d, J = 1.6 Hz 1 H), 7.95-7.92 (m, 1 H), 7.87-7.84 (m, 1 H), 7.79 (d, J = 2.0 Hz, 1 H), 7.72 (d, J = 8.8 Hz, 1 H), 7.13 (s, 1 H), 4.15 (s, 2 H), 3.50 (br. s, 4 H), 3.31 (overlapping with solvent, 2 H), 1.77-1.68 (m, 4 H), 1.27 (s, 6 H), 0.98 (br. s, 6 H); m/z: [M + H]$^+$ 502. |
| 1-7-6 | CH$_3$-S(O)$_2$-NH-CH$_2$-CH$_2$- | $^1$H NMR (400 MHz, CD$_3$OD): δ 8.38 (d, J = 8.4 Hz, 1 H), 8.35 (s, 1 H), 8.00-7.98 (m, 1 H), 7.93-7.89 (m, 1 H), 7.86-7.82 (m, 1 H), 7.77-7.76 (m, 1 H), 7.72 (d, J = 8.0 Hz, 1 H), 7.11 (s, 1 H), 4.23 (t, J = 5.6 Hz, 2 H), 3.55-3.43 (m, 6 H), 3.40-3.35 (m, 2 H), 2.91 (s, 3 H), 1.77-1.65 (m, 4 H), 0.97 (br. s, 6 H); m/z: [M + H]$^+$ 551. |

Embodiment 52: Synthesis of Compounds 1-8-1~1-8-22

Compounds 1-8-1~1-8-22 were synthesized following the synthetic method to the one used for Embodiment 43 compound 1-1-1, by reaction of corresponding compound 18.4, 16.21, 16.24, 17.4, 22.4, 22.5, 16.32, 20.6, 16.36, 16.39, 22.11, 22.6, 16.44, 16.60, 16.63, 16.64, 28.4, 16.66, 16.67, 16.73 or 16.75 which was used in place of 6-bromoisoquinolin-1(2H)-one in step 1, with compound 1.20:

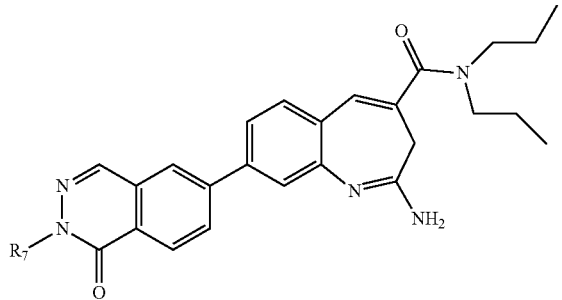

1-8-1~1-8-22

| No. | R<sub>7</sub> | ¹H NMR and/or MS |
|---|---|---|
| 1-8-1 | H₂N-C(O)-CH₂CH₂- | ¹H NMR (400 MHz, CD₃OD): δ 8.51-8.39 (m, 2 H), 8.24 (d, J = 4.0 Hz, 1 H), 8.19 (dd, J = 8.0, 4.0 Hz, 1 H), 7.87 (dd, J = 8.0, 4.0 Hz, 1 H), 7.78 (d, J = 4.0 Hz, 1 H), 7.71 (d, J = 8.0 Hz, 1 H), 7.11 (s, 1 H), 4.92-4.91 (m, 2 H), 3.47 (br. s., 4 H), 3.39-3.33 (m, 2 H), 1.77-1.62 (m, 4 H), 0.99-0.86 (m, 6 H); m/z: [M + H]⁺ 487. |
| 1-8-2 | CH₃NH-C(O)-CH₂CH₂- | ¹H NMR (400 MHz, CD₃OD): δ 8.49-8.41 (m, 2 H), 8.24 (d, J = 4.0 Hz, 1 H), 8.20 (dd, J = 8.0, 4.0 Hz, 1 H), 7.86 (dd, J = 8.0, 4.0 Hz 1 H), 7.79 (s, 1 H), 7.71 (d, J = 8.0 Hz, 1 H), 7.11 (s, 1 H), 4.73 (s, 2 H), 3.47 (br. s., 4 H), 3.39-3.32 (m, 2 H), 2.79 (s, 3 H), 1.70 (qd, J = 16.0, 8.0 Hz, 4 H), 1.04-0.83 (m, 6 H); m/z: [M + H]⁺ 501. |
| 1-8-3 | HO-CH₂CH₂CH₂- | ¹H NMR (400 MHz, CD₃OD): δ 8.49 (d, J = 10.4 Hz, 1 H), 8.48 (s, 1 H), 8.26-8.21 (m, 2 H), 7.90-7.88 (m, 1 H), 7.80 (d, J = 2.0 Hz, 1 H), 7.74 (d, J = 8.0 Hz, 1 H), 7.14 (s, 1 H), 4.42 (t, J = 5.6 Hz, 2 H), 4.01 (t, J = 5.6 Hz, 2 H), 3.50 (br. s, 4 H), 3.38 (s, 2 H), 1.77-1.68 (m, 4 H), 0.98 (br. s, 6 H); m/z: [M + H]⁺ 474. |
| 1-8-4 | HO-C(CH₃)₂-CH₂- | ¹H NMR (400 MHz, CD₃OD): δ 8.49-8.47 (m, 2 H), 8.25-8.20 (m, 2 H), 7.88-7.82 (m, 2 H), 7.72 (d, J = 8.0 Hz, 1 H), 7.13 (s, 1 H), 4.35 (s, 2 H), 3.50 (br. s, 4 H), 3.31 (overlapping with solvent, 2 H), 1.77-1.68 (m. 4 H), 1.30 (s, 6 H), 0.98 (br. s, 6 H); m/z: [M + H]⁺ 502. |
| 1-8-5 | CH₃SO₂-CH₂CH₂- | ¹H NMR (400 MHz, CD₃OD): δ 8.49 (s, 1 H), 8.48 (d, J = 9.6 Hz, 1 H), 8.25 (d, J = 1.6 Hz, 1 H), 8.21 (dd, J = 8.0, 1.6 Hz, 1 H), 7.88 (dd, J = 8.0, 1.6 Hz, 1 H), 7.80 (d, J = 1.6 Hz, 1 H), 7.73 (d, J = 8.4 Hz, 1 H), 7.13 (s, 1 H), 4.75 (t, J = 7.2 Hz, 2 H), 3.72 (t, J = 7.2 Hz, 2 H), 3.50 (br. s, 4 H), 3.33 (overlapping with solvent, 2 H), 3.10 (s, 3 H), 1.76-1.70 (m, 4 H), 0.98 (br. s, 6 H); m/z: [M + H]⁺ 536. |
| 1-8-6 | CH₃SO₂-CH₂CH₂CH₂- | ¹H NMR (400 MHz, CD₃OD): δ 8.47-8.41 (m, 2 H), 8.20-8.18 (m, 2 H), 7.56 (s, 1 H), 7.49 (s, 2 H), 6.92 (s, 1 H), 4.42 (t, J = 6.8 Hz, 2 H), 3.47-3.44 (m, 4 H), 3.33 (overlapping with solvent, 2 H), 3.28 (t, J = 7.8 Hz, 2 H), 3.00 (s, 3 H), 2.43-2.35 (m, 2 H), 1.76-1.68 (m, 4 H), 0.98 (br. s, 6 H); m/z: [M + H]⁺ 550. |
| 1-8-7 | H₂N-C(O)-CH₂CH₂CH₂- | ¹H NMR (400 MHz, CD₃OD): δ 8.47-8.40 (m, 2 H), 8.24-8.15 (m, 2 H), 7.88-7.82 (m, 1 H), 7.80-7.77 (m, 1 H), 7.71 (d, J = 8.4 Hz, 1 H), 7.11 (s, 1 H), 4.52 (t, J = 7.2 Hz, 2 H), 3.48 (br. s, 4 H), 3.31 (overlapping with solvent, 2 H), 2.79 (t, J = 7.2 Hz, 2 H), 1.77-1.65 (m, 4 H), 0.95 (br. s, 6 H); m/z: [M + H]⁺ 501. |
| 1-8-8 | CH₃SO₂-NH-CH₂CH₂- | ¹H NMR (400 MHz, CD₃OD): δ 8.50-8.44 (m, 2 H), 8.25-8.20 (m, 2 H), 7.89-7.84 (m, 1 H), 7.80-7.77 (m, 1 H), 7.74-7.70 (m, 1 H), 7.12 (s, 1 H), 4.41 (t, J = 6.4 Hz, 2 H), 3.58 (t, J = 6.4 Hz, 2 H), 3.50 (br. s, 4 H), 3.40-3.36 (m, 2 H), 2.92 (s, 3 H), 1.78-1.65 (m, 4 H), 0.98 (br. s, 6 H); m/z: [M + H]⁺ 551. |
| 1-8-9 | CH₃O-CH₂CH₂- | ¹H NMR (400 MHz, CD₃OD): δ 8.44 (s, 1 H), 8.42-8.38 (m, 1 H), 8.19-8.13 (m, 2 H), 7.55 (s, 1 H), 7.49-7.45 (m, 2 H), 6.90 (s, 1 H), 4.44 (t, J = 5.6 Hz, 2 H), 3.85 (t, J = 5.6 Hz, 2 H), 3.48-3.40 (m, 4 H), 3.36 (s, 3 H), 3.31 (overlapping with solvent, 2 H), 1.77-1.60 (m, 4 H), 0.95(br. s, 6 H); m/z: [M + H]⁺ 488. |
| 1-8-10 | thiazol-2-yl-CH₂- | ¹H NMR (400 MHz, CD₃OD): δ 8.51-8.43 (m, 2 H), 8.26-8.23 (m, 1 H), 8.23-8.18 (m, 1 H), 7.88-7.82 (m, 1 H), 7.80-7.77 (m, 1 H), 7.76-7.73 (m, 1 H), 7.73-7.68 (m, 1 H), 7.60-7.56 (m, 1 H), 7.11 (s, 1 H), 5.74 (s, 2 H), 3.48 (br. s, 4 H), 3.31 (overlapping with solvent, 2 H), 1.78-1.62 (m, 4 H), 0.95 (br. s, 6 H); m/z: [M + H]⁺ 527. |

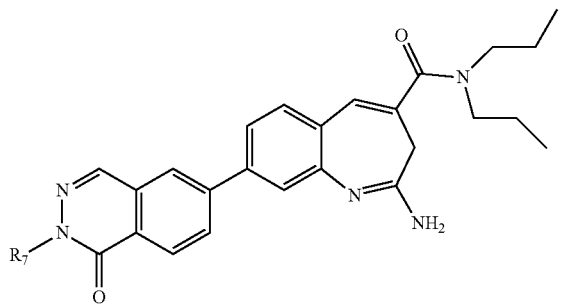

1-8-1~1-8-22

| No. | R₇ | ¹H NMR and/or MS |
|---|---|---|
| 1-8-11 | methyl sulfinyl ethyl | ¹H NMR (400 MHz, CD₃OD): δ 8.49-8.42 (m, 2 H), 8.26-8.17 (m, 2 H), 7.88-7.82 (m, 1 H), 7.80-7.76 (m, 1 H), 7.74-7.68 (m, 1 H), 7.11 (s, 1 H), 4.76-4.63 (m, 2 H), 3.57-3.37 (m, 5 H), 3.33-3.25 (overlapping with solvent, 3 H), 2.73 (s, 3 H), 1.77-1.64 (m, 4 H), 0.95 (br. s, 6 H); m/z: [M + H]⁺ 520. |
| 1-8-12 | ethyl sulfonyl ethyl | ¹H NMR (400 MHz, CD₃OD): δ 8.48-8.45 (m, 2 H), 8.25-8.20 (m, 2 H), 7.88-7.86 (m, 1 H), 7.82-7.79 (m, 1 H), 7.73 (d, J = 8.4 Hz, 1 H), 7.13 (s, 1 H), 4.73 (t, J = 7.2 Hz, 2 H), 3.68 (t, J = 7.2 Hz, 2 H), 3.50 (br. s, 4 H), 3.34 (overlapping with solvent, 2 H), 3.24 (q, J = 7.6 Hz, 2 H), 1.77-1.68 (m, 4 H), 1.39 (t, J = 7.6 Hz, 3 H), 0.98 (br. s, 6 H); m/z: [M + H]⁺ 550. |
| 1-8-13 | pyrazolyl ethyl | ¹H NMR (400 MHz, CD₃OD): δ 8.40 (d, J = 8.4 Hz, 1 H), 8.35 (s, 1 H), 8.21-8.14 (m, 2 H), 7.86-7.82 (m, 1 H), 7.79-7.75 (m, 1 H), 7.71 (d, J = 8.4 Hz, 1 H), 7.54-7.50 (m, 1 H), 7.42-7.38 (m, 1 H), 7.11 (s, 1 H), 6.20 (t, J = 2.2 Hz, 1 H), 4.69-4.60 (m, 4 H), 3.48 (br. s, 4 H), 3.40-3.34 (m, 2 H), 1.77-1.65 (m, 4 H), 0.95 (br. s, 6 H); m/z: [M + H]⁺ 524. |
| 1-8-14 | diethyl phosphonate ethyl | ¹H NMR (400 MHz, CD₃OD): δ 8.46 (d, J = 7.2 Hz, 2 H), 8.26-8.17 (m, 2 H), 7.85 (dd, J = 8.0, 1.6 Hz, 1 H), 7.79 (s, 1 H), 7.71 (d, J = 8.2 Hz, 1 H), 7.11 (s, 1 H), 4.55-4.46 (m, 2 H), 4.21-4.05 (m, 4 H), 3.48 (s, 4 H), 3.31 (overlapping with solvent, 2 H), 2.50-2.37 (m, 2 H), 1.78-1.65 (m, 4 H), 1.30 (t, J = 7.0 Hz, 6 H), 0.95 (s, 6 H); m/z: [M + H]⁺ 594. |
| 1-8-15 | oxazolyl methyl | ¹H NMR (400 MHz, CD₃OD): δ 8.50-8.43 (m, 2 H), 8.28-8.24 (m, 1 H), 8.23-8.18 (m, 1 H), 7.93-7.90 (m, 1 H), 7.89-7.84 (m, 1 H), 7.81-7.78 (m, 1 H), 7.72 (d, J = 8.4 Hz, 1 H), 7.16 (s, 1 H), 7.12 (s, 1 H), 5.57 (s, 2 H), 3.48 (br. s, 4 H), 3.31 (overlapping with solvent, 2 H), 1.77-1.64 (m, 4 H), 0.95 (br. s, 6 H); m/z: [M + H]⁺ 511. |
| 1-8-16 | pyrimidinyl methyl | ¹H NMR (400 MHz, CD₃OD): δ 8.73 (d, J = 4.4 Hz, 2 H), 8.51-8.44 (m, 2 H), 8.23-8.15 (m, 2 H), 7.82-7.79 (m, 2 H), 7.67 (d, J = 8.4 Hz, 1 H), 7.37 (t, J = 5.2 Hz, 1 H), 7.05 (s, 1 H), 5.69 (s, 2 H), 3.48 (s, 4 H), 3.31 (overlapping with solvent, 2 H), 1.78-1.66 (m, 4 H), 0.97 (br. s, 6 H); m/z: [M + H]⁺ 522. |
| 1-8-17 | 4,6-dimethylpyrimidinyl methyl | ¹H NMR (400 MHz, MeOD:CDCl₃ = 1:1): δ 8.50 (d, J = 8.4 Hz, 1 H), 8.44 (s, 1 H), 8.19 (s, 1 H), 8.16 (dd, J = 8.4, 1.8 Hz, 1 H), 7.83-7.79 (m, 2 H), 7.67 (s, 1 H), 7.07 (s, 1 H), 7.04 (s, 1 H), 5.60 (s, 2 H), 3.48 (s, 4 H), 3.31 (overlapping with solvent, 2 H), 2.44 (s, 6 H), 1.76-1.66 (m, 4 H), 0.97 (s, 6 H); m/z: [M + H]⁺ 550. |
| 1-8-18 | ethyl methyl phosphinate ethyl | ¹H NMR (400 MHz, CD₃OD): δ 8.50-8.44 (m, 2 H), 8.26-8.17 (m, 2 H), 7.90-7.84 (m, 1 H), 7.82-7.78 (m, 1 H), 7.72 (d, J = 8.0 Hz, 1 H), 7.12 (s, 1 H), 4.63-4.45 (m, 2 H), 4.11-4.01 (m, 2 H), 3.48 (br. s, 4 H), 3.41-3.36 (m, 2 H), 2.51-2.39 (m, 2 H), 1.77-1.68 (m, 4 H), 1.64 (d, J = 14.0 Hz, 3 H), 1.25 (t, J = 7.0 Hz, 3 H), 0.95 (br. s, 6 H); m/z: [M + H]⁺ 564. |

-continued

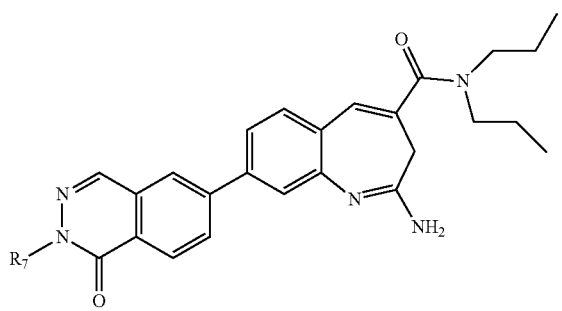

1-8-1~1-8-22

| No. | R₇ | ¹H NMR and/or MS |
|---|---|---|
| 1-8-19 | benzyl | ¹H NMR (400 MHz, CD₃OD): δ 8.55-8.39 (m, 2 H), 8.31-8.13 (m, 2 H), 7.91-7.66 (m, 3 H), 7.47-7.22 (m, 5 H), 7.12 (s, 1 H), 5.43 (s, 2 H), 3.48 (br. s, 4 H), 3.31 (overlapping with solvent, 2 H), 1.80-1.59 (m, 4 H), 0.95 (br. s, 6 H); m/z: [M + H]⁺ 520. |
| 1-8-20 | (pyridin-2-yl)methyl | ¹H NMR (400 MHz, CD₃OD): δ 8.56-8.44 (m, 3 H), 8.27 (d, J = 1.6 Hz, 1 H), 8.24-8.18 (m, 1 H), 7.96-7.84 (m, 2 H), 7.80 (d, J = 1.6 Hz, 1 H), 7.72 (d, J = 8.4 Hz, 1 H), 7.48-7.39 (m, 2 H), 7.12 (s, 1 H), 5.60 (s, 2 H), 3.48 (br. s, 4 H), 3.42-3.34 (m, 2 H), 1.77-1.64 (m, 4 H), 0.96 (br. s, 6 H); m/z: [M + H]⁺ 521. |
| 1-8-21 | (4,6-dimethoxypyrimidin-2-yl)methyl | ¹H NMR (400 MHz, CD₃OD): δ8.49 (s, 1 H), 8.47 (d, J = 8.4 Hz, 1 H), 8.27 (d, J = 1.6 Hz, 1 H), 8.24-8.19 (m, 1 H), 7.90-7.85 (m, 1 H), 7.80 (d, J = 2.0 Hz, 1 H), 7.72 (d, J = 8.4 Hz, 1 H), 7.12 (s, 1 H), 6.00 (s, 1 H), 5.46 (s, 2 H), 3.75 (s, 6 H), 3.48 (br. s., 4 H), 3.31 (overlapping with solvent, 2 H), 1.77-1.65 (m, 4 H), 0.96 (br. s., 6 H); m/z: [M + H]⁺ 582. |
| 1-8-22 | (pyrimidin-2-yl)methyl | ¹H NMR (400 MHz, CD₃OD:CDCl₃ = 1:1) δ 9.02 (d, J = 4.8 Hz, 2 H), 8.59 (d, J = 8.4 Hz, 1 H), 8.55 (s, 1 H), 8.25 (d, J = 1.4 Hz, 1 H), 8.22 (dd, J = 8.4, 1.7 Hz, 1 H), 7.85-7.81 (m, 2 H), 7.67 (d, J = 8.0 Hz, 1 H), 7.62 (t, J = 5.0 Hz, 1 H), 7.05 (s, 1 H), 3.48 (br. s, 4 H), 3.31 (overlapping with solvent, 2 H), 1.76-1.68 (m, 4 H), 0.98 (br. s, 6 H); m/z: [M + H]⁺ 508. |

Embodiment 53: Synthesis of Compounds 1-9-1~1-9-6

Compounds 1-9-1~1-9-6 were synthesized following the synthetic method to the one used for Embodiment 43 compound 1-1-1, by reaction of corresponding compound 17.3, 23.1, 24.1, 24.2, 25.1 or 20.4 which was used in place of 6-bromoisoquinolin-1(2H)-one in step 1, with compound 1.20:

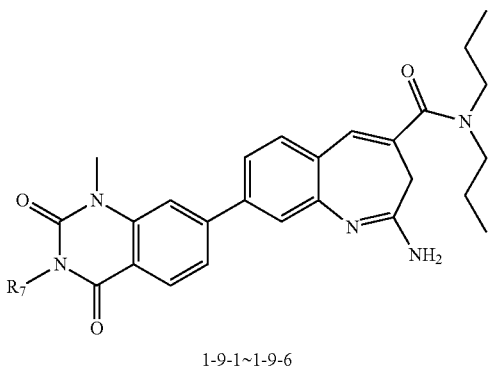

1-9-1~1-9-6

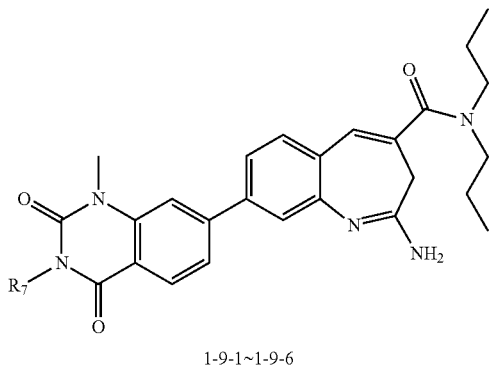

1-9-1~1-9-6

| No. | R$_7$ | $^1$H NMR and/or MS |
|---|---|---|
| 1-9-1 | 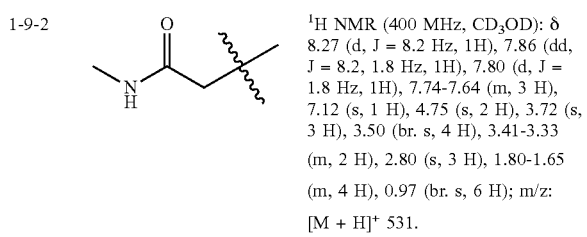 | $^1$H NMR (400 MHz, CD$_3$OD): δ 8.27 (d, J = 8.0 Hz, 1 H), 7.88-7.83 (m, 1 H), 7.80 (s, 1 H), 7.74-7.63 (m, 3 H), 7.12 (s, 1 H), 4.73 (t, J = 5.2 Hz, 0.5 H), 4.52 (t, J = 5.2 Hz, 0.5 H), 4.28 (t, J = 6.2 Hz, 1.5 H), 3.83 (t, J = 6.2 Hz, 1.5 H), 3.72 (s, 3 H), 3.50 (br. s, 4 H), 3.40 (s, 2 H), 1.79-1.67 (m, 4 H), 0.97 (br. s, 6 H); m/z: [M + H]$^+$ 504. |
| 1-9-2 |  | $^1$H NMR (400 MHz, CD$_3$OD): δ 8.27 (d, J = 8.2 Hz, 1H), 7.86 (dd, J = 8.2, 1.8 Hz, 1H), 7.80 (d, J = 1.8 Hz, 1H), 7.74-7.64 (m, 3 H), 7.12 (s, 1 H), 4.75 (s, 2 H), 3.72 (s, 3 H), 3.50 (br. s, 4 H), 3.41-3.33 (m, 2 H), 2.80 (s, 3 H), 1.80-1.65 (m, 4 H), 0.97 (br. s, 6 H); m/z: [M + H]$^+$ 531. |
| 1-9-3 |  | $^1$H NMR (400 MHz, CD$_3$OD): δ 8.24 (d, J = 8.0 Hz, 1 H), 7.83 (dd, J = 8.0, 4.0 Hz, 1 H), 7.76 (s, 1 H), 7.68 (d, J = 8.0 Hz, 2 H), 7.63 (d, J = 8.0 Hz, 1 H), 7.09 (s, 1 H), 4.76 (s, 2 H), 3.69 (s, 3H), 3.47 (br. s, 4 H), 3.34 (s, 2 H), 1.77-1.65 (m, 4 H), 0.94 (br. s, 6 H); m/z: [M + H]$^+$ 517. |
| 1-9-4 |  | $^1$H NMR (400 MHz, CD$_3$OD): δ 8.26 (d, J = 8.0 Hz, 1 H), 7.83 (dd, J = 8.0, 4.0 Hz, 1 H), 7.76 (d, J = 4.0 Hz, 1 H), 7.69 (d, J = 8.0 Hz, 1 H), 7.67-7.60 (m, 2 H), 7.10 (s, 1 H), 4.55 (t, J = 7.0 Hz, 2 H), 3.70 (s, 3 H), 3.56-3.41 (m, 6 H), 3.36 (d, J = 8.0 Hz, 2 H), 3.12 (s, 3 H), 1.75-1.65 (m, 4 H), 0.94 (br. s, 6 H); m/z: [M + H]$^+$ 566. |
| 1-9-5 | 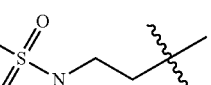 | m/z: [M + H]$^+$ 532. |
| 1-9-6 | | m/z: [M + H]$^+$ 581. |

Embodiment 54: Synthesis of Compounds 1-10-1~1-10-11

Compounds 1-10-1~1-10-11 were synthesized following the synthetic method to the one used for Embodiment 43 compound 1-1-1, by replacing 6-bromoisoquinolin-1(2H)-one and compound 1.20 to corresponding compound 18.1, 22.4, 16.22, 22.3, 24.1, 16.21, 16.34, 16.18, 16.33, 22.2, or 22.1 and 1.22 in step 1:

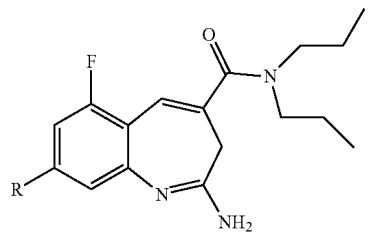

1-10-1~1-10-13

| No. | R | ¹H NMR and/or MS |
|---|---|---|
| 1-10-1 | (2-(carbamoylmethyl)-1-oxo-1,2-dihydroisoquinolin-6-yl) | ¹H NMR (400 MHz, CD₃OD): δ 8.43 (d, J = 8.0 Hz, 1 H), 8.02 (s, 1 H), 7.87 (dd, J = 8.0, 4.0 Hz, 1 H), 7.70 (d, J = 12.0 Hz, 1 H), 7.64 (s, 1 H), 7.41 (d, J = 8.0 Hz, 1 H), 7.14 (d, J = 4.0 Hz, 1 H), 6.82 (d, J = 4.0 Hz, 1 H), 4.77 (s, 2 H), 3.50 (br. s, 4 H), 3.44 (s, 2 H), 1.81-1.68 (m, 4 H), 0.98 (br. s, 6 H); m/z: [M + H]⁺ 504. |
| 1-10-2 | (2-(2-methylsulfonylethyl)-1-oxo-phthalazin-6-yl) | ¹H NMR (400 MHz, CD₃OD): δ 8.49-8.48 (m, 2 H), 8.27-8.20 (m, 2 H), 7.75-7.72 (m, 1 H), 7.66 (s, 1 H), 7.17-7.12 (m, 1 H), 4.76 (t, J = 6.8 Hz, 2 H), 3.72 (t, J = 6.8 Hz, 2 H), 3.50 (br. s, 4 H), 3.34 (overlapping with solvent, 2 H), 3.11 (s, 3 H), 1.77-1.72 (m, 4 H), 0.98 (br. s, 6 H); m/z: [M + H]⁺ 554. |
| 1-10-3 | (2-(N-methylcarbamoylmethyl)-1-oxo-1,2-dihydroisoquinolin-6-yl) | ¹H NMR (400 MHz, CD₃OD:CDCl₃ = 1:1): δ 8.44 (d, J = 8.4 Hz, 1 H), 7.91 (d, J = 1.6 Hz, 1 H), 7.80-7.78 (m, 1 H), 7.59-7.52 (m, 2 H), 7.30 (d, J = 7.6 Hz, 1 H), 7.10-7.06 (m, 1 H), 6.76 (d, J = 7.2 Hz, 1 H), 4.67 (s, 2 H), 3.50 (br. s, 4 H), 3.33 (overlapping with solvent, 2 H), 2.81 (s, 3 H), 1.81-1.65 (m, 4 H), 0.97 (br. s, 6 H); m/z: [M + H]⁺ 518. |
| 1-10-4 | (2-(2-methylsulfonylethyl)-1-oxo-1,2-dihydroisoquinolin-6-yl) | ¹H NMR (400 MHz, CD₃OD): δ 8.42 (d, J = 8.4 Hz, 1 H), 8.00-7.96 (m, 1 H), 7.89-7.83 (m, 1 H), 7.69-7.63 (m, 1 H), 7.61 (s, 1 H), 7.49 (d, J = 7.2 Hz, 1 H), 7.14-7.08 (m, 1 H), 6.79 (d, J = 7.2 Hz, 1 H), 4.51 (t, J = 6.8 Hz, 2 H), 3.67 (t, J = 6.8 Hz, 2 H), 3.48 (br. s, 4 H), 3.31 (overlapping with solvent, 2 H), 3.04 (s, 3 H), 1.79-1.64 (m, 4 H), 0.97 (br. s, 6 H); m/z: [M + H]⁺ 553. |
| 1-10-5 | (1-methyl-3-(N-methylcarbamoylmethyl)-2,4-dioxo-1,2,3,4-tetrahydroquinazolin-7-yl) | ¹H NMR (400 MHz, CD₃OD): δ 8.29 (d, J = 8.4 Hz, 1 H), 7.77-7.65 (m, 4 H), 7.14 (m, 1 H), 4.76 (s, 2 H), 3.73 (s, 3 H), 3.51 (br. s, 4 H), 3.33 (overlapping with solvent, 2 H), 2.80 (s, 3 H), 1.81-1.67 (m, 4 H), 0.99 (br. s, 6 H); m/z: [M + H]⁺ 549. |
| 1-10-6 | (2-(N-methylcarbamoylmethyl)-1-oxo-phthalazin-6-yl) | ¹H NMR (400 MHz, CD₃OD): δ 8.50-8.47 (m, 2 H), 8.29 (m, 1 H), 8.23-8.21 (m, 1 H), 7.77-7.74 (m, 1 H), 7.67 (s, 1 H), 7.17-7.14 (m, 1 H), 4.91 (s, 2 H), 3.50 (br. s, 4 H), 3.33 (overlapping with solvent, 2 H), 2.81 (s, 3 H), 1.80-1.69 (m, 4 H), 0.99 (br. s, 6 H); m/z: [M + H]⁺ 519. |
| 1-10-7 | (2-(N-ethylcarbamoylmethyl)-1-oxo-1,2-dihydroisoquinolin-6-yl) | ¹H NMR (400 MHz, CD₃OD): δ 8.43 (d, J = 8.4 Hz, 1 H), 8.04-8.01 (m, 1 H), 7.88-7.86 (m, 1 H), 7.72-7.69 (m, 1 H), 7.63 (s, 1 H), 7.41 (d, J = 7.2 Hz, 1 H), 7.16-7.12 (m, 1 H), 6.81 (d, J = 7.2 Hz, 1 H), 4.73 (s, 2 H), 3.50 (br. s, 4 H), 3.33 (overlapping with solvent, 2 H), 3.31-3.26 (m, 2 H), 1.82-1.65 (m, 4 H), 1.19 (t, J = 7.2 Hz, 3 H), 0.99 (br. s, 6H); m/z: [M + H]⁺ 532. |

-continued

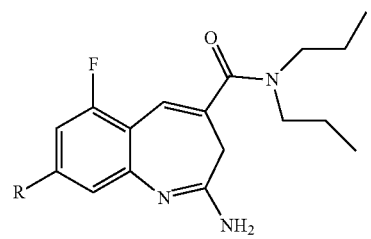

1-10-1~1-10-13

| No. | R | ¹H NMR and/or MS |
|---|---|---|
| 1-10-8 | 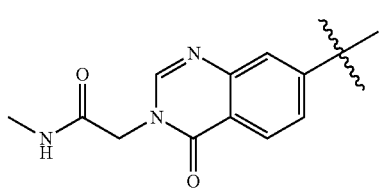 [SMILES: *c1ccc2c(=O)n(CC(=O)NC)cnc2c1] | ¹H NMR (400 MHz, CD$_3$OD): δ 8.38-8.36 (m, 2 H), 8.03 (s, 1 H), 7.94-7.91 (m, 1 H), 7.70 (d, J = 10.4 Hz, 1 H), 7.65 (s, 1 H), 7.16-7.12 (m, 1 H), 4.77 (s, 2 H), 3.50 (br. s, 4 H), 3.34 (overlapping with solvent, 2 H), 2.83 (s, 3 H), 1.77-1.68 (m, 4 H), 0.99 (br. s, 6 H); m/z: [M + H]$^+$ 519. |
| 1-10-9 | 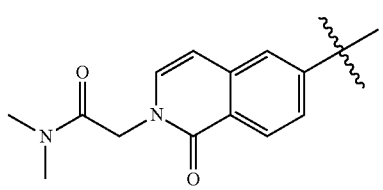 [SMILES: *c1ccc2c(=O)n(CC(=O)N(C)C)ccc2c1] | ¹H NMR (400 MHz, CD$_3$OD): δ 8.44 (d, J = 8.4 Hz, 1 H), 8.02 (s, 1 H), 7.87 (d, J = 9.2 Hz, 1 H), 7.71 (d, J = 10.8 Hz, 1 H), 7.63 (s, 1 H), 7.37 (d, J = 7.6 Hz, 1 H), 7.14 (s, 1 H), 6.82 (d, J = 7.6 Hz, 1 H), 4.99 (s, 2 H), 3.50 (br. s, 4 H), 3.33 (overlapping with solvent, 2 H), 3.23 (s, 3 H), 3.03 (s, 3 H), 1.81-1.68 (m, 4 H), 0.99 (br. s, 6 H); m/z: [M + H]$^+$ 532. |
| 1-10-10 | 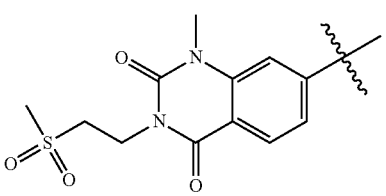 [SMILES: *c1ccc2c(=O)n(CCS(C)(=O)=O)c(=O)n(C)c2c1] | ¹H NMR (400 MHz, CD$_3$OD): δ 8.29 (d, J = 8.4 Hz, 1 H), 7.74-7.64 (m, 4 H), 7.16-7.12 (m, 1 H), 4.59 (t, J = 6.8 Hz, 2 H), 3.72 (s, 3 H), 3.54 (t, J = 6.8 Hz, 2 H), 3.50 (br. s, 4 H), 3.33 (overlapping with solvent, 2 H), 3.15 (s, 3 H), 1.77-1.72 (m, 4 H), 0.99 (br. s, 6 H); m/z: [M + H]$^+$ 584. |
| 1-10-11 | 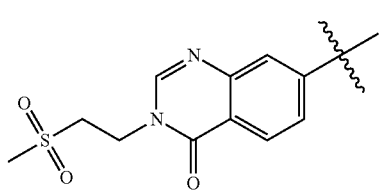 [SMILES: *c1ccc2c(=O)n(CCS(C)(=O)=O)cnc2c1] | m/z: [M + H]$^+$ 554. |
| 1-10-12 | 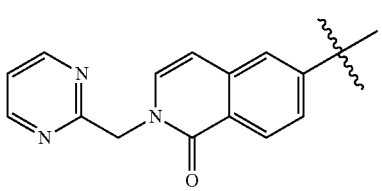 [SMILES: *c1ccc2c(=O)n(Cc3ncccn3)ccc2c1] | ¹H NMR (400 MHz, CD$_3$OD): δ 8.74 (d, J = 4.8 Hz, 2 H), 8.41 (d, J = 8.6 Hz, 1 H), 8.05 (d, J = 1.6 Hz, 1 H), 7.87 (dd, J = 8.6, 1.6 Hz, 1 H), 7.71 (dd, J = 10.8, 1.6 Hz, 1 H), 7.65 (s, 1 H), 7.57 (d, J = 7.4 Hz, 1 H), 7.40 (t, J = 4.98 Hz, 1 H), 7.14 (d, J = 1.4 Hz, 1 H), 6.87 (d, J = 7.2 Hz, 1 H), 5.50 (s, 2 H), 3.60-3.42 (m, 6 H), 1.82-1.69 (m, 4 H), 0.99 (s, 6 H); m/z: [M + H]$^+$ 539. |
| 1-10-13 | 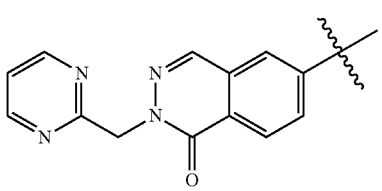 [SMILES: *c1ccc2c(=O)n(Cc3ncccn3)ncc2c1] | ¹H NMR (400 MHz, CD$_3$OD:CDCl$_3$ = 1:1) δ 8.72 (d, J = 5.0 Hz, 2 H), 8.50 (d, J = 8.4 Hz, 1 H), 8.46 (s, 1 H), 8.22 (d, J = 1.5 Hz, 1 H), 8.16 (dd, J = 8.4, 1.8 Hz, 1 H), 7.65-7.59 (m, 2 H), 7.37 (t, J = 5.0 Hz, 1 H), 7.11 (d, J = 1.4 Hz, 1 H), 5.70 (s, 2 H), 3.49 (s, 4 H), 3.31 (overlapping with solvent, 2 H), 1.73 (dd, J = 14.2, 7.0 Hz, 4 H), 0.98 (s, 6 H); m/z: [M + H]$^+$ 540. |

Embodiment 56: Synthesis of Compound 1-11-1

Compound 1-11-1 was synthesized following the synthetic method to the one used for Embodiment 43 compound 1-1-1, by replacing 6-bromoisoquinolin-1(2H)-one and compound 1.20 to corresponding compound 18.1 and 1.21 in step 1:

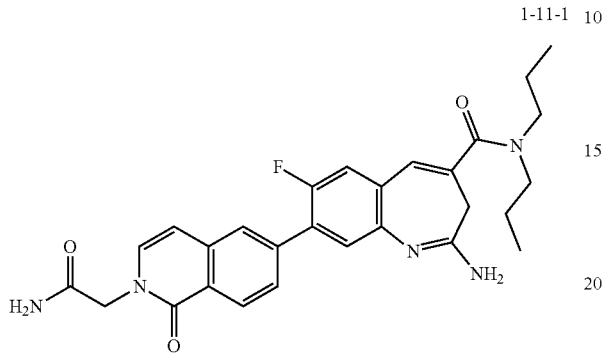

1-11-1

$^1$H NMR (400 MHz, CD$_3$OD): δ 8.42 (d, J=8.4 Hz, 1H), 7.91 (s, 1H), 7.75 (d, J=8.4 Hz, 1H), 7.62 (d, J=6.8 Hz, 1H), 7.51 (d, J=11.2 Hz, 1H), 7.39 (d, J=7.6 Hz, 1H), 7.08 (s, 1H), 6.77 (d, J=7.2 Hz, 1H), 4.76 (s, 2H), 3.55-3.41 (m, 4H), 3.32 (overlapping with solvent, 2H), 1.77-1.65 (m, 4H), 1.05-0.85 (m, 6H); m/z: [M+H]$^+$504.

Embodiment 57: Synthesis of Compound 1-12-1

Compound 1-12-1 was synthesized following the synthetic method to the one used for Embodiment 43 compound 1-1-1, by replacing 6-bromoisoquinolin-1(2H)-one and compound 1.20 to corresponding compound 18.4 and 1.19 in step 1:

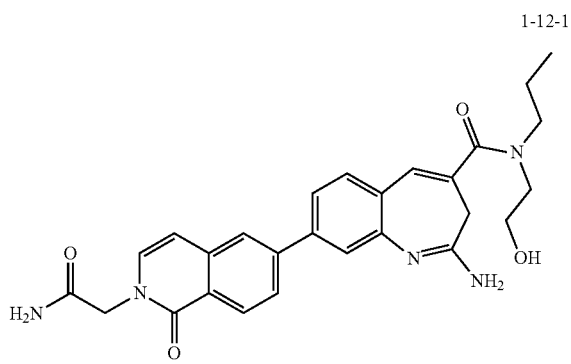 [SMILES: CCCN(CCO)C(=O)C1=Cc2ccc(-c3ccc4c(=O)n(CC(N)=O)ccc4c3)cc2N=C(N)C1]

1-12-1

$^1$H NMR (400 MHz, CD$_3$OD): δ 8.40 (d, J=8.0 Hz, 1H), 7.98 (s, 1H), 7.90-7.79 (m, 2H), 7.78-7.65 (m, 2H), 7.37 (d, J=8.0 Hz, 1H), 7.16 (s, 1H), 6.79 (d, J=8.0 Hz, 1H), 4.75 (s, 2H), 3.71-3.44 (m, 6H), 3.25-3.23 (m, 2H), 1.76-1.64 (m, 2H), 1.03-0.80 (m, 3H); m/z: [M+H] $^+$488.

Embodiment 58: Synthesis of Compounds 1-14-1~1-14-8

Compounds 1-14-1~1-14-8 were synthesized following the synthetic method to the one used for Embodiment 43 compound 1-1-1, by reaction of corresponding compound 29.1, 29.2, 30.1, 30.2, 30.3, 30.4, 30.5 or 30.6 which was used in place of 6-bromoisoquinolin-1(2H)-one in step 1, with compound 1.20:

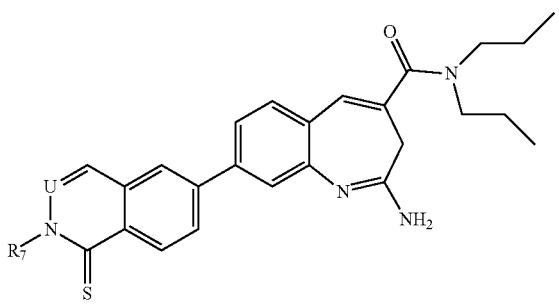

1-14-1~1-14-8

| No. | U | R$_7$ | $^1$H NMR and/or MS |
|---|---|---|---|
| 1-14-1 | N | ![pyrimidinylmethyl] | $^1$H NMR (400 MHz, CD$_3$OD:CDCl$_3$ = 3:1): δ 9.00 (d, J = 8.6 Hz, 1H), 8.73-8.70 (m, 3H), 8.23-8.17 (m, 2H), 7.86 (dd, J = 8.2, 1.8 Hz, 1H), 7.79 (d, J = 1.8 Hz, 1H), 7.69 (d, J = 8.2 Hz, 1H), 7.37 (t , J = 5.0 Hz, 1H), 7.07 (s, 1H), 6.22 (s, 2H), 3.50 (br. S, 4H), 3.36 (s, 2H), 1.76-1.68 (m, 4H), 0.97 (br. S, 6H); m/z: [M + H]$^+$ 538. |
| 1-14-2 | N | ![methylsulfonylpropyl] | $^1$H NMR (400 MHz, CD$_3$OD): δ8.99 (d, J = 9.2 Hz, 1H), 8.72 (s, 1H), 8.29-8.18 (m, 2H), 7.88 (dd, J = 8.4, 2.0 Hz, 1H), 7.82 (d, J = 1.6 Hz, 1H), 7.73 (d, J = 8.4 Hz, 1H), 7.13 (s, 1H), 5.26 (t, J = 6.8 Hz, 2H), 3.86 (t, J = 6.8 Hz, 2H), 3.51 (br. s, 4H), 3.33 (s, 2H), 3.14 (s, 3H), 1.83-1.65 (m, 4H), 0.98 (br. s, 6H); m/z: [M + H]$^+$ 552. |

-continued

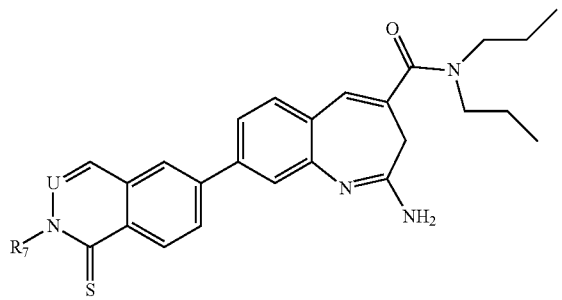

1-14-1~1-14-8

| No. | U | R₇ | ¹H NMR and/or MS |
|---|---|---|---|
| 1-14-3 | CH | pyrimidin-2-ylmethyl | ¹H NMR (400 MHz, CD₃OD): δ9.02 (d, J = 8.8 Hz, 1 H), 8.82-8.66 (m, 2 H), 8.62-8.35 (m, 1 H), 8.06-7.94 (m, 1 H), 7.93-7.74 (m, 3 H), 7.69-7.62 (m, 1 H), 7.48, 7.36 (two t, J = 5.0 Hz, 1 H), 7.18 (d, J = 7.6 Hz, 1 H), 7.14-7.05 (m, 1 H), 6.25, 6.06 (two s, 2 H), 3.48 (br. S., 4 H), 3.31 (overlapping with solvent, 2 H), 1.77-1.64 (m, 4 H), 0.96 (br. S, 6 H); m/z: [M + H]⁺ 537. |
| 1-14-4 | CH | (4,6-dimethoxypyrimidin-2-yl)methyl | ¹H NMR (400 MHz, CD₃OD): δ☐ 9.04 (d, J = 8.8 Hz, 1 H), 8.01 (d, J = 1.6 Hz, 1 H), 7.88-7.75 (m, 4 H), 7.64 (d, J = 8.4 Hz, 1 H), 7.16 (d, J = 8.0 Hz, 1 H), 7.07 (s, 1 H), 5.97 (s, 1 H), 5.90 (s, 2 H), 3.79-3.72 (m, 6 H), 3.48 (br. S, 4 H), 3.31 (overlapping with solvent, 2 H), 1.77-1.64 (m, 4 H), 0.96 (br. S., 6 H). m/z: [M + H]⁺ 597. |
| 1-14-5 | CH | pyrazin-2-ylmethyl | ¹H NMR (400 MHz, CD₃OD:CDCl₃ = 3:1): δ 9.08 (d, J = 8.8 Hz, 1 H), 8.73 (s, 1 H), 8.55 (s, 1 H), 8.48 (d, J = 2.4 Hz, 1 H), 8.05-7.99 (m, 2 H), 7.90 (d, J = 8.8 Hz, 1 H), 7.84 (dd, J = 8.2, 1.6 Hz, 1 H), 7.77 (s, 1 H), 7.68 (d, J = 8.2 Hz, 1 H), 7.21 (d, J = 7.4 Hz, 1 H), 7.08 (s, 1 H), 6.04 (s, 2 H), 3.49 (s, 4 H), 3.36 (t, 2 H), 1.74-1.68 (m, 4 H), 0.98 (br. s, 6 H); m/z: [M + H]⁺ 537. |
| 1-14-6 | N | pyrazin-2-ylmethyl | ¹H NMR (400 MHz, CD₃OD:CDCl₃ = 3:1): δ 8.98 (d, J = 8.6 Hz, 1 H), 8.74 (s, 1H), 8.65 (s, 1H), 8.57-8.48 (m, 2H), 8.26-8.18 (m, 2H), 7.84 (d, J = 8.4 Hz, 1H), 7.77 (s, 1H), 7.69 (d, J = 8.4 Hz, 1H), 7.07 (s, 1H), 6.19 (s, 2H), 3.49 (s, 4H), 3.31 (overlapping with solvent, 2 H), 1.77-1.63 (m, 4H), 0.97 (bs. s, 6H). m/z: [M + H]⁺ 538. |
| 1-14-7 | N | (4,6-dimethoxypyrimidin-2-yl)methyl | ¹H NMR (400 MHz, CD₃OD): δ9.01 (d, J = 8.4 Hz, 1 H), 8.73 (s, 1H), 8.26 (d, J = 1.6 Hz, 1 H), 8.24-8.19 (m, 1 H), 7.92-7.88 (m, 1 H), 7.81 (d, J = 1.6 Hz, 1 H), 7.73 (d, J = 8.4 Hz, 1 H), 7.12 (s, 1 H), 6.00 (s, 2 H), 5.99 (s, 1 H), 3.76 (s, 6 H), 3.48 (br. S., 4 H), 3.31 (overlapping with solvent, 2 H), 1.77-1.64 (m, 4 H), 0.96 (br. S., 6 H); m/z: [M + H]⁺ 598. |
| 1-14-8 | CH | (1-methyl-1H-imidazol-2-yl)methyl | ¹H NMR (400 MHz, CD₃OD): δ 9.06 (d, J = 8.8 Hz, 1H), 8.15 (d, J = 2.0 Hz, 1H), 8.02-7.96 (m, 2H), 7.92-7.88 (m, 1H), 7.83 (d, J = 1.6 Hz, 1H), 7.73 (d, J = 8.0 Hz, 1H), 7.54 (d, J = 2.0 Hz, 1H), 7.41 (d, J = 2.0 Hz, 1H), 7.34 (d, J = 7.2 Hz, 1H), 7.13 (s, 1H), 6.00 (s, 2H), 4.03 (s, 3H), 3.50 (br. s, 4H), 3.42-3.37 (m, 2H), 1.79-1.67 (m, 4H), 0.96 (br. s, 6H); m/z: [M + H]⁺ 539. |

179
Embodiment 59: Synthesis of Compound 1-4-10

180
Embodiment 60: Synthesis of Compound 2-1-1

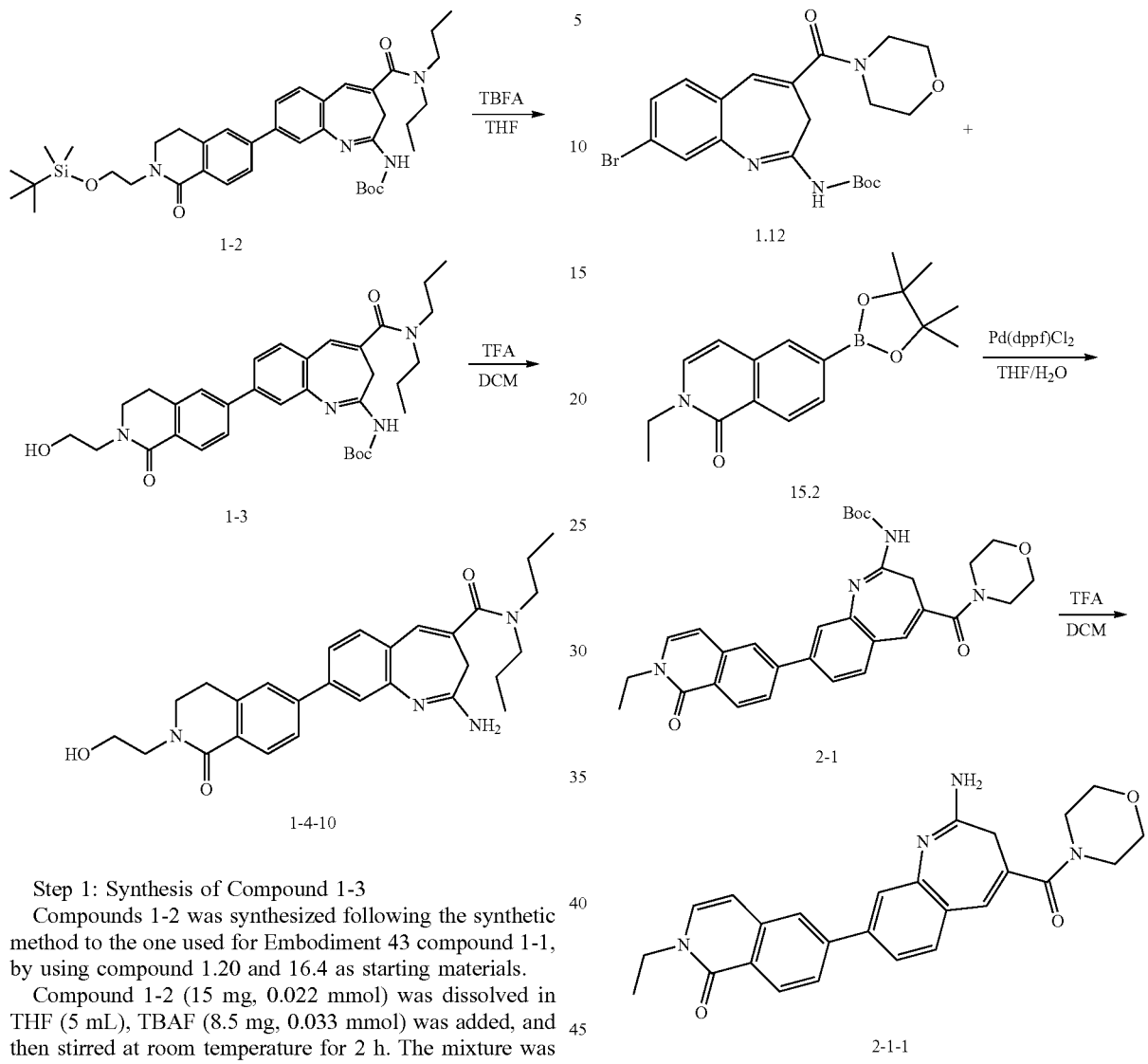

Step 1: Synthesis of Compound 1-3

Compounds 1-2 was synthesized following the synthetic method to the one used for Embodiment 43 compound 1-1, by using compound 1.20 and 16.4 as starting materials.

Compound 1-2 (15 mg, 0.022 mmol) was dissolved in THF (5 mL), TBAF (8.5 mg, 0.033 mmol) was added, and then stirred at room temperature for 2 h. The mixture was added to the aqueous solution of saturated sodium bicarbonate (10 mL) and extracted with ethyl acetate (10 mL×2). The combined organic layers were washed with brine, dried over anhydrous sodium sulfate, filtered, the solvent was evaporated under reduced pressure, the residue was purified by prep-TLC (ethyl acetate) to afford compound 1-3 (12 mg, yield: 96%) as a yellow solid.

m/z: [M+H] $^+$575

Step 2: Synthesis of Compound 1-4-10

Compound 1-3 (12 mg, 0.021 mmol) was dissolved in DCM (2 mL), TFA (1 mL) was added under an ice-water bath, and then removed the ice-water bath and stirred at room temperature for 1 h. The mixture was directly concentrated to dryness under reduced pressure. The residue was purified by prep-HPLC to afford compound 1-4-10 (1.55 mg, yield: 16%) as a yellow solid.

$^1$H NMR (400 MHz, CD$_3$OD): δ 8.07-8.04 (m, 1H), 7.78-7.74 (m, 1H), 7.72-7.67 (m, 2H), 7.67-7.62 (m, 2H), 7.09 (s, 1H), 3.84-3.69 (m, 6H), 3.55-3.40 (m, 4H), 3.38-3.33 (m, 2H), 3.16-3.11 (m, 2H), 1.76-1.65 (m, 4H), 1.02-0.88 (m, 6H); m/z: [M+H] $^+$475.

Step 1: Synthesis of Compound 2-1

To a solution of compound 1.12 (30 mg, 0.07 mmol) in THF (1 mL) was successively added aqueous solution of sodium carbonate (2.0 M, 0.5 mL), Pd(dppf)Cl$_2$ (10 mg, 0.01 mmol) and compound 15.2 (30 mg, 0.10 mmol) under N$_2$ protection. After the addition, the reaction system was replaced 3 times by N$_2$, stirred at 80° C. for 30 min. The reaction was quenched by addition of water (25 mL), the mixture was extracted with ethyl acetate (10 mL×2), the combined organic layers were washed with brine, separation of organic layer, dried over anhydrous sodium sulfate, filtered and concentrated. The residue was purified by column chromatography on silica gel (ethyl acetate:petroleum ether=1:1) to afford compound 2-1 (35 mg, yield: 97%) as a white solid.

Step 2: Synthesis of Compound 2-1-1

To an ice-cooling solution of compound 2-1 (35 mg, 0.07 mmol) in DCM (1 mL) was added TFA (1 mL), and then the reaction system was stirred at 20° C. for 2 h. The reaction was quenched by addition of water (10 mL), the mixture was extracted with ethyl acetate (10 mL×2), the combined organic layers were washed with brine, separation of organic phase, dried over anhydrous sodium sulfate, filtered and concentrated, the residue was purified by prep-HPLC to afford compound 2-1-1 (15 mg, yield: 55%) as a white solid.

$^1$H NMR (400 MHz, CD$_3$OD): δ 8.42 (d, J=8.2 Hz, 1H), 7.97 (s, 1H), 7.88-7.80 (m, 2H), 7.75 (s, 1H), 7.70 (d, J=8.0 Hz, 1H), 7.45 (d, J=7.2 Hz, 1H), 7.16 (s, 1H), 6.80 (d, J=7.2 Hz, 1H), 4.11 (q, J=7.2 Hz, 2H), 3.73 (s, 8H), 3.38 (s, 2H), 1.38 (t, J=7.2 Hz, 3H); m/z: [M+H]$^+$443.

Embodiment 61: Synthesis of Compounds 2-1-2~2-1-4

Compounds 2-1-2~2-1-4 were synthesized following the synthetic method to the one used for Embodiment 60 compound 2-1-1, by reaction of corresponding compound 1.9, 1.11 or 1.13 which was used in place of compound 1.12 in step 1, with compound 15.2:

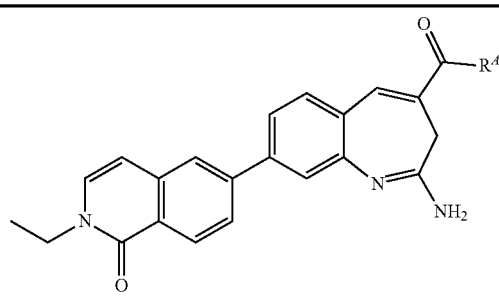

2-1-2~2-1-4

| No. | R$^A$ | $^1$H NMR and/or MS |
|---|---|---|
| 2-1-2 | 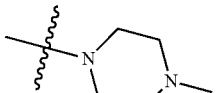 | $^1$H NMR (400 MHz, CD$_3$OD): δ 8.44 (d, J = 8.8 Hz, 1 H), 8.00-7.97 (m 1 H), 7.89-7.82 (m, 2 H), 7.78-7.70 (m, 2 H), 7.47 (d, J = 7.6 Hz, 1 H), 7.34 (s, 1 H), 6.81 (d, J = 7.6 Hz, 1 H), 4.13 (q, J = 7.2 Hz, 2 H), 3.80-3.71 (m, 2 H), 3.61-3.54 (m, 2 H), 3.45-3.37 (m, 2 H), 2.08-1.95 (m, 4 H), 1.39 (t, J = 7.2 Hz, 3 H); m/z: [M + H]$^+$ 427. |
| 2-1-3 | 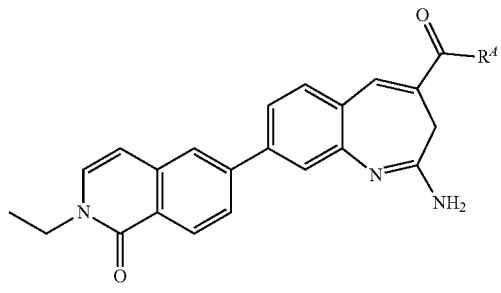 | $^1$H NMR (400 MHz, CD$_3$OD): δ 8.45 (d, J = 8.8 Hz, 1 H), 8.00 (s, 1 H), 7.89-7.85 (m, 2 H), 7.80 (s, 1 H), 7.75 (d, J = 8.4 Hz, 1 H), 7.48 (d, J = 7.2 Hz, 1 H), 7.27 (s, 1 H), 6.83 (d, J = 6.8 Hz, 1 H), 4.14 (q, J = 7.2 Hz, 2 H), 3.42 (s, 3 H), 3.23 (s, 2 H), 3.01-2.99 (m, 4 H), 1.41 (t, J = 7.2 Hz, 3 H), 1.21-1.20 (m, 4 H); m/z: [M + H]$^+$ 456. |
| 2-1-4 | 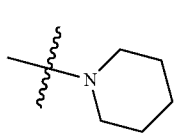 [SMILES: *N1CCCCC1] | $^1$H NMR (400 MHz, CD$_3$OD): δ 8.44 (d, J = 8.0 Hz, 1 H), 7.98 (s, 1 H), 7.89-7.71 (m, 3 H), 7.69 (s, 1 H), 7.47 (d. J = 8.0 Hz, 1 H), 7.12 (s, 1 H), 6.82 (d, J = 8.0 Hz, 1 H), 4.13 (q, J = 8.0 Hz, 2 H), 3.70-3.64 (m, 4 H), 3.39 (s, 2 H), 1.80-1.64 (m, 4 H), 1.41 (t, J = 7.6 Hz, 3 H), 1.38-1.28 (m, 2 H); m/z: [M + H]$^+$ 441. |

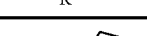

Embodiment 62: Synthesis of Compounds 2-2-1~2-2-4

Compounds 2-2-1~2-2-4 were synthesized following the synthetic method to the one used for Embodiment 60 compound 2-1-1, by reaction of corresponding compound 1.14, 1.15, 1.16 or 1.17 which was used in place of compound 1.12 in step 1, with compound 22.7:

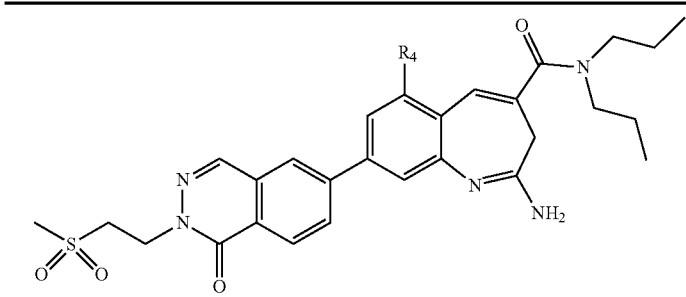

2-2-1~2-2-4

| No. | R$_4$ | $^1$H NMR and/or MS |
|---|---|---|
| 2-2-1 | methoxy | $^1$H NMR (400 MHz, CD$_3$OD): δ 8.49-8.46 (m, 2 H), 8.27-8.21 (m, 2 H), 7.74-7.37 (m, 2 H), 7.20 (s, 1 H), 4.75 (t, J = 6.8 Hz, 2 H), 4.09 (s, 3 H), 372 (t, J = 6.8 Hz, 2 H), 3.50 (br. s, 4 H), 3.31 (overlapping with solvent, 2 H), 3.11 (s, 3 H), 1.75 (br. s, 4 H), 0.99 (t, J = 7.6 Hz, 6 H); m/z: [M + H]$^+$ 566. |

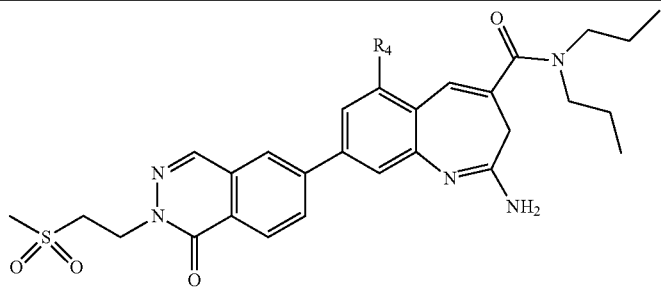

2-2-1~2-2-4

| No. | R$_4$ | $^1$H NMR and/or MS |
|---|---|---|
| 2-2-2 | methyl | $^1$H NMR (400 MHz, CD$_3$OD): δ 8.49-8.46 (m, 2 H), 8.24-8.19 (m, 2 H), 7.77 (s, 1 H), 7.65 (s, 1 H ), 7.14 (s, 1 H), 4.75 (t, J = 6.8 Hz, 2 H), 3.72 (t, J = 6.8 Hz, 2 H), 3.50 (br. s, 4 H), 3.31 (overlapping with solvent, 2 H), 3.10 (s, 3 H), 2.59 (s, 3 H), 1.78-1.73 (m, 4 H), 0.98 (br. s, 6 H); m/z: [M + H]$^+$ 550. |
| 2-2-3 | Cl | $^1$H NMR (400 MHz, CD$_3$OD): δ 8.49-8.42 (m, 2 H), 8.26-8.22 (m, 1 H), 8.21-8.16 (m, 1 H), 8.02-7.98 (m, 1 H), 7.76-7.72 (m, 1 H), 7.19 (s, 1 H), 4.73 (t, J = 7.2 Hz, 2 H), 3.70 (t, J = 6.8 Hz, 2 H), 3.61-3.38 (m, 4 H), 3.31 (overlapping with solvent, 2 H), 3.09 (s, 3 H), 1.75 (br. s, 4 H), 0.97 (br. s, 6 H); m/z: [M + H]$^+$ 570. |
| 2-2-4 | D | $^1$H NMR (400 MHz, DMSO-d$_6$): δ 9.86 (br. s, 1 H), 9.18 (br. s, 1 H), 8.56 (s, 1 H), 8.41 (d, J = 8.4 Hz, 1 H), 8.35 (d, J = 2.0 Hz, 1 H), 8.23 (dd, J = 8.0, 1.6 Hz, 1 H), 7.87-7.82 (m, 2 H), 7.08 (s, 1 H), 4.60 (t, J = 7.2 Hz, 2 H), 3.66 (t, J = 7.2 Hz, 2 H), 3.36 (overlapping with solvent, 6 H), 3.10 (s, 3 H), 1.62-1.57 (m, 4 H), 0.90 (br. s, 6 H); m/z: [M + H]$^+$ 537. |

Embodiment 63: Synthesis of Compounds 2-3-1~2-3-3

Compounds 2-3-1~2-3-3 were synthesized following the synthetic method to the one used for Embodiment 60 compound 2-1-1, by reaction of corresponding compound 1.15, 1.16 or 1.17 which was used in place of compound 1.12 in step 1, with compound 22.8:

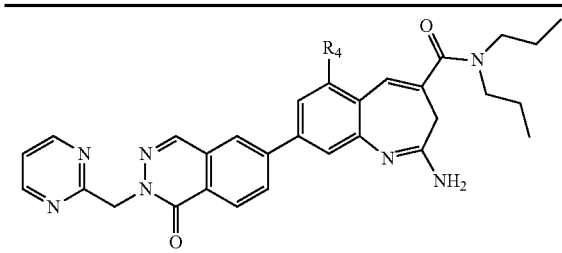

2-3-1~2-3-3

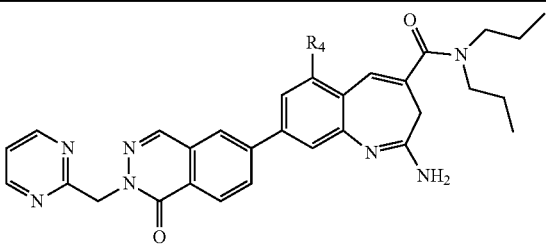

2-3-1~2-3-3

| No. | R$_4$ | $^1$H NMR and/or MS |
|---|---|---|
| 2-3-1 | Cl | $^1$H NMR (400 MHz, CD$_3$OD): δ 8.73 (d, J = 5.2 Hz, 2 H), 8.51-8.44 (m, 2 H), 8.29 (d, J = 1.6 Hz, 1 H), 8.21 (dd, J = 1.6, 8.6 Hz, 1 H), 8.05 (d, J = 1.6 Hz, 1 H), 7.77 (d, J = 1.6 Hz, 1 H), 7.39 (t, J = 5.0 Hz, 1 H), 7.21 (s, 1 H), 5.66 (s, 2 H), 3.61-3.41 (m, 4 H), 3.31 (overlapping with solvent, 2 H), 1.75 (br. s., 4 H), 0.98 (br. s, 6 H); m/z: [M + H]$^+$ 556. |
| 2-3-2 | methyl | $^1$H NMR (400 MHz, CD$_3$OD): δ 8.75 (d, J = 4.8 Hz, 2 H), 8.50 (s, 1 H), 8.46 (d, J = 8.4 Hz, 1 H), 8.28 (d, J = 1.2 Hz, 1 H), 8.22 (dd, J = 1.6, 8.4 Hz, 1 H), 7.79 (s, 1 H), 7.67 (s, 1 H), 7.41 (t, J = 4.8 Hz, 1 H), 7.15 (s, 1 H), 5.68 (s, 2 H), 3.50 (br. s, 4 H), 3.36 (s, 2 H), 2.59 (s, 3 H), 1.76-1.68 (m, 4 H), 0.99 (br. s, 6 H); m/z: [M + H]$^+$ 536. |
| 2-3-3 | D | $^1$H NMR (400 MHz, CD$_3$OD): δ 8.75 (d, J = 4.4 Hz, 2 H), 8.50 (s, 1 H), 8.48 (d, J = 8.8 Hz, 1 H), 8.30 (d, J = 2.0 Hz, 1 H), 8.23 (dd, J = 2.0, 8.0 Hz, 1 H), 7.90 (d, J = 2.0 Hz, 1 H), 7.82 (d, J = 1.2 Hz, 1 H), 7.41 (t, J = 4.8 Hz, 1 H), 7.15 (s, 1 H), 5.68 (s, 2 H), 3.50 (br. s, 4 H), 3.41 (s, 2 H), 1.76-1.68 (m, 4 H), 0.98 (br. s, 6 H); m/z: [M + H]$^+$ 523. |

EMBODIMENTS OF BIOASSAYS

Embodiment 1: TLR8 Cell Based Assay

In this assay, the bioactivity of compound of formula Iw as measured using a cell based assay. The assay was performed in human embryonic kidney cells (HEK293) expressing TLR8 or other TLR family members such as TLR4, TLR7 and TLR9 (for selectivity screens). The activity of specific TLR agonists was assessed using the secretory embryonic alkaline phosphatase (SEAP) reporter gene that is linked to NF-κB activation in response to TLR stimulation. The SEAP activity was measured using the Quanti-Blue substrate (InvivoGen) after TLR agonist treatment.

The detailed experimental method is as follow:

HEK-BLUE-hTLR8 cell line was purchased from InvivoGen. The cells were cultured in Dulbecco's Modified Eagle's Media containing 4.5 g/L L-glucose (Sigma-Aldrich) and 10% FBS. The cells were cultured at 37° C., 95% humidity and 5% $CO_2$.

Test concentrations of the compounds ranged from 0.5 nM to 15 μM with 10 points. A known TLR8 agonist was added as positive control and 1 μl of DMSO was added as negative control.

The cells were prepared as follows: The cells were removed from the incubator and growth medium was discarded. The cells were gently rinsed with pre-warmed 10 ml PBS for a T-150 flask. 12 ml pre-warmed growth medium was added, and the cells were detached by tapping the flask. Cell clumps were dissociated by gently pipetting up and down. The cells were counted. Single cell suspension was prepared at 200,000 cells per ml in growth medium and 200 μl of the cell suspension (40,000 cells per well) were immediately added to each well of the plate. The final DMSO concentration of each well was 0.5%.

The cells were cultured and treated with the compounds at 37° C., 5% CO2 for 24 h.

20 μL of the supernatant of each well were added to 180 μL of QUANTI-Blue, and the plates were incubated at 37° C. for 1.5 hour. Optical density was measured using a spectrophotometer at 650 nm (OD data). Activation was calculated by using the equation below:

Activation %=(Compound OD mean value−DMSO OD mean value)/(positive control OD mean value−DMSO OD mean value)×100

The data were analyzed using the GraphPad to get EC50 values and fitting dose response curves of the compounds.

Embodiment 2: TLR7 Cell Based Assay

In this assay, the bioactivity of compound of formula (I) was measured using a cell based assay. The assay was performed in human embryonic kidney cells (HEK293) expressing TLR7 or other TLR family members such as TLR4, and TLR9 (for selectivity screens). The activity of specific TLR agonists was assessed using the secretory embryonic alkaline phosphatase (SEAP) reporter gene that is linked to NF-κB activation in response to TLR stimulation. The SEAP activity was measured using the Quanti-Blue substrate (InvivoGen) after TLR agonist treatment.

The detailed experimental method is as follow:

HEK-BLUE-hTLR7 cell line was purchased from InvivoGen. The cells were cultured in Dulbecco's Modified Eagle's Media containing 4.5 g/L L-glucose (Sigma-Aldrich) and 10% FBS. The cells were cultured at 37° C., 95% humidity and 5% $CO_2$.

Test concentrations of the compounds ranged from 0.5 nM to 15 μM with 10 points. A known TLR8 agonist was added as positive control and 1 μl of DMSO was added as negative control.

The cells were prepared as follows. The cells were removed from the incubator and growth medium was discarded. The cells were gently rinsed with pre-warmed 10 ml PBS for a T-150 flask. 12 ml pre-warmed growth medium was added, and the cells were detached by tapping the flask. Cell clumps were dissociated by gently pipetting up and down. The cells were counted. Single cell suspension was prepared at 200,000 cells per ml in growth medium and 200 μl of the cell suspension (40,000 cells per well) were immediately added to each well of the plate. The final DMSO concentration of each well was 0.5%.

The cells were cultured and treated with the compounds at 37° C., 5% CO2 for 24 hours.

20 μL of the supernatant of each well were added to 180 μL of QUANTI-Blue, and the plates were incubated at 37° C. for 1.5 hour. Optical density was measured using a spectrophotometer at 650 nm (OD data). Activation was calculated by using the equation below:

Activation %=(Compound OD mean value−DMSO OD mean value)/(positive control OD mean value−DMSO OD mean value)×100

The data were analyzed using the GraphPad to get EC50 values and fitting dose response curves of the compounds.

The TLR8 and TLR9 $EC_{50}$ value range is as follow: − represents >50 μM, −− represents 10-50 μM, + represents 1-10 μM, ++ represents 0.1-1 μM, +++ represents <0.1 μM, / represents Not done.

| Compound No. | TLR8 EC50 | TLR7 EC50 |
| --- | --- | --- |
| 1-1-1 | + | / |
| 1-2-1 | + | / |
| 1-2-2 | ++ | / |
| 1-2-3 | ++ | / |
| 1-2-5 | ++ | / |
| 1-2-6 | +++ | / |
| 1-2-7 | ++ | / |
| 1-2-8 | +++ | − |
| 1-2-9 | +++ | − |
| 1-2-10 | +++ | − |
| 1-2-11 | +++ | / |
| 1-2-12 | ++ | / |
| 1-2-13 | +++ | − |
| 1-2-14 | +++ | − |
| 1-2-15 | + | / |
| 1-2-16 | +++ | − |
| 1-2-17 | +++ | − |
| 1-2-18 | +++ | − |
| 1-2-19 | +++ | − |
| 1-2-20 | ++ | / |
| 1-2-21 | +++ | − |
| 1-2-22 | +++ | − |
| 1-2-23 | +++ | − |
| 1-2-24 | +++ | / |
| 1-2-25 | +++ | / |
| 1-2-26 | +++ | / |
| 1-2-27 | ++ | / |
| 1-2-28 | +++ | −− |
| 1-2-29 | ++ | / |
| 1-2-30 | +++ | / |
| 1-2-31 | +++ | −− |
| 1-2-32 | +++ | + |
| 1-2-33 | +++ | − |
| 1-2-34 | +++ | / |
| 1-2-35 | +++ | − |
| 1-2-36 | +++ | −− |
| 1-2-37 | +++ | / |
| 1-2-38 | + | / |
| 1-2-39 | +++ | / |
| 1-2-40 | +++ | − |
| 1-2-41 | +++ | / |
| 1-2-42 | + | / |
| 1-2-43 | ++ | − |
| 1-2-44 | +++ | / |
| 1-2-45 | +++ | −− |
| 1-2-46 | +++ | / |
| 1-2-47 | ++ | / |
| 1-2-49 | +++ | / |
| 1-2-50 | ++ | / |
| 1-2-51 | + | / |
| 1-3-1 | +++ | / |
| 1-3-2 | +++ | − |

-continued

| Compound No. | TLR8 EC50 | TLR7 EC50 |
|---|---|---|
| 1-4-1 | ++ | / |
| 1-4-2 | +++ | − |
| 1-4-10 | ++ | − |
| 1-5-1 | + | / |
| 1-5-2 | + | / |
| 1-6-1 | ++ | / |
| 1-6-2 | ++ | / |
| 1-7-1 | ++ | / |
| 1-7-2 | ++ | − |
| 1-7-3 | +++ | / |
| 1-7-4 | +++ | − |
| 1-7-5 | +++ | / |
| 1-7-6 | ++ | / |
| 1-8-1 | +++ | − |
| 1-8-2 | +++ | − |
| 1-8-3 | +++ | − |
| 1-8-4 | +++ | − |
| 1-8-5 | +++ | − |
| 1-8-6 | +++ | / |
| 1-8-7 | +++ | / |
| 1-8-8 | +++ | / |
| 1-8-9 | +++ | / |
| 1-8-10 | +++ | / |
| 1-8-11 | +++ | / |
| 1-8-12 | +++ | −− |
| 1-8-13 | +++ | / |
| 1-8-14 | +++ | / |
| 1-8-15 | +++ | −− |
| 1-8-17 | +++ | / |
| 1-8-18 | +++ | / |
| 1-8-19 | ++ | / |
| 1-8-20 | +++ | / |
| 1-8-21 | +++ | / |
| 1-8-22 | +++ | / |
| 1-9-1 | +++ | − |
| 1-9-2 | +++ | − |
| 1-9-3 | ++ | / |
| 1-9-4 | ++ | − |
| 1-9-5 | ++ | / |
| 1-9-6 | +++ | / |
| 1-10-1 | +++ | − |
| 1-10-2 | +++ | / |
| 1-10-3 | +++ | / |
| 1-10-4 | +++ | / |
| 1-10-5 | +++ | / |
| 1-10-6 | +++ | / |
| 1-10-7 | +++ | / |
| 1-10-8 | +++ | / |
| 1-10-9 | +++ | + |
| 1-10-10 | ++ | / |
| 1-11-1 | + | − |
| 1-12-1 | ++ | / |
| 1-14-1 | +++ | / |
| 1-14-2 | +++ | / |
| 1-14-3 | +++ | / |
| 1-14-4 | ++ | / |
| 1-14-5 | +++ | / |
| 1-14-6 | +++ | / |
| 1-14-7 | ++ | / |
| 1-14-8 | +++ | − |
| 2-2-1 | ++ | / |
| 2-2-2 | +++ | −− |
| 2-2-3 | ++ | / |
| 2-2-4 | +++ | / |
| 2-3-1 | +++ | / |
| 2-3-2 | +++ | / |
| 2-3-3 | +++ | / |
| Positive Control | ++ | / |

Note:
The Positive Control is VTX-2337(motolimod), Chemical Name is 2-amino-N,N-dipropyl-8-(4-(pyrrolidine-1-carbonyl)phenyl)-3H-benzo[b]azepine-4-carboxamide Wherein, the TLR8 $EC_{50}$ values for compounds 1-2-21, 1-2-24, 1-2-25, 1-2-26, 1-2-30, 1-2-31, 1-2-33, 1-2-34, 1-2-35, 1-2-39, 1-2-40, 1-2-41, 1-2-44, 1-8-4, 1-8-5, 1-8-6, 1-8-8, 1-8-9, 1-8-12, 1-8-15, 1-8-17, 1-8-20, 1-8-22, 1-10-3, 1-10-6, 1-10-7, 1-10-9, 1-14-1, 1-14-2, 1-14-3, 1-14-8, 2-2-4, 2-3-2 and 2-3-3 are less than 0.01 μM.

It is to be understood that the foregoing description of preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A compound of formula (I), an isomer, a prodrug, a stable isotopic derivative or a pharmaceutically acceptable salt thereof:

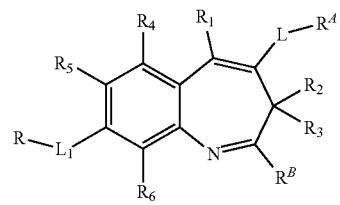

(I)

wherein, L is —C(O)—, —C(S)— or —S(O)$_2$—;
L$_1$ is a bond, C$_{2-6}$ alkenylene, C$_{2-6}$ alkynylene, —(CR$_a$R$_b$)$_m$—, —(CR$_a$R$_b$)$_u$O(CR$_a$R$_b$)$_v$—, —(CR$_a$R$_b$)$_u$C(O)(CR$_a$R$_b$)$_v$—, —(CR$_a$R$_b$)$_u$C(O)O(CR$_a$R$_b$)$_v$—, —(CR$_a$R$_b$)$_u$OC(O)(CR$_a$R$_b$)$_v$—, —(CR$_a$R$_b$)$_u$N(R$_c$)C(O)(CR$_a$R$_b$)$_v$—, —(CR$_a$R$_b$)$_u$N(R$_c$)C(O)N(R$_c$)(CR$_a$R$_b$)$_v$—, —(CR$_a$R$_b$)$_u$C(O)N(R$_c$)(CR$_a$R$_b$)$_v$—, —(CR$_a$R$_b$)$_u$C(S)(CR$_a$R$_b$)$_v$, —(CR$_a$R$_b$)$_u$S(O)$_{0-2}$(CR$_a$R$_b$)$_v$, —(CR$_a$R$_b$)$_u$S(O)$_{1-2}$N(R$_c$)(CR$_a$R$_b$)$_v$, —(CR$_a$R$_b$)$_u$N(R$_c$)S(O)$_2$N(R$_c$)(CR$_a$R$_b$)$_v$ or —(CR$_a$R$_b$)$_u$N(R$_c$)S(O)$_{1-2}$(CR$_a$R$_b$)$_v$;
R is a 9 to 15 membered bicyclic or tricyclic fused ring, one ring of which is an aromatic ring, the other 1 to 2 rings being non-aromatic rings, and the 9 to 15 membered bicyclic or tricyclic fused ring contains 1 to 3 N atoms, and the non-aromatic ring further contains 1 to 2

and/or

and the 9 to 15 membered bicyclic or tricyclic fused ring is unsubstituted or selectively substituted at any position by one or more than one substituent selected from the group consisting of halogen, alkyl, haloalkyl, haloalkoxy, alkenyl, alkynyl, Cy$^1$, -L$_2$-Cy$^1$, —CN, —NO$_2$, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —C(O)NR$_d$S(O)$_2$R$_e$, —C(O)N(R$_d$)OR$_e$, —C(=NH)R$_e$, —C(=NH)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$ and —NR$_d$ $S(O)_2NR_dR_e$; the alkyl, alkenyl or alkynyl is unsubstituted or selectively substituted at any position by one or more than one substituent selected from the group consisting of —CN, —NO$_2$, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —C(O)NR$_d$S(O)$_2$R$_e$, —NR$_d$R$_e$, —NR$_d$C(O)R$_e$, —N(R$_d$)C(O)OR$_e$, —N(R$_d$)C(O)NR$_d$R$_e$, —NR$_d$C(=NH)R$_e$, —NR$_d$C(=NH)NR$_d$R$_e$, —NR$_d$S(O)$_2$R$_e$, —NR$_d$S(O)$_2$NR$_d$R$_e$, —N(R$_d$)C(O)N(R$_d$)S(O)$_2$R$_e$, —S(O)$_{1\text{-}2}$R$_e$, —S(O)$_2$NR$_d$R$_e$, —S(O)(=NCN)R$_e$, —S(O)(=NR$_d$)R$_e$, —S(O)(=NSO$_2$R$_d$)R$_e$, —S(O)$_2$N(R$_d$)C(O)R$_e$, —S(O)$_2$N(R$_d$)C(O)NR$_d$R$_e$, —P(O)(OR$_d$)$_2$, —OP(O)(OR$_d$)$_2$ or —B(OR$_d$)$_2$;

L$_2$ is a bond, C$_{2\text{-}6}$ alkenylene, C$_{2\text{-}6}$ alkynylene, —(CR$_{a1}$R$_{b1}$)$_m$—, —(CR$_{a1}$R$_{b1}$)$_u$O(CR$_{a1}$R$_{b1}$)$_v$—, —(CR$_{a1}$R$_{b1}$)$_u$C(O)(CR$_{a1}$R$_{b1}$)$_v$—, —(CR$_{a1}$R$_{b1}$)$_u$C(O)O(CR$_{a1}$R$_{b1}$)$_v$—, —(CR$_{a1}$R$_{b1}$)$_u$OC(O)(CR$_{a1}$R$_{b1}$)$_v$—, —(CR$_{a1}$R$_{b1}$)$_u$N(R$_{c1}$)C(O)(CR$_{a1}$R$_{b1}$)$_v$—, —(CR$_a$R$_b$)$_u$C(O)N(R$_{c1}$)(CR$_{a1}$R$_{b1}$)$_v$—, —(CR$_{a1}$R$_{b1}$)$_u$N(R$_c$)C(O)N(R$_{c1}$)(CR$_{a1}$R$_{b1}$)$_v$—, —(CR$_{a1}$R$_{b1}$)$_u$C(S)(CR$_{a1}$R$_{b1}$)$_v$, —(CR$_{a1}$R$_{b1}$)$_u$S(O)$_{0\text{-}2}$(CR$_{a1}$R$_{b1}$)$_v$, —(CR$_{a1}$R$_{b1}$)$_u$S(O)$_{1\text{-}2}$N(R$_{c1}$)(CR$_{a1}$R$_{b1}$)$_v$, —(CR$_{a1}$R$_{b1}$)$_u$N(R$_{c1}$)S(O)$_2$N(R$_{c1}$)(CR$_{a1}$R$_{b1}$)$_v$ or —(CR$_{a1}$R$_{b1}$)$_u$N(R$_{c1}$)S(O)$_{1\text{-}2}$(CR$_{a1}$R$_{b1}$)$_v$;

each of Cy$^1$ is independently cycloalkyl, heterocycloalkyl, aryl or heteroaryl; the Cy$^1$ is unsubstituted or selectively substituted at any position by one or more than one substituent selected from the group consisting of halogen, alkyl, haloalkyl, haloalkoxy, hydroxyalkyl, aminoalkyl, alkenyl, alkynyl, —CN, —NO$_2$, —SR$_{d2}$, —OR$_{d2}$, —OC(O)R$_{d2}$, —OC(O)OR$_{d2}$, —OC(O)NR$_{d2}$R$_{e2}$, —C(O)OR$_{d2}$, —C(O)R$_{d2}$, —C(O)NR$_{d2}$R$_{e2}$, —NR$_{d2}$R$_{e2}$, —NR$_{d2}$C(O)R$_{e2}$, —N(R$_{d2}$)C(O)OR$_{e2}$, —N(R$_{d2}$)C(O)NR$_{d2}$R$_{e2}$, —NR$_{d2}$S(O)$_2$R$_{e2}$, —NR$_{d2}$C(=NH)R$_{e2}$, —NR$_{d2}$C(=NH)NR$_{d2}$R$_{e2}$, —S(O)$_{1\text{-}2}$R$_{e2}$, —S(O)$_2$NR$_{d2}$R$_{e2}$ and —NR$_{d2}$S(O)$_2$NR$_{d2}$R$_{e2}$;

R$_1$, R$_2$ and R$_3$ are independently selected from hydrogen, deuterium, or alkyl;

or, R$_2$ and R$_3$ together with the C atom to which they are attached, form a C$_{3\text{-}8}$ cycloalkyl or a 3 to 8 membered heterocycloalkyl;

R$_4$, R$_5$ and R$_6$ are independently selected from hydrogen, deuterium, halogen, amino, cyano, nitro, C$_{1\text{-}6}$ alkyl, C$_{1\text{-}6}$ haloalkyl, C$_{1\text{-}6}$ haloalkoxy, C$_{1\text{-}6}$ alkoxy, C$_{2\text{-}6}$ alkenyl, C$_{2\text{-}6}$ alkynyl, C$_{1\text{-}6}$ hydroxyalkyl, C$_{3\text{-}8}$ cycloalkyl, 3 to 8 membered heterocycloalkyl, phenyl or 5 to 6 membered heteroaryl;

R$^A$ is —NR$_{d1}$R$_{e1}$;

R$^B$ is —NR$_{d1}$R$_{e1}$;

each of R$_a$, R$_b$, R$_{a1}$ and R$_{b1}$ is independently selected from hydrogen, deuterium, halogen, C$_{1\text{-}6}$ alkyl, C$_{1\text{-}6}$ alkoxy, C$_{2\text{-}6}$ alkenyl, C$_{2\text{-}6}$ alkynyl, C$_{3\text{-}8}$ cycloalkyl, 3 to 8 membered heterocycloalkyl, C$_{6\text{-}10}$ aryl, 5 to 6 membered heteroaryl, C$_{3\text{-}8}$ cycloalkyl C$_{1\text{-}6}$ alkyl, 3 to 8 membered heterocycloalkyl C$_{1\text{-}6}$ alkyl, phenyl C$_{1\text{-}6}$ alkyl or 5 to 6 membered heteroaryl C$_{1\text{-}6}$ alkyl; the C$_{1\text{-}6}$ alkyl, C$_{1\text{-}6}$ alkoxy, C$_{2\text{-}6}$ alkenyl, C$_{2\text{-}6}$ alkynyl, C$_{3\text{-}8}$ cycloalkyl, 3 to 8 membered heterocycloalkyl, C$_{6\text{-}10}$ aryl or 5 to 6 membered heteroaryl is unsubstituted or substituted at any position by 1 to 3 substituent selected from the group consisting of halogen, hydroxyl, amino, carboxyl, C$_{2\text{-}6}$ alkenyl, C$_{2\text{-}6}$ alkynyl, C$_{1\text{-}6}$ alkyl, C$_{1\text{-}6}$ haloalkyl, C$_{1\text{-}6}$ alkoxy and C$_{1\text{-}6}$ haloalkoxy;

or, R$_a$ and R$_b$, or R$_{a1}$ and R$_{b1}$ together with the C atom to which they are attached, form a C$_{3\text{-}8}$ cycloalkyl or a 3 to 8 membered heterocycloalkyl;

each of R$_c$ and R$_d$ is independently selected from hydrogen, C$_{1\text{-}4}$ alkyl, C$_{3\text{-}8}$ cycloalkyl or 3 to 8 membered heterocycloalkyl;

each of R$_d$, R$_e$, R$_{d1}$ and R$_{e1}$ is independently selected from hydrogen, C$_{1\text{-}6}$ alkyl, C$_{2\text{-}6}$ alkenyl, C$_{2\text{-}6}$ alkynyl, C$_{3\text{-}8}$ cycloalkyl, 3 to 8 membered heterocycloalkyl, C$_{6\text{-}10}$ aryl, 5 to 6 membered heteroaryl, C$_{3\text{-}8}$ cycloalkyl C$_{1\text{-}6}$ alkyl, 3 to 8 membered heterocycloalkyl C$_{1\text{-}6}$ alkyl, phenyl C$_{1\text{-}6}$ alkyl or 5 to 6 membered heteroaryl C$_{1\text{-}6}$ alkyl; R$_d$, R$_e$, R$_{d1}$ or R$_{e1}$ is unsubstituted or substituted at any position by 1 to 3 substituent selected from the group consisting of halogen, hydroxyl, amino, carboxyl, C$_{1\text{-}6}$ alkyl, C$_{1\text{-}6}$ alkoxy, C$_{1\text{-}6}$ alkylamino, C$_{1\text{-}6}$ haloalkyl, C$_{1\text{-}6}$ haloalkoxy, C$_{2\text{-}6}$ alkenyl and C$_{2\text{-}6}$ alkynyl;

or, R$_d$ and R$_e$, or R$_{d1}$ and R$_{e1}$ together with the N atom to which they are attached, form a 3 to 8 membered heterocycloalkyl; the heterocycloalkyl can further comprise 1 to 3 heteroatom selected from the group consisting of N, O and S; the heterocycloalkyl is unsubstituted or substituted at any position by 1 to 3 substituent selected from the group consisting of halogen, amino, hydroxyl, carboxyl, cyano, C$_{1\text{-}6}$ alkyl, C$_{1\text{-}6}$ haloalkyl, C$_{2\text{-}6}$ alkenyl, C$_{2\text{-}6}$ alkynyl, C$_{1\text{-}3}$ alkyl, amino C$_{1\text{-}3}$ alkyl, —OR$_{d2}$, —OC(O)R$_{d2}$, —OC(O)OR$_{d2}$, —OC(O)NR$_{d2}$R$_{e2}$, —C(O)OR$_{d2}$, —C(O)R$_{d2}$, —C(O)NR$_{d2}$R$_{e2}$, —NR$_{d2}$R$_{e2}$, —NR$_{d2}$C(O)R$_{e2}$, —N(R$_{d2}$)C(O)OR$_{e2}$, —N(R$_{d2}$)C(O)NR$_{d2}$R$_{e2}$, —NR$_{d2}$S(O)$_2$R$_{e2}$, —NR$_{d2}$C(=NH)R$_{e2}$, —NR$_{d2}$C(=NH)NR$_{d2}$R$_{e2}$, —NR$_{d2}$S(O)$_2$NR$_{d2}$R$_{e2}$, —S(O)$_{1\text{-}2}$R$_{d2}$ and —S(O)$_2$NR$_{d2}$R$_{e2}$;

each of R$_{d2}$ and R$_{e2}$ is independently selected from hydrogen, C$_{1\text{-}6}$ alkyl, C$_{2\text{-}6}$ alkenyl, C$_{2\text{-}6}$ alkynyl, C$_{3\text{-}8}$ cycloalkyl, 3 to 8 membered heterocycloalkyl, C$_{6\text{-}10}$ aryl, 5 to 6 membered heteroaryl, C$_{3\text{-}8}$ cycloalkyl C$_{1\text{-}6}$ alkyl, 3 to 8 membered heterocycloalkyl C$_{1\text{-}6}$ alkyl, phenyl C$_{1\text{-}6}$ alkyl or 5 to 6 membered heteroaryl C$_{1\text{-}6}$ alkyl; R$_{d2}$ or R$_{e2}$ is unsubstituted or substituted at any position by 1 to 3 substituent selected from the group consisting of halogen, hydroxyl, amino, carboxyl, C$_{1\text{-}6}$ alkyl, C$_{1\text{-}6}$ alkoxy, C$_{1\text{-}6}$ alkylamino, C$_{1\text{-}6}$ haloalkyl, C$_{1\text{-}6}$ haloalkoxy, C$_{2\text{-}6}$ alkenyl and C$_{2\text{-}6}$ alkynyl; or, R$_{d2}$ and R$_{e2}$ together with the N atom to which they are attached, form a 3 to 8 membered heterocycloalkyl;

each of u is independently 0, 1, 2, or 3;

each of v is independently 0, 1, 2, or 3;

each of m is 1, 2, 3, 4, 5, or 6.

2. The compound of formula (I), the isomer, the prodrug, the stable isotopic derivative or the pharmaceutically acceptable salt thereof according to claim 1, wherein each of R$_1$, R$_2$ and R$_3$ is H; each of R$_4$, R$_5$ and R$_6$ is independently selected from H, D, F, Cl, Br, —CN, —NH$_2$, —CH$_3$, —OCH$_3$, —OCF$_3$, —CH$_2$F, —CHF$_2$ or —CF$_3$.

3. The compound of formula (I), the isomer, the prodrug, the stable isotopic derivative or the pharmaceutically acceptable salt thereof according to claim 1, wherein L$_1$ is a bond, —CH$_2$—, —NH—, —O—, —CH$_2$O— or —OCH$_2$—.

4. The compound of formula (I), the isomer, the prodrug, the stable isotopic derivative or the pharmaceutically acceptable salt thereof according to claim 1, wherein each of R$_{d1}$ and R$_{e1}$ is independently selected from hydrogen, C$_{1\text{-}6}$ alkyl, C$_{1\text{-}6}$ haloalkyl, C$_{3\text{-}8}$ cycloalkyl or a 3 to 8 membered heterocycloalkyl; R$_{d1}$ or R$_{e1}$ is unsubstituted or substituted at any position by one hydroxyl;

or, R$_{d1}$ and R$_{e1}$ together with the N atom to which they are attached, form a C$_{3\text{-}8}$ heterocycloalkyl; the heterocycloalkyl may further contain 1-3 hetero atoms selected from N, O, and S; the heterocycloalkyl is unsubstituted or substituted at any position by one substituent selected from the group consisting of $C_{1-4}$ alkyl, $C_{1-3}$ haloalkyl, $C_{1-3}$ hydroxyalkyl and $C_{1-3}$ aminoalkyl.

5. The compound of formula (I), the isomer, the prodrug, the stable isotopic derivative or the pharmaceutically acceptable salt thereof according to claim 1, wherein $R^B$ is —NH$_2$.

6. The compound of formula (I), the isomer, the prodrug, the stable isotopic derivative or the pharmaceutically acceptable salt thereof according to claim 1, wherein R is selected from the group consisting of R-1 to R-19:

R-1
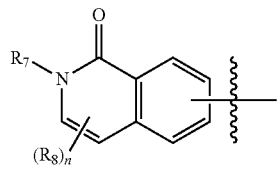

R-2
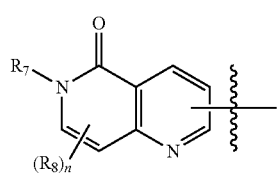

R-3
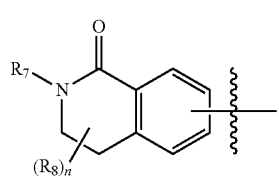

R-4
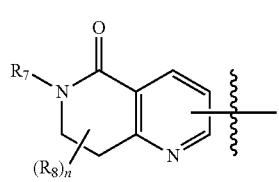

R-5
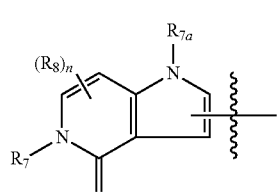

R-6
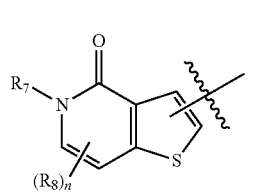

R-7
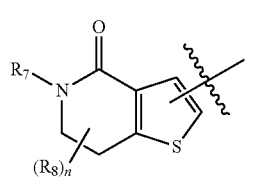

-continued

R-8
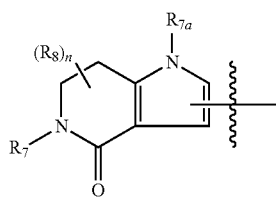

R-9
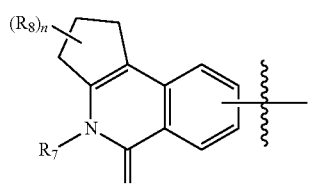

R-10
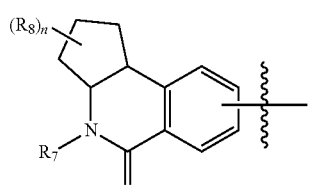

R-11
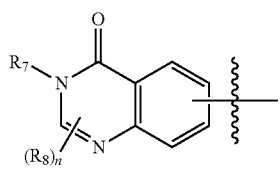

R-12
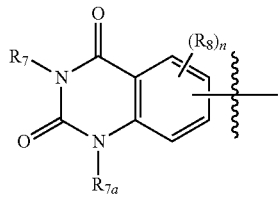

R-13
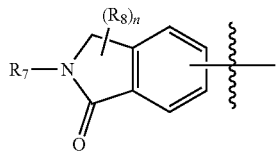

R-14
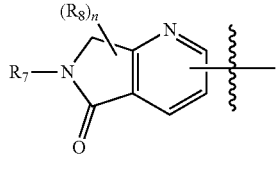

R-15
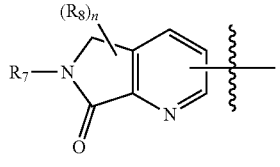

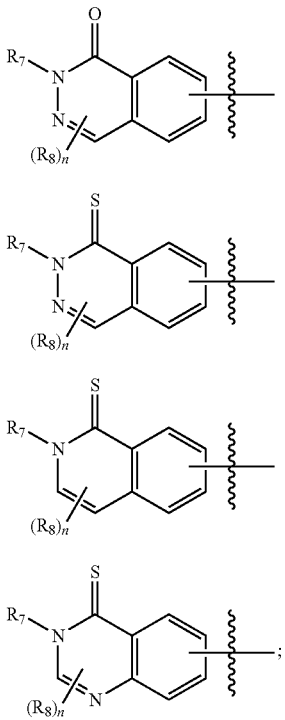

each of $R_7$ and $R_{7a}$ is independently selected from hydrogen, halogen, alkyl, haloalkyl, alkenyl, alkynyl, $Cy^1$, -$L_2$-$Cy^1$, —$SR_d$, —$OR_d$, —$C(O)OR_d$, —$C(O)R_d$, —$C(O)NR_dR_e$, —$C(O)NR_dS(O)_2R_e$, —$C(=NH)R_e$, —$C(=NH)NR_dR_e$, —$S(O)_2R_e$ and —$S(O)_2NR_dR_e$; wherein the alkyl, alkenyl or alkynyl is unsubstituted or substituted at any position by one or more than one substituent selected from the group consisting of —CN, —$NO_2$, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$C(O)NR_dS(O)_2R_e$, —$NR_dR_e$, —$NR_dC(O)R_e$, —$N(R_d)C(O)OR_e$, —$N(R_d)C(O)NR_dR_e$, —$NR_dC(=NH)R_e$, —$NR_dC(=NH)NR_dR_e$, —$NR_dS(O)_2R_e$, —$NR_dS(O)_2NR_dR_e$, —$N(R_d)C(O)N(R_d)S(O)_2R_e$, —$S(O)_{1-2}R_e$, —$S(O)_2NR_dR_e$, —$S(O)(=NCN)R_e$, —$S(O)(=NR_d)R_e$, —$S(O)(=NSO_2R_d)R_e$, —$S(O)_2N(R_d)C(O)R_e$, —$S(O)_2N(R_d)C(O)NR_dR_e$, —$P(O)(OR_d)_2$, —$OP(O)(OR_d)_2$ or —$B(OR_d)_2$;

each of $R_8$ is independently hydrogen, halogen, alkyl, haloalkyl, haloalkoxy, alkenyl, alkynyl, $Cy^1$, -$L_2$-$Cy^1$, —CN, —$NO_2$, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$C(O)NR_dS(O)_2R_e$, —$C(=NH)R_e$, —$C(=NH)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(=NH)R_e$, —$NR_dC(=NH)NR_dR_e$, —$S(O)_{1-2}R_e$, —$S(O)_2NR_dR_e$ and —$NR_dS(O)_2NR_dR_e$; wherein the alkyl, alkenyl or alkynyl is unsubstituted or substituted at any position by one or more than one substituent selected from the group consisting of —CN, —$NO_2$, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$C(O)NR_dS(O)_2R_e$, —$NR_dR_e$, —$NR_dC(O)R_e$, —$N(R_d)C(O)OR_e$, —$N(R_d)C(O)NR_dR_e$, —$NR_dC(=NH)R_e$, —$NR_dC(=NH)NR_dR_e$, —$NR_dS(O)_2R_e$, —$NR_dS(O)_2NR_dR_e$, —$N(R_d)C(O)N(R_d)S(O)_2R_e$, —$S(O)_{1-2}R_e$, —$S(O)_2NR_dR_e$, —$S(O)_2N(R_d)C(O)R_e$ or —$S(O)_2N(R_d)C(O)NR_dR_e$;

each of n is independently 1, 2 or 3;
wherein, $L_2$, $Cy^1$, $R_d$ and $R_e$ are defined as claim 1.

7. The compound of formula (I), the isomer, the prodrug, the stable isotopic derivative or the pharmaceutically acceptable salt thereof according to claim 6, wherein, each of $R_7$ is independently hydrogen, $C_{1-6}$ alkyl, $C_{1-6}$ haloalkyl, $C_{2-6}$ alkenyl, $C_{2-6}$ alkynyl, $Cy^1$, -$L_2$-$Cy^1$, —$SR_d$, —$OR_d$, —$C(O)OR_d$, —$C(O)R_d$, —$C(O)NR_dR_e$, —$C(=NH)R_e$, —$C(=NH)NR_dR_e$, —$S(O)_2R_e$ or —$S(O)_2NR_dR_e$; wherein the $C_{1-6}$ alkyl, $C_{2-6}$ alkenyl or $C_{2-6}$ alkynyl is unsubstituted or substituted at any position by 1 to 3 substituent selected from the group consisting of —CN, —$NO_2$, —CN, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(=NH)R_e$, —$NR_dC(=NH)NR_dR_e$, —$S(O)_{1-2}R_e$, —$S(O)_2NR_dR_e$, —$S(O)(=NCN)R_e$, —$S(O)(=NR_d)R_e$, —$S(O)(=NSO_2R_d)R_e$, —$NR_dS(O)_2NR_dR_e$ or —$P(O)(OR_d)_2$, —$OP(O)(OR_d)_2$ or —$B(OR_d)_2$;

and/or, each of $R_{7a}$ is independently hydrogen or $C_{1-6}$ alkyl;

and/or, each of $R_8$ is independently hydrogen, methyl, ethyl, n-propyl, tert-butyl, isopropyl, isobutyl, n-butyl, —CN, —$NO_2$, —$NH_2$, —$CF_3$, —$OCF_3$, —$CH_3$, —$OCH_3$, F, Cl or Br;

and/or, $L_2$ is a bond, —$CH_2$—, —$CH_2CH_2$—, —$CH_2CH_2CH_2$—, —$CH_2CH_2C(CH_3)_2$—, —$CH_2CH_2CH_2CH_2$— or —$CH_2CH(CH_3)CH_2$—;

and/or, each of $Cy^1$ is independently $C_{3-10}$ cycloalkyl, 3 to 10 membered heterocycloalkyl, $C_{6-10}$ aryl or 5 to 10 membered heteroaryl; the $Cy^1$ is unsubstituted or substituted at any position by 1 to 3 substituent selected from the group consisting of F, Cl, Br, $C_{1-4}$ alkyl, $C_{1-3}$ haloalkyl, $C_{1-3}$ haloalkoxy, $C_{1-3}$ hydroxyalkyl, $C_{1-3}$ aminoalkyl, $C_{2-6}$ alkenyl, $C_{2-6}$ alkynyl, —CN, —$NO_2$, —$SR_{d2}$, —$OR_{d2}$, —$OC(O)R_{d2}$, —$OC(O)OR_{d2}$, —$OC(O)NR_{d2}R_{e2}$, —$C(O)OR_{d2}$, —$C(O)R_{d2}$, —$C(O)NR_{d2}R_{e2}$, —$NR_{d2}R_{e2}$, —$NR_{d2}C(O)R_{e2}$, —$N(R_{d2})C(O)OR_{e2}$, —$N(R_{d2})C(O)NR_{d2}R_{e2}$, —$NR_{d2}S(O)_2R_{e2}$, —$NR_{d2}C(=NH)R_{e2}$, —$NR_{d2}C(=NH)NR_{d2}R_{e2}$, —$S(O)_{1-2}R_{e2}$, —$S(O)_2NR_{d2}R_{e2}$ and —$NR_{d2}S(O)_2NR_{d2}R_{e2}$;

and/or, each of $R_d$, $R_e$, $R_{d2}$ and $R_{e2}$ is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, 3 to 8 membered heterocycloalkyl, $C_{6-10}$ aryl, 5 to 6 membered heteroaryl, $C_{3-8}$ cycloalkyl $C_{1-6}$ alkyl, 3 to 8 membered heterocycloalkyl $C_{1-6}$ alkyl, phenyl $C_{1-6}$ alkyl or 5 to 6 membered heteroaryl $C_{1-6}$ alkyl; $R_d$, $R_e$, $R_{d2}$ or $R_{e2}$ is unsubstituted or substituted at any position by 1 to 3 substituent selected from the group consisting of halogen, hydroxyl, amino, carboxyl, $C_{1-4}$ alkyl, $C_{1-3}$ haloalkyl, $C_{1-3}$ haloalkoxy, $C_{1-3}$ alkoxy, $C_{1-3}$ alkylamino, $C_{2-6}$ alkenyl and $C_{2-6}$ alkynyl;

or, $R_d$ and $R_e$ together with the N atom to which they are attached, form a 3 to 8 membered heterocycloalkyl; the heterocycloalkyl may further contain 1 to 3 hetero atom selected from N, O, and S;

or, $R_{d2}$ and $R_{e2}$ together with the N atom to which they are attached, form a 3 to 8 membered heterocycloalkyl.

8. The compound of formula (I), the isomer, the prodrug, the stable isotopic derivative or the pharmaceutically acceptable salt thereof according to claim 6, wherein each of $R_7$ is independently hydrogen, methyl, ethyl, n-propyl, tert-butyl, isopropyl, isobutyl, n-butyl, neopentyl, tert-amyl, cyclopropyl, cyclobutyl, cyclopentyl, cyclohexyl, phenyl, pyridyl, pyrimidinyl, benzyl,
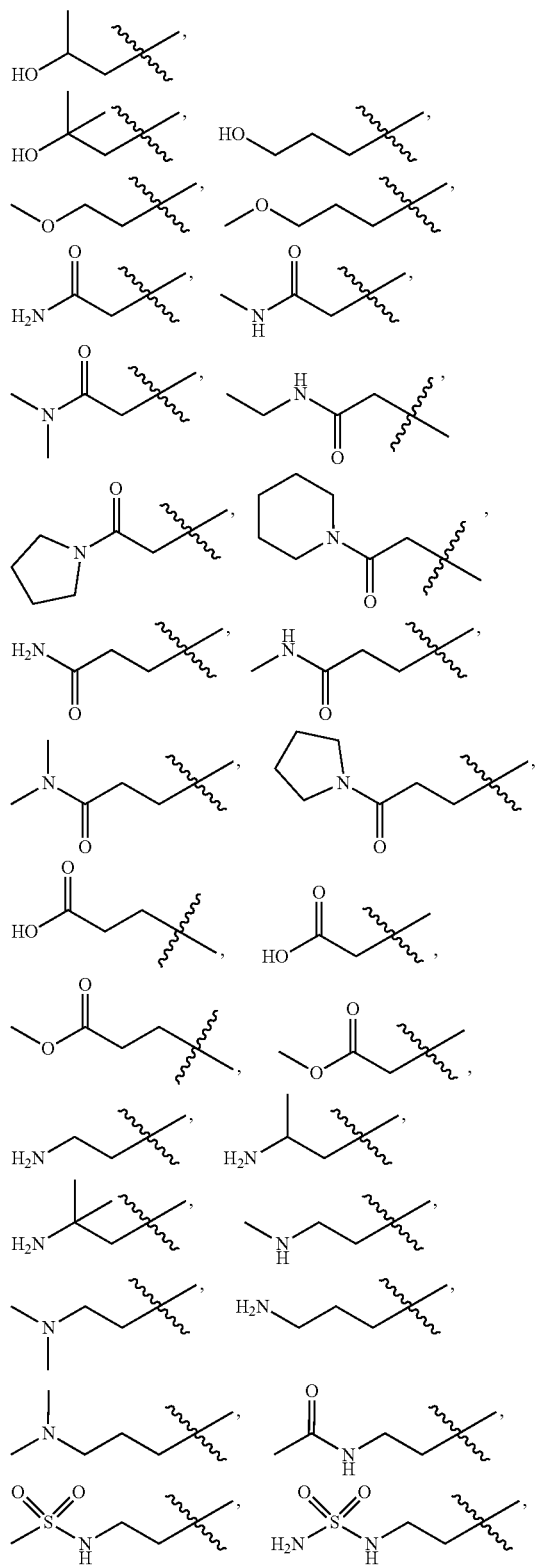
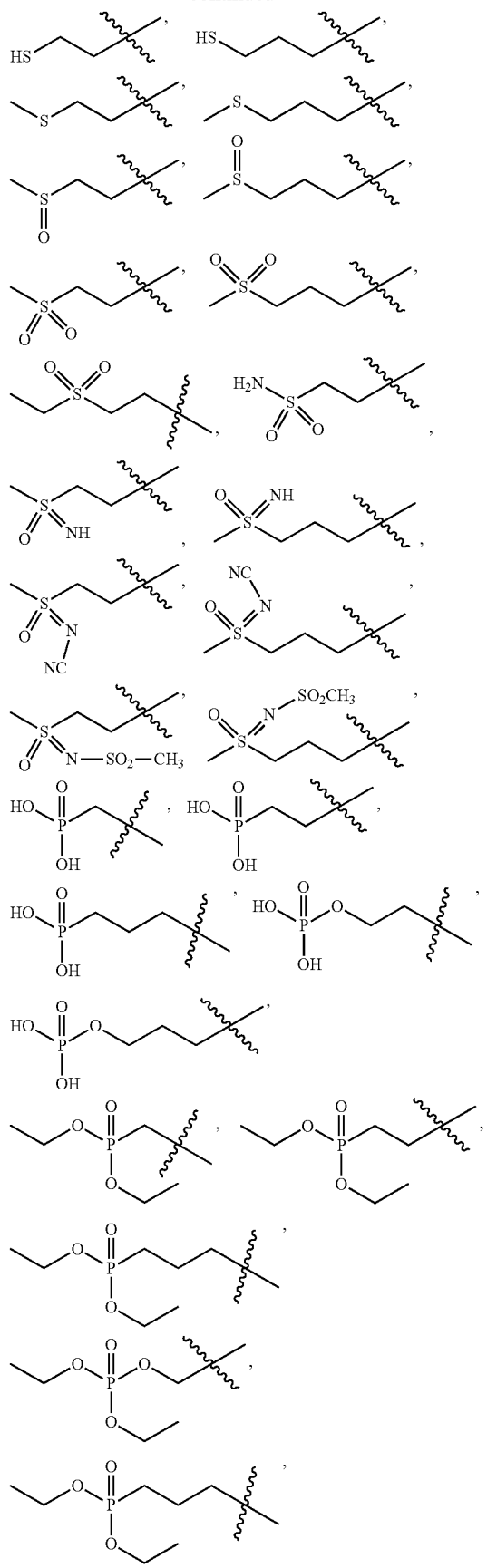

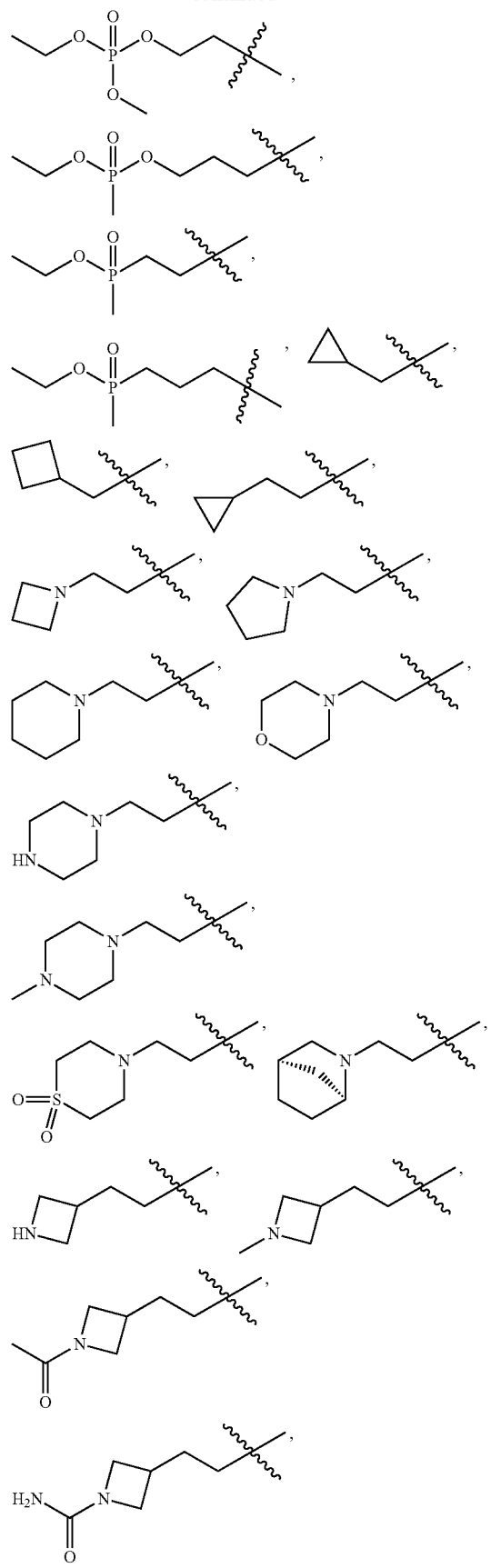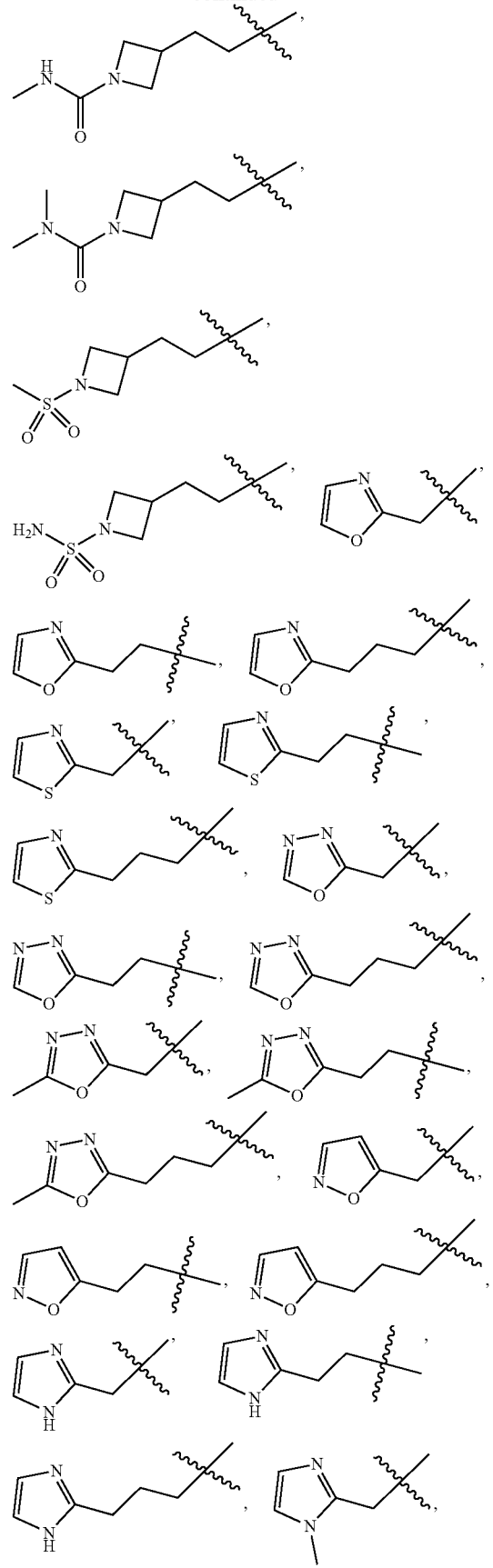

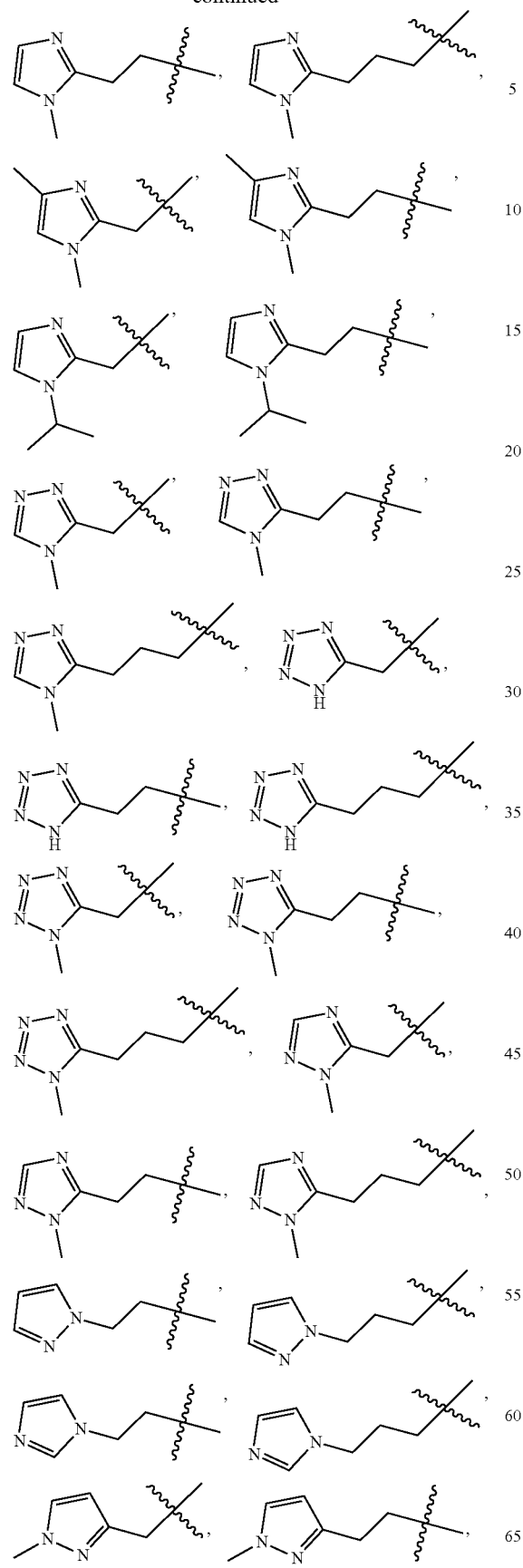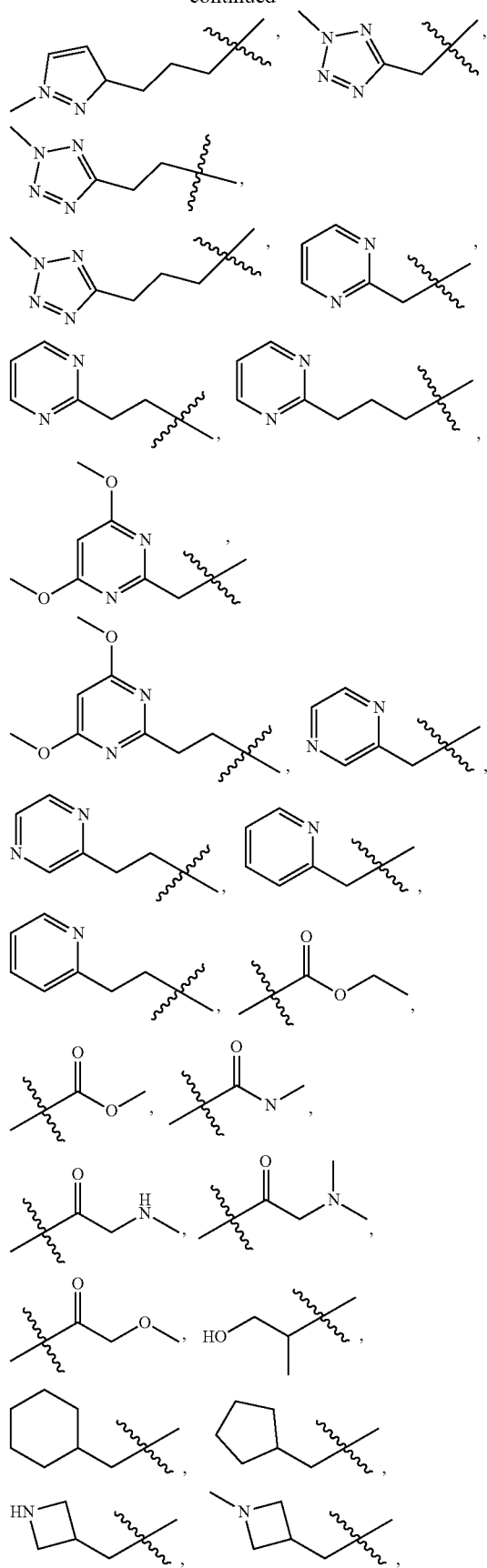

201
-continued

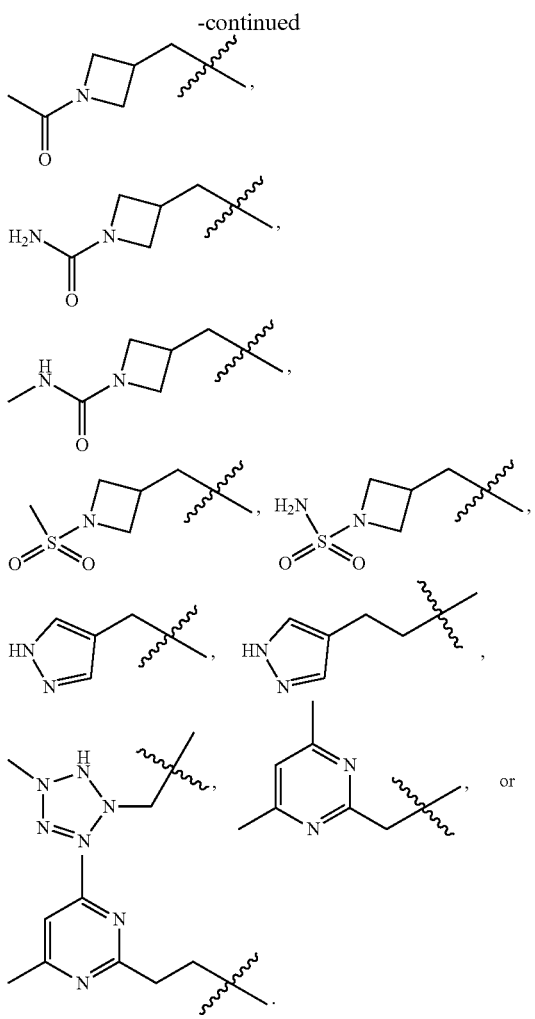

9. The compound of formula (I), the isomer, the prodrug, the stable isotopic derivative or the pharmaceutically acceptable salt thereof according to claim 1, which is shown as the compound of formula (IA), the isomer, the prodrug, the stable isotopic derivative or the pharmaceutically acceptable salt thereof:

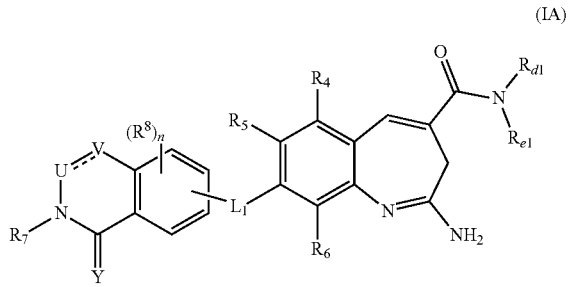

(IA)

wherein, ═══ is a single bond or a double bond;
Y is O or S;
U is N, C($R_8$) or C(O), V is N, C($R_8$) or N($R_{7a}$); and, ═══, U and V are any combination of the followings:
1) ═══ is a double bond, U is N, V is C($R_8$);
2) ═══ is a double bond, U is C($R_8$), V is N;
3) ═══ is a double bond, U is C($R_8$), V is C($R_8$);

202

4) ═══ is a single bond, U is C($R_8$), V is C($R_8$);
5) ═══ is a single bond, U is C(O), V is N($R_{7a}$);

each of $R_7$ and $R_{7a}$ is independently selected from hydrogen, halogen, alkyl, haloalkyl, alkenyl, alkynyl, $Cy^1$, -$L_2$-$Cy^1$, —C(O)O$R_d$, —C(O)$R_d$, —C(O)N$R_dR_e$, —C(O)N$R_dS(O)_2R_e$, —C(═NH)$R_e$, —C(═NH)N$R_dR_e$, —S(O)$_2R_e$ and —S(O)$_2$N$R_dR_e$; wherein the alkyl, alkenyl or alkynyl is unsubstituted or substituted at any position by one or more than one substituent selected from the group consisting of —CN, —NO$_2$, —S$R_d$, —O$R_d$, —OC(O)$R_d$, —OC(O)O$R_d$, —OC(O)N$R_dR_e$, —C(O)O$R_d$, —C(O)$R_d$, —C(O)N$R_dR_e$, —C(O)N$R_dS(O)_2R_e$, —N$R_dR_e$, —N$R_dC(O)R_e$, —N(R)C(O)O$R_e$, —N($R_d$)C(O)N$R_dR_e$, —N$R_dC$(═NH)$R_e$, —N$R_dC$(═NH)N$R_dR_e$, —N$R_dS(O)_2R_e$, —N$R_dS(O)_2NR_dR_e$, —N($R_d$)C(O)N($R_d$)S(O)$_2R_e$, —S(O)$_{1-2}R_e$, —S(O)$_2$N$R_dR_e$, —S(O)(═NCN)$R_e$, —S(O)(═N$R_d$)$R_e$, —S(O)(═NSO$_2R_d$)$R_e$, —S(O)$_2$N($R_d$)C(O)$R_e$, —S(O)$_2$N($R_d$)C(O)N$R_dR_e$, —P(O)(O$R_d$)$_2$, —OP(O)(O$R_d$)$_2$ or —B(O$R_d$)$_2$;

each of $R_8$ is independently hydrogen, halogen, alkyl, haloalkyl, haloalkoxy, alkenyl, alkynyl, $Cy^1$, -$L_2$-$Cy^1$, —CN, —NO$_2$, —S$R_d$, —O$R_4$, —OC(O)$R_d$, —OC(O)O$R_d$, —OC(O)N$R_dR_e$, —C(O)O$R_d$, —C(O)$R_d$, —C(O)N$R_dR_e$, —C(O)N$R_dS(O)_2R_e$, —C(═NH)$R_e$, —C(═NH)N$R_dR_e$, —N$R_dR_e$, —N$R_dC(O)R_e$, —N(R)C(O)O$R_e$, —N(R)C(O)N$R_dR_e$, —N$R_dS(O)_2R_e$, —N$R_dC$(═NH)$R_e$, —N$R_dC$(═NH)N$R_dR_e$, —S(O)$_{1-2}R_e$, —S(O)$_2$N$R_dR_e$ and —N$R_dS(O)_2NR_dR_e$; wherein the alkyl, alkenyl or alkynyl is unsubstituted or substituted at any position by one or more than one substituent selected from the group consisting of —CN, —NO$_2$—S$R_d$, —O$R_d$, —OC(O)$R_d$, —OC(O)O$R_d$, —OC(O)N$R_dR_e$, —C(O)O$R_d$, —C(O)$R_d$, —C(O)N$R_dR_e$, —C(O)N$R_dS(O)_2R_e$, —N$R_dR_e$, —N$R_dC(O)R_e$, —N($R_d$)C(O)O$R_e$, —N($R_d$)C(O)N$R_dR_e$, —N$R_dC$(═NH)$R_e$, —N$R_dC$(═NH)N$R_dR_e$, —N$R_dS(O)_2R_e$, —N$R_dS(O)_2NR_dR_e$, —N($R_d$)C(O)N($R_d$)S(O)$_2R_e$, —S(O)$_{1-2}R_e$, —S(O)$_2$N$R_dR_e$, —S(O)$_2$N($R_d$)C(O)$R_e$ or —S(O)$_2$N($R_d$)C(O)N$R_dR_e$;

n is 1;

$L_1$, $R_{d1}$, $R_{e1}$, $R_4$, $R_5$, and $R_6$ and X are defined as claim 1.

10. The compound of formula (I), the isomer, the prodrug, the stable isotopic derivative or the pharmaceutically acceptable salt thereof according to claim 1, wherein the compound of formula (I) is selected from the group consisting of

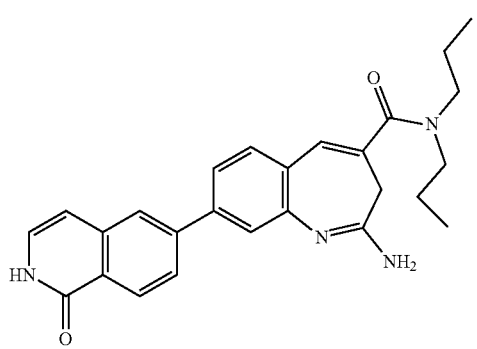

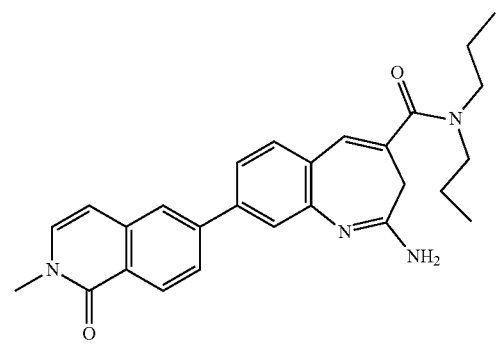
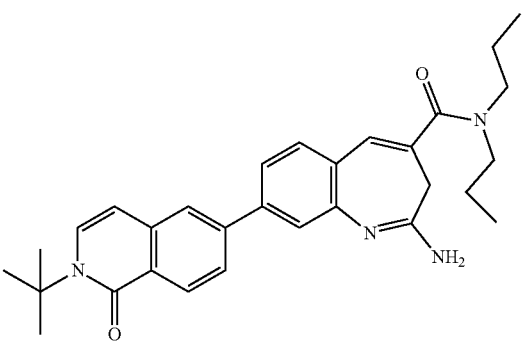
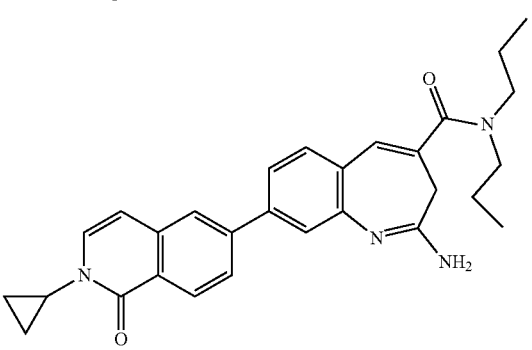
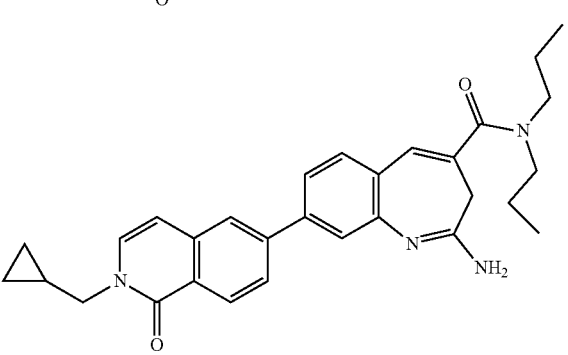
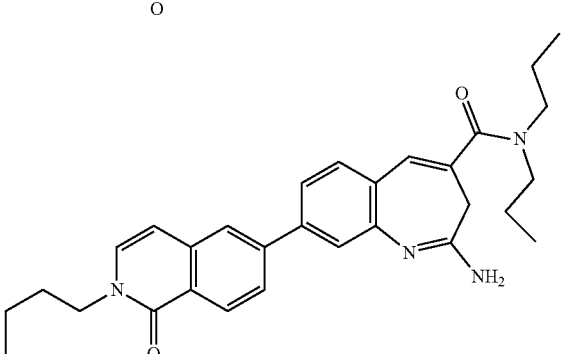
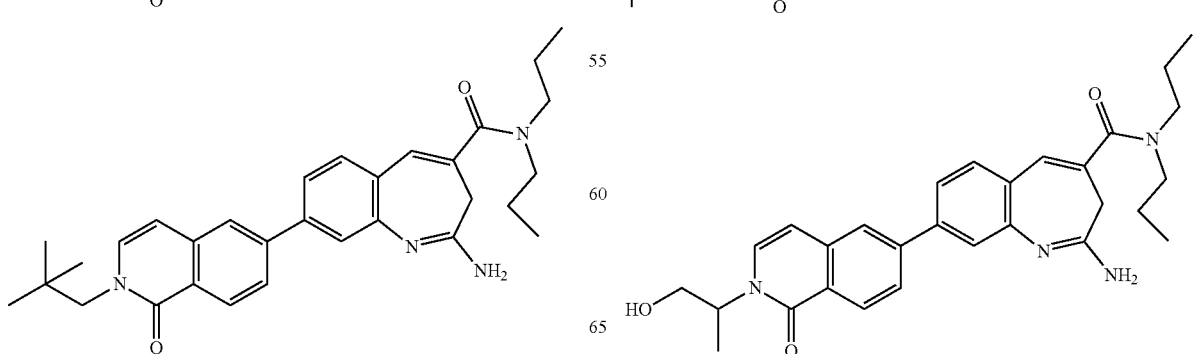

205
-continued
206
-continued
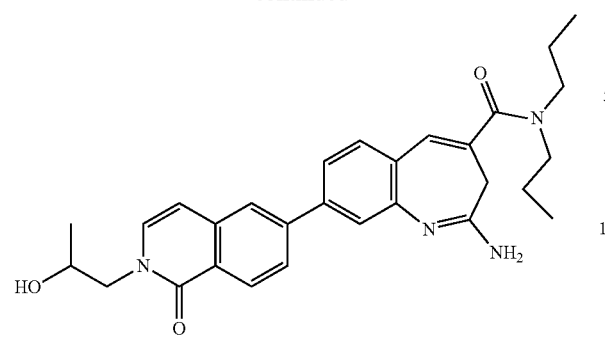
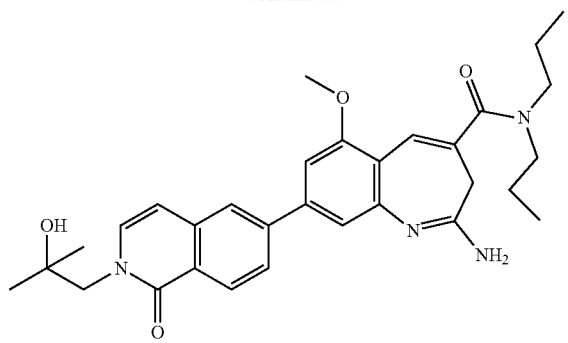

207
-continued
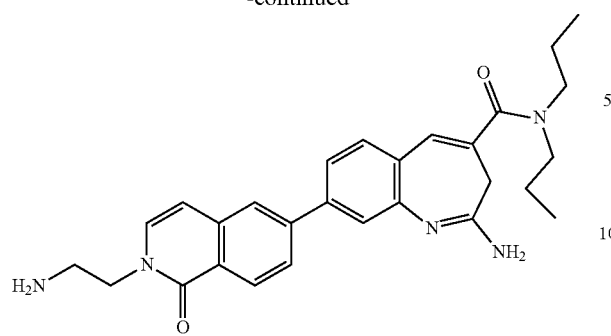
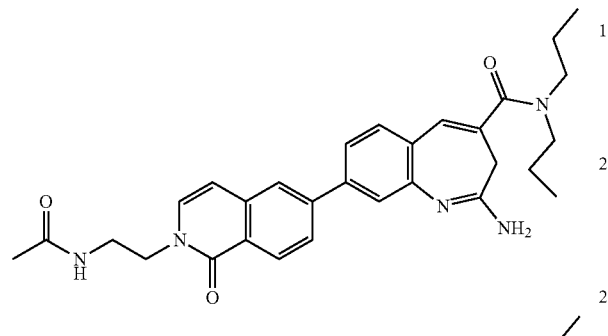
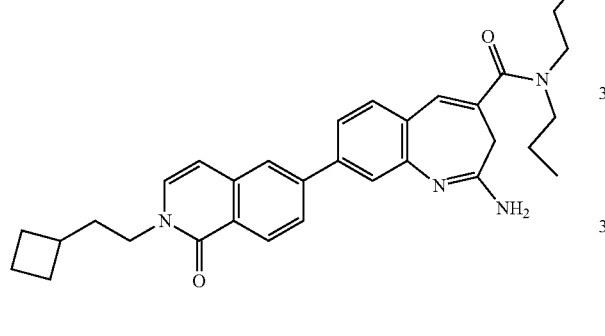
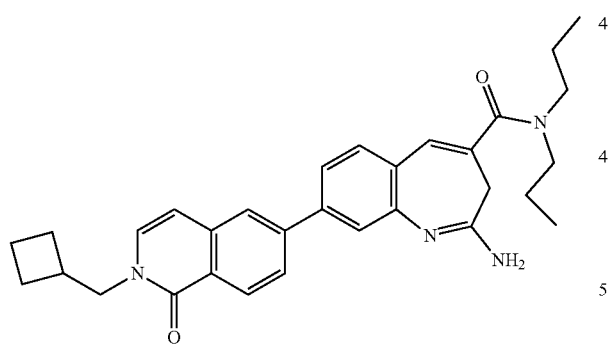
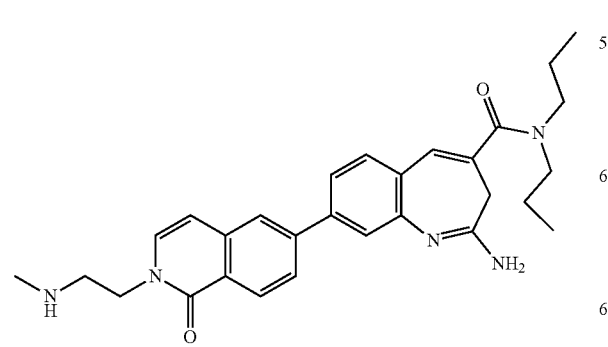
208
-continued
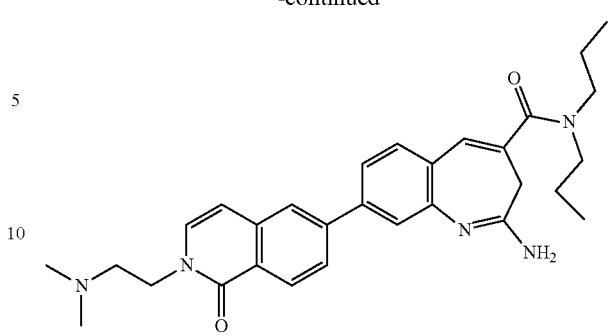
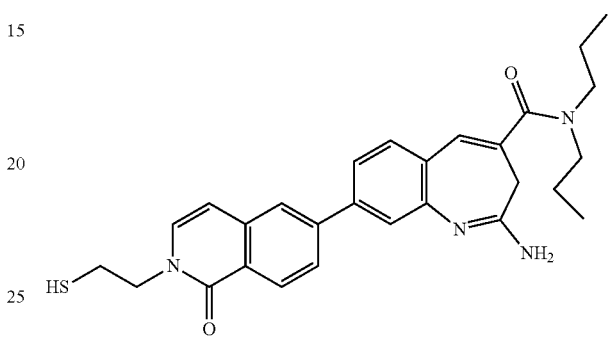
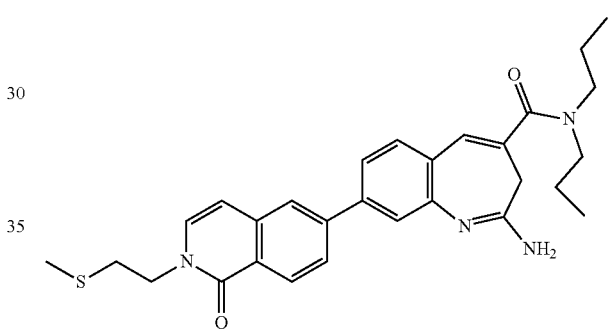
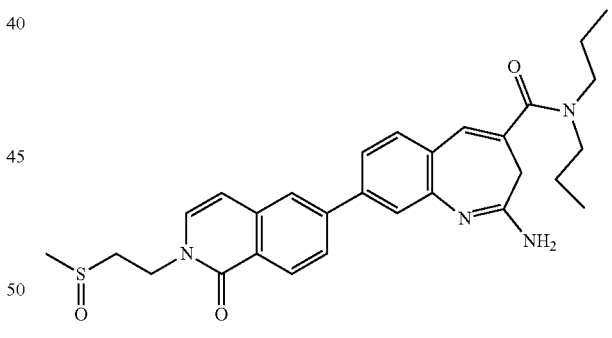
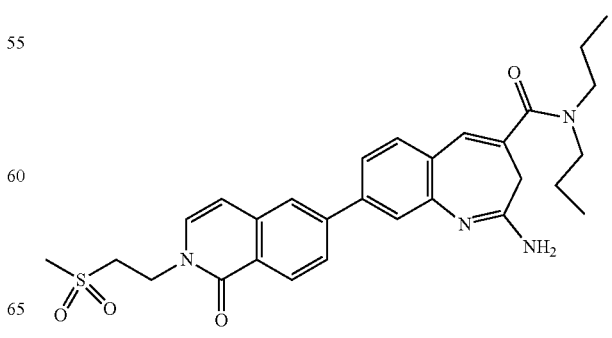

-continued
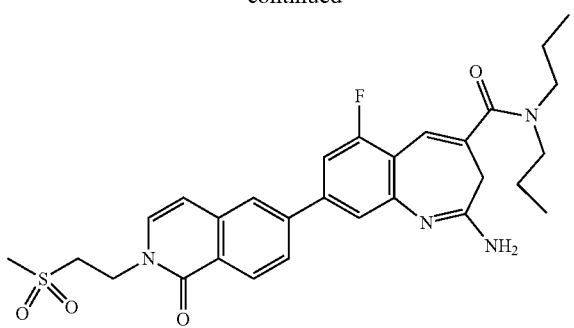
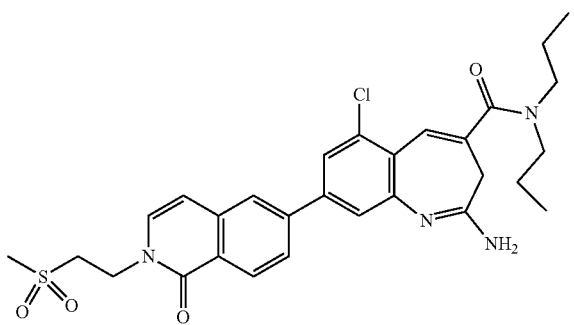
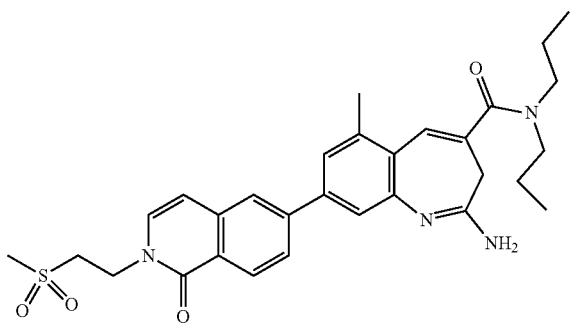
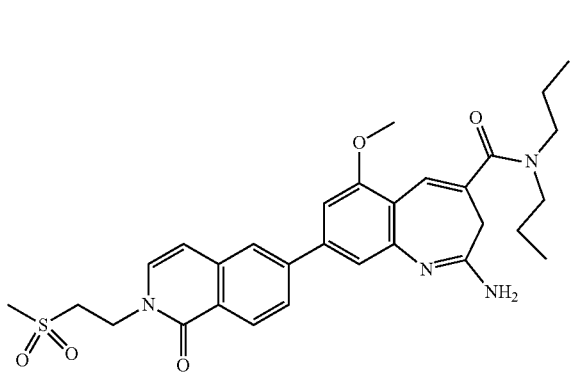
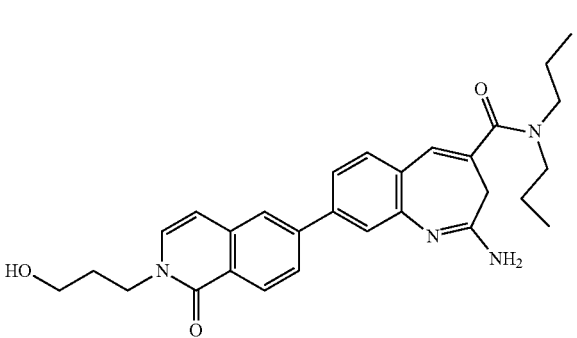
-continued
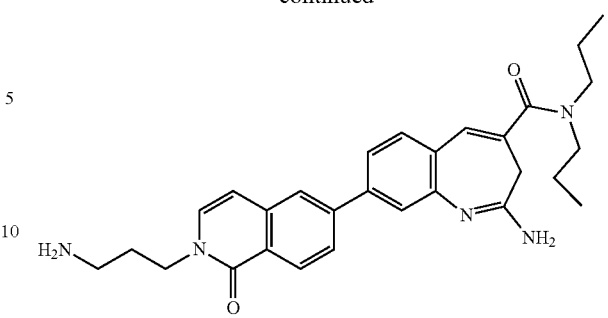
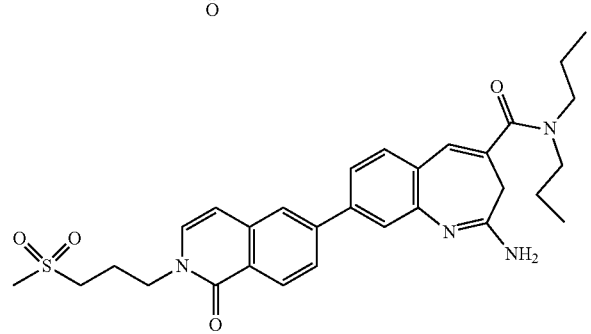
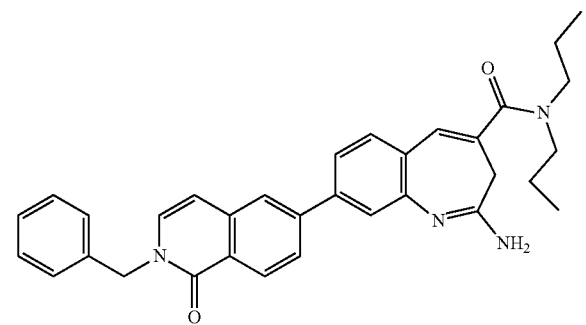
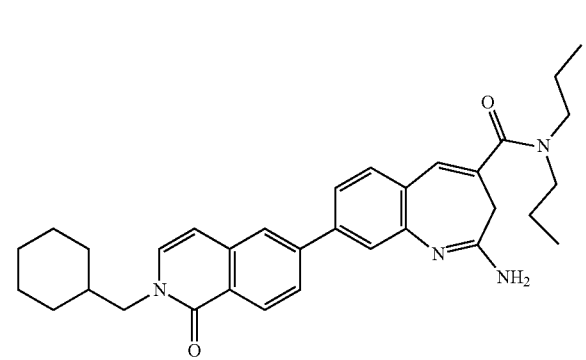
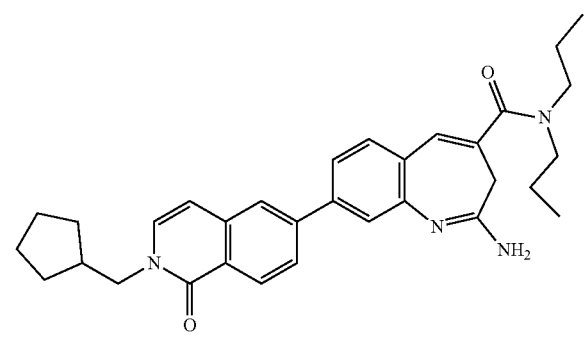

211
-continued
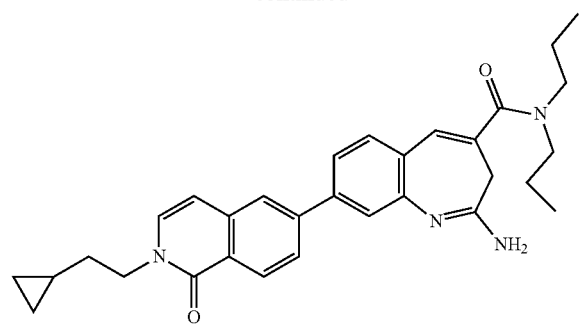
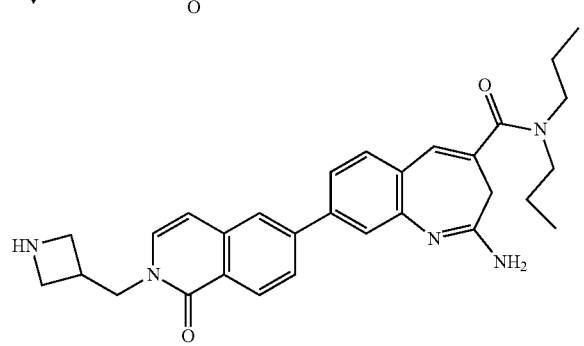
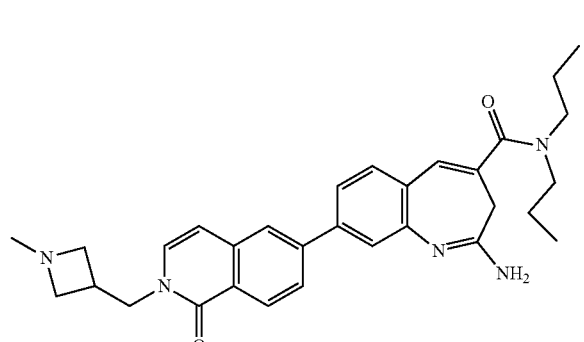
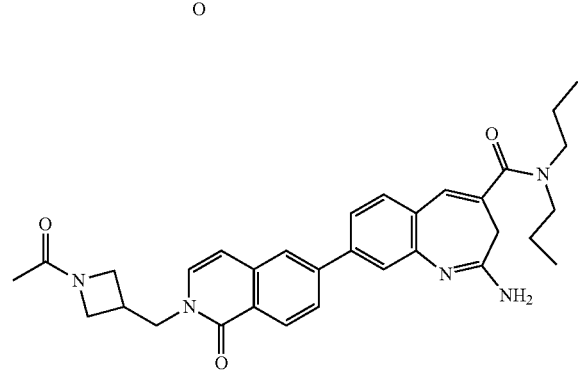
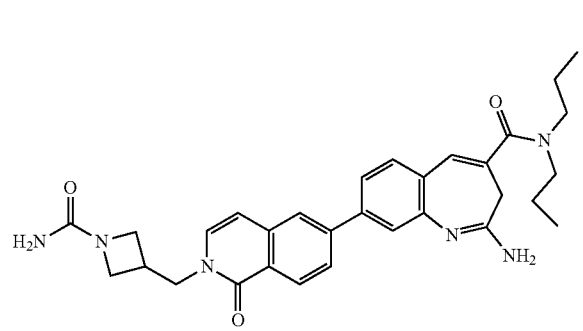
212
-continued
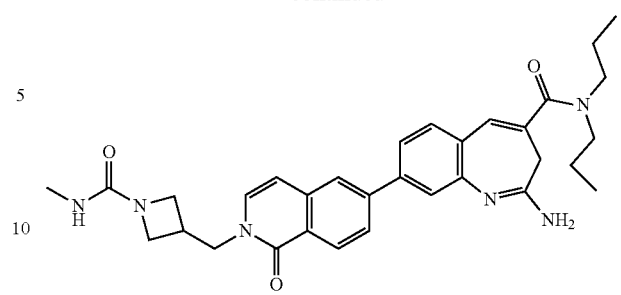
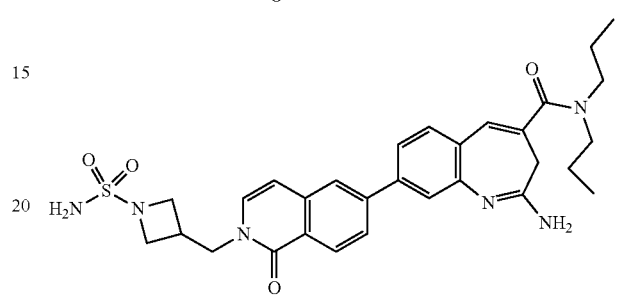
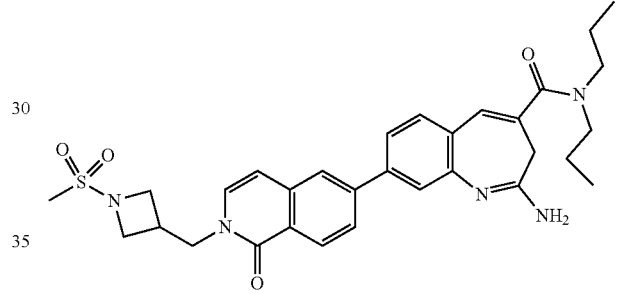
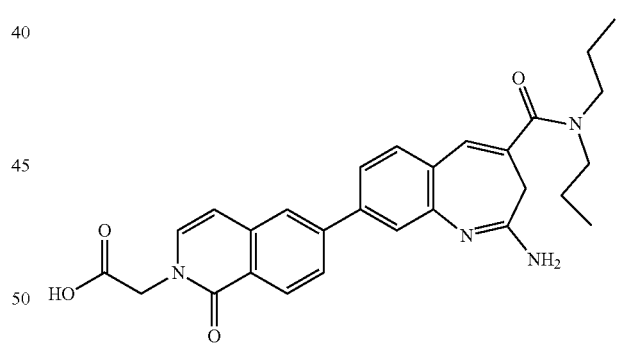
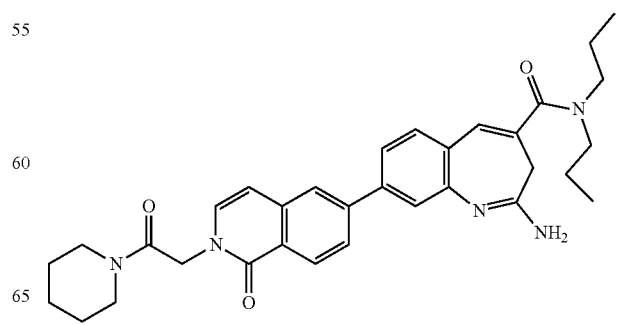

213
-continued
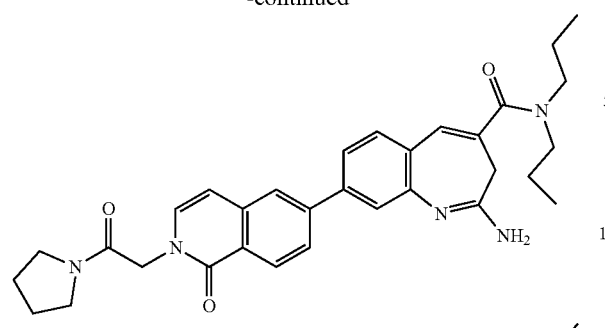
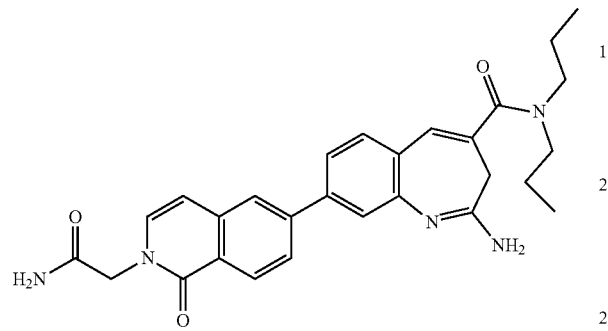
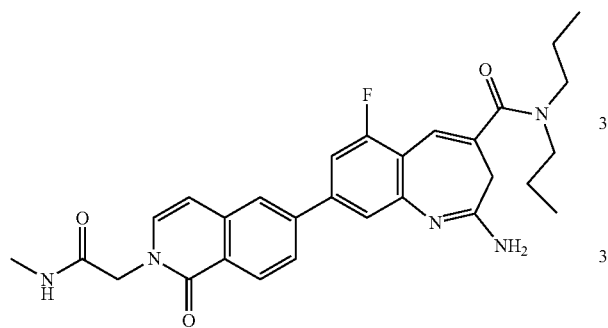
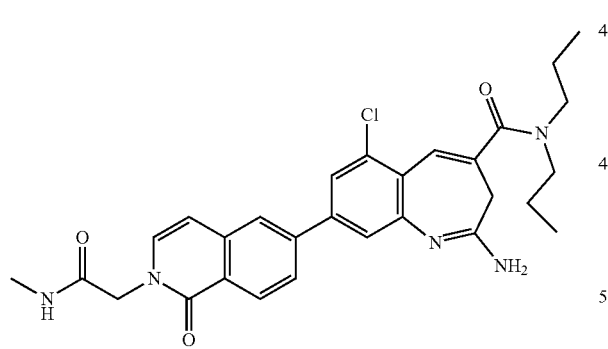
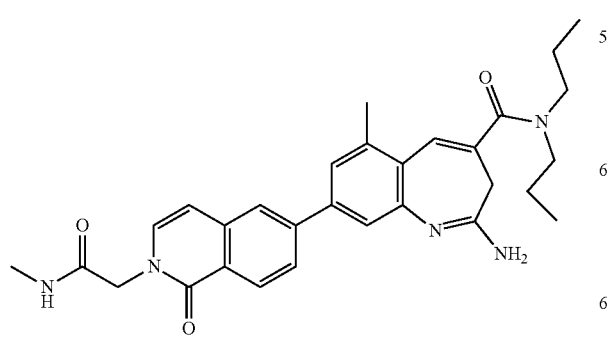
214
-continued
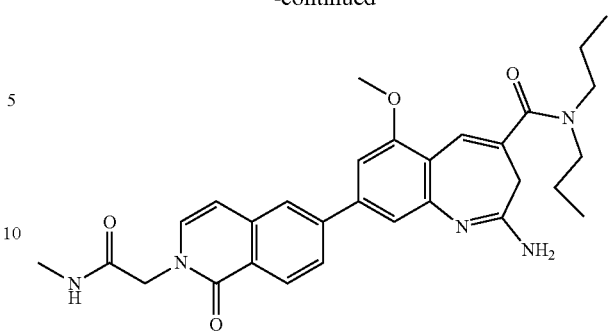
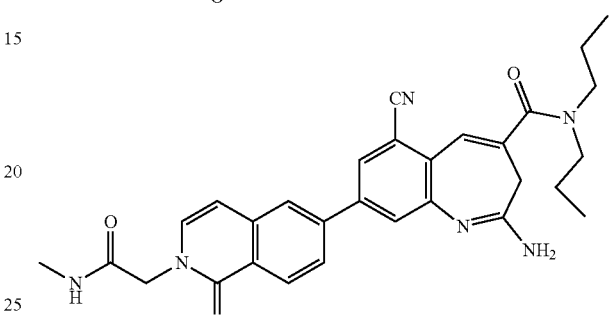
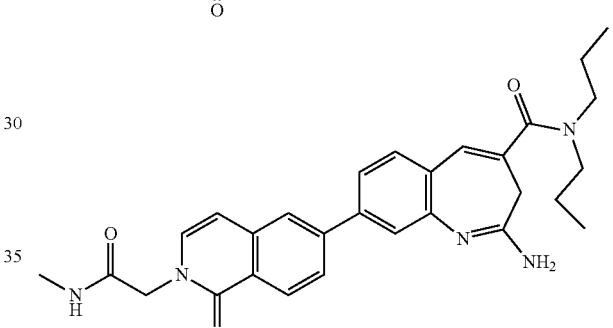
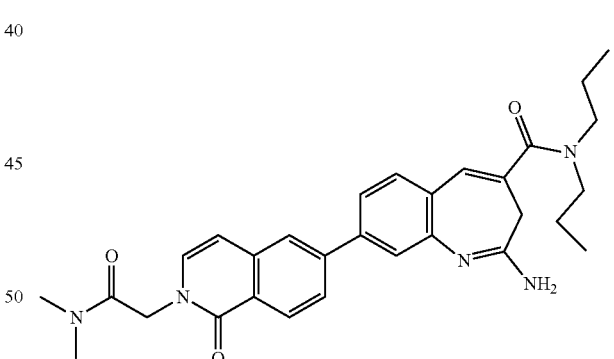
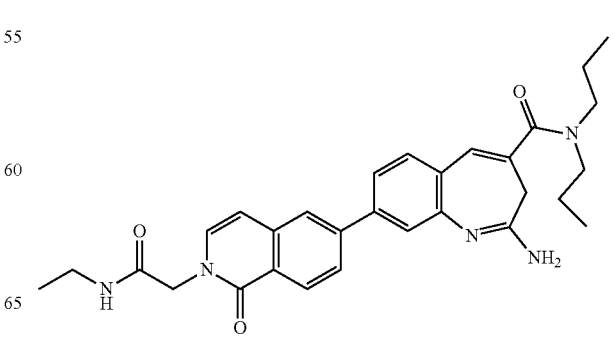

215
-continued
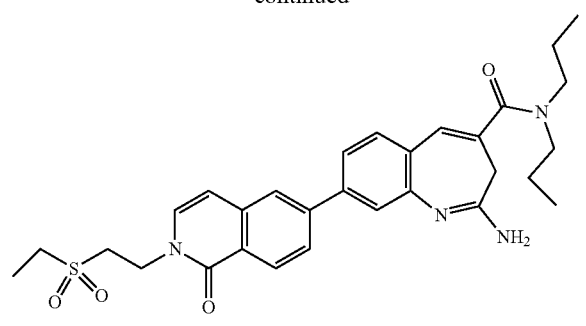
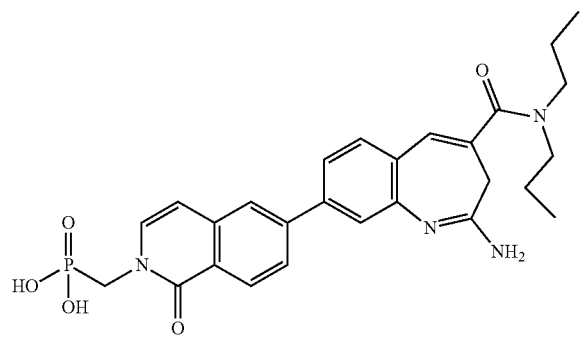
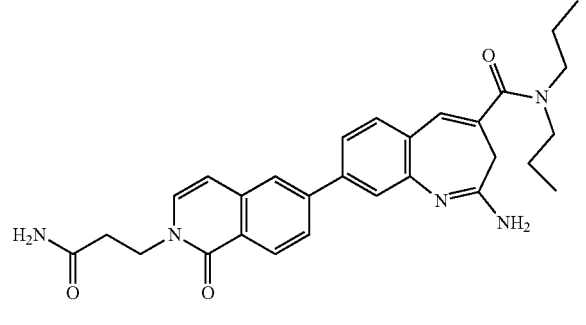
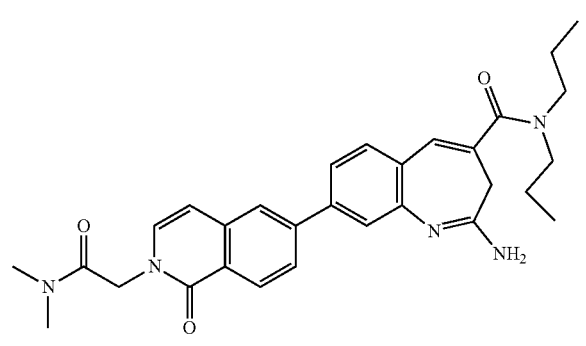
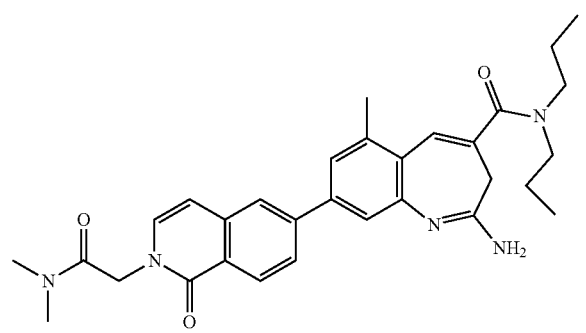
216
-continued
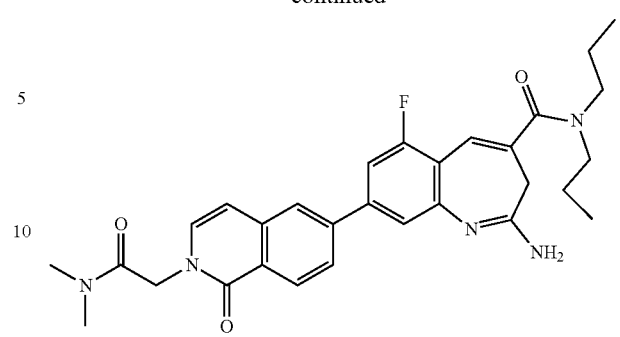
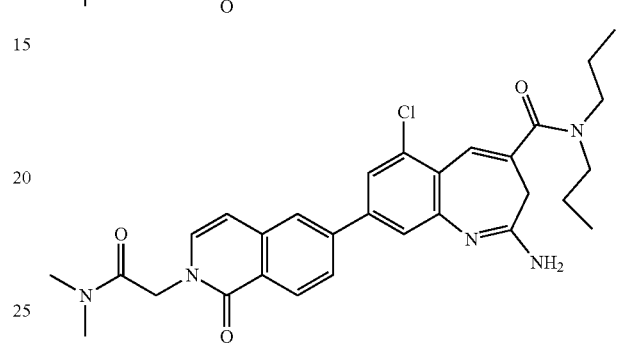
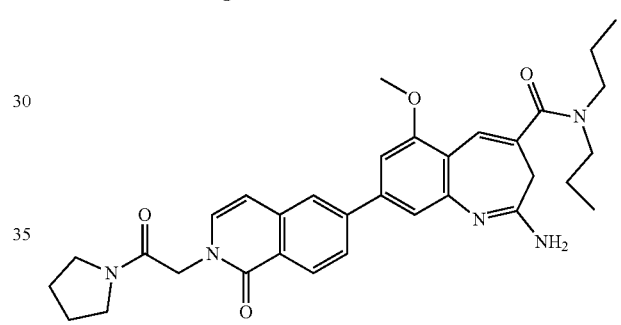
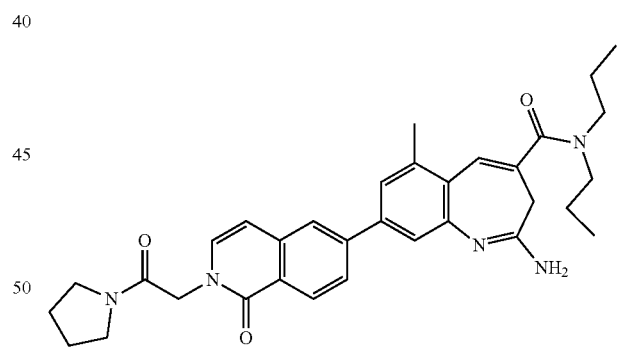
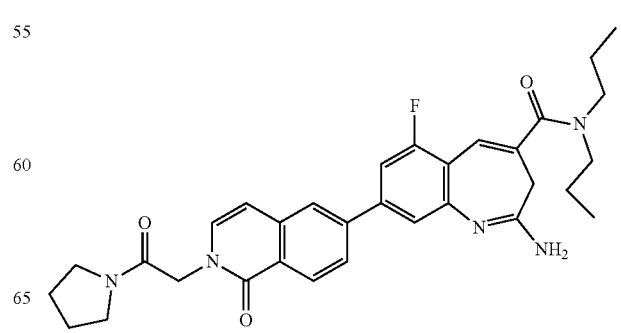

217
-continued
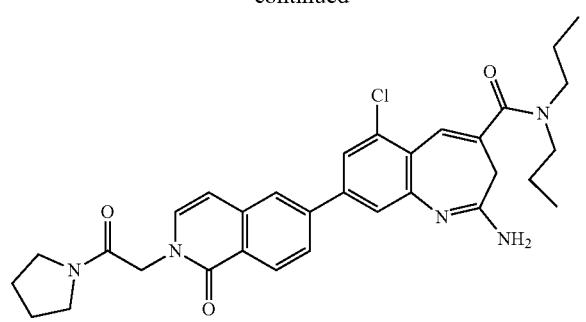
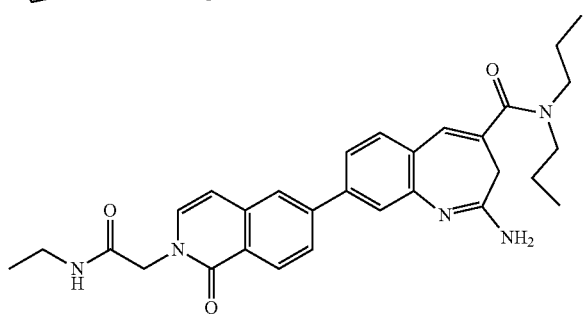
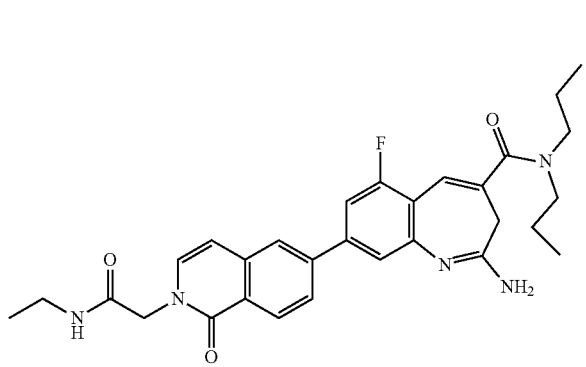
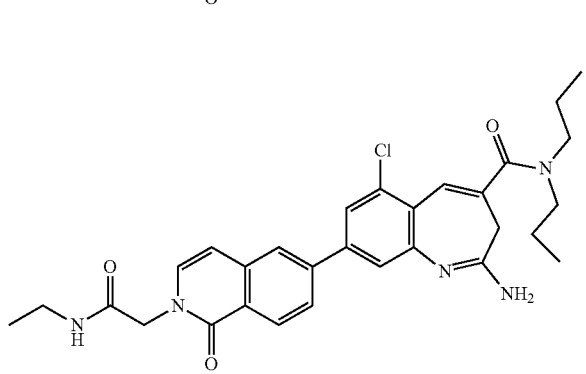
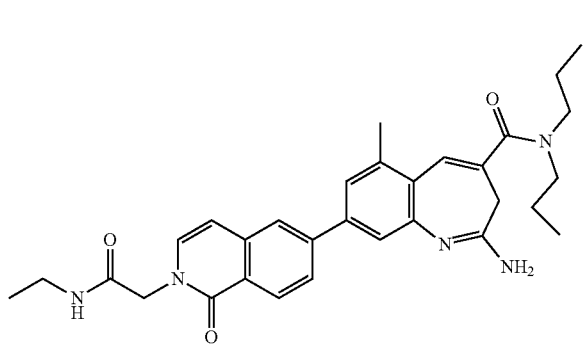
218
-continued
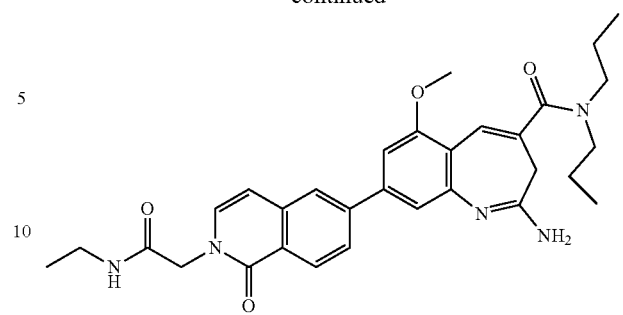
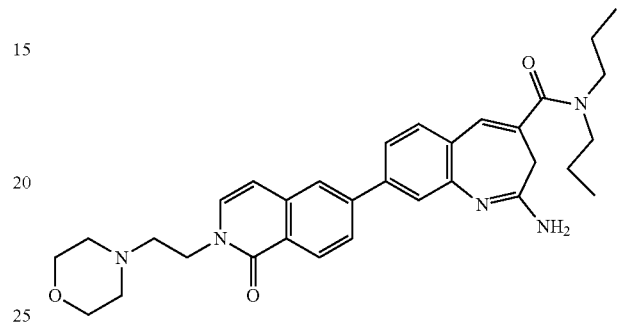
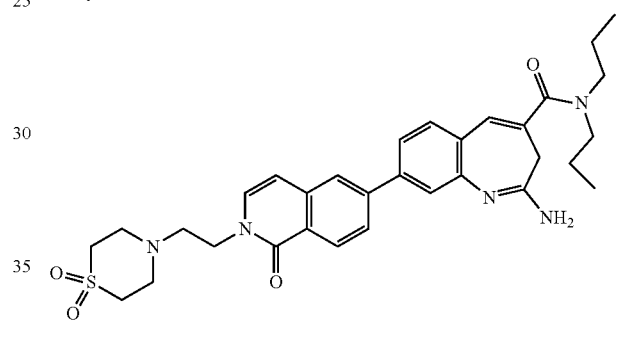
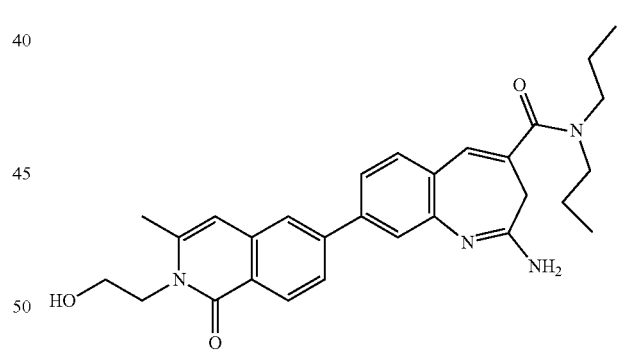
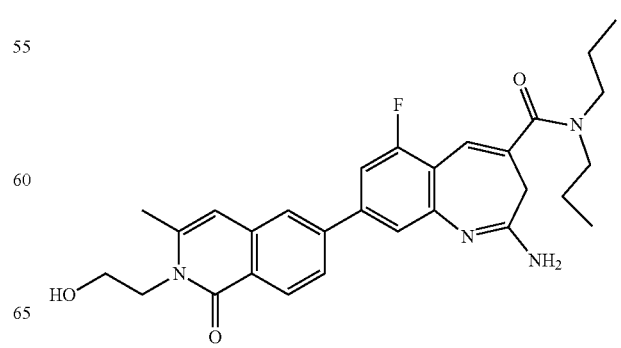

219
-continued
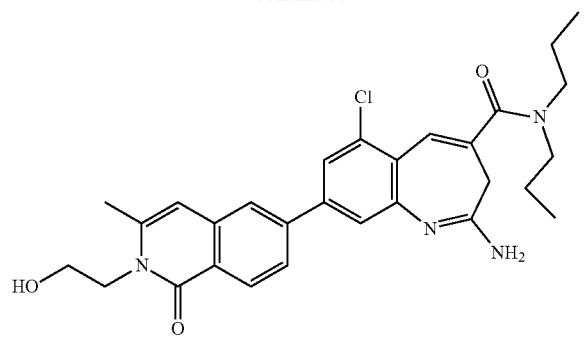
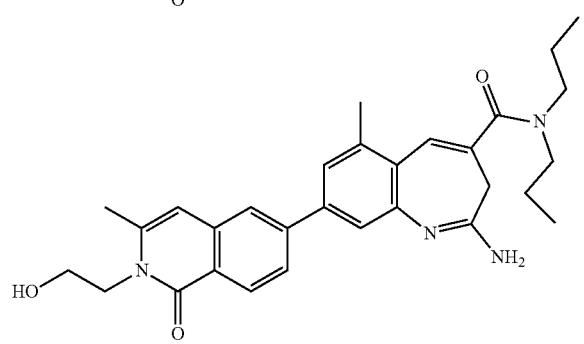
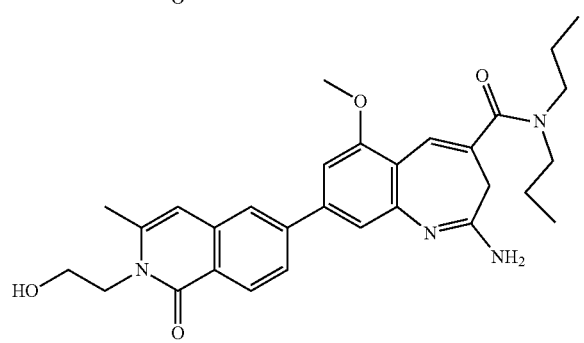
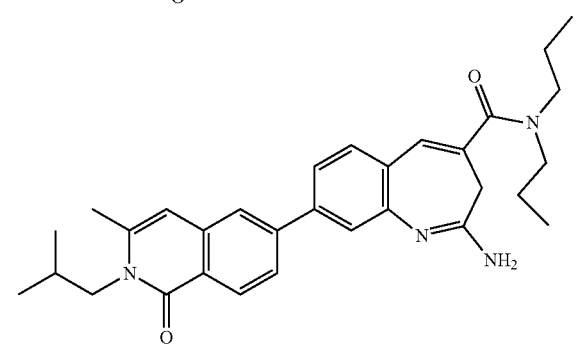
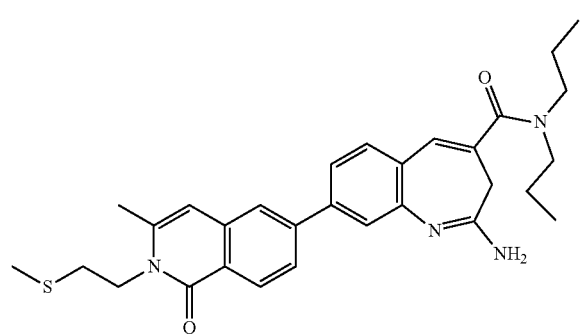
220
-continued
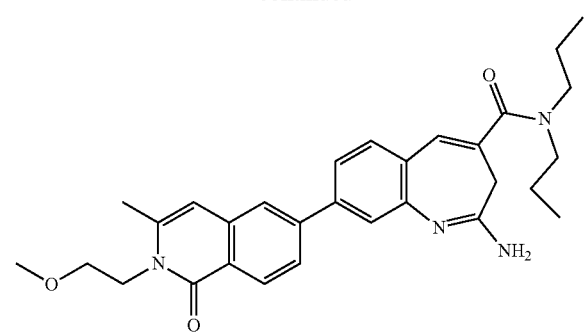
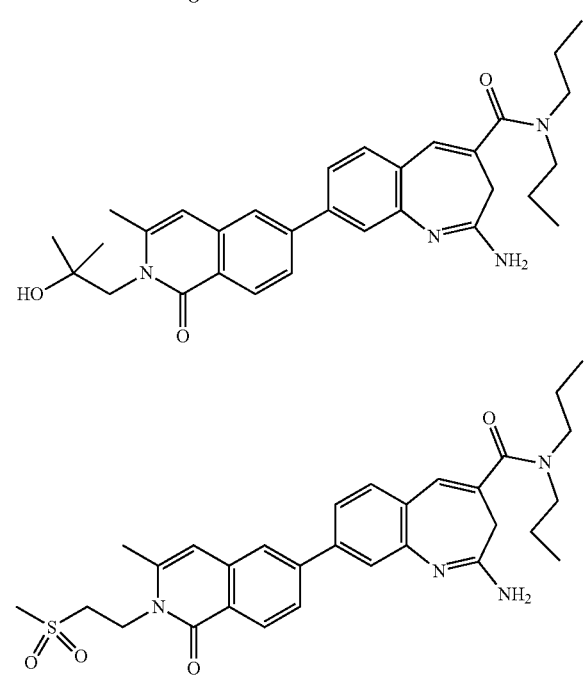
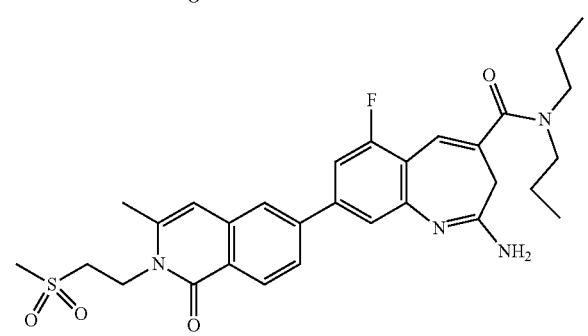
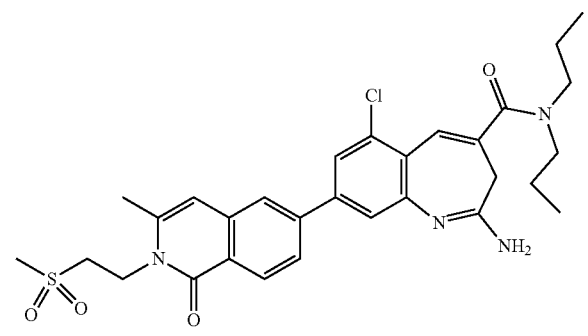

221
-continued
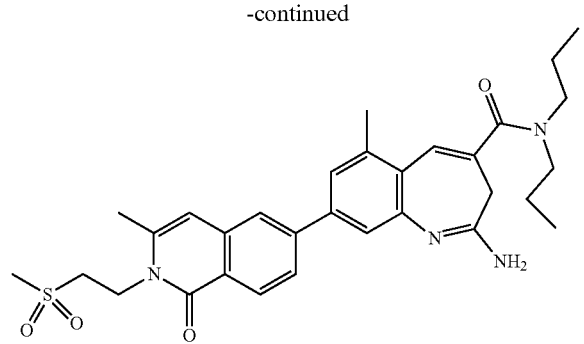
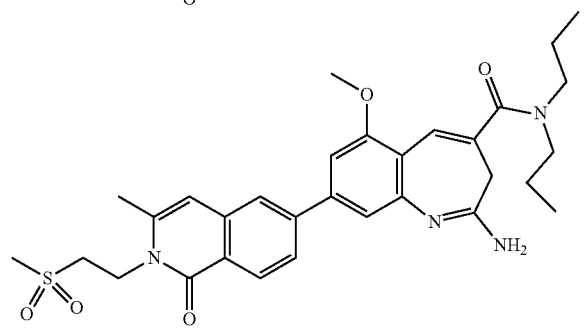
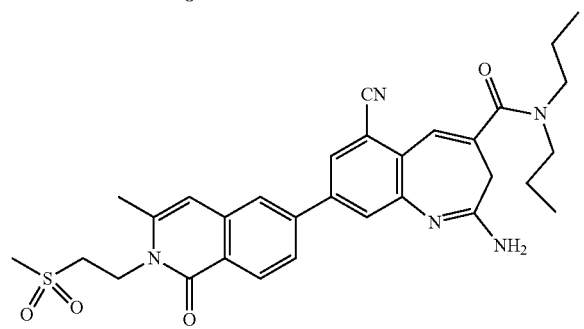
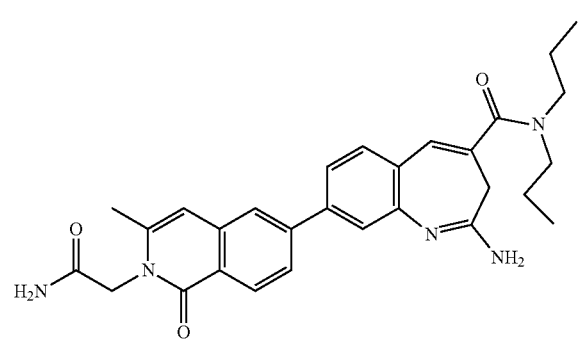
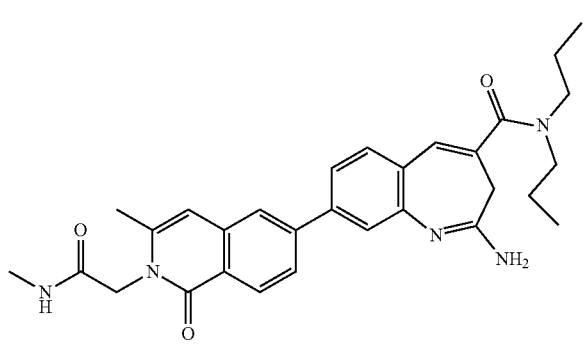
222
-continued
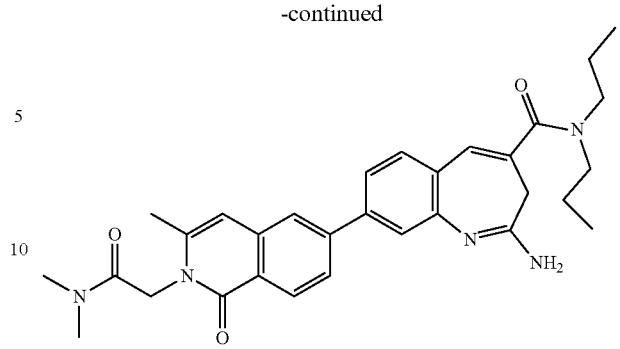
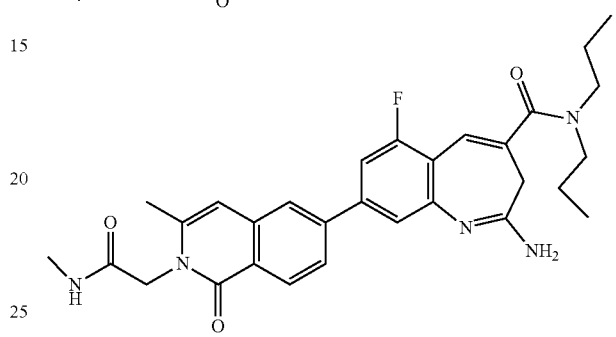
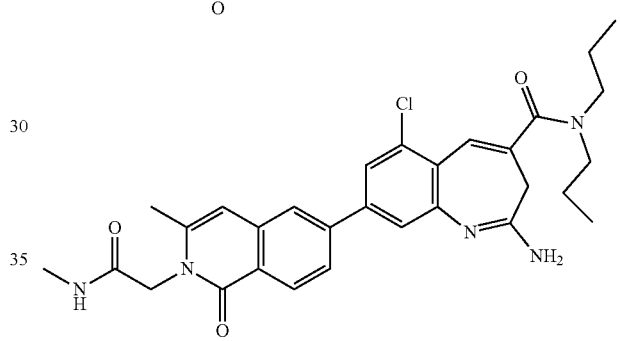
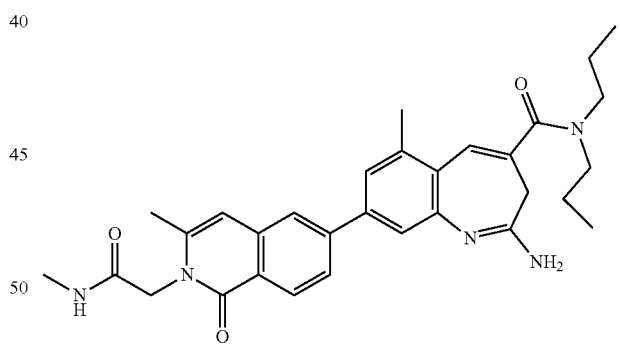
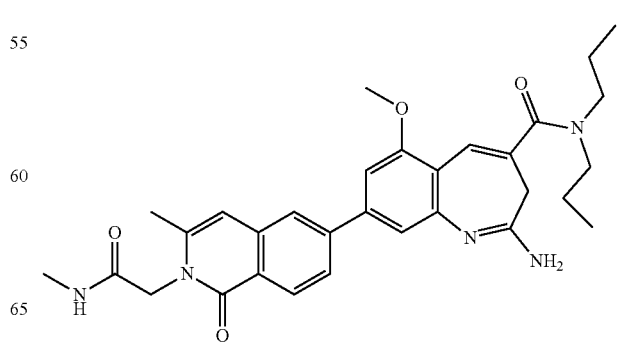

223
-continued
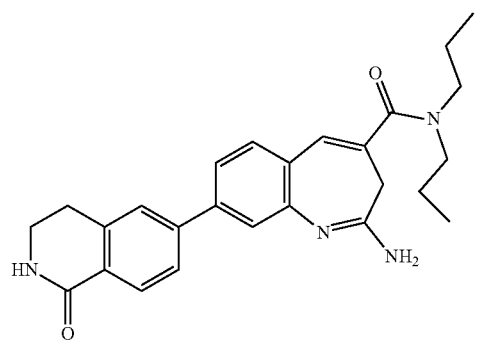
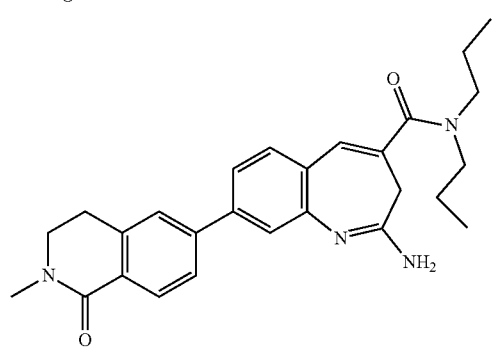
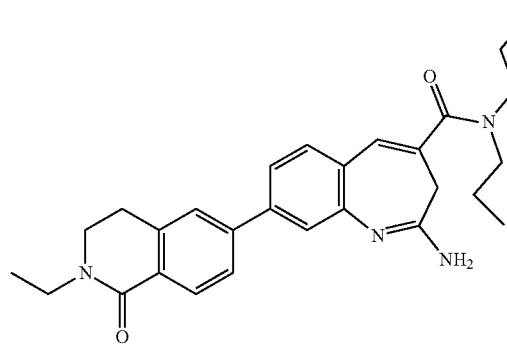
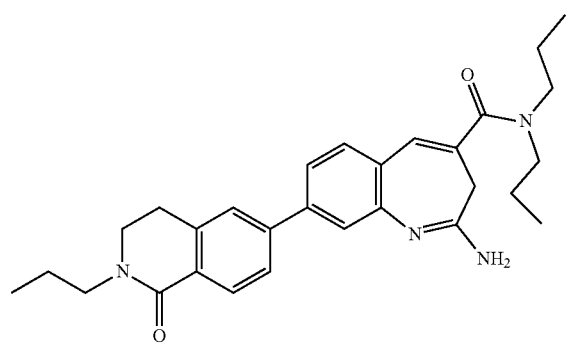
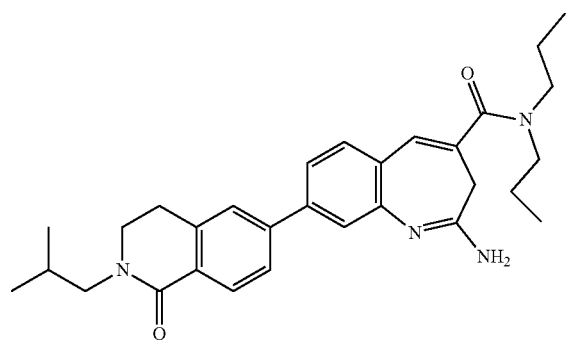
224
-continued
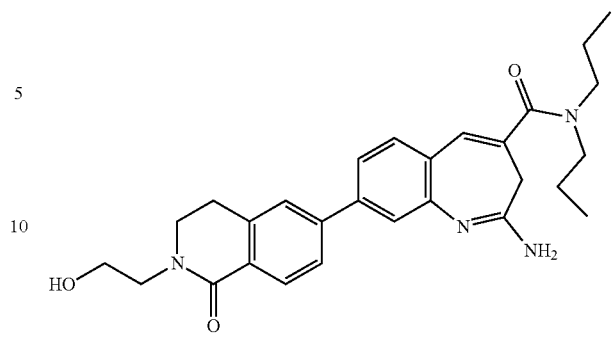
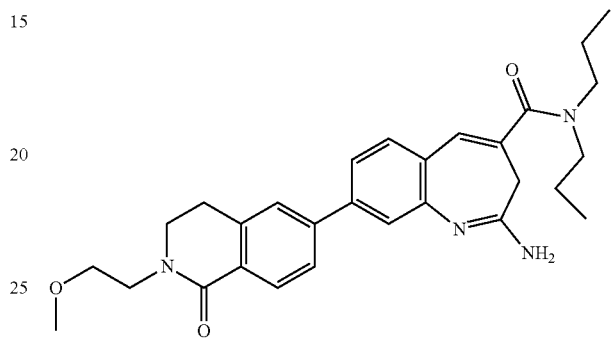
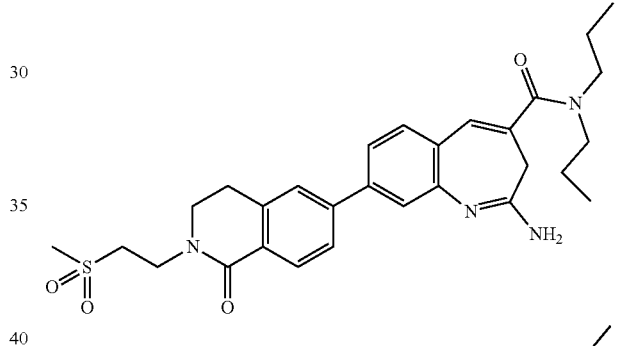
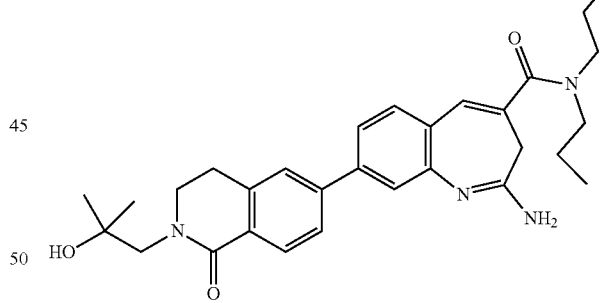
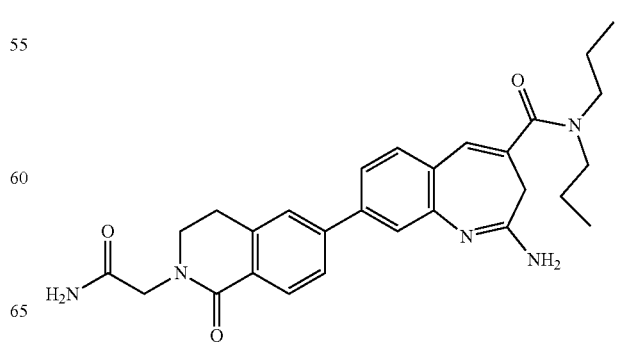

225
-continued
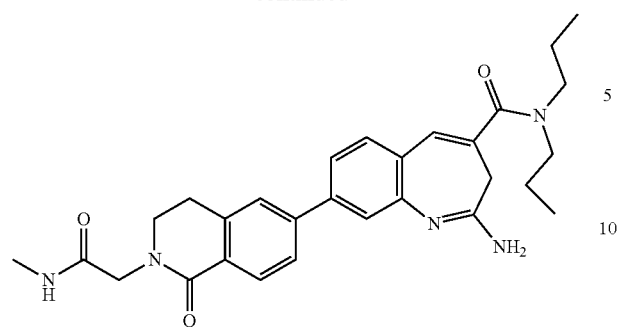
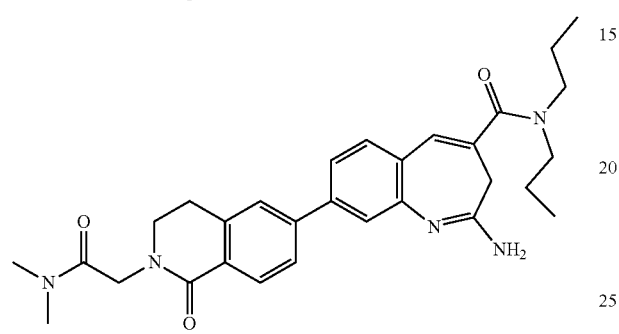
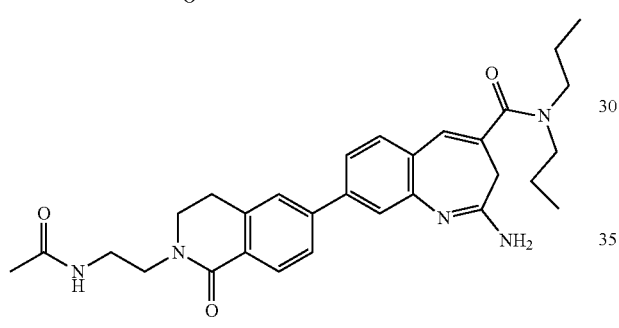
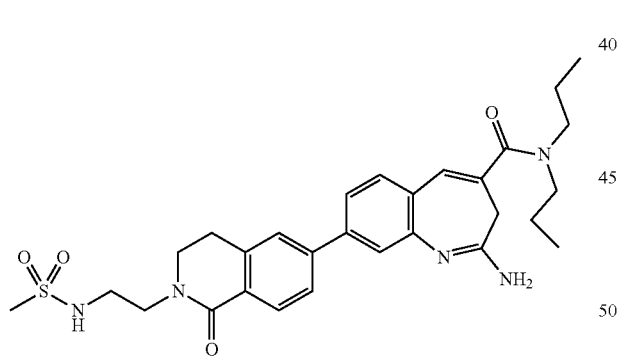
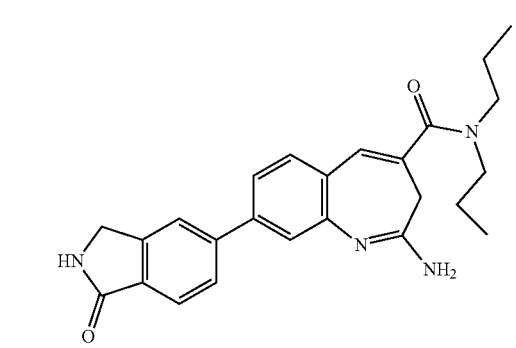
226
-continued
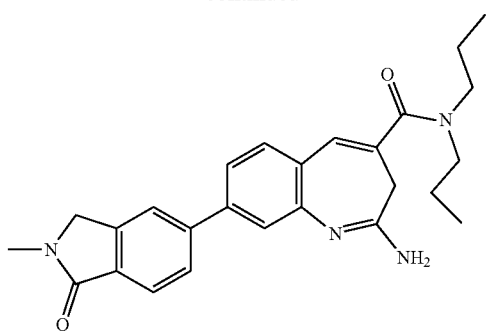
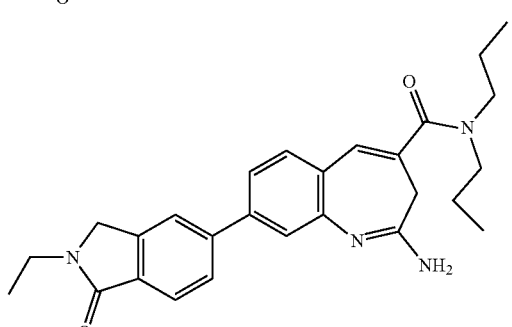
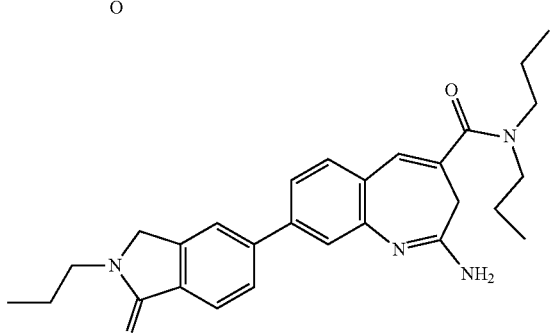
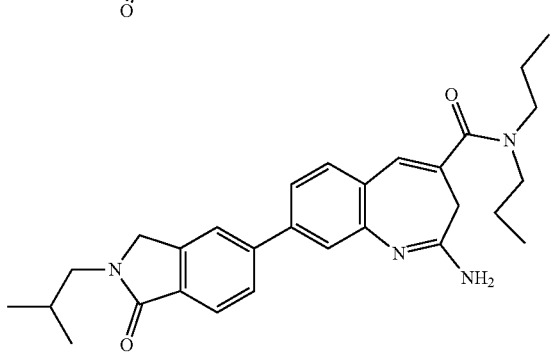
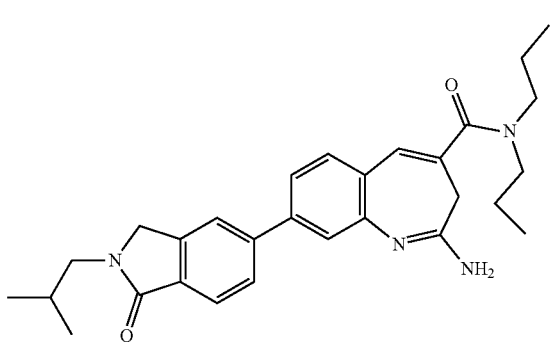

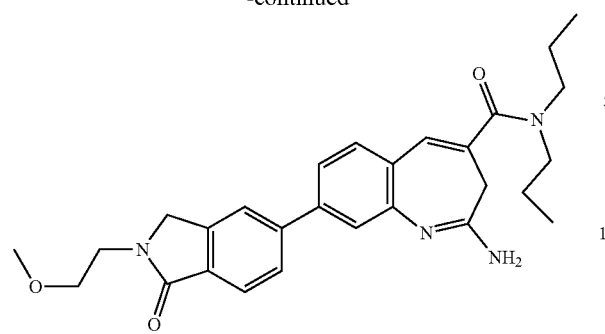
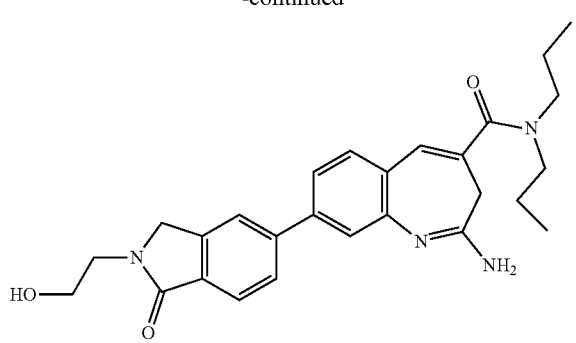
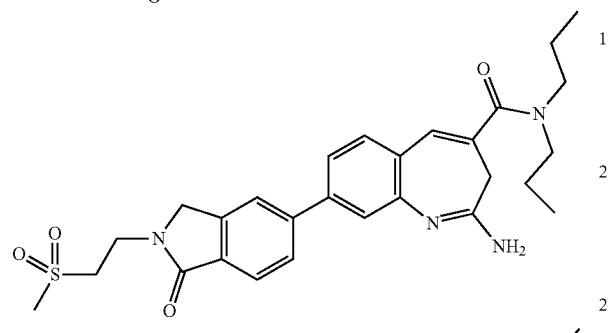
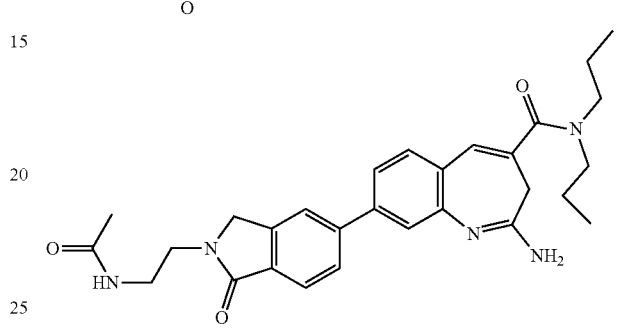
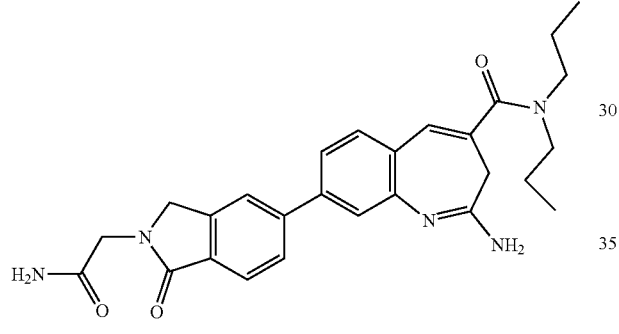
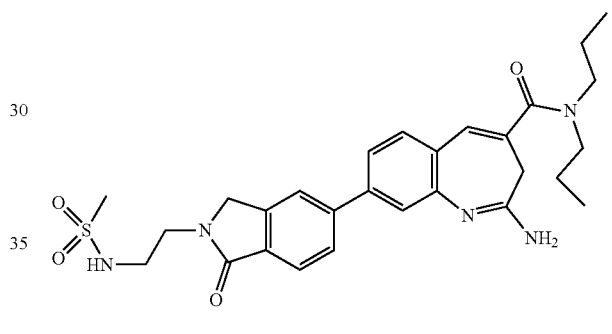
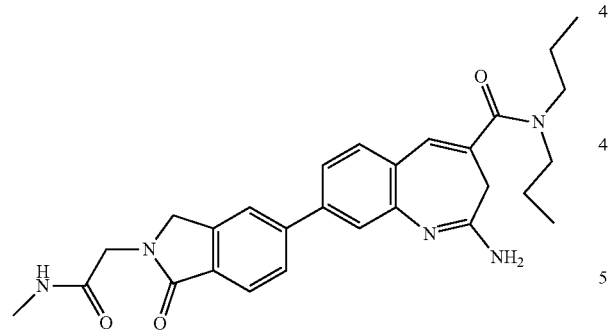
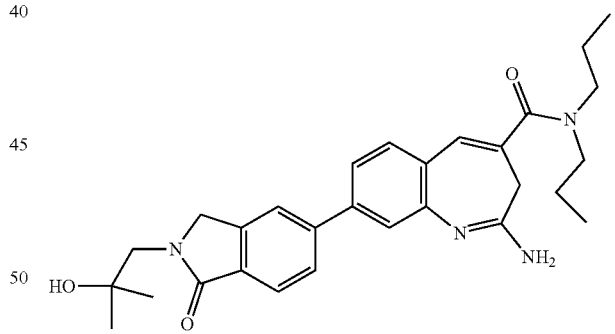
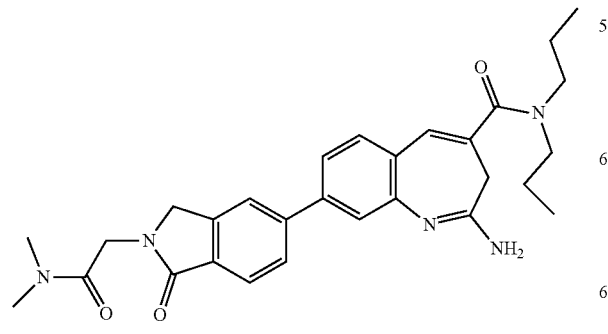
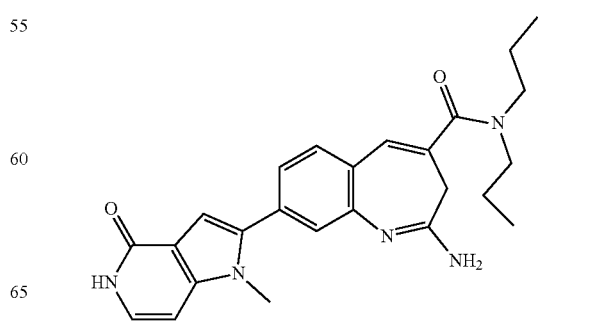

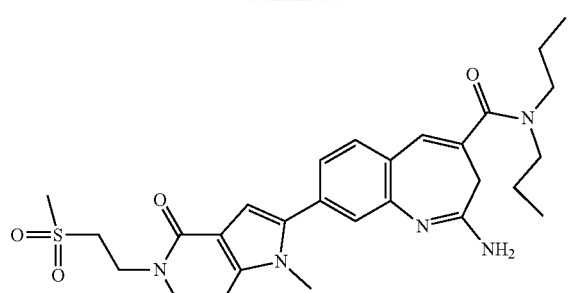
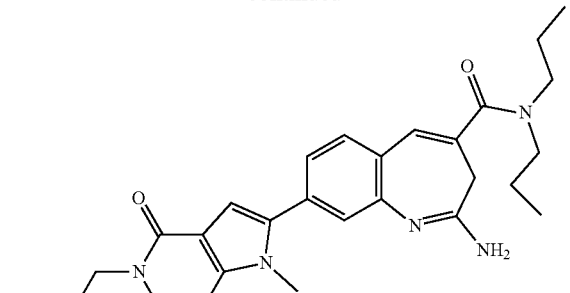
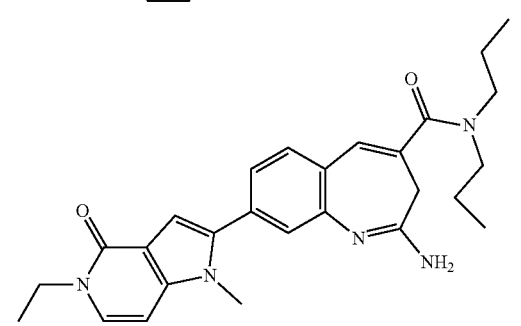
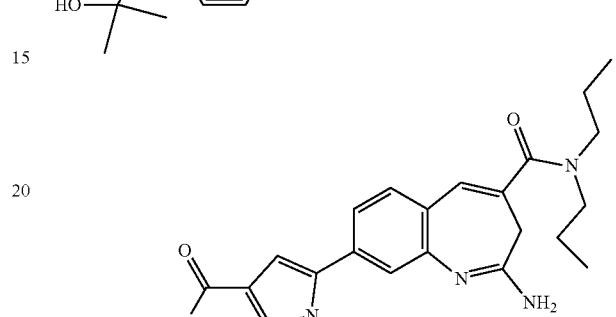
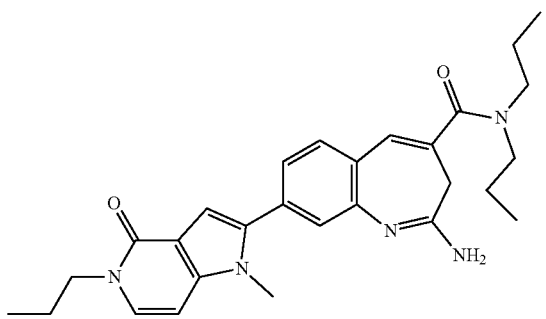
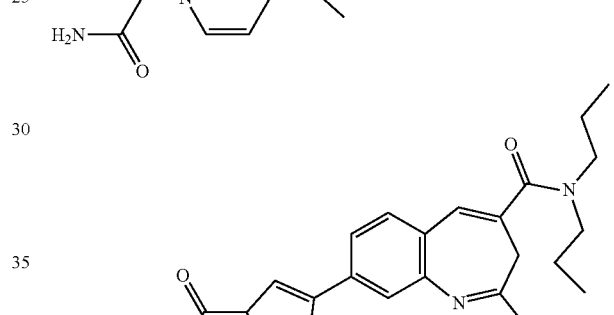
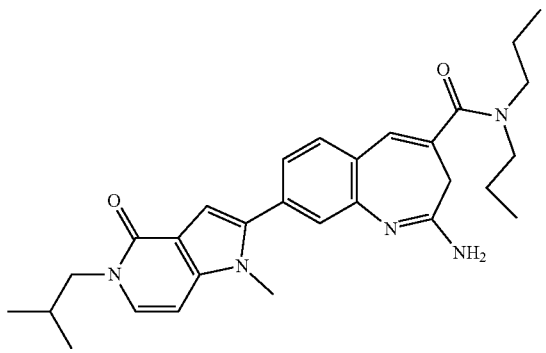
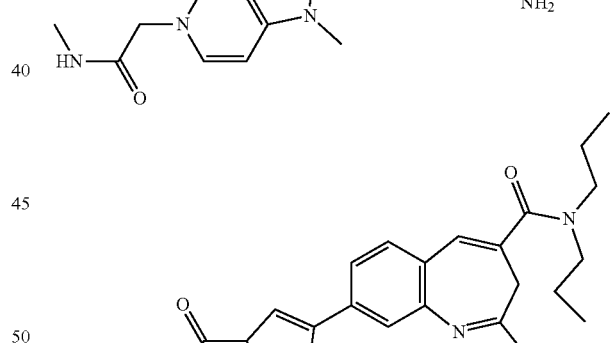
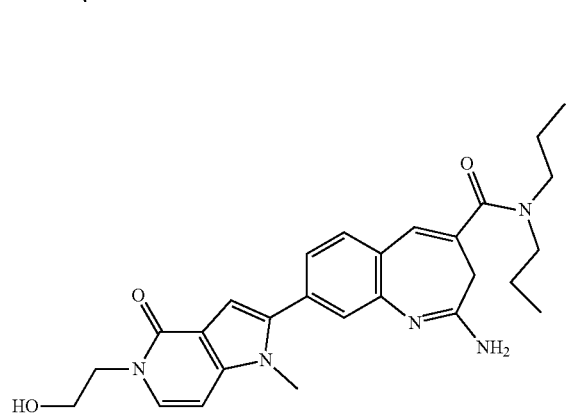
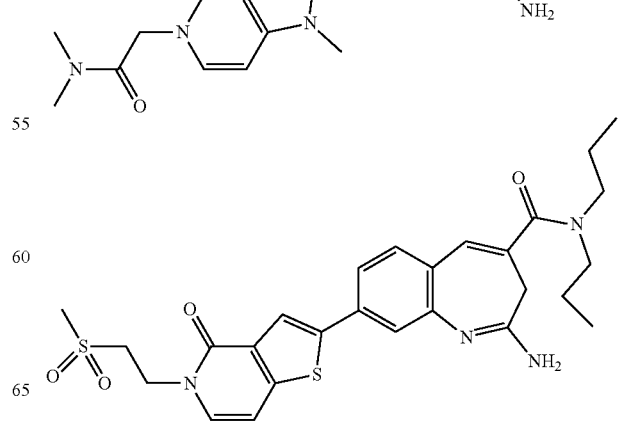

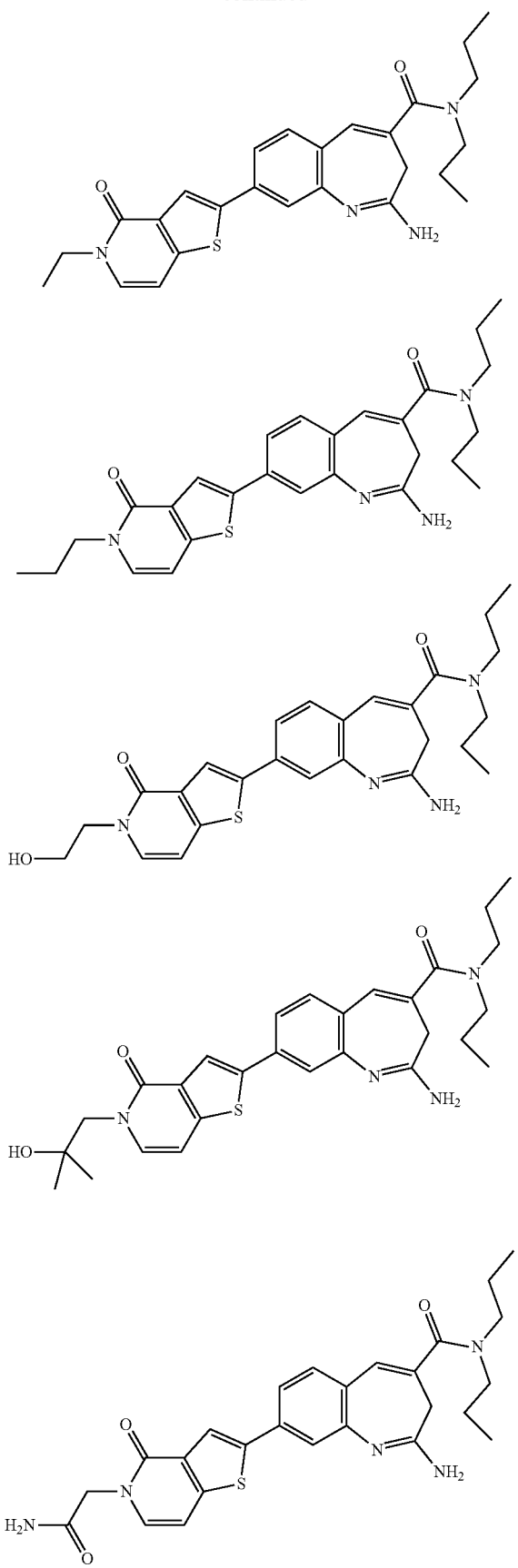
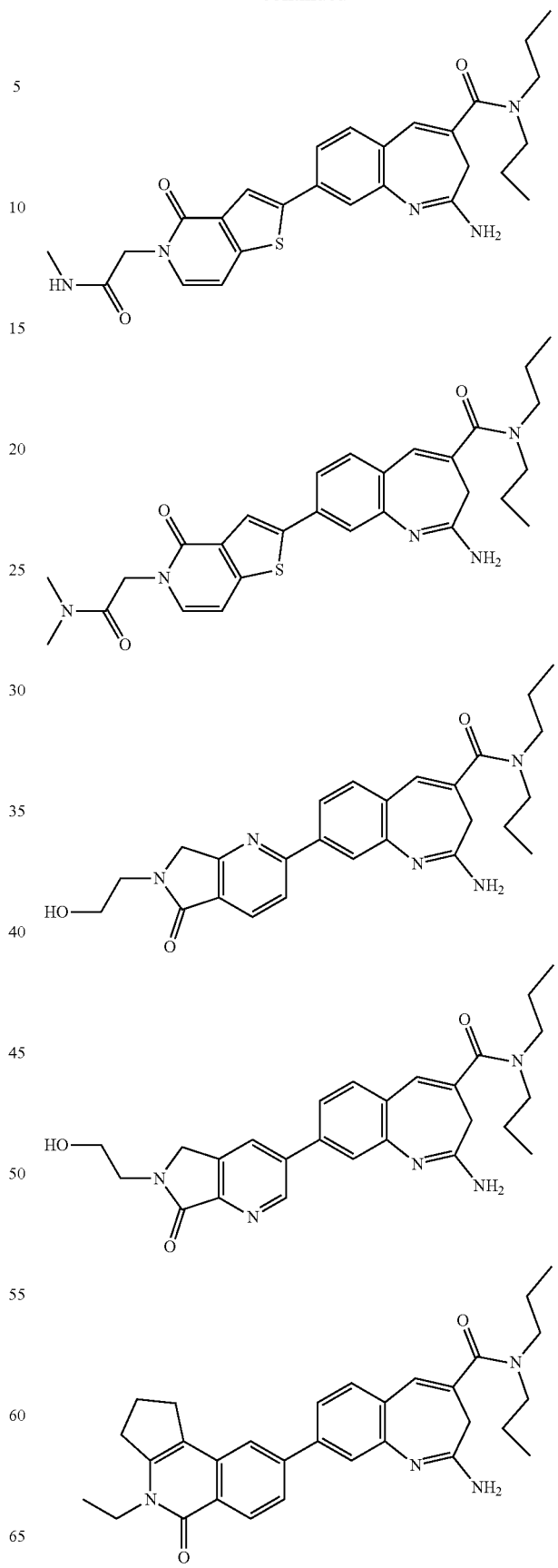

233
-continued
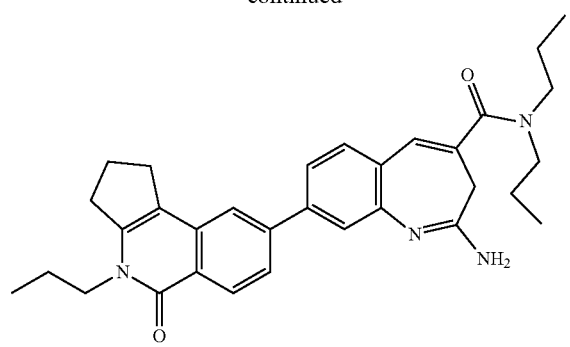
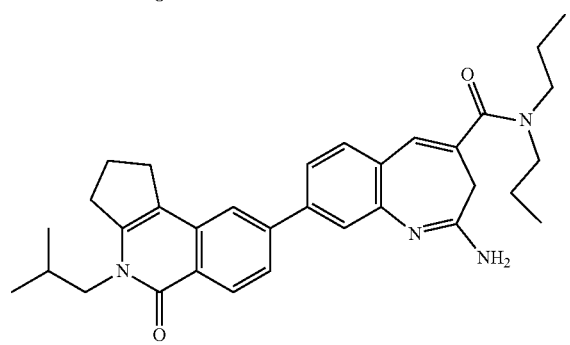
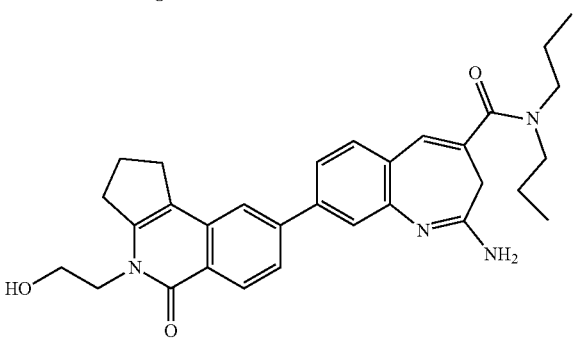
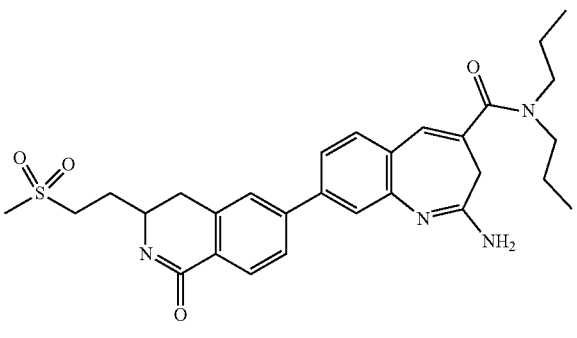
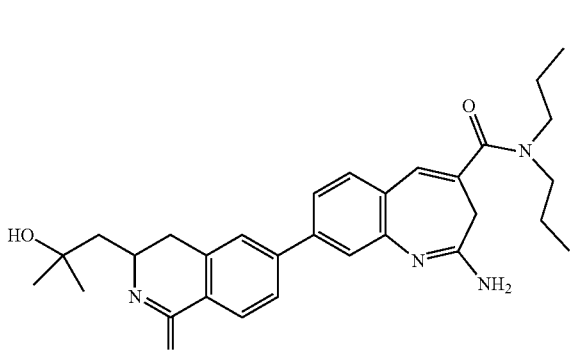
234
-continued
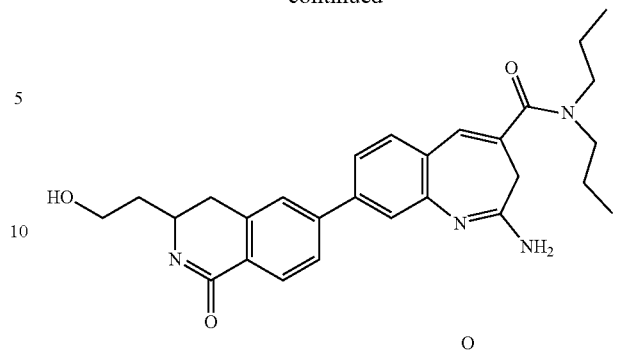
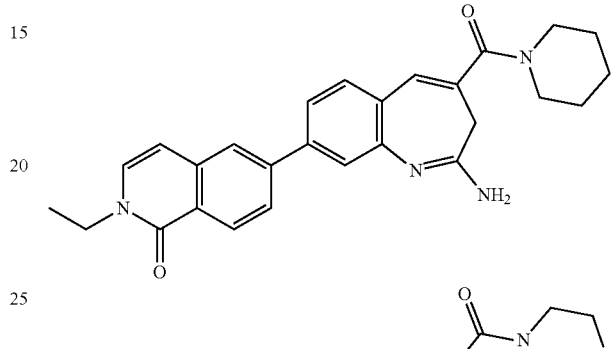
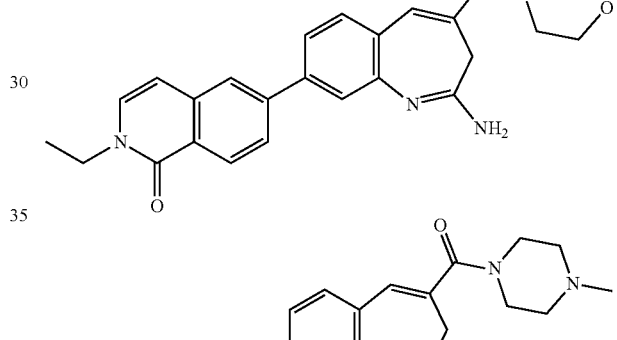
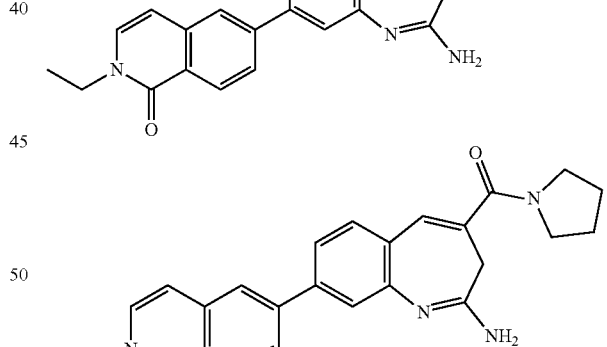
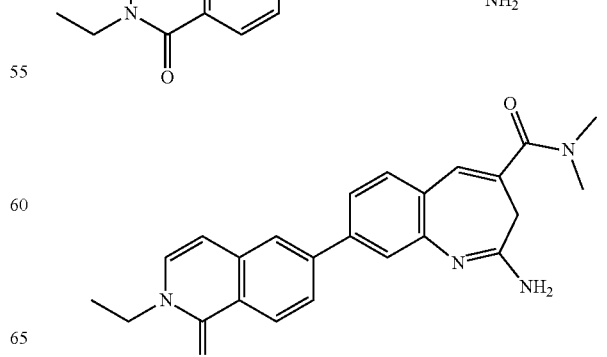

235
-continued
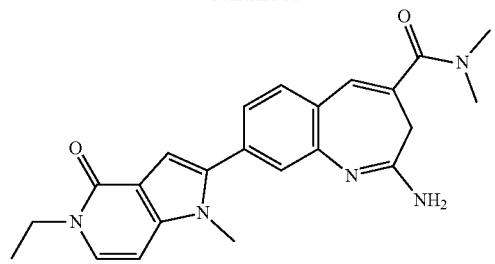
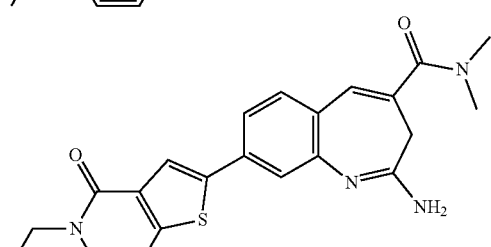
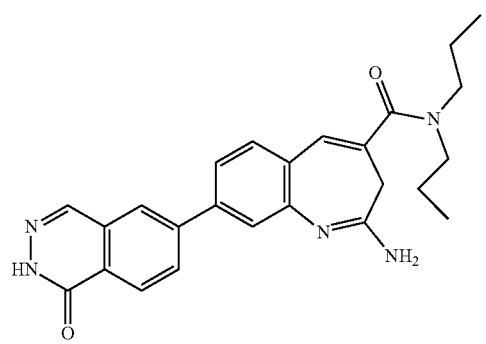
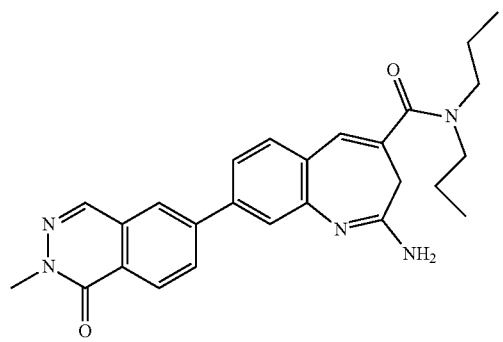
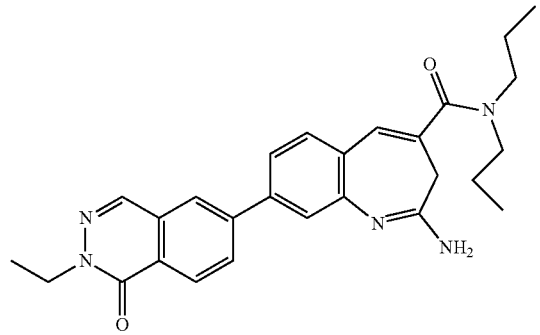
236
-continued
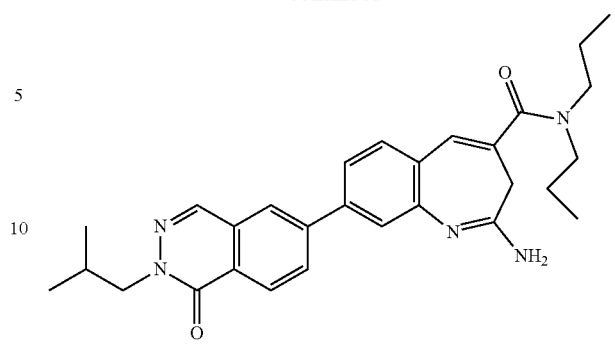
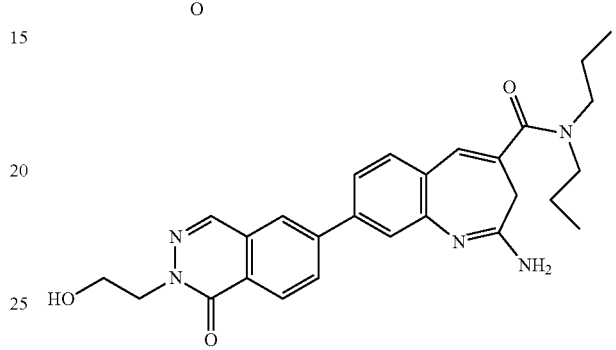
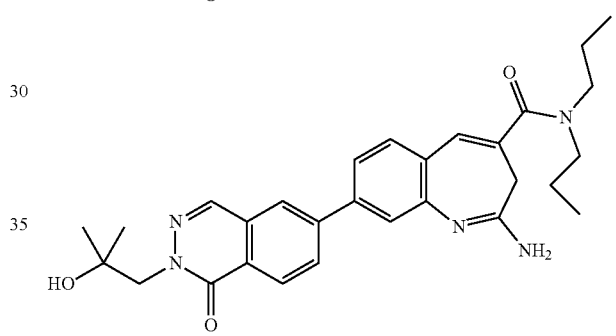
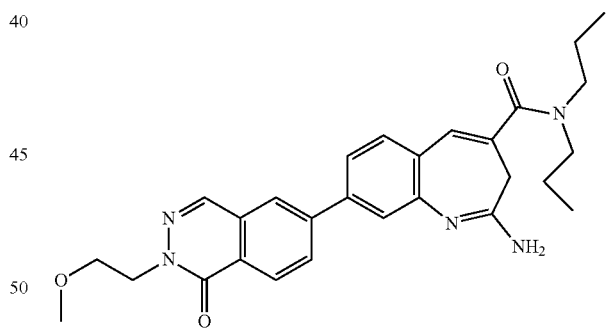
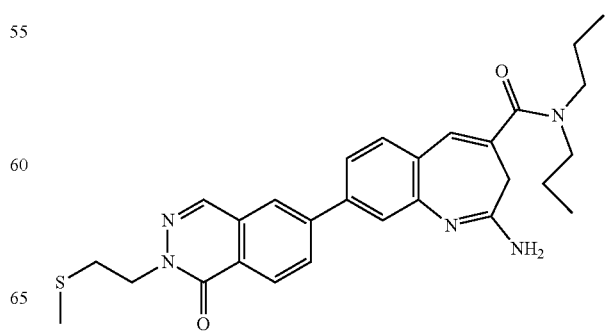

237
-continued
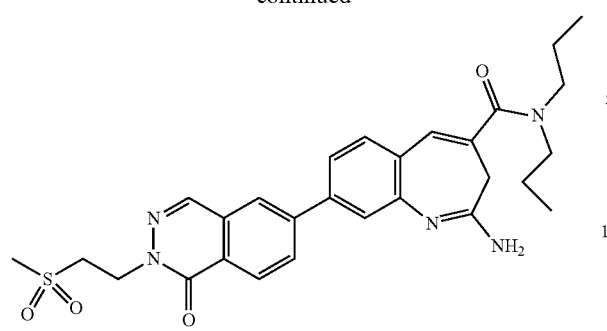
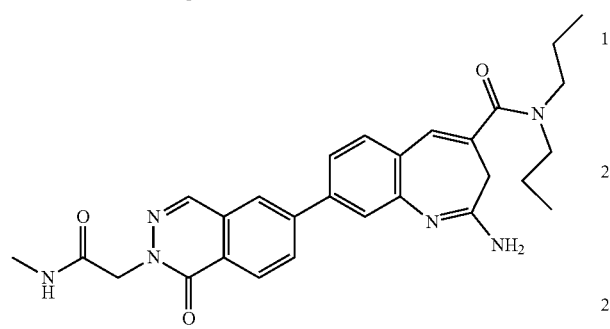
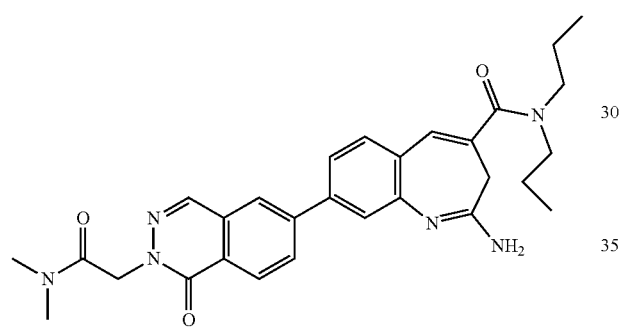
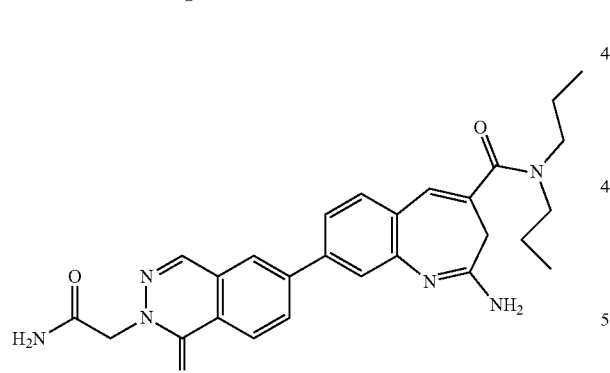
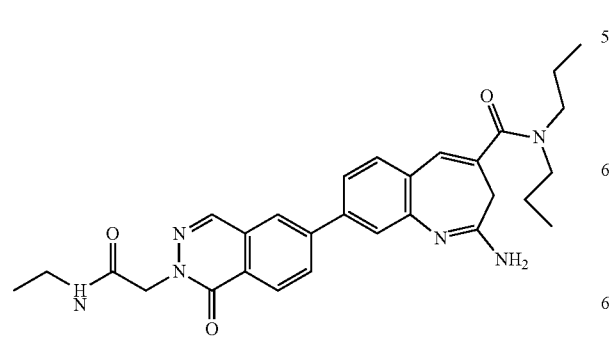
238
-continued
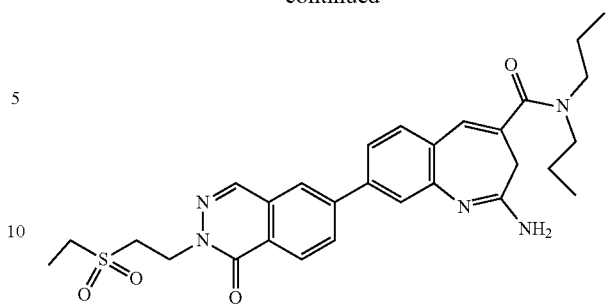
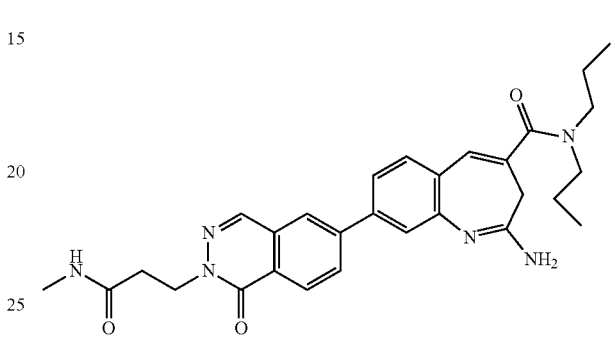
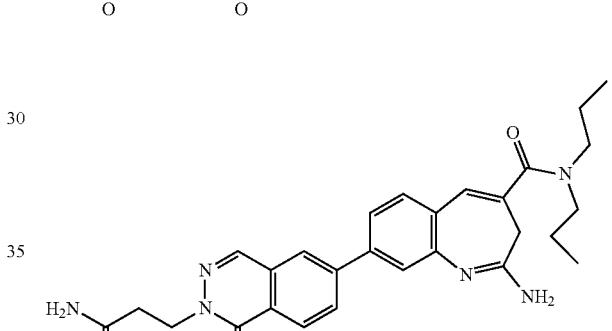
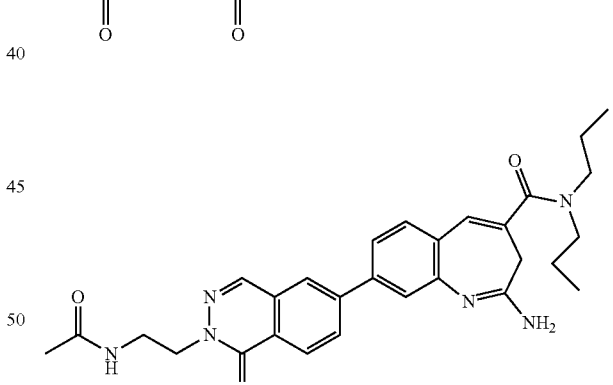
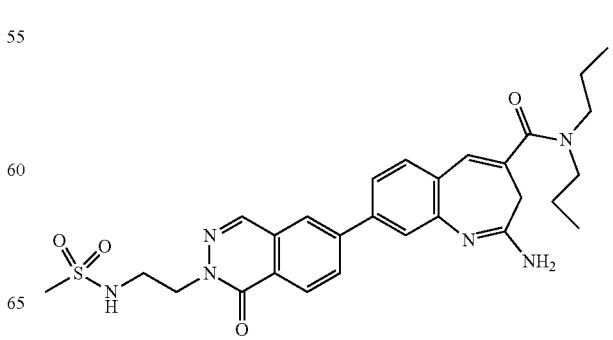

239
-continued
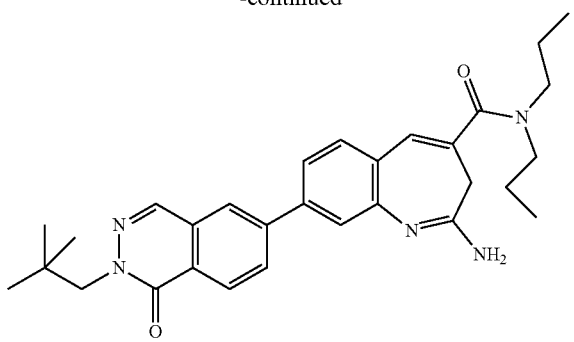
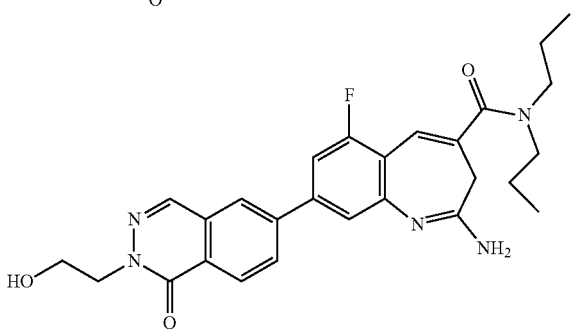
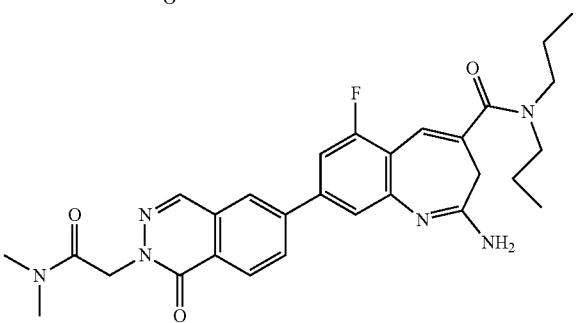
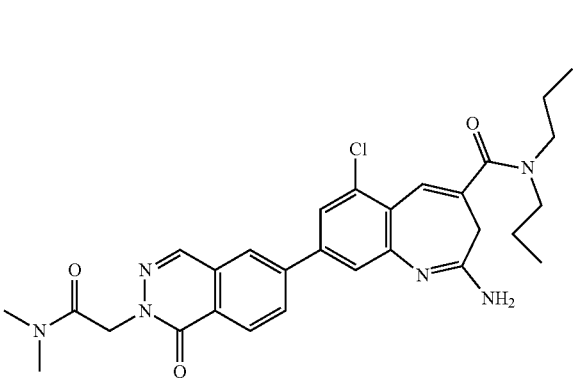
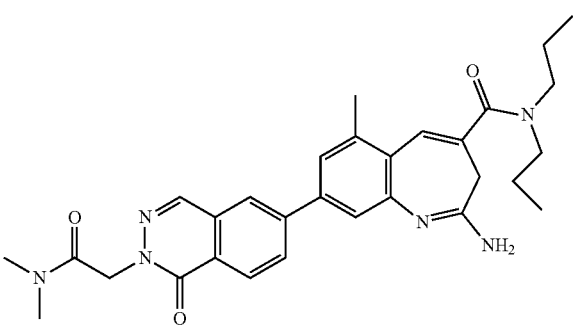
240
-continued
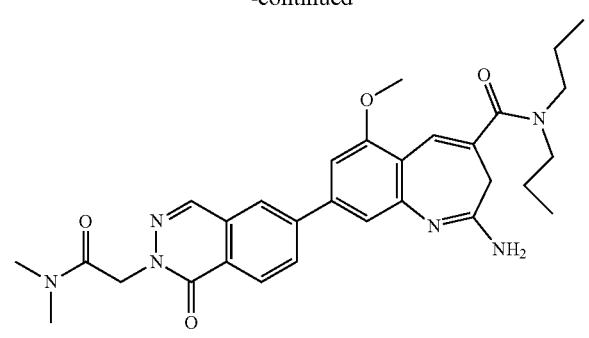
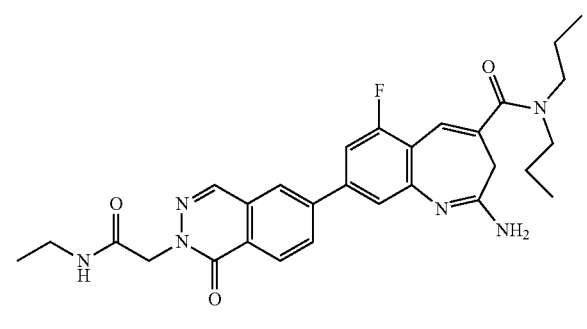
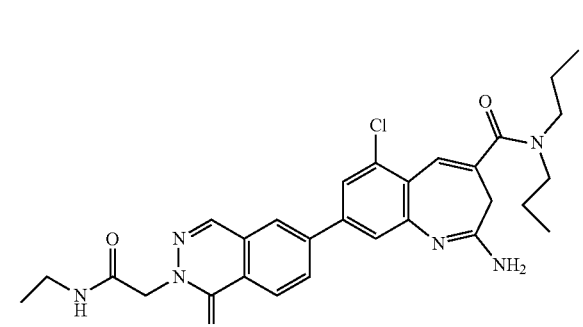
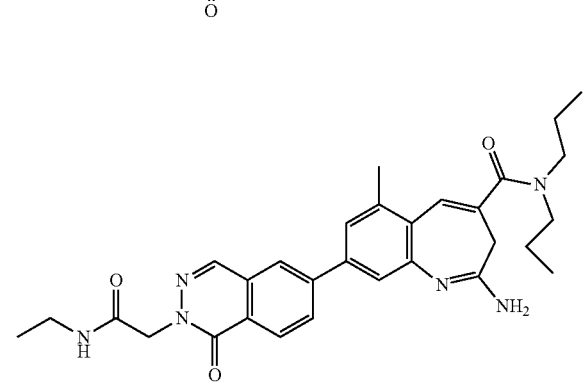
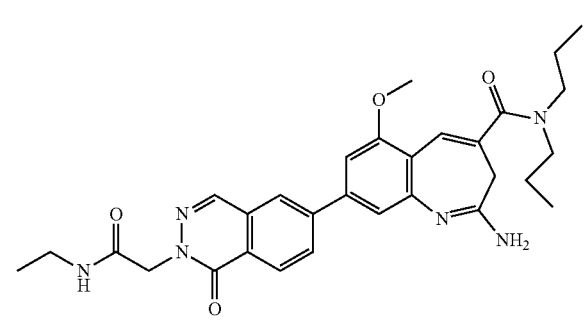

241
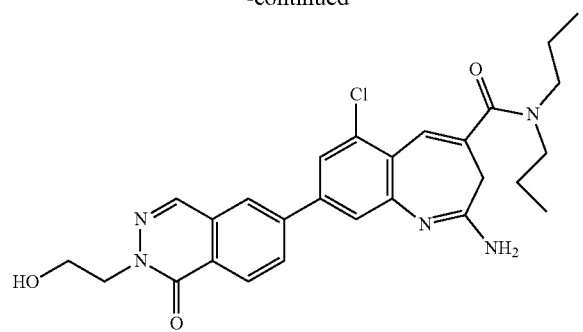
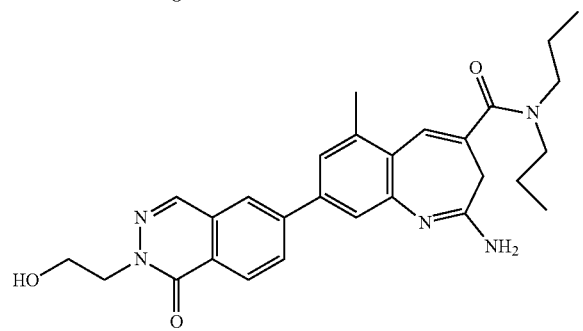
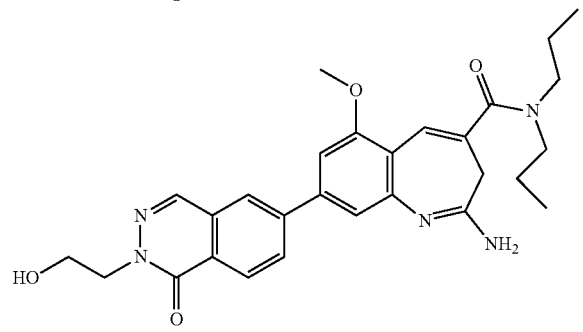
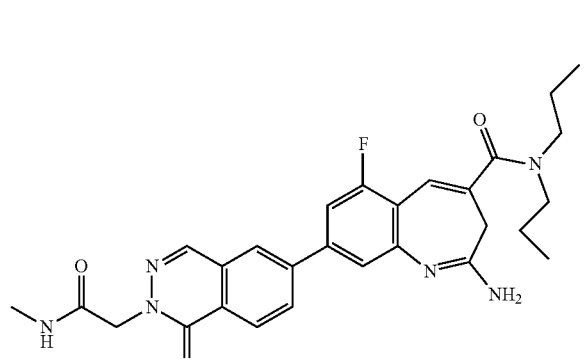
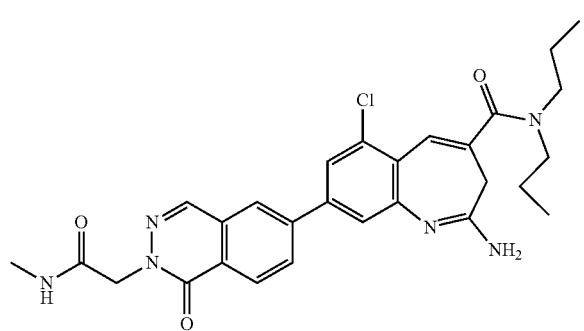
242
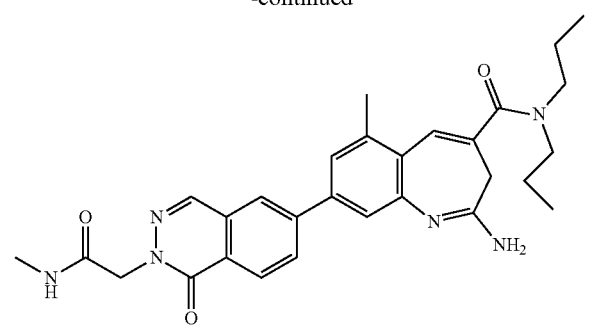
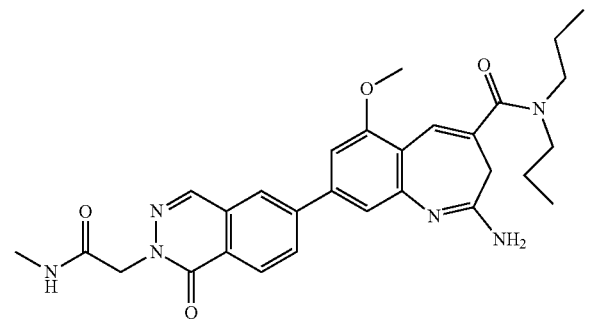
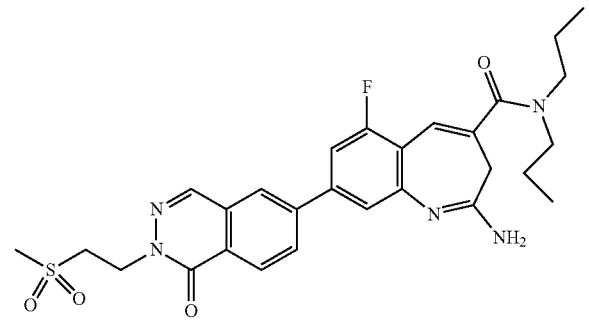
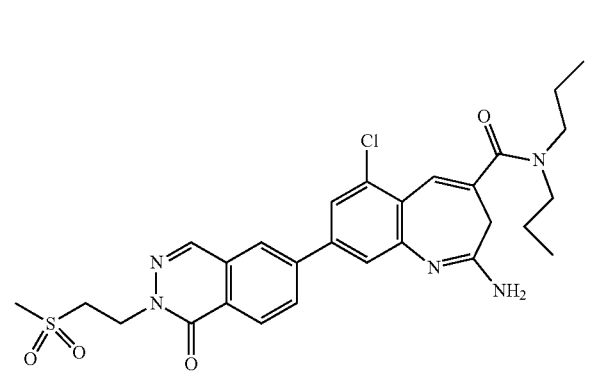
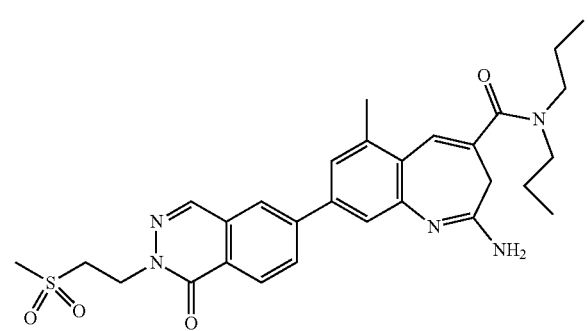

243
-continued
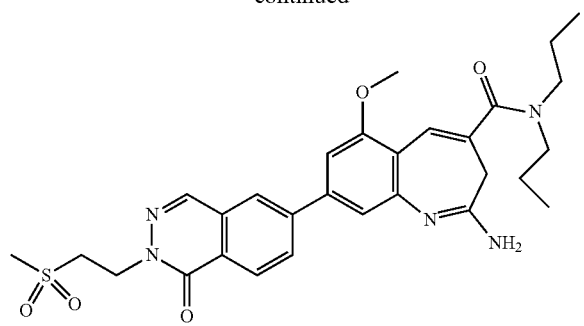
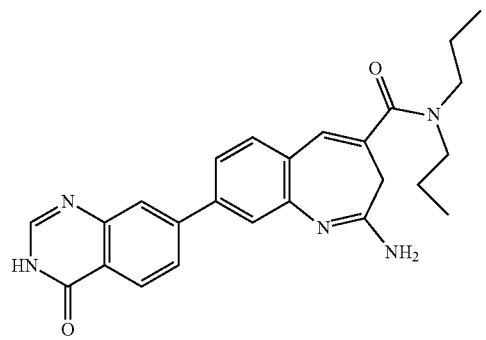
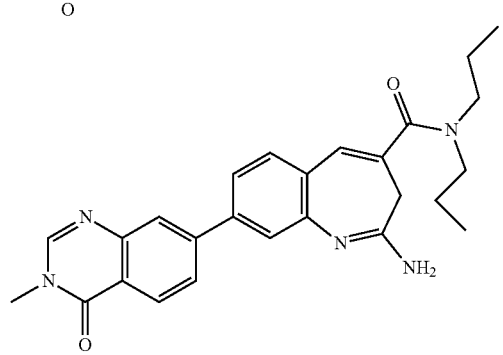
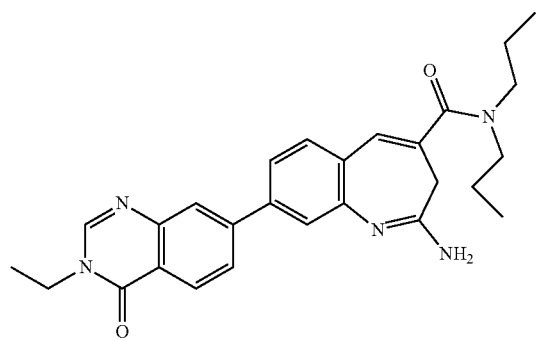
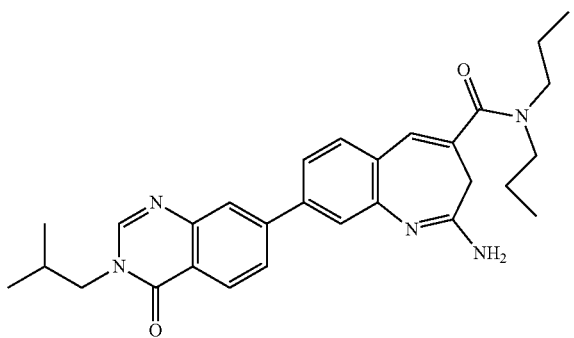
244
-continued
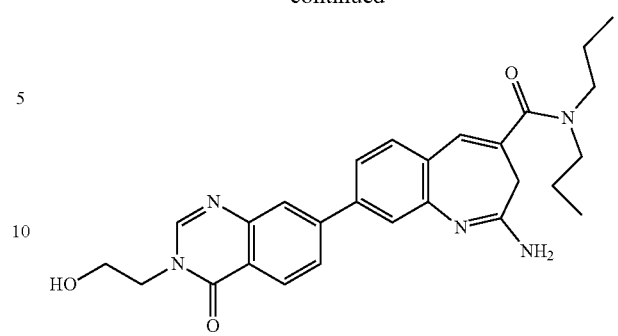
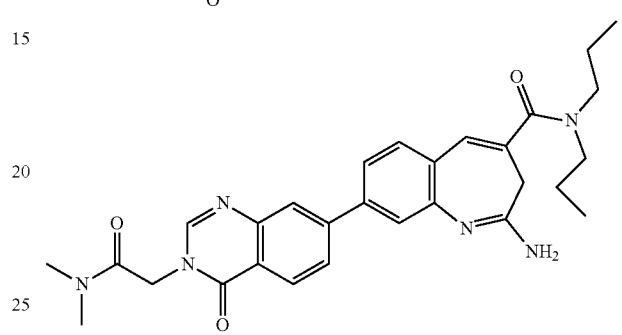
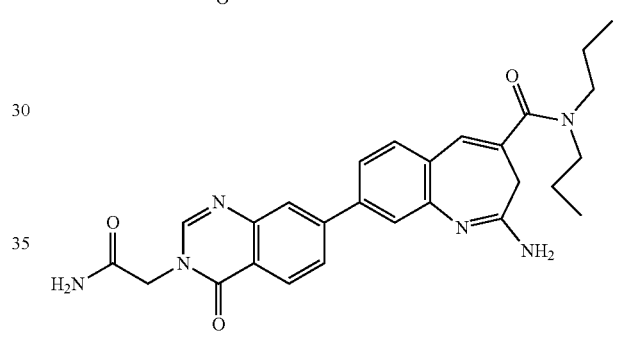
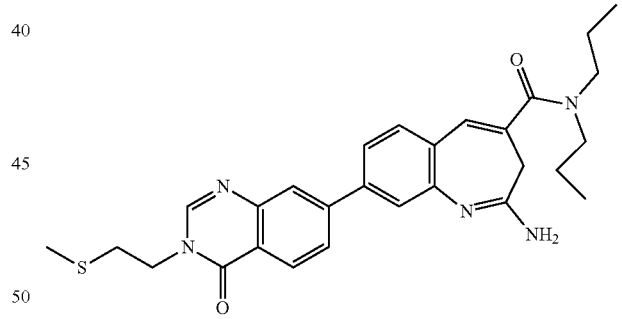
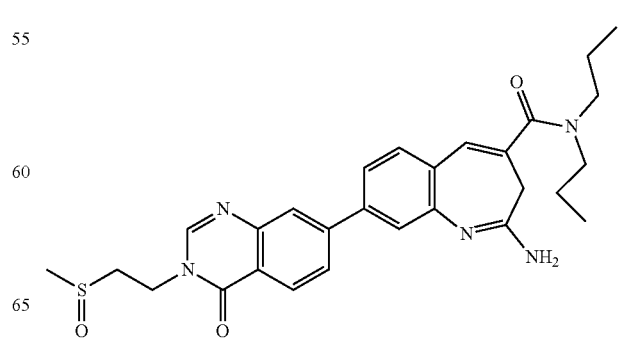

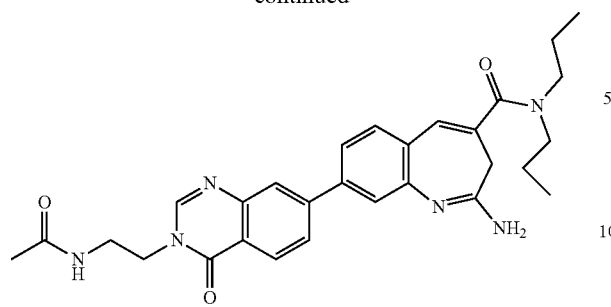
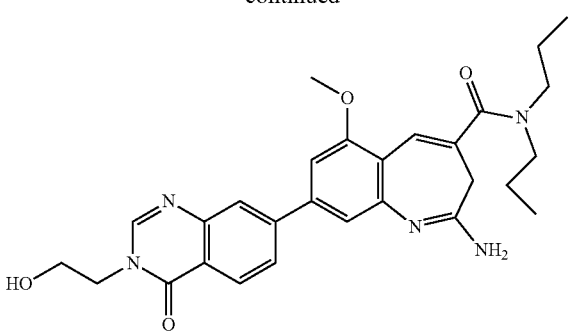

247
-continued
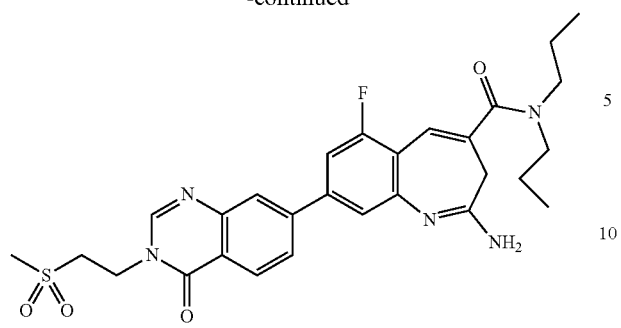
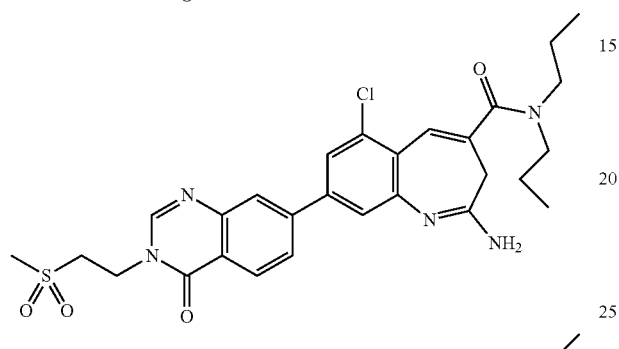
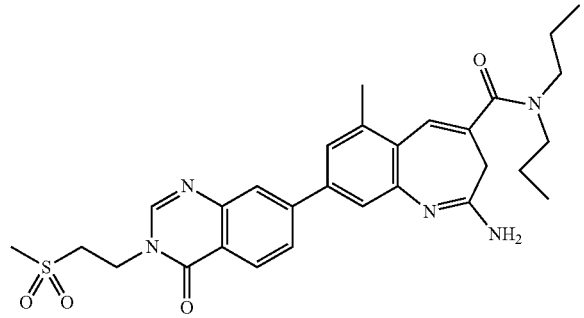
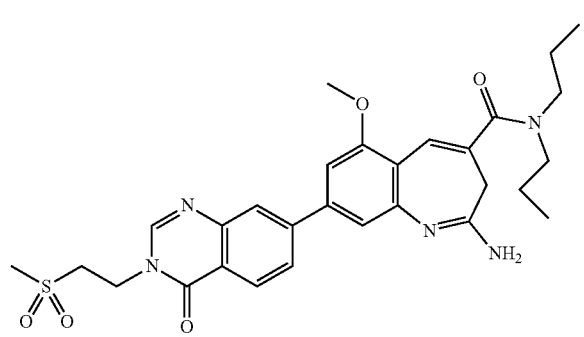
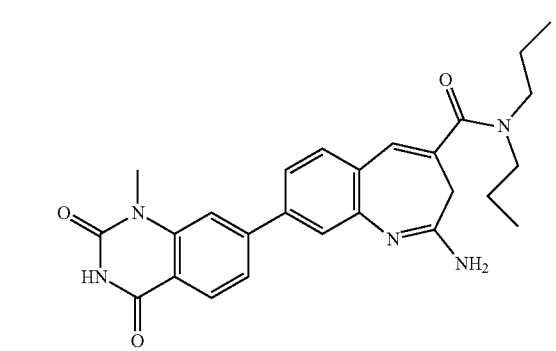
248
-continued
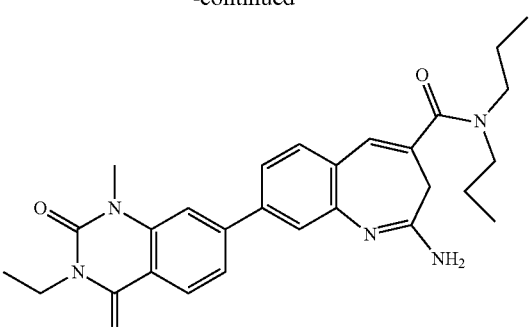
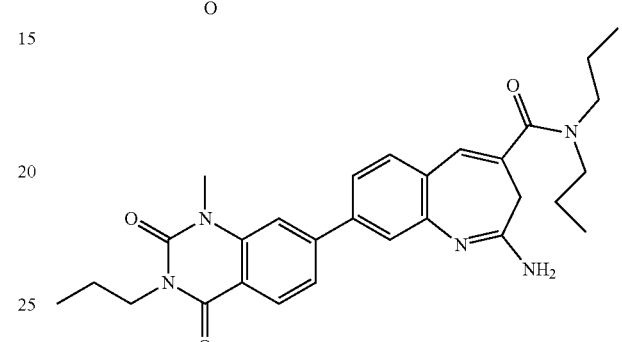
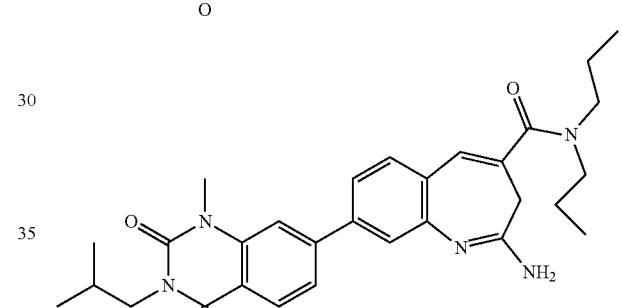
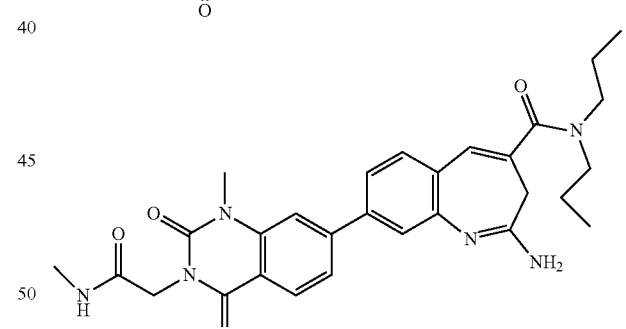
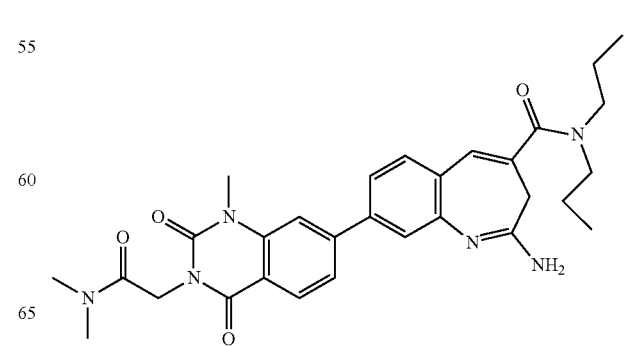

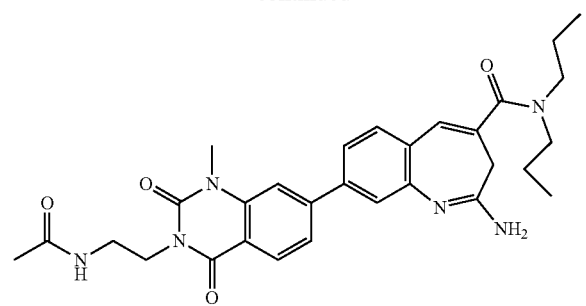
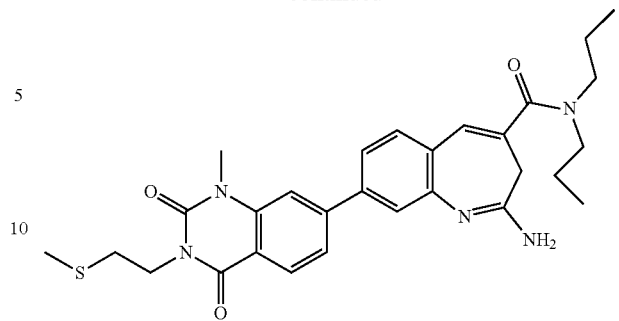
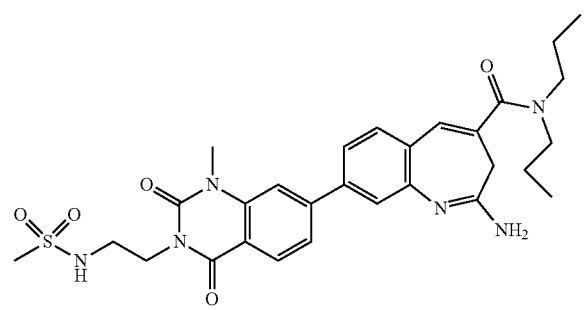
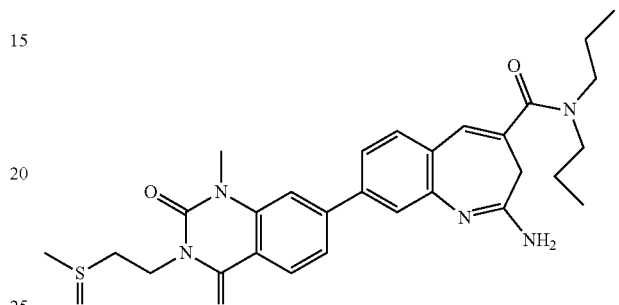
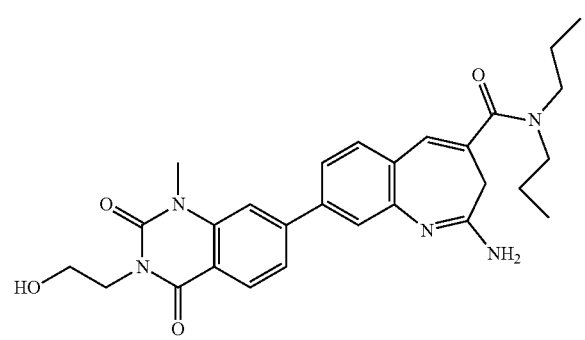
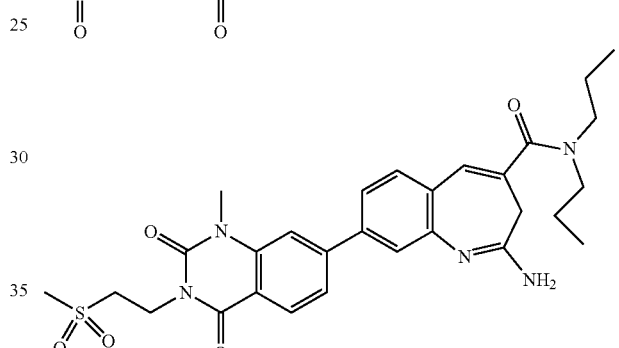
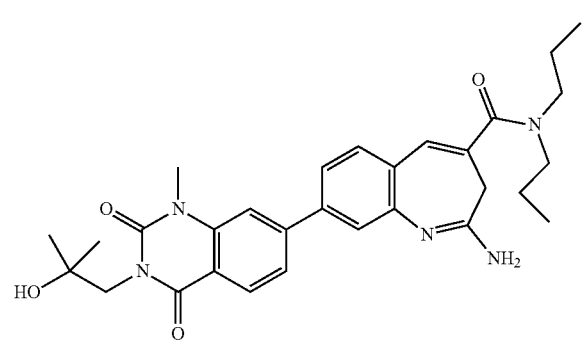
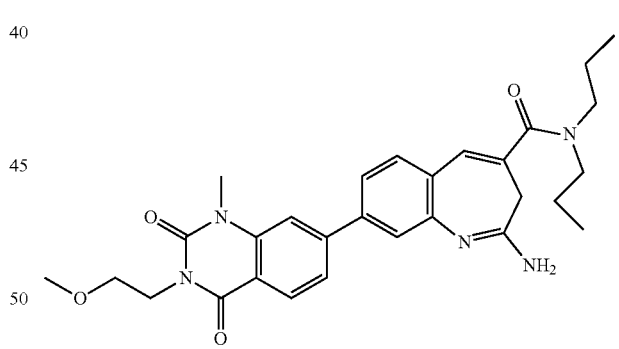
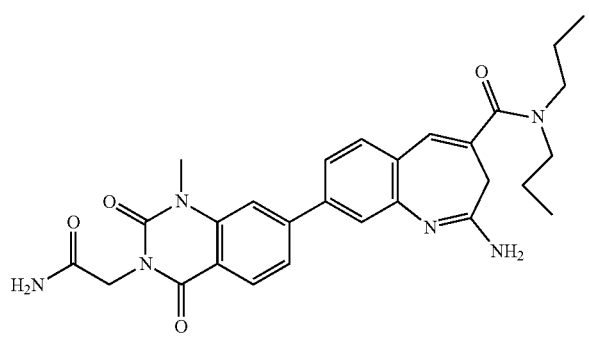
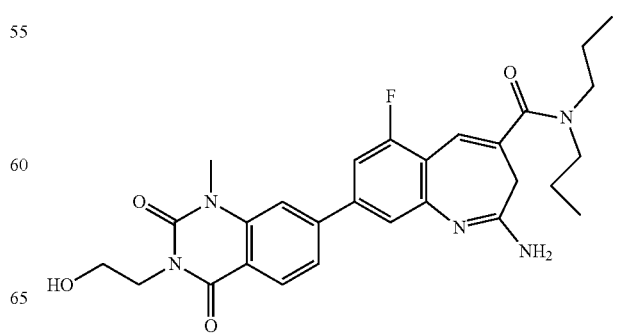

251
-continued
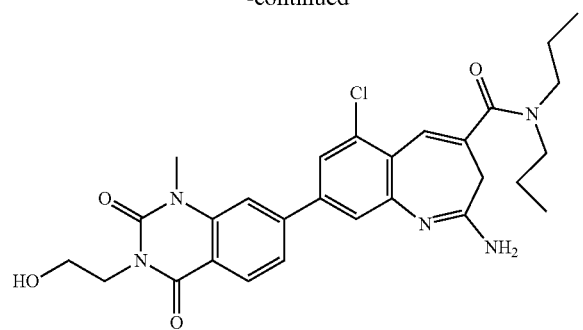
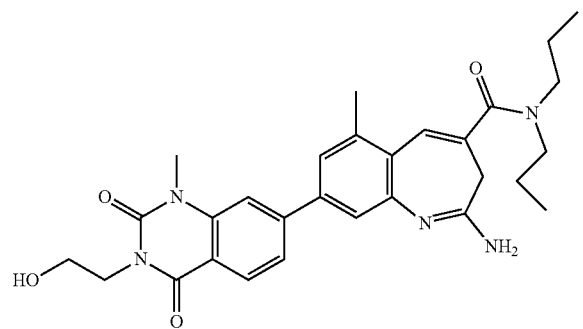
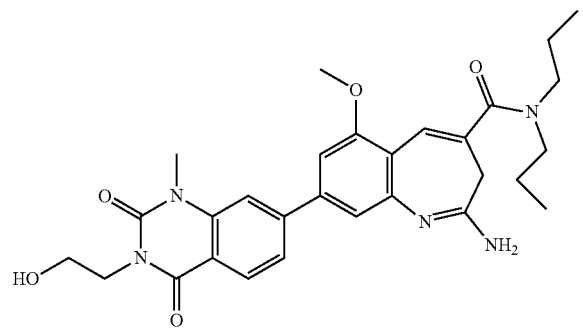
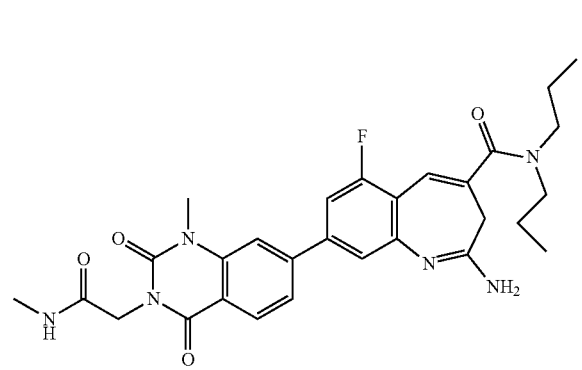
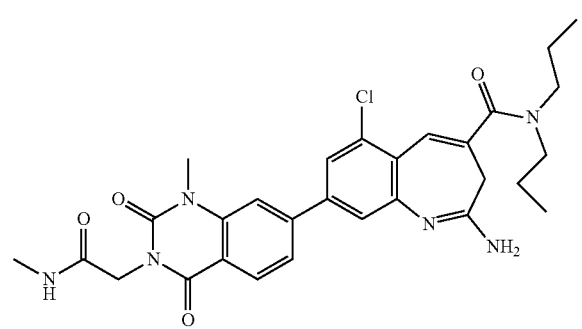
252
-continued
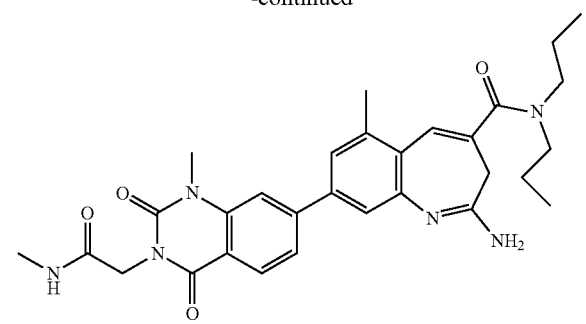
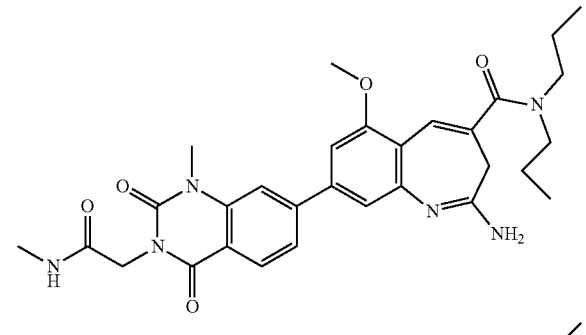
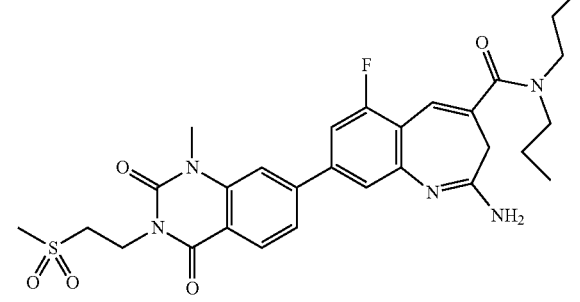
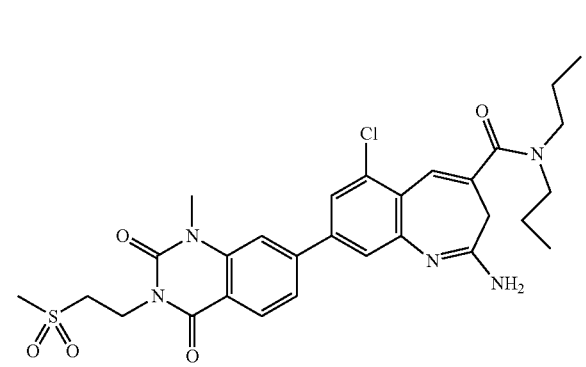
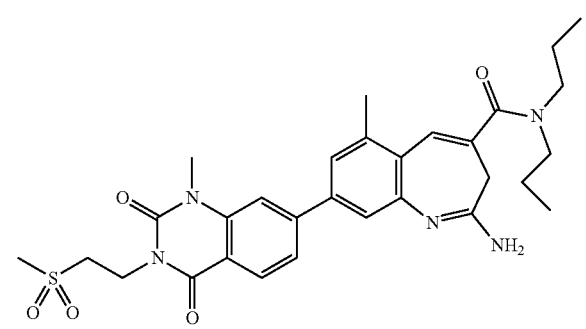

253
-continued
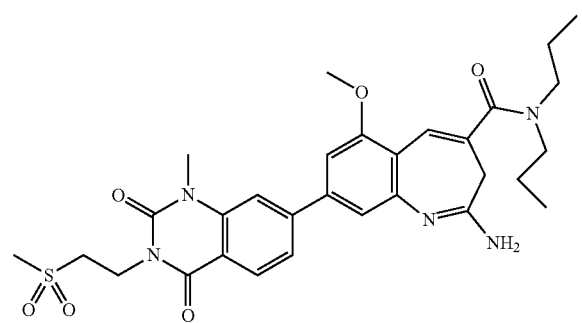
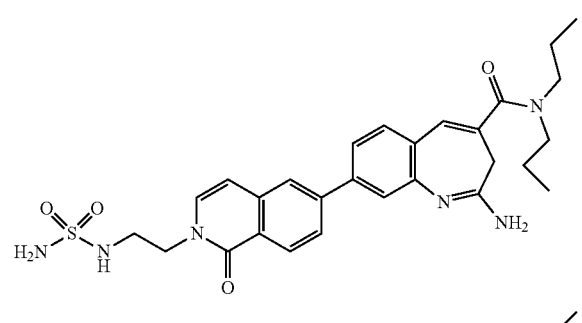
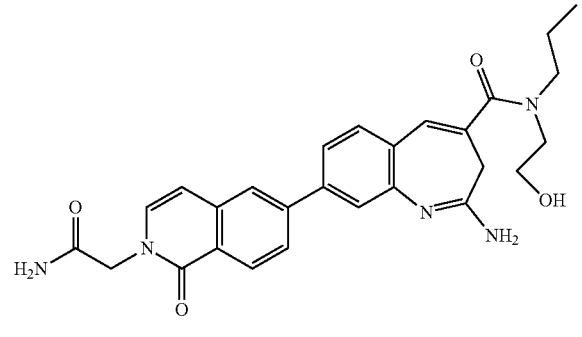
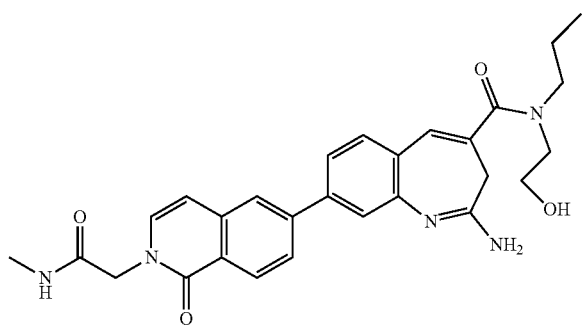
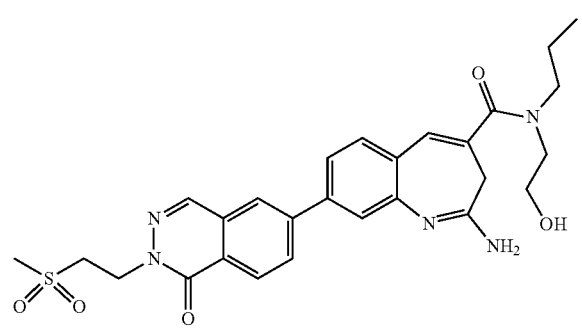
254
-continued
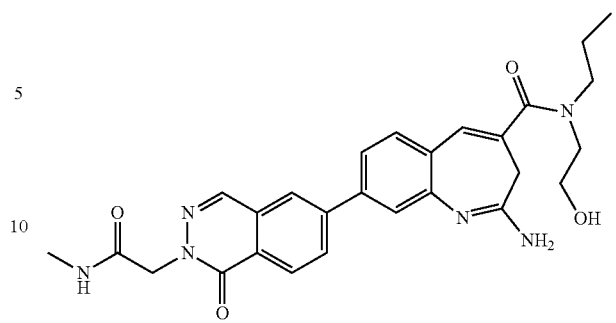
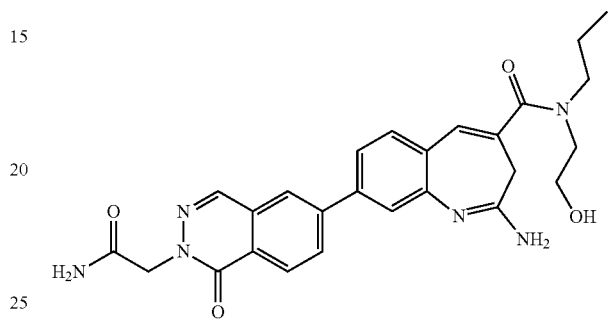
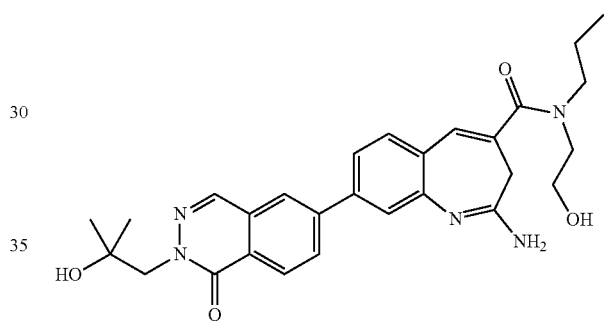
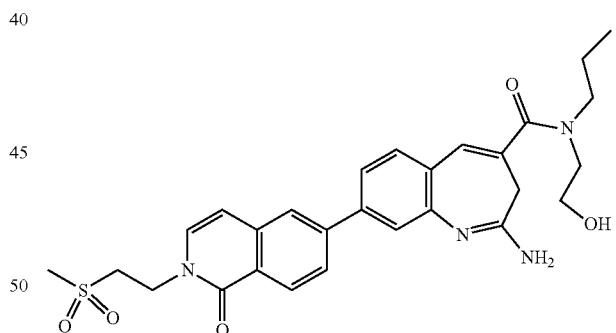
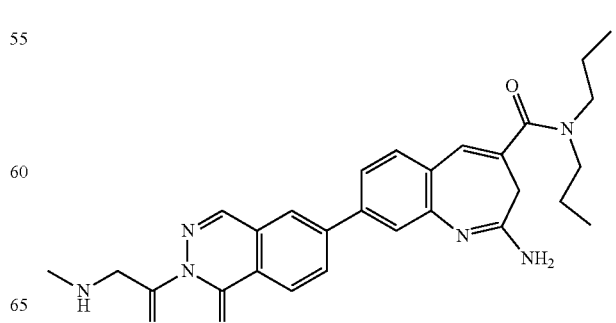

255
-continued
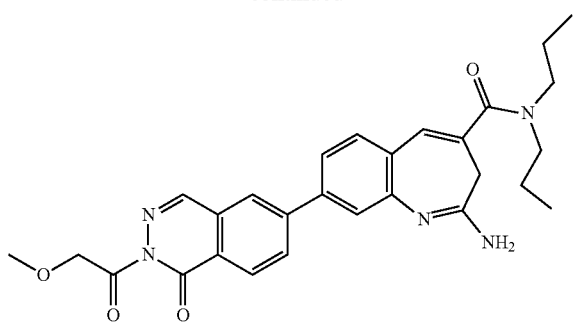
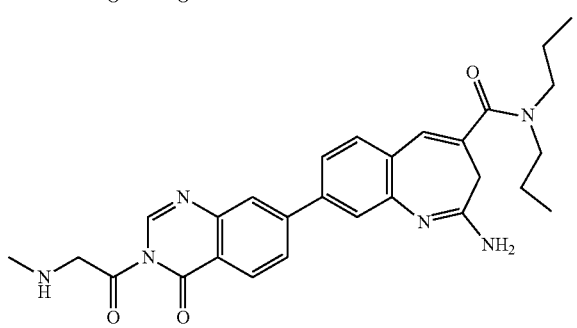
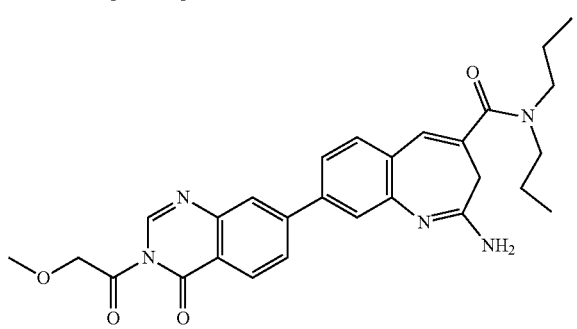
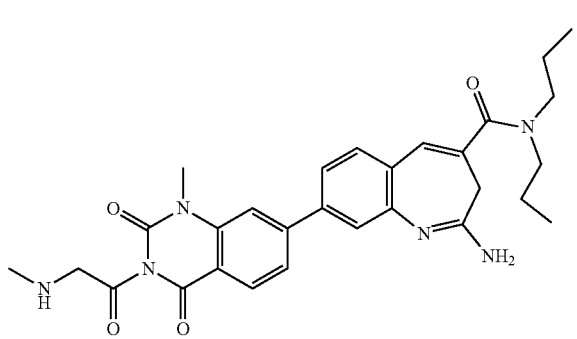
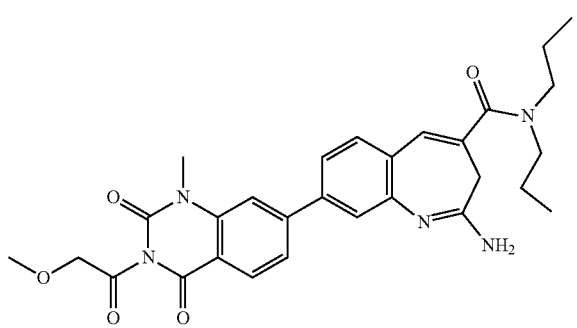
256
-continued
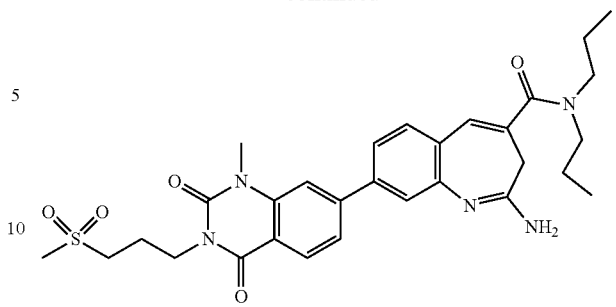
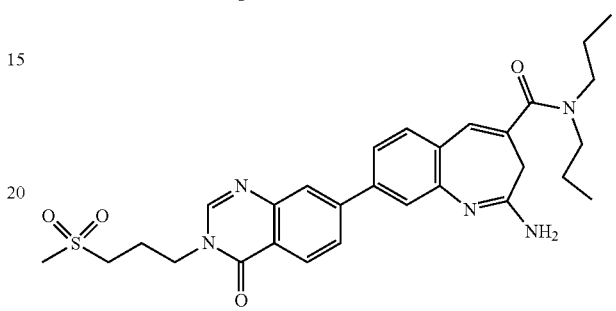
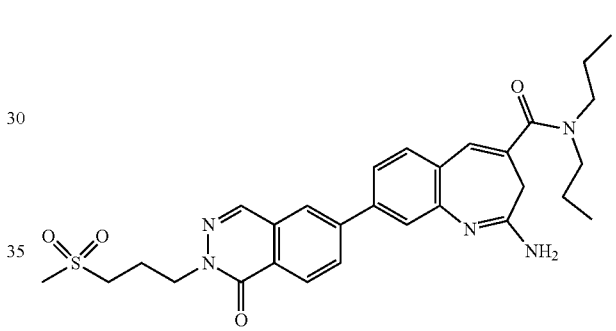
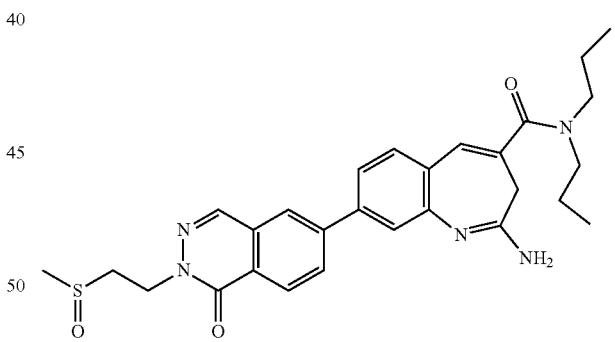
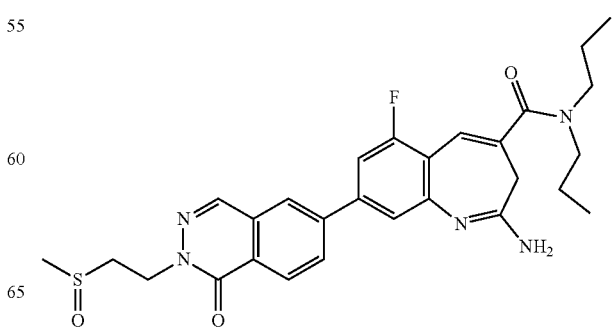

257
-continued
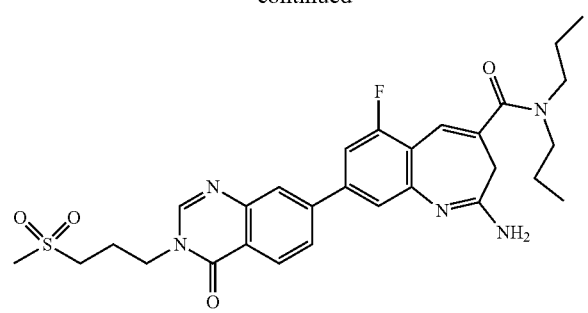
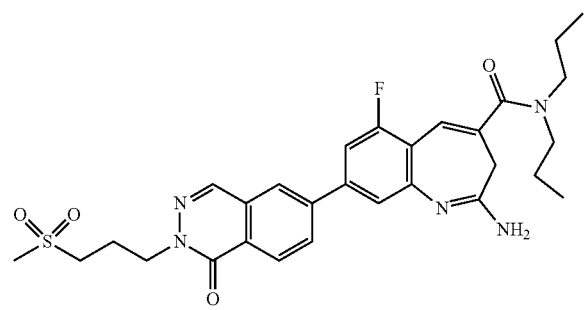
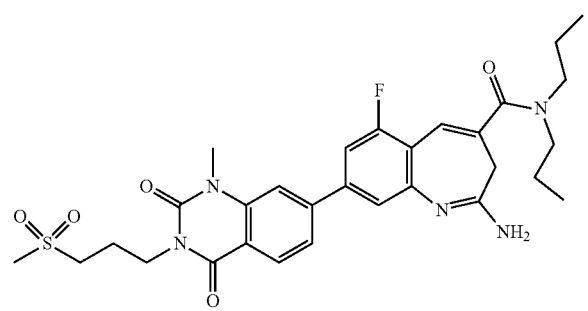
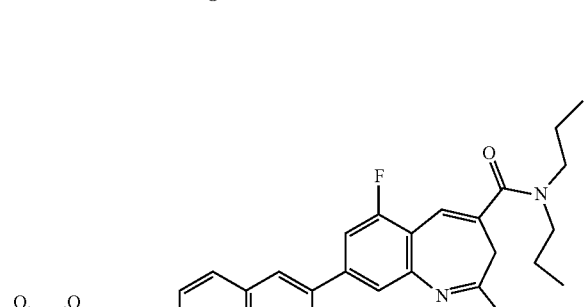
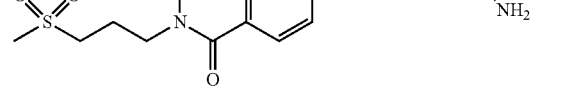
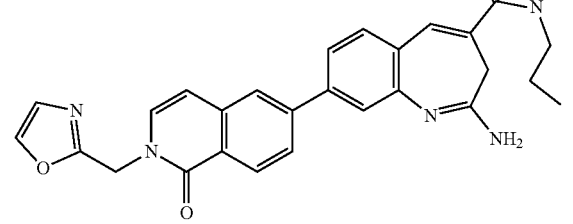
258
-continued
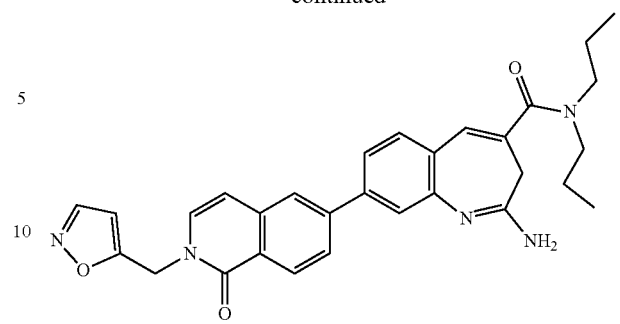
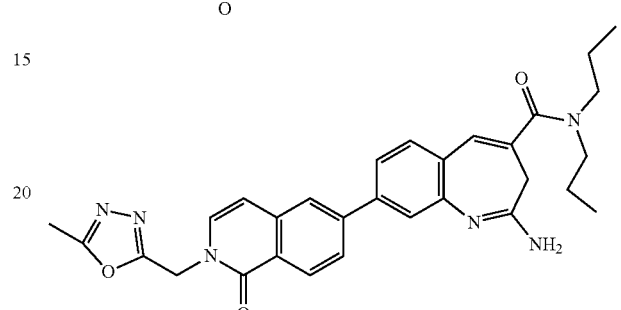
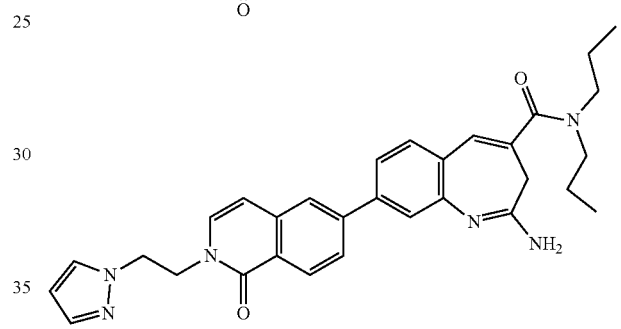
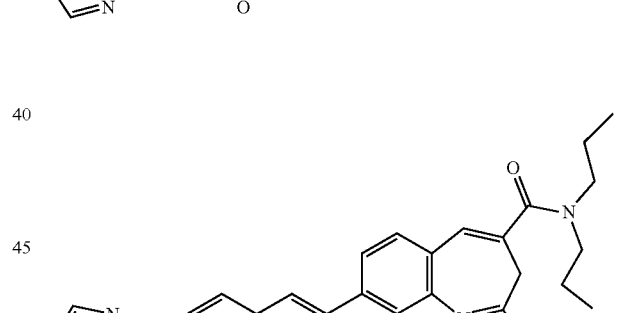
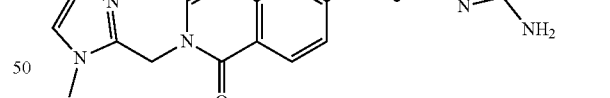
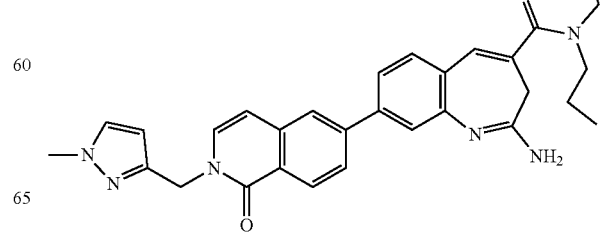

259
-continued
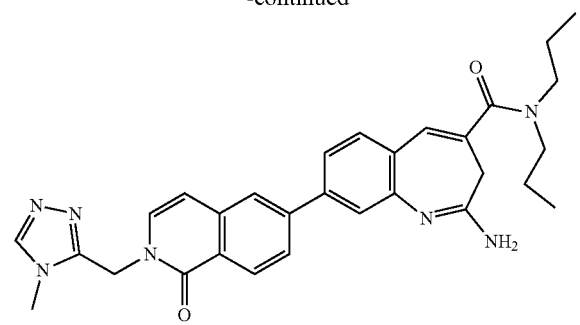
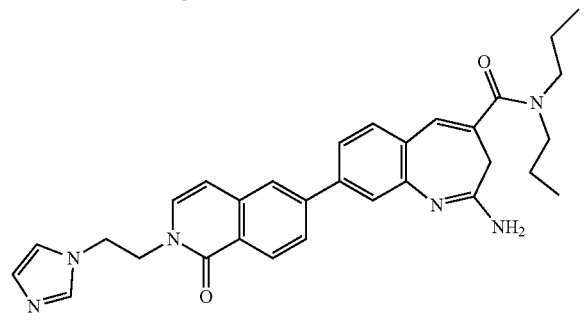
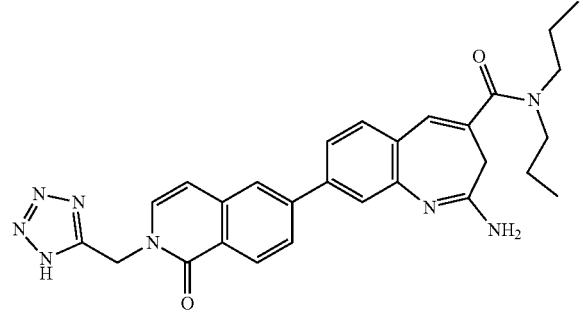
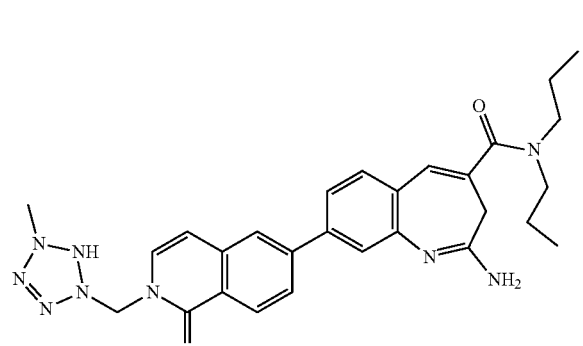
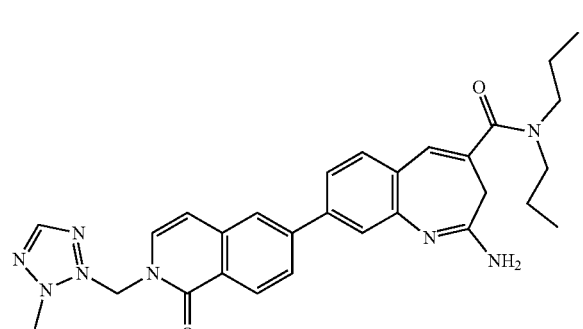
260
-continued
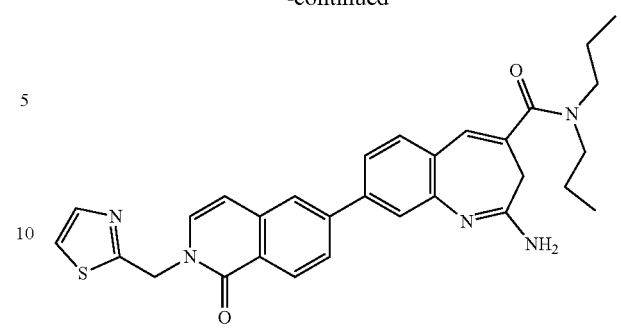
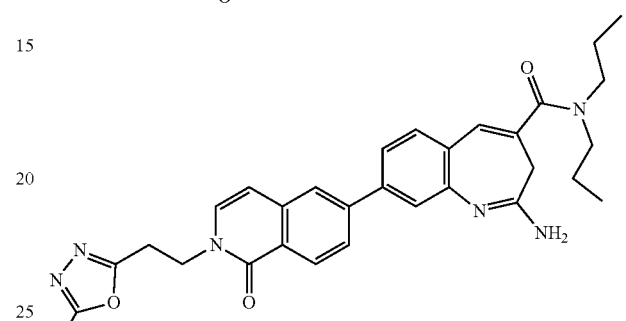
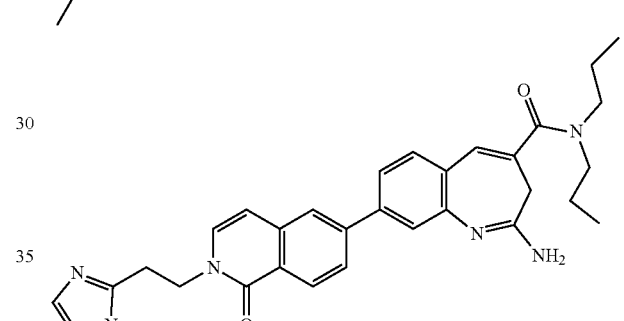
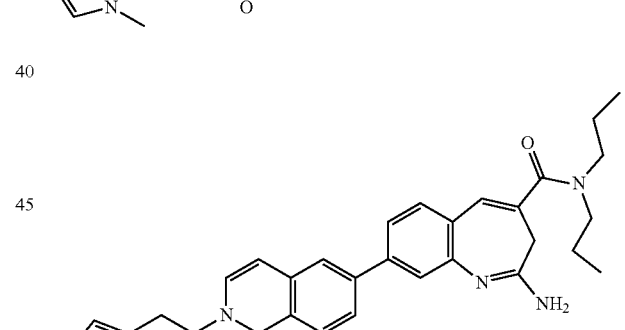
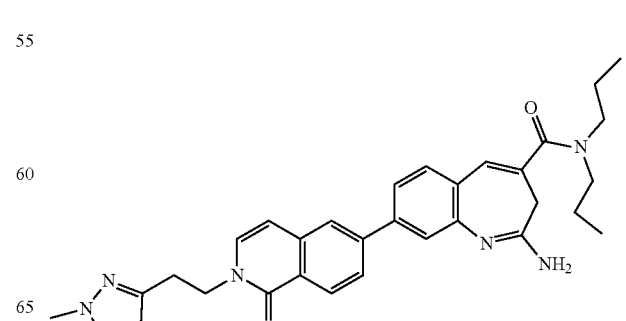

261
-continued
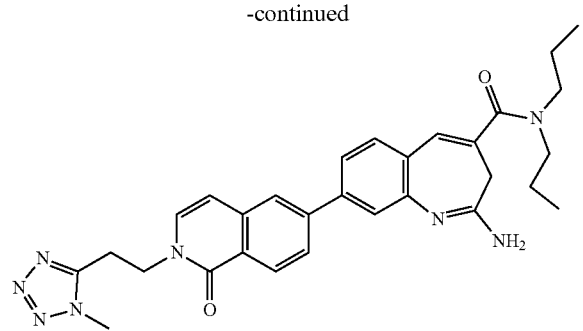
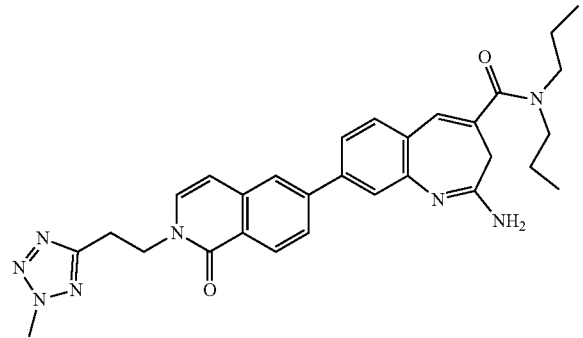
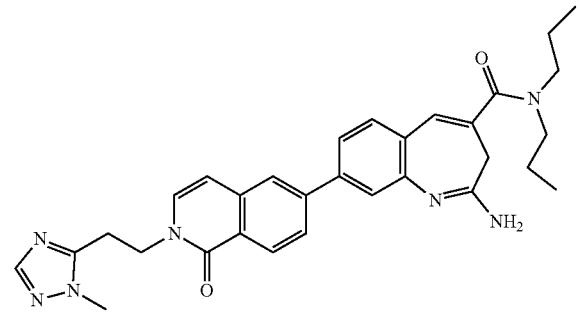
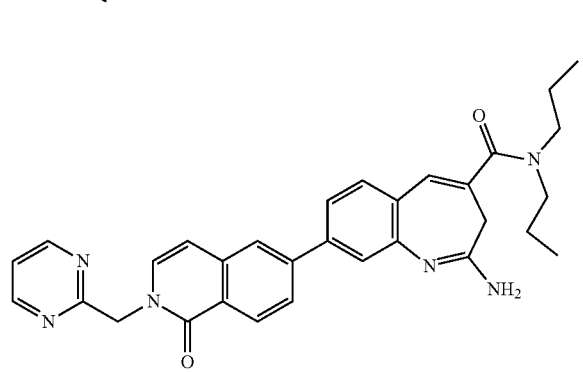
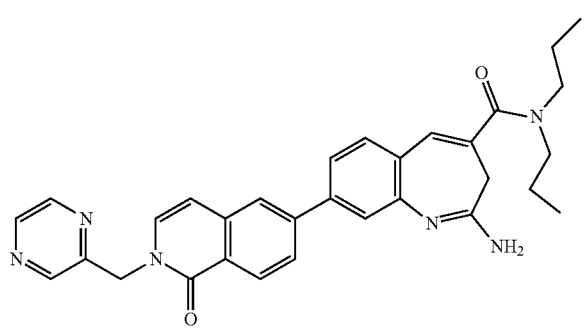
262
-continued
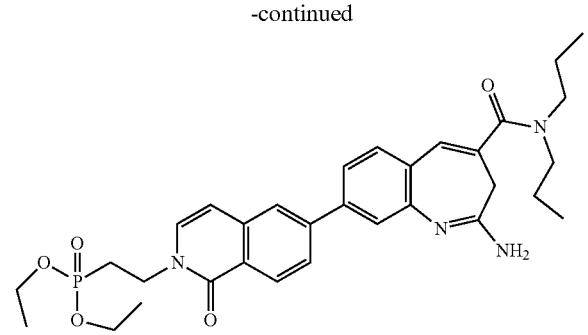
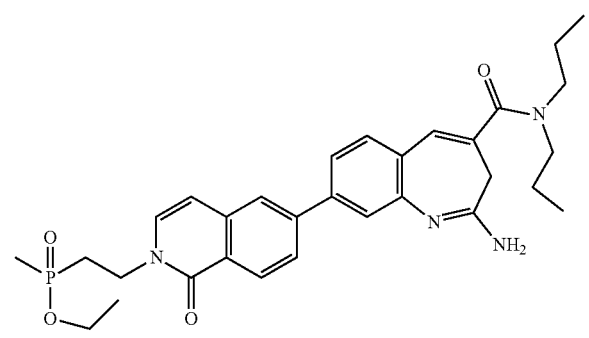
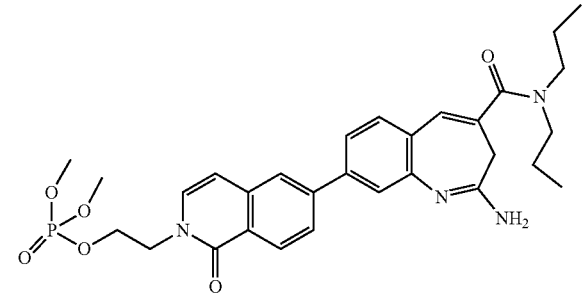
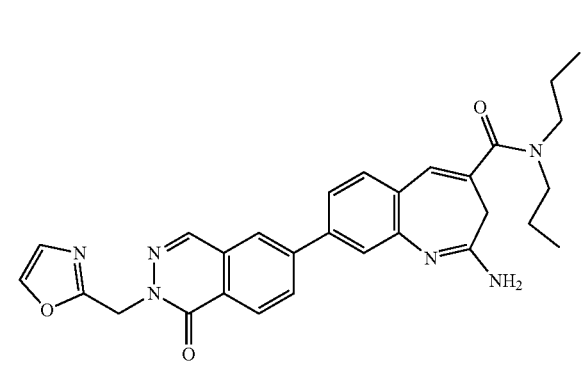
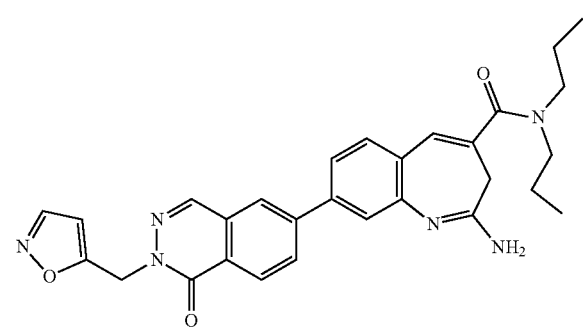

263
-continued
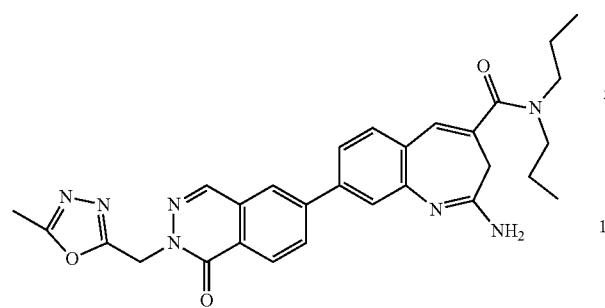
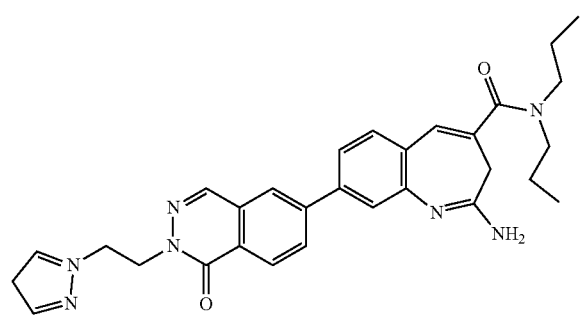
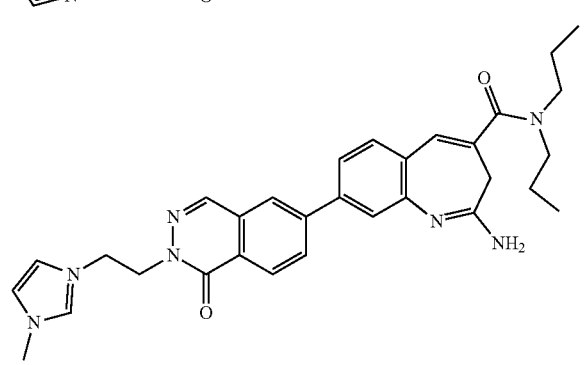
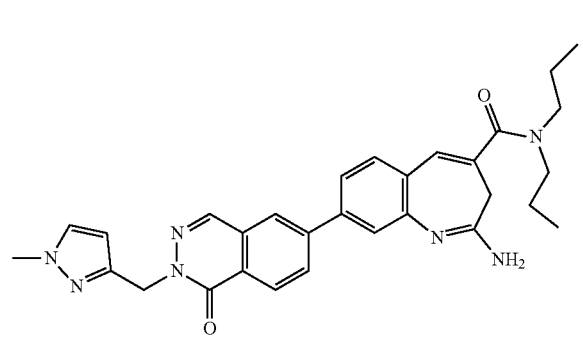
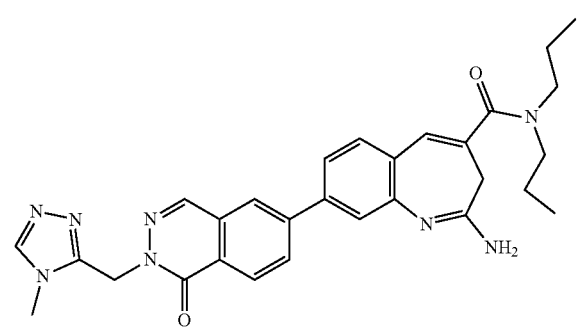
264
-continued
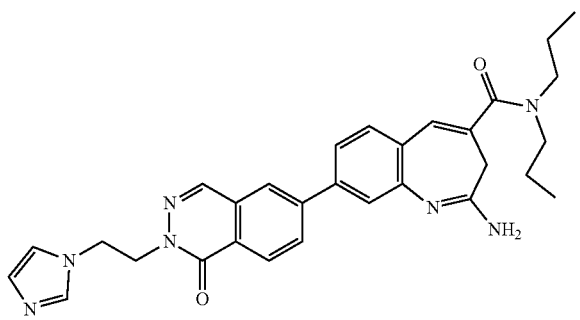
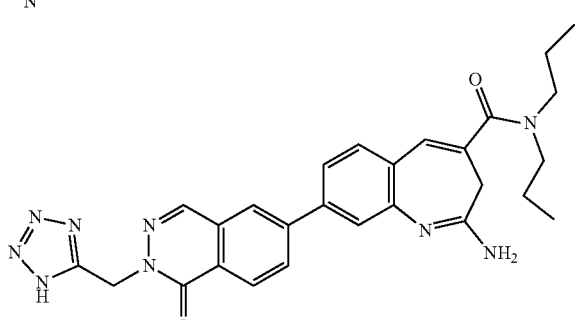
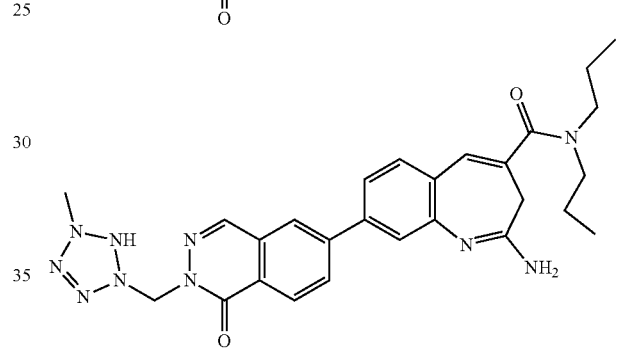
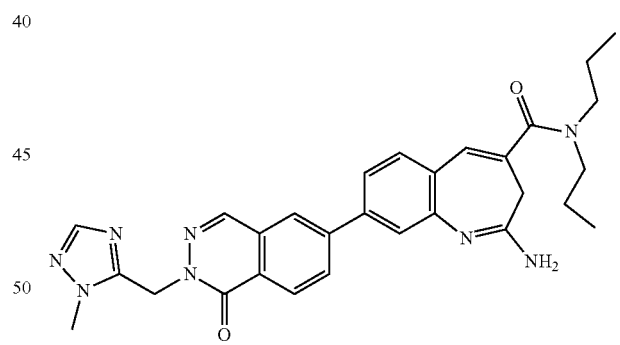
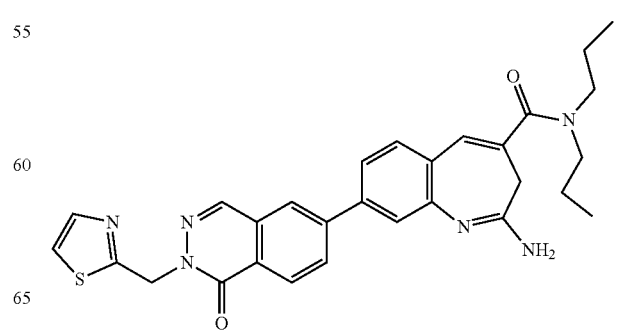

265
-continued
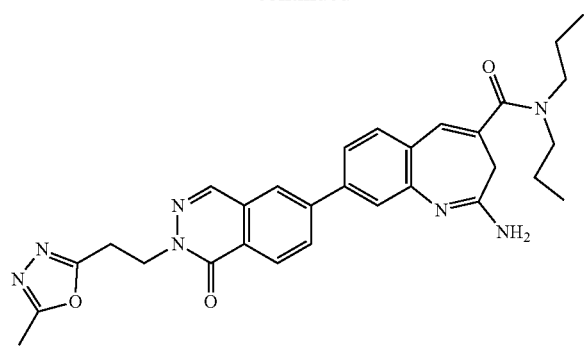
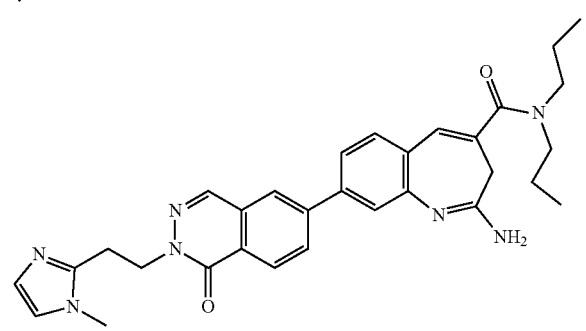
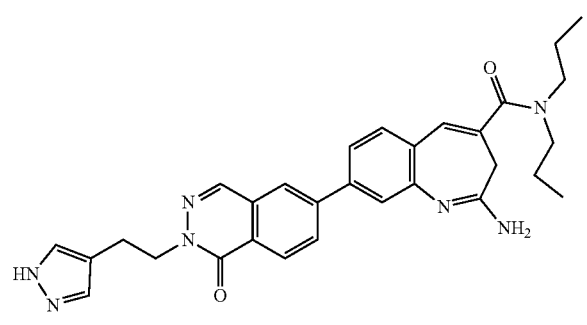
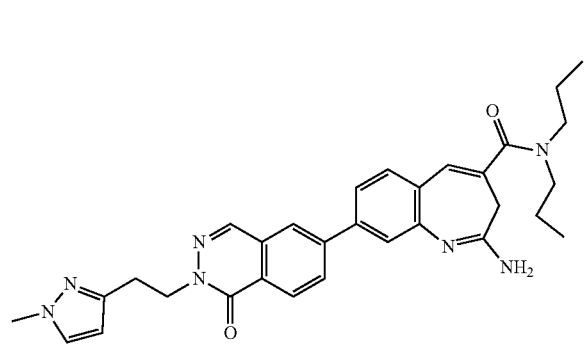
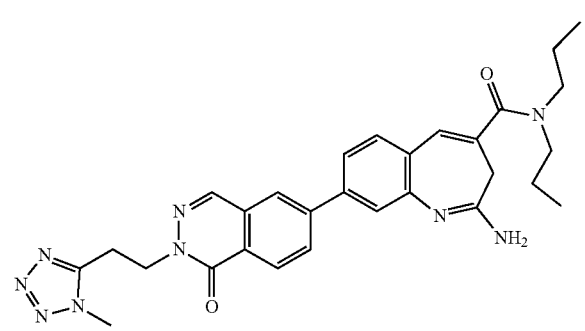
266
-continued
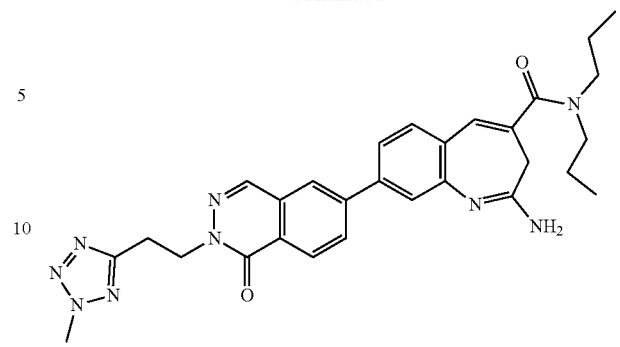
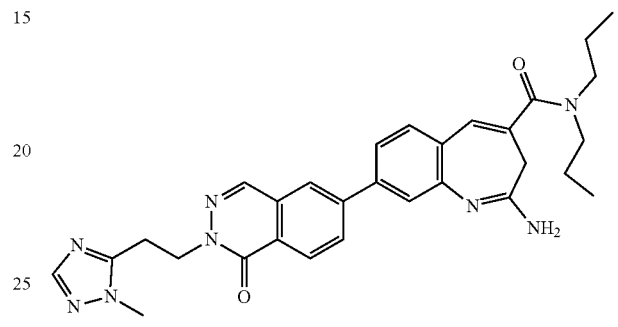
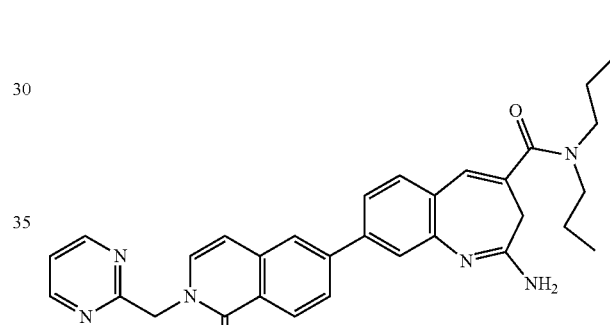
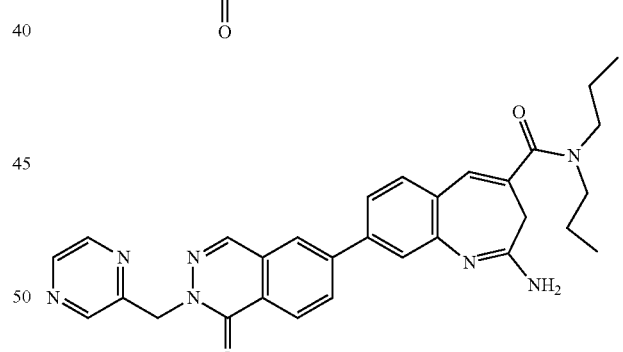
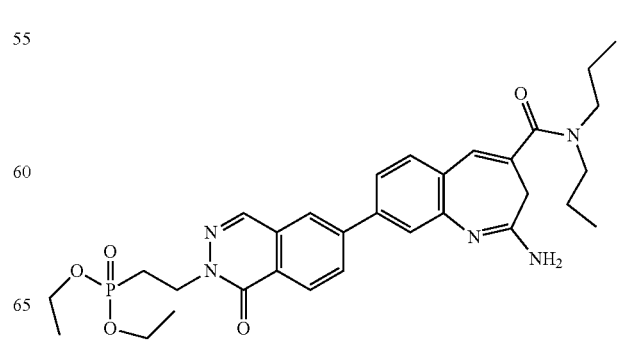

267
-continued
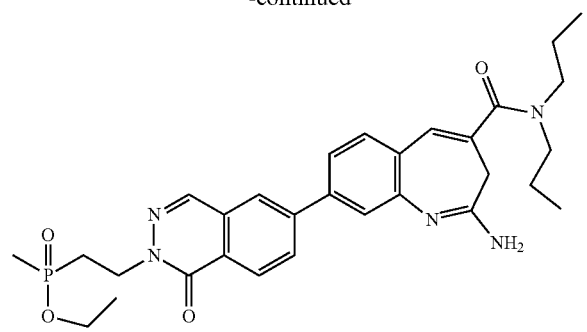
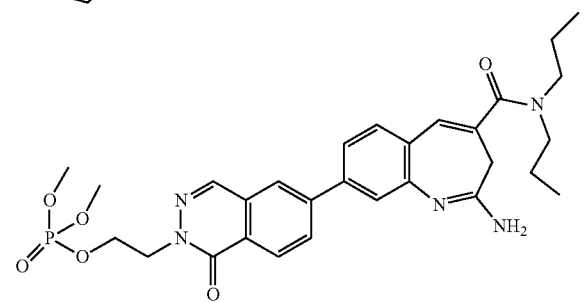
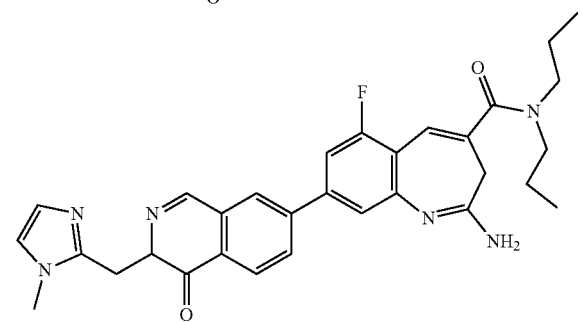
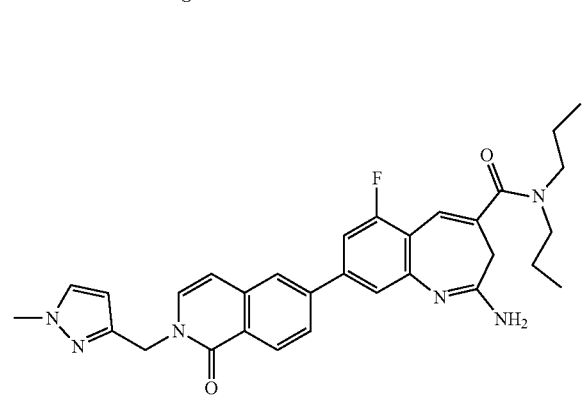
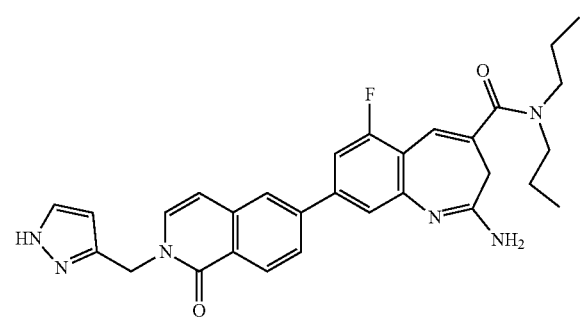
268
-continued
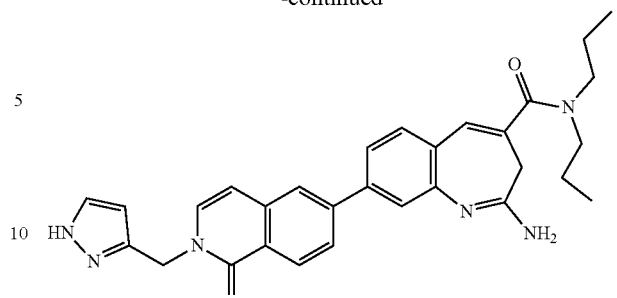
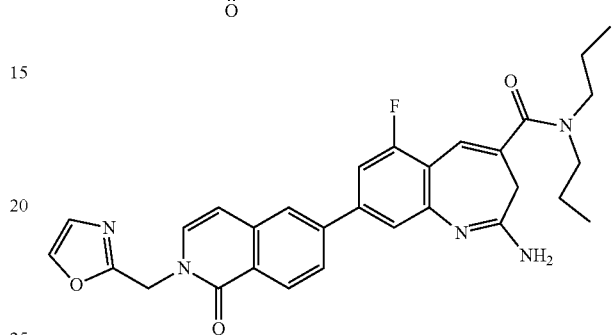
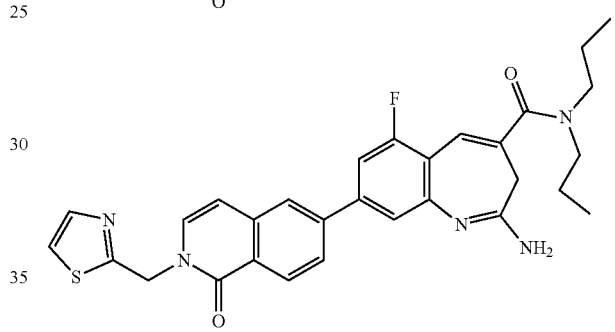
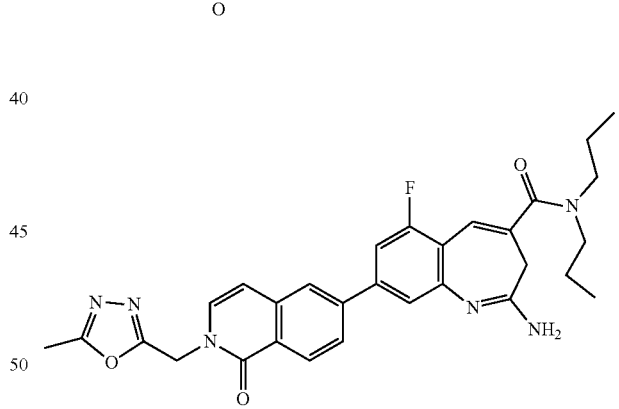
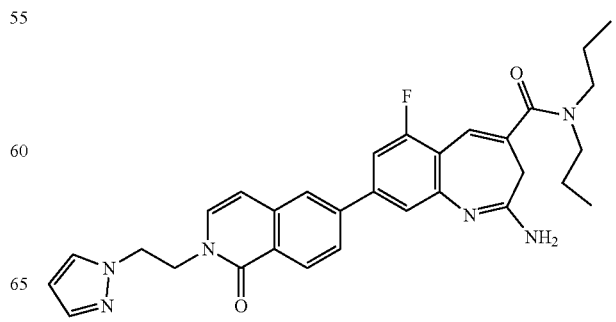

269
-continued
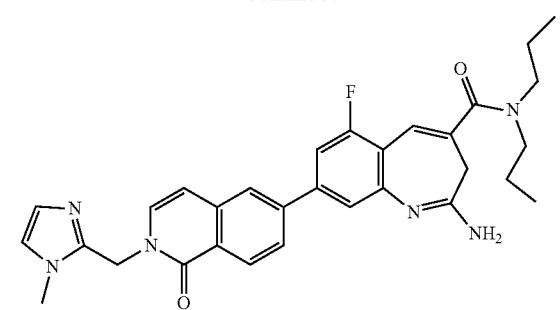
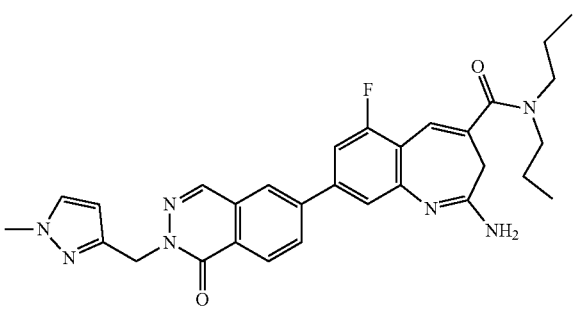
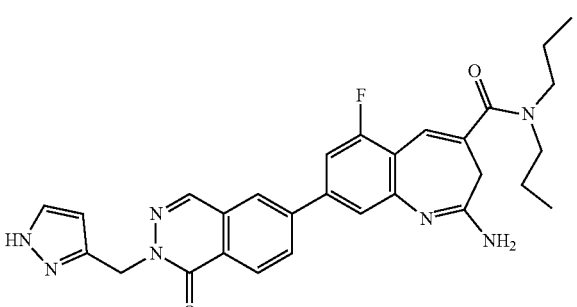
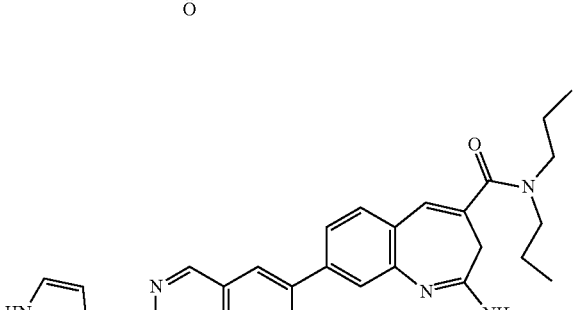
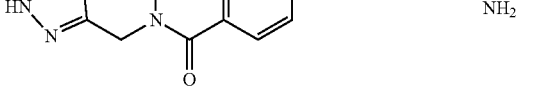
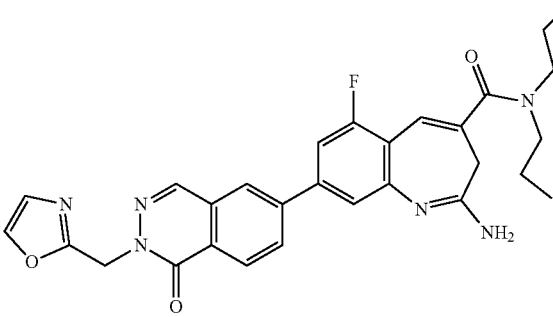
270
-continued
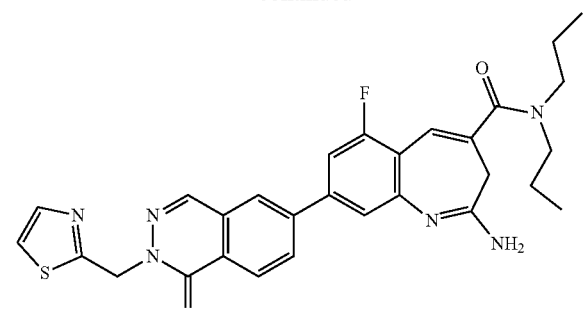
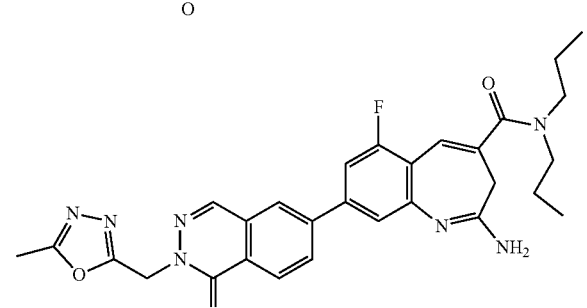
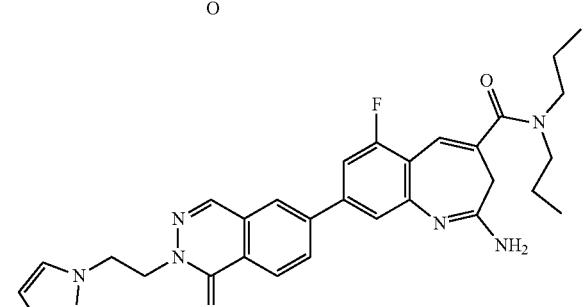
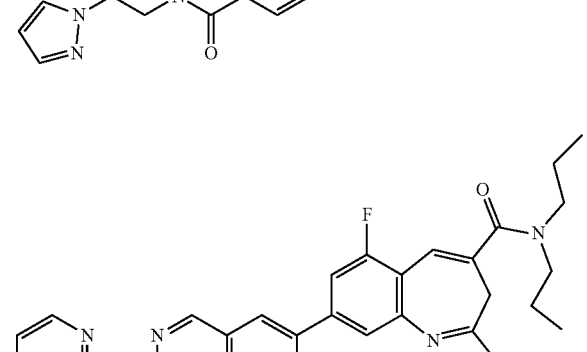
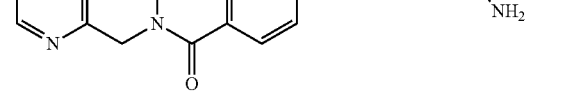
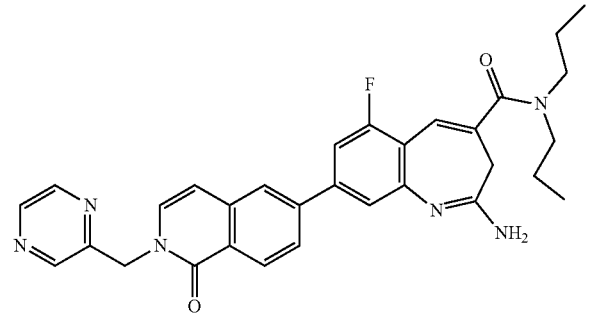

271
-continued
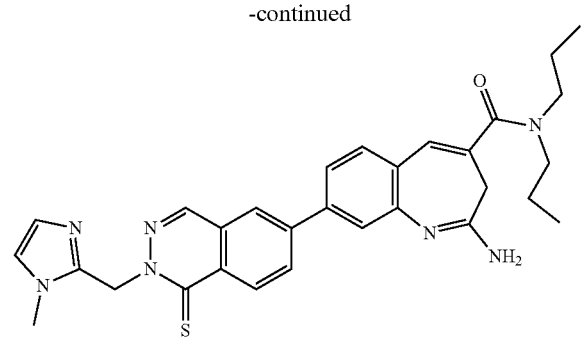
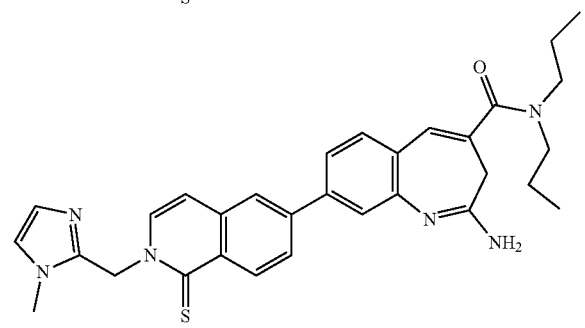
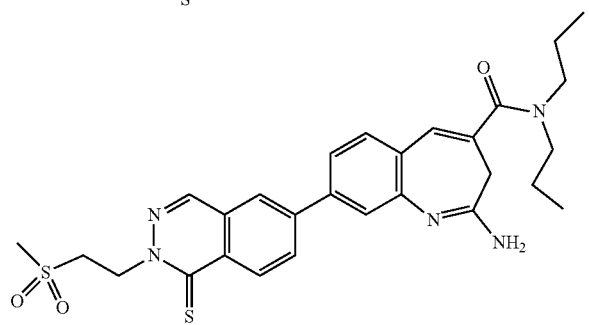
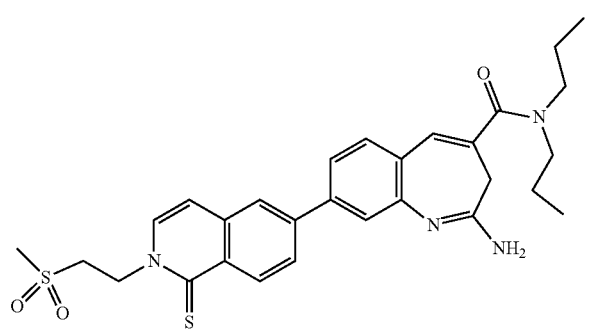
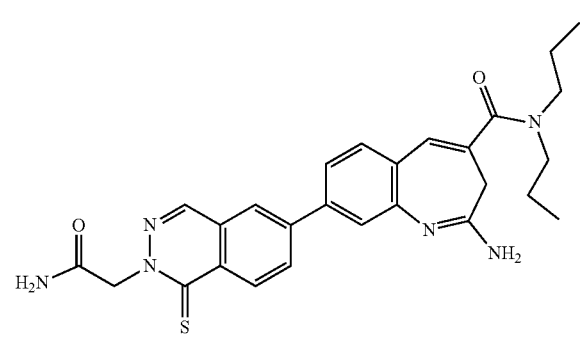
272
-continued
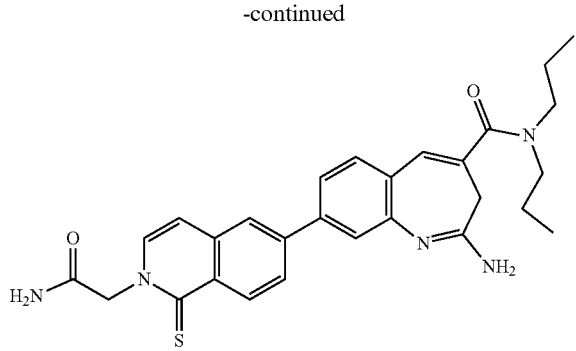
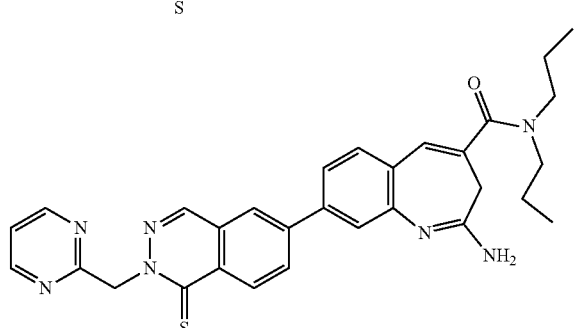
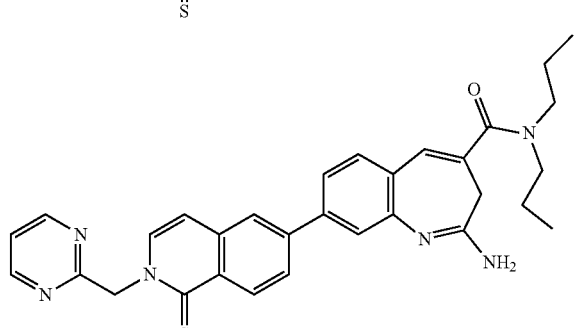
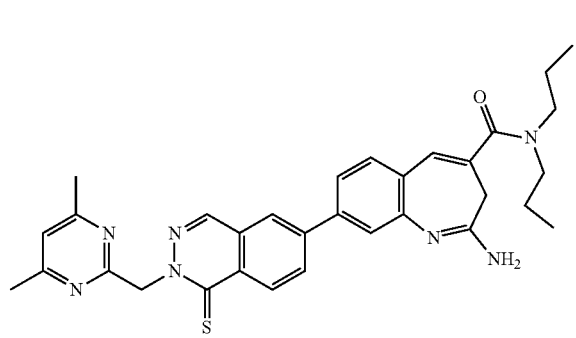
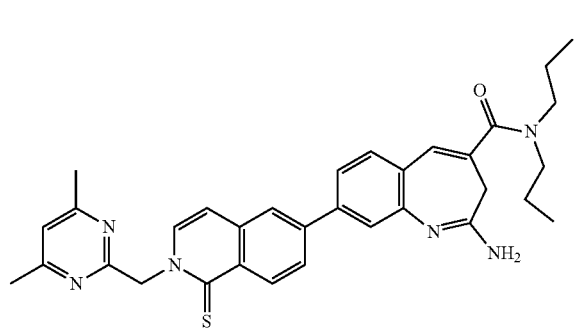

273
-continued
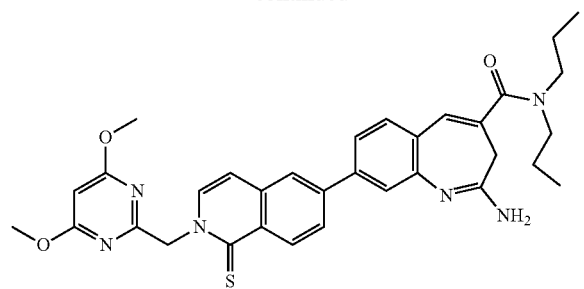
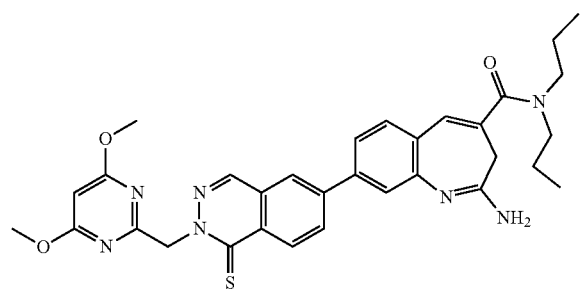
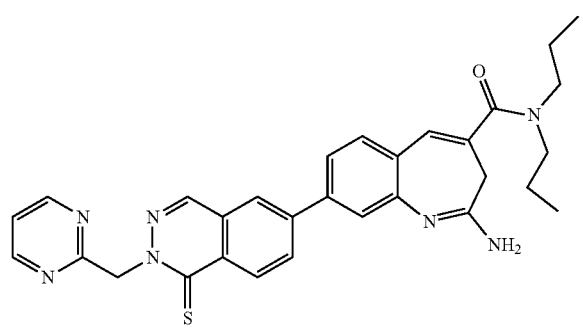
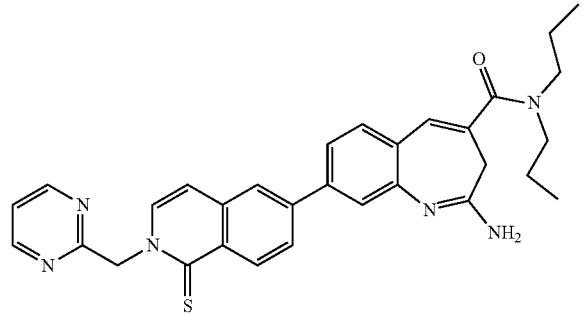
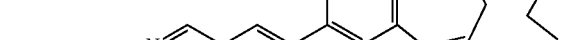
274
-continued
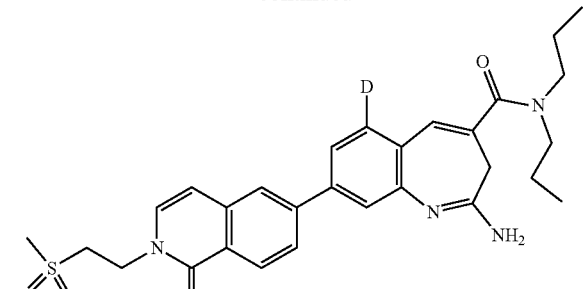
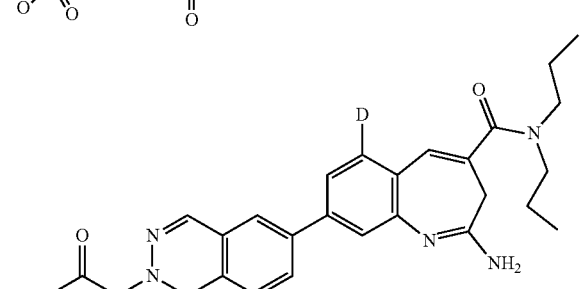
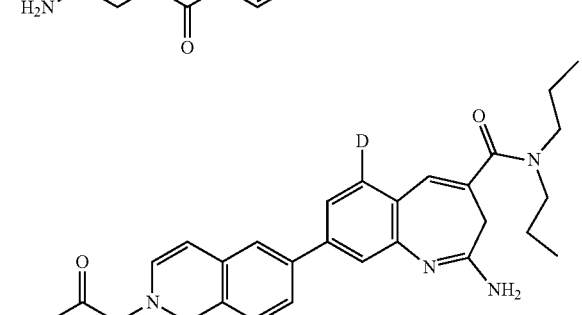
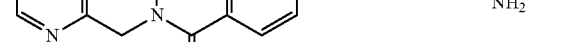

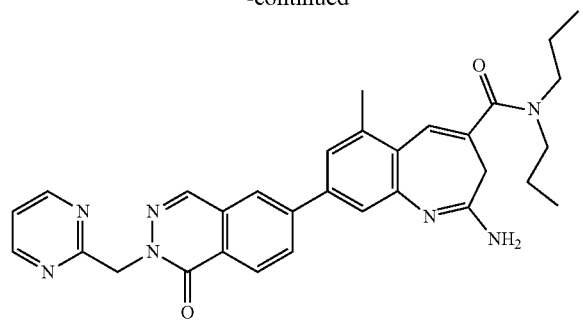
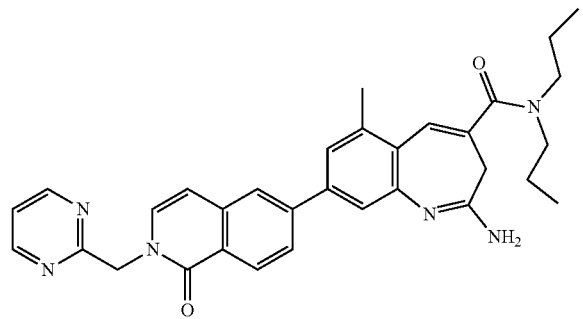
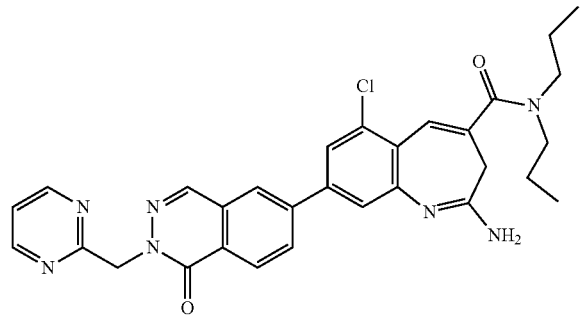
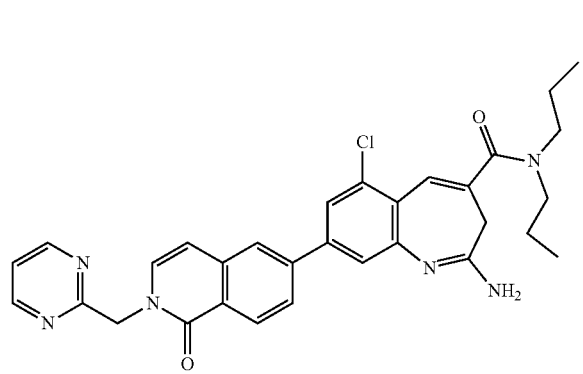
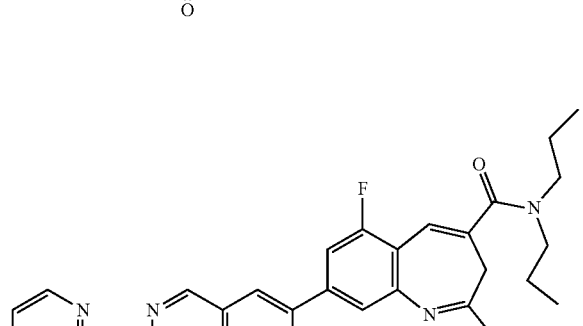
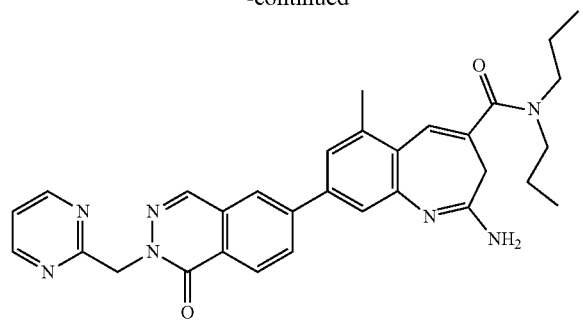
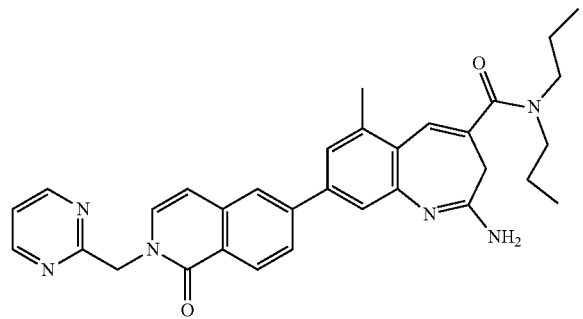
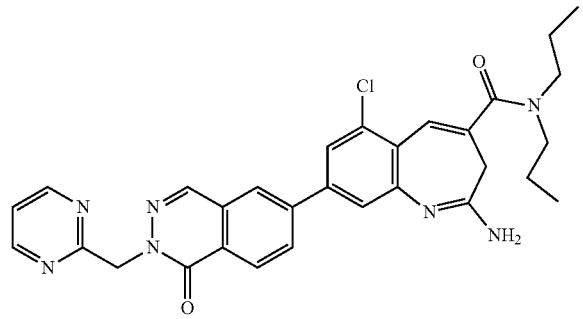
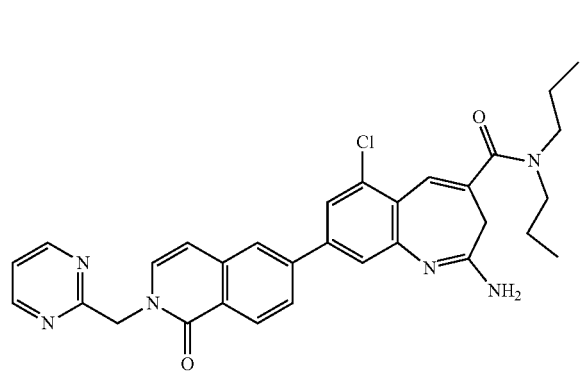
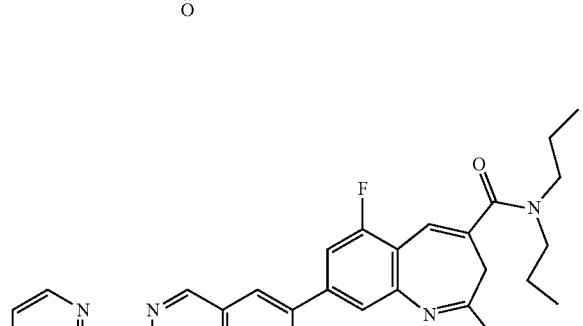

277
-continued
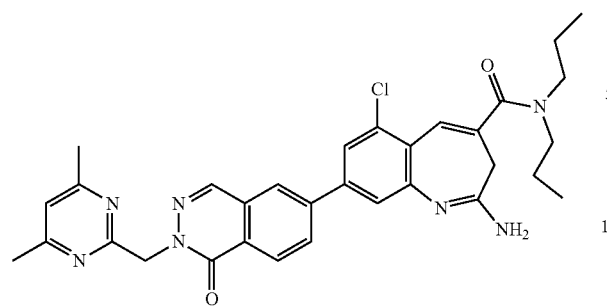
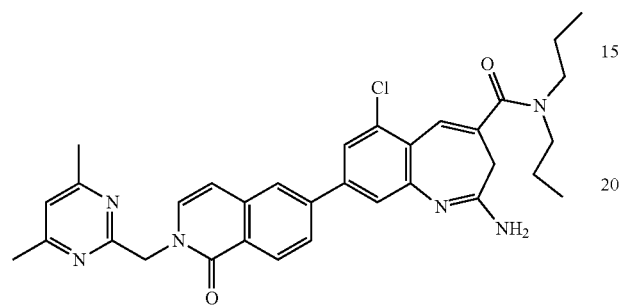
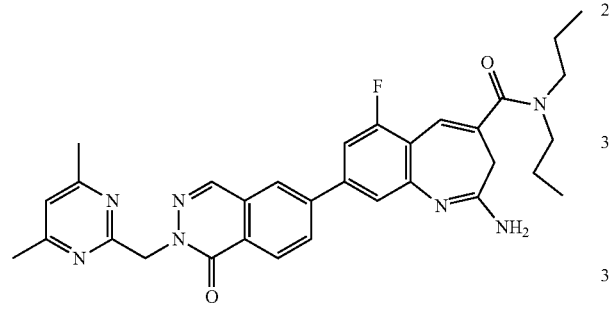
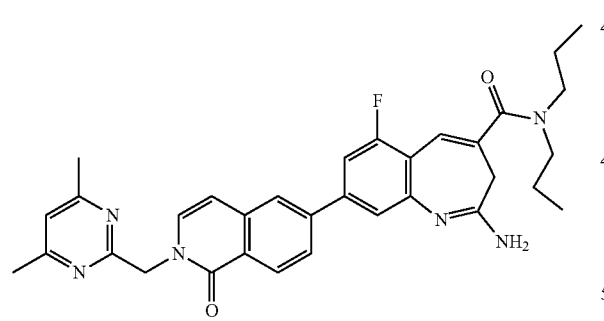
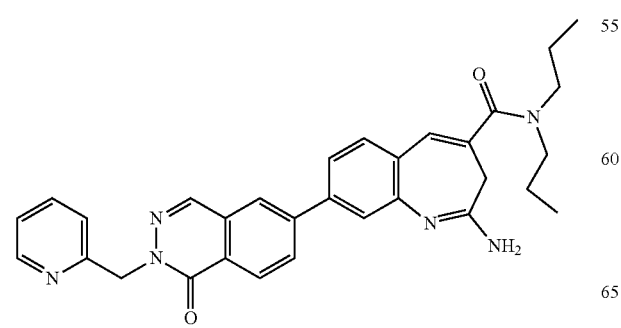
278
-continued
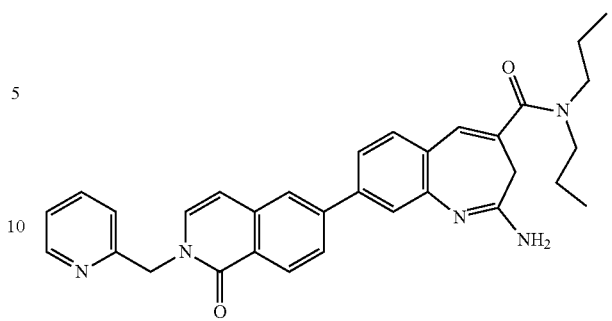
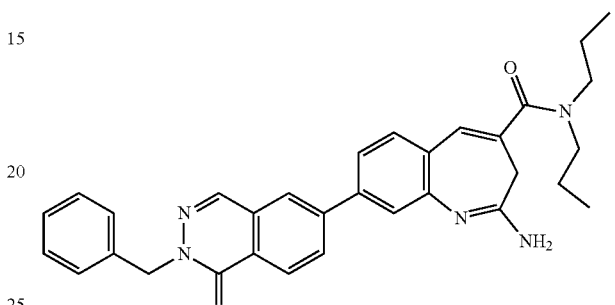
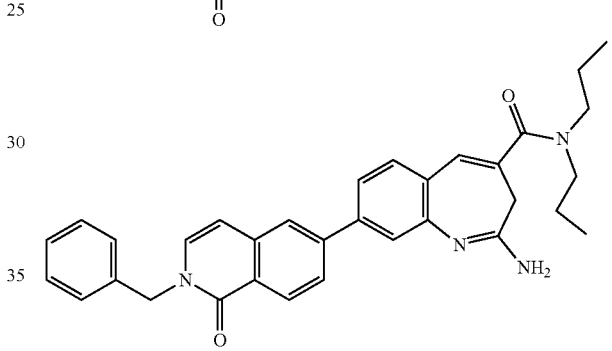
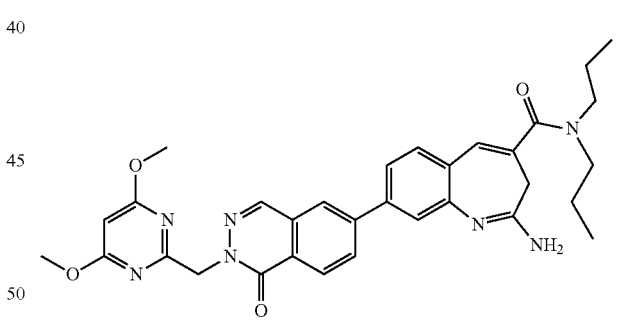
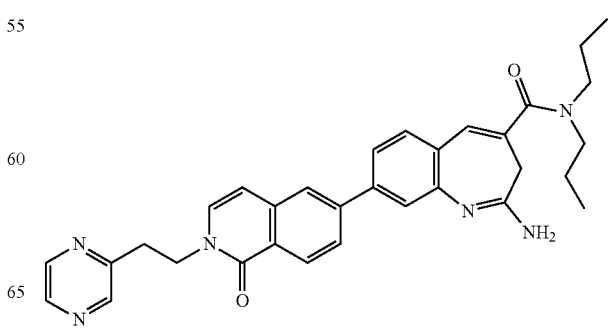

279
-continued
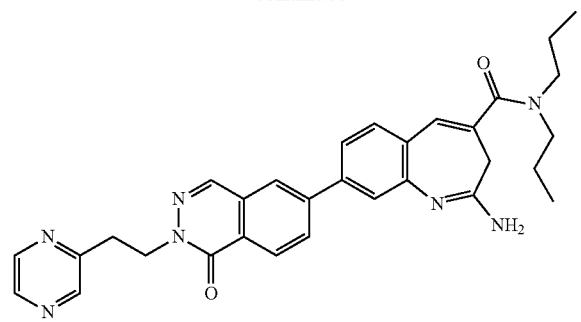
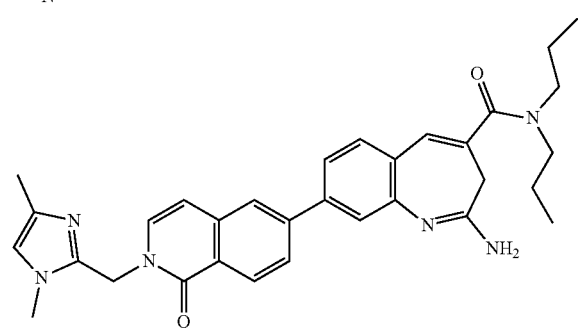
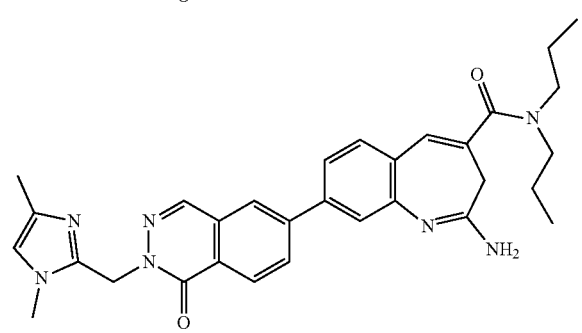
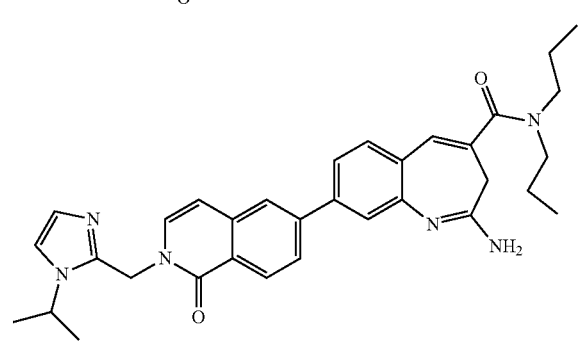
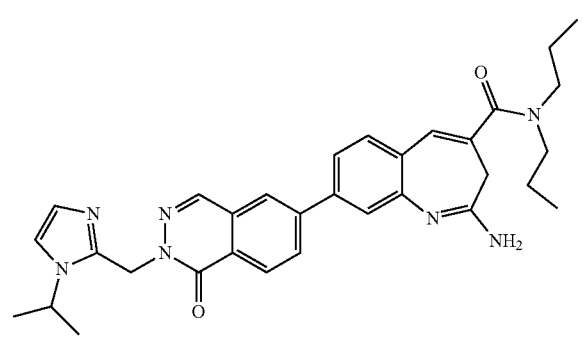
280
-continued
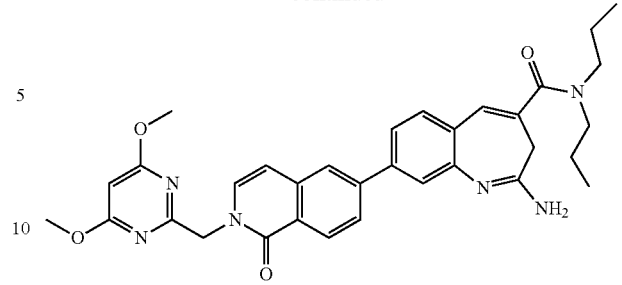
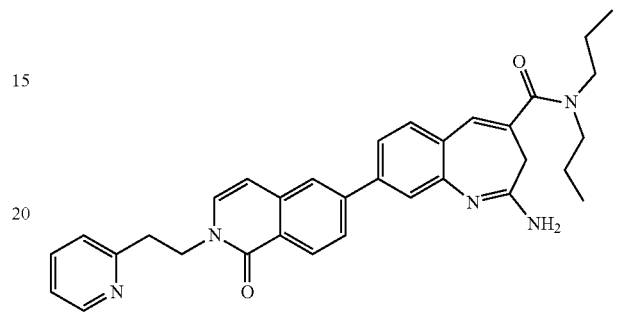
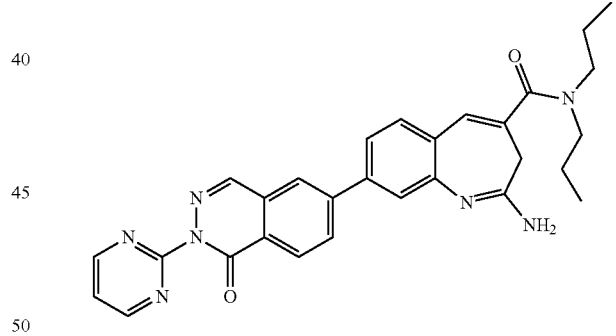
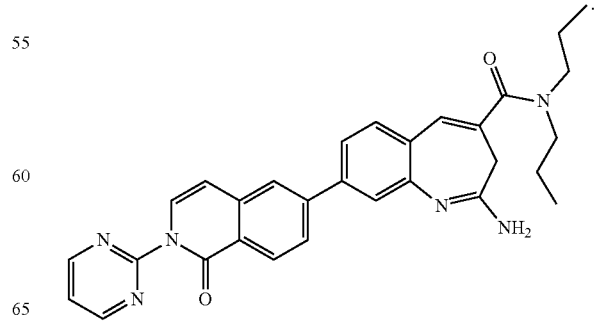

-continued and

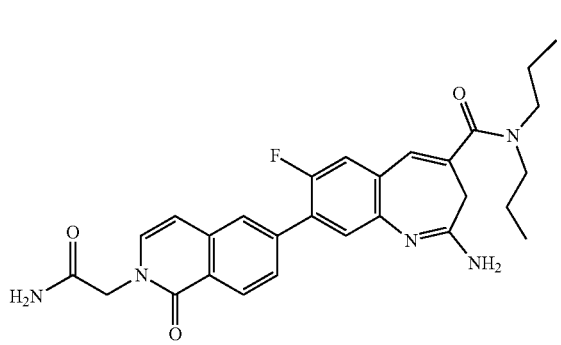

11. The preparation method of the compound of formula (I), the isomer, the prodrug, the stable isotopic derivative or the pharmaceutically acceptable salt thereof according to claim 1, which is any one of the following methods:

method 1 comprising conducting a suzuki coupling reaction with the compound of formula I-a and

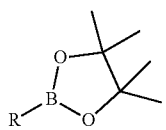

to obtain the compound of formula (I);

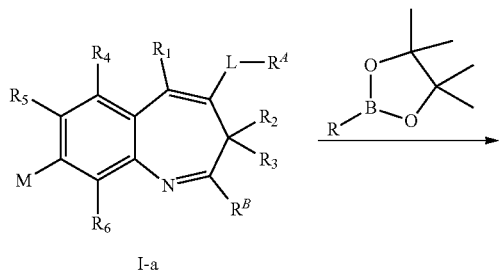

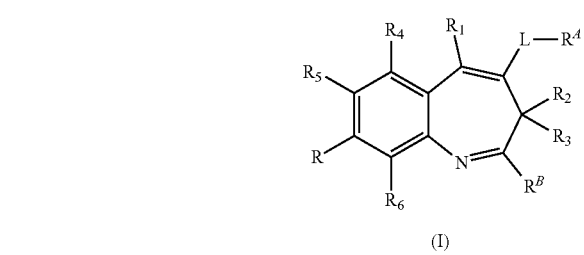

method 2 comprising conducting a suzuki coupling reaction with the compound I-b and R-M to obtain the compound of formula (I);

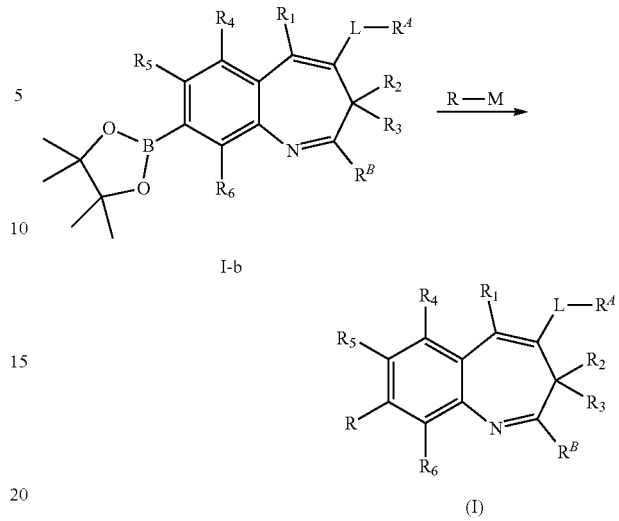

wherein, M is bromine, chlorine, iodine or —OS(O)$_2$CF$_3$; $R_1$, $R_3$, $R_4$, $R_5$, $R_6$, $R^A$, $R^B$, R and L are defined as claim 1.

12. A pharmaceutical composition, comprising a therapeutically effective amount of the compound of formula (I), the tautomer, the prodrug, the stable isotopic derivative or the pharmaceutically acceptable salt thereof according to claim 1, and pharmaceutically acceptable excipient(s).

13. A method for treating, and/or alleviating preventing cancers, viral infections, inflammations, autoimmune diseases, transplant rejections and transplant-versus-host diseases in a subject in need thereof, comprising administering an effective amount of the compound of formula (I), the tautomer, the prodrug, the stable isotopic derivative or the pharmaceutically acceptable salt thereof according to claim 1 to the subject.

14. The method according to claim 13, wherein the compound of formula (I), the tautomer, the prodrug, the stable isotopic derivative or the pharmaceutically acceptable salt thereof according to claim 1 is further used in combination with one or more than one other kinds of therapeutic agents and/or therapeutic methods.

15. The compound of formula (I), the isomer, the prodrug, the stable isotopic derivative or the pharmaceutically acceptable salt thereof according to claim 9, which is shown as the compound of formula (IB), (IC), (ID), (IE), (IF), (IG), (IH) or (II), the isomer, the prodrug, the stable isotopic derivative or the pharmaceutically acceptable salt thereof:

the compound of formula (IB) or (IC), the isomer, the prodrug, the stable isotopic derivative or the pharmaceutically acceptable salt thereof:

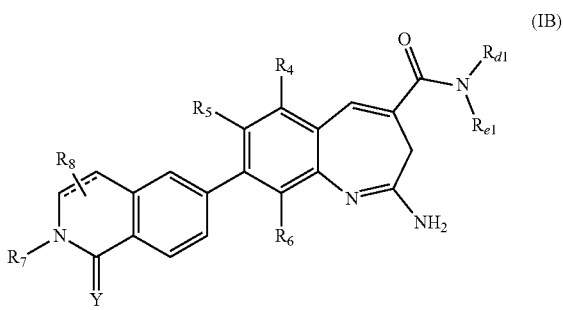

(IC)

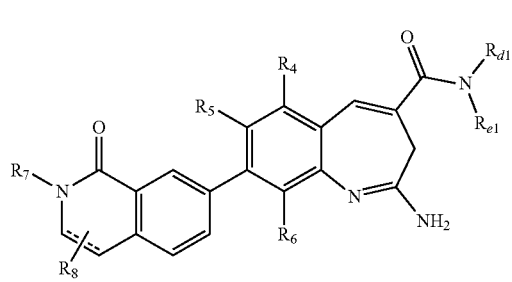

wherein, ═══ is a single bond or a double bond;
$R_{d1}$, $R_{e1}$, $R_4$, $R_5$, $R_6$, $R_7$, $R_8$ and Y are defined as claim 9;

the compound of formula (ID) or (IE), the isomer, the prodrug, the stable isotopic derivative or the pharmaceutically acceptable salt thereof:

(ID)

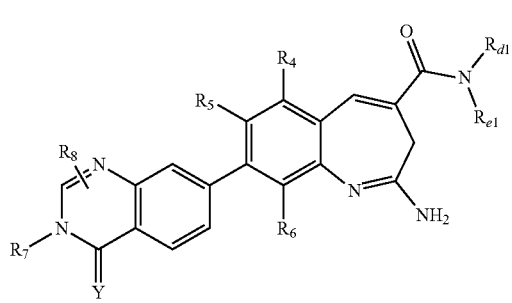

(IE)

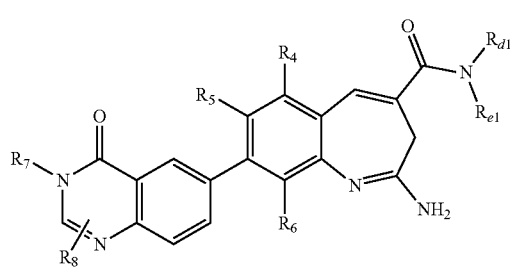

wherein, $R_{d1}$, $R_{e1}$, $R_4$, $R_5$, $R_6$, $R_7$, $R_8$ and Y are defined as claim 9;

the compound of formula (IF) or (IG), the isomer, the prodrug, the stable isotopic derivative, or the pharmaceutically acceptable salt thereof:

(IF)

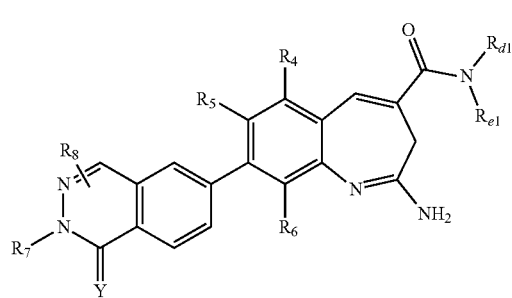

(IG)

wherein, $R_{d1}$, $R_{e1}$, $R_4$, $R_5$, $R_6$, $R_7$, $R_8$ and Y are defined as claim 9;

the compound of formula (IH) or (II), the isomer, the prodrug, the stable isotopic derivative, or the pharmaceutically acceptable salt thereof:

(IH)

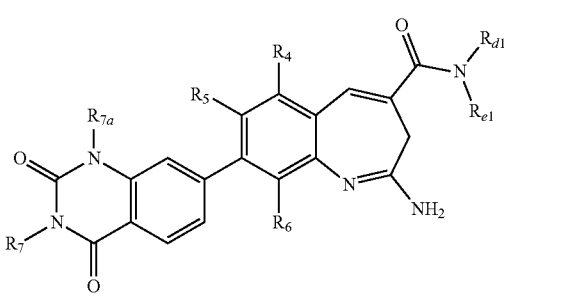

(II)

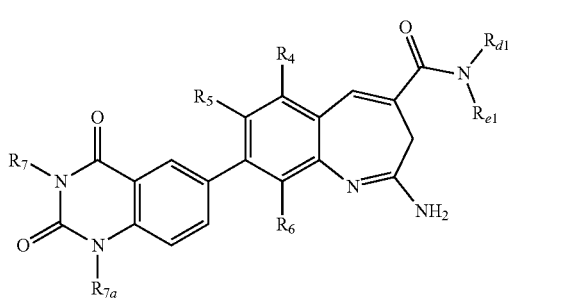

wherein, $R_{d1}$, $R_{e1}$, $R_4$, $R_5$, $R_6$, $R_7$ and $R_{7a}$ are defined as claim 9.

16. The compound of formula (I), the isomer, the prodrug, the stable isotopic derivative or the pharmaceutically acceptable salt thereof according to claim 1, which is shown as the compound of formula (IJ), the isomer, the prodrug, the stable isotopic derivative or the pharmaceutically acceptable salt thereof:

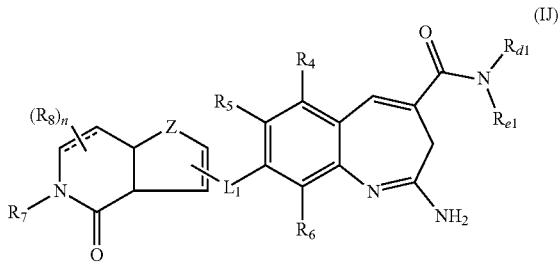

(IJ)

wherein, ═══ is a single bond or a double bond; Z is N($R_{7a}$) or S;

each of $R_7$ and $R_{7a}$ is independently selected from hydrogen, halogen, alkyl, haloalkyl, alkenyl, alkynyl, $Cy^1$, -$L_2$-$Cy^1$, —$SR_d$, —$OR_d$, —C(O)$OR_d$, —C(O)$R_d$, —C(O)$NR_dR_e$, —C(O)$NR_dS(O)_2R_e$, —C(=NH)$R_e$, —C(=NH)$NR_dR_e$, —$S(O)_2R_e$ and —$S(O)_2NR_dR_e$; wherein the alkyl, alkenyl or alkynyl is unsubstituted or substituted at any position by one or more than one substituent selected from the group consisting of —CN, —$NO_2$, —$SR_d$, —$OR_d$, —OC(O)$R_d$, —OC(O)$OR_d$, —OC(O)$NR_dR_e$, —C(O)$OR_d$, —C(O)$R_d$, —C(O)$NR_dR_e$, —C(O)$NR_dS(O)_2R_e$, —$NR_dR_e$, —$NR_dC(O)R_e$, —N($R_d$)C(O)$OR_e$, —N($R_d$)C(O)$NR_dR_e$, —$NR_dC$(=NH)$R_e$, —$NR_dC$(=NH)$NR_dR_e$, —$NR_dS(O)_2R_e$, —$NR_dS(O)_2NR_dR_e$, —N($R_d$)C(O)N($R_d$)$S(O)_2R_e$, —$S(O)_{1-2}R_e$, —$S(O)_2NR_dR_e$, —S(O)(=NCN)$R_e$, —S(O)(=N$R_d$)$R_e$, —S(O)(=$NSO_2R_d$)$R_e$, —$S(O)_2N$($R_d$)C(O)$R_e$, —$S(O)_2N$($R_d$)C(O)$NR_dR_e$, —P(O)($OR_d$)$_2$, —OP(O)($OR_d$)$_2$ or —B($OR_d$)$_2$;

each of $R_8$ is independently hydrogen, halogen, alkyl, haloalkyl, haloalkoxy, alkenyl, alkynyl, $Cy^1$, -$L_2$-$Cy^1$, —CN, —$NO_2$, —$SR_d$, —$OR_d$, —OC(O)$R_d$, —OC(O)$OR_d$, —OC(O)$NR_dR_e$, —C(O)$OR_d$, —C(O)$R_d$, —C(O)$NR_dR_e$, —C(O)$NR_dS(O)_2R_e$, —C(=NH)$R_e$, —C(=NH)$NR_dR_e$, —$NR_dR_e$, —$NR_dC(O)R_e$, —N($R_d$)C(O)$OR_e$, —N($R_d$)C(O)$NR_dR_e$, —$NR_dS(O)_2R_e$, —$NR_dC$(=NH)$R_e$, —$NR_dC$(=NH)$NR_dR_e$, —$S(O)_{1-2}R_e$, —$S(O)_2NR_dR_e$ and —$NR_dS(O)_2NR_dR_e$; wherein the alkyl, alkenyl or alkynyl is unsubstituted or substituted at any position by one or more than one substituent selected from the group consisting of —CN, —$NO_2$, —$SR_d$, —$OR_d$, —OC(O)$R_d$, —OC(O)$OR_d$, —OC(O)$NR_dR_e$, —C(O)$OR_d$, —C(O)$R_d$, —C(O)$NR_dR_e$, —C(O)$NR_dS(O)_2R_e$, —$NR_dR_e$, —$NR_dC(O)R_e$, —N($R_d$)C(O)$OR_e$, —N($R_d$)C(O)$NR_dR_e$, —$NR_dC$(=NH)$R_e$, —$NR_dC$(=NH)$NR_dR_e$, —$NR_dS(O)_2R_e$, —$NR_dS(O)_2NR_dR_e$, —N($R_d$)C(O)N($R_d$)$S(O)_2R_e$, —$S(O)_{1-2}R_e$, —$S(O)_2NR_dR_e$, —$S(O)_2N$($R_d$)C(O)$R_e$ or —$S(O)_2N$($R_d$)C(O)$NR_dR_e$;

n is 1 or 2;

$L_1$, $R_{d1}$, $R_{e1}$, $R_4$, $R_5$ and $R_6$ are defined as claim 1.

17. The compound of formula (I), the isomer, the prodrug, the stable isotopic derivative or the pharmaceutically acceptable salt thereof according to claim 16, which is shown as the compound of formula (IK) or (IL), the isomer, the prodrug, the stable isotopic derivative or the pharmaceutically acceptable salt thereof:

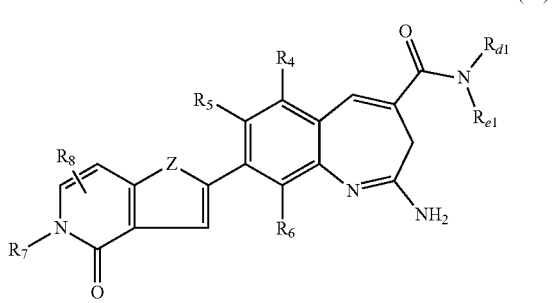

(IK)

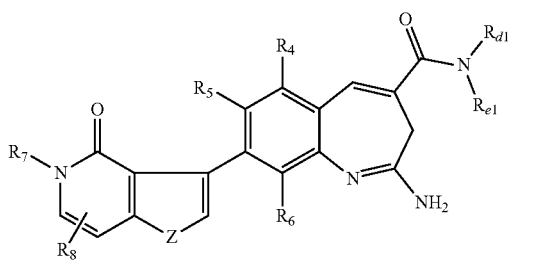

(IL)

wherein, Z is NH, N($CH_3$) or S;

$R_{d1}$, $R_{e1}$, $R_4$, $R_5$, $R_6$, $R_7$ and $R_8$ are defined as claim 16.

* * * * *